United States Patent
Kaiser et al.

(12) 
(10) Patent No.: US 6,562,611 B1
(45) Date of Patent: May 13, 2003

(54) FEN-1 ENDONUCLEASES, MIXTURES AND CLEAVAGE METHODS

(75) Inventors: Michael W. Kaiser, Madison, WI (US); Victor I. Lyamichev, Madison, WI (US); Natasha Lyamicheva, Madison, WI (US)

(73) Assignee: Third Wave Technologies, Ins., Madison, WI (US)

( * ) Notice: Subject to any disclaimer, the term of this patent is extended or adjusted under 35 U.S.C. 154(b) by 0 days.

(21) Appl. No.: 09/308,825

(22) PCT Filed: Nov. 26, 1997

(86) PCT No.: PCT/US97/21783

§ 371 (c)(1), (2), (4) Date: Oct. 8, 1999

(87) PCT Pub. No.: WO98/23774

PCT Pub. Date: Jun. 4, 1998

Related U.S. Application Data

(63) Continuation of application No. 08/757,653, filed on Nov. 29, 1996, now Pat. No. 5,843,669, which is a continuation of application No. 08/758,314, filed on Dec. 2, 1996, now Pat. No. 6,090,606.

(51) Int. Cl.[7] .................................................. C12N 9/22
(52) U.S. Cl. ...................................... 435/199; 435/975
(58) Field of Search ................................. 435/199, 975

(56) References Cited

U.S. PATENT DOCUMENTS

| | | | |
|---|---|---|---|
| 4,511,502 A | 4/1985 | Builder et al. ............... | 260/112 |
| 4,511,503 A | 4/1985 | Olson et al. ................ | 260/112 |
| 4,512,922 A | 4/1985 | Jones et al. ................ | 260/112 |
| 4,518,526 A | 5/1985 | Olson ........................ | 260/112 |
| 4,683,194 A | 7/1987 | Saiki et al. ................... | 435/6 |
| 4,683,195 A | 7/1987 | Mullis et al. ................. | 435/6 |
| 4,683,202 A | 7/1987 | Mullis ......................... | 435/91 |
| 4,775,619 A | 10/1988 | Urdea ........................ | 435/6 |
| 4,876,187 A | 10/1989 | Duck et al. ................... | 435/6 |
| 5,011,769 A | 4/1991 | Duck et al. ................... | 435/6 |
| 5,108,892 A | 4/1992 | Burke et al. .................. | 435/6 |
| 5,118,605 A | 6/1992 | Urdea ........................ | 435/6 |
| 5,144,019 A | 9/1992 | Rossi ......................... | 536/27 |
| 5,210,015 A | 5/1993 | Gelfand et al. ............... | 435/6 |
| 5,380,833 A | 1/1995 | Urdea ........................ | 536/22.1 |
| 5,403,711 A | 4/1995 | Walder et al. ................. | 435/6 |
| 5,422,253 A | 6/1995 | Dahlberg et al. ........ | 435/91.53 |
| 5,427,930 A | 6/1995 | Birkenmeyer et al. ........ | 435/91 |
| 5,487,972 A | 1/1996 | Geland et al. ................. | 435/6 |
| 5,494,810 A | 2/1996 | Barany et al. ........... | 435/91.52 |
| 5,545,729 A | 8/1996 | Goodchild et al. ........ | 536/24.5 |
| 5,698,400 A | 12/1997 | Cotton et al. ................. | 435/6 |
| 5,783,392 A | 7/1998 | Seibl et al. .................... | 435/6 |
| 5,792,614 A | 8/1998 | Western et al. ............... | 435/6 |
| 5,830,664 A | 11/1998 | Rosemeyer et al. .......... | 435/6 |
| 5,843,669 A | 12/1998 | Kaiser et al. ................. | 435/6 |
| 5,874,283 A | 2/1999 | Harrington et al. ........ | 435/252 |
| 5,882,867 A | 3/1999 | Ullman et al. ................ | 435/6 |
| 5,888,780 A | 3/1999 | Dahlberg et al. ........ | 435/91.53 |
| 5,985,557 A | 11/1999 | Prudent et al. ................ | 435/6 |
| 5,994,069 A | 11/1999 | Hall et al. ..................... | 435/6 |

FOREIGN PATENT DOCUMENTS

| | | |
|---|---|---|
| EP | 0 411 186 A1 | 2/1991 |
| EP | 0 482 714 A1 | 10/1991 |
| WO | 89/09284 | 10/1989 |
| WO | 90/01069 | 2/1990 |
| WO | 91/09950 | 7/1991 |
| WO | 92/06200 | 4/1992 |
| WO | 94/29482 | 12/1994 |
| WO | 95/14106 | 5/1995 |
| WO | 96/20287 | 7/1996 |

OTHER PUBLICATIONS

Kelnk, H–P., et al. (1997) Nature 390, 364–370.*
Nolan, J.P., et al. (1996) Biochemistry 35, 11668–11676.*
Wu, X, et al. (1996) Nucl. Acids Res. 24(11), 2036–2043.*
Li, X, et al. (1995) J. Biol. Chem. 270(38), 22109–22112.*
Harrington, J.J., et al. (1995) J. Biol. Chem. 270(9), 4503–4508.*
Harrington, J.J., et al. (1994) Embo J. 13(5), 1235–1246.*
Akhmetzjanov and Vakhitov, "Molecular cloning and nucleotide sequence of the DNA polymerase gene from *Thermus flavus*," *Nucl. Acids Res.* 20:5839 (1992).
Altamirano et al., "Identification of Hepatitis C Virus Genotypes among Hospitalized Patients in British Columbia, Canada," *J. Infect. Dis.* 171:1034–1038 (1995).
Anderson and Young, "Quantitative Filter Hybridization", in *Nucleic Acid Hybridization*, Eds Hames & Higgins, IRL Press, Washington, DC, pp. 73–111 (1985).
*Electrophoresis*, 2nd Edition, ed. Anthony T. Andrews, Clarendon Press, New York, New York (1986), pp. 153–154.
Antao et al. "A thermodynamic study of unusually stable RNA and DNA hairpins," *Nucl. Acids Res.* 19:5901–5905 (1991).
Barany, "Genetic disease detection and DNA amplification using cloned thermostable ligase," *Proc. Natl. Acad. Sci.*, 88:189–193 (1991);Bambara et al., "Enzymes and Reactions at the Eukaryotic DNA Replication Fork," *J. Biol. Chem.* 272:4647–4650 (1997).
Barany, "The Ligase Chain Reaction in a PCR World," *PCR Methods and Applic.*, 1:5–16 (1991).

(List continued on next page.)

Primary Examiner—Charles L. Patterson, Jr.
(74) Attorney, Agent, or Firm—Medlen & Carroll, LLP

(57) ABSTRACT

The present invention relates to means for the detection and characterization of nucleic acid sequences, as well as variations in nucleic acid sequences. The present invention also relates to improved cleavage means for the detection and characterization of nucleic acid sequences. Structure-specific nucleases derived from a variety of thermostable organisms are provided. These structure-specific nucleases are used to cleave target-dependent cleavage structures, thereby indicating the presence of specific nucleic acid sequences or specific variations thereof.

47 Claims, 185 Drawing Sheets

OTHER PUBLICATIONS

Bardwell et al., "Specific Cleavage of Model Recombination and Repair Intermediates by the Yeast Rad1–Rad10 DNA Endonuclease," *Science* 265:2082–2085 (1994).

Barnes eta al., "Mechanism of Tracking and Cleavage of Adduct–damaged DNA Substrates by the Mammalian 5'- to 3'Exonuclease/Endonuclease RAD2 Homologue 1 or Flap Endonuclease 1", *J. Biol. Chem.* 271:29624–29632 (1996).

Bergseid et al., "A High Fidelity Thermostable DNA Polymerase Isolated from *Pyrococcus Furiosus*," *Strategies* 4:34–35 (1991).

Bhagwat et al., "The 5'–Exonuclease Activity of Bacteriophage T4 RNase H is Stimulated by the T4 Gene 32 Single–stranded DNA–binding Protein, but Its Flap Endonuclease Is Inhibited," *J. Biol. Chem.* 272:28523–28530 (1997).

Bonch–Osmolovskaya, et al., *Microbiology* (Engl. Transl. of Mikrobiologiya) 57:78–85 (1988).

Brutiag et al., "An Active Fragment of DNA Polymerase Produced By Proteolytic Cleavage," *Biochem. Biophys. Res. Commun.* 37:982–989 (1969).

Brow et al., "Differentiation of Bacterial 16S rRNA Genes and Intergenic Regions and *Mycobacterium tuberculosis* katG Genes by Structure–Specific Endonuclease Cleavage," *J. of Clin. Micro.* 34:3129–3137 (1996).

Carballeira et al., "Purification of a Thermostable DNA Polymerase from *Thermus thermophilus* HB8, Useful in the Polymerase Chain Reaction," *Biotechniques* 9:276–281 (1990).

Ceska et al., "A helical arch allowing single–stranded DNA to thread through T5 5'–exonuclease," *Nature* 382:90–93 (1996).

Ceska et al., "Structure–specific DNA cleavage by 5' nucleases," *TIPS 23* (1998), 331.

Chamberlin and Ryan, "Bacteriophage DNA–Dependent RNA Polymerases", *The Enzymes*, XV:87–108 (1982).

Copley and Boot, "Exonuclease Cycling Assay: An Amplified Assay for the Detection for the Detection of Specific DNA Sequences," *BioTechniques* 13:888–891 (1992).

Cuthbert, "Hepatitis C:Progress and Problems," *Clin. Microbiol. Rev.* 7:505–532 (1994).

DeMott et al., "Human RAD2 Homolog 1 5'–3'–Exo/Endonuclease Can Efficiently Excise a Displaced DNA Fragment Containing a 5'–Terminal Abasic Lesion by Endonuclease Activity," *J. Biol. Chem.* 271:30068–30076 (1996).

Donnabella et al., "Isolation of the Gene for the β Subunit of RNA Polymerase from Rifampicin–resistant *Mycobacterium tuberculosis* and Identification of New Mutations,"*Am. J. Respir. Dis.* 11:639–643 (1994).

Doty et al., "Strand Separation and Specific Recombination in Deoxyribonucleic Acids: Physical Chemical Studies," *Proc. Natl. Acad. Sci. USA* 46:461–476 (1960).

Duck et al., "Probe Amplifier System Based on Chimeric Cycling Oligonucleotides," *BioTech*, 9:142–147 (1990).

Dunn et al., "Complete Nucleotide Sequence of Bacteriophage T7 DNA and the Locations of T7 Genetic Elements," *J. Mol. Biol.* 166:477–535 (1983).

Engelke, "Purification of *Thermus Aquaticus* DNA Polymerase Expressed in *Escherichia coli*," *Anal. Biochem.* 191:396–400 (1990).

Eom et al., "Structure of Taq polymerase with DNA at the polymerase active site," *Nature* 382:278–282 (1996).

Erlich et al., "Recent Advances in the Polymerase Chain Reaction," *Science* 252:1643–1651 (1991).

Fahy et al., "Self–sustained Sequence Replication (3SR): An Isothermal Transcription–based Amplification System Alternative to PCR," *PCR Meth. Appl.*, 1:25–33 (1991).

Gaforth et al., "Structure–specific DNA binding by bacteriophage T5 5'→3' exonuclease," *Nucleic Acids Res.* 25:2801–3807 (1997).

Gelfand, *PCR Technology—Principles and Applications for DNA Amplification* (H.A. Erlich, Ed.), Stockton Press, New York, p. 19 (1989).

Guatelli et al., "Isothermal, in vitro amplification of nucleic acids by a multienzyme reaction modeled after retroviral replication," *Proc. Natl. Acad. Sci.*, 87:1874–1878 (1990) with an erratum at *Proc. Natl. Acad. Sci.*, 87:1874–1878 (1990).

Harrington et al., "DNA Structural Elements Required for FEN–1 Binding," *J. Biol. Chem.* 270:4503–4508 (1995).

Harrington et al., "The characterization of a mammalian DNA structure–specific endonuclease," *EMBO Journ.* 13:1235–1246 (1994).

Harrington and Lieber, "Functional domains with FEN–1 and RAD2 define a family a family of structure–specific endonucleases: implications for nucleotide excision repair," *Genes and Develop.* 8:1344–1355 (1994).

Hiraro et al. "Most compact hairpin–turn structure exerted by a short DNA fragment, d(GGGAAGC) in solution: an extraordinarily stable structure resistant to nucleases and heat," *Nuc. Acids Res.* 22:576–582 (1994).

Holland et al., "Detection of specific polymerase chain reaction product by utilizing the 5'–3' exonuclease activity of *Thermus aquaticus* DNA polymerase," *Proc. Natl. Acad. Sci. USA* 88:7276–7280 (1991).

Hosfield et al., "Structure of the DNA Repair and Replication Endonuclease and Exonuclease FEN–1: Coupling DNA and PCNA Binding to FEN–1 Activity," *Cell* 95:135–146 (1996).

Hosfield et al., "Newly Discovered Archaebacterial Flap Endonuclease Show a Structure–Specific Mechanism for DNA Substrate Binding and Catalysis Resembling Human Flap Endonuclease–1," *J. Biol. Chem.* 273:27154–17161.

Huang et al., "Role of Calf RTH–1 Nuclease in Removal of 5'–Ribonucleotides during Okazaki Frament Processing," *Biochemistry* 35:9266–9277 (1996).

Hwang et al., "The crystal structure of flap endonuclease–1 from *Methanococcus jannaschii*," *Nature Structural Biology* 5:707–713 (1998); Inchauspe et al., "Use of Conserved Sequences from Hepatitis C Virus for the Detection of Viral RNA in Infected Sera by Polymerase Chain Reaction," *Nature Structural Biol.* 5(8), 702–713 (1998).

Inchauspe et al., "Use of Conserved Sequences from Hepatitis C Virus for the Detection of Viral RNA in Infected Sera by Polymerase Chain Reaction," *Hepatology* 14:595–600 (1991).

Ito et al., "Compilation and alignment of DNA polymerase sequences," *Nucl. Acids Res.* 19:4045–4057 (1991).

Johnson et al., "Requirement of the Yeast RTHI 5' to 3' Exonuclease for the Stability of Simple Repetitive DNA," *Science* 269:238–240 (1995).

Kaledin et al., "Isolation and Properties of DNA Polymerase From the Extremely Thermophilic Bacterium *Thermus flavus*," *Biokhimiya* 46(9):1576–1584 (1981).

Kim et al., "Crystal structure of *Thermus aquaticus* DNA polymerase," *Nature* 376:612–616 (1995).

Kornberg, *DNA Replication*, W.H. Freeman and Co., San Francisco, pp. 127–139 (1980).

Kotler et al., "DNA sequencing: Modular primers assembled from a library of hexamers or pentamers," *Proc. Natl. Acad. Sci. USA* 90:4241–4245 (1993).

Kwoh et al., "Transcription–based amplification system and detection of amplified human immunodeficiency virus type I with a bead–based sandwich hybridization format," *Proc. Natl. Acad. Sci.*, 86:1173–1177 (1989).

Kwok et al., "Effects of primer–template mismatches on the polymerase chain reaction: Human immunodeficiency virus type 1 model studies," *Nucl. Acids Res.*, 18:999–1005 (1990).

Laemmli, "Cleavage of Structural proteins during the Assembly of the Head of Bacteriophage T4," *Nature* 277:680–685 (1970).

Landegren, "Molecular mechanics of nucleic acid sequence amplification," *Trends in Genetics* 9:199–204 (1993).

Lawyer et al., "Isolation, Characterization, and Expression in *Escherichia coli* of the DNA Polymerase Gene from *Thermus aquaticus*," *J. Biol. Chem.* 264:6427–6437 (1989).

Lee et al., "Polymerase chain reaction in detection of CMV DNA in renal allograft recipients," *Aust. NZ J. Med.* 22:249–255 (1992).

Leirmo et al., "Replacement of Potassium Chloride by Potassium Glutamate Dramatically Enhances Protein–DNA Interactions in Vitro," *Biochem.* 26:2095–2101 (1987).

Li et al., "Lagging Strand DNA Synthesis at the Eukaryotic Replication Fork Involves Binding and Stimulation of FEN–1 by Proliferating Cell Nuclear Antigen," *J. Biol. Chem.* 270:22109–22112 (1995).

Lieber, "The FEN–1 family of structure–specific nucleases in eukaryotic DNA replication, recombination and repair," *BioEssays* 19:233–240 (1997).

Lindahl, et al., "Deoxyribonuclease IV: A New Exonuclease From Mammalian Tissues," *Proc. N.A.S.* 62:597–603.

Lindahl and Karlström, "Heat–Induced Depyrimidination of Deoxyribonucleic Acid in Neutral Solution," *Biochem.* 12:5151–5154 (1973).

Longley et al. "Characterization of the 5' to 3' exonuclease associated with *Thermus aquaticus* DNA polymerase," *Nucl. Acids Res.* 18:7317–7322 (1990).

Lundquist, et al., "Transient Generation of Displaced Single–Stranded DNA during Nick Translation," *Cell* 32:53–60.

Lyamichev et al."Structure–Specific Endonucleolytic Cleavage of Nucleic Acids by Eubacterial DNA Polymerases," *Science* 260:778–783 (1993).

Marmur and Lane, "Strand Separation and Specific Recombination in Deoxyribonucleic acids: Biological Studies," *Proc. Natl. Acad. Sci. USA* 46:453–461 (1960).

Mathur et al., "The DNA polymerase gene from the hyperthermophilic marine archaebacterium *Pyrococcus furiosus*, shows sequence homology with α–like DNA polymerases," *Nucl. Acids Res.* 19:6952 (1991).

Mulius, "The Polymerase Chain Reaction in an Anemic Mode: How to Avoid Cold Oligodeoxyribonuclear Fusion," *PCR Methods Applic.*, 1:1–4 (1991).

Mullis and Faloona, "Specific Synthesis of DNA in Vitro via a Polymerase–Catalyzed Chain Reaction," *Methods in Enzymology* 155:335–350 (1987).

Murante et al., "Calf 5' to 3' Exo/Endonuclease Must Slide from a 5' End of the Substrate to Perform Structure–specific Cleavage," *J. Biol. Chem.* 270:30377–30383 (1995).

Murante et al., "The Calf 5'– to 3'–Exonuclease Is Also an Endonuclease with Both Activities Dependent on Primers Annealed Upstream of the Point of Cleavage," *J. Biol. Chem.* 269:1191–1196 (1994).

Murray et al., "Structural and Functional Conversation of the Human Homolog of the *Schizosaccharomyces pombe* rad2 gene, Which is Required for Chromosome Segregation and Recovery from DNA Damage," *Molecular and Cellular Biology* 14:4878–4888 (1994).

Myers et al., "Reverse Transcription and DNA amplification by a *Thermus thermophilus* DNA Polymerase," *Biochem.* 30:7661–7666 (1991).

Nelson and Long, "A General Method of Site–Specific Mutagenesis Using a Modification of the *Thermus aquaticus* Polymerase Chain Reaction," *Analytical Biochem.* 180:147–151 (1989).

Nielsen PE et al., "Peptide nucleic acids (PNAs): Potential anti–sense and anti–gene agents," *Anticancer Drug Des.* 8:53–63 (1993).

Nolan et al., "Kinetic Analysis of Human Flap Endonuclease–1 by Flow Cytometry," *Biochemistry* 35:11668–11677 (1996).

Nugent et al., "Characterization of the Apurinic Endonuclease Activity of Drosophila Rrp1," *Biochemistry* 32:11445–11452 (1993).

Perler et al., "Intervening sequences in an Archae DNA polymerase gene," *Proc. Natl. Acad. Sci. USA* 89:5577–5581 (1992).

Pontius and Berg, "Rapid renaturation of complementary DNA strands mediated by cationic detergents: A role for high–probability binding domains in enhancing the kinetics of molecular assembly processes," *Proc. Natl. Acad. Sci. USA* 88:8237–8241 (1991).

Rao et al., "*Methanococcus jannaschii* Flap Endonuclease: Expression, Purification, and Substrate Requirements," *J. of Bacteriology* 180:5406–5412.

Reagan et al., "Characterization of a Mutant Strain of *Saccharomyces cerevisia* with a Deletion of the RAD27 Gene, a Structural Homolog of the RAD2 Nucleotide Excision Repair Gene," *J. of Bacteriology* 177:364–371 (1995).

Saiki et al., "Primer–Directed Enzymatic Amplification of DNA with a Thermostable DNA Polymerase," *Science* 239:487–491 (1988).

Sambrook et al., *Molecular Cloning. A Laboratory Manual*, Cold Spring Harbor Laboratory Press, Cold Spring Harbor, pp. 1.63–1.69 (1989).

Schenborn and Mierendorf, Jr., "A novel transcription property of SP6 and T7 RNA polymerases: dependence on template structure," *Nucl. Acids. Res.* 13:6223–6236, 6223 (1985).

Setlow and Kornberg, "Deoxyribonucleic Acid Polymerase: Two Distinct Enzymes in One Polypeptide," *J. Biol. Chem.* 247:232–240 (1972).

Siegal et al, "A 5' to 3' exonuclease functionally interacts with calf DNA polymerase ε," *Proc. Natl. Acad. Sci. USA* 89:9377–9381 (1992).

Shen et al., "Flap endonuclease homologs in archaebacteria exist as independent proteins," *TIBS* 23 (1998).

Shen et al., "Essential Amino Acids for Substrate Binding and Catalysis of Human Flap Endonuclease 1," *J. of Biol. Chem.* 271:9173–9176 (1996).

Sommers et al., "Conditional Lethality of Nuli Mutations in RTH1 That Encodes the Yeast Counterpart of a Mammalian 5'– to 3'–Exonuclease Required for Lagging Strand DNA Synthesis in Reconstituted Systems," *J. of Biol. Chem.* 270:4193–4196 (1995).

Stark, "Multicopy expression vectors carrying the lac repressor gene for regulated high–level expression of genes in *Escherichia coli*," *Gene* 5:255–267 (1987).

Studier and Moffatt, "Use of Bacteriophage T7 RNA Polymerase to Direct Selective High–level Expression of Cloned Genes," *J. Mol. Biol.* 189:113–130 (1986).

Tindall and Kunkel, "Fidelity of DNA by the *Thermus aquatics* DNA Polymerase," *Biochem.* 27:6008–6013 (1988).

Tuerk and Gold, "Systematic Evolution of Ligands by Exponential Enrichment: RNA Ligands to Bacteriophage T4 DNA Polymerase," *Science* 249:505–510 (1990).

Turchi et al., "Enzymatic completion of mammalian lagging–strand DNa replication," *Proc. Natl. Acad. Sci. USA* 91:9803–9807 (1994).

Urdea et al., "A novel method for the rapid detection of specific nucleotide sequences in crude biological samples without blotting or radioactivity; application to the analysis if hepatitis B virus in human serum," *Gene* 61:253–264 (1987).

Wu and Wallace, "The Ligation Amplification (LAR)—Amplification of Specific DNA Sequences Using Sequential Rounds of Template–Dependent Ligation," *Genomics* 4:560–569 (1989).

Wu et al., "Processing of branched DNA intermediates by a complex of human FEN–1 and PCNA," *Nucleic Acids Research* 24:2036–2043 (1996).

Xu et al., "Biochemical and Mutational Studies of the 5'–3' Exonuclease of DNA Polymerase 1 of *Escherichia coli*," *J. Mol. Biol.* 268:284–302 (1997).

Zwickl et al., "Glyceraldehyde–3–Phosphate Dehydrogenase from the Hyperthermophilic Archaebacterium *Pyrococcus woesei*: Characterization of the Enzyme, Cloning and Sequencing of the Gene, and Expression in *Escherichia coli*," *J. Bact.* 172:4329–4338 (1990).

Hiraoka et al., "Sequence of human FEN–1, a stucture specific endonuclease, and chromosomal localization of the gene (FEN1) in mouse and human," *Genomics* 25:220–225 (1995).

Sigman et al., "Chemical Nucleases," *Chem. Rev.* 93:2295 (1993).

Youil et al., "Screening for Mutations by Enzyme Mismatch Cleavage with T4 Endonuclease VII," *Proc. Natl. Acad. Sci. USA* 92:87–91 (1995).

Abramson et al., "Characterization of the 5'–3' Exonuclease Activity of *Thermus Aquatics* DNA Polymerase," *FASEB J.* 5(4) 386 (1991).

* cited by examiner

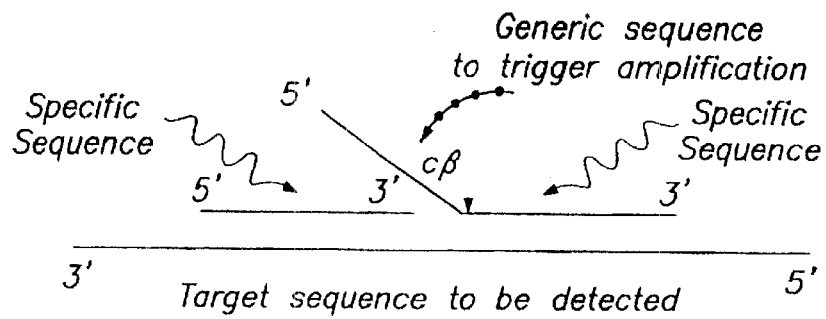
FIG. 1B PART ONE: TRIGGER REACTION
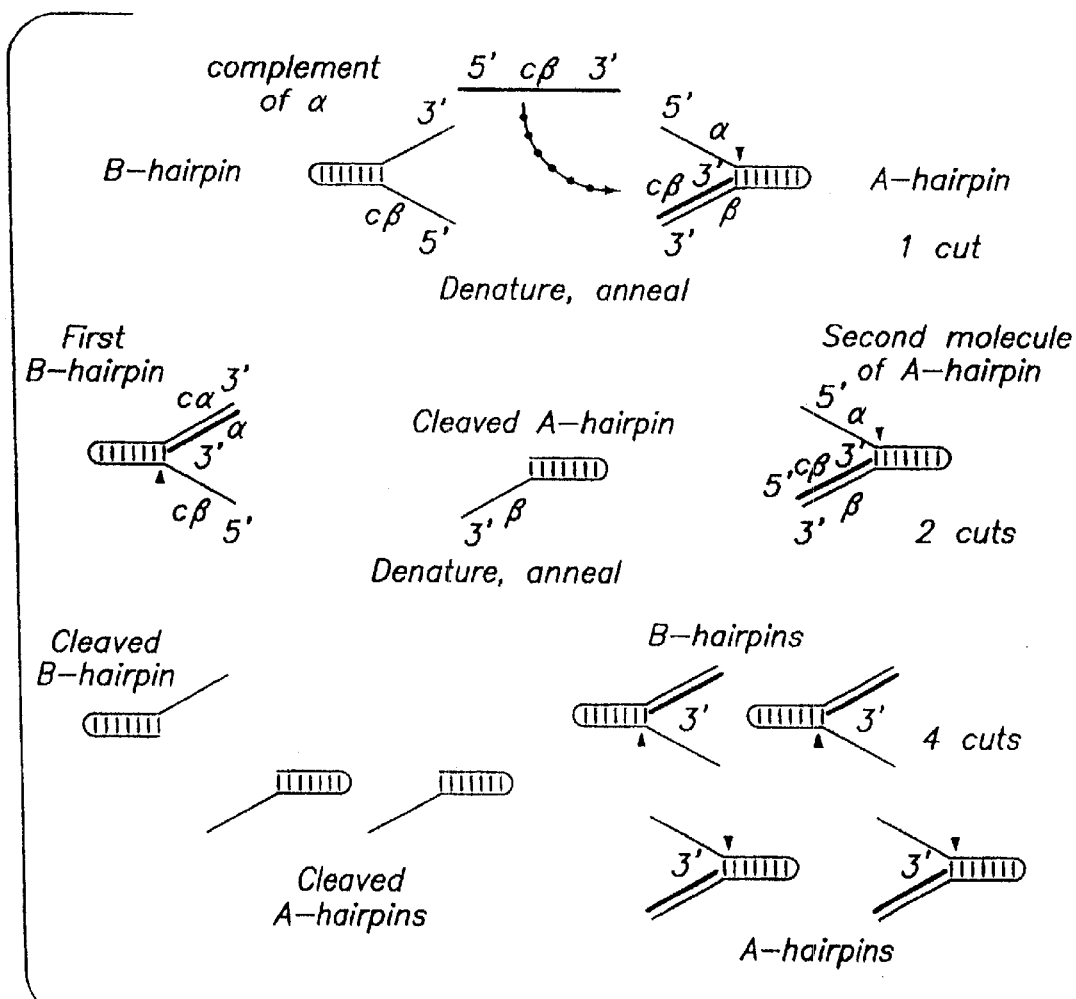
FIG. 1C PART TWO: DETECTION REACTION

FIG. 2A

```
MAJORITY [SEQ ID NO:7] ATGXXGGCGATGCTTCCCCTCTTTGAGCCCAAAGCCCGGGTCCTCCTGGTGGACGGGCCACCACCTGGCCT

DNAPTAQ  [SEQ ID NO:1]  .....AG..G........G.............................G..................... 70
DNAPTFL  [SEQ ID NO:2]  ........................................................C..G........... 67
DNAPTTH  [SEQ ID NO:3]  .....GA.........................A........................................ 70

MAJORITY ACCGCACCTTCTTCGCCCTGAAGGGCCTCACCACCAGCCGGGGGGAACCGGTCCAGGCCGGTCTACGGCTT

DNAPTAQ  ..............CA..................................G..G................. 140
DNAPTFL  ..............A...T.........C.....................................C..T. 137
DNAPTTH  ...............................G........................................ 140

MAJORITY CGGCCAAGAGCCTCCTCAAGGCCCTGAAGGAGGACGGGGACACGGGGACXXGGGGGTGXTCGTGGTCTTTGACGCCAAG

DNAPTAQ  .........................C..............................A.............. 207
DNAPTFL  ..............A................................GT..T.................... 204
DNAPTTH  .......................................T..AA...C..CT.................... 210

MAJORITY GCCCCCTCCTTCCGGCACGAGGCCTACGAGGCCTACAAGGCCGGGCGGGCCCCACCCCGGAGGACTTTC

DNAPTAQ  ........................G..GG.........................G............... 277
DNAPTFL  ....................................................GA....G.....C...... 274
DNAPTTH  .................................................................C..... 280

MAJORITY CCCGGCAGCTCGGCCCTCATCAAGGAGCTGGTGGACCTCCTGGGGCCTTGCCCGCCCTCAGGTCCCCGGCTA

DNAPTAQ  ......A............................................G................... 347
DNAPTFL  ........G..........................T...........A..C...T..G..G...T......T 344
DNAPTTH  ..................................................T..A..C............... 350
```

Sequence alignment figure showing MAJORITY [SEQ ID NO:7] compared with DNAPTAQ [SEQ ID NO:1], DNAPTFL [SEQ ID NO:2], and DNAPTTH [SEQ ID NO:3] across nucleotide positions 2164–2450.

FIG. 2H

```
MAJORITY [SEQ ID NO:7]    GCCCCTGGAGGTGGAGGTGGGGATGGGGAGGACTGGCTCTCCCCAAGGAGTAG

DNAPTAQ  [SEQ ID NO:1]    ....................A...............................GA
DNAPTFL  [SEQ ID NO:2]    ..............CC................................
DNAPTTH  [SEQ ID NO:3]    ...........................................T......GT...
```

FIG. 3A

```
MAJORITY [SEQ ID NO:8]   MXAML PLFEPKGRVLLVDGHHLAYRTFFALKGLTTSRGEPVQAVYGFAKSLLKALKEDG-DAVXVVFDAK

TAQ PRO  [SEQ ID NO:4]   ..RG..............H..............................................I....    69
TFL PRO  [SEQ ID NO:5]   ..........................................................V.V......    68
TTH PRO  [SEQ ID NO:6]   ..E......................................................YK..F.....    70

MAJORITY                 APSFRHEAYEAYKAGRAPTPEDFPROLALIKELVDLLGLXRLEVPGYEADDVLATLAKKAEKEGYEVRIL

TAQ PRO                  ......................GG..........................A.................S....    139
TFL PRO                  .........................................V......F.............R........    138
TTH PRO                  ..................................FT.............................       140

MAJORITY                 TADRDLYQLLSDRIAVLHPEGYLITPAWLWEKYGLRPEQWVDYRALXGDPSDNLPGVKGIGEKTAXKLLX

TAQ PRO                  ......K.............H...............................D.A......T..E....R...E    209
TFL PRO                  ....................E..I......Y..............................A.......QR.IR    208
TTH PRO                  ..............V..V..........H...E...........................F..V........L...K    210

MAJORITY                 EWGSLENLLKNLDRVKP-XXREKIXAHMEDLXLSXXLSXVRTDLPLEVDFAXRREPDREGLRAFLERLEF

TAQ PRO                  ........A..........L....AI......L.....D...K..WD.AK...................K........R........    278
TFL PRO                  .......FQH.Q.......SL....LQ.G..A.A..RK..Q.H......................GR..T..NL............    277
TTH PRO                  ........ENV.........K.L....R..LE...R...............................L.QG...........    280

MAJORITY                 GSLLHEFGLLEXPKALEEAPWPPPEGAFVGFVLSRPEPMWAELLALAAARXGRVHRAXDPLXGLRDLKEV

TAQ PRO                  .........S..............K............D.................G.......PE..YKA......A    348
TFL PRO                  .......G..A............L..SF...........................G.WE..L...Q....R.....G.    347
TTH PRO                  .......A.AP.......................K......C.D...............A...A...K.......    350
```

FIG. 3B

```
MAJORITY [SEQ ID NO:8]  RGLLAKDLAVLALREGLDLXPGDDPMLLAYLLDPSNTTPEGVARRYGGEWTEDAGERALLSERLFXNLXX

TAQ PRO [SEQ ID NO:4]   ...........S.............G.P..................E.............A..WG  418
TFL PRO [SEQ ID NO:5]   ...I.........S.........F.E...........................A......QT.KE  417
TTH PRO [SEQ ID NO:6]   .............S.........V.........AH.................A.......HR.LK  420

MAJORITY                RLEGEERLLWLYXEVEKPLSRVLAHMEATGVRLDVAYLQALSLEVAEEIRRLEEEVFRLAGHPFNLNSRD

TAQ PRO                 .........................R......R......A....A....................  488
TFL PRO                 ..K..........................E.........EA.V.Q.....................  487
TTH PRO                 .....K......H................R.................L..................  490

MAJORITY                QLERVLFDELGLPAIGKTEKTGKRSTSAAVLEALREAHPIVEKILQYRELTKLKNTYIDPLPXLVHPRTG

TAQ PRO                 ....................................................S..........D.I.  558
TFL PRO                 .................DR..................................A....K......  557
TTH PRO                 ............R..L..Q.................H...................V....S...  560

MAJORITY                RLHTRFNQTATATGRLSSSDPNLQNIPVRTPLGQRIRRAFVAEEGWXLVALDYSQIELRVLAHLSGDENL

TAQ PRO                 .................................................L................  628
TFL PRO                 ....................................................V..V.........  627
TTH PRO                 .................................................A..A.............  630

MAJORITY                IRVFQEGRDIHTQTASWMFGVPPEAVDPLMRRAAKTINFGVLYGMSAHRLSQELAIPYEEAVAFIERYFQ

TAQ PRO                 .................E................R..............................Q.  698
TFL PRO                 ..K....................S.G........................G.S.............  697
TTH PRO                 ...........................V.......................................  700
```

FIG. 3C

```
MAJORITY [SEQ ID NO:8]  SFPKVRAWIEKTLEEGRRRGYVETLFGRRRYVPDLNARVKSVREAAERMAFNMPVQGTAADLMKLAMVKL

TAQ PRO  [SEQ ID NO:4]  .........Y......G....................E..................R.........    768
TFL PRO  [SEQ ID NO:5]  .........Y......G............................................R....    767
TTH PRO  [SEQ ID NO:6]  ................................K...................................    770

MAJORITY  FPRLXEMGARMLQVHDELVLEAPKXRAEXVAALAKEVMEGVYPLAVPLEVEVGXGEDWLSAKEX

TAQ PRO   ....E...............E...A...R.................I........................    833
TFL PRO   ....Q.L.............D...R...........W..Q.......L........................    831
TTH PRO   ....R..............QA...E..........A..KA...............M...............G   835
```

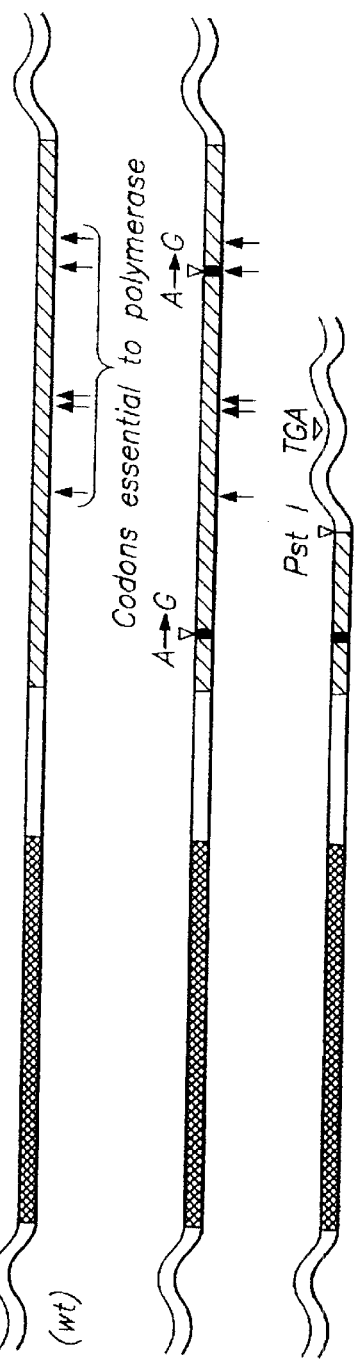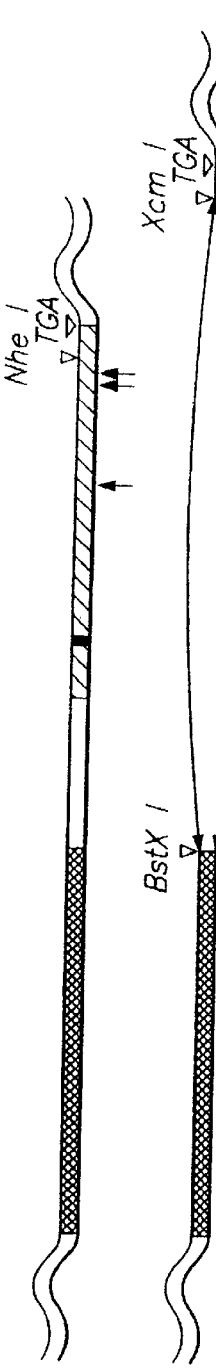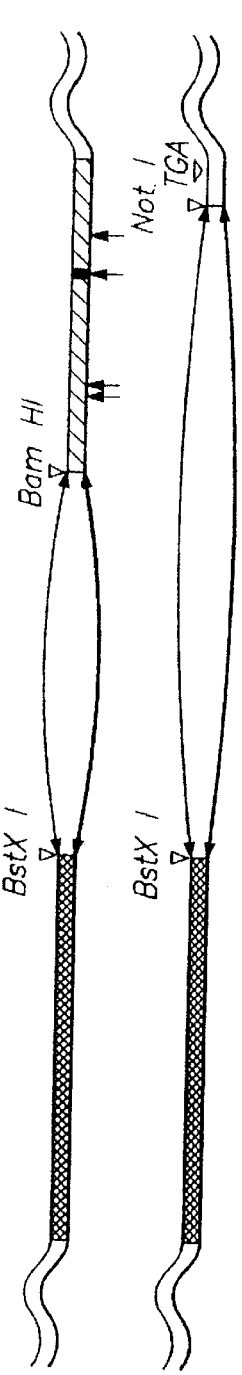
FIG. 4A
FIG. 4B
FIG. 4C
FIG. 4D
FIG. 4E
FIG. 4F
FIG. 4G

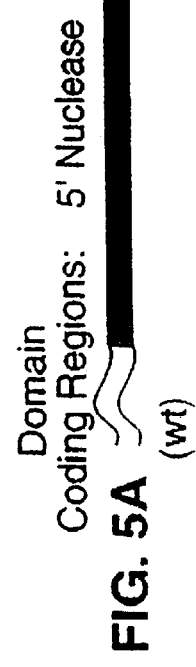
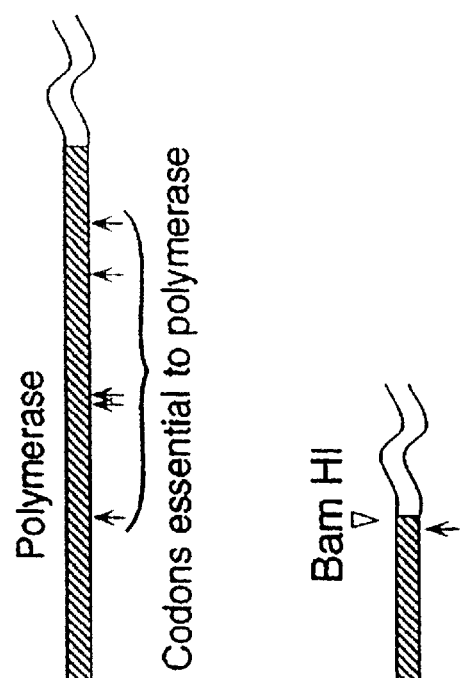
FIG. 5A
FIG. 5B

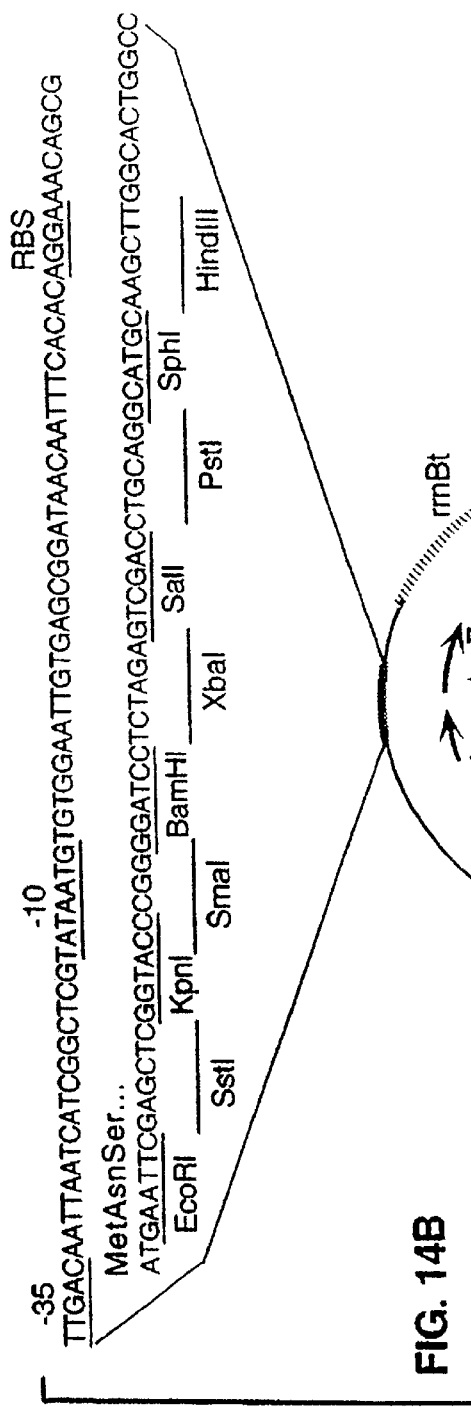
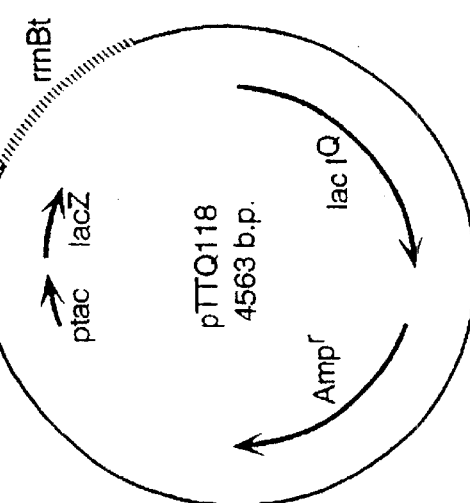
FIG. 14B
FIG. 14A
FIG. 14C
RBS: Ribosome binding site
ptac: Synthetic tac promoter
lac IQ: Lac repressor gene
lacZ: Beta-galactosidase alpha fragment
rrnBt: E. coli rrnB transcription terminator P φ10: Bacteriophage T7 φ10 promoter        RBS: Ribosome binding site
Tφ: T7 φ Terminator

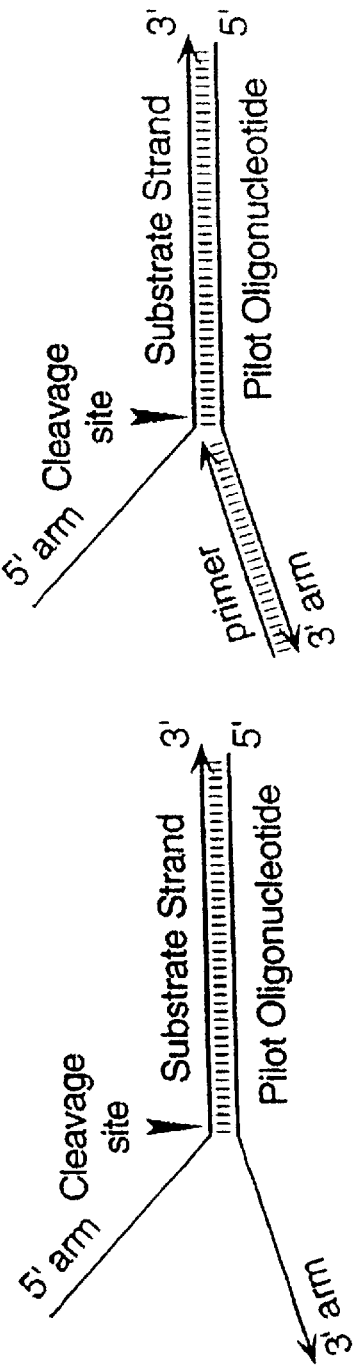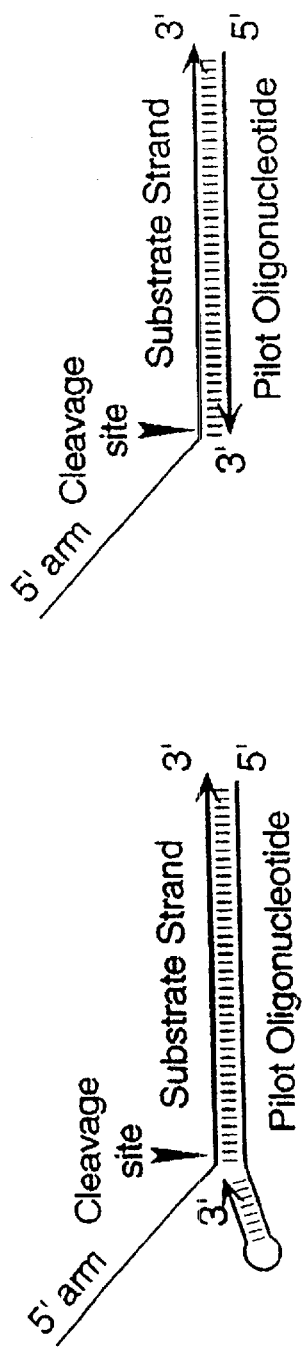
FIG. 16A  FIG. 16B  FIG. 16C  FIG. 16D

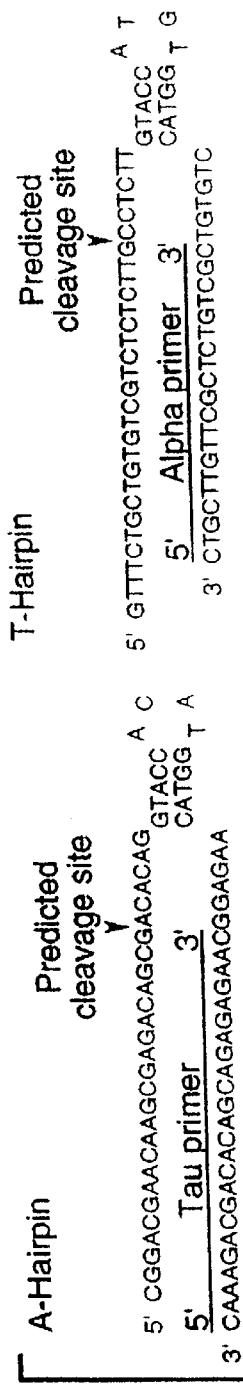
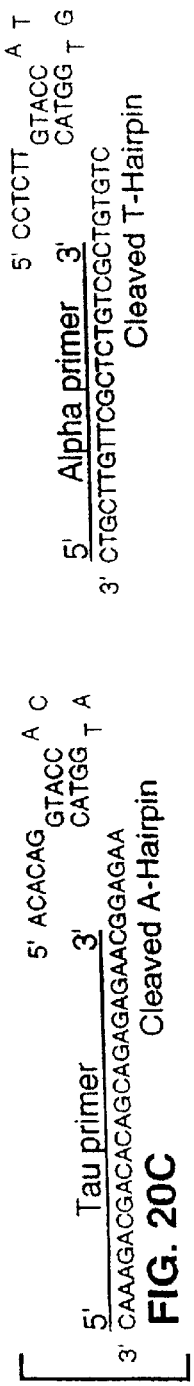
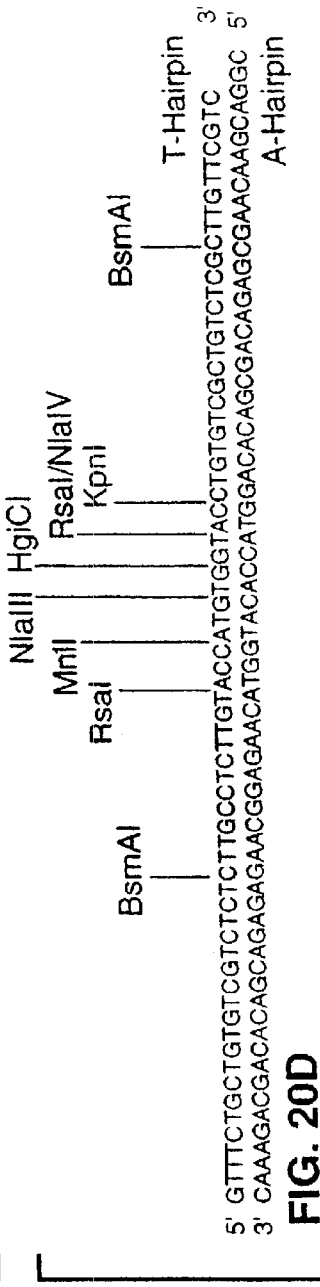
FIG. 20A
FIG. 20B
FIG. 20C
FIG. 20D

FIG. 30

INVASIVE CLEAVAGE DIRECTING OLIGO

CLEAVAGE SITE

5'-cy-3 
    agaaaggA agggaagaaagcgaaaggt-3' ← PROBE OLIGO
5'-gccggcgaacgtgggcgagaaagga
3'-ctgccccttttcggccgttgcaccgctcttccttcccttttcgctttcc-5'

FIG. 41

```
           10            20            30            40            50            60            70
   1  MGVQ-----FGDFIPK--NIISFEDLKGKKVAIDGMNALYQFLTSIRLRDGSPLRNRKGEITSAYNGVFY  MJAFEN1.PRO
   1  MGVP-----IGEIIPR--KEIELENLYGKKIAIDALNAIYQFLSTIRQKDGTPLMDSKGRITSHLSGLFY  PFUFEN1.PRO
   1  MGIQGLAKLIADVAPSAIRENDIKSYFGRKVAIDASMSIYQFLIAVRQ-GGDVLQNEEGETTSHLMGMFY  HUMFEN1.PRO
   1  MGIHGLAKLIADVAPSAIRENDIKSYFGRKVAIDASMSIYQFLIAVRQ-GGDVLQNEEGETTS-LMGMFY  MUSFEN1.PRO
   1  MGIKGLNAIISEHVPSAIRKSDIKSFFGRKVAIDASMSLYQFLIAVRQQDGGQLTNEAGETTSHLMGMFY  YST510.PRO
   1  MGVHSFWDIAG-----PTARPVRLESLEDKRMAVDASIWIYQFLKAVRDQEGNAVKN------SHITGFFR  YSTRAD2.PRO
   1  MGVSGLWNILE-----PVKRPVKLETLVNKRLAIDASIWIYQFLKAVRDKEGNQLKS------SHVVGFFR  SPORAD13.PRO
   1  MGVQGLWKLLE-----CSGROVSPEALEGKILAVDISIWLNQALKGVRDRHGNSIEN------PHLLTLFH  HUMXPG.PRO
   1  MGVQGLWKLLE-----CSGHRVSPEALEGKVLAVDISIWLNQALKGVRDSHGNVIEN------AHLLTLFH  MUSXPG.PRO
   1  MGVQGLWKLLE-----CSGRPINPGTLEGKILAVDISIWLNQAVKGARDRQGNAIQN------AHLLTLFH  XENXPG.PRO
   1  MTINGIWEWANHVV----RKVPNETMRDKTLSIDGHIWLYESLKGCEAHHQQT-------PNSYLVTFFT  CELRAD2.PRO 80            90           100           110           120           130           140
  64  KTIHLLENDITPIWVFDGEPPKLKEKTRKVRREMKEKAELKMKEAIKK-----EDFEEAAKYAKRVSYLTP  MJAFEN1.PRO
  64  RTINLMEAGIKPVYVFDGEPPEFKKKELEKRREAEEEAEEKWREALEK-----GEIEEARKYAQRATRVNE  PFUFEN1.PRO
  70  RTIRMMENGIKPVYVFDGKPPQLKSGELAKRSERRAEAEKQLQQAQAA-----GAEOEVEKFTKRLVKVTK  HUMFEN1.PRO
  69  RTIRM-ENGIKPVYVFDGKPPQLKSGELAKRSERRAEAEKQLQQAQEA-----GMEEEVEKFTKRLVKVTK  MUSFEN1.PRO
  71  RTLRMIDNGIKPCYVFDGKPPDLKSHELTKRSSRRVETEKKLA----EA-----TTELEKMQERRLVKVSK  YST510.PRO
  61  RICKLLYFGIRPVFDGGVPVLKRETIRQKERRQGKRESAKSTARKLLALQLQNGSNDNKRDSDEVTM  YSTRAD2.PRO
  61  RICKLLFFGIKPVFVFDGGAPSLKRQTIQKRQARRLDREENATVTANKLLALQMRHQAMLLKRDADEVTQ  SPORAD13.PRO
  61  RLCKLLFFRIRPIFVFDGDAPLLKKQTLVKRRQRKDLASSDSRKTTEKLLTEKLLKTFLKRQAIKTERIAATVTG  HUMXPG.PRO
  61  RLCKLLFFRIRPIFVFDGDAPLLKKQTLAKRRQRKDSASIDSRKTTEKLLKTFLKRQALKTDRIAASVTG  MUSXPG.PRO
  61  RLCKLLFFRIRPIFVFDGEAPLLKRQTLAKRRQRTDKASNDARKTNEKLLRTFLKRQAIKAERIAATVTG  XENXPG.PRO
  60  RIQRLLETLKIIPIVVFDNINASSSAHESKDQNEFVPRKRRSFGDSPFTNLV--------------  CELRAD2.PRO
```

FIG. 70A

| Pos | Sequence | File |
|---|---|---|
| 130 | KMVENCKYLLSLMGIPYVEAPSEGEAQASYMAKKGDVWAVVSQDYDALLYGAPRVVRNLTTTKEM---- | MJAFEN1.PRO |
| 130 | MLIEDAKKLLELMGIPIVQAPSEGEAQAAYMAAKGSVYASASQDYDSLLFGAPRLVRNLTITGKRKLPGK | PFUFEN1.PRO |
| 136 | QHNDECKHLLSLMGIPYLDAPSEAEASCAALVKAGKVYAAATEDMDCLTFGSPVLMRHLTASEAKKLPIQ | HUMFEN1.PRO |
| 134 | QHNDECKHLLSLMGIPYLDAPSEAEASCAALAKAGKVYAAATEDMDCLTFGSPVLMRHLTASEAKKLPIQ | MUSFEN1.PRO |
| 134 | EHNEEAQKLLGLMGIPYIIAPTEAEAQCAELLQLNLVDGIITDDSDVFLFGGTKIYKNMFHEKNY---VE | YST510.PRO |
| 131 | DMIKEVQELLSRFGIPYITAPMEAEAQCAELLQLNLVDGIITDDSDVFLFGGTKIYKNMFHEKNY---VE | YSTRAD2.PRO |
| 131 | VMIKECQELLRLFGLPYIVAPOEAEAQCSKLLELKLVDGIVTDDSDVFLFGGTRVYRNMFNQNKF---VE | SPORAD13.PRO |
| 131 | QMFLESQELLRLFGIPYIQAPMEAEAQCAILDLTDQTSGTITDDSDIWLFGARHVYRNFFNKNKF---VE | HUMXPG.PRO |
| 131 | QMFLESQELLRLFGVPYIQAPMEAEAOCAVLDLSDQTSGTITDDSDIWLFGARHVYKNFFNKNKF---VE | MUSXPG.PRO |
| 131 | QMCLESQELLQLFGIPYIVAPMEAEAQCAILDLTDQTSGTITDDSDIWLFGARHVYKNFFSQNKH---VE | XENXPG.PRO |
| 111 | DHVYKTNALLTELGIKVIIAPGDGEAQCARLEQLGVTSGCITTDFDYFLFGGKNLYRFDFTAGT----- | CELRAD2.PRO |

| Pos | Sequence | File |
|---|---|---|
| 195 | ------PELIELNEVLEDLRISLDDLIDIAIFMGTDYNPGGV--K--GIGFKRAYELVRSGVAK--DV | MJAFEN1.PRO |
| 200 | NVYVE-IKPELIILEEVLKELKLTREKLIELAILVGTDYNPGGI--K--GIGLKKALEIVRHSKDPLAKF | PFUFEN1.PRO |
| 206 | EFHLSRILQELGLNQEQFVDLCILLGSDYCESIRGIGPKRAVDLIQK--HKSIEEIVRRLDPN----KY | HUMFEN1.PRO |
| 204 | EFHLSRVLQELGLNQEQFVDLCILLGSDYCESIRGIAKRAVDLIQK--HKSIEEIVRRLDPS----KY | MUSFEN1.PRO |
| 204 | EIDTELVLRGLDLTIEQFVDLTIEQFVDLCIMLGCDYCESIRGVGPVTALKLIKT--HGSIEKIVEFIESGESNNTKW | YST510.PRO |
| 198 | FYDAESILKLLGLDRKNMIELAQLLGSDYTNGLKGMGPVSSIEVIAEF---GNLKNFKDWYNNGOFDKRK | YSTRAD2.PRO |
| 198 | LYLMDDMKREFNVNQMDLIKLAHLLGSDYTMGLSRVGPVLALEILHEFPGDTGLFEFKKWFQRLSTGHAS | SPORAD13.PRO |
| 198 | YYQYVDFHNQLGLDRNKLINLAYLLGSDYTEGIPTVGCVTAMEILNEFPGHGLEPLLKFSEWWHEAQKNP | HUMXPG.PRO |
| 119 | YYQYVDFYSQLGLDRNKLINLAYLLGSDYTEGIPTVGCVTAMEILNEFPGRGLDPLLKFSEWWHEAQNNK | MUSXPG.PRO |
| 198 | YYQYADIHNOLGLDRSKLINLAYLLGSDYTEGIPTVGYVSAMEILNEFPGQGLEPLVKFKEWWSEAQKDK | XENXPG.PRO |
| 175 | ---------SSTACLHDIMHLSLGRMFM--------- | CELRAD2.PRO |

FIG. 70B

```
251 LKKEVEYYDEIKRIFKEPKV-----------------------TD--NYSLSLKLPDKEGIIKFLVDENDFNYD  MJAFEN1.PRO
265 QKQSDVDLYAIKEFFLNPPV-----------------------TD--NYNLVWRDPEEGILKFLCDEHDFSEE  PFUFEN1.PRO
269 PVPENWLHKEAHQLFLEPEV---------------------LDPESVELKWSEPNEEELIKFMCGEKQFSEE  HUMFEN1.PRO
267 PVPENWLHKEAQQLFLEPEV---------------------VDPESVELKWSEPNEEELVKFMCGEKQFSEE  MUSFEN1.PRO
272 KIPEDWPYKQARMLFLDPEV---------------------IDGNEINLKWSPPKEKELIEYLCDDKKFSEE  YST510.PRO
265 QETENKFEKDLRKKLVNNEIILDDDFPSVMVYDAYMRPEVDHDTTPFVWGVPDLDMLRSFMKTQLGWPHE    YSTRAD2.PRO
268 KNDVNTPVKKRINKLVGK-IILPSEFPNPLVDEAYLHPAVDDSKQSFQWGIPDLDELRQFLMATVGWSKQ    SPORAD13.PRO
268 KIRPNPHDTKVKKKL--RTLQLTPGFPNPAVADAYLKPVVDDSKGSFLWGKPDLDKIREFCQRYFGWNRT    HUMXPG.PRO
268 KVAENPYDTKVKKKL--RKLQLTPGFPNPAVADAYLRPVVDDSRGSFLWGKPDVDKIREFCORYFGWNRM    MUSXPG.PRO
268 KMRPNPNDTKVKKKL--RLLDLQQSFPNPAVASAYLKPVVDESKSAFSWGRPDLEQIREFCESRFGWYRL    XENXPG.PRO
194 -----EKKVSRPHLISTAILLGCDYFORGVQNIGIVSVFD-ILGEFGDDGNEEIDPHVILDRFASYVRE    CELRAD2.PRO

300 RVKKHVDKLYNLIA-----------------------------------------------------  MJAFEN1.PRO
314 RVKNGLERLKKAI------------------------------------------------------  PFUFEN1.PRO
320 RIRSGVKRLSKSRQGS-TQGRLDDFFKVT--------------------------------------  HUMFEN1.PRO
318 RIRSGVKRLSKSRQGS-TQGRLDDFFKVT--------------------------------------  MUSFEN1.PRO
323 RVKSGISRLKKGLKSG-IQGRLDGFFOVV--------------------------------------  YST510.PRO
335 KSDEILIPLIRDVNKRKK----------------------------------------KGKQ      YSTRAD2.PRO
337 RTNEVLLPVIQDMHKKOF----------------------------------------VGTQ      SPORAD13.PRO
336 KTDESLFPVLKQLDAQQTQLRIDSFFRLAQQEKEDAKRIKSQRLNRAVTCMLRKEKEAAASEIEAVSVAM  HUMXPG.PRO
336 KTDESLYPVLKHLNAHQTQLRIDSFFRLAQQEKQDAKLIKSHRLSRAVTCMLRKEREEKAPELTKVTEAM  MUSXPG.PRO
336 KTDEVLLPVLKQLNAQQTQLRIDSFFRLEQHEAAG---LKSQRLRRAVTCMKRKERDVEAEEVEAAVAVM  XENXPG.PRO
257 EIPARSEDTQRKLRLRRKKYNFPVGFPNCDAVHNAITMYLRPPVSSEIPKIIPR----AANFQQVAEIM  CELRAD2.PRO
```

FIG. 70C

```
314 ----------------------------------------                          MJAFEN1.PRO
327 ----------------------------------------                          PFUFEN1.PRO
348 ----------------------------------------GSLS                      HUMFEN1.PRO
346 ----------------------------------------GSLS                      MUSFEN1.PRO
351 ----------------------------------------PK-T                      YST510.PRO
357 KRINEFF---------------------------------                          YSTRAD2.PRO
359 SNLTQFFEGGNTNVYAPRVAYHFKSKRLENALSSFKNQISNQSPMSEEIQADADAFGESKGSDELQSRIL  SPORAD13.PRO
406 EKEFELLDKAKRKTQKRGITNTLEESSLKRKRLSDSKRKNTCGGFLGETCLSESSDGSSEHAESSSLM    HUMXPG.PRO
406 EKEFELLDDAKGKTOKRELPYK------KETSVPKRRPSGNGGFLGDPYCSESPQESSCEDGEGSSVM    MUSXPG.PRO
403 ERECTNQRKGQKTNTKS-----------QGTKRRKPTECSQEDQDPGGGFIGIELKTLSSKAYSSD---   XENXPG.PRO
322 MKECGWPATRTQKELALSIRRKVHLTTTVAQTRIPDFFAATKSKNFTPIVEPCESLEDYISANN-----T  CELRAD2.PRO

314 ---------------------------------NKTKQKTL                         MJAFEN1.PRO
327 ---------------------------------KSGKQSTL                         PFUFEN1.PRO
352 SAKRKEPEPKGST--------------------KKKAKTGAAG                       HUMFEN1.PRO
350 SAKRKEPEPKGPA--------------------KKKAKTGGAG                       MUSFEN1.PRO
354 KEQLAAAAKRAQE--------------------NKKLNKNKNK                       YST510.PRO
364 -----------------PREYISGDKKLNTSKRISTATGKL--KK                      YSTRAD2.PRO
429 RRKKMMASKNSSDSDSDSEDNFLASLTPKTNSSSISIENLPRKTKLSTSLL------KKP       SPORAD13.PRO
476 NVQRRTAAKEPKTSASDSONSVKEAPVKNGGATTSSSSDSDDDGGKEKMVLVTARSVFGKKRRLRRARG   HUMXPG.PRO
469 SARQRSAAESSKIGCSDVPDLVRDSPHGRQGCVSTSSSDSEDGEDKAKTVLVTARPVFGKKRRKLKSMK-  MUSXPG.PRO
458 ---GSSSDAEDLPSGLIDKQSQSGIVGROKASNKVESSSSSDDEDRTVMVTAKPVFQGKKTKSKTMKE    XENXPG.PRO
387 WMRKRKRSESPQILQHHAKRQVPDRK--------------------RSVKIRAFKPYPTDVI     CELRAD2.PRO
```

FIG. 70D

| | | |
|---|---|---|
| 322 | DAWFKZ | MJAFEN1.PRO |
| 335 | ESWFKR | PFUFEN1.PRO |
| 375 | KFKRGK | HUMFEN1.PRO |
| 373 | KFRRGK | MUSFEN1.PRO |
| 377 | VTKGRR | YST510.PRO |
| 390 | ---RKM | YSTRAD2.PRO |
| 483 | SKRRRK | SPORAD13.PRO |
| 546 | RKRKTZ | HUMXPG.PRO |
| 538 | RRKKKT | MUSXPG.PRO |
| 523 | TVKRK | XENXPG.PRO |
| 429 | ELGDSD | CELRAD2.PRO |

5' GTTCTCTGCTCTCTGGT
                   1819
                   ↓↓
                   CGCTGTCTCGCTTGT G
                                    A
                   GCGACAGAGCGAACA A
                                    A
3'GCTCTCTGGT

5'GTTCTCTGCTCTCTGGTCGCT
                       2122
                       ↓↓
                       GTCTCGCTTGT G
                                    A
3'GCTCTCTGGTGCGACAGAGCGAACA A
                            A
5'CGAGAGACCACGCT
         P15      G

FIG. 89B

INVADER 3'-END SUBSTITUENTS

3'-PHOSPHATE C ARABINOSE

3'-CYTOSINE ARABINOSE

2'-OMETHYL CYTOSINE

3'-NITROPYROLE

5'-NITROINDOLE

ACRIDINE

3'-DEOXY-ADENINE

CONCENTRATION OF PROBE W/ AND W/O STACKER vs TEMP

Hairpin Substrate

A)

```
5' Fl-TTTT ▼
         CGCTGTCTCGCT G
                       A
3' TTT GCGACAGAGCGA A
       25-65-1
```

Invader (IT) substrate

B)

```
        5' Fl-TTT
                 T▼
  A ACGAGCGTCTTT G  CGCTGTCTCGCT G
 A                                A
 A TGCTCGCAGAAA — GCGACAGAGCGA A
  G
       25-184-5
```

FEN-1 ENDONUCLEASES, MIXTURES AND CLEAVAGE METHODS

This application is a national entry of International Application Number PCT/US97/21783 filed Nov. 26, 1997, which claims priority to U.S. patent applications Ser. No. 08/757,653 filed Nov. 29, 1996 now U.S. Pat. No. 5,843,669 and Ser. No. 08/758,314 filed Dec. 2, 1996 now U.S. Pat. No. 6,090,606.

This invention was made with United States Government support under Cooperative Agreement Number 70NANB5H1030, awarded by the National Institute of Standards and Technology (NIST). The United States Government has certain rights in the invention.

FIELD OF THE INVENTION

The present invention relates to means for the detection and characterization of nucleic acid sequences and variations in nucleic acid sequences. The present invention relates to methods for forming a nucleic acid cleavage structure on a target sequence and cleaving the nucleic acid cleavage structure in a site-specific manner. The 5' nuclease activity of a variety of enzymes is used to cleave the target-dependent cleavage structure, thereby indicating the presence of specific nucleic acid sequences or specific variations thereof. The present invention further provides novel methods and devices for the separation of nucleic acid molecules based by charge.

BACKGROUND OF THE INVENTION

The detection and characterization of specific nucleic acid sequences and sequence variations has been utilized to detect the presence of viral or bacterial nucleic acid sequences indicative of an infection, the presence of variants or alleles of mammalian genes associated with disease and cancers and the identification of the source of nucleic acids found in forensic samples, as well as in paternity determinations.

Various methods are known to the art which may be used to detect and characterize specific nucleic acid sequences and sequence variants. Nonetheless, as nucleic acid sequence data of the human genome, as well as the genomes of pathogenic organisms accumulates, the demand for fast, reliable, cost-effective and user-friendly tests for the detection of specific nucleic acid sequences continues to grow. Importantly, these tests must be able to create a detectable signal from samples which contain very few copies of the sequence of interest. The following discussion examines two levels of nucleic acid detection assays currently in use. I. Signal Amplification Technology for detection of rare sequences; and II. Direct Detection Technology for detection of higher copy number sequences.

I. Signal Amplification Technology Methods For Amplification

The "Polymerase Chain Reaction" (PCR) comprises the first generation of methods for nucleic acid amplification. However, several other methods have been developed that employ the same basis of specificity, but create signal by different amplification mechanisms. These methods include the "Ligase Chain Reaction" (LCR), "Self-Sustained Synthetic Reaction" (3SR/NASBA), and "Qβ-Replicase" (Qβ).

Polymerase Chain Reaction (PCR)

The polymerase chain reaction (PCR), as described in U.S. Pat. Nos. 4,683,195 and 4,683,202 to Mullis and Mullis et al. (the disclosures of which are hereby incorporated by reference), describe a method for increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR)

The ligase chain reaction (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. Segev, PCT Public. No. WO9001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

Self-Sustained Synthetic Reaction (3SR/NASBA)

The self-sustained sequence replication reaction (3SR) (Guatelli et al., Proc. Natl. Acad. Sci., 87:1874–1878 [1990], with an erratum at Proc. Natl. Acad. Sci., 87:7797 [1990]) is a transcription-based in vitro amplification system (Kwok et al., Proc. Natl. Acad. Sci., 86:1173–1177 [1989]) that can exponentially amplify RNA sequences at a uniform temperature. The amplified RNA can then be utilized for mutation detection (Fahy et al., PCR Meth. Appl., 1:25–33 [1991]). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200–300 base pairs).

Q-Beta (Qβ) Replicase

In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37° C.). This prevents the use of high temperature as a means of achieving specificity as in the LCR, the ligation event can be used to detect a mutation at the junction site, but not elsewhere.

Table 1 below, lists some of the features desirable for systems useful in sensitive nucleic acid diagnostics, and summarizes the abilities of each of the major amplification methods (See also, Landgren, Trends in Genetics 9:199 [1993]).

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55° C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

TABLE 1

| | METHOD: | | | | |
|---|---|---|---|---|---|
| FEATURE | PCR | LCR | PCR & LCR | 3SR NASBA | Qβ |
| Amplifies Target | + | + | + | + | |
| Recognition of Independent Sequences Required | + | + | + | + | + |
| Performed at High Temp. | + | + | | | |
| Operates at Fixed Temp. | | | | + | + |
| Exponential Amplification | + | + | + | + | + |
| Generic Signal Generation | | | | | + |
| Easily Automatable | | | | | |

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1 [1991]). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999 [1990]).

A similar 3'-mismatch strategy is used with greater effect to prevent ligation in the LCR (Barany, PCR Meth. Applic., 1:5 [1991]). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

II. Direct Detection Technology

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA)

The cycling probe reaction (CPR) (Duck et al., BioTech., 9:142 [1990]), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may be carried through sample preparation.

Branched DNA (bDNA), described by Urdea et al., Gene 61:253–264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

While both of these methods have the advantages of direct detection discussed above, neither the CPR or bDNA methods can make use of the specificity allowed by the requirement of independent recognition by two or more probe (oligonucleotide) sequences, as is common in the signal amplification methods described in section I. above. The requirement that two oligonucleotides must hybridize to a target nucleic acid in order for a detectable signal to be generated confers an extra measure of stringency on any detection assay. Requiring two oligonucleotides to bind to a target nucleic acid reduces the chance that false "positive" results will be produced due to the non-specific binding of a probe to the target. The further requirement that the two oligonucleotides must bind in a specific orientation relative to the target, as is required in PCR, where oligonucleotides must be oppositely but appropriately oriented such that the DNA polymerase can bridge the gap between the two oligonucleotides in both directions, further enhances specificity of the detection reaction. However, it is well known to those in the art that even though PCR utilizes two oligonucleotide probes (termed primers) "non-specific" amplification (i.e., amplification of sequences not directed by the two primers used) is a common artifact. This is in part because the DNA polymerase used in PCR can accommodate very large distances, measured in nucleotides, between the oligonucleotides and thus there is a large window in which non-specific binding of an oligonucleotide can lead to exponential amplification of inappropriate product. The LCR, in contrast, cannot proceed unless the oligonucleotides used are bound to the target adjacent to each other and so the full benefit of the dual oligonucleotide hybridization is realized.

An ideal direct detection method would combine the advantages of the direct detection assays (e.g., easy quantification and minimal risk of carry-over contamination) with the specificity provided by a dual oligonucleotide hybridization assay.

SUMMARY OF THE INVENTION

The present invention relates to means for cleaving a nucleic acid cleavage structure in a site-specific manner. In one embodiment, the means for cleaving is a cleaving enzyme comprising 5' nucleases derived from thermostable DNA polymerases. These polymerases form the basis of a novel method of detection of specific nucleic acid sequences. The present invention contemplates use of novel detection methods for various uses, including, but not limited to clinical diagnostic purposes.

In one embodiment, the present invention contemplates a DNA sequence encoding a DNA polymerase altered in sequence (i.e., a "mutant" DNA polymerase) relative to the native sequence, such that it exhibits altered DNA synthetic activity from that of the native (i.e., "wild type") DNA polymerase. It is preferred that the encoded DNA polymerase is altered such that it exhibits reduced synthetic activity compared to that of the native DNA polymerase. In this manner, the enzymes of the invention are predominantly 5' nucleases and are capable of cleaving nucleic acids in a structure-specific manner in the absence of interfering synthetic activity.

Importantly, the 5' nucleases of the present invention are capable of cleaving linear duplex structures to create single discrete cleavage products. These linear structures are either 1) not cleaved by the wild type enzymes (to any significant degree), or 2) are cleaved by the wild type enzymes so as to create multiple products. This characteristic of the 5' nucleases has been found to be a consistent property of enzymes derived in this manner from thermostable polymerases across eubacterial thermophilic species.

It is not intended that the invention be limited by the nature of the alteration necessary to render the polymerase synthesis-deficient. Nor is it intended that the invention be limited by the extent of the deficiency. The present invention contemplates various structures, including altered structures (primary, secondary, etc.), as well as native structures, that may be inhibited by synthesis inhibitors.

Where the polymerase structure is altered, it is not intended that the invention be limited by the means by which the structure is altered. In one embodiment, the alteration of the native DNA sequence comprises a change in a single nucleotide. In another embodiment, the alteration of the native DNA sequence comprises a deletion of one or more nucleotides. In yet another embodiment, the alteration of the native DNA sequence comprises an insertion of one or more nucleotides. It is contemplated that the change in DNA sequence may manifest itself as change in amino acid sequence.

The present invention contemplates structure-specific nucleases from a variety of sources, including mesophilic, psychrophilic, thermophilic, and hyperthermophilic organisms. The preferred structure-specific nucleases are thermostable. Thermostable structure-specific nucleases are contemplated as particularly useful in that they operate at temperatures where nucleic acid hybridization is extremely specific, allowing for allele-specific detection (including single-base mismatches). In one embodiment, the thermostable structure-specific are thermostable 5' nucleases which are selected from the group consisting of altered polymerases derived from the native polymerases of Thermus species, including, but not limited to *Thermus aquaticus, Thermus flavus,* and *Thermus thermophilus*. However, the invention is not limited to the use of thermostable 5' nucleases. Thermostable structure- specific nucleases from the FEN-1, RAD2 and XPG class of nucleases are also preferred.

The present invention provides a composition comprising a cleavage structure, the cleavage structure comprising: a) a target nucleic acid, the target nucleic acid having a first region, a second region, a third region and a fourth region, wherein the first region is located adjacent to and downstream from the second region, the second region is located adjacent to and downstream from the third region and the third region is located adjacent to and downstream from the fourth region; b) a first oligonucleotide complementary to the fourth region of the target nucleic acid; c) a second oligonucleotide having a 5' portion and a 3' portion wherein the 5' portion of the second oligonucleotide contains a sequence complementary to the second region of the target nucleic acid and wherein the 3' portion of the second oligonucleotide contains a sequence complementary to the third region of the target nucleic acid; and d) a third oligonucleotide having a 5' portion and a 3' portion wherein the 5' portion of the third oligonucleotide contains a sequence complementary to the first region of the target nucleic acid and wherein the 3' portion of the third oligonucleotide contains a sequence complementary to the second region of the target nucleic acid.

The present invention is not limited by the length of the four regions of the target nucleic acid. In one embodiment, the first region of the target nucleic acid has a length of 11 to 50 nucleotides. In another embodiment, the second region of the target nucleic acid has a length of one to three nucleotides. In another embodiment, the third region of the target nucleic acid has a length of six to nine nucleotides. In yet another embodiment, the fourth region of the target nucleic acid has a length of 6 to 50 nucleotides.

The invention is not limited by the nature or composition of the of the first, second, third and fourth oligonucleotides; these oligonucleotides may comprise DNA, RNA, PNA and combinations thereof as well as comprise modified nucleotides, universal bases, adducts, etc. Further, one or more of the first, second, third and the fourth oligonucleotides may contain a dideoxynucleotide at the 3' terminus.

In one preferred embodiment, the target nucleic acid is not completely complementary to at least one of the first, the second, the third and the fourth oligonucleotides. In a particularly preferred embodiment, the target nucleic acid is not completely complementary to the second oligonucleotide.

As noted above, the present invention contemplates the use of structure-specific nucleases in detection methods. In one embodiment, the present invention provides a method of detecting the presence of a target nucleic acid molecule by detecting non-target cleavage products comprising: a) providing: i) a cleavage means, ii) a source of target nucleic acid, the target nucleic acid having a first region, a second region, a third region and a fourth region, wherein the first region is located adjacent to and downstream from the second region, the second region is located adjacent to and downstream from the third region and the third region is located adjacent to and downstream from the fourth region; iii) a first oligonucleotide complementary to the fourth region of the target nucleic acid; iv) a second oligonucleotide having a 5' portion and a 3' portion wherein the 5' portion of the second oligonucleotide contains a sequence complementary to the second region of the target nucleic acid and wherein the 3' portion of the second oligonucleotide contains a sequence complementary to the third region of the target nucleic acid; iv) a third oligonucleotide having a 5' and a 3' portion wherein the 5' portion of the third oligonucleotide contains a sequence complementary to the first region of the target nucleic acid and wherein the 3' portion of the third oligonucleotide contains a sequence complementary to the second region of the target nucleic acid; b) mixing the cleavage means, the target nucleic acid, the first oligonucleotide, the second oligonucleotide and the third oligonucleotide to create a reaction mixture under reaction conditions such that the first oligonucleotide is annealed to the fourth region of the target nucleic acid and wherein at least the 3' portion of the second oligonucleotide is annealed to the target nucleic acid and wherein at least the 5' portion of the third oligonucleotide is annealed to the target nucleic acid so as to create a cleavage structure and wherein cleavage of the cleavage structure occurs to generate non-target cleavage products, each non-target cleavage product having a 3'-hydroxyl group; and c) detecting the non-target cleavage products.

The invention is not limited by the nature of the target nucleic acid. In one embodiment, the target nucleic acid comprises single-stranded DNA. In another embodiment, the target nucleic acid comprises double-stranded DNA and prior to step c), the reaction mixture is treated such that the double-stranded DNA is rendered substantially single-stranded. In another embodiment, the target nucleic acid comprises RNA and the first and second oligonucleotides comprise DNA.

The invention is not limited by the nature of the cleavage means. In one embodiment, the cleavage means is a structure-specific nuclease; particularly preferred structure-specific nucleases are thermostable structure-specific nucleases. In one preferred embodiment, the thermostable structure-specific nuclease is encoded by a DNA sequence selected from the group consisting of SEQ ID NOS:1–3, 9, 10, 12, 21, 30, 31, 101, 106, 110, 114, 129, 131, 132, 137, 140, 141, 142, 143, 144, 145, 147, 150, 151, 153, 155, 156, 157, 158, 161, 163, 178, 180, and 182.

In another preferred embodiment, the thermostable structure-specific nuclease is a nuclease from the FEN-1/RAD2/XPG class of nucleases. In another preferred embodiment the thermostable structure specific nuclease is a chimeric nuclease.

In an alternative preferred embodiment, the detection of the non-target cleavage products comprises electrophoretic separation of the products of the reaction followed by visualization of the separated non-target cleavage products.

In another preferred embodiment, one or more of the first, second, and third oligonucleotides contain a dideoxynucleotide at the 3' terminus. When dideoxynucleotide-containing oligonucleotides are employed, the detection of the non-target cleavage products preferably comprises: a) incubating the non-target cleavage products with a template-independent polymerase and at least one labeled nucleoside triphosphate under conditions such that at least one labeled nucleotide is added to the 3'-hydroxyl group of the non-target cleavage products to generate labeled non-target cleavage products; and b) detecting the presence of the labeled non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase are employed in the detection step, the second oligonucleotide may contain a 5' end label, the 5' end label being a different label than the label present upon the labeled nucleoside triphosphate. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In another embodiment, detecting the non-target cleavage products comprises: a) incubating the non-target cleavage products with a template-independent polymerase and at least one nucleoside triphosphate under conditions such that at least one nucleotide is added to the 3'-hydroxyl group of the non-target cleavage products to generate tailed non-target cleavage products; and b) detecting the presence of the tailed non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase are employed in the detection step, the second oligonucleotide may contain a 5' end label. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In a preferred embodiment, the reaction conditions comprise providing a source of divalent cations; particularly preferred divalent cations are $Mn^{2+}$ and $Mg^{2+}$ ions.

The present invention further provides a method of detecting the presence of a target nucleic acid molecule by detecting non-target cleavage products comprising: a) providing: i) a cleavage means, ii) a source of target nucleic acid, the target nucleic acid having a first region, a second region and a third region, wherein the first region is located adjacent to and downstream from the second region and wherein the second region is located adjacent to and downstream from the third region; iii) a first oligonucleotide having a 5' and a 3' portion wherein the 5' portion of the first oligonucleotide contains a sequence complementary to the second region of the target nucleic acid and wherein the 3' portion of the first oligonucleotide contains a sequence complementary to the third region of the target nucleic acid; iv) a second oligonucleotide having a length between eleven to fifteen nucleotides and further having a 5' and a 3' portion wherein the 5' portion of the second oligonucleotide contains a sequence complementary to the first region of the target nucleic acid and wherein the 3' portion of the second oligonucleotide contains a sequence complementary to the second region of the target nucleic acid; b) mixing the cleavage means, the target nucleic acid, the first oligonucleotide and the second oligonucleotide to create a reaction mixture under reaction conditions such that at least the 3' portion of the first oligonucleotide is annealed to the target nucleic acid and wherein at least the 5' portion of the second oligonucleotide is annealed to the target nucleic acid so as to create a cleavage structure and wherein cleavage of the cleavage structure occurs to generate non-target cleavage products, each non-target cleavage product having a 3'-hydroxyl group; and c) detecting the non-target cleavage products. In a preferred embodiment the cleavage means is a structure-specific nuclease, preferably a thermostable structure-specific nuclease.

The invention is not limited by the length of the various regions of the target nucleic acid. In a preferred embodiment, the second region of the target nucleic acid has a length between one to five nucleotides. In another preferred embodiment, one or more of the first and the second oligonucleotides contain a dideoxynucleotide at the 3' terminus. When dideoxynucleotide-containing oligonucleotides are employed, the detection of the non-target cleavage products preferably comprises: a) incubating the non-target cleavage products with a template-independent polymerase and at least one labeled nucleoside triphosphate under conditions such that at least one labeled nucleotide is added to the 3'-hydroxyl group of the non-target cleavage products to generate labeled non-target cleavage products; and b) detecting the presence of the labeled non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase is employed in the detection step, the second oligonucleotide may contain a 5' end label, the 5' end label being a different label than the label present upon the labeled nucleoside triphosphate. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In another embodiment, detecting the non-target cleavage products comprises: a) incubating the non-target cleavage products with a template-independent polymerase and at least one nucleoside triphosphate under conditions such that at least one nucleotide is added to the 3'-hydroxyl group of the non-target cleavage products to generate tailed non-target cleavage products; and b) detecting the presence of the tailed non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase are employed in the detection step, the second oligonucleotide may contain a 5' end label. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

The novel detection methods of the invention may be employed for the detection of target DNAs and RNAs including, but not limited to, target DNAs and RNAs comprising wild type and mutant alleles of genes, including genes from humans or other animals that are or may be associated with disease or cancer. In addition, the methods of the invention may be used for the detection of and/or identification of strains of microorganisms, including bacteria, fungi, protozoa, ciliates and viruses (and in particular for the detection and identification of RNA viruses, such as HCV).

The present invention further provides improved enzymatic cleavage means. In one embodiment, the present invention provides a thermostable structure-specific nuclease having an amino acid sequence selected from the group consisting of SEQ ID NOS:102, 107, 130, 132, 179, 181, 183, 184, 185, 186, 187, and 188. In another embodiment, the nuclease is encoded by a DNA sequence selected from the group consisting of SEQ ID NOS:101, 106, 129 131, 178, 180, and 182.

The present invention also provides a recombinant DNA vector comprising DNA having a nucleotide sequence encoding a structure-specific nuclease, the nucleotide sequence selected from the group consisting of SEQ ID NOS:101, 106, 129 131, 137, 140, 141, 142, 143, 144, 145, 147, 150, 151, 153, 155, 156, 157, 158, 161, 163, 178, 180, and 182. In a preferred embodiment, the invention provides a host cell transformed with a recombinant DNA vector comprising DNA having a nucleotide sequence encoding a structure-specific nuclease, the nucleotide sequence selected from the group consisting of SEQ ID NOS:101, 106, 129, 131, 178, 180, and 182. The invention is not limited by the nature of the host cell employed. The art is well aware of expression vectors suitable for the expression of nucleotide sequences encoding structure-specific nucleases which can be expressed in a variety of prokaryotic and eukaryotic host cells. In a preferred embodiment, the host cell is an *Escherichia coli* cell.

The present invention provides purified FEN-1 endonucleases. In one embodiment, the present invention provides *Pyrococcus woesei* FEN-1 endonuclease. In a preferred embodiment, the purified *Pyrococcus woesei* FEN-1 endonuclease has a molecular weight of about 38.7 kilodaltons (the molecular weight may be conveniently estimated using SDS-PAGE as described in Ex. 28).

The present invention further provides an isolated oligonucleotide encoding a *Pyrococcus woesei* FEN-1 endonuclease, the oligonucleotide having a region capable of hybridizing to an oligonucleotide sequence selected from the group consisting of SEQ ID NOS:116–119. In a preferred embodiment, the oligonucleotide encoding the purified *Pyrococcus woesei* FEN-1 endonuclease is operably linked to a heterologous promoter. The present invention is not limited by the nature of the heterologous promoter employed; in a preferred embodiment, the heterologous promoter is an inducible promoter (the promoter chosen will depend upon the host cell chosen for expression as is known in the art). The invention is not limited by the nature of the inducible promoter employed. Preferred inducible promoter include the $\lambda$-$P_L$ promoter, the tac promoter, the trp promoter and the trc promoter.

In another preferred embodiment, the invention provides a recombinant DNA vector comprising an isolated oligonucleotide encoding a *Pyrococcus woesei* (Pwo) FEN-1 endonuclease, the oligonucleotide having a region capable of hybridizing to an oligonucleotide sequence selected from the group consisting of SEQ ID NOS:116–119. Host cells transformed with these recombinant vectors are also provided. In a preferred embodiment, the invention provides a host cell transformed with a recombinant DNA vector comprising DNA having a region capable of hybridizing to an oligonucleotide sequence selected from the group consisting of SEQ ID NOS: 116–119; these vectors may further comprise a heterologous promoter operably linked to the Pwo FEN-1-encoding polynucleotides. The invention is not limited by the nature of the host cell employed. The art is well aware of expression vectors suitable for the expression of Pwo FEN-1-encoding polynucleotides which can be expressed in a variety of prokaryotic and eukaryotic host cells. In a preferred embodiment, the host cell is an *Escherichia coli* cell.

In yet another embodiment, the invention provides an isolated oligonucleotide comprising a gene encoding a *Pyrococcus woesei* FEN-1 endonuclease having a molecular weight of about 38.7 kilodaltons. In another embodiment, the encoding a *Pyrococcus woesei* FEN-1 endonuclease is operably linked to a heterologous promoter. The present invention is not limited by the nature of the heterologous promoter employed; in a preferred embodiment, the heterologous promoter is an inducible promoter (the promoter chosen will depend upon the host cell chosen for expression as is known in the art). The invention is not limited by the nature of the inducible promoter employed. Preferred inducible promoter include the $\lambda$-$P_L$ promoter, the tac promoter, the trp promoter and the trc promoter.

The invention further provides recombinant DNA vectors comprising DNA having a nucleotide sequence encoding FEN-1 endonucleases. In one preferred embodiment, the present invention provides a *Pyrococcus woesei* FEN-1 endonuclease having a molecular weight of about 38.7 kilodaltons. Still further, a host cell transformed with a recombinant DNA vector comprising DNA having a nucleotide sequence encoding FEN-1 endonuclease. In a preferred embodiment, the host cell is transformed with a recombinant DNA vector comprising DNA having a nucleotide sequence encoding a *Pyrococcus woesei* FEN-1 endonuclease having a molecular weight of about 38.7 kilodaltons is provided. The invention is not limited by the nature of the host cell employed. The art is well aware of expression vectors suitable for the expression of Pwo FEN-1-encoding polynucleotides which can be expressed in a variety of prokaryotic and eukaryotic host cells. In a preferred embodiment, the host cell is an *Escherichia coli* cell.

Thus, the present invention provides multiple purified FEN-1 endonucleases, both purified native forms of the endonucleases, as well as recombinant endonucleases. In preferred embodiments, the purified FEN-1 endonucleases are obtained from archaebacterial or eubacterial organisms. In particularly preferred embodiments, the FEN-1 endonucleases are obtained from organisms selected from the group consisting of *Archaeoglobus fulgidus* and *Methanobacterium thermoautotrophicum*. In a preferred embodiment, the purified FEN-1 endonucleases have molecular weights of about 39 kilodaltons (the molecular weight may be conveniently estimated using SDS-PAGE as described in Ex. 28).

The present invention further provides isolated oligonucleotides encoding *Archaeoglobus fulgidus* and *Methanobacterium thermoautotrophicum* FEN-1 endonucleases, the oligonucleotides each having a region capable of hybridizing to at least a portion of an oligonucleotide sequence, wherein the oligonucleotide sequence is selected from the group consisting of SEQ ID NOS:170, 171, 172, and 173. In some preferred embodiment, the oligonucleotides encoding the *Archaeoglobus fulgidus* and *Methanobacterium thermoautotrophicum* FEN-1 endonucleases are operably linked to heterologous promoters. However, it is not intended that the present invention be limited by the nature of the heterologous promoter employed. It is contemplated that the promoter chosen will depend upon the host cell chosen for expression as is known in the art. In some preferred embodiments, the heterologous promoter is an inducible promoter. The invention is not limited by the nature of the inducible promoter employed. Preferred inducible promoters include the $\lambda$-$P_L$ promoter, the tac promoter, the trp promoter and the trc promoter.

In another preferred embodiment, the invention provides recombinant DNA vectors comprising isolated oligonucleotides encoding *Archaeoglobus fulgidus* or *Methanobacterium thermoautotrophicum* FEN-1 endonucleases, each oligonucleotides having a region capable of hybridizing to at least a portion of an oligonucleotide sequence, wherein the oligonucleotide sequence is selected from the group consisting of SEQ ID NOS:170, 171, 172, and 173. The present invention further provides host cells transformed with these recombinant vectors. In a preferred embodiment, the invention provides a host cell transformed with a recombinant DNA vector comprising DNA having a region capable of hybridizing to at least a portion of an oligonucleotide sequence, wherein the oligonucleotide sequence is selected from the group consisting of SEQ ID NOS:170, 171, 172 and 173. In some embodiments, these vectors may further comprise a heterologous promoter operably linked to the FEN-1-encoding polynucleotides. The invention is not limited by the nature of the host cell employed. The art is well aware of expression vectors suitable for the expression of FEN-1-encoding polynucleotides which can be expressed in a variety of prokaryotic and eukaryotic host cells. In a preferred embodiment, the host cell is an *Escherichia coli* cell.

The present invention further provides chimeric structure-specific nucleases. In one embodiment, the present invention provides chimeric endonucleases comprising amino acid portions derived from the endonucleases selected from the group of FEN-1, XPG and RAD homologs. In a preferred embodiment, the chimeric endonucleases comprise amino acid portions derived from the FEN-1 endonucleases selected from the group of *Pyrococcus furiosus, Methanococcus jannaschi, Pyrococcus woesei, Archaeoglobus fulgidus* and *Methanobacterium thermoautotrophicum*. In a more preferred embodiment, the chimeric FEN-1 endonucleases have molecular weights of about 39 kilodaltons (the molecular weight may be conveniently estimated using SDS-PAGE as described in Ex. 28).

The present invention further provides isolated oligonucleotides encoding chimeric endonucleases. In one embodiment, the oligonucleotides encoding the chimeric endonucleases comprise nucleic acid sequences derived from the genes selected from the group of FEN-1, XPG and RAD homologs. In a preferred embodiment the oligonucleotides encoding the chimeric endonucleases comprise nucleic acid sequences derived from the genes encoding the FEN-1 endonucleases selected from the group of *Pyrococcus furiosus, Methanococcus jannaschi, Pyrococcus woesei, Archaeoglobus fulgidus* and *Methanobacterium thermoautotrophicum*. In a particularly preferred embodiment, the genes for the chimeric endonucleases are operably linked to heterologous promoters. The present invention is not limited by the nature of the heterologous promoter employed. It is contemplated that the promoter chosen will depend upon the host cell selected for expression, as is known in the art. In preferred embodiments, the heterologous promoter is an inducible promoter. The invention is not limited by the nature of the inducible promoter employed. Preferred inducible promoter include the λ-$P_L$ promoter, the tac promoter, the trp promoter and the trc promoter.

In another preferred embodiment, the invention provides recombinant DNA vectors comprising isolated oligonucleotides encoding the chimeric endonucleases described above. In one embodiment, the recombinant DNA vectors comprise isolated oligonucleotides encoding nucleic acid sequences derived from the genes selected from the group of FEN-1, XPG and RAD homologs. In a preferred embodiment, the recombinant DNA vectors comprise isolated oligonucleotides encoding the chimeric endonucleases comprising nucleic acid sequences derived from the genes encoding the FEN-1 endonucleases selected from the group of *Pyrococcus furiosus, Methanococcus jannaschi, Pyrococcus woesei, Archaeoglobus fulgidus* and *Methanobacterium thermoautotrophicum*. These vectors may further comprise a heterologous promoter operably linked to the chimeric nuclease-encoding polynucleotides.

Host cells transformed with these recombinant vectors are also provided. The invention is not limited by the nature of the host cell employed. The art is well aware of expression vectors suitable for the expression of FEN-1-encoding polynucleotides which can be expressed in a variety of prokaryotic and eukaryotic host cells. In a preferred embodiment, the host cell is an *Escherichia coli* cell.

The present invention further provides mixtures comprising a first structure-specific nuclease, wherein the first nuclease consists of a purified FEN-1 endonuclease and a second structure-specific nuclease. In preferred embodiments, the second structure-specific nuclease of the mixture is selected from the group consisting *Pyrococcus woesei* FEN-1 endonuclease, *Pyrococcus furiosus* FEN-1, *Methanococcus jannaschii* FEN-1 endonuclease, *Methanobacterium thermoautotrophicum* FEN-1 endonuclease, *Archaeoglobus fulgidus* FEN-1, and chimerical FEN-1 endonucleases. In alternative embodiments, the purified FEN-1 endonuclease of the mixture is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, and chimerical FEN-1 endonucleases. In yet other preferred embodiments of the mixture, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In some preferred embodiments of the mixture, the second nuclease is selected from the group consisting of the Cleavase® BN enzyme, *Thermus aquaticus* DNA polymerase, *Thermus thermophilus* DNA polymerase, *Escherichia coli* Exo III, *Saccharomyces cerevisiae* Rad1/Rad10 complex.

The present invention also provides methods for treating nucleic acid, comprising: a) providing a purified FEN-1 endonuclease; and a nucleic acid substrate; b) treating the nucleic acid substrate under conditions such that the substrate forms one or more cleavage structures; and c) reacting the endonuclease with the cleavage structures so that one or more cleavage products are produced. In some embodiments, the purified FEN-1 endonuclease is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, and chimerical FEN-1 endonucleases. In other embodiments, the method further comprises providing a structure-specific nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase.

In alternative embodiments of the methods, a portion of the amino acid sequence of the second nuclease is homologous to a portion of the amino acid sequence of a thermostable DNA polymerase derived from a eubacterial thermophile of the genus Thermus. In yet other embodiments, the thermophile is selected from the group consisting of *Thermus aquaticus, Thermus flavus* and *Thermus thermophilus*. In some alternative embodiments. the structure-specific nuclease is selected from the group consisting of the Cleavase® BN enzyme, *Thermus aquaticus* DNA polymerase, *Thermus thermophilus* DNA polymerase, *Escherichia coli* Exo III, *Saccharomyces cerevisiae* Rad1/Rad10 complex. In some preferred embodiments, the structure-specific nuclease is the Cleavase® BN nuclease. In yet other embodiments, the nucleic acid of step (a) is substantially single-stranded. In further embodiments, the nucleic acid is selected from the group consisting of RNA and DNA. In yet further embodiments, the nucleic acid of step (a) is double stranded.

In other embodiments of the methods, the treating of step (b) comprises: rendering the double-stranded nucleic acid substantially single-stranded; and exposing the single-stranded nucleic acid to conditions such that the single-stranded nucleic acid has secondary structure. In some preferred embodiments, the double stranded nucleic acid is rendered substantially single-stranded by the use of increased temperature. In alternative preferred embodiments, the method further comprises the step of detecting the one or more cleavage products.

The present invention also provides methods for treating nucleic acid, comprising: a) providing: a first structure-specific nuclease consisting of a purified FEN-1 endonuclease in a solution containing manganese; and a nucleic acid substrate; b) treating the nucleic acid substrate with increased temperature such that the substrate is substantially single-stranded; c) reducing the temperature under conditions such that the single-stranded substrate forms one or more cleavage structures; d) reacting the cleavage means with the cleavage structures so that one or more cleavage products are produced; and e) detecting the one or more cleavage products. In some embodiments of the methods, the purified FEN-1 endonuclease is selected from the group consisting Pyrococcus woesei FEN-1 endonuclease, Pyrococcus furiosus FEN-1 endonuclease, Methanococcus jannaschii FEN-1 endonuclease, Methanobacterium thermoautotrophicum FEN-1 endonuclease, Archaeoglobus fulgidus FEN-1, and chimerical FEN-1 endonucleases. In alternative embodiments, the methods further comprise providing a second structure-specific nuclease. In some preferred embodiments, the second nuclease is selected from the group consisting of the Cleavase® BN enzyme, Thermus aquaticus DNA polymerase, Thermus thermophilus DNA polymerase, Escherichia coli Exo III, and the Saccharomyces cerevisiae Rad1/Rad10 complex. In yet other preferred embodiments, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In yet other embodiments, the nucleic acid is selected from the group consisting of RNA and DNA. In further embodiments, the nucleic acid of step (a) is double stranded.

The present invention also provides nucleic acid treatment kits, comprising: a) a composition comprising at least one purified FEN-1 endonuclease; and b) a solution containing manganese. In some embodiments of the kits, the purified FEN-1 endonuclease is selected from the group consisting Pyrococcus woesei FEN-1 endonuclease, Pyrococcus furiosus FEN-1 endonuclease, Methanococcus jannaschii FEN-1 endonuclease, Methanobacterium thermoautotrophicum FEN-1 endonuclease, Archaeoglobus fulgidus FEN-1, and chimerical FEN-1 endonucleases. In other embodiments, the kits further comprise at least one second structure-specific nuclease. In some preferred embodiments, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In yet other embodiments of the kits, the portion of the amino acid sequence of the second nuclease is homologous to a portion of the amino acid sequence of a thermostable DNA polymerase derived from a eubacterial thermophile of the genus Thermus. In further embodiments, the thermophile is selected from the group consisting of Thermus aquaticus, Thermus flavus and Thermus thermophilus. In yet other preferred embodiments, the kits further comprise reagents for detecting the cleavage products.

DESCRIPTION OF THE DRAWINGS

FIG. 1B provides a schematic of a second embodiment of the detection method of the present invention.

FIG. 1C provides a schematic of a second part of the detection method shown in FIG. 1B, with an annealing of the fragment of the second oligonucleotide liberated by the cleavage of the first cleavage structure formed in the triggering reaction, to a first hairpin structure.

Figure 2B:
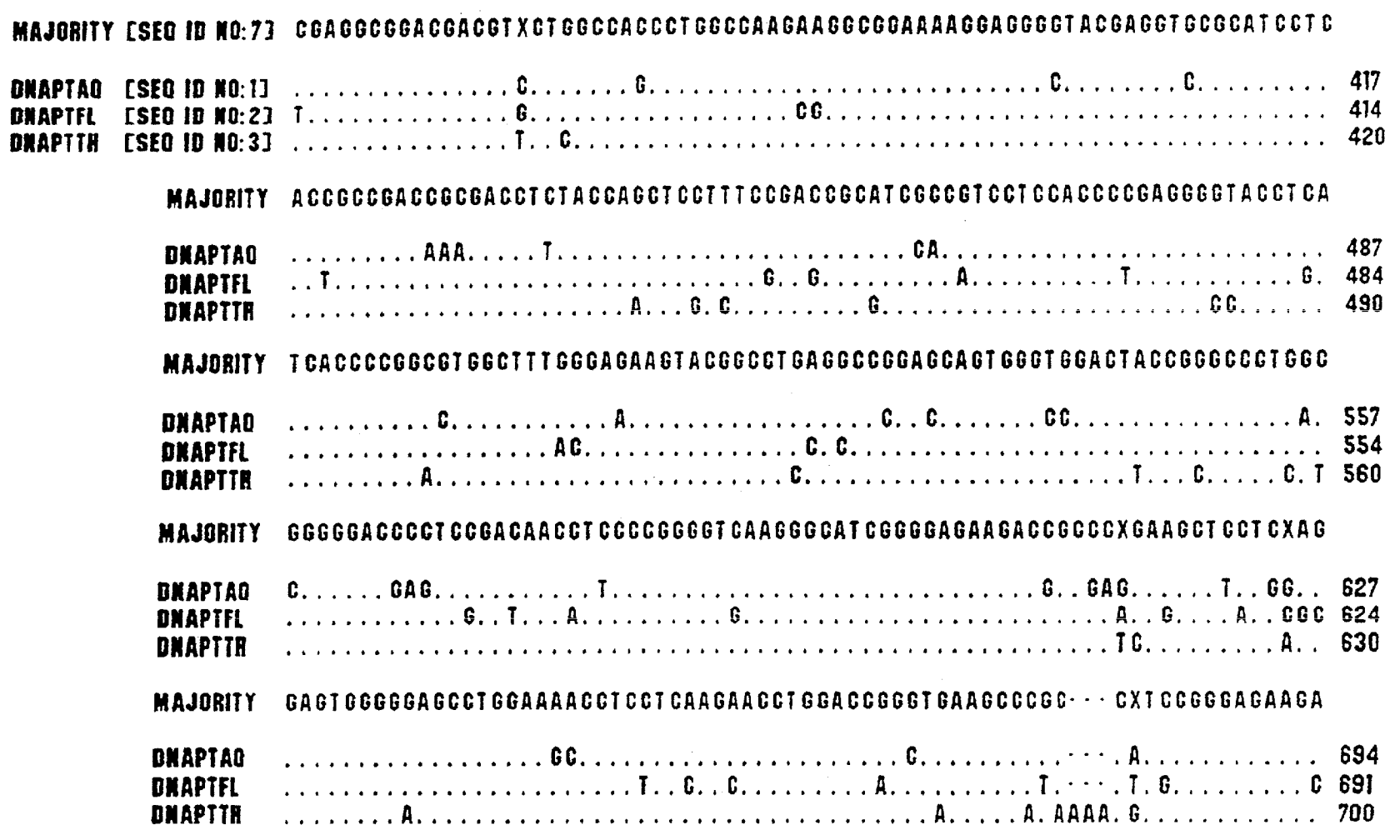
Figure 2C:
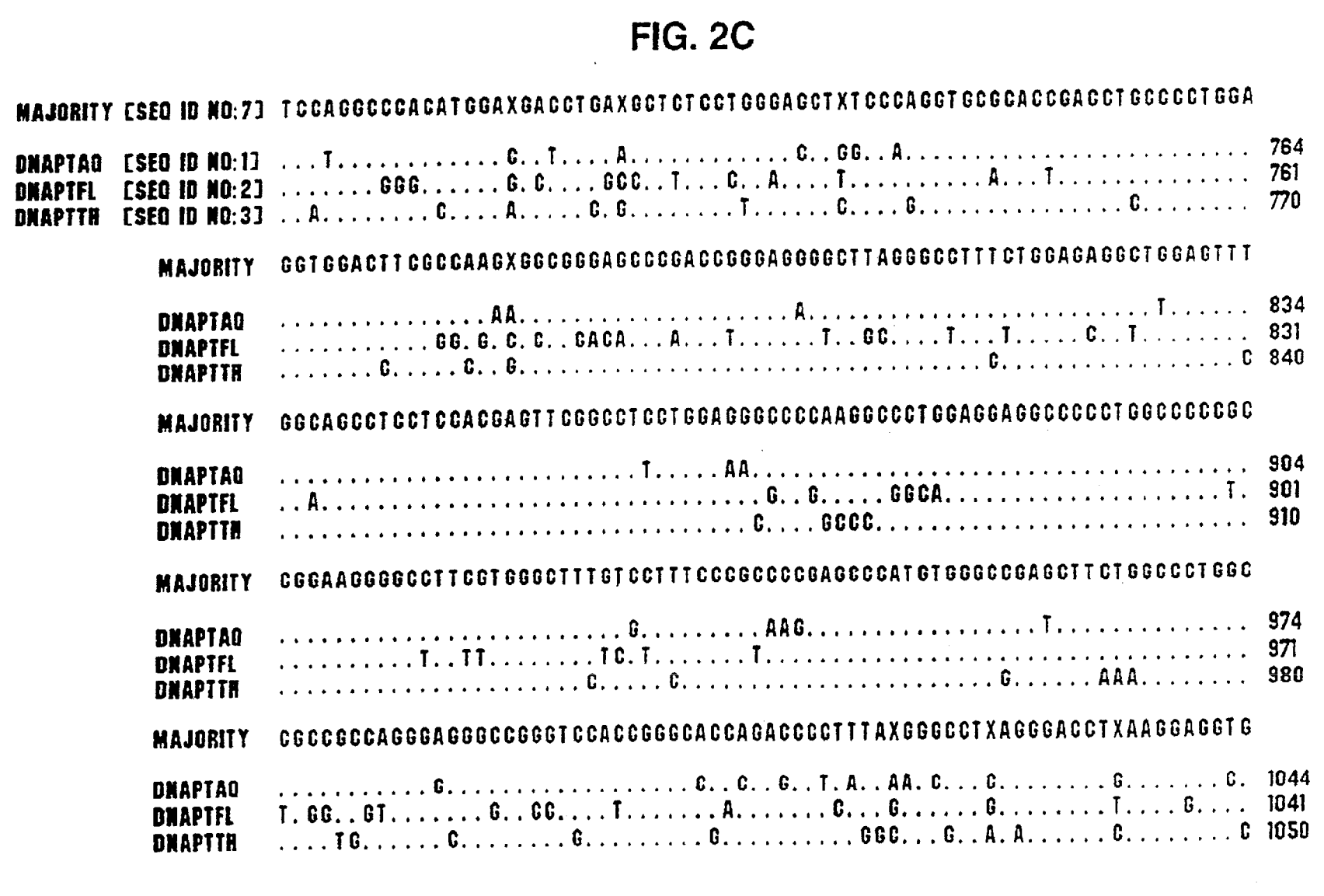
Figure 2D:
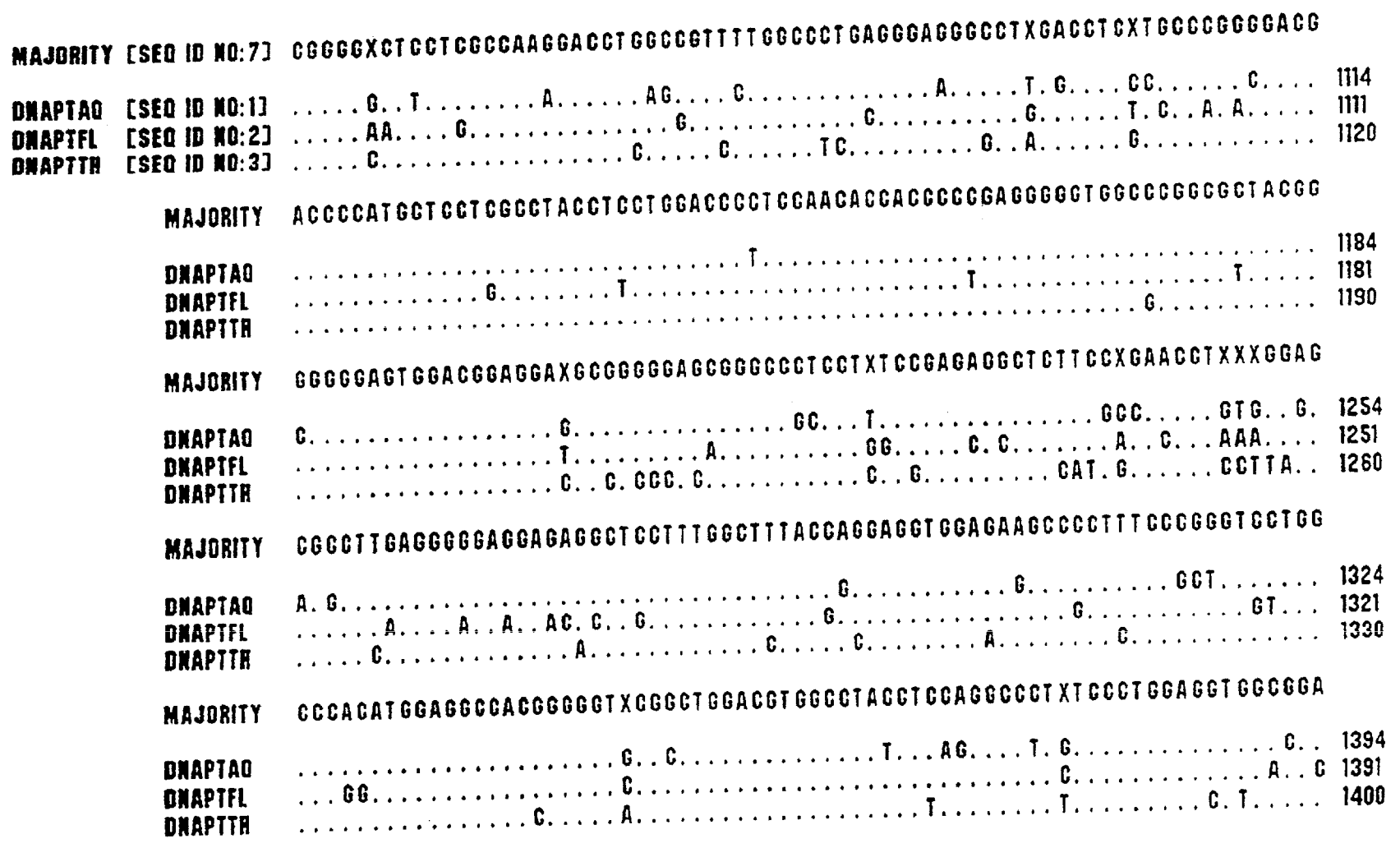
Figure 2E:
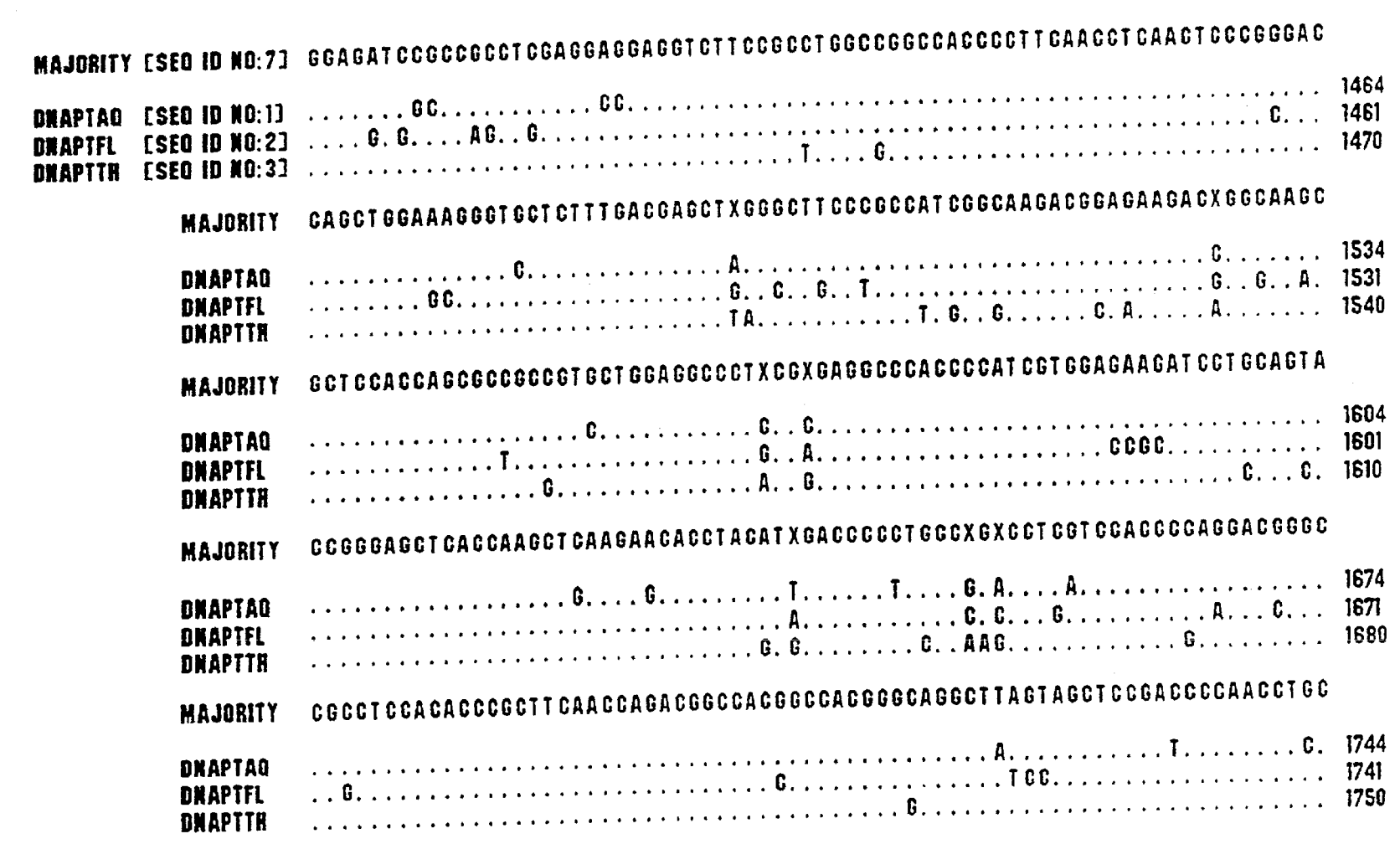
Figure 2F:
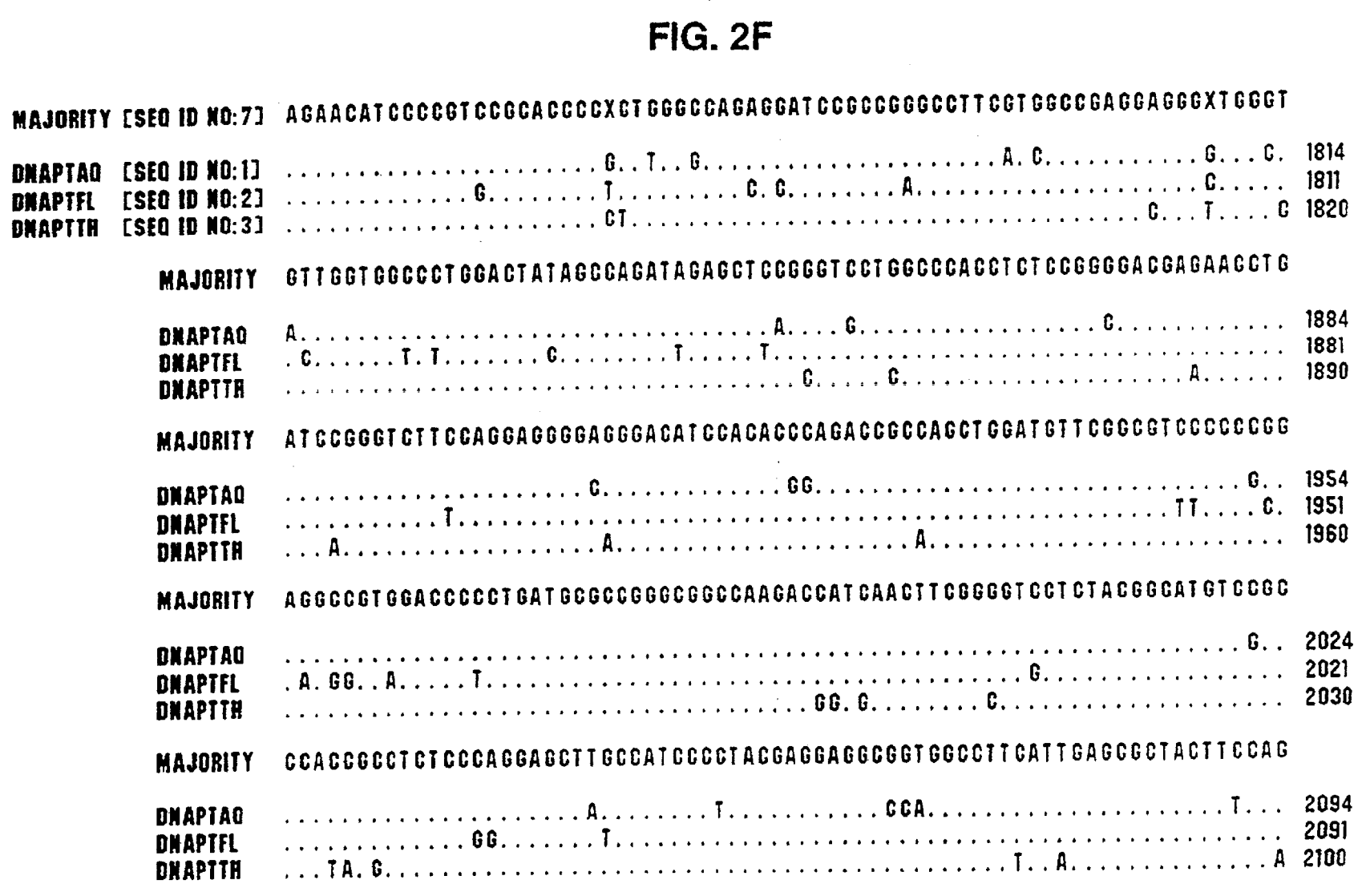

FIG. 2 is a comparison of the nucleotide structure of the DNAP genes isolated from Thermus aquaticus (SEQ ID NO:1), Thermus flavus (SEQ ID NO:2) and Thermus thermophilus (SEQ ID NO:3); the consensus sequence (SEQ ID NO:7) is shown at the top of each row.

FIG. 3 is a comparison of the amino acid sequence of the DNAP isolated from Thermus aquaticus (SEQ ID NO:4), Thermus flavus (SEQ ID NO:5), and Thermus thermophilus (SEQ ID NO:6); the consensus sequence (SEQ ID NO:8) is shown at the top of each row.

FIGS. 4A–G are a set of diagrams of wild-type and synthesis-deficient DNAPTaq genes.

FIG. 5A depicts the wild-type Thermus flavus polymerase gene.

FIG. 5B depicts a synthesis-deficient Thermus flavus polymerase gene.

FIG. 14 is a diagram of vector pTTQ18.

FIGS. 16A–E depicts a set of molecules which are suitable substrates for cleavage by the 5' nuclease activity of DNAPs.

FIG. 20A shows the A- and T-hairpin molecules used in the trigger/detection assay.

FIG. 20B shows the sequence of the alpha primer used in the trigger/detection assay.

FIG. 20C shows the structure of the cleaved A- (SEQ ID NO:28) and T-hairpin molecules.

FIG. 20D depicts the complementarity between the A- and T-hairpin molecules.

FIG. 30 provides a schematic showing the S-60 hairpin oligonucleotide (SEQ ID NO:40) with the annealed P-15 oligonucleotide (SEQ ID NO:41).

FIG. 41 provides a schematic showing an arrangement of a target-specific invader oligonucleotide (SEQ ID NO:50) and a target-specific probe oligonucleotide (SEQ ID NO:49) bearing a 5' Cy3 label along a target nucleic acid (SEQ ID NO:42).

FIG. 70 provides an alignment of the amino acid sequences of several FEN-1 nucleases including the *Methanococcus jannaschii* FEN-1 protein (MJAFENI.PRO), the *Pyrococcus furiosus* FEN-1 protein (PFUFEN1.PRO), the human FEN-1 protein (HUMFEN1.PRO), the mouse FEN-1 protein (MUSFEN1.PRO), the *Saccharomyces cerevisiae* YKL510 protein (YST510.PRO), the *Saccharomyces cerevisiae* RAD2 protein (YSTRAD2.PRO), the *Shizosaccharomyces pombe* RAD 13 protein (SPORAD13.PRO), the human XPG protein (HUMXPG.PRO), the mouse XPG protein (MUSXPG.PRO), the *Xenopus laevis* XPG protein (XENXPG.PRO) and the *C. elegans* RAD2 protein (CELRAD2.PRO); portions of the amino acid sequence of some of these proteins were not shown in order to maximize the alignment between proteins. The numbers to the left of each line of sequence refers to the amino acid residue number; dashes represent gaps introduced to maximize alignment.

FIGS. 89A–C show the sequence of the S-60 hairpin (SEQ ID NO:40) (A), and the P-15 oligonucleotide (SEQ ID NO:41) (shown annealed to the S-60 hairpin in B) and the image generated by a fluorescence imager showing the products produced by cleavage of the S-60 hairpin in the presence of various Invader™ oligonucleotides.

FIG. 107 shows the two substrates. Panel A shows the structure and sequence of the hairpin substrate (25-65-1) (SEQ ID NO:176), while Panel B shows the structure and sequence of the invader (IT) substrate (25-184-5)(SEQ ID NO:177).

DEFINITIONS

Figure 1A:
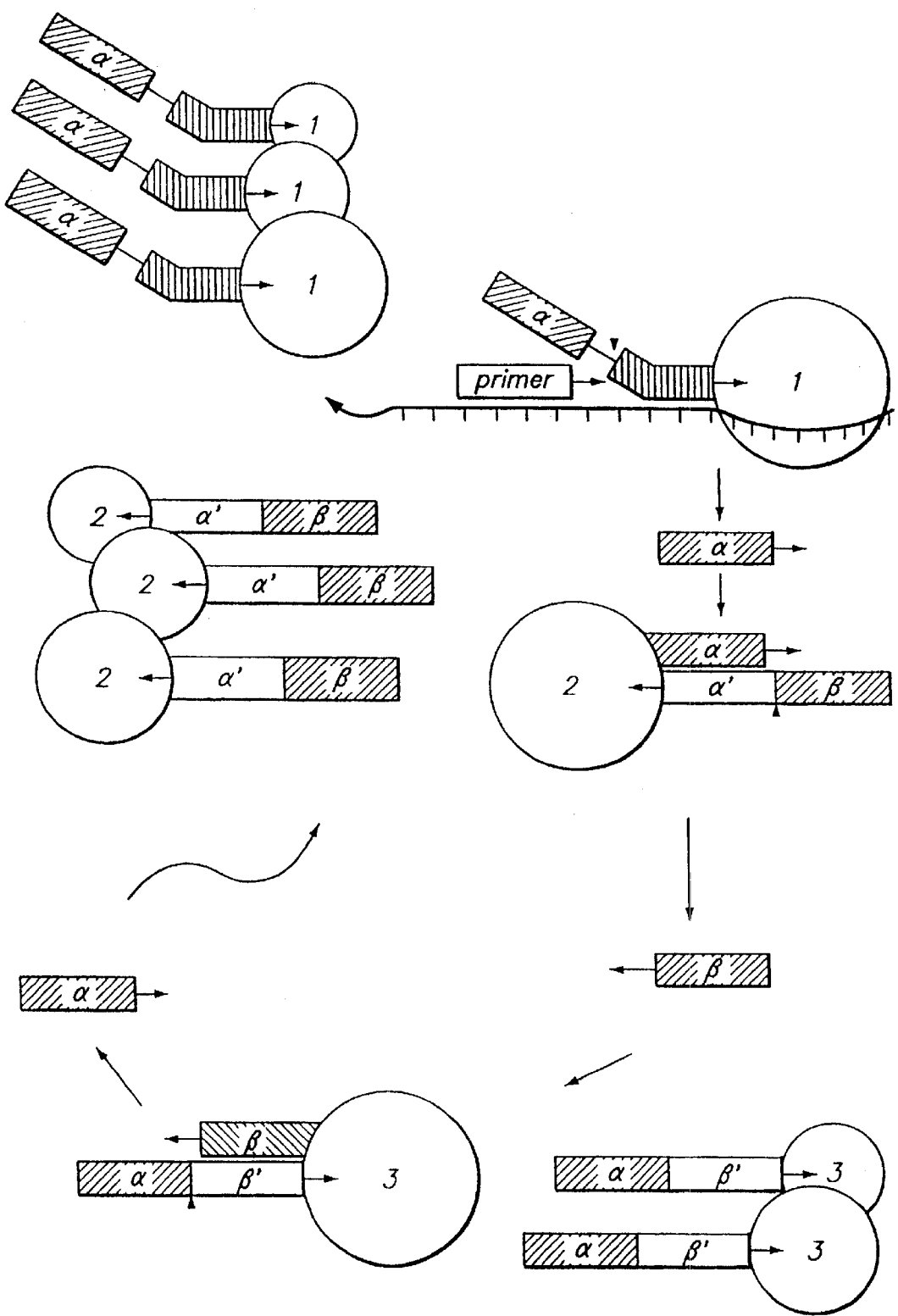
FIG. 1A provides a schematic of one embodiment of the detection method of the present invention.

As used herein, the terms "complementary" or "complementarity" are used in reference to polynucleotides (i.e., a sequence of nucleotides such as an oligonucleotide or a target nucleic acid) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of identity. There may be partial homology or complete homology. A partially identical sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defined as a molecule comprised of two or more deoxyribonucleotides or ribonucleotides, preferably at least 5 nucleotides, more preferably at least about 10–15 nucleotides and more preferably at least about 15 to 30 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected; the detection of this sequence may be by either direct or indirect means). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology.

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral.

The term "cleavage structure" as used herein, refers to a structure which is formed by the interaction of a probe oligonucleotide and a target nucleic acid to form a duplex, the resulting structure being cleavable by a cleavage means, including but not limited to an enzyme. The cleavage structure is a substrate for specific cleavage by the cleavage means in contrast to a nucleic acid molecule which is a substrate for non-specific cleavage by agents such as phosphodiesterases which cleave nucleic acid molecules without regard to secondary structure (i.e., no formation of a duplexed structure is required).

The term "folded cleavage structure" as used herein, refers to a region of a single-stranded nucleic acid substrate containing secondary structure, the region being cleavable by an enzymatic cleavage means. The cleavage structure is a substrate for specific cleavage by the cleavage means in contrast to a nucleic acid molecule which is a substrate for non-specific cleavage by agents such as phosphodiesterases which cleave nucleic acid molecules without regard to secondary structure (i.e., no folding of the substrate is required).

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "cleavage means" as used herein refers to any means which is capable of cleaving a cleavage structure, including but not limited to enzymes. The cleavage means may include native DNAPs having 5' nuclease activity (e.g., Taq DNA polymerase, *E. coli* DNA polymerase I) and, more specifically, modified DNAPs having 5' nuclease but lacking synthetic activity. The ability of 5' nucleases to cleave naturally occurring structures in nucleic acid templates (structure-specific cleavage) is useful to detect internal sequence differences in nucleic acids without prior knowledge of the specific sequence of the nucleic acid. In this manner, they are structure-specific enzymes. "Structure-specific nucleases" or "structure-specific enzymes" are enzymes which recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means is not restricted to enzymes having solely 5' nuclease activity. The cleavage means may include nuclease activity provided from a variety of sources including the Cleavase® enzymes, the FEN-1 endonucleases (including RAD2 and XPG proteins), Taq DNA polymerase and *E. coli* DNA polymerase I.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule which contains a sequence which has at least partial complementarity with at least a probe oligonucleotide and may also have at least partial complementarity with an invader oligonucleotide. The target nucleic acid may comprise single- or double-stranded DNA or RNA.

The term "probe oligonucleotide" refers to an oligonucleotide which interacts with a target nucleic acid to form a cleavage structure in the presence or absence of an invader oligonucleotide. When annealed to the target nucleic acid, the probe oligonucleotide and target form a cleavage structure and cleavage occurs within the probe oligonucleotide. In the presence of an invader oligonucleotide upstream of the probe oligonucleotide along the target nucleic acid will shift the site of cleavage within the probe oligonucleotide (relative to the site of cleavage in the absence of the invader).

The term "non-target cleavage product" refers to a product of a cleavage reaction which is not derived from the target nucleic acid. As discussed above, in the methods of the present invention, cleavage of the cleavage structure occurs within the probe oligonucleotide. The fragments of the probe oligonucleotide generated by this target nucleic acid-dependent cleavage are "non-target cleavage products."

The term "invader oligonucleotide" refers to an oligonucleotide which contains sequences at its 3' end which are substantially the same as sequences located at the 5' end of a probe oligonucleotide; these regions will compete for hybridization to the same segment along a complementary target nucleic acid.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism which is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample which contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "charge-balanced" oligonucleotide refers to an oligonucleotide (the input oligonucleotide in a reaction) which has been modified such that the modified oligonucleotide bears a charge, such that when the modified oligonucleotide is either cleaved (i.e., shortened) or elongated, a resulting product bears a charge different from the input oligonucleotide (the "charge-unbalanced" oligonucleotide) thereby permitting separation of the input and reacted oligonucleotides on the basis of charge. The term "charge-balanced" does not imply that the modified or balanced oligonucleotide has a net neutral charge (although this can be the case). Charge-balancing refers to the design and modification of an oligonucleotide such that a specific reaction product generated from this input oligonucleotide can be separated on the basis of charge from the input oligonucleotide.

For example, in an invader-directed cleavage assay in which the probe oligonucleotide bears the sequence: 5'-TTCTTTTCACCAGCGAGACGGG-3' (i.e., SEQ ID NO:61 without the modified bases) and cleavage of the probe occurs between the second and third residues, one possible charge-balanced version of this oligonucleotide would be: 5'-Cy3-AminoT-Amino-TCTTTTCACCAGC GAGAC GGG-3'. This modified oligonucleotide bears a net negative charge. After cleavage, the following oligonucleotides are generated: 5'-Cy3-AminoT-Amino-T-3' and 5'-CTTTTCACCAGCGAGACGGG-3' (residues 3–22 of SEQ ID NO:61). 5'-Cy3-AminoT-Amino-T-3' bears a detectable moiety (the positively-charged Cy3 dye) and two amino-modified bases. The amino-modified bases and the Cy3 dye contribute positive charges in excess of the negative charges contributed by the phosphate groups and thus the 5'-Cy3-AminoT-Amino-T-3' oligonucleotide has a net positive charge. The other, longer cleavage fragment, like the input probe, bears a net negative charge. Because the 5'-Cy3-AminoT-Amino-T-3' fragment is separable on the basis of charge from the input probe (the charge-balanced oligonucleotide), it is referred to as a charge-unbalanced oligonucleotide. The longer cleavage product cannot be separated on the basis of charge from the input oligonucleotide as both oligonucleotides bear a net negative charge; thus, the longer cleavage product is not a charge-unbalanced oligonucleotide.

The term "net neutral charge" when used in reference to an oligonucleotide, including modified oligonucleotides, indicates that the sum of the charges present (i.e., R-NH$^{3+}$ groups on thymidines, the N3 nitrogen of cytosine, presence or absence or phosphate groups, etc.) under the desired reaction conditions is essentially zero. An oligonucleotide having a net neutral charge would not migrate in an electrical field.

The term "net positive charge" when used in reference to an oligonucleotide, including modified oligonucleotides, indicates that the sum of the charges present (i.e., R-NH$^{3+}$ groups on thymidines, the N3 nitrogen of cytosine, presence or absence or phosphate groups, etc.) under the desired reaction conditions is +1 or greater. An oligonucleotide having a net positive charge would migrate toward the negative electrode in an electrical field.

The term "net negative charge" when used in reference to an oligonucleotide, including modified oligonucleotides, indicates that the sum of the charges present (i.e., R-NH$^{3+}$ groups on thymidines, the N3 nitrogen of cytosine, presence or absence or phosphate groups, etc.) under the desired reaction conditions is −1 or lower. An oligonucleotide having a net negative charge would migrate toward the positive electrode in an electrical field.

The term "polymerization means" refers to any agent capable of facilitating the addition of nucleoside triphosphates to an oligonucleotide. Preferred polymerization means comprise DNA polymerases.

The term "ligation means" refers to any agent capable of facilitating the ligation (i.e., the formation of a phosphodiester bond between a 3'-OH and a 5'-P located at the termini of two strands of nucleic acid). Preferred ligation means comprise DNA ligases and RNA ligases.

The term "reactant" is used herein in its broadest sense. The reactant can comprise an enzymatic reactant, a chemical reactant or ultraviolet light (ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

The term "adduct" is used herein in its broadest sense to indicate any compound or element which can be added to an oligonucleotide. An adduct may be charged (positively or negatively) or may be charge neutral. An adduct may be added to the oligonucleotide via covalent or non-covalent linkages. Examples of adducts, include but are not limited to indodicarbocyanine dye amidites, amino-substituted nucleotides, ethidium bromide, ethidium homodimer, (1,3-propanediamino)propidium, (diethylenetriamino)propidium, thiazole orange, (N-N'-tetramethyl-1,3-propanediamino)propyl thiazole orange, (N-N'-tetramethyl-1,2-ethanediamino)propyl thiazole orange, thiazole orange-thiazole orange homodimer (TOTO), thiazole orange-thiazole blue heterodimer (TOTAB), thiazole orange-ethidium heterodimer 1 (TOED1), thiazole orange-ethidium heterodimer 2 (TOED2) and fluorescein-ethidium heterodimer (FED), psoralens, biotin, streptavidin, avidin, etc.

Where a first oligonucleotide is complementary to a region of a target nucleic acid and a second oligonucleotide has complementary to the same region (or a portion of this region) a "region of overlap" exists along the target nucleic acid. The degree of overlap will vary depending upon the nature of the complementarity (see, e.g., region "X" in FIGS. 29 and 67 and the accompanying discussions).

As used herein, the term "purified" or "to purify" refers to the removal of contaminants from a sample. For example, recombinant Cleavase® nucleases are expressed in bacterial host cells and the nucleases are purified by the removal of host cell proteins; the percent of these recombinant nucleases is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

As used herein the term "portion" when in reference to a protein (as in "a portion of a given protein") refers to fragments of that protein. The fragments may range in size from four amino acid residues to the entire amino acid sequence minus one amino acid.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence.

"Peptide nucleic acid" ("PNA") as used herein refers to a molecule which comprises an oligomer to which an amino acid residue, such as lysine, and an amino group have been added. These small molecules, also designated anti-gene agents, stop transcript elongation by binding to their complementary strand of nucleic acid [Nielsen P E et al. (1993) Anticancer Drug Des. 8:53–63].

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

An isolated oligonucleotide (or polynucleotide) encoding a *Pyrococcus woesei* (Pwo) FEN-1 endonuclease having a region capable of hybridizing to SEQ ID NO:116 is an oligonucleotide containing sequences encoding at least the amino-terminal portion of Pwo FEN-1 endonuclease. An isolated oligonucleotide (or polynucleotide) encoding a Pwo FEN-1 endonuclease having a region capable of hybridizing to SEQ ID NO:117 is an oligonucleotide containing sequences encoding at least the carboxy-terminal portion of Pwo FEN-1 endonuclease. An isolated oligonucleotide (or polynucleotide) encoding a Pwo FEN-1 endonuclease having a region capable of hybridizing to SEQ ID NOS:118 and 119 is an oligonucleotide containing sequences encoding at least portions of Pwo FEN-1 endonuclease protein located internal to either the amino or carboxy-termini of the Pwo FEN-1 endonuclease protein.

As used herein, the term "fusion protein" refers to a chimeric protein containing the protein of interest (i.e., Cleavase® BN/thrombin nuclease and portions or fragments thereof) joined to an exogenous protein fragment (the fusion partner which consists of a non-Cleavase® BN/thrombin nuclease protein). The fusion partner may enhance solubility of recombinant chimeric protein (e.g., the Cleavase® BN/thrombin nuclease) as expressed in a host cell, may provide an affinity tag (e.g., a his-tag) to allow purification of the recombinant fusion protein from the host cell or culture supernatant, or both. If desired, the fusion protein may be removed from the protein of interest (e.g., Cleavase® BN/thrombin nuclease or fragments thereof) by a variety of enzymatic or chemical means known to the art.

As used herein, the terms "chimeric protein" and "chimerical protein" refer to a single protein molecule that comprises amino acid sequences portions derived from two or more parent proteins. These parent molecules may be from similar proteins from genetically distinct origins, different proteins from a single organism, or different proteins from different organisms. By way of example but not by way of limitation, the a chimeric structure-specific nuclease of the present invention may contain a mixture of amino acid sequences that have been derived from FEN-1 genes from two or more of the organisms having such genes, combined to form a non-naturally occurring nuclease. The term "chimerical" as used herein is not intended to convey any particular proportion of contribution from the naturally occurring genes, nor limit the manner in which the portions are combined. Any chimeric structure-specific nuclease constructs having cleavage activity as determined by the testing methods described herein are improved cleavage agents within the scope of the present invention.

DESCRIPTION OF THE INVENTION

The present invention relates to methods and compositions for treating nucleic acid, and in particular, methods and compositions for detection and characterization of nucleic acid sequences and sequence changes.

The present invention relates to means for cleaving a nucleic acid cleavage structure in a site-specific manner. In particular, the present invention relates to a cleaving enzyme having 5' nuclease activity without interfering nucleic acid synthetic ability.

This invention provides 5' nucleases derived from thermostable DNA polymerases which exhibit altered DNA synthetic activity from that of native thermostable DNA polymerases. The 5' nuclease activity of the polymerase is retained while the synthetic activity is reduced or absent. Such 5' nucleases are capable of catalyzing the structure-specific cleavage of nucleic acids in the absence of interfering synthetic activity. The lack of synthetic activity during a cleavage reaction results in nucleic acid cleavage products of uniform size.

The novel properties of the nucleases of the invention form the basis of a method of detecting specific nucleic acid sequences. This method relies upon the amplification of the detection molecule rather than upon the amplification of the target sequence itself as do existing methods of detecting specific target sequences.

DNA polymerases (DNAPs), such as those isolated from *E. coli* or from thermophilic bacteria of the genus Thermus, are enzymes that synthesize new DNA strands. Several of the known DNAPs contain associated nuclease activities in addition to the synthetic activity of the enzyme.

Some DNAPs are known to remove nucleotides from the 5' and 3' ends of DNA chains (Kornberg, *DNA Replication*, W.H. Freeman and Co., San Francisco, pp. 127–139 [1980]). These nuclease activities are usually referred to as 5' exonuclease and 3' exonuclease activities, respectively. For example, the 5' exonuclease activity located in the N-terminal domain of several DNAPs participates in the removal of RNA primers during lagging strand synthesis during DNA replication and the removal of damaged nucleotides during repair. Some DNAPs, such as the *E. coli* DNA polymerase (DNAPEc1), also have a 3' exonuclease activity responsible for proof-reading during DNA synthesis (Kornberg, supra).

A DNAP isolated from *Thermus aquaticus*, termed Taq DNA polymerase (DNAPTaq), has a 5' exonuclease activity, but lacks a functional 3' exonucleolytic domain (Tindall and Kunkell, Biochem., 27:6008 [1988]). Derivatives of DNAPEc1 and DNAPTaq, respectively called the Klenow and Stoffel fragments, lack 5' exonuclease domains as a result of enzymatic or genetic manipulations (Brutlag et al., Biochem. Biophys. Res. Commun., 37:982 [1969]; Erlich et al., Science 252:1643 [1991]; Setlow and Kornberg, J. Biol. Chem.. 247:232 [1972]).

The 5' exonuclease activity of DNAPTaq was reported to require concurrent synthesis (Gelfand, *PCR Technology—Principles and Applications for DNA Amplification*, H. A. Erlich, [Ed.], Stockton Press, New York, p. 19 [1989]). Although mononucleotides predominate among the digestion products of the 5' exonucleases of DNAPTaq and DNAPEc1, short oligonucleotides ($\leq 12$ nucleotides) can also be observed implying that these so-called 5' exonucleases can function endonucleolytically (Setlow, supra; Holland et al., Proc. Natl. Acad. Sci. USA 88:7276 [1991]).

In WO 92/06200, Gelfand et al. show that the preferred substrate of the 5' exonuclease activity of the thermostable DNA polymerases is displaced single-stranded DNA. Hydrolysis of the phosphodiester bond occurs between the displaced single-stranded DNA and the double-helical DNA with the preferred exonuclease cleavage site being a phosphodiester bond in the double helical region. Thus, the 5' exonuclease activity usually associated with DNAPs is a structure-dependent single-stranded endonuclease and is more properly referred to as a 5' nuclease. Exonucleases are enzymes which cleave nucleotide molecules from the ends of the nucleic acid molecule. Endonucleases, on the other hand, are enzymes which cleave the nucleic acid molecule at internal rather than terminal sites. The nuclease activity associated with some thermostable DNA polymerases cleaves endonucleolytically but this cleavage requires contact with the 5' end of the molecule being cleaved. Therefore, these nucleases are referred to as 5' nucleases.

When a 5' nuclease activity is associated with a eubacterial Type A DNA polymerase, it is found in the one-third N-terminal region of the protein as an independent functional domain. The C-terminal two-thirds of the molecule constitute the polymerization domain which is responsible for the synthesis of DNA. Some Type A DNA polymerases also have a 3' exonuclease activity associated with the two-third C-terminal region of the molecule.

The 5' exonuclease activity and the polymerization activity of DNAPs have been separated by proteolytic cleavage or genetic manipulation of the polymerase molecule. To date thermostable DNAPs have been modified to remove or reduce the amount of 5' nuclease activity while leaving the polymerase activity intact.

The Klenow or large proteolytic cleavage fragment of DNAPEc1 contains the polymerase and 3' exonuclease activity but lacks the 5' nuclease activity. The Stoffel fragment of DNAPTaq (DNAPStf) lacks the 5' nuclease activity due to a genetic manipulation which deleted the N-terminal 289 amino acids of the polymerase molecule (Erlich et al., Science 252:1643 [1991]). WO 92/06200 describes a thermostable DNAP with an altered level of 5' to 3' exonuclease. U.S. Pat. No. 5,108,892 describes a *Thermus aquaticus* DNAP without a 5' to 3' exonuclease. However, the art of molecular biology lacks a thermostable DNA polymerase with a lessened amount of synthetic activity.

The present invention provides 5' nucleases derived from thermostable Type A DNA polymerases that retain 5' nuclease activity but have reduced or absent synthetic activity. The ability to uncouple the synthetic activity of the enzyme from the 5' nuclease activity proves that the 5' nuclease activity does not require concurrent DNA synthesis as was previously reported (Gelfand, *PCR Technology*, supra).

The description of the invention is divided into: I. Detection of Specific Nucleic Acid Sequences Using 5' Nucleases; II. Generation of 5' Nucleases Derived From Thermostable DNA Polymerases; III. Detection of Specific Nucleic Acid Sequences Using 5' Nucleases in an Invader-Directed Cleavage Assay; IV. A Comparison Of Invasive Cleavage And Primer-Directed Cleavage; V. Fractionation Of Specific Nucleic Acids By Selective Charge Reversal; VI. Invader™-Directed Cleavage Using Miniprobes And Mid-Range Probes; VII. Signal Enhancement By Tailing Of Reaction Products In The Invader™-Directed Cleavage Assay ; VIII. Improved Enzymes For Use In Invader™-Directed Cleavage Reactions; and IX. Improved Enzymes For Use in The CFLP® Method.

I. Detection Of Specific Nucleic Acid Sequences Using 5' Nucleases

The 5' nucleases of the invention form the basis of a novel detection assay for the identification of specific nucleic acid sequences. This detection system identifies the presence of specific nucleic acid sequences by requiring the annealing of two oligonucleotide probes to two portions of the target sequence. As used herein, the term "target sequence" or "target nucleic acid sequence" refers to a specific nucleic acid sequence within a polynucleotide sequence. such as genomic DNA or RNA, which is to be either detected or cleaved or both.

FIG. 1A provides a schematic of one embodiment of the detection method of the present invention. The target sequence is recognized by two distinct oligonucleotides in the triggering or trigger reaction. It is preferred that one of these oligonucleotides is provided on a solid support. The other can be provided free. In FIG. 1A the free oligonucleotide is indicated as a "primer" and the other oligonucleotide is shown attached to a bead designated as type 1. The target nucleic acid aligns the two oligonucleotides for specific cleavage of the 5' arm (of the oligonucleotide on bead 1) by the DNAPs of the present invention (not shown in FIG. 1A).

The site of cleavage (indicated by a large solid arrowhead) is controlled by the distance between the 3' end of the "primer" and the downstream fork of the oligonucleotide on bead 1. The latter is designed with an uncleavable region (indicated by the striping). In this manner neither oligonucleotide is subject to cleavage when misaligned or when unattached to target nucleic acid.

Successful cleavage releases a single copy of what is referred to as the alpha signal oligonucleotide. This oligonucleotide may contain a detectable moiety (e.g., fluorescein). On the other hand, it may be unlabelled.

In one embodiment of the detection method, two more oligonucleotides are provided on solid supports. The oligonucleotide shown in FIG. 1A on bead 2 has a region that is complementary to the alpha signal oligonucleotide (indicated as alpha prime) allowing for hybridization. This structure can be cleaved by the DNAPs of the present invention to release the beta signal oligonucleotide. The beta signal oligonucleotide can then hybridize to type 3 beads having an oligonucleotide with a complementary region (indicated as beta prime). Again, this structure can be cleaved by the DNAPs of the present invention to release a new alpha oligonucleotide.

At this point, the amplification has been linear. To increase the power of the method, it is desired that the alpha signal oligonucleotide hybridized to bead type 2 be liberated after release of the beta oligonucleotide so that it may go on to hybridize with other oligonucleotides on type 2 beads. Similarly, after release of an alpha oligonucleotide from type 3 beads, it is desired that the beta oligonucleotide be liberated.

The liberation of "captured" signal oligonucleotides can be achieved in a number of ways. First, it has been found that the DNAPs of the present invention have a true 5' exonuclease capable of "nibbling" the 5' end of the alpha (and beta) prime oligonucleotide (discussed below in more detail). Thus, under appropriate conditions, the hybridization is destabilized by nibbling of the DNAP. Second, the alpha—alpha prime (as well as the beta—beta prime) complex can be destabilized by heat (e.g., thermal cycling).

With the liberation of signal oligonucleotides by such techniques, each cleavage results in a doubling of the number of signal oligonucleotides. In this manner, detectable signal can quickly be achieved.

FIG. 1B provides a schematic of a second embodiment of the detection method of the present invention. Again, the target sequence is recognized by two distinct oligonucleotides in the triggering or trigger reaction and the target nucleic acid aligns the two oligonucleotides for specific cleavage of the 5' arm by the DNAPs of the present invention (not shown in FIG. 1B). The first oligonucleotide is completely complementary to a portion of the target sequence. The second oligonucleotide is partially complementary to the target sequence; the 3' end of the second oligonucleotide is fully complementary to the target sequence while the 5' end is non-complementary and forms a single-stranded arm. The non-complementary end of the second oligonucleotide may be a generic sequence which can be used with a set of standard hairpin structures (described below). The detection of different target sequences would require unique portions of two oligonucleotides: the entire first oligonucleotide and the 3' end of the second oligonucleotide. The 5' arm of the second oligonucleotide can be invariant or generic in sequence.

The annealing of the first and second oligonucleotides near one another along the target sequence forms a forked cleavage structure which is a substrate for the 5' nuclease of DNA polymerases. The approximate location of the cleavage site is again indicated by the large solid arrowhead in FIG. 1B.

The 5' nucleases of the invention are capable of cleaving this structure but are not capable of polymerizing the extension of the 3' end of the first oligonucleotide. The lack of polymerization activity is advantageous as extension of the first oligonucleotide results in displacement of the annealed region of the second oligonucleotide and results in moving the site of cleavage along the second oligonucleotide. If polymerization is allowed to occur to any significant amount, multiple lengths of cleavage product will be generated. A single cleavage product of uniform length is desirable as this cleavage product initiates the detection reaction.

The trigger reaction may be run under conditions that allow for thermocycling. Thermocycling of the reaction allows for a logarithmic increase in the amount of the trigger oligonucleotide released in the reaction.

The second part of the detection method allows the annealing of the fragment of the second oligonucleotide liberated by the cleavage of the first cleavage structure formed in the triggering reaction (called the third or trigger oligonucleotide) to a first hairpin structure. This first hairpin structure has a single-stranded 5' arm and a single-stranded 3' arm. The third oligonucleotide triggers the cleavage of this first hairpin structure by annealing to the 3' arm of the hairpin thereby forming a substrate for cleavage by the 5' nuclease of the present invention. The cleavage of this first hairpin structure generates two reaction products: 1) the cleaved 5' arm of the hairpin called the fourth oligonucleotide, and 2) the cleaved hairpin structure which now lacks the 5' arm and is smaller in size than the uncleaved hairpin. This cleaved first hairpin may be used as a detection molecule to indicate that cleavage directed by the trigger or third oligonucleotide occurred. Thus, this indicates that the first two oligonucleotides found and annealed to the target sequence thereby indicating the presence of the target sequence in the sample.

The detection products are amplified by having the fourth oligonucleotide anneal to a second hairpin structure. This hairpin structure has a 5' single-stranded arm and a 3' single-stranded arm. The fourth oligonucleotide generated by cleavage of the first hairpin structure anneals to the 3' arm of the second hairpin structure thereby creating a third cleavage structure recognized by the 5' nuclease. The cleavage of this second hairpin structure also generates two reaction products: 1) the cleaved 5' arm of the hairpin called the fifth oligonucleotide which is similar or identical in sequence to the third nucleotide, and 2) the cleaved second hairpin structure which now lacks the 5' arm and is smaller in size than the uncleaved hairpin. This cleaved second hairpin may be as a detection molecule and amplifies the signal generated by the cleavage of the first hairpin structure. Simultaneously with the annealing of the forth oligonucleotide, the third oligonucleotide is dissociated from the cleaved first hairpin molecule so that it is free to anneal to a new copy of the first hairpin structure. The disassociation of the oligonucleotides from the hairpin structures may be accomplished by heating or other means suitable to disrupt base-pairing interactions.

Further amplification of the detection signal is achieved by annealing the fifth oligonucleotide (similar or identical in sequence to the third oligonucleotide) to another molecule of the first hairpin structure. Cleavage is then performed and the oligonucleotide that is liberated then is annealed to another molecule of the second hairpin structure. Successive rounds of annealing and cleavage of the first and second hairpin structures, provided in excess, are performed to generate a sufficient amount of cleaved hairpin products to be detected. The temperature of the detection reaction is cycled just below and just above the annealing temperature for the oligonucleotides used to direct cleavage of the hairpin structures, generally about 55° C. to 70° C. The number of cleavages will double in each cycle until the amount of hairpin structures remaining is below the $K_m$ for the hairpin structures. This point is reached when the hairpin structures are substantially used up. When the detection reaction is to be used in a quantitative manner, the cycling reactions are stopped before the accumulation of the cleaved hairpin detection products reach a plateau.

Detection of the cleaved hairpin structures may be achieved in several ways. In one embodiment detection is achieved by separation on agarose or polyacrylamide gels followed by staining with ethidium bromide. In another embodiment, detection is achieved by separation of the cleaved and uncleaved hairpin structures on a gel followed by autoradiography when the hairpin structures are first labeled with a radioactive probe and separation on chromatography columns using HPLC or FPLC followed by detection of the differently sized fragments by absorption at $OD_{260}$. Other means of detection include detection of changes in fluorescence polarization when the single-stranded 5' arm is released by cleavage, the increase in fluorescence of an intercalating fluorescent indicator as the amount of primers annealed to 3' arms of the hairpin structures increases. The formation of increasing amounts of duplex DNA (between the primer and the 3' arm of the hairpin) occurs if successive rounds of cleavage occur.

The hairpin structures may be attached to a solid support, such as an agarose, styrene or magnetic bead, via the 3' end of the hairpin. A spacer molecule may be placed between the 3' end of the hairpin and the bead, if so desired. The advantage of attaching the hairpin structures to a solid support is that this prevents the hybridization of the two hairpin structures to one another over regions which are complementary. If the hairpin structures anneal to one another, this would reduce the amount of hairpins available for hybridization to the primers released during the cleavage reactions. If the hairpin structures are attached to a solid support, then additional methods of detection of the products of the cleavage reaction may be employed. These methods include, but are not limited to, the measurement of the released single-stranded 5' arm when the 5' arm contains a label at the 5' terminus. This label may be radioactive, fluorescent, biotinylated, etc. If the hairpin structure is not cleaved, the 5' label will remain attached to the solid support. If cleavage occurs, the 5' label will be released from the solid support.

The 3' end of the hairpin molecule may be blocked through the use of dideoxynucleotides. A 3' terminus containing a dideoxynucleotide is unavailable to participate in reactions with certain DNA modifying enzymes, such as terminal transferase. Cleavage of the hairpin having a 3' terminal dideoxynucleotide generates a new, unblocked 3' terminus at the site of cleavage. This new 3' end has a free hydroxyl group which can interact with terminal transferase thus providing another means of detecting the cleavage products.

The hairpin structures are designed so that their self-complementary regions are very short (generally in the range of 3–8 base pairs). Thus, the hairpin structures are not stable at the high temperatures at which this reaction is performed (generally in the range of 50–75° C.) unless the hairpin is stabilized by the presence of the annealed oligonucleotide on the 3' arm of the hairpin. This instability prevents the polymerase from cleaving the hairpin structure in the absence of an associated primer thereby preventing false positive results due to non-oligonucleotide directed cleavage.

As discussed above, the use of the 5' nucleases of the invention which have reduced polymerization activity is advantageous in this method of detecting specific nucleic acid sequences. Significant amounts of polymerization during the cleavage reaction would cause shifting of the site of cleavage in unpredictable ways resulting in the production of a series of cleaved hairpin structures of various sizes rather than a single easily quantifiable product. Additionally, the primers used in one round of cleavage could, if elongated, become unusable for the next cycle, by either forming an incorrect structure or by being too long to melt off under moderate temperature cycling conditions. In a pristine system (i.e., lacking the presence of dNTPs), one could use the unmodified polymerase, but the presence of nucleotides (dNTPs) can decrease the per cycle efficiency enough to give a false negative result. When a crude extract (genomic DNA preparations, crude cell lysates, etc.) is employed or where a sample of DNA from a PCR reaction, or any other sample that might be contaminated with dNTPs, the 5' nucleases of the present invention that were derived from thermostable polymerases are particularly useful.

II. Generation Of 5' Nucleases From Thermostable DNA Polymerases

The genes encoding Type A DNA polymerases share about 85% homology to each other on the DNA sequence level. Preferred examples of thermostable polymerases include those isolated from *Thermus aquaticus, Thermus flavus*, and *Thermus thermophilus*. However, other thermostable Type A polymerases which have 5' nuclease activity are also suitable. FIGS. 2 and 3 compare the nucleotide and amino acid sequences of the three above mentioned polymerases. In FIGS. 2 and 3, the consensus or majority sequence derived from a comparison of the nucleotide (FIG. 2) or amino acid (FIG. 3) sequence of the three thermostable DNA polymerases is shown on the top line. A dot appears in the sequences of each of these three polymerases whenever an amino acid residue in a given sequence is identical to that contained in the consensus amino acid sequence. Dashes are used to introduce gaps in order to maximize alignment between the displayed sequences. When no consensus nucleotide or amino acid is present at a given position, an "X" is placed in the consensus sequence. SEQ ID NOS:1–3 display the nucleotide sequences and SEQ ID NOS:4–6 display the amino acid sequences of the three wild-type polymerases. SEQ ID NO:1 corresponds to the nucleic acid sequence of the wild type *Thermus aquaticus* DNA polymerase gene isolated from the YT-1 strain (Lawyer et al., J. Biol. Chem., 264:6427 [1989]). SEQ ID NO:2 corresponds to the nucleic acid sequence of the wild type *Thermus flavus* DNA polymerase gene (Akhmetzjanov and Vakhitov, Nucl. Acids Res., 20:5839 [1992]). SEQ ID NO:3 corresponds to the nucleic acid sequence of the wild type *Thermus thermophilus* DNA polymerase gene (Gelfand et al., WO 91/09950 [1991]). SEQ ID NOS:7–8 depict the consensus nucleotide and amino acid sequences, respectively for the above three DNAPs (also shown on the top row in FIGS. 2 and 3).

The 5' nucleases of the invention derived from thermostable polymerases have reduced synthetic ability, but retain substantially the same 5' exonuclease activity as the native DNA polymerase. The term "substantially the same 5' nuclease activity" as used herein means that the 5' nuclease activity of the modified enzyme retains the ability to function as a structure-dependent single-stranded endonuclease but not necessarily at the same rate of cleavage as compared to the unmodified enzyme. Type A DNA polymerases may also be modified so as to produce an enzyme which has increases 5' nuclease activity while having a reduced level of synthetic activity. Modified enzymes having reduced synthetic activity and increased 5' nuclease activity are also envisioned by the present invention.

By the term "reduced synthetic activity" as used herein it is meant that the modified enzyme has less than the level of synthetic activity found in the unmodified or "native" enzyme. The modified enzyme may have no synthetic activity remaining or may have that level of synthetic activity that will not interfere with the use of the modified enzyme in the detection assay described below. The 5' nucleases of the present invention are advantageous in situations where the cleavage activity of the polymerase is desired, but the synthetic ability is not (such as in the detection assay of the invention).

As noted above, it is not intended that the invention be limited by the nature of the alteration necessary to render the polymerase synthesis deficient. The present invention contemplates a variety of methods, including but not limited to: 1) proteolysis; 2) recombinant constructs (including mutants); and 3) physical and/or chemical modification and/or inhibition.

1. Proteolysis

Thermostable DNA polymerases having a reduced level of synthetic activity are produced by physically cleaving the unmodified enzyme with proteolytic enzymes to produce fragments of the enzyme that are deficient in synthetic activity but retain 5' nuclease activity. Following proteolytic digestion, the resulting fragments are separated by standard chromatographic techniques and assayed for the ability to synthesize DNA and to act as a 5' nuclease. The assays to determine synthetic activity and 5' nuclease activity are described below.

2. Recombinant Constructs

The examples below describe a preferred method for creating a construct encoding a 5' nuclease derived from a thermostable DNA polymerasc. As the Type A DNA polymerases are similar in DNA sequence, the cloning strategies employed for the *Thermus aquaticus* and *T. flavus* polymerases are applicable to other thermostable Type A polymerases. In general, a thermostable DNA polymerase is cloned by isolating genomic DNA using molecular biological methods from a bacteria containing a thermostable Type A DNA polymerase. This genomic DNA is exposed to primers which are capable of amplifying the polymerase gene by PCR.

This amplified polymerase sequence is then subjected to standard deletion processes to delete the polymerase portion of the gene. Suitable deletion processes are described below in the examples.

The example below discusses the strategy used to determine which portions of the DNAPTaq polymerase domain could be removed without eliminating the 5' nuclease activity. Deletion of amino acids from the protein can be done either by deletion of the encoding genetic material, or by introduction of a translational stop codon by mutation or frame shift. In addition, proteolytic treatment of the protein molecule can be performed to remove segments of the protein.

In the examples below, specific alterations of the Taq gene were: a deletion between nucleotides 1601 and 2502 (the end of the coding region), a 4 nucleotide insertion at position 2043, and deletions between nucleotides 1614 and 1848 and between nucleotides 875 and 1778 (numbering is as in SEQ ID NO:1). These modified sequences are described below in the examples and at SEQ ID NOS:9–12.

Those skilled in the art understand that single base pair changes can be innocuous in terms of enzyme structure and function. Similarly, small additions and deletions can be present without substantially changing the exonuclease or polymerase function of these enzymes.

Other deletions are also suitable to create the 5' nucleases of the present invention. It is preferable that the deletion decrease the polymerase activity of the 5' nucleases to a level at which synthetic activity will not interfere with the use of the 5' nuclease in the detection assay of the invention. Most preferably, the synthetic ability is absent. Modified polymerases are tested for the presence of synthetic and 5' nuclease activity as in assays described below. Thoughtful consideration of these assays allows for the screening of candidate enzymes whose structure is heretofore as yet unknown. In other words, construct "X" can be evaluated according to the protocol described below to determine whether it is a member of the genus of 5' nucleases of the present invention as defined functionally, rather than structurally.

In the example below, the PCR product of the amplified *Thermus aquaticus* genomic DNA did not have the identical nucleotide structure of the native genomic DNA and did not have the same synthetic ability of the original clone. Base pair changes which result due to the infidelity of DNAPTaq during PCR amplification of a polymerase gene are also a method by which the synthetic ability of a polymerase gene may be inactivated. The examples below and FIGS. 4A and 5A indicate regions in the native *Thermus aquaticus* and *flavus* DNA polymerases likely to be important for synthetic ability. There are other base pair changes and substitutions that will likely also inactivate the polymerase.

It is not necessary, however, that one start out the process of producing a 5' nuclease from a DNA polymerase with such a mutated amplified product. This is the method by which the examples below were performed to generate the synthesis-deficient DNAPTaq mutants, but it is understood by those skilled in the art that a wild-type DNA polymerase sequence may be used as the starting material for the introduction of deletions, insertion and substitutions to produce a 5' nuclease. For example, to generate the synthesis-deficient DNAPTfl mutant, the primers listed in SEQ ID NOS:13–14 were used to amplify the wild type DNA polymerase gene from *Thermus flavus* strain AT-62. The amplified polymerase gene was then subjected to restriction enzyme digestion to delete a large portion of the domain encoding the synthetic activity.

The present invention contemplates that the nucleic acid construct of the present invention be capable of expression in a suitable host. Those in the art know methods for attaching various promoters and 3' sequences to a gene structure to achieve efficient expression. The examples below disclose two suitable vectors and six suitable vector constructs. Of course, there are other promoter/vector combinations that would be suitable. It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega Corporation, Madison, Wis.).

Once a suitable nucleic acid construct has been made, the 5' nuclease may be produced from the construct. The examples below and standard molecular biological teachings enable one to manipulate the construct by different suitable methods.

Once the 5' nuclease has been expressed, the polymerase is tested for both synthetic and nuclease activity as described below.

3. Physical And/Or Chemical Modification And/Or Inhibition

The synthetic activity of a thermostable DNA polymerase may be reduced by chemical and/or physical means. In one embodiment, the cleavage reaction catalyzed by the 5' nuclease activity of the polymerase is run under conditions which preferentially inhibit the synthetic activity of the polymerase. The level of synthetic activity need only be reduced to that level of activity which does not interfere with cleavage reactions requiring no significant synthetic activity.

As shown in the examples below, concentrations of $Mg^{++}$ greater than 5 mM inhibit the polymerization activity of the native DNAPTaq. The ability of the 5' nuclease to function under conditions where synthetic activity is inhibited is tested by running the assays for synthetic and 5' nuclease activity, described below, in the presence of a range of $Mg^{++}$ concentrations (5 to 10 mM). The effect of a given concentration of $Mg^{++}$ is determined by quantitation of the amount of synthesis and cleavage in the test reaction as compared to the standard reaction for each assay.

The inhibitory effect of other ions, polyamines, denaturants, such as urea, formamide, dimethylsulfoxide, glycerol and non-ionic detergents (Triton X-100 and Tween-20), nucleic acid binding chemicals such as, actinomycin D, ethidium bromide and psoralens, are tested by their addition to the standard reaction buffers for the synthesis and 5' nuclease assays. Those compounds having a preferential inhibitory effect on the synthetic activity of a thermostable poiymerase are then used to create reaction conditions under which 5' nuclease activity (cleavage) is retained while synthetic activity is reduced or eliminated.

Physical means may be used to preferentially inhibit the synthetic activity of a polymerase. For example, the synthetic activity of thermostable polymerases is destroyed by exposure of the polymerase to extreme heat (typically 96 to 100° C.) for extended periods of time (greater than or equal to 20 minutes). While these are minor differences with respect to the specific heat tolerance for each of the enzymes, these are readily determined. Polymerases are treated with heat for various periods of time and the effect of the heat treatment upon the synthetic and 5' nuclease activities is determined.

III. Detection Of Specific Nucleic Acid Sequences Using 5' Nucleases In An Invader-Directed Cleavage Assay The present invention provides means for forming a nucleic acid cleavage structure which is dependent upon the presence of a target nucleic acid and cleaving the nucleic acid cleavage structure so as to release distinctive cleavage products. 5' nuclease activity is used to cleave the target-dependent cleavage structure and the resulting cleavage products are indicative of the presence of specific target nucleic acid sequences in the sample.

The present invention further provides assays in which the target nucleic acid is reused or recycled during multiple rounds of hybridization with oligonucleotide probes and cleavage without the need to use temperature cycling (i.e., for periodic denaturation of target nucleic acid strands) or nucleic acid synthesis (i.e., for the displacement of target nucleic acid strands). Through the interaction of the cleavage means (e.g., a 5' nuclease) an upstream oligonucleotide, the cleavage means can be made to cleave a downstream oligonucleotide at an internal site in such a way that the resulting fragments of the downstream oligonucleotide dissociate from the target nucleic acid, thereby making that region of the target nucleic acid available for hybridization to another, uncleaved copy of the downstream oligonucleotide.

Figure 29:
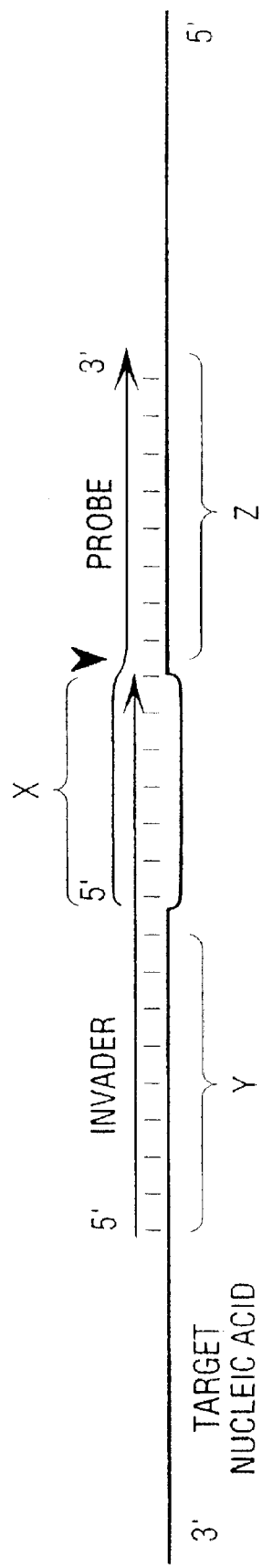
FIG. 29 provides a schematic drawing of a target nucleic acid with an invader oligonucleotide and a probe oligonucleotide annealed to the target.

As illustrated in FIG. 29, the methods of the present invention employ at least a pair of oligonucleotides that interact with a target nucleic acid to form a cleavage structure for a structure-specific nuclease. More specifically, the cleavage structure comprises i) a target nucleic acid that may be either single-stranded or double-stranded (when a double-stranded target nucleic acid is employed, it may be rendered single stranded, e.g., by heating); ii) a first oligonucleotide, termed the "probe," which defines a first region of the target nucleic acid sequence by being the complement of that region (regions X and Z of the target as shown in FIG. 29); iii) a second oligonucleotide, termed the "invader," the 5' part of which defines a second region of the same target nucleic acid sequence (regions Y and X in FIG. 29), adjacent to and downstream of the first target region (regions X and Z), and the second part of which overlaps into the region defined by the first oligonucleotide (region X depicts the region of overlap). The resulting structure is diagrammed in FIG. 29.

While not limiting the invention or the instant discussion to any particular mechanism of action, the diagram in FIG. 29 represents the effect on the site of cleavage caused by this type of arrangement of a pair of oligonucleotides. The design of such a pair of oligonucleotides is described below in detail. In FIG. 29, the 3' ends of the nucleic acids (i.e., the target and the oligonucleotides) are indicated by the use of the arrowheads on the ends of the lines depicting the strands of the nucleic acids (and where space permits, these ends are also labeled "3'"). It is readily appreciated that the two oligonucleotides (the invader and the probe) are arranged in a parallel orientation relative to one another, while the target nucleic acid strand is arranged in an anti-parallel orientation relative to the two oligonucleotides. Further it is clear that the invader oligonucleotide is located upstream of the probe oligonucleotide and that with respect to the target nucleic acid strand, region Z is upstream of region X and region X is upstream of region Y (that is region Y is downstream of region X and region X is downstream of region Z). Regions of complementarity between the opposing strands are indicated by the short vertical lines. While not intended to indicate the precise location of the site(s) of cleavage, the area to which the site of cleavage within the probe oligonucleotide is shifted by the presence of the invader oligonucleotide is indicated by the solid vertical arrowhead. An alternative representation of the target/invader/probe cleavage structure is shown in FIG. 32c. Neither diagram (i.e., FIG. 29 or FIG. 32c) is intended to represent the actual mechanism of action or physical arrangement of the cleavage structure and further it is not intended that the method of the present invention be limited to any particular mechanism of action.

It can be considered that the binding of these oligonucleotides divides the target nucleic acid into three distinct regions: one region that has complementarity to only the probe (shown as "Z"); one region that has complementarity only to the invader (shown as "Y"); and one region that has complementarity to both oligonucleotides (shown as "X").

Design of these oligonucleotides (i.e., the invader and the probe) is accomplished using practices which are standard in the art. For example, sequences that have self complementarity, such that the resulting oligonucleotides would either fold upon themselves, or hybridize to each other at the expense of binding to the target nucleic acid, are generally avoided.

One consideration in choosing a length for these oligonucleotides is the complexity of the sample containing the target nucleic acid. For example, the human genome is approximately $3 \times 10^9$ basepairs in length. Any 10 nucleotide sequence will appear with a frequency of $1:4^{10}$, or 1:1048,576 in a random string of nucleotides, which would be approximately 2,861 times in 3 billion basepairs. Clearly an oligonucleotide of this length would have a poor chance of binding uniquely to a 10 nucleotide region within a target having a sequence the size of the human genome. If the target sequence were within a 3 kb plasmid, however, such an oligonucleotide might have a very reasonable chance of binding uniquely. By this same calculation it can be seen that an oligonucleotide of 16 nucleotides (i.e., a 16-mer) is the minimum length of a sequence which is mathematically likely to appear once in $3 \times 10^9$ basepairs.

A second consideration in choosing oligonucleotide length is the temperature range in which the oligonucleotides will be expected to function. A 16-mer of average base content (50% G-C basepairs) will have a calculated $T_m$ (the temperature at which 50% of the sequence is dissociated) of about 41° C., depending on, among other things, the concentration of the oligonucleotide and its target, the salt content of the reaction and the precise order of the nucleotides. As a practical matter, longer oligonucleotides are usually chosen to enhance the specificity of hybridization. Oligonucleotides 20 to 25 nucleotides in length are often used as they are highly likely to be specific if used in reactions conducted at temperatures which are near their $T_m$s (within about 5° of the $T_m$). In addition, with calculated $T_m$s in the range of 50° to 70° C., such oligonucleotides (i.e., 20 to 25-mers) are appropriately used in reactions catalyzed by thermostable enzymes, which often display optimal activity near this temperature range.

The maximum length of the oligonucleotide chosen is also based on the desired specificity. One must avoid choosing sequences that are so long that they are either at a high risk of binding stably to partial complements, or that they cannot easily be dislodged when desired (e.g., failure to disassociate from the target once cleavage has occurred).

The first step of design and selection of the oligonucleotides for the invader-directed cleavage is in accordance with these sample general principles. Considered as sequence-specific probes individually, each oligonucleotide may be selected according to the guidelines listed above. That is to say, each oligonucleotide will generally be long enough to be reasonably expected to hybridize only to the intended target sequence within a complex sample, usually in the 20 to 40 nucleotide range. Alternatively, because the invader-directed cleavage assay depends upon the concerted action of these oligonucleotides, the composite length of the 2 oligonucleotides which span/bind to the X, Y, Z regions may be selected to fall within this range, with each of the individual oligonucleotides being in approximately the 13 to 17 nucleotide range. Such a design might be employed if a non-thermostable cleavage means were employed in the reaction, requiring the reactions to be conducted at a lower temperature than that used when thermostable cleavage means are employed. In some instances, it may be desirable to have these oligonucleotides bind multiple times within a target nucleic acid (e.g., which bind to multiple variants or multiple similar sequences within a target). It is not intended that the method of the present invention be limited to any particular size of the probe or invader oligonucleotide.

The second step of designing an oligonucleotide pair for this assay is to choose the degree to which the upstream "invader" oligonucleotide sequence will overlap into the downstream "probe" oligonucleotide sequence, and consequently, the sizes into which the probe will be cleaved. A key feature of this assay is that the probe oligonucleotide can be made to "turn over," that is to say cleaved probe can be made to depart to allow the binding and cleavage of other copies of the probe molecule, without the requirements of thermal denaturation or displacement by polymerization. While in one embodiment of this assay probe turnover may be facilitated by an exonucleolytic digestion by the cleavage agent, it is central to the present invention that the turnover does not require this exonucleolytic activity.

1. Choosing The Amount Of Overlap (Length Of The X Region)

One way of accomplishing such turnover can be envisioned by considering the diagram in FIG. 29. It can be seen that the $T_m$ of each oligonucleotide will be a function of the full length of that oligonucleotide: i.e., the $T_m$ of the invader=Tm(Y+X), and the Tm of the probe=$Tm_{(X+Y)}$ for the probe. When the probe is cleaved the X region is released, leaving the Z section. If the Tm of Z is less than the reaction temperature, and the reaction temperature is less than the Tm$_{(X+Z)}$, then cleavage of the probe will lead to the departure of Z, thus allowing a new (X+Z) to hybridize. It can be seen from this example that the X region must be sufficiently long that the release of X will drop the Tm of the remaining probe section below the reaction temperature: a G-C rich X section may be much shorter than an A-T rich X section and still accomplish this stability shift.

2. Designing Oligonucleotides Which Interact With The Y And Z Regions

If the binding of the invader oligonucleotide to the target is more stable than the binding of the probe (e.g., if it is long, or is rich in G-C basepairs in the Y region), then the copy of X associated with the invader may be favored in the competition for binding to the X region of the target, and the probe may consequently hybridize inefficiently, and the assay may give low signal. Alternatively, if the probe binding is particularly strong in the Z region, the invader will still cause internal cleavage, because this is mediated by the enzyme, but portion of the probe oligonucleotide bound to the Z region may not dissociate at the reaction temperature, turnover may be poor, and the assay may again give low signal.

It is clearly beneficial for the portions of the oligonucleotide which interact with the Y and Z regions so be similar in stability, i.e., they must have similar melting temperatures. This is not to say that these regions must be the same length. As noted above, in addition to length, the melting temperature will also be affected by the base content and the specific sequence of those bases. The specific stability designed into the invader and probe sequences will depend on the temperature at which one desires to perform the reaction.

This discussion is intended to illustrate that (within the basic guidelines for oligonucleotide specificity discussed above) it is the balance achieved between the stabilities of the probe and invader sequences and their X and Y component sequences, rather than the absolute values of these stabilities, that is the chief consideration in the selection of the probe and invader sequences.

3. Design Of The Reaction Conditions

Target nucleic acids that may be analyzed using the methods of the present invention which employ a 5' nuclease as the cleavage means include many types of both RNA and DNA. Such nucleic acids may be obtained using standard molecular biological techniques. For example, nucleic acids (RNA or DNA) may be isolated from a tissue sample (e.g., a biopsy specimen), tissue culture cells, samples containing bacteria and/or viruses (including cultures of bacteria and/or viruses), etc. The target nucleic acid may also be transcribed in vitro from a DNA template or may be chemically synthesized or generated in a PCR. Furthermore, nucleic acids may be isolated from an organism, either as genomic material or as a plasmid or similar extrachromosomal DNA, or they may be a fragment of such material generated by treatment with a restriction endonuclease or other cleavage agents or it may be synthetic.

Assembly of the target, probe, and invader nucleic acids into the cleavage reaction of the present invention uses principles commonly used in the design of oligonucleotide base enzymatic assays, such as dideoxynucleotide sequencing and polymerase chain reaction (PCR). As is done in these assays, the oligonucleotides are provided in sufficient excess that the rate of hybridization to the target nucleic acid is very rapid. These assays are commonly performed with 50 fmoles to 2 pmoles of each oligonucleotide per μl of reaction mixture. In the Examples described herein, amounts of oligonucleotides ranging from 250 fmoles to 5 pmoles per μl of reaction volume were used. These values were chosen for the purpose of ease in demonstration and are not intended to limit the performance of the present invention to these concentrations. Other (e.g., lower) oligonucleotide concentrations commonly used in other molecular biological reactions are also contemplated.

It is desirable that an invader oligonucleotide be immediately available to direct the cleavage of each probe oligonucleotide that hybridizes to a target nucleic acid. For this reason, in the Examples described herein, the invader oligonucleotide is provided in excess over the probe oligonucleotide; often this excess is 10-fold. While this is an effective ratio, it is not intended that the practice of the present invention be limited to any particular ratio of invader-to-probe (a ratio of 2- to 100-fold is contemplated).

Buffer conditions must be chosen that will be compatible with both the oligonucleotide/target hybridization and with the activity of the cleavage agent. The optimal buffer conditions for nucleic acid modification enzymes, and particularly DNA modification enzymes, generally included enough mono- and di-valent salts to allow association of nucleic acid strands by base-pairing. If the method of the present invention is performed using an enzymatic cleavage agent other than those specifically described here, the reactions may generally be performed in any such buffer reported to be optimal for the nuclease function of the cleavage agent. In general, to test the utility of any cleavage agent in this method, test reactions are performed wherein the cleavage agent of interest is tested in the MOPS/MnCl$_2$/KCl buffer or Mg-containing buffers described herein and in whatever buffer has been reported to be suitable for use with that agent, in a manufacturer's data sheet, a journal article, or in personal communication.

The products of the invader-directed cleavage reaction are fragments generated by structure-specific cleavage of the input oligonucleotides. The resulting cleaved and/or uncleaved oligonucleotides may be analyzed and resolved by a number of methods including electrophoresis (on a variety of supports including acrylamide or agarose gels, paper, etc.), chromatography, fluorescence polarization, mass spectrometry and chip hybridization. The invention is illustrated using electrophoretic separation for the analysis of the products of the cleavage reactions. However, it is noted that the resolution of the cleavage products is not limited to electrophoresis. Electrophoresis is chosen to illustrate the method of the invention because electrophoresis is widely practiced in the art and is easily accessible to the average practitioner.

The probe and invader oligonucleotides may contain a label to aid in their detection following the cleavage reaction. The label may be a radioisotope (e.g., a $^{32}$P or $^{35}$S-labelled nucleotide) placed at either the 5' or 3' end of the oligonucleotide or alternatively, the label may be distributed throughout the oligonucleotide (i.e., a uniformly labeled oligonucleotide). The label may be a nonisotopic detectable moiety, such as a fluorophore, which can be detected directly, or a reactive group which permits specific recognition by a secondary agent. For example, biotinylated oligonucleotides may be detected by probing with a streptavidin molecule which is coupled to an indicator (e.g., alkaline phosphatase or a fluorophore) or a hapten such as dioxigenin may be detected using a specific antibody coupled to a similar indicator.

4. Optimization Of Reaction Conditions

The invader-directed cleavage reaction is useful to detect the presence of specific nucleic acids. In addition to the considerations listed above for the selection and design of the invader and probe oligonucleotides, the conditions under which the reaction is to be performed may be optimized for detection of a specific target sequence.

One objective in optimizing the invader-directed cleavage assay is to allow specific detection of the fewest copies of a target nucleic acid. To achieve this end, it is desirable that the combined elements of the reaction interact with the maximum efficiency, so that the rate of the reaction (e.g., the number of cleavage events per minute) is maximized. Elements contributing to the overall efficiency of the reaction include the rate of hybridization, the rate of cleavage, and the efficiency of the release of the cleaved probe.

The rate of cleavage will be a function of the cleavage means chosen, and may be made optimal according to the manufacturer's instructions when using commercial preparations of enzymes or as described in the examples herein. The other elements (rate of hybridization, efficiency of release) depend upon the execution of the reaction, and optimization of these elements is discussed below.

Three elements of the cleavage reaction that significantly affect the rate of nucleic acid hybridization are the concentration of the nucleic acids, the temperature at which the cleavage reaction is performed and the concentration of salts and/or other charge-shielding ions in the reaction solution.

The concentrations at which oligonucleotide probes are used in assays of this type are well known in the art, and are discussed above. One example of a common approach to optimizing an oligonucleotide concentration is to choose a starting amount of oligonucleotide for pilot tests; 0.01 to 2 $\mu$M is a concentration range used in many oligonucleotide-based assays. When initial cleavage reactions are performed, the following questions may be asked of the data: Is the reaction performed in the absence of the target nucleic acid substantially free of the cleavage product?; Is the site of cleavage specifically shifted in accordance with the design of the invader oligonucleotide?; Is the specific cleavage product easily detected in the presence of the uncleaved probe (or is the amount of uncut material overwhelming the chosen visualization method)?

A negative answer to any of these questions would suggest that the probe concentration is too high, and that a set of reactions using serial dilutions of the probe should be performed until the appropriate amount is identified. Once identified for a given target nucleic acid in a give sample type (e.g., purified genomic DNA, body fluid extract, lysed bacterial extract), it should not need to be re-optimized. The sample type is important because the complexity of the material present may influence the probe optimum.

Conversely, if the chosen initial probe concentration is too low, the reaction may be slow, due to inefficient hybridization. Tests with increasing quantities of the probe will identify the point at which the concentration exceeds the optimum. Since the hybridization will be facilitated by excess of probe, it is desirable, but not required, that the reaction be performed using probe concentrations just below this point.

The concentration of invader oligonucleotide can be chosen based on the design considerations discussed above. In a preferred embodiment, the invader oligonucleotide is in excess of the probe oligonucleotide. In a particularly preferred embodiment, the invader is approximately 10-fold more abundant than the probe.

Temperature is also an important factor in the hybridization of oligonucleotides. The range of temperature tested will depend in large part, on the design of the oligonucleotides, as discussed above. In a preferred embodiment, the reactions are performed at temperatures slightly below the $T_m$ of the least stable oligonucleotide in the reaction. Melting temperatures for the oligonucleotides and for their component regions (X, Y and Z, FIG. 29), can be estimated through the use of computer software or, for a more rough approximation, by assigning the value of 2° C. per A-T basepair, and 4° C. per G-C basepair, and taking the sum across an expanse of nucleic acid. The latter method may be used for oligonucleotides of approximately 10–30 nucleotides in length. Because even computer prediction of the $T_m$ of a nucleic acid is only an approximation, the reaction temperatures chosen for initial tests should bracket the calculated $T_m$. While optimizations are not limited to this, 5° C. increments are convenient test intervals in these optimization assays.

When temperatures are tested, the results can be analyzed for specificity (the first two of the questions listed above) in the same way as for the oligonucleotide concentration determinations. Non-specific cleavage (i.e., cleavage of the probe at many or all positions along its length) would indicate non-specific interactions between the probe and the sample material, and would suggest that a higher temperature should be employed. Conversely, little or no cleavage would suggest that even the intended hybridization is being prevented, and would suggest the use of lower temperatures. By testing several temperatures, it is possible to identify an approximate temperature optimum, at which the rate of specific cleavage of the probe is highest. If the oligonucleotides have been designed as described above, the $T_m$ of the Z-region of the probe oligonucleotide should be below this temperature, so that turnover is assured.

A third determinant of hybridization efficiency is the salt concentration of the reaction. In large part, the choice of solution conditions will depend on the requirements of the cleavage agent, and for reagents obtained commercially, the manufacturer's instructions are a resource for this information. When developing an assay utilizing any particular cleavage agent, the oligonucleotide and temperature optimizations described above should be performed in the buffer conditions best suited to that cleavage agent.

A "no enzyme" control allows the assessment of the stability of the labeled oligonucleotides under particular reaction conditions, or in the presence of the sample to be tested (i.e., in assessing the sample for contaminating nucleases). In this manner, the substrate and oligonucleotides are placed in a tube containing all reaction components, except the enzyme and treated the same as the enzyme-containing reactions. Other controls may also be included. For example, a reaction with all of the components except the target nucleic acid will serve to confirm the dependence of the cleavage on the presence of the target sequence.

5. Probing For Multiple Alleles

The invader-directed cleavage reaction is also useful in the detection and quantification of individual variants or alleles in a mixed sample population. By way of example, such a need exists in the analysis of tumor material for mutations in genes associated with cancers. Biopsy material from a tumor can have a significant complement of normal cells, so it is desirable to detect mutations even when present in fewer than 5% of the copies of the target nucleic acid in a sample. In this case, it is also desirable to measure what fraction of the population carries the mutation. Similar analyses may also be done to examine allelic variation in other gene systems, and it is not intended that the method of the present invention by limited to the analysis of tumors.

As demonstrated below, reactions can be performed under conditions that prevent the cleavage of probes bearing even a single-nucleotide difference mismatch within the region of the target nucleic acid termed "Z" in FIG. 29, but that permit cleavage of a similar probe that is completely complementary to the target in this region. Thus, the assay may be used to quantitate individual variants or alleles within a mixed sample.

The use of multiple, differently labeled probes in such an assay is also contemplated. To assess the representation of different variants or alleles in a sample, one would provide a mixture of probes such that each allele or variant to be detected would have a specific probe (i.e., perfectly matched to the Z region of the target sequence) with a unique label (e.g., no two variant probes with the same label would be used in a single reaction). These probes would be characterized in advance to ensure that under a single set of reaction conditions, they could be made to give the same rate of signal accumulation when mixed with their respective target nucleic acids. Assembly of a cleavage reaction comprising the mixed probe set, a corresponding invader oligonucleotide, the target nucleic acid sample, and the appropriate cleavage agent, along with performance of the cleavage reaction under conditions such that only the matched probes would cleave, would allow independent quantification of each of the species present, and would therefore indicate their relative representation in the target sample.

IV. A Comparison Of Invasive Cleavage And Primer-Directed Cleavage

As discussed herein, the terms "invasive" or "invader-directed" cleavage specifically denote the use of a first, upstream oligonucleotide, as defined below, to cause specific cleavage at a site within a second, downstream sequence. To effect such a direction of cleavage to a region within a duplex, it is required that the first and second oligonucleotides overlap in sequence. That is to say, a portion of the upstream oligonucleotide, termed the "invader", has significant homology to a portion of the downstream "probe" oligonucleotide, so that these regions would tend to basepair with the same complementary region of the target nucleic acid to be detected. While not limiting the present invention to any particular mechanism, the overlapping regions would be expected to alternate in their occupation of the shared hybridization site. When the probe oligonucleotide fully anneals to the target nucleic acid, and thus forces the 3' region of the invader to remain unpaired, the structure so formed is not a substrate for the 5' nucleases of the present invention. By contrast, when the inverse is true, the structure so formed is substrate for these enzymes, allowing cleavage and release of the portion of the probe oligonucleotide that is displaced by the invader oligonucleotide. The shifting of the cleavage site to a region the probe oligonucleotide that would otherwise be basepaired to the target sequence is one hallmark of the invasive cleavage assay (i.e., the invader-directed cleavage assay) of the present invention.

It is beneficial at this point to contrast the invasive cleavage as described above with two other forms of probe cleavage that may lead to internal cleavage of a probe oligonucleotide, but which do not comprise invasive cleavage. In the first case, a hybridized probe may be subject to duplex-dependent 5' to 3' exonuclease "nibbling," such that the oligonucleotide is shortened from the 5' end until it cannot remain bound to the target (see, e.g., Examples 6–8 and FIGS. 26–28). The site at which such nibbling stops can appear to be discrete, and, depending on the difference between the melting temperature of the full-length probe and the temperature of the reaction, this stopping point may be 1 or several nucleotides into the probe oligonucleotide sequence. Such "nibbling" is often indicated by the presence of a "ladder" of longer products ascending size up to that of the full length of the probe, but this is not always the case. While any one of the products of such a nibbling reaction may be made to match in size and cleavage site the products of an invasive cleavage reaction, the creation of these nibbling products would be highly dependent on the temperature of the reaction and the nature of the cleavage agent, but would be independent of the action of an upstream oligonucleotide, and thus could not be construed to involve invasive cleavage.

Figure 40A:
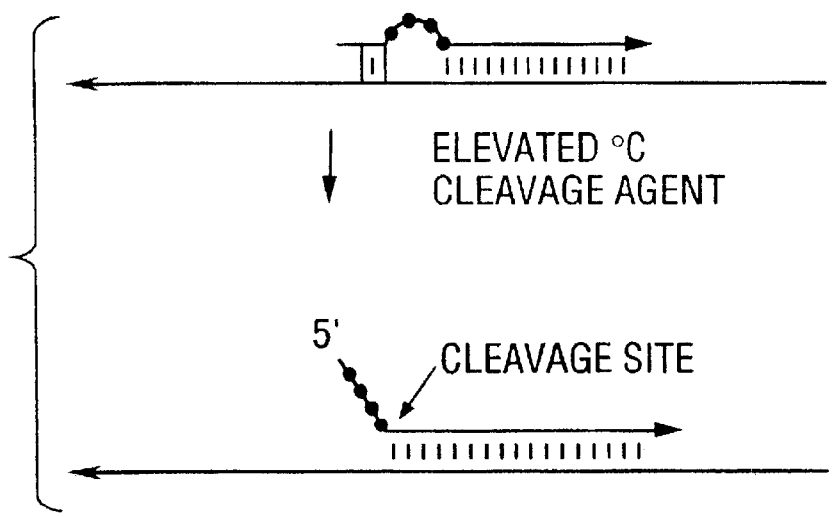
FIG. 40A provides a schematic showing the effect of elevated temperature upon the annealing and cleavage of a probe oligonucleotide along a target nucleic acid wherein the probe contains a region of noncomplementarity with the target.

A second cleavage structure that may be considered is one in which a probe oligonucleotide has several regions of complementarity with the target nucleic acid, interspersed with one or more regions or nucleotides of noncomplementarity. These noncomplementary regions may be thought of as "bubbles" within the nucleic acid duplex. As temperature is elevated, the regions of complementarity can be expected to "melt" in the order of their stability, lowest to highest. When a region of lower stability is near the end of a segment of duplex, and the next region of complementarity along the strand has a higher melting temperature, a temperature can be found that will cause the terminal region of duplex to melt first, opening the first bubble, and thereby creating a preferred substrate structure of the cleavage by the 5' nucleases of the present invention (FIG. 40a). The site of such cleavage would be expected to be on the 5' arm, within 2 nucleotides of the junction between the single and double-stranded regions (Lyamichev et al., supra. and U.S. Pat. No. 5,422,253)

Figure 6:
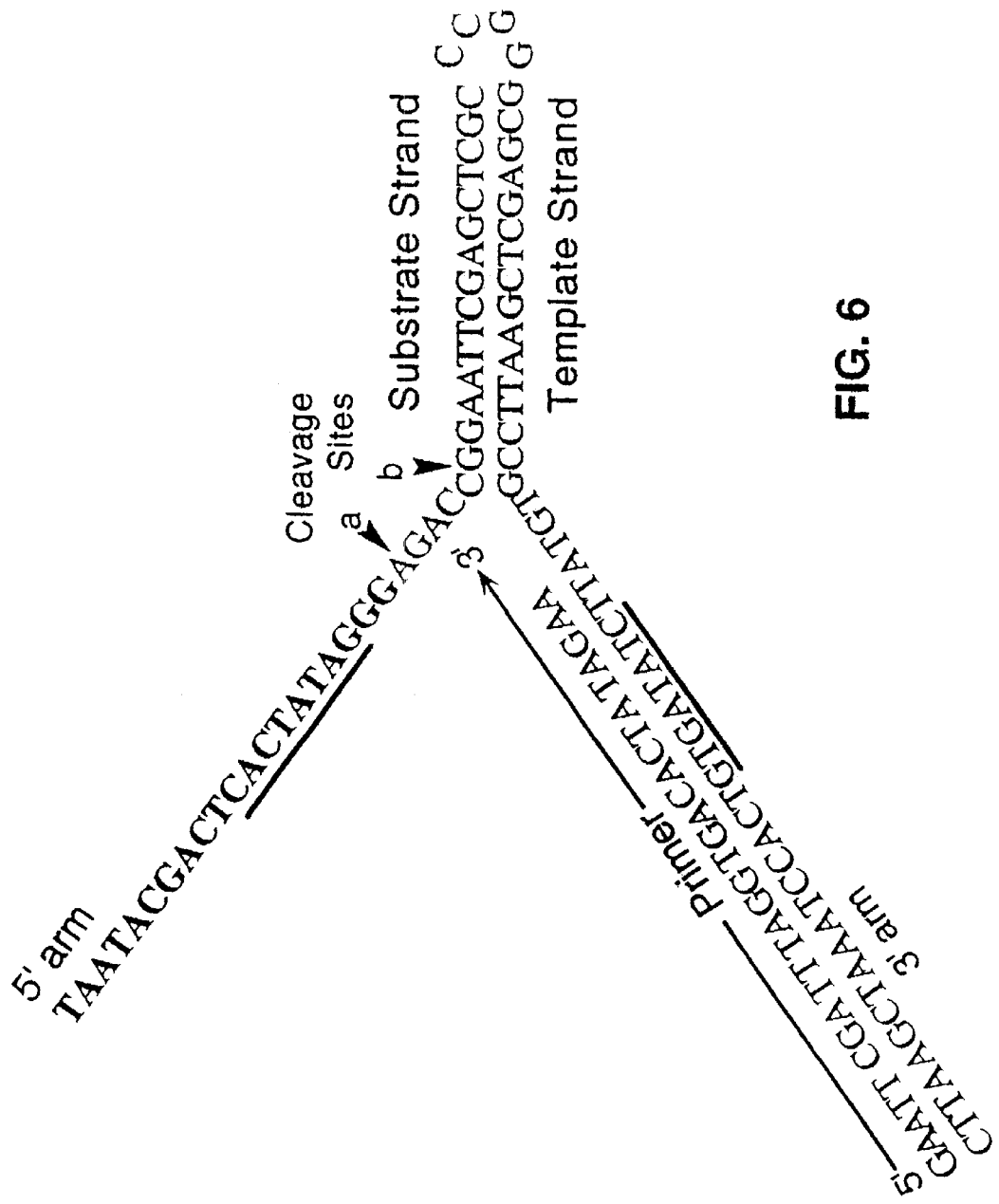
FIG. 6 depicts a structure which cannot be amplified using DNAPTaq.
Figure 40B:
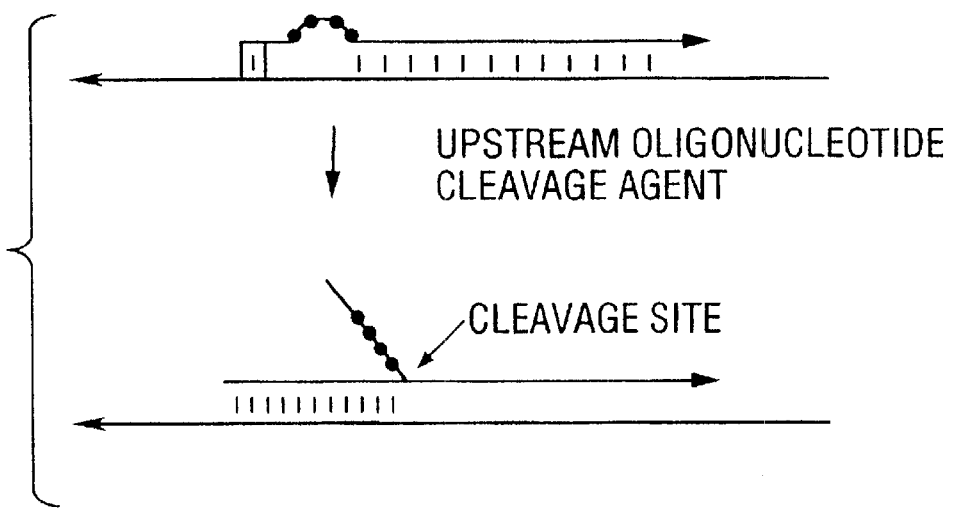
FIG. 40B provides a schematic showing the effect of adding an upstream oligonucleotide upon the annealing and cleavage of a probe oligonucleotide along a target nucleic acid wherein the probe contains a region of noncomplementarity with the target.

An additional oligonucleotide could be introduced to basepair along the target nucleic acid would have a similar effect of opening this bubble for subsequent cleavage of the unpaired 5' arm (FIG. 40b and FIG. 6). Note in this case, the 3' terminal nucleotides of the upstream oligonucleotide anneals along the target nucleic acid sequence in such a manner that the 3' end is located within the "bubble" region. Depending on the precise location of the 3' end of this oligonucleotide, the cleavage site may be along the newly unpaired 5' arm, or at the site expected for the thermally opened bubble structure as described above. In the former case the cleavage is not within a duplexed region, and is thus not invasive cleavage, while in the latter the oligonucleotide is merely an aide in inducing cleavage at a site that might otherwise be exposed through the use of temperature alone (i.e., in the absence of the additional oligonucleotide), and is thus not considered to be invasive cleavage.

In summary, any arrangement of oligonucleotides used for the cleavage-based detection of a target sequence can be analyzed to determine if the arrangement is an invasive cleavage structure as contemplated herein. An invasive cleavage structure supports cleavage of the probe in a region that, in the absence of an upstream oligonucleotide, would be expected to be basepaired to the target nucleic acid.

Ex. 26 below provides further guidance for the design and execution of a experiments which allow the determination of whether a given arrangement of a pair of upstream and downstream (i.e., the probe) oligonucleotides when annealed along a target nucleic acid would form an invasive cleavage structure.

V. Fractionation Of Specific Nucleic Acids By Selective Charge Reversal

Some nucleic acid-based detection assays involve the elongation and/or shortening of oligonucleotide probes. For example, as described herein, the primer-directed, primer-independent, and invader-directed cleavage assays, as well as the "nibbling" assay all involve the cleavage (i.e., shortening) of oligonucleotides as a means for detecting the presence of a target nucleic sequence. Examples of other detection assays which involve the shortening of an oligonucleotide probe include the "TaqMan" or nick-translation PCR assay described in U.S. Pat. No. 5,210,015 to Gelfand et al. (the disclosure of which is herein incorporated by reference), the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), and the cycling probe assay described in U.S. Pat. Nos. 4,876,187 and 5,011,769 to Duck et al. (the disclosures of which are herein incorporated by reference). Examples of detection assays which involve the elongation of an oligonucleotide probe (or primer) include the polymerase chain reaction (PCR) described in U.S. Pat. Nos. 4,683,195 and 4,683,202 to Mullis and Mullis et al. (the disclosures of which are herein incorporated by reference) and the ligase chain reaction (LCR) described in U.S. Pat. Nos. 5,427,930 and 5,494,810 to Birkenmeyer et al. and Barany et al. (the disclosures of which are herein incorporated by reference). The above examples are intended to be illustrative of nucleic acid-based detection assays that involve the elongation and/or shortening of oligonucleotide probes and do not provide an exhaustive list.

Typically, nucleic acid-based detection assays that involve the elongation and/or shortening of oligonucleotide probes require post-reaction analysis to detect the products of the reaction. It is common that, the specific reaction product(s) must be separated from the other reaction components, including the input or unreacted oligonucleotide probe. One detection technique involves the electrophoretic separation of the reacted and unreacted oligonucleotide probe. When the assay involves the cleavage or shortening of the probe, the unreacted product will be longer than the reacted or cleaved product. When the assay involves the elongation of the probe (or primer), the reaction products will be greater in length than the input. Gel-based electrophoresis of a sample containing nucleic acid molecules of different lengths separates these fragments primarily on the basis of size. This is due to the fact that in solutions having a neutral or alkaline pH, nucleic acids having widely different sizes (i.e., molecular weights) possess very similar charge-to-mass ratios and do not separate (Andrews, *Electrophoresis,* 2nd Edition, Oxford University Press [1986], pp. 153–154). The gel matrix acts as a molecular sieve and allows nucleic acids to be separated on the basis of size and shape (e.g., linear, relaxed circular or covalently closed supercoiled circles).

Unmodified nucleic acids have a net negative charge due to the presence of negatively charged phosphate groups contained within the sugar-phosphate backbone of the nucleic acid. Typically, the sample is applied to gel near the negative pole and the nucleic acid fragments migrate into the gel toward the positive pole with the smallest fragments moving fastest through the gel.

The present invention provides a novel means for fractionating nucleic acid fragments on the basis of charge. This novel separation technique is related to the observation that positively charged adducts can affect the electrophoretic behavior of small oligonucleotides because the charge of the adduct is significant relative to charge of the whole complex. In addition, to the use of positively charged adducts (e.g., Cy3 and Cy5 amidite fluorescent dyes, the positively charged heterodimeric DNA-binding dyes shown in FIG. 66, etc.), the oligonucleotide may contain amino acids (particularly useful amino acids are the charged amino acids: lysine, arginine, asparate, glutamate), modified bases, such as amino-modified bases, and/or a phosphonate backbone (at all or a subset of the positions). In addition as discussed further below, a neutral dye or detection moiety (e.g., biotin, streptavidin, etc.) may be employed in place of a positively charged adduct in conjunction with the use of amino-modified bases and/or a complete or partial phosphonate backbone.

This observed effect is of particular utility in assays based on the cleavage of DNA molecules. Using the assays described herein as an example, when an oligonucleotide is shortened through the action of a Cleavase® enzyme or other cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis; Ex. 24 provides examples of devices suitable for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer.

An important benefit of this type of readout is the absolute nature of the partition of products from substrates, i.e., the separation is virtually 100%. This means that an abundance of uncleaved probe can be supplied to drive the hybridization step of the probe-based assay, yet the unconsumed (i.e., unreacted) probe can, in essence, be subtracted from the result to reduce background by virtue of the fact that the unreacted probe will not migrate to the same pole as the specific reaction product.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which lack a 3' phosphate, and the products of thermal degradation, which retain a 3' phosphate (and thus two additional negative charges). Examples 23 and 24 demonstrate the ability to separate positively charged reaction products from a net negatively charged substrate oligonucleotide. As discussed in these examples, oligonucleotides may be transformed from net negative to net positively charged compounds. In Ex. 24, the positively charged dye, Cy3 was incorporated at the 5' end of a 22-mer (SEQ ID NO:61) which also contained two amino-substituted residues at the 5' end of the oligonucleotide; this oligonucleotide probe carries a net negative charge. After cleavage, which occurred 2 nucleotides into the probe, the following labeled oligonucleotide was released: 5'-Cy3-AminoT-AminoT-3' (as well as the remaining 20 nucleotides of SEQ ID NO:61). This short fragment bears a net positive charge while the remainder of the cleaved oligonucleotide and the unreacted or input oligonucleotide bear net negative charges.

Figure 56:
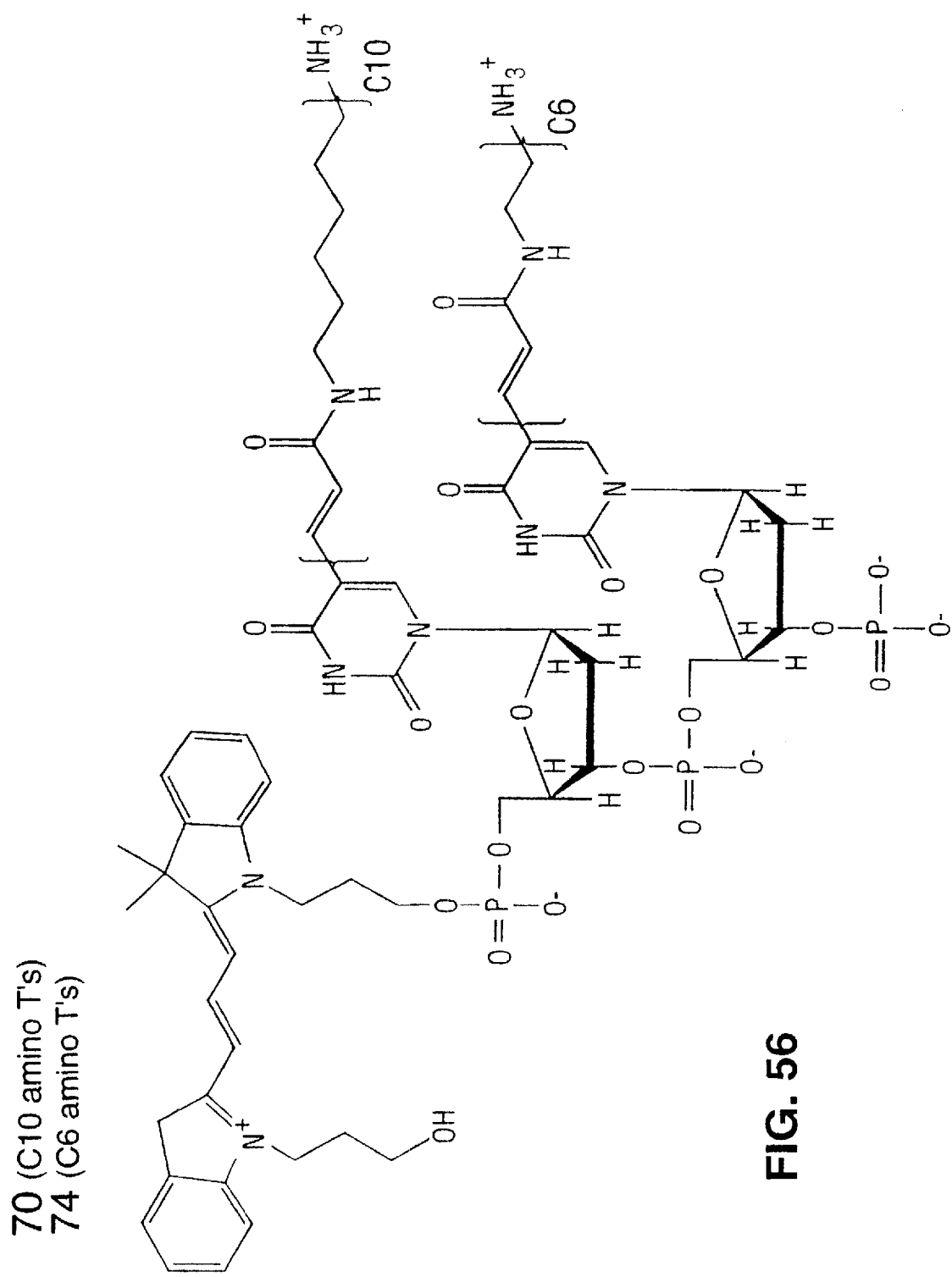
FIG. 56 depicts the structure of amino-modified oligonucleotides 70 and 74.
Figure 57:
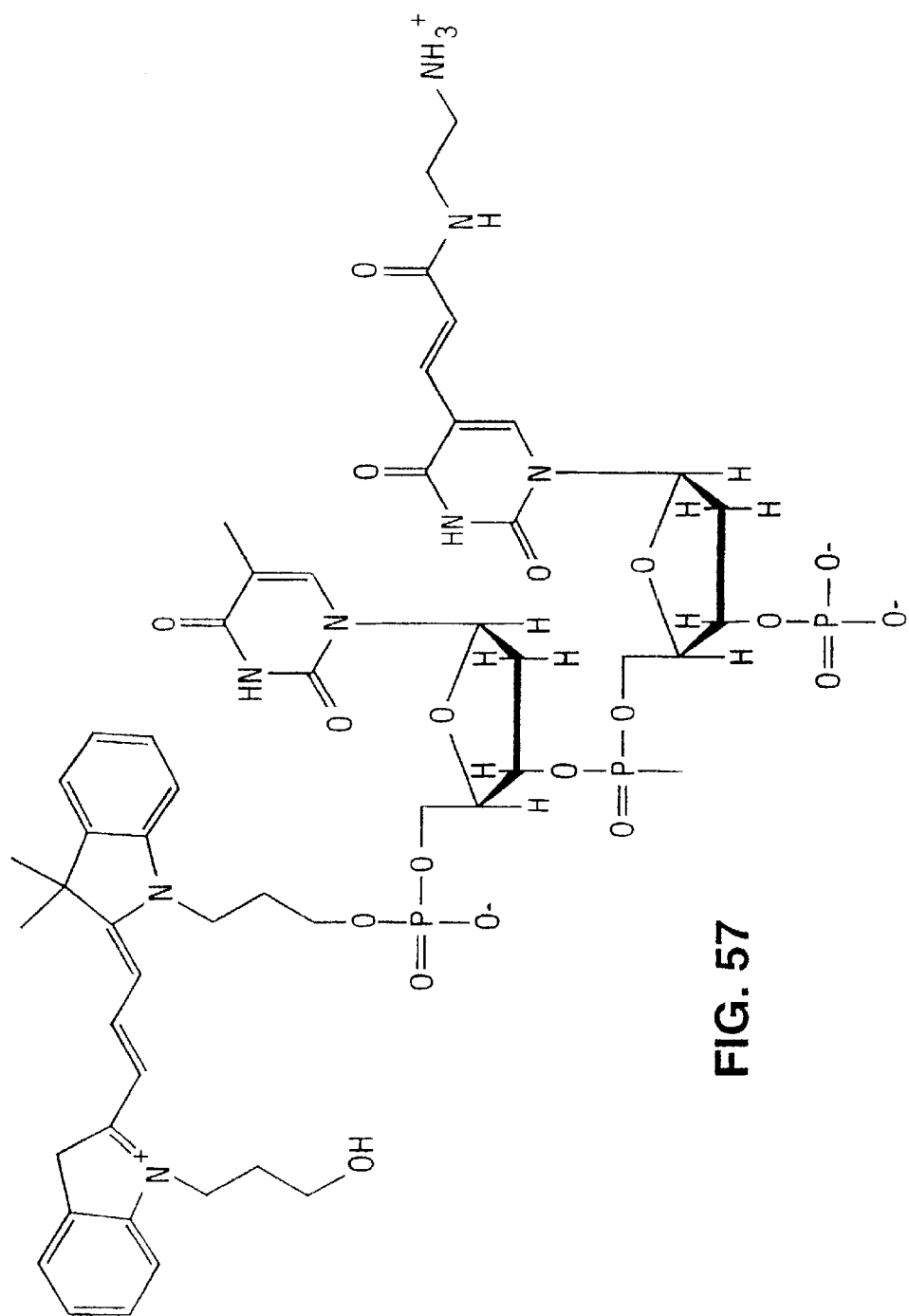
FIG. 57 depicts the structure of amino-modified oligonucleotide 75

The present invention contemplates embodiments wherein the specific reaction product produced by any cleavage of any oligonucleotide can be designed to carry a net positive charge while the unreacted probe is charge neutral or carries a net negative charge. The present invention also contemplates embodiments where the released product may be designed to carry a net negative charge while the input nucleic acid carries a net positive charge. Depending on the length of the released product to be detected, positively charged dyes may be incorporated at the one end of the probe and modified bases may be placed along the oligonucleotide such that upon cleavage, the released fragment containing the positively charged dye carries a net positive charge. Amino-modified bases may be used to balance the charge of the released fragment in cases where the presence of the positively charged adduct (e.g., dye) alone is not sufficient to impart a net positive charge on the released fragment. In addition, the phosphate backbone may be replaced with a phosphonate backbone at a level sufficient to impart a net positive charge (this is particularly useful when the sequence of the oligonucleotide is not amenable to the use of amino-substituted bases); FIGS. 56 and 57 show the structure of short oligonucleotides containing a phosphonate group on the second T residue). An oligonucleotide containing a fully phosphonate-substituted backbone would be charge neutral (absent the presence of modified charged residues bearing a charge or the presence of a charged adduct) due to the absence of the negatively charged phosphate groups. Phosphonate-containing nucleotides (e.g., methylphosphonate-containing nucleotides are readily available and can be incorporated at any position of an oligonucleotide during synthesis using techniques which are well known in the art.

In essence, the invention contemplates the use of charge-based separation to permit the separation of specific reaction products from the input oligonucleotides in nucleic acid-based detection assays. The foundation of this novel separation technique is the design and use of oligonucleotide probes (typically termed "primers" in the case of PCR) which are "charge balanced" so that upon either cleavage or elongation of the probe it becomes "charge unbalanced," and the specific reaction products may be separated from the input reactants on the basis of the net charge.

In the context of assays which involve the elongation of an oligonucleotide probe (i.e., a primer), such as is the case in PCR, the input primers are designed to carry a net positive charge. Elongation of the short oligonucleotide primer during polymerization will generate PCR products which now carry a net negative charge. The specific reaction products may then easily be separated and concentrated away from the input primers using the charge-based separation technique described herein (the electrodes will be reversed relative to the description in Ex. 24, as the product to be separated and concentrated after a PCR will carry a negative charge).

VI. Invader™-Directed Cleavage Using Miniprobes And Mid-Range Probes

As discussed in section III above, the Invader™-directed cleavage assay may be performed using invader and probe oligonucleotides which have a length of about 13–25 nucleotides (typically 20–25 nucleotides). It is also contemplated that the oligonucleotides that span the X, Y and Z regions (see FIG. 29), the invader and probe oligonucleotides, may themselves be composed of shorter oligonucleotide sequences that align along a target strand but that are not covalently linked. This is to say that there is a nick in the sugar-phosphate backbone of the composite oligonucleotide, but that there is no disruption in the progression of base-paired nucleotides in the resulting duplex. When short strands of nucleic acid align contiguously along a longer strand the hybridization of each is stabilized by the hybridization of the neighboring fragments because the basepairs can stack along the helix as though the backbone was in fact uninterrupted. This cooperativity of binding can give each segment a stability of interaction in excess of what would be expected for the segment hybridizing to the longer nucleic acid alone. One application of this observation has been to assemble primers for DNA sequencing, typically about 18 nucleotides long, from sets of three hexamer oligonucleotides that are designed to hybridize in this way (Kotler et al., Proc. Natl. Acad. Sci. USA 90:4241 [1993]). The resulting doubly-nicked primer can be extended enzymatically in reactions performed at temperatures that might be expected to disrupt the hybridization of hexamers, but not of 18-mers.

The use of composite or split oligonucleotides is applied with success in the Invader™-directed cleavage assay. The probe oligonucleotide may be split into two oligonucleotides which anneal in a contiguous and adjacent manner along a target oligonucleotide as diagrammed in FIG. 68. In this figure, the downstream oligonucleotide (analogous to the probe of FIG. 29) is assembled from two smaller pieces: a short segment of 6–10 nts (termed the "miniprobe"), that is to be cleaved in the course of the detection reaction, and an oligonucleotide that hybridizes immediately downstream of the miniprobe (termed the "stacker"), which serves to stabilize the hybridization of the probe. To form the cleavage structure, an upstream oligonucleotide (the "InvaderTM" oligonucleotide) is provided to direct the cleavage activity to the desired region of the miniprobe. Assembly of the probe from non-linked pieces of nucleic acid (i.e., the miniprobe and the stacker) allows regions of sequences to be changed without requiring the re-synthesis of the entire proven sequence, thus improving the cost and flexibility of the detection system. In addition, the use of unlinked composite oligonucleotides makes the system more stringent in its requirement of perfectly matched hybridization to achieve signal generation, allowing this to be used as a sensitive means of detecting mutations or changes in the target nucleic acid sequences.

Figure 67:
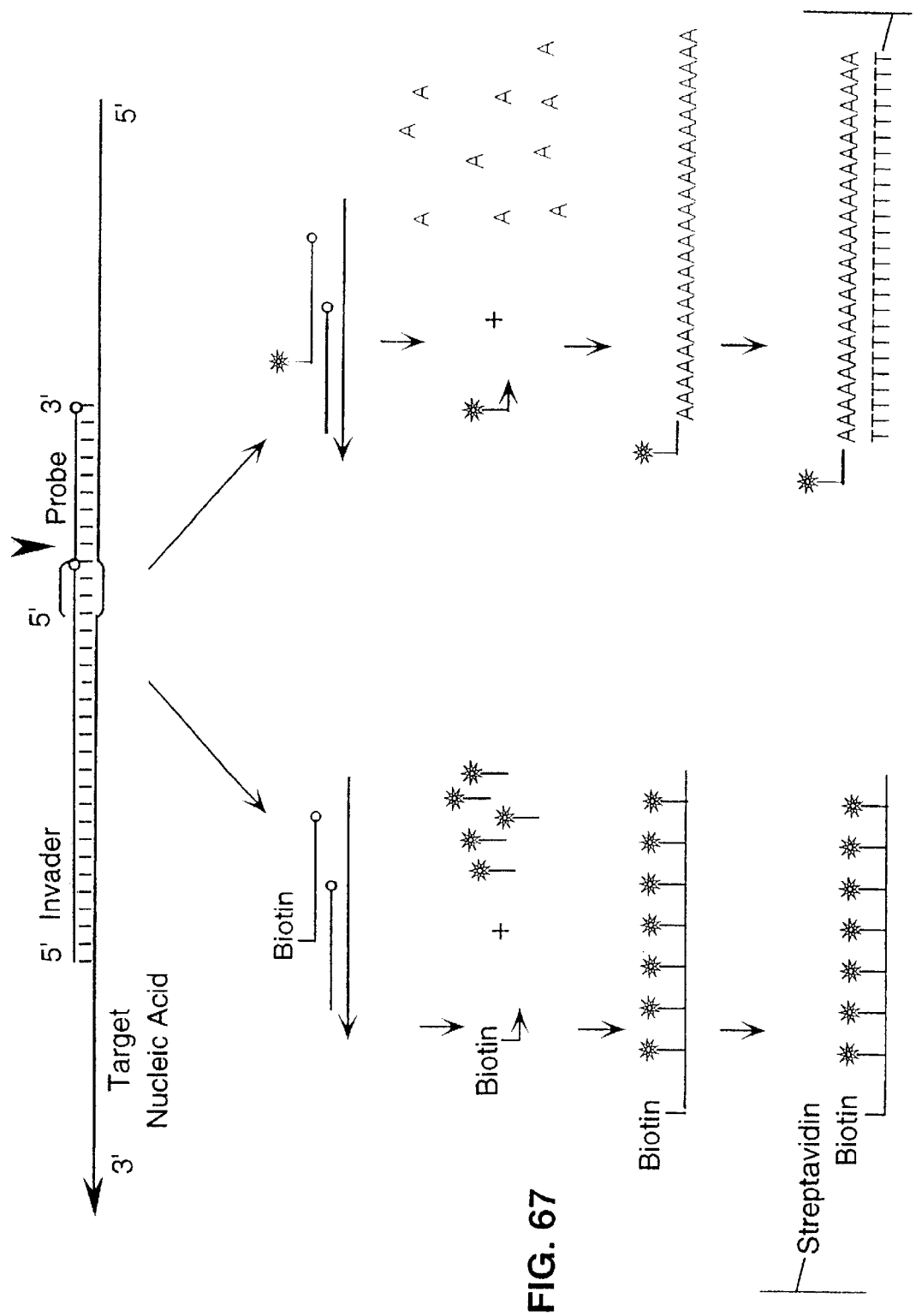
FIG. 67 is a schematic showing alternative methods for the tailing and detection of specific cleavage products in the context of the Invader™-directed cleavage assay.
Figure 68:
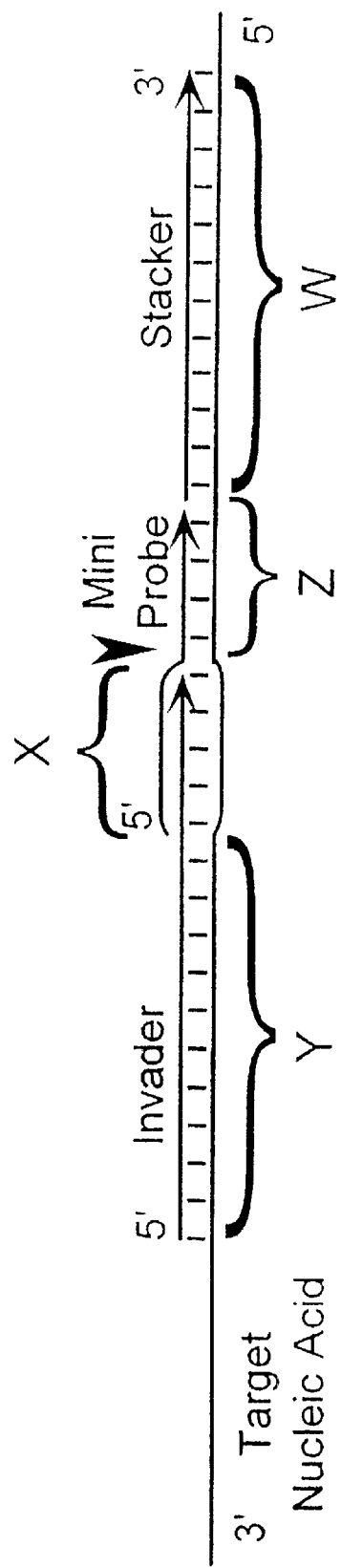
FIG. 68 provides a schematic drawing of a target nucleic acid with an Invader™ oligonucleotide, a miniprobe, and a stacker oligonucleotide annealed to the target.

As illustrated in FIG. 68, in one embodiment, the methods of the present invention employ at least three oligonucleotides that interact with a target nucleic acid to form a cleavage structure for a structure-specific nuclease. More specifically, the cleavage structure comprises i) a target nucleic acid that may be either single-stranded or double-stranded (when a double-stranded target nucleic acid is employed, it may be rendered single-stranded, e.g., by heating); ii) a first oligonucleotide, termed the "stacker," which defines a first region of the target nucleic acid sequence by being the complement of that region (region W of the target as shown in FIG. 67); iii) a second oligonucleotide, termed the "miniprobe," which defines a second region of the target nucleic acid sequence by being the complement of that region (regions X and Z of the target as shown in FIG. 67); iv) a third oligonucleotide, termed the "invader," the 5' part of which defines a third region of the same target nucleic acid sequence (regions Y and X in FIG. 67), adjacent to and downstream of the second target region (regions X and Z), and the second or 3' part of which overlaps into the region defined by the second oligonucleotide (region X depicts the region of overlap). The resulting structure is diagranmned in FIG. 68.

While not limiting the invention or the instant discussion to any particular mechanism of action, the diagram in FIG.

68 represents the effect on the site of cleavage caused by this type of arrangement of three oligonucleotides. The design of these three oligonucleotides is described below in detail. In FIG. 68, the 3' ends of the nucleic acids (i.e., the target and the oligonucleotides) are indicated by the use of the arrowheads on the ends of the lines depicting the strands of the nucleic acids (and where space permits, these ends are also labeled "3'"). It is readily appreciated that the three oligonucleotides (the invader, the miniprobe and the stacker) are arranged in a parallel orientation relative to one another, while the target nucleic acid strand is arranged in an antiparallel orientation relative to the three oligonucleotides. Further it is clear that the invader oligonucleotide is located upstream of the miniprobe oligonucleotide and that the miniprobe oligonucleotide is located upstream of the stacker oligonucleotide and that with respect to the target nucleic acid strand, region W is upstream of region Z, region Z is upstream of upstream of region X and region X is upstream of region Y (that is region Y is downstream of region X, region X is downstream of region Z and region Z is downstream of region W). Regions of complementarity between the opposing strands are indicated by the short vertical lines. While not intended to indicate the precise location of the site(s) of cleavage, the area to which the site of cleavage within the miniprobe oligonucleotide is shifted by the presence of the invader oligonucleotide is indicated by the solid vertical arrowhead. FIG. 68 is not intended to represent the actual mechanism of action or physical arrangement of the cleavage structure and further it is not intended that the method of the present invention be limited to any particular mechanism of action.

It can be considered that the binding of these oligonucleotides divides the target nucleic acid into four distinct regions: one region that has complementarity to only the stacker (shown as "W"); one region that has complementarity to only the miniprobe (shown as "Z"); one region that has complementarity only to the Invader™ oligonucleotide (shown as "Y"); and one region that has complementarity to both the Invader™ and miniprobe oligonucleotides (shown as "X").

In addition to the benefits cited above, the use of a composite design for the oligonucleotides which form the cleavage structure allows more latitude in the design of the reaction conditions for performing the Invader™-directed cleavage assay. When a longer probe (e.g., 16–25 nt), as described in section III above, is used for detection in reactions that are performed at temperatures below the $T_m$ of that probe, the cleavage of the probe may play a significant role in destabilizing the duplex of which it is a part, thus allowing turnover and reuse of the recognition site on the target nucleic acid. In contrast, with miniprobes, reaction temperatures that are at or above the $T_m$ of the probe mean that the probe molecules are hybridizing and releasing from the target quite rapidly even without cleavage of the probe. When an upstream Invader™ oligonucleotide and a cleavage means are provided the miniprobe will be specifically cleaved, but the cleavage will not be necessary to the turnover of the miniprobe. If a long probe (e.g., 16–25 nt) were to be used in this way the temperatures required to achieve this state would be quite high, around 65 to 70° C. for a 25-mer of average base composition. Requiring the use of such elevated temperatures limits the choice of cleavage agents to those that are very thermostable, and may contribute to background in the reactions, depending of the means of detection, through thermal degradation of the probe oligonucleotides. Thus, the shorter probes are preferable for use in this way.

The miniprobe of the present invention may vary in size depending on the desired application. In one embodiment, the probe may be relatively short compared to a standard probe (e.g., 16–25 nt), in the range of 6 to 10 nucleotides. When such a short probe is used reaction conditions can be chosen that prevent hybridization of the miniprobe in the absence of the stacker oligonucleotide. In this way a short probe can be made to assume the statistical specificity and selectivity of a longer sequence. In the event of a perturbation in the cooperative binding of the miniprobe and stacker nucleic acids, as might be caused by a mismatch within the short sequence (i.e., region "Z" which is the region of the miniprobe which does not overlap with the invader) or at the junction between the contiguous duplexes, this cooperativity can be lost, dramatically reducing the stability of the shorter oligonucleotide (ie., the miniprobe), and thus reducing the level of cleaved product in the assay of the present invention.

It is also contemplated that probes of intermediate size may be used. Such probes, in the 11 to 15 nucleotide range, may blend some of the features associated with the longer probes as originally described, these features including the ability to hybridize and be cleaved absent the help of a stacker oligonucleotide. At temperatures below the expected $T_m$ of such probes, the mechanisms of turnover may be as discussed above for probes in the 20 nt range, and be dependent on the removal of the sequence in the 'X' region for destabilization and cycling.

The mid-range probes may also be used at elevated temperatures, at or above their expected $T_m$, to allow melting rather than cleavage to promote probe turnover. In contrast to the longer probes described above, however, the temperatures required to allow the use of such a thermally driven turnover are much lower (about 40 to 60° C.), thus preserving both the cleavage means and the nucleic acids in the reaction from thermal degradation. In this way, the mid-range probes may perform in some instances like the miniprobes described above. In a further similarity to the miniprobes, the accumulation of cleavage signal from a mid-range probe may be helped under some reaction conditions by the presence of a stacker.

To summarize, a standard long probe usually does not benefit from the presence of a stacker oligonucleotide downstream (the exception being cases where such an oligonucleotide may also disrupt structures in the target nucleic acid that interfere with the probe binding), and it is usually used in conditions requiring several nucleotides to be removed to allow the oligonucleotide to release from the target efficiently.

The miniprobe is very short and performs optimally in the presence of a downstream stacker oligonucleotide. The miniprobes are well suited to reactions conditions that use the temperature of the reaction to drive rapid exchange of the probes on the target regardless of whether any bases have been cleaved. In reactions with sufficient amount of the cleavage means, the probes that do bind will be rapidly cleaved before they melt off. The mid-range or midiprobe combines features of these probes and can be used in reactions like those designed long probes, with longer regions of overlap ("X" regions) to drive probe turnover at lower temperature. In a preferred embodiment, the midrange probes are used at temperatures sufficiently high that the probes are hybridizing to the target and releasing rapidly regardless of cleavage. This is known to be the behavior of oligonucleotides at or near their melting temperature. This mode of turnover is more similar to that used with miniprobe/stacker combinations than with long probes. The mid-range probe may have enhanced performance in the presence of a stacker under some circumstances. For example, with a probe in the lower end of the mid-range, e.g., 11 nt, or one with exceptional A/T content, in a reaction performed well in excess of the $T_m$ of the probe (e.g., >10° C. above) the presence of a stacker would be likely to enhance the performance of the probe, while at a more moderate temperature the probe may be indifferent to a stacker.

The distinctions between the mini-, midi- (i.e., mid-range) and long probes are not contemplated to be inflexible and based only on length. The performance of any given probe may vary with its specific sequence, the choice of solution conditions, the choice of temperature and the selected cleavage means.

It is shown in Ex. 18 that the assemblage of oligonucleotides that comprises the cleavage structure of the present invention is sensitive to mismatches between the probe and the target. The site of the mismatch used in Ex. 18 provides one example and is not intended to be a limitation in location of a mismatch affecting cleavage. It is also contemplated that a mismatch between the Invader™ oligonucleotide and the target may be used to distinguish related target sequences. In the 3-oligonucleotide system, comprising an Invader™, a probe and a stacker oligonucleotide, it is contemplated that mismatches may be located within any of the regions of duplex formed between these oligonucleotides and the target sequence. In a preferred embodiment, a mismatch to be detected is located in the probe. In a particularly preferred embodiment, the mismatch is in the probe, at the basepair immediately upstream (i.e., 5') of the site that is cleaved when the probe is not mismatched to the target.

In another preferred embodiment, a mismatch to be detected is located within the region 'Z' defined by the hybridization of a miniprobe. In a particularly preferred embodiment, the mismatch is in the miniprobe, at the basepair immediately upstream (i.e., 5') of the site that is cleaved when the miniprobe is not mismatched to the target. It is also contemplated that different sequences may be detected in a single reaction. Probes specific for the different sequences may be differently labeled. For example, the probes may have different dyes or other detectable moieties, different lengths, or they may have differences in net charges of the products after cleavage. When differently labeled in one of these ways, the contribution of each specific target sequence to final product can be tallied. This has application in detecting the quantities of different versions of a gene within a mixture. Different genes in a mixture to be detected and quantified may be wild type and mutant genes, e.g., as may be found in a tumor sample (e.g., a biopsy). In this embodiment, one might design the probes to precisely the same site, but one to match the wild-type sequence and one to match the mutant. Quantitative detection of the products of cleavage from a reaction performed for a set amount of time will reveal the ratio of the two genes in the mixture. Such analysis may also be performed on unrelated genes in a mixture. This type of analysis is not intended to be limited to two genes. Many variants within a mixture may be similarly measured.

Alternatively, different sites on a single gene may be monitored and quantified to verify the measurement of that gene. In this embodiment, the signal from each probe would be expected to be the same.

It is also contemplated that multiple probes may be used that are not differently labeled, such that the aggregate signal is measured. This may be desirable when using many probes designed to detect a single gene to boost the signal from that gene. This configuration may also be used for detecting unrelated sequences within a mix. For example, in blood banking it is desirable to know if any one of a host of infectious agents is present in a sample of blood. Because the blood is discarded regardless of which agent is present, different signals on the probes would not be required in such an application of the present invention, and may actually be undesirable for reasons of confidentiality.

Just as described for the two-oligonucleotide system, above, the specificity of the detection reaction will be influenced by the aggregate length of the target nucleic acid sequences involved in the hybridization of the complete set of the detection oligonucleotides. For example, there may be applications in which it is desirable to detect a single region within a complex genome. In such a case the set of oligonucleotides may be chosen to require accurate recognition by hybridization of a longer segment of a target nucleic acid, often in the range of 20 to 40 nucleotides. In other instances it may be desirable to have the set of oligonucleotides interact with multiple sites within a target sample. In these cases one approach would be to use a set of oligonucleotides that recognize a smaller, and thus statistically more common, segment of target nucleic acid sequence.

In one preferred embodiment, the invader and stacker oligonucleotides may be designed to be maximally stable, so that they will remain bound to the target sequence for extended periods during the reaction. This may be accomplished through any one of a number of measures well known to those skilled in the art, such as adding extra hybridizing sequences to the length of the oligonucleotide (up to about 50 nts in total length), or by using residues with reduced negative charge, such as phosphorothioates or peptide-nucleic acid residues, so that the complementary strands do not repel each other to degree that natural strands do. Such modifications may also serve to make these flanking oligonucleotides resistant to contaminating nucleases, thus further ensuring their continued presence on the target strand during the course of the reaction. In addition, the Invader™ and stacker oligonucleotides may be covalently attached to the target (e.g., through the use of psoralen cross-linking).

The use of the reaction temperatures at or near the $T_m$ of the probe oligonucleotide, rather than the used of cleavage, to drive the turnover of the probe oligonucleotide in these detection reactions means that the amount of the probe oligonucleotide cleaved off may be substantially reduced without adversely affecting the turnover rate. It has been determined that the relationship between the 3' end of the upstream oligonucleotide and the desired site of cleavage on the probe must be carefully designed. It is known that the preferred site of cleavage for the types of structure specific endonucleases employed herein is one basepair into a duplex (Lyamichev et al., supra). It was previously believed that the presence of an upstream oligonucleotide or primer allowed the cleavage site to be shifted away from this preferred site, into the single stranded region of the 5' arm (Lyamichev et al., supra and U.S. Pat. No. 5,422,253, herein incorporated by reference). In contrast to this previously proposed mechanism, and while not limiting the present invention to any particular mechanism, it is believed that the nucleotide immediately 5', or upstream of the cleavage site on the probe (including miniprobe and mid-range probes) must be able to basepair with the target for efficient cleavage to occur. In the case of the present invention, this would be the nucleotide in the probe sequence immediately upstream of the intended cleavage site. In addition, as described herein, it has been observed that in order to direct cleavage to that same site in the probe, the upstream oligonucleotide must have its 3' base (i.e., nt) immediately upstream of the intended cleavage site of the probe. This places the 3' terminal nucleotide of the upstream oligonucleotide and the base of the probe oligonucleotide 5' of the cleavage site in competition for pairing with the corresponding nucleotide of the target strand.

To examine the outcome of this competition (i.e. which base is paired during a successful cleavage event), substitutions were made in the probe and invader oligonucleotides such that either the probe or the Invader™ oligonucleotide were mismatched with the target sequence at this position. The effects of both arrangements on the rates of cleavage were examined. When the Invader™ oligonucleotide is unpaired at the 3' end, the rate of cleavage was not reduced. If this base was removed, however, the cleavage site was shifted upstream of the intended site. In contrast, if the probe oligonucleotide was not base-paired to the target just upstream of the site to which the Invader™ oligonucleotide was directing cleavage, the rate of cleavage was dramatically reduced, suggesting that when a competition exists, the probe oligonucleotide was the molecule to be base-paired in this position.

It appears that the 3' end of the upstream invader oligonucleotide is unpaired during cleavage, and yet is required for accurate positioning of the cleavage. To examine which is part(s) of the 3' terminal nucleotide are required for the positioning of cleavage, Invader™ oligonucleotides were designed that terminated on this end with nucleotides that were altered in a variety of ways. Sugars examined included 2' deoxyribose with a 3' phosphate group, a dideoxyribose, 3' deoxyribose, 2' O-methyl ribose, arabinose and arabinose with a 3' phosphate. Abasic ribose, with and without 3' phosphate were tested. Synthetic "universal" bases such at 3-nitropyrrole and 5-3nitroindole on ribose sugars were tested. Finally, a base-like aromatic ring structure, acridine, linked to the 3' end the previous nucleotide without a sugar group was tested. The results obtained support the conclusion that the aromatic ring of the base (at the 3' end of the invader oligonucleotide) is the required moiety for accomplishing the direction of cleavage to the desired site within the downstream probe.

VII. Signal Enhancement By Tailing Of Reaction Products In The Invader™-Directed Cleavage Assay It has been determined that when oligonucleotide probes are used in cleavage detection assays at elevated temperature, some fraction of the truncated probes will have been shortened by nonspecific thermal degradation, and that such breakage products can make the analysis of the target-specific cleavage data more difficult. Background cleavage such as this can, when not resolved from specific cleavage products, reduce the accuracy of quantitation of target nucleic acids based on the amount of accumulated product in a set timeframe. One means of distinguishing the specific from the nonspecific products is disclosed above, and is based on partitioning the products of these reactions by differences in the net charges carried by the different molecular species in the reaction. As was noted in that discussion, the thermal breakage products usually retain 3' phosphates after breakage, while the enzyme-cleaved products do not. The two negative charges on the phosphate facilitate charge-based partition of the products.

The absence of a 3' phosphate on the desired subset of the probe fragments may be used to advantage in enzymatic assays as well. Nucleic acid polymerases, both non-templated (e.g., terminal deoxynucleotidyl transferase, polyA polymerase) and template-dependent (e.g., Pol I-type DNA polymerases), require an available 3' hydroxyl by which to attach further nucleotides. This enzymatic selection of 3' end structure may be used as an effective means of partitioning specific from non-specific products.

In addition to the benefits of the partitioning described above, the addition of nucleotides to the end of the specific product of an invader-specific cleavage offers an opportunity to either add label to the products, to add capturable tails to facilitate solid-support based readout systems, or to do both of these things at the same time. Some possible embodiments of this concept are illustrated in FIG. 67.

In FIG. 67, an Invader™ cleavage structure comprising an Invader™ oligonucleotide containing a blocked or non-extendible 3' end (e.g., a 3' dideoxynucleotide) and a probe oligonucleotide containing a blocked or non-extendible 3' end (the open circle at the 3' end of the oligonucleotides represents a non-extendible nucleotide) and a target nucleic acid is shown; the probe oligonucleotide may contain a 5' end label such as a biotin or a fluorescein (indicated by the stars) label (cleavage structures which employ a 5' biotin-labeled probe or a 5' fluorescein-labeled probe are shown below the large diagram of the cleavage structure to the left and the right, respectively). Following, cleavage of the probe (the site of cleavage is indicated by the large arrowhead), the cleaved biotin-labeled probe is extended using a template-independent polymerase (e.g., TdT) and fluoresceinated nucleotide triphosphates. The fluorescein tailed cleaved probe molecule is then captured by binding via its 5' biotin label to streptavidin and the fluorescence is then measured. Alternatively, following, cleavage of a 5'-fluoresceinated probe, the cleaved probe is extended using a template-independent polymerase (e.g., TdT) and dATP. The polyadenylated (A-tailed) cleaved probe molecule is then captured by binding via the polyA tail to oligonucleotide dT attached to a solid support.

Figure 66:
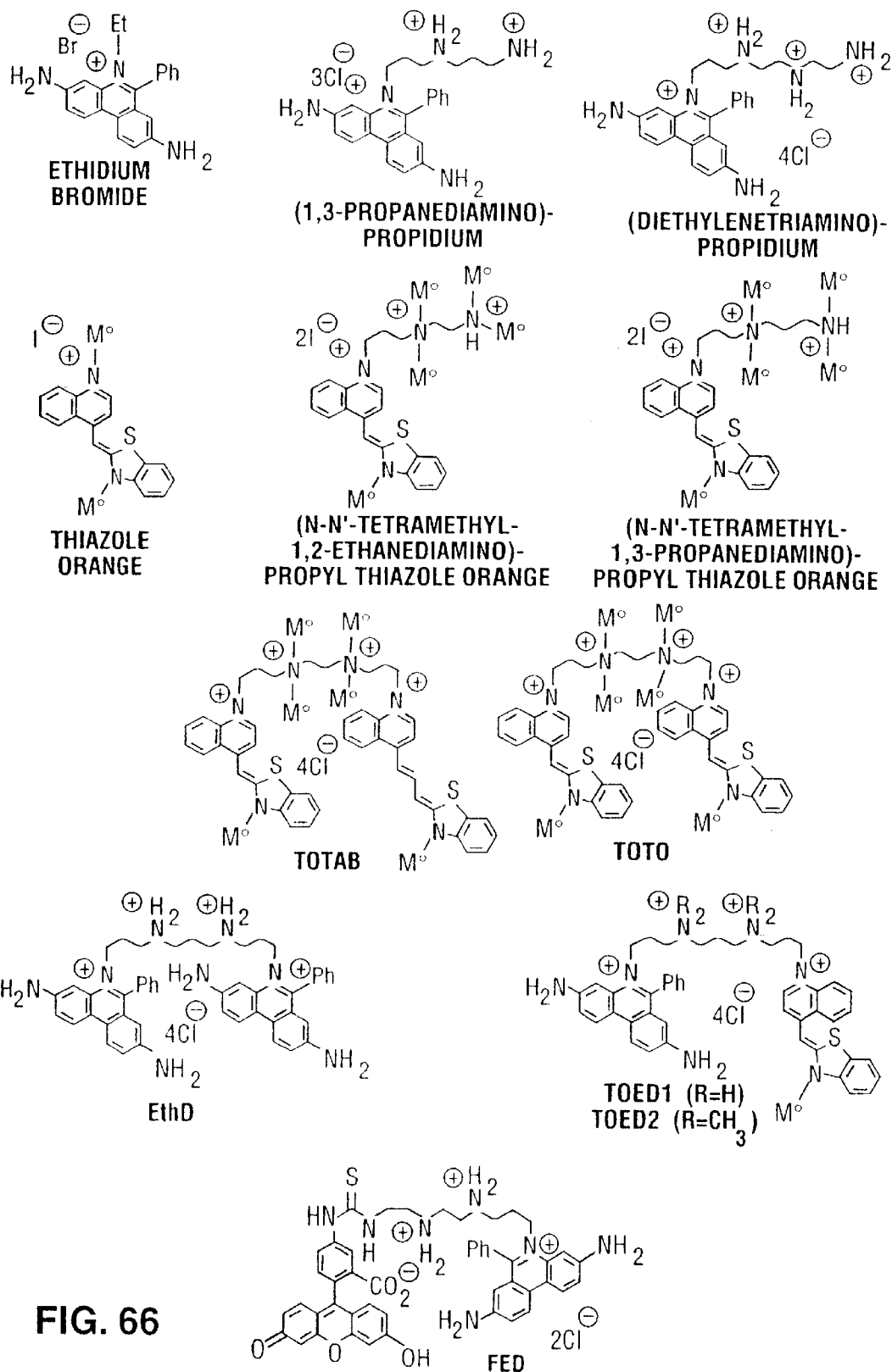
FIG. 66 shows the chemical structure of several positively charged heterodimeric DNA-binding dyes.

The examples described in FIG. 66 are based on the use of TdT to tail the specific products of Invader™-directed cleavage. The description of the use of this particular enzyme is presented by way of example and is not intended as a limitation (indeed, when probe oligonucleotides comprising RNA are employed, cleaved RNA probes may be extended using polyA polymerase). It is contemplated that an assay of this type could be configured to use a template-dependent polymerase, as described above. While this would require the presence of a suitable copy template distinct from the target nucleic acid, on which the truncated oligonucleotide could prime synthesis, it can be envisaged that a probe which before cleavage would be unextendible, due to either mismatch or modification of the 3' end, could be activated as a primer when cleaved by an invader directed cleavage. A template directed tailing reaction also has the advantage of allowing greater selection and control of the nucleotides incorporated.

The use of nontemplated tailing does not require the presence of any additional nucleic acids in the detection reaction, avoiding one step of assay development and troubleshooting. In addition, the use of non templated synthesis eliminated the step of hybridization, potentially speeding up the assay. Furthermore, the TdT enzyme is fast, able to add at least >700 nucleotides to substrate oligonucleotides in a 15 minute reaction.

As mentioned above, the tails added can be used in a number of ways. It can be used as a straight-forward way of adding labeled moieties to the cleavage product to increase signal from each cleavage event. Such a reaction is depicted in the left side of FIG. 66. The labeled moieties may be anything that can, when attached to a nucleotide, be added by the tailing enzyme, such as dye molecules, haptens such as digoxigenin, or other binding groups such as biotin.

In a preferred embodiment the assay includes a means of specifically capturing or partitioning the tailed invader-directed cleavage products in the mixture. It can be seen that target nucleic acids in the mixture may be tailed during the reaction. If a label is added, it is desirable to partition the tailed invader-directed cleavage products from these other labeled molecules to avoid background in the results. This is easily done if only the cleavage product is capable of being captured. For example, consider a cleavage assay of the present invention in which the probe used has a biotin on the 5' end and is blocked from extension on the 3' end, and in which a dye is added during tailing. Consider further that the products are to be captured onto a support via the biotin moiety, and the captured dye measured to assess the presence of the target nucleic acid. When the label is added by tailing, only the specifically cleaved probes will be labeled. The residual uncut probes can still bind in the final capture step, but they will not contribute to the signal. In the same reaction, nicks and cuts in the target nucleic acid may be tailed by the enzyme, and thus become dye labeled. In the final capture these labeled targets will not bind to the support and thus, though labeled, they will not contribute to the signal. If the final specific product is considered to consist of two portions, the probe-derived portion and the tail portion, can be seen from this discussion that it is particularly preferred that when the probe-derived portion is used for specific capture, whether by hybridization, biotin/streptavidin, or other method, that the label be associated with the tail portion. Conversely, if a label is attached to the probe-derived portion, then the tail portion may be made suitable for capture, as depicted on the right side of FIG. 66. Tails may be captured in a number of ways, including hybridization, biotin incorporation with streptavidin capture, or by virtue if the fact that the longer molecules bind more predictably and efficiently to a number of nucleic acid minding matrices, such as nitrocellulose, nylon, or glass, in membrane, paper, resin, or other form. While not required for this assay, this separation of functions allows effective exclusion from signal of both unreacted probe and tailed target nucleic acid.

In addition to the supports described above, the tailed products may be captured onto any support that contains a suitable capture moiety. For example, biotinylated products are generally captured with avidin-treated surfaces. These avidin surfaces may be in microtitre plate wells, on beads, on dipsticks, to name just a few of the possibilities. Such surfaces can also be modified to contain specific oligonucleotides, allowing capture of product by hybridization. Capture surfaces as described here are generally known to those skilled in the art and include nitrocellulose dipsticks (e.g., GeneComb, BioRad, Hercules, Calif.).

VIII. Improved Enzymes For Use In Invader™-Directed Cleavage Reactions

A cleavage structure is defined herein as a structure which is formed by the interaction of a probe oligonucleotide and a target nucleic acid to form a duplex, the resulting structure being cleavable by a cleavage means, including but not limited to an enzyme. The cleavage structure is further defined as a substrate for specific cleavage by the cleavage means in contrast to a nucleic acid molecule which is a substrate for nonspecific cleavage by agents such as phosphodiesterases. Examples of some possible cleavage structures are shown in FIG. 16. In considering improvements to enzymatic cleavage means, one may consider the action of said enzymes on any of these structures, and on any other structures that fall within the definition of a cleavage structure. The cleavage sites indicated on the structures in FIG. 16 are presented by way of example. Specific cleavage at any site within such a structure is contemplated.

Improvements in an enzyme may be an increased or decreased rate of cleavage of one or more types of structures. Improvements may also result in more or fewer sites of cleavage on one or more of said cleavage structures. In developing a library of new structure-specific nucleases for use in nucleic acid cleavage assays, improvements may have many different embodiments, each related to the specific substrate structure used in a particular assay.

As an example, one embodiment of the Invader™-directed cleavage assay of the present invention may be considered. In the Invader™ directed cleavage assay, the accumulation of cleaved material is influenced by several features of the enzyme behavior. Not surprisingly, the turnover rate, or the number of structures that can be cleaved by a single enzyme molecule in a set amount of time, is very important in determining the amount of material processed during the course of an assay reaction. If an enzyme takes a long time to recognize a substrate (e.g., if it is presented with a less-than-optimal structure), or if it takes a long time to execute cleavage, the rate of product accumulation is lower than if these steps proceeded quickly. If these steps are quick, yet the enzyme "holds on" to the cleaved structure, and does not immediately proceed to another uncut structure, the rate will be negatively affected.

Enzyme turnover is not the only way in which enzyme behavior can negatively affect the rate of accumulation of product. When the means used to visualize or measure product is specific for a precisely defined product, products that deviate from that definition may escape detection, and thus the rate of product accumulation may appear to be lower than it is. For example, if one had a sensitive detector for trinucleotides that could not see di- or tetranucleotides, or any sized oligonucleotide other that 3 residues, in the Invader™-directed cleavage assay of the present invention any errant cleavage would reduce the detectable signal proportionally. It can be seen from the cleavage data presented here that, while there is usually one site within a probe that is favored for cleavage, there are often products that arise from cleavage one or more nucleotides away from the primary cleavage site. These are products that are target dependent, and are thus not non-specific background. Nevertheless, if a subsequent visualization system can detect only the primary product, these represent a loss of signal. One example of such a selective visualization system is the charge reversal readout presented herein, in which the balance of positive and negative charges determines the behavior of the products. In such a system the presence of an extra nucleotide or the absence of an expected nucleotide can excluded a legitimate cleavage product from ultimate detection by leaving that product with the wrong balance of charge. It can be easily seen that any assay that can sensitively distinguish the nucleotide content of an oligonucleotide, such as standard stringent hybridization, suffers in sensitivity when some fraction of the legitimate product is not eligible for successful detection by that assay.

These discussions suggest two highly desirable traits in any enzyme to be used in the method of the present invention. First, the more rapidly the enzyme executes an entire cleavage reaction, including recognition, cleavage and release, the more signal it may potentially created in the invader-directed cleavage assay. Second, the more successful an enzyme is at focusing on a single cleavage site within a structure, the more of the cleavage product can be successfully detected in a selective read-out.

The rationale cited above for making improvements in enzymes to be used in the Invader™-directed cleavage assay are meant to serve as an example of one direction in which improvements might be sought, but not as a limit on either the nature or the applications of improved enzyme activities. As another direction of activity change that would be appropriately considered improvement, the DNAP-associated 5' nucleases may be used as an example. In creating some of the polymerase-deficient 5' nucleases described herein it was found that the those that were created by deletion of substantial portions of the polymerase domain, as depicted in FIG. 4, assumed activities that were weak or absent in the parent proteins. These activities included the ability to cleave the non-forked structure shown in FIG. 16D, a greatly enhanced ability to exonucleolytically remove nucleotides from the 5' ends of duplexed strands, and a nascent ability to cleave circular molecules without benefit of a free 5' end. These features have contributed to the development of detection assays such as the one depicted in FIG. 1A.

IX. Improved Enzymes For Use in The CFLP® Method

As defined herein, a folded cleavage structure is a single-stranded nucleic acid molecule which contains one or more regions containing secondary structure, said region(s) being cleavable by a cleavage means, including but not limited to an enzyme. The folded cleavage structure is further defined as a substrate for specific cleavage by said cleavage means in contrast to a nucleic acid molecule which is a substrate for nonspecific cleavage by agents such as phosphodiesterases. Examples of some possible cleavage structures are shown in FIG. 16.

In considering improvements to enzymatic cleavage means, the action of structure-specific enzymes on any of these folded structures, and on any other structures that fall within the definition of a cleavage structure may be taken into consideration. The cleavage sites indicated on the structures in FIG. 16 are presented by way of example. The present invention contemplates specific cleavage at any site within such a structure. It is also contemplated that improvements of an enzyme may encompass an increased or decreased rate of cleavage of one or more types of structures folded or otherwise. Improvements may also result in more or fewer sites of cleavage on one or more of cleavage structures. In developing a library of new or additional structure-specific nucleases for use in nucleic acid cleavage assays, improvements may have many different embodiments, each related to the specific substrate structure used in a particular assay.

As an example, one embodiment of the CFLP® assay of the present invention may be considered. In the CFLP® assay, the distribution of cleavage products is influenced by several features of the enzyme's behavior. In some instances it has been observed that DNAs (i.e., a DNA substrate) may have regions of sequence that are resistant to cleavage by a particular structure-specific nuclease, such as the Cleavase® BN nuclease or other nucleases of the present invention. Although an understanding of the mechanisms is not necessary in order to use the present invention, these regions may be unstructured (i.e., lack secondary structure), or the structures that form are not well recognized by these nucleases. In the latter case, it is contemplated that the use of a nuclease that does cleave in such a region will allow additional existing structural information to be visualized. The data presented in Examples 38 and 40 demonstrate this particular advantage provided through use of an alternative nuclease in CFLP® analysis, one with either a different substrate recognition specificity, so that a different set of structures are represented in the cleavage pattern.

In addition, there may be cases in which no single enzyme (e.g., nuclease) provides sufficient cleavage across an entire nucleic acid fragment of interest. An optimal cleavage pattern is considered to be one in which the bands are evenly spaced, the bands are as even in intensity as possible, and the fragment sizes run from full-length (to assure representation of the larger fragments) down to the size of the shortest cleavable fragment (about 15 to 20 nt). More detailed patterns (i.e., ones that contain many bands (> about 15) rather than a few bands (< about 5)) are also more likely to show differences in response to sequence changes (e.g., a single point mutation between two forms of a substrate, such as a mutant and a wild-type form). When the spacing and intensity distribution of a CFLP® pattern, or the cleavage frequency (e.g., number of bands) of a fragment of interest is not optimal using a single enzyme, it is contemplated that in some embodiments of the present invention, mixtures of enzymes provides the desired enhancement of the cleavage pattern. The enhancing effect of mixing nucleases which have slightly different substrate specificities is demonstrated in the experiment shown in FIG. 100.

In addition to the 5' nucleases derived from DNA polymerases, the present invention also contemplates the use of structure-specific nucleases that are not derived from DNA polymerases. For example, a class of eukaryotic and archaebacterial endonucleases have been identified which have a similar substrate specificity to 5' nucleases of Pol I-type DNA polymerases. These are the FEN-1 (Flap EndoNuclease), RAD2, and XPG (Xeroderma Pigmentosa-complementation group G) proteins. These proteins are involved in DNA repair, and have been shown to favor the cleavage of structures that resemble a 5' arm that has been displaced by an extending primer during polymerization, similar to the model depicted in FIG. 16B. Similar DNA repair enzymes have been isolated from single cell and higher eukaryotes and from archaea, and there are related DNA repair proteins in eubacteria. Similar 5' nucleases have also be associated with bacteriophage such as T5 and T7.

Surprisingly, and contrary to reports in the literature, it is demonstrated herein that the FEN-1 proteins can also effectively cleavage folded structures similar to that depicted in FIG. 16A. This type of structure is the structure formed when nucleic acids assume secondary structures. Literature defining the FEN class of nucleases states that no activity is observed on either single strands of DNA, or on structures lacking a primer upstream of the cleavage site (such as that in FIG. 16A). (See Harrington and Lieber, supra).

Figure 69:
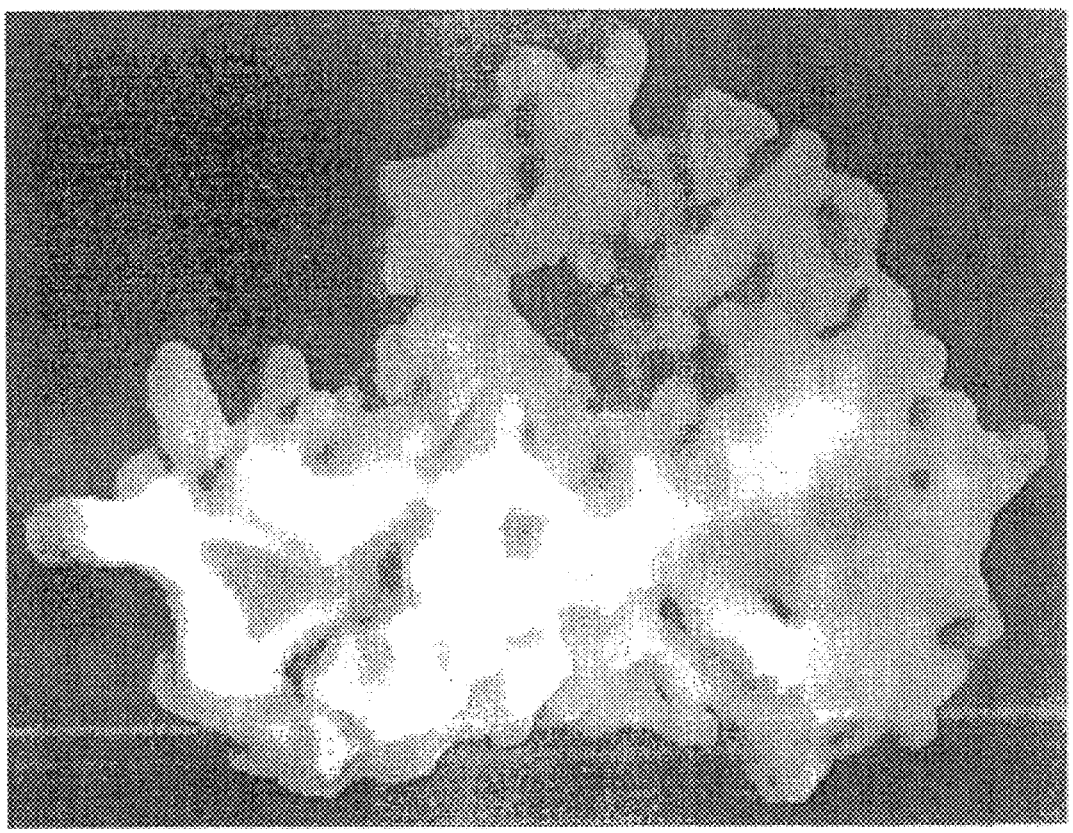
FIG. 69 provides a space-filling model of the 3-dimensional structure of the T5 5'-exonuclease.

Recently, the 3-dimensional structures of DNAPTaq and T5 phage 5'-exonuclease (FIG. 69) were determined by X-ray diffraction (Kim et al., Nature 376:612 [1995] and Ceska et al., Nature 382:90 [1995]). The two enzymes have very similar 3-dimensional structures despite limited amino acid sequence similarity. The most striking feature of the T5 5'-exonuclease structure is the existence of a triangular hole formed by the active site of the protein and two alpha helices (FIG. 69). This same region of DNAPTaq is disordered in the crystal structure, indicating that this region is flexible, and thus is not shown in the published 3-dimensional structure. However, the 5' nuclease domain of DNAPTaq is likely to have the same structure, based its overall 3-dimensional similarity to T5 5'-exonuclease, and that the amino acids in the disordered region of the DNAPTaq protein are those associated with alpha helix formation. The existence of such a hole or groove in the 5' nuclease domain of DNAPTaq was predicted based on its substrate specificity (Lyamichev et al., supra).

It has been suggested that the 5' arm of a cleavage structure must thread through the helical arch described above to position said structure correctly for cleavage (Ceska et al., supra). One of the modifications of 5' nucleases described herein opened up the helical arch portion of the protein to allow improved cleavage of structures that cut poorly or not at all (e.g., structures on circular DNA targets that would preclude such threading of a 5' arm). The gene construct that was chosen as a model to test this approach was the one called Cleavase® BN, which was derived from DNAPTaq but does not contain the polymerase domain (See, Ex. 2). It comprises the entire 5' nuclease domain of DNAP Taq, and thus should be very close in structure to the T5 5' exonuclease. This 5' nuclease was chosen to demonstrate the principle of such a physical modification on proteins of this type. The arch-opening modification of the present invention is not intended to be limited to the 5' nuclease domains of DNA polymerases, and is contemplated for use on any structure-specific nuclease which includes such an aperture as a limitation on cleavage activity. The present invention contemplates the insertion of a thrombin cleavage site into the helical arch of DNAPs derived from the genus Thermus as well as 5' nucleases derived from DNAPs derived from the genus Thermus. The specific example shown herein using the Cleavase® BN/thrombin nuclease merely illustrates the concept of opening the helical arch located within a nuclease domain. As the amino acid sequence of DNAPs derived from the genus Thermus are highly conserved, the teachings of the present invention enable the insertion of a thrombin site into the helical arch present in these DNAPs and 5' nucleases derived from these DNAPs.

The opening of the helical arch was accomplished by insertion of a protease site in the arch. This allowed post-translational digestion of the expressed protein with the appropriate protease to open the arch at its apex. Proteases of this type recognize short stretches of specific amino acid sequence. Such proteases include thrombin and factor Xa. Cleavage of a protein with such a protease depends on both the presence of that site in the amino acid sequence of the protein and the accessibility of that site on the folded intact protein. Even with a crystal structure it can be difficult to predict the susceptibility of any particular region of a protein to protease cleavage. Absent a crystal structure it must be determined empirically.

In selecting a protease for a site-specific cleavage of a protein that has been modified to contain a protease cleavage site, a first step is to test the unmodified protein for cleavage at alternative sites. For example, DNAPTaq and Cleavase® BN nuclease were both incubated under protease cleavage conditions with factor Xa and thrombin proteases. Both nuclease proteins were cut with factor Xa within the 5' nuclease domain, but neither nuclease was digested with large amounts of thrombin. Thus, thrombin was chosen for initial tests on opening the arch of the Cleavase® BN enzyme.

In the protease/Cleavase® modifications described herein the factor Xa protease cleaved strongly in an unacceptable position in the unmodified nuclease protein, in a region likely to compromise the activity of the end product. Other unmodified nucleases contemplated herein may not be sensitive to the factor Xa, but may be sensitive to thrombin or other such proteases. Alternatively, they may be sensitive to these or other such proteases at sites that are immaterial to the function of the nuclease sought to be modified. In approaching any protein for modification by addition of a protease cleavage site, the unmodified protein should be tested with the proteases under consideration to determine which proteases give acceptable levels of cleavage in other regions.

Working with the cloned segment of DNAPTaq from which the Cleavase® BN protein is expressed, nucleotides encoding a thrombin cleavage site were introduced in-frame near the sequence encoding amino acid 90 of the nuclease gene. This position was determined to be at or near the apex of the helical arch by reference to both the 3-dimensional structure of DNAPTaq, and the structure of T5 5' exonuclease.

The encoded amino acid sequence, LVPRGS, was inserted into the apex of the helical arch by site-directed mutagenesis of the nuclease gene. The proline (P) in the thrombin cleavage site was positioned to replace a proline normally in this position in Cleavase® BN because proline is an alpha helix-breaking amino acid, and may be important for the 3-dimensional structure of this arch. This construct was expressed, purified and then digested with thrombin. The digested enzyme was tested for its ability to cleave a target nucleic acid, bacteriophage M13 genomic DNA, that does not provide free 5' ends to facilitate cleavage by the threading model.

While the helical arch in this nuclease was opened by protease cleavage, it is contemplated that a number of other techniques could be used to achieve the same end. For example, the nucleotide sequence could be rearranged such that, upon expression, the resulting protein would be configured so that the top of the helical arch (amino acid 90) would be at the amino terminus of the protein, the natural carboxyl and amino termini of the protein sequence would be joined, and the new carboxyl terminus would lie at natural amino acid 89. This approach has the benefit that no foreign sequences are introduced and the enzyme is a single amino acid chain, and thus may be more stable that the cleaved 5' nuclease. In the crystal structure of DNAPTaq, the amino and carboxyl termini of the 5'-exonuclease domain lie in close proximity to each other, which suggests that the ends may be directly joined without the use of a flexible linker peptide sequence as is sometimes necessary. Such a rearrangement of the gene, with subsequent cloning and expression could be accomplished by standard PCR recombination and cloning techniques known to those skilled in the art.

The present invention also contemplates the use of nucleases isolated from a organisms that grow under a variety of conditions. The genes for the FEN-1/XPG class of enzymes are found in organisms ranging from bacteriophage to humans to the extreme thermophiles of Kingdom Archaea. For assays in which high temperature is to be used, it is contemplated that enzymes isolated from extreme thermophiles may exhibit the thermostability required of such an assay. For assays in which it might be desirable to have peak enzyme activity at moderate temperature or in which it might be desirable to destroy the enzyme with elevated temperature, those enzymes from organisms that favor moderate temperatures for growth may be of particular value.

An alignment of a collection of FEN-1 proteins sequenced by others is shown in FIGS. 70A–E. It can be seen from this alignment that there are some regions of conservation in this class of proteins, suggesting that they are related in function, and possibly in structure. Regions of similarity at the amino acid sequence level can be used to design primers for in vitro amplification (PCR) by a process of back translating the amino acid sequence to the possible nucleic acid sequences, then choosing primers with the fewest possible variations within the sequences. These can be used in low stringency PCR to search for related DNA sequences. This approach permits the amplification of DNA encoding a FEN-1 nuclease without advance knowledge of the actual DNA sequence.

It can also be seen from this alignment that there are regions in the sequences that are not completely conserved. The degree of difference observed suggests that the proteins may have subtle or distinct differences is substrate specificity. In other words, they may have different levels of cleavage activity on the cleavage structures of the present invention. When a particular structure is cleaved at a higher rate than the others, this is referred to a preferred substrate, while a structure that is cleaved slowly is considered a less preferred substrate. The designation of preferred or less preferred substrates in this context is not intended to be a limitation of the present invention. It is contemplated that some embodiments the present invention will make use of the interactions of an enzyme with a less preferred substrate. Candidate enzymes are tested for suitability in the cleavage assays of the present invention using the assays described below.

As noted above, the variations in structure-specific nucleases from organism to organism, or between different natural structure specific nucleases within a single organism can lead to the observation of different activities in both the test systems and the final assay applications of these nucleases. It has been noted that it may be desirable in some cases to use two or more of these nucleases in combination, within a single assay to make use of the combines abilities of the proteins. It is also noted above that many of these nucleases have similar morphological features when crystal structures are compared, even when the primary nucleic acid and amino acid sequences are quite divergent.

It is contemplated that the functions of the nucleases of the present invention may be modified and improved by combining different regions of the proteins within a single nuclease molecule. One method in which this may be accomplished is by the construction and expression of genes containing the coding regions for the desired portions of each protein. While it is not intended to limit the structure and/or composition of such nucleases, it is contemplated that chimerical nucleases may be composed of portions derived from two distinct natural enzymes. It is further contemplated that portions of more than two natural enzymes may by combined in a single chimeric nuclease.

The conservation of structure of the 5' nucleases allows the primary sequences to be aligned sufficiently that regions that are likely to have the same function within the protein can be identified. While these common regions may perform similar functions, this is not to say that the functions are performed with identical mechanisms or with the same performance characteristics (e.g., turnover rate, substrate Km, ion requirements). For example, the segment of sequence likely to correspond to the "loop region" described herein can be located on each protein sequence, by both location within the amino acid sequence and by conservation within the amino acid sequence. As used in this instance, conservation in the amino acid sequence comprises not only precise amino acid identity, but also resulting character of the sequence, including but not limited to hydrophobicity, hydrophilicity, positive or negative charge, α-helix or β-sheet forming nature or steric features.

The portions of sequence used to make the chimeric nucleases of the present invention may be chosen such that the final construct has a single representative of each putative domain. In a preferred embodiment the sequence domains are arranged so as to mimic the domain alignments of the natural enzymes.

The improvements to be gained by the creation of chimeric nucleases are not limited to any particular feature of such a nuclease. As described above, improvements in an enzyme may include an increased or decreased rate of cleavage of one or more types of structures. Improvements may also result in more or fewer sites of cleavage on one or more of said cleavage structures. Improvements may also result in changes in the stability of the enzyme with or without any changes in the cleavage functions cited above. In developing a library of new structure-specific nucleases for use in nucleic acid cleavage assays, improvements may have many different embodiments, each related to the specific substrate structure used in a particular assay.

1. Structure-Specific Nuclease Assay

Testing candidate nucleases for structure-specific activities in these assays is done in much the same way as described for testing modified DNA polymerases in Ex. 2, but with the use of a different library of model structures. In addition to assessing the enzyme performance in primer-independent and primer-directed cleavage, a set of synthetic hairpins are used to examine the length of duplex downstream of the cleavage site preferred by the enzyme.

The FEN-1 and XPG 5' nucleases used in the present invention must be tested for activity in the assays in which they are intended to be used, including but not limited to the Invader™-directed cleavage detection assay of the present invention and the CFLP® method of characterizing nucleic acids (the CFLP® method is described in co-pending application Ser. Nos. 08/337,164, 08/402,601, 08/484,956 and 08/520,946; the disclosures of these applications are incorporated herein by reference). The Invader™ assay uses a mode of cleavage that has been termed "primer directed" of "primer dependent" to reflect the influence of the an oligonucleotide hybridized to the target nucleic acid upstream of the cleavage site. In contrast, the CFLP® reaction is based on the cleavage of folded structure, or hairpins, within the target nucleic acid, in the absence of any hybridized oligonucleotide. The tests described herein are not intended to be limited to the analysis of nucleases with any particular site of cleavage or mode of recognition of substrate structures. It is contemplated that enzymes may be described as 3' nucleases, utilizing the 3' end as a reference point to recognize structures, or may have a yet a different mode of recognition. Further, the use of the term 5' nucleases is not intended to limit consideration to enzymes that cleave the cleavage structures at any particular site. It refers to a general class of enzymes that require some reference or access to a 5' end to effect cleavage of a structure.

Figure 71:
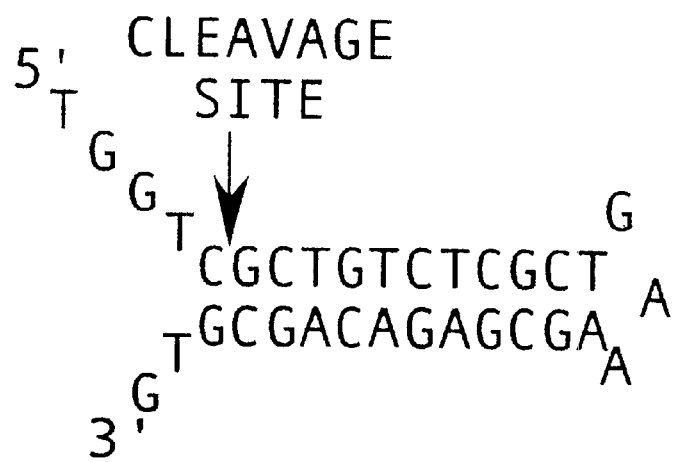
FIG. 71 is a schematic showing the S-33 (SEQ ID NO:120) and 11-8-0 (SEQ ID NO:121) oligonucleotides in a folded configuration; the cleavage site is indicated by the arrowhead.
Figure 71:
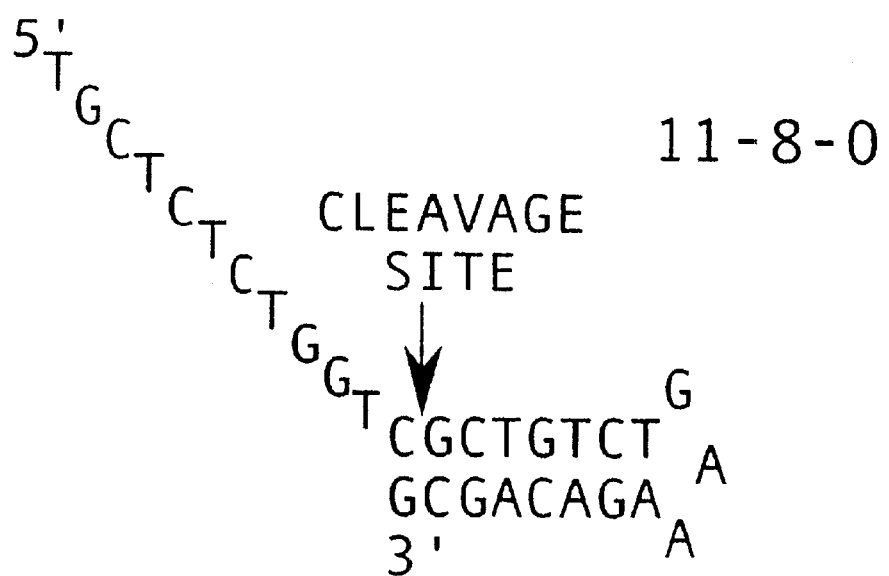

A set of model cleavage structures have been created to allow the cleavage ability of unknown enzymes on such structures to be assessed. Each of the model structures is constructed of one or more synthetic oligonucleotides made by standard DNA synthesis chemistry. Examples of such synthetic model substrate structures are shown in FIGS. 30 and 71. These are intended only to represent the general folded configuration desirable is such test structures. While a sequence that would assume such a structure is indicated in the figures, there are numerous other sequence arrangements of nucleotides that would be expected to fold in such ways. The essential features to be designed into a set of oligonucleotides to perform the tests described herein are the presence or absence of a sufficiently long 3' arm to allow hybridization of an additional nucleic acid to test cleavage in a "primer-directed" mode, and the length of the duplex region. In the set depicted in FIG. 71, the duplex lengths of the S-33 and the 11-8-0 structures are 12 and 8 basepairs, respectively. This difference in length in the test molecules facilitates detection of discrimination by the candidate nuclease between longer and shorter duplexes. Additions to this series expanding the range of duplex molecules presented to the enzymes, both shorter and longer, may be used. The use of a stabilizing DNA tetraloop (Antao et al., Nucl. Acids Res. 19:5901 [1991]) or triloop (Hiraro et al., Nuc. Acids Res. 22:576 [1994]) at the closed end of the duplex helps ensure formation of the expected structure by the oligonucleotide.

The effects of specific modifications on the activities of the nucleases of the present invention may be assessed by making such modifications in a test structure. For example, positively charged moieties such as Cy3 dye and amine groups may be added to the 5' end of a probe to be cleaved, in order to assess the performance of these cleavage agents in the charge reversal method described above and in Ex. 23.

The model substrate for testing primer directed cleavage, the "S-60 hairpin" (SEQ ID NO:40) is described in Ex. 11 In the absence of a primer this hairpin is usually cleaved to release 5' arm fragments of 18 and 19 nucleotides length. An oligonucleotide, termed P-14 (5'-CGAGAGACCACGCT-3')(SEQ ID NO:122), that extends to the base of the duplex when hybridized to the 3' arm of the S-60 hairpin gives cleavage products of the same size, but at a higher rate of cleavage.

To test invasive cleavage a different primer is used, termed P-15 (5'-CGAGAGACCACGCTG-3')(SEQ ID NO:41). In a successful invasive cleavage the presence of this primer shifts the site of cleavage of S-60 into the duplex region, usually releasing products of 21 and 22 nucleotides length.

The S-60 hairpin may also be used to test the effects of modifications of the cleavage structure on either primer-directed or invasive cleavage. Such modifications include, but are not limited to, use of mismatches or base analogs in the hairpin duplex at one, a few or all positions, similar disruptions or modifications in the duplex between the primer and the 3' arm of the S-60, chemical or other modifications to one or both ends of the primer sequence, or attachment of moieties to, or other modifications of the 5' arm of the structure. In all of the analyses using the S-60 or a similar hairpin described herein, activity with and without a primer may be compared using the same hairpin structure.

The assembly of these test reactions, including appropriate amounts of hairpin, primer and candidate nuclease are described in Ex. 2. As cited therein, the presence of cleavage products is indicated by the presence of molecules which migrate at a lower molecular weight than does the uncleaved test structure. When the reversal of charge of a label is used the products will carry a different net charge than the uncleaved material. Any of these cleavage products indicate that the candidate nuclease has the desired structure-specific nuclease activity. By "desired structure-specific nuclease activity" it is meant only that the candidate nuclease cleaves one or more test molecules. It is not necessary that the candidate nuclease cleave at any particular rate or site of cleavage to be considered successful cleavage.

EXPERIMENTAL

The following examples serve to illustrate certain preferred embodiments and aspects of the present invention and are not to be construed as limiting the scope thereof.

In the disclosure which follows, the following abbreviations apply: Afu (*Archaeoglobus fulgidus*); Mth (*Methanobacterium thermoautotrophicum*); Mja (*Methanococcus jannaschii*); Pfu (*Pyrococcus furiosus*); Pwo (*Pyrococcus woesei*); Taq (*Thermus aquaticus*); Taq DNAP, DNAPTaq, and Taq Pol I (*T. aquaticus* DNA polymerase I); DNAPStf (the Stoffel fragment of DNAPTaq); DNAPEcl (*E. coli* DNA polymerase I); Tth (*Thermus thermophilus*); Ex. (Example); Fig. (Figure);° C. (degrees Centigrade); g (gravitational field); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); p (plasmid); $\mu$l (microliters); ml (milliliters); $\mu$g (micrograms); pmoles (picomoles); mg (milligrams); M (molar); mM (milliMolar); $\mu$M (microMolar); nm (nanometers); kdal (kilodaltons); OD (optical density); EDTA (ethylene diamine tetra-acetic acid); FITC (fluorescein isothiocyanate); SDS (sodium dodecyl sulfate); $NaPO_4$ (sodium phosphate); Tris (tris (hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); ATCC (American Type Culture Collection, Rockville, Md.); DSMZ (Deutsche Sammlung von Mikroorganismen und Zellculturen, Braunschweig, Germany); Sigma (Sigma Chemical Company, St. Louis, Mo.); Dynal (Dynal A. S., Oslo, Norway); Gull (Gull Laboratories, Salt Lake City, Utah); Epicentre (Epicentre Technologies, Madison, Wis.); MJ Research (MJ Research, Watertown, Mass.); National Biosciences (Plymouth, Minn.); New England Biolabs (Beverly, Mass.); Novagen (Novagen, Inc., Madison, Wis.); Perkin Elmer (Norwalk, Conn.); Promega Corp. (Madison, Wis.); Stratagene (Stratagene Cloning Systems, La Jolla, Calif.); Clonetech (Clonetech, Palo Alto, Calif.) Pharmacia (Pharmacia, Piscataway, N.J.); Milton Roy (Milton Roy, Rochester, N.Y.); Amersham (Amersham International, Chicago, Ill.); and USB (U.S. Biochemical, Cleveland, Ohio).

EXAMPLE 1

Characteristics Of Native Thermostable DNA Polymerases

A. 5' Nuclease Activity Of DNAPTaq

During the polymerase chain reaction (PCR) (Saiki et al., Science 239:487 [1988]; Mullis and Faloona, *Methods in Enzymology* 155:335 [1987]), DNAPTaq is able to amplify many, but not all, DNA sequences. One sequence that cannot be amplified using DNAPTaq is shown in FIG. 6 (Hairpin structure is SEQ ID NO:15, PRIMERS are SEQ ID NOS: 16–17.) This DNA sequence has the distinguishing characteristic of being able to fold on itself to form a hairpin with two single-stranded arms, which correspond to the primers used in PCR.

To test whether this failure to amplify is due to the 5' nuclease activity of the enzyme, we compared the abilities of DNAPTaq and DNAPStf to amplify this DNA sequence during 30 cycles of PCR. Synthetic oligonucleotides were obtained from The Biotechnology Center at the University of Wisconsin-Madison. The DNAPTaq and DNAPStf were from Perkin Elmer (i.e., Amplitaq™ DNA polymerase and the Stoffel fragment of Amplitaq™ DNA polymerase). The substrate DNA comprised the hairpin structure shown in FIG. 6 cloned in a double-stranded form into pUC19. The primers used in the amplification are listed as SEQ ID NOS:16–17. Primer SEQ ID NO:17 is shown annealed to the 3' arm of the hairpin structure in FIG. 6. Primer SEQ ID NO: 16 is shown as the first 20 nucleotides in bold on the 5' arm of the hairpin in FIG. 6.

Polymerase chain reactions comprised 1 ng of supercoiled plasmid target DNA, 5 pmoles of each primer, 40 $\mu$M each dNTP, and 2.5 units of DNAPTaq or DNAPStf, in a 50 $\mu$l solution of 10 mM Tris•Cl pH 8.3. The DNAPTaq reactions included 50 mM KCl and 1.5 mM $MgCl_2$. The temperature profile was 95° C. for 30 sec., 55° C. for 1 min. and 72° C. for 1 min., through 30 cycles. Ten percent of each reaction was analyzed by gel electrophoresis through 6% polyacrylamide (cross-linked 29:1) in a buffer of 45 mM Tris•Borate, pH 8.3, 1.4 mM EDTA.

Figure 7:
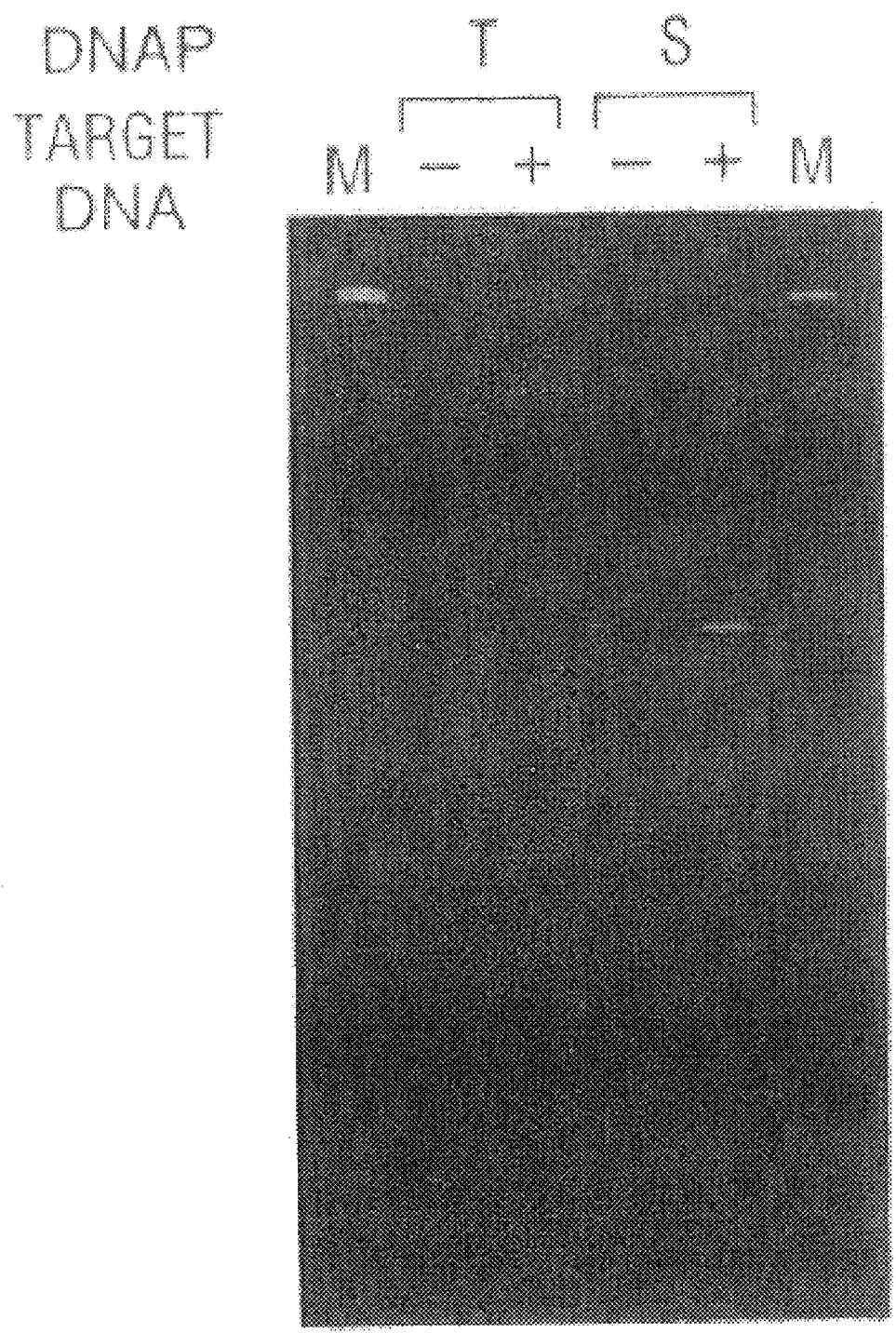
FIG. 7 is a ethidium bromide-stained gel demonstrating attempts to amplify a bifurcated duplex using either DNAPTaq or DNAPStf (i.e., the Stoffel fragment of DNAPTaq).

The results are shown in FIG. 7. The expected product was made by DNAPStf (indicated simply as "S") but not by DNAPTaq (indicated as "T"). We conclude that the 5' nuclease activity of DNAPTaq is responsible for the lack of amplification of this DNA sequence.

Figure 8:
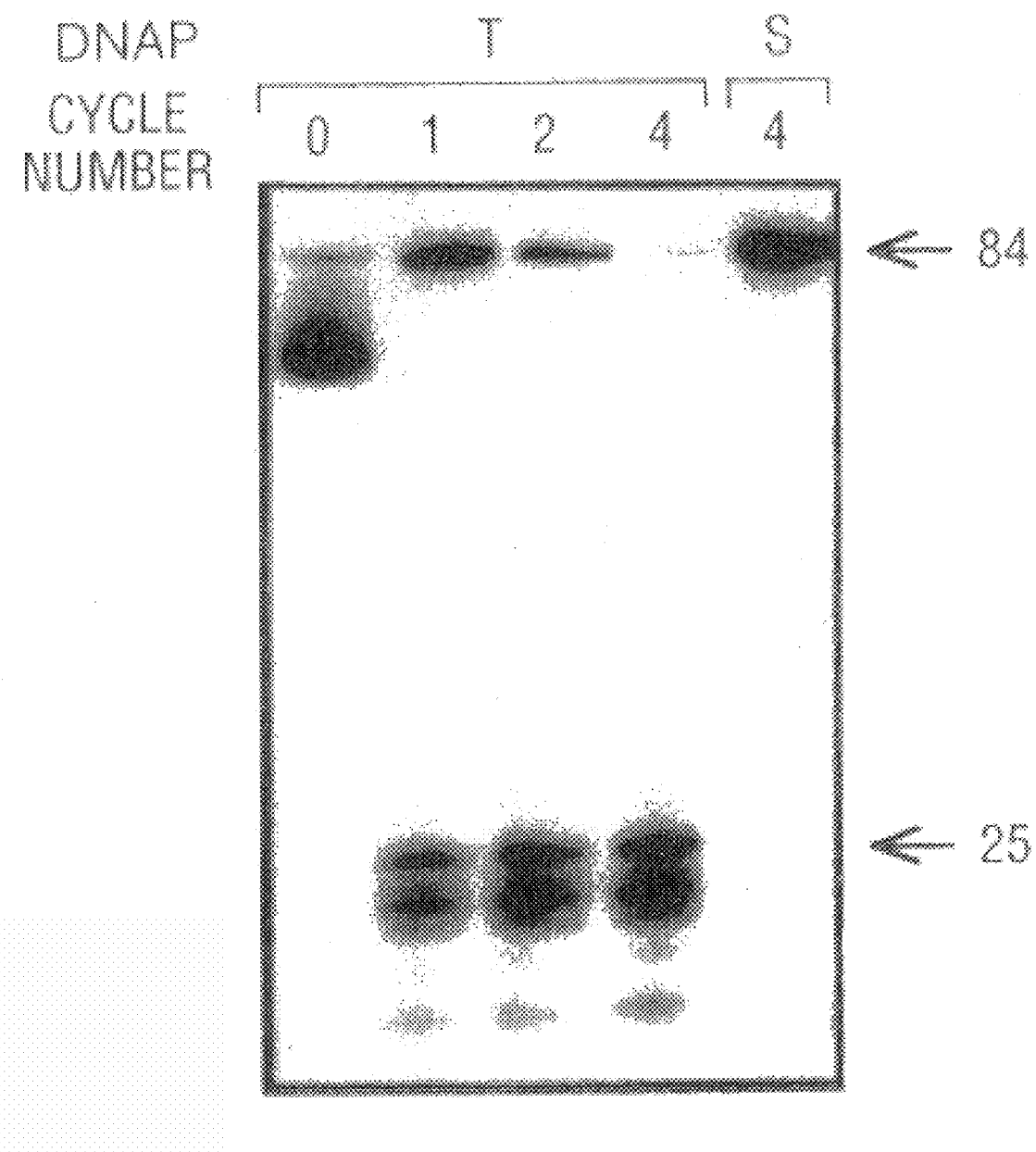
FIG. 8 is an autoradiogram of a gel analyzing the cleavage of a bifurcated duplex by DNAPTaq and lack of cleavage by DNAPStf.

To test whether the 5' unpaired nucleotides in the substrate region of this structured DNA are removed by DNAPTaq, the fate of the end-labeled 5' arm during four cycles of PCR was compared using the same two polymerases (FIG. 8). The hairpin templates, such as the one described in FIG. 6, were made using DNAPStf and a $^{32}$P-5'-end-labeled primer. The 5'-end of the DNA was released as a few large fragments by DNAPTaq but not by DNAPStf. The sizes of these fragments (based on their mobilities) show that they contain most or all of the unpaired 5' arm of the DNA. Thus, cleavage occurs at or near the base of the bifurcated duplex. These released fragments terminate with 3' OH groups, as evidenced by direct sequence analysis, and the abilities of the fragments to be extended by terminal deoxynucleotidyl transferase.

FIGS. 9–11 show the results of experiments designed to characterize the cleavage reaction catalyzed by DNAPTaq. Unless otherwise specified, the cleavage reactions comprised 0.01 pmoles of heat-denatured, end-labeled hairpin DNA (with the unlabeled complementary strand also present), 1 pmole primer (complementary to the 3' arm) and 0.5 units of DNAPTaq (estimated to be 0.026 pmoles) in a total volume of 10 μl of 10 mM Tris-Cl, pH 8.5, 50 mM KCl and 1.5 mM $MgCl_2$. As indicated, some reactions had different concentrations of KCl, and the precise times and temperatures used in each experiment are indicated in the individual figures. The reactions that included a primer used the one shown in FIG. 6 (SEQ ID NO:17). In some instances, the primer was extended to the junction site by providing polymerase and selected nucleotides.

Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes. The $T_m$ calculations listed were made using the Oligo™ primer analysis software from National Biosciences, Inc. These were determined using 0.25 μM as the DNA concentration, at either 15 or 65 mM total salt (the 1.5 mM $MgCl_2$ in all reactions was given the value of 15 mM salt for these calculations).

Figure 9A:
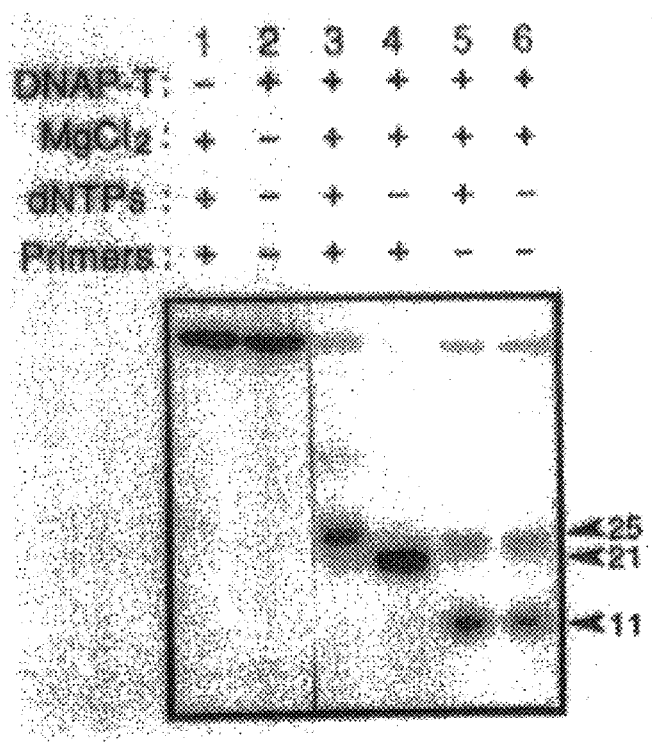
FIGS. 9A–B are a set of autoradiograms of gels analyzing cleavage or lack of cleavage upon addition of different reaction components and change of incubation temperature during attempts to cleave a bifurcated duplex with DNAPTaq.
Figure 9B:
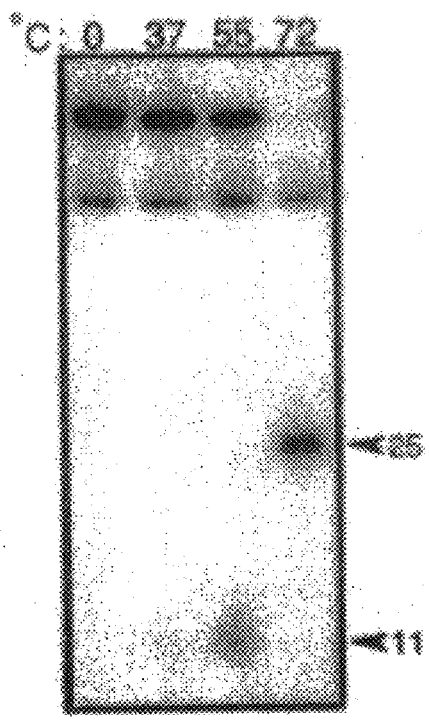

FIG. 9 is an autoradiogram containing the results of a set of experiments and conditions on the cleavage site. FIG. 9A is a determination of reaction components that enable cleavage. Incubation of 5'-end-labeled hairpin DNA was for 30 minutes at 55° C., with the indicated components. The products were resolved by denaturing polyacrylamide gel electrophoresis and the lengths of the products, in nucleotides, are indicated. FIG. 9B describes the effect of temperature on the site of cleavage in the absence of added primer. Reactions were incubated in the absence of KCl for 10 minutes at the indicated temperatures. The lengths of the products, in nucleotides, are indicated.

Surprisingly, cleavage by DNAPTaq requires neither a primer nor dNTPs (see FIG. 9A). Thus, the 5' nuclease activity can be uncoupled from polymerization. Nuclease activity equires magnesium ions, though manganese ions can be substituted, albeit with potential changes in specificity and activity. Neither zinc nor calcium ions support the cleavage reaction. The reaction occurs over a broad temperature range, from 25° C. to 85° C., with the rate of cleavage increasing at higher temperatures.

Still referring to FIG. 9, the primer is not elongated in the absence of added dNTPs. However, the primer influences both the site and the rate of cleavage of the hairpin. The change in the site of cleavage (FIG. 9A) apparently results from disruption of a short duplex formed between the arms of the DNA substrate. In the absence of primer, the sequences indicated by underlining in FIG. 6 could pair, forming an extended duplex. Cleavage at the end of the extended duplex would release the 11 nucleotide fragment seen on the FIG. 9A lanes with no added primer. Addition of excess primer (FIG. 9A, lanes 3 and 4) or incubation at an elevated temperature (FIG. 9B) disrupts the short extension of the duplex and results in a longer 5' arm and, hence, longer cleavage products.

The location of the 3' end of the primer can influence the precise site of cleavage. Electrophoretic analysis revealed that in the absence of primer (FIG. 9B), cleavage occurs at the end of the substrate duplex (either the extended or shortened form, depending on the temperature) between the first and second base pairs. When the primer extends up to the base of the duplex, cleavage also occurs one nucleotide into the duplex. However, when a gap of four or six nucleotides exists between the 3' end of the primer and the substrate duplex, the cleavage site is shifted four to six nucleotides in the 5' direction.

Figures 10A, 10B:
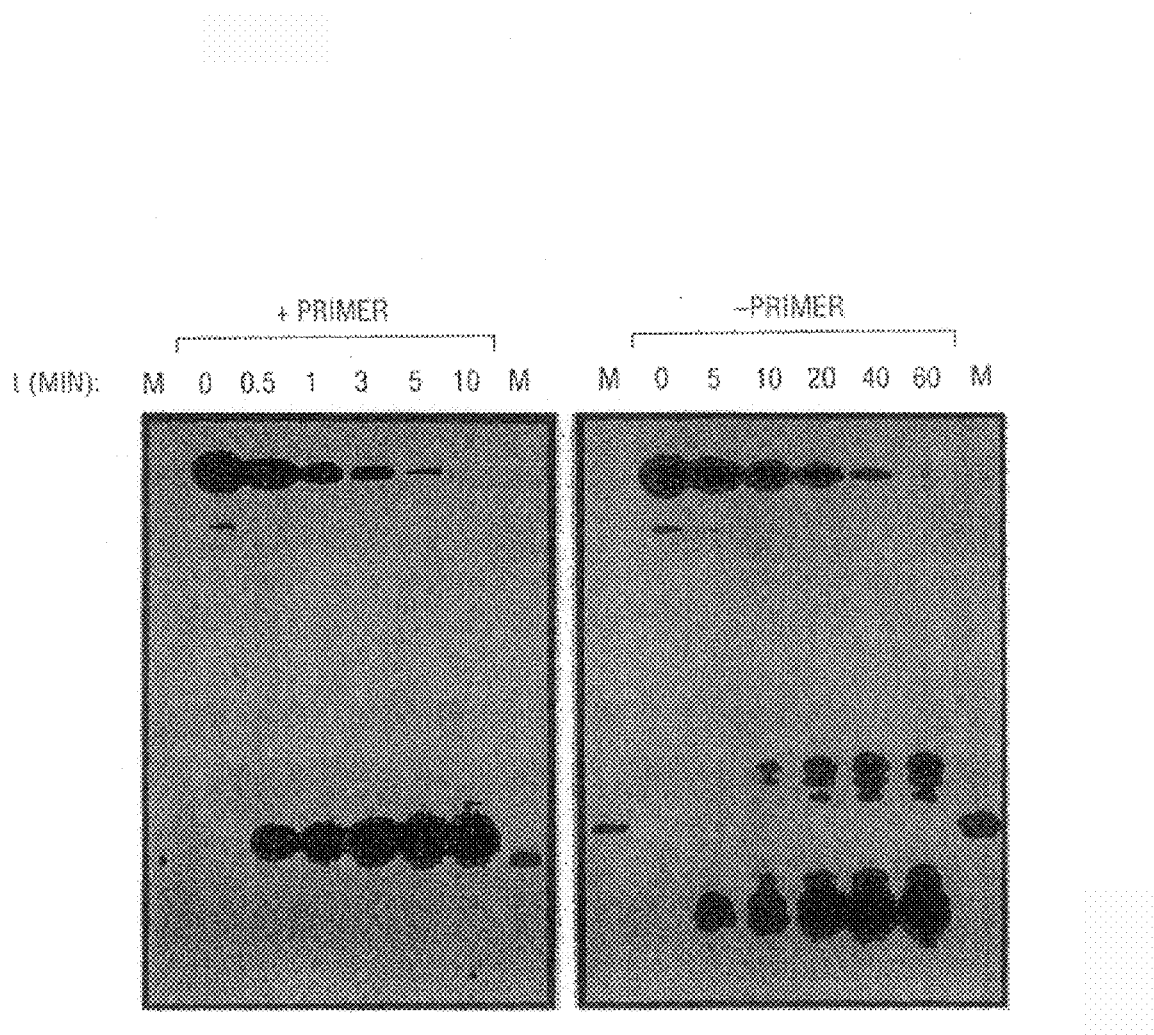
FIGS. 10A–B are an autoradiogram displaying timed cleavage reactions, with and without prirner.

FIG. 10 describes the kinetics of cleavage in the presence (FIG. 10A) or absence (FIG. 10B) of a primer oligonucleotide. The reactions were run at 55° C. with either 50 mM KCl (FIG. 10A) or 20 mM KCl (FIG. 10B). The reaction products were resolved by denaturing polyacrylamide gel electrophoresis and the lengths of the products, in nucleotides, are indicated. "M", indicating a marker, is a 5' end-labeled 19-nt oligonucleotide. Under these salt conditions, FIGS. 10A and 10B indicate that the reaction appears to be about twenty times faster in the presence of primer than in the absence of primer. This effect on the efficiency may be attributable to proper alignment and stabilization of the enzyme on the substrate.

The relative influence of primer on cleavage rates becomes much greater when both reactions are run in 50 mM KCl. In the presence of primer, the rate of cleavage increases with KCl concentration, up to about 50 mM. However, inhibition of this reaction in the presence of primer is apparent at 100 mM and is complete at 150 mM KCl. In contrast, in the absence of primer the rate is enhanced by concentration of KCl up to 20 mM, but it is reduced at concentrations above 30 mM. At 50 mM KCl, the reaction is almost completely inhibited. The inhibition of cleavage by KCl in the absence of primer is affected by temperature, being more pronounced at lower temperatures.

Recognition of the 5' end of the arm to be cut appears to be an important feature of substrate recognition. Substrates that lack a free 5' end, such as circular M13 DNA, cannot be cleaved under any conditions tested. Even with substrates having defined 5' arms, the rate of cleavage by DNAPTaq is influenced by the length of the arm. In the presence of primer and 50 mM KCl, cleavage of a 5' extension that is 27 nucleotides long is essentially complete within 2 minutes at 55° C. In contrast, cleavages of molecules with 5' arms of 84 and 188 nucleotides are only about 90% and 40% complete after 20 minutes. Incubation at higher temperatures reduces the inhibitory effects of long extensions indicating that secondary structure in the 5' arm or a heat-labile structure in the enzyme may inhibit the reaction. A mixing experiment, run under conditions of substrate excess, shows that the molecules with long arms do not preferentially tie up the available enzyme in non-productive complexes. These results may indicate that the 5' nuclease domain gains access to the cleavage site at the end of the bifurcated duplex by moving down the 5' arm from one end to the other. Longer 5' arms would be expected to have more adventitious secondary structures (particularly when KCl concentrations are high), which would be likely to impede this movement.

Cleavage does not appear to be inhibited by long 3' arms of either the substrate strand target molecule or pilot nucleic acid, at least up to 2 kilobases. At the other extreme, 3' arms of the pilot nucleic acid as short as one nucleotide can support cleavage in a primer-independent reaction, albeit inefficiently. Fully paired oligonucleotides do not elicit cleavage of DNA templates during primer extension.

The ability of DNAPTaq to cleave molecules even when the complementary strand contains only one unpaired 3' nucleotide may be useful in optimizing allele-specific PCR. PCR primers that have unpaired 3' ends could act as pilot oligonucleotides to direct selective cleavage of unwanted templates during preincubation of potential template-primer complexes with DNAPTaq in the absence of nucleoside triphosphates.

B. 5' Nuclease Activities Of Other DNAPs

To determine whether other 5' nucleases in other DNAPs would be suitable for the present invention, an array of enzymes, several of which were reported in the literature to be free of apparent 5' nuclease activity, were examined. The ability of these other enzymes to cleave nucleic acids in a structure-specific manner was tested using the hairpin substrate shown in FIG. 6 under conditions reported to be optimal for synthesis by each enzyme.

DNAPEcl and DNAP Klenow were obtained from Promega Corporation; the DNAP of *Pyrococcus furious* ("Pfu", Bargseid et al., Strategies 4:34 [1991]) was from Strategene; the DNAP of *Thermococcus litoralis* ("Tli", Vent™(exo-), Perler et al., Proc. Natl. Acad. Sci., USA 89:5577 [1992]) was from New England Biolabs; the DNAP of *Thermus flavus* ("Tfl", Kaledin et al., *Biokhimiya* 46:1576 [1981]) was from Epicentre Technologies; and the DNAP of *Thermus thermophilus* ("Tth", Carballeira et al., Biotechniques 9:276 [1990]; Myers et al., Biochem., 30:7661 [1991]) was from U.S. Biochemical.

In this Example, 0.5 units of each DNA polymerase was assayed in a 20 µl reaction, using either the buffers supplied by the manufacturers for the primer-dependent reactions, or 10 mM Tris•Cl, pH 8.5, 1.5 mM MgCl$_2$, and 2 mM KCl. Reaction mixtures were at held 72° C. before the addition of enzyme.

Figures 11A, 11B:
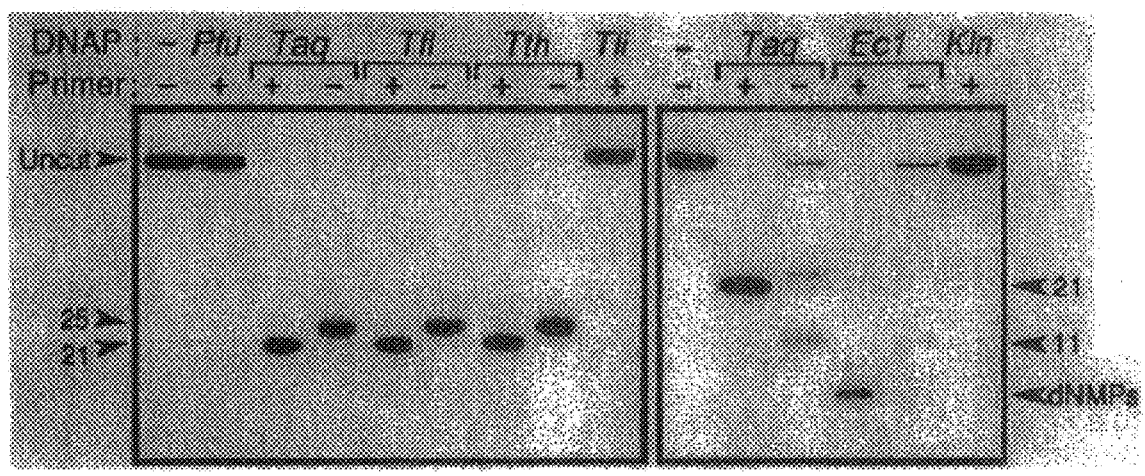
FIGS. 11A–B are a set of autoradiograms of gels demonstrating attempts to cleave a bifurcated duplex (with and without primer) with various DNAPs.

FIG. 11 is an autoradiogram recording the results of these tests. FIG. 11A demonstrates reactions of endonucleases of DNAPs of several thermophilic bacteria. The reactions were incubated at 55° C. for 10 minutes in the presence of primer or at 72° C. for 30 minutes in the absence of primer, and the products were resolved by denaturing polyacrylamide gel electrophoresis. The lengths of the products, in nucleotides, are indicated. FIG. 11B demonstrates endonucleolytic cleavage by the 5' nuclease of DNAPEcl. The DNAPEcl and DNAP Klenow reactions were incubated for 5 minutes at 37° C. Note the light band of cleavage products of 25 and 11 nucleotides in the DNAPEcl lanes (made in the presence and absence of primer, respectively). FIG. 7B also demonstrates DNAPTaq reactions in the presence (+) or absence (−) of primer. These reactions were run in 50 mM and 20 mM KCl, respectively, and were incubated at 55° C. for 10 minutes.

Referring to FIG. 11A, DNAPs from the eubacteria *Thermus thermophilus* and *Thermus flavus* cleave the substrate at the same place as DNAPTaq, both in the presence and absence of primer. In contrast, DNAPs from the archaebacteria *Pyrococcus furiosus* and *Thermococcus litoralis* are unable to cleave the substrates endonucleolytically. The DNAPs from *Pyrococcus furious* and *Thermococcus litoralis* share little sequence homology with eubacterial enzymes (Ito et al., Nucl. Acids Res., 19:4045 [1991]; Mathur et al., Nucl. Acids Res., 19:6952 [1991]; See also Perler et al.). Referring to FIG. 11B, DNAPEcl also cleaves the substrate, but the resulting cleavage products are difficult to detect unless the 3' exonuclease is inhibited. The amino acid sequences of the 5' nuclease domains of DNAPEcl and DNAPTaq are about 38% homologous (Gelfand, supra).

The 5' nuclease domain of DNAPTaq also shares about 19% homology with the 5' exonuclease encoded by gene 6 of bacteriophage T7 (Dunn et al., J. Mol. Biol. 166:477 [1983]). This nuclease, which is not covalently attached to a DNAP polymerization domain, is also able to cleave DNA endonucleolytically, at a site similar or identical to the site that is cut by the 5' nucleases described above, in the absence of added primers.

C. Transcleavage

Figure 12A:
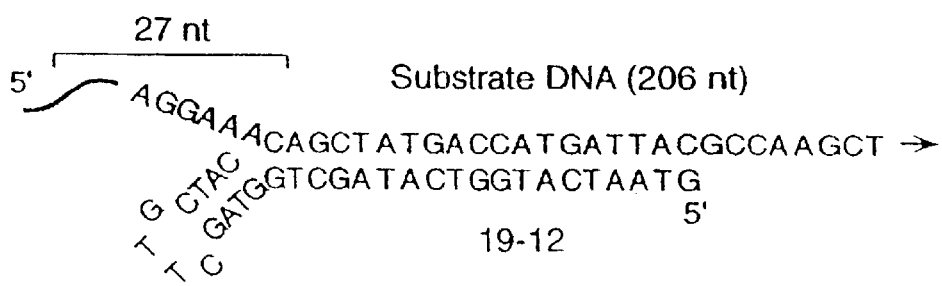
FIG. 12A shows the substrates and oligonucleotides used to test the specific cleavage of substrate DNAs targeted by pilot oligonucleotides.
Figure 12A:
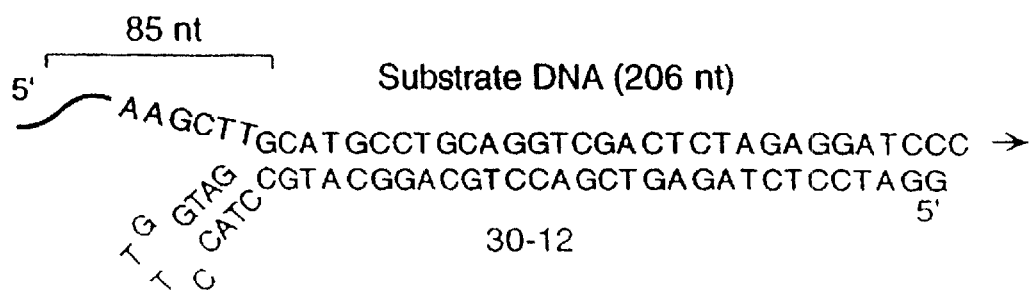

The ability of a 5' nuclease to be directed to cleave efficiently at any specific sequence was demonstrated in the following experiment. A partially complementary oligonucleotide termed a "pilot oligonucleotide" was hybridized to sequences at the desired point of cleavage. The non-complementary part of the pilot oligonucleotide provided a structure analogous to the 3' arm of the template (See, FIG. 6), whereas the 5' region of the substrate strand became the 5' arm. A primer was provided by designing the 3' region of the pilot so that it would fold on itself creating a short hairpin with a stabilizing tetra-loop (Antao et al., Nucl. Acids Res., 19:5901 [1991]). Two pilot oligonucleotides are shown in FIG. 12A. Oligonucleotides 19-12 (SEQ ID NO:18), 30-12 (SEQ ID NO:19) and 30-0 (SEQ ID NO:20) are 31, 42 or 30 nucleotides long, respectively. However, oligonucleotides 19-12 (SEQ ID NO:18) and 34-19 (SEQ ID NO:19) have only 19 and 30 nucleotides, respectively, that are complementary to different sequences in the substrate strand. The pilot oligonucleotides are calculated to melt off their complements at about 50° C. (19-12) and about 75° C. (30-12). Both pilots have 12 nucleotides at their 3' ends, which act as 3' arms with base-paired primers attached.

To demonstrate that cleavage could be directed by a pilot oligonucleotide, we incubated a single-stranded target DNA with DNAPTaq in the presence of two potential pilot oligonucleotides. The transcleavage reactions, where the target and pilot nucleic acids are not covalently linked, includes 0.01 pmoles of single end-labeled substrate DNA, 1 unit of DNAPTaq and 5 pmoles of pilot oligonucleotide in a volume of 20 µl of the same buffers. These components were combined during a one minute incubation at 95° C., to denature the PCR-generated double-stranded substrate DNA, and the temperatures of the reactions were then reduced to their final incubation temperatures. Oligonucleotides 30-12 and 19-12 can hybridize to regions of the substrate DNAs that are 85 and 27 nucleotides from the 5' end of the targeted strand.

Figure 21:
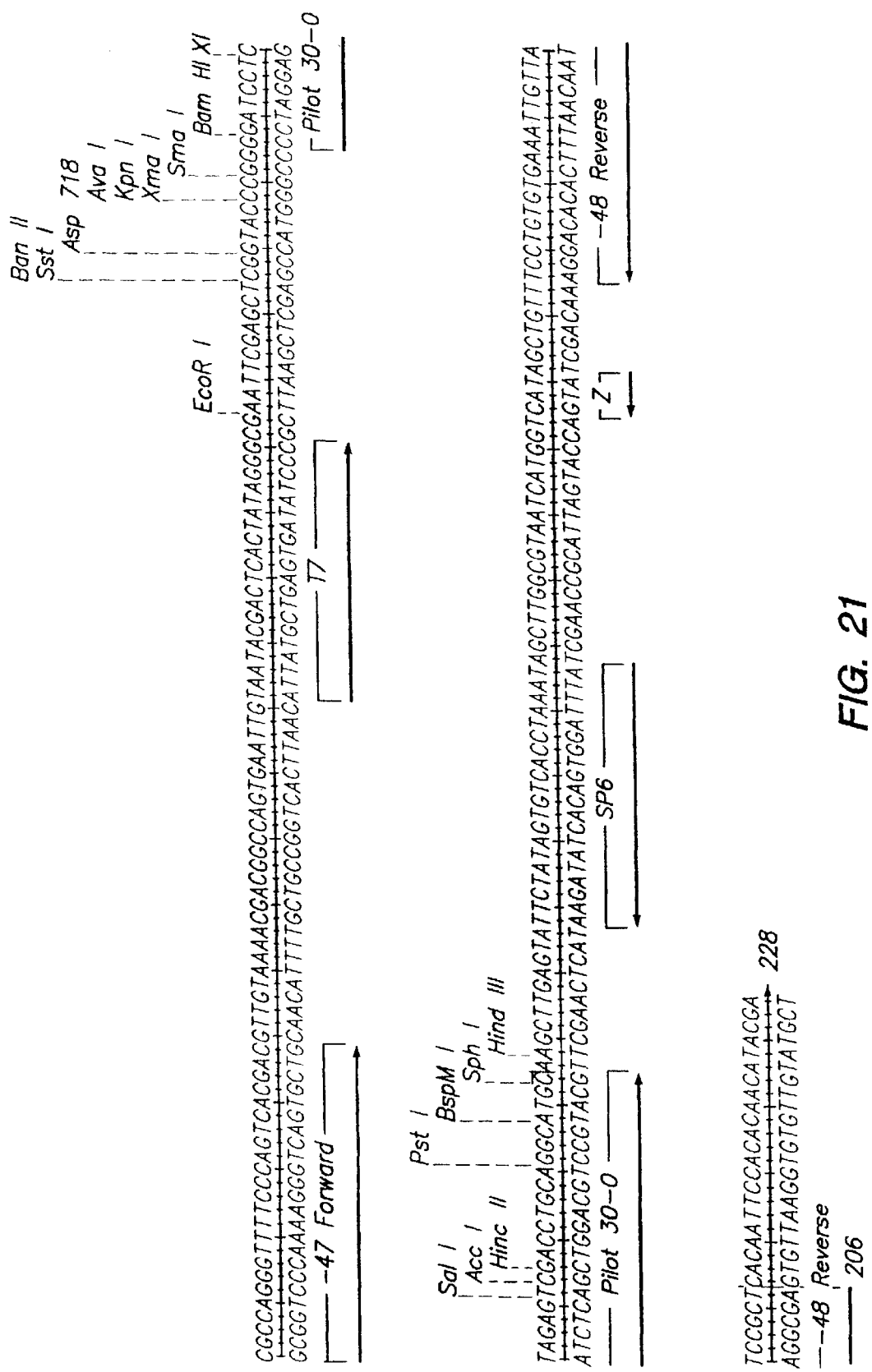
FIG. 21 provides the complete 206-mer duplex sequence employed as a substrate for the 5' nucleases of the present invention FIGS. 22A and B show the cleavage of linear nucleic acid substrates (based on the 206-mer of FIG. 21) by wild type DNAPs and 5' nucleases isolated from *Thermus aquaticus* and *Thermus flavus*.

FIG. 21 shows the complete 206-mer sequence (SEQ ID NO:32). The 206-mer was generated by PCR. The M13/pUC 24-mer reverse sequencing (−48) primer and the M13/pUC sequencing (−47) primer from New England Biolabs (catalogue nos. 1233 and 1224 respectively) were used (50 pmoles each) with the pGEM3z(f+) plasmid vector (Promega Corp.) as template (10 ng) containing the target sequences. The conditions for PCR were as follows: 50 µM of each dNTP and 2.5 units of Taq DNA polymerase in 100 µl of 20 mM Tris-Cl, pH 8.3, 1.5 mM MgCl$_2$, 50 mM KCl with 0.05% Tween-20 and 0.05% NP-40. Reactions were cycled 35 times through 95° C. for 45 seconds, 63° C. for 45 seconds, then 72° C. for 75 seconds. After cycling, reactions were finished off with an incubation at 72° C. for 5 minutes. The resulting fragment was purified by electrophoresis through a 6% polyacrylamide gel (29:1 cross link) in a buffer of 45 mM Tris-Borate, pH 8.3, 1.4 mM EDTA, visualized by ethidium bromide staining or autoradiography, excised from the gel, eluted by passive diffusion, and concentrated by ethanol precipitation.

Figure 12B:
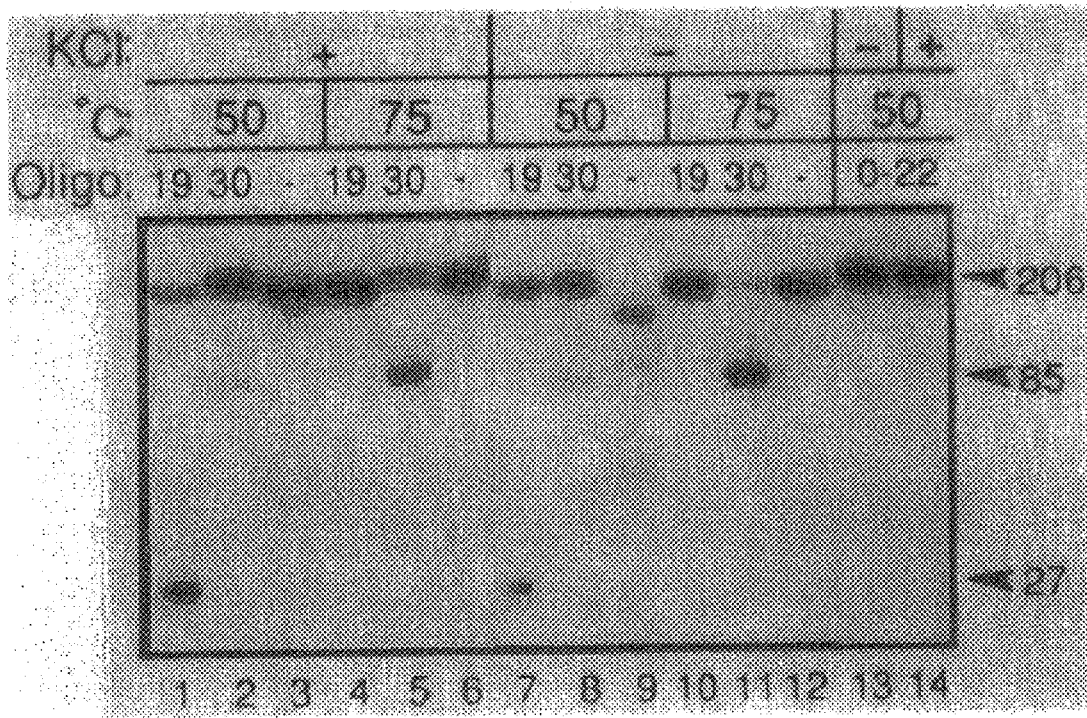
FIG. 12B shows an autoradiogram of a gel showing the results of cleavage reactions using the substrates and oligonucleotides shown FIG. 12A.

Cleavage of the substrate DNA occurred in the presence of the pilot oligonucleotide 19-12 at 50° C. (FIG. 12B. lanes 1 and 7) but not at 75° C. (lanes 4 and 10). In the presence of oligonucleotide 30-12 cleavage was observed at both temperatures. Cleavage did not occur in the absence of added oligonucleotides (lanes 3, 6 and 12) or at about 80° C. even though at 50° C. adventitious structures in the substrate allowed primer-independent cleavage in the absence of KCl (FIG. 12B, lane 9). A non-specific oligonucleotide with no complementarity to the substrate DNA did not direct cleavage at 50° C., either in the absence or presence of 50 mM KCl (lanes 13 and 14). Thus, the specificity of the cleavage reactions can be controlled by the extent of complementarity to the substrate and by the conditions of incubation.

D. Cleavage Of RNA

An shortened RNA version of the sequence used in the transcleavage experiments discussed above was tested for its ability to serve as a substrate in the reaction. The RNA is cleaved at the expected place, in a reaction that is dependent upon the presence of the pilot oligonucleotide. The RNA substrate, made by T7 RNA polymerase in the presence of [α-$^{32}$P]UTP, corresponds to a truncated version of the DNA substrate used in FIG. 12B. Reaction conditions were similar to those in used for the DNA substrates described above, with 50 mM KCl; incubation was for 40 minutes at 55° C. The pilot oligonucleotide used is termed 30-0 (SEQ ID NO:20) and is shown in FIG. 13A.

Figure 13B:
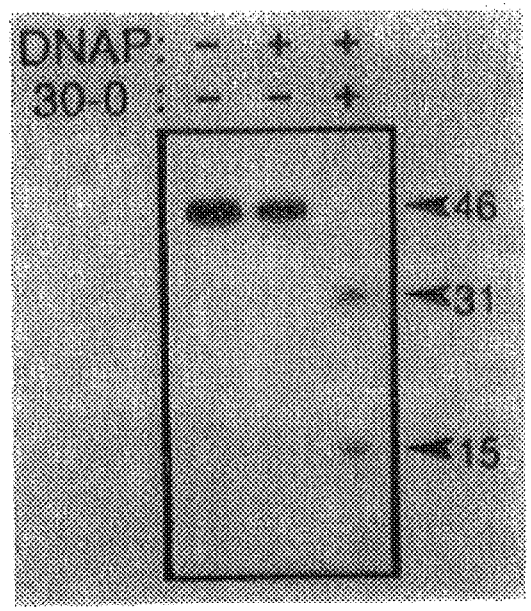
FIG. 13B shows an autoradiogram of a gel showing the results of a cleavage reaction using the substrate and oligonucleotide shown in FIG. 13A.
Figure 13A:
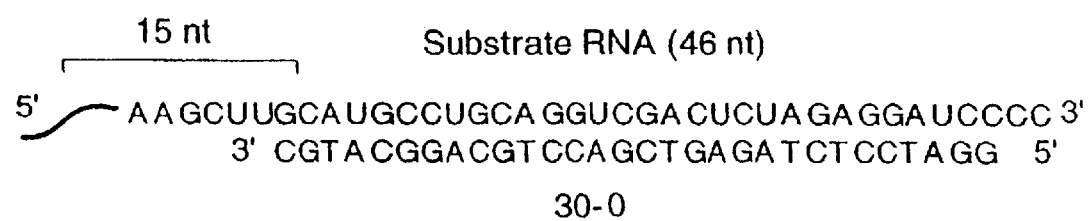
FIG. 13A shows the substrate and oligonucleotide used to test the specific cleavage of a substrate RNA targeted by a pilot oligonucleotide.

The results of the cleavage reaction is shown in FIG. 13B. The reaction was run either in the presence or absence of DNAPTaq or pilot oligonucleotide as indicated in FIG. 13B.

Strikingly, in the case of RNA cleavage, a 3' arm is not required for the pilot oligonucleotide. It is very unlikely that this cleavage is due to previously described RNaseH, which would be expected to cut the RNA in several places along the 30 base-pair long RNA-DNA duplex. The 5' nuclease of DNAPTaq is a structure-specific RNaseH that cleaves the RNA at a single site near the 5' end of the heteroduplexed region.

It is surprising that an oligonucleotide lacking a 3' arm is able to act as a pilot in directing efficient cleavage of an RNA target because such oligonucleotides are unable to direct efficient cleavage of DNA targets using native DNAPs. However, some 5' nucleases of the present invention (for example, clones E, F and G of FIG. 4) can cleave DNA in the absence of a 3' arm. In other words, a non-extendable cleavage structure is not required for specific cleavage with some 5' nucleases of the present invention derived from thermostable DNA polymerases.

We tested whether cleavage of an RNA template by DNAPTaq in the presence of a fully complementary primer could help explain why DNAPTaq is unable to extend a DNA oligonucleotide on an RNA template, in a reaction resembling that of reverse transcriptase. Another thermophilic DNAP, DNAPTth, is able to use RNA as a template, but only in the presence of Mn++, so we predicted that this enzyme would not cleave RNA in the presence of this cation. Accordingly, we incubated an RNA molecule with an appropriate pilot oligonucleotide in the presence of DNAPTaq or DNAPTth, in buffer containing either Mg++ or Mn++. As expected, both enzymes cleaved the RNA in the presence of Mg++. However, DNAPTaq, but not DNAPTth, degraded the RNA in the presence of Mn++. We conclude that the 5' nuclease activities of many DNAPs may contribute to their inability to use RNA as templates.

EXAMPLE 2

Generation Of 5' Nucleases From Thermostable DNA Polymerases

Thermostable DNA polymerases were generated which have reduced synthetic activity, an activity that is an undesirable side-reaction during DNA cleavage in the detection assay of the invention, yet have maintained thermostable nuclease activity. The result is a thermostable polymerase which cleaves nucleic acids DNA with extreme specificity.

Type A DNA polymerases from eubacteria of the genus Thermus share extensive protein sequence identity (90% in the polymerization domain, using the Lipman-Pearson method in the DNA analysis software from DNAStar, Wis.) and behave similarly in both polymerization and nuclease assays. Therefore, we have used the genes for the DNA polymerase of *Thermus aquaticus* (DNAPTaq) and *Thermus flavus* (DNAPTfl) as representatives of this class. Polymerase genes from other eubacterial organisms, such as *Thermus thermophilus*, Thermus sp., *Thermotoga maritima*, *Thermosipho africanus* and *Bacillus stearothermophilus* are equally suitable. The DNA polymerases from these thermophilic organisms are capable of surviving and performing at elevated temperatures, and can thus be used in reactions in which temperature is used as a selection against non-specific hybridization of nucleic acid strands.

The restriction sites used for deletion mutagenesis, described below, were chosen for convenience. Different sites situated with similar convenience are available in the *Thermus thermophilus* gene and can be used to make similar constructs with other Type A polymerase genes from related organisms.

A. Creation Of 5' Nuclease Constructs

1. Modified DNAPTaq Genes

The first step was to place a modified gene for the Taq DNA polymerase on a plasmid under control of an inducible promoter. The modified Taq polymerase gene was isolated as follows: The Taq DNA polymerase gene was amplified by polymerase chain reaction from genomic DNA from Thermus aquaticus, strain YT-1 (Lawyer et al., supra), using as primers the oligonucleotides described in SEQ ID NOS:13-14. The resulting fragment of DNA has a recognition sequence for the restriction endonuclease EcoRI at the 5' end of the coding sequence and a BglII sequence at the 3' end. Cleavage with BglII leaves a 5' overhang or "sticky end" that is compatible with the end generated by BamHI. The PCR-amplified DNA was digested with EcoRI and BamHI. The 2512 bp fragment containing the coding region for the polymerase gene was gel purified and then ligated into a plasmid which contains an inducible promoter.

In one embodiment of the invention, the pTTQ18 vector, which contains the hybrid trp-lac (tac) promoter, was used [M. J. R. Stark, *Gene* 5:255 (1987)] and shown in FIG. 14.

The tac promoter is under the control of the E. coli lac repressor. Repression allows the synthesis of the gene product to be suppressed until the desired level of bacterial growth has been achieved, at which point repression is removed by addition of a specific inducer, isopropyl-β-D-thiogalactopyranoside (IPTG). Such a system allows the expression of foreign proteins that may slow or prevent growth of transformants.

Figures 15A, 15B, 15C:
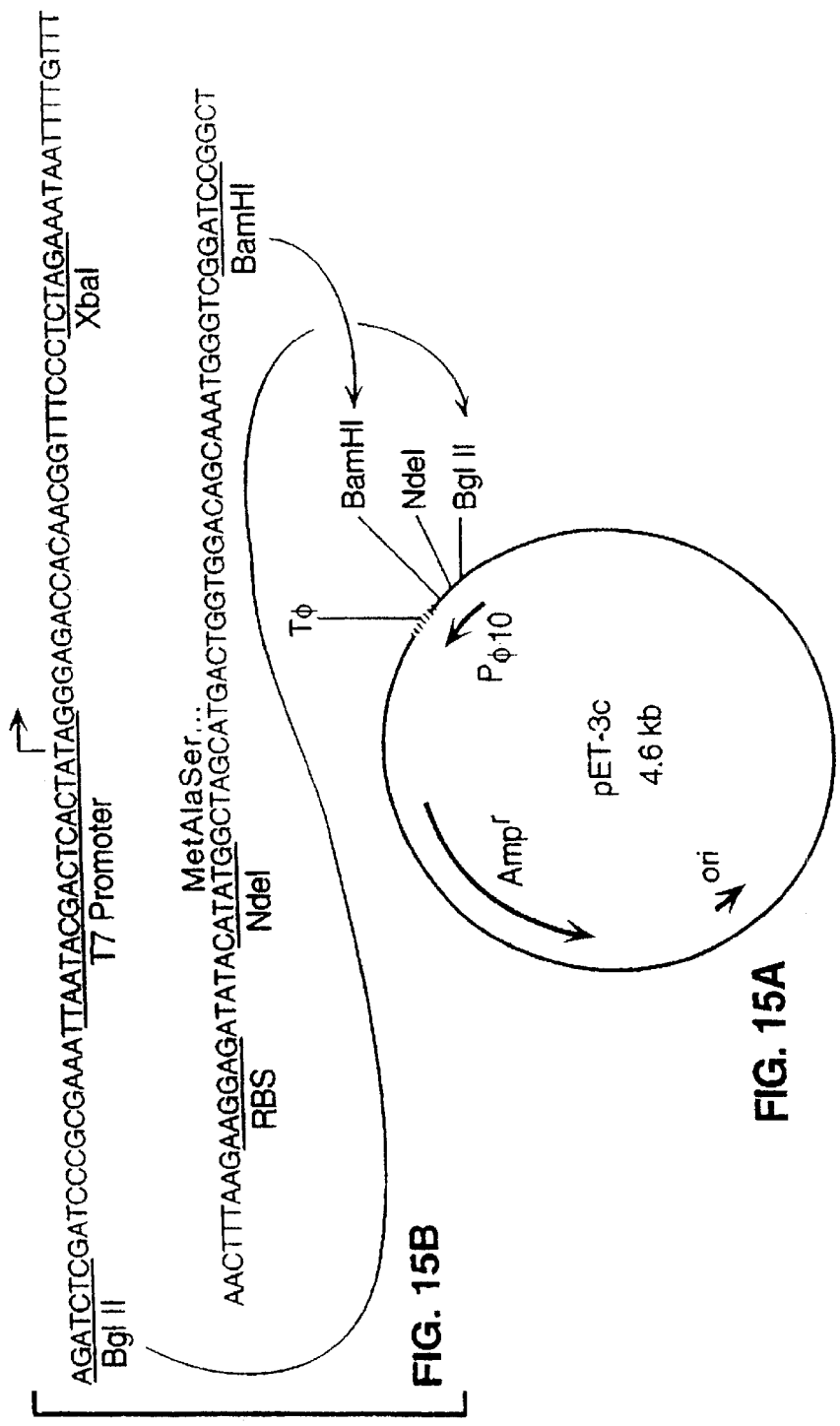
FIG. 15 is a diagram of vector pET-3c.

Bacterial promoters, such as tac, may not be adequately suppressed when they are present on a multiple copy plasmid. If a highly toxic protein is placed under control of such a promoter, the small amount of expression leaking through can be harmful to the bacteria. In another embodiment of the invention, another option for repressing synthesis of a cloned gene product was used. The non-bacterial promoter, from bacteriophage T7, found in the plasmid vector series pET-3 was used to express the cloned mutant Taq polymerase genes [FIG. 15; Studier and Moffatt, J. Mol. Biol. 189:113 (1986)]. This promoter initiates transcription only by T7 RNA polymerase. In a suitable strain, such as BL21 (DE3)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy.

For ligation into the pTTQ18 vector (FIG. 14), the PCR product DNA containing the Taq polymerase coding region (mutTaq, clone 4B, SEQ ID NO:21) was digested with EcoRI and BglII and this fragment was ligated under standard "sticky end" conditions [Sambrook et al. Molecular Cloning, Cold Spring Harbor Laboratory Press, Cold Spring Harbor, pp. 1.63–1.69 (1989)] into the EcoRI and BamHI sites of the plasmid vector pTTQ18. Expression of this construct yields a translational fusion product in which the first two residues of the native protein (Met-Arg) are replaced by three from the vector (Met-Asn-Ser), but the remainder of the natural protein would not change. The construct was transformed into the JM109 strain of E. coli and the transformants were plated under incompletely repressing conditions that do not permit growth of bacteria expressing the native protein. These plating conditions allow the isolation of genes containing pre-existing mutations, such as those that result from the infidelity of Taq polymerase during the amplification process.

Using this amplification/selection protocol, we isolated a clone (depicted in FIG. 4B) containing a mutated Taq polymerase gene (mutTaq, clone 4B). The mutant was first detected by its phenotype, in which temperature-stable 5' nuclease activity in a crude cell extract was normal, but polymerization activity was almost absent (approximately less than 1% of wild type Taq polymerase activity).

DNA sequence analysis of the recombinant gene showed that it had changes in the polymerase domain resulting in two amino acid substitutions: an A to G change at nucleotide position 1394 causes a Glu to Gly change at amino acid position 465 (numbered according to the natural nucleic and amino acid sequences, SEQ ID NOS:1 and 4) and another A to G change at nucleotide position 2260 causes a Gln to Arg change at amino acid position 754. Because the Gln to Gly mutation is at a nonconserved position and because the Glu to Arg mutation alters an amino acid that is conserved in virtually all of the known Type A polymerases, this latter mutation is most likely the one responsible for curtailing the synthesis activity of this protein. The nucleotide sequence for the FIG. 4B construct is given in SEQ ID NO:21. The enzyme encoded by this sequence is referred to as Cleavase® A/G.

Subsequent derivatives of DNAPTaq constructs were made from the mutTaq gene, thus, they all bear these amino acid substitutions in addition to their other alterations, unless these particular regions were deleted. These mutated sites are indicated by black boxes at these locations in the diagrams in FIG. 4. In FIG. 4, the designation "3' Exo" is used to indicate the location of the 3' exonuclease activity associated with Type A polymerases which is not present in DNAPTaq. All constructs except the genes shown in FIGS. 4E, F and G were made in the pTTQ18 vector.

The cloning vector used for the genes in FIGS. 4E and F was from the commercially available pET-3 series, described above. Though this vector series has only a BamHI site for cloning downstream of the T7 promoter, the series contains variants that allow cloning into any of the three reading frames. For cloning of the PCR product described above, the variant called pET-3c was used (FIG. 15). The vector was digested with BamHI, dephosphorylated with calf intestinal phosphatase, and the sticky ends were filled in using the Klenow fragment of DNAPEcl and dNTPs. The gene for the mutant Taq DNAP shown in FIG. 4B (mutTaq, clone 4B) was released from pTTQ18 by digestion with EcoRi and SalI, and the "sticky ends" were filled in as was done with the vector. The fragment was ligated to the vector under standard blunt-end conditions (Sambrook et al., Molecular Cloning, supra), the construct was transformed into the BL21(DE3)pLYS strain of E. coli, and isolates were screened to identify those that were ligated with the gene in the proper orientation relative to the promoter. This construction yields another translational fusion product, in which the first two amino acids of DNAPTaq (Met-Arg) are replaced by 13 from the vector plus two from the PCR primer (Met-Ala-Ser-Met-Thr-Gly-Gly-Gln-Gln-Met-Gly-Arg-Ile-Asn-Ser) (SEQ ID NO:29).

Our goal was to generate enzymes that lacked the ability to synthesize DNA, but retained the ability to cleave nucleic acids with a 5' nuclease activity. The act of primed, templated synthesis of DNA is actually a coordinated series of events, so it is possible to disable DNA synthesis by disrupting one event while not affecting the others. These steps include, but are not limited to, primer recognition and binding, dNTP binding and catalysis of the inter-nucleotide phosphodiester bond. Some of the amino acids in the polymerization domain of DNAPEcI have been linked to these functions, but the precise mechanisms are as yet poorly defined.

One way of destroying the polymerizing ability of a DNA polymerase is to delete all or part of the gene segment that encodes that domain for the protein, or to otherwise render the gene incapable of making a complete polymerization domain. Individual mutant enzymes may differ from each other in stability and solubility both inside and outside cells. For instance, in contrast to the 5' nuclease domain of DNAPEcI, which can be released in an active form from the polymerization domain by gentle proteolysis (Setlow and Kornberg, J. Biol. Chem., 247:232 [1972]), the Thermus nuclease domain, when treated similarly, becomes less soluble and the cleavage activity is often lost.

Using the mutant gene shown in FIG. 4B as starting material, several deletion constructs were created. All cloning technologies were standard (Sambrook et al., supra) and are summarized briefly, as follows:

FIG. 4C: The mutTaq construct was digested with PstI, which cuts once within the polymerase coding region, as indicated, and cuts immediately downstream of the gene in the multiple cloning site of the vector. After release of the fragment between these two sites, the vector was re-ligated, creating an 894-nucleotide deletion, and bringing into frame a stop codon 40 nucleotides downstream of the junction. The nucleotide sequence of this 5' nuclease (clone 4C) is given in SEQ ID NO:9.

FIG. 4D: The mutTaq construct was digested with NheI, which cuts once in the gene at position 2047. The resulting four-nucleotide 5' overhanging ends were filled in, as described above, and the blunt ends were re-ligated. The resulting four-nucleotide insertion changes the reading frame and causes termination of translation ten amino acids downstream of the mutation. The nucleotide sequence of this 5' nuclease (clone 4D) is given in SEQ ID NO:10.

FIG. 4E: The entire mutTaq gene was cut from pTTQ18 using EcoRI and SalI and cloned into pET-3c, as described above. This clone was digested with BstXI and XcmI, at unique sites that are situated as shown in FIG. 4E. The DNA was treated with the Klenow fragment of DNAPEcl and dNTPs, which resulted in the 3' overhangs of both sites being trimmed to blunt ends. These blunt ends were ligated together, resulting in an out-of-frame deletion of 1540 nucleotides. An in-frame termination codon occurs 18 triplets past the junction site. The nucleotide sequence of this 5' nuclease (clone 4E) is given in SEQ ID NO: 11, with the appropriate leader sequence given in SEQ ID NO:30. It is also referred to as Cleavase® BX.

FIG. 4F: The entire mutTaq gene was cut from pTTQ18 using EcoRI and SalI and cloned into pET-3c, as described above. This clone was digested with BstXI and BamHI, at unique sites that are situated as shown in the diagram. The DNA was treated with the Klenow fragment of DNAPEcl and dNTPs, which resulted in the 3' overhang of the BstXI site being trimmed to a blunt end, while the 5' overhang of the BamHI site was filled in to make a blunt end. These ends were ligated together, resulting in an in-frame deletion of 903 nucleotides. The nucleotide sequence of the 5' nuclease (clone 4F) is given in SEQ ID NO:12. It is also referred to as Cleavase® BB.

FIG. 4G: This polymerase is a variant of that shown in FIG. 4E. It was cloned in the plasmid vector pET-21 (Novagen). The non-bacterial promoter from bacteriophage T7, found in this vector, initiates transcription only by T7 RNA polymerase. See Studier and Moffatt, supra. In a suitable strain, such as (DES)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy. Because the expression of these mutant genes is under this tightly controlled promoter, potential problems of toxicity of the expressed proteins to the host cells are less of a concern.

The pET-21 vector also features a "His*Tag", a stretch of six consecutive histidine residues that are added on the carboxy terminus of the expressed proteins. The resulting proteins can then be purified in a single step by metal chelation chromatography, using a commercially available (Novagen) column resin with immobilized $Ni^{++}$ ions. The 2.5 ml columns are reusable, and can bind up to 20 mg of the target protein under native or denaturing (guanidine*HCl or urea) conditions.

E. coli (DES)pLYS cells are transformed with the constructs described above using standard transformation techniques, and used to inoculate a standard growth medium (e.g., Luria-Bertani broth). Production of T7 RNA polymerase is induced during log phase growth by addition of IPTG and incubated for a further 12 to 17 hours. Aliquots of culture are removed both before and after induction and the proteins are examined by SDS-PAGE. Staining with Coomassie Blue allows visualization of the foreign proteins if they account for about 3–5% of the cellular protein and do not co-migrate with any of the major protein bands. Proteins that co-migrate with major host protein must be expressed as more than 10% of the total protein to be seen at this stage of analysis.

Some mutant proteins are sequestered by the cells into inclusion bodies. These are granules that form in the cytoplasm when bacteria are made to express high levels of a foreign protein, and they can be purified from a crude lysate, and analyzed by SDS-PAGE to determine their protein content. If the cloned protein is found in the inclusion bodies, it must be released to assay the cleavage and polymerase activities. Different methods of solubilization may be appropriate for different proteins, and a variety of methods are known. See e.g., Builder & Ogez, U.S. Pat. No. 4,511,502 (1985); Olson, U.S. Pat. No. 4,518,526 (1985); Olson & Pai, U.S. Pat. No. 4,511,503 (1985); Jones et al., U.S. Pat. No. 4,512,922 (1985), all of which are hereby incorporated by reference.

The solubilized protein is then purified on the $Ni^{++}$ column as described above, following the manufacturers instructions (Novagen). The washed proteins are eluted from the column by a combination of imidazole competitor (1 M) and high salt (0.5 M NaCl), and dialyzed to exchange the buffer and to allow denature proteins to refold. Typical recoveries result in approximately 20 μg of specific protein per ml of starting culture. The DNAP mutant is referred to as the Cleavase® BN nuclease and the sequence is given in SEQ ID NO:31 (the amino acid sequence of the Cleavase® BN nuclease is obtained by translating the DNA sequence of SEQ ID NO:31).

2. Modified DNAPTfl Gene

The DNA polymerase gene of *Thermus flavus* was isolated from the "*T. flavus*" AT-62 strain obtained from the ATCC (ATCC #33923). This strain has a different restriction map then does the *T. flavus* strain used to generate the sequence published by Akhmetzjanov and Vakhitov, supra. The published sequence is listed as SEQ ID NO:2. No sequence data has been published for the DNA polymerase gene from the AT-62 strain of *T. flavus*.

Genomic DNA from *T. flavus* was amplified using the same primers used to amplify the *T. aquaticus* DNA polymerase gene (SEQ ID NOS:13–14). The approximately 2500 base pair PCR fragment was digested with EcoRI and BamHI. The over-hanging ends were made blunt with the Klenow fragment of DNAPEcl and dNTPs. The resulting approximately 1800 base pair fragment containing the coding region for the N-terminus was ligated into pET-3c, as described above. This construct, clone 5B, is depicted in FIG. 5B. The wild type *T. flavus* DNA polymerase gene is depicted in FIG. 5A. The 5B clone has the same leader amino acids as do the DNAPTaq clones 4E and F which were cloned into pET-3c; it is not known precisely where translation termination occurs, but the vector has a strong transcription termination signal immediately downstream of the cloning site.

B. Growth And Induction Of Transformed Cells

Bacterial cells were transformed with the constructs described above using standard transformation techniques and used to inoculate 2 mls of a standard growth medium (e.g., Luria-Bertani broth). The resulting cultures were incubated as appropriate for the particular strain used, and induced if required for a particular expression system. For all of the constructs depicted in FIGS. 4 and 5, the cultures were grown to an optical density (at 600 nm wavelength) of 0.5 OD.

To induce expression of the cloned genes, the cultures were brought to a final concentration of 0.4 mM IPTG and the incubations were continued for 12 to 17 hours. 50 µl aliquots of each culture were removed both before and after induction and were combined with 20 µl of a standard gel loading buffer for sodium dodecyl sulfate-polyacrylamide gel electrophoresis (SDS-PAGE). Subsequent staining with Coomassie Blue (Sambrook et al., supra) allows visualization of the foreign proteins if they account for about 3–5% of the cellular protein and do not co-migrate with any of the major *E. coli* protein bands. Proteins that do co-migrate with a major host protein must be expressed as more than 10% of the total protein to be seen at this stage of analysis.

C. Heat Lysis And Fractionation

Expressed thermostable proteins, i.e., the 5' nucleases, were isolated by heating crude bacterial cell extracts to cause denaturation and precipitation of the less stable *E. coli* proteins. The precipitated *E. coli* proteins were then, along with other cell debris, removed by centrifugation. 1.7 mls of the culture were pelleted by microcentrifugation at 12,000 to 14,000 rpm for 30 to 60 seconds. After removal of the supernatant, the cells were resuspended in 400 µl of buffer A (50 mM Tris-HCl, pH 7.9, 50 mM dextrose, 1 mM EDTA), re-centrifuged, then resuspended in 80 µl of buffer A with 4 mg/ml lysozyme. The cells were incubated at room temperature for 15 minutes, then combined with 80 µl of buffer B (10 mM Tris-HCl, pH 7.9, 50 mM KCl, 1 mM EDTA, 1 mM PMSF, 0.5% Tween-20, 0.5% Nonidet-P40).

This mixture was incubated at 75° C. for 1 hour to denature and precipitate the host proteins. This cell extract was centrifuged at 14,000 rpm for 15 minutes at 4° C., and the supernatant was transferred to a fresh tube. An aliquot of 0.5 to 1 µl of this supernatant was used directly in each test reaction, and the protein content of the extract was determined by subjecting 7 µl to electrophoretic analysis, as above. The native recombinant Taq DNA polymerase [Englke, Anal. Biochem 191:396 (1990)], and the double point mutation protein shown in FIG. 4B are both soluble and active at this point.

The foreign protein may not be detected after the heat treatments due to sequestration of the foreign protein by the cells into inclusion bodies. These are granules that form in the cytoplasm when bacteria are made to express high levels of a foreign protein, and they can be purified from a crude lysate, and analyzed SDS PAGE to determine their protein content. Many methods have been described in the literature, and one approach is described below.

D. Isolation And Solubilization Of Inclusion Bodies

A small culture was grown and induced as described above. A 1.7 ml aliquot was pelleted by brief centrifugation, and the bacterial cells were resuspended in 100 µl of Lysis buffer (50 mM Tris-HCl, pH 8.0, 1 mM EDTA, 100 mM NaCl). 2.5 µl of 20 mM PMSF were added for a final concentration of 0.5 mM, and lysozyme was added to a concentration of 1.0 mg/ml. The cells were incubated at room temperature for 20 minutes, deoxycholic acid was added to 1 mg/ml (1 µl of 100 mg/ml solution), and the mixture was further incubated at 37° C. for about 15 minutes or until viscous. DNAse I was added to 10 µg/ml and the mixture was incubated at room temperature for about 30 minutes or until it was no longer viscous.

From this mixture the inclusion bodies were collected by centrifugation at 14,000 rpm for 15 minutes at 4° C., and the supernatant was discarded. The pellet was resuspended in 100 µl of lysis buffer with 10 mM EDTA (pH 8.0) and 0.5% Triton X-100. After 5 minutes at room temperature, the inclusion bodies were pelleted as before, and the supernatant was saved for later analysis. The inclusion bodies were resuspended in 50 µl of distilled water, and 5 µl was combined with SDS gel loading buffer (which dissolves the inclusion bodies) and analyzed electrophoretically, along with an aliquot of the supernatant.

If the cloned protein is found in the inclusion bodies, it may be released to assay the cleavage and polymerase activities and the method of solubilization must be compatible with the particular activity. Different methods of solubilization may be appropriate for different proteins, and a variety of methods are discussed in *Molecular Cloning* (Sambrook et al., supra). The following is an adaptation we have used for several of our isolates.

Twenty µl of the inclusion body-water suspension were pelleted by centrifugation at 14,000 rpm for 4 minutes at room temperature, and the supernatant was discarded. To further wash the inclusion bodies, the pellet was resuspended in 20 µl of lysis buffer with 2 M urea, and incubated at room temperature for one hour. The washed inclusion bodies were then resuspended in 2 µl of lysis buffer with 8 M urea; the solution clarified visibly as the inclusion bodies dissolved. Undissolved debris was removed by centrifugation at 14,000 rpm for 4 minutes at room temperature, and the extract supernatant was transferred to a fresh tube.

To reduce the urea concentration, the extract was diluted into KH2PO$_4$. A fresh tube was prepared containing 180 µl of 50 mM KH$_2$PO$_4$, pH 9.5, 1 mM EDTA and 50 mM NaCl. A 2 µl aliquot of the extract was added and vortexed briefly to mix. This step was repeated until all of the extract had been added for a total of 10 additions. The mixture was allowed to sit at room temperature for 15 minutes, during which time some precipitate often forms. Precipitates were removed by centrifugation at 14,000 rpm, for 15 minutes at room temperature, and the supernatant was transferred to a fresh tube. To the 200 µl of protein in the KH$_2$PO$_4$ solution, 140–200 µl of saturated (NH$_4$)$_2$SO$_4$ were added, so that the resulting mixture was about 41% to 50% saturated (NH$_4$)$_2$SO$_4$. The mixture was chilled on ice for 30 minutes to allow the protein to precipitate, and the protein was then collected by centrifugation at 14,000 rpm, for 4 minutes at room temperature. The supernatant was discarded, and the pellet was dissolved in 20 µl Buffer C (20 mM HEPES, pH 7.9, 1 mM EDTA, 0.5% PMSF, 25 mM KCl and 0.5% each of Tween-20 and Nonidet P 40). The protein solution was centrifuged again for 4 minutes to pellet insoluble materials, and the supernatant was removed to a fresh tube. The protein contents of extracts prepared in this manner were visualized by resolving 1–4 µl by SDS-PAGE; 0.5 to 1 µl of extract was tested in the cleavage and polymerization assays as described.

E. Protein Analysis For Presence Of Nuclease And Synthetic Activity

The 5' nucleases described above and shown in FIGS. 4 and 5 were analyzed by the following methods.

1. Structure Specific Nuclease Assay

A candidate modified polymerase is tested for 5' nuclease activity by examining its ability to catalyze structure-specific cleavages. By the term "cleavage structure" as used herein, is meant a nucleic acid structure which is a substrate for cleavage by the 5' nuclease activity of a DNAP.

The polymerase is exposed to test complexes that have the structures shown in FIG. 16. Testing for 5' nuclease activity involves three reactions: 1) a primer-directed cleavage (FIG. 16B) is performed because it is relatively insensitive to variations in the salt concentration of the reaction and can, therefore, be performed in whatever solute conditions the modified enzyme requires for activity; this is generally the same conditions preferred by unmodified polymerases; 2) a similar primer-directed cleavage is performed in a buffer which permits primer-independent cleavage, i.e., a low salt buffer, to demonstrate that the enzyme is viable under these conditions; and 3) a primer-independent cleavage (FIG. 16A) is performed in the same low salt buffer.

The bifurcated duplex is formed between a substrate strand and a template strand as shown in FIG. 16. By the term "substrate strand" as used herein, is meant that strand of nucleic acid in which the cleavage mediated by the 5' nuclease activity occurs. The substrate strand is always depicted as the top strand in the bifurcated complex which serves as a substrate for 5' nuclease cleavage (FIG. 16). By the term "template strand" as used herein, is meant the strand of nucleic acid which is at least partially complementary to the substrate strand and which anneals to the substrate strand to form the cleavage structure. The template strand is always depicted as the bottom strand of the bifurcated cleavage structure (FIG. 16). If a primer (a short oligonucleotide of 19 to 30 nucleotides in length) is added to the complex, as when primer-dependent cleavage is to be tested, it is designed to anneal to the 3' arm of the template strand (FIG. 16B). Such a primer would be extended along the template strand if the polymerase used in the reaction has synthetic activity.

Figure 16E:
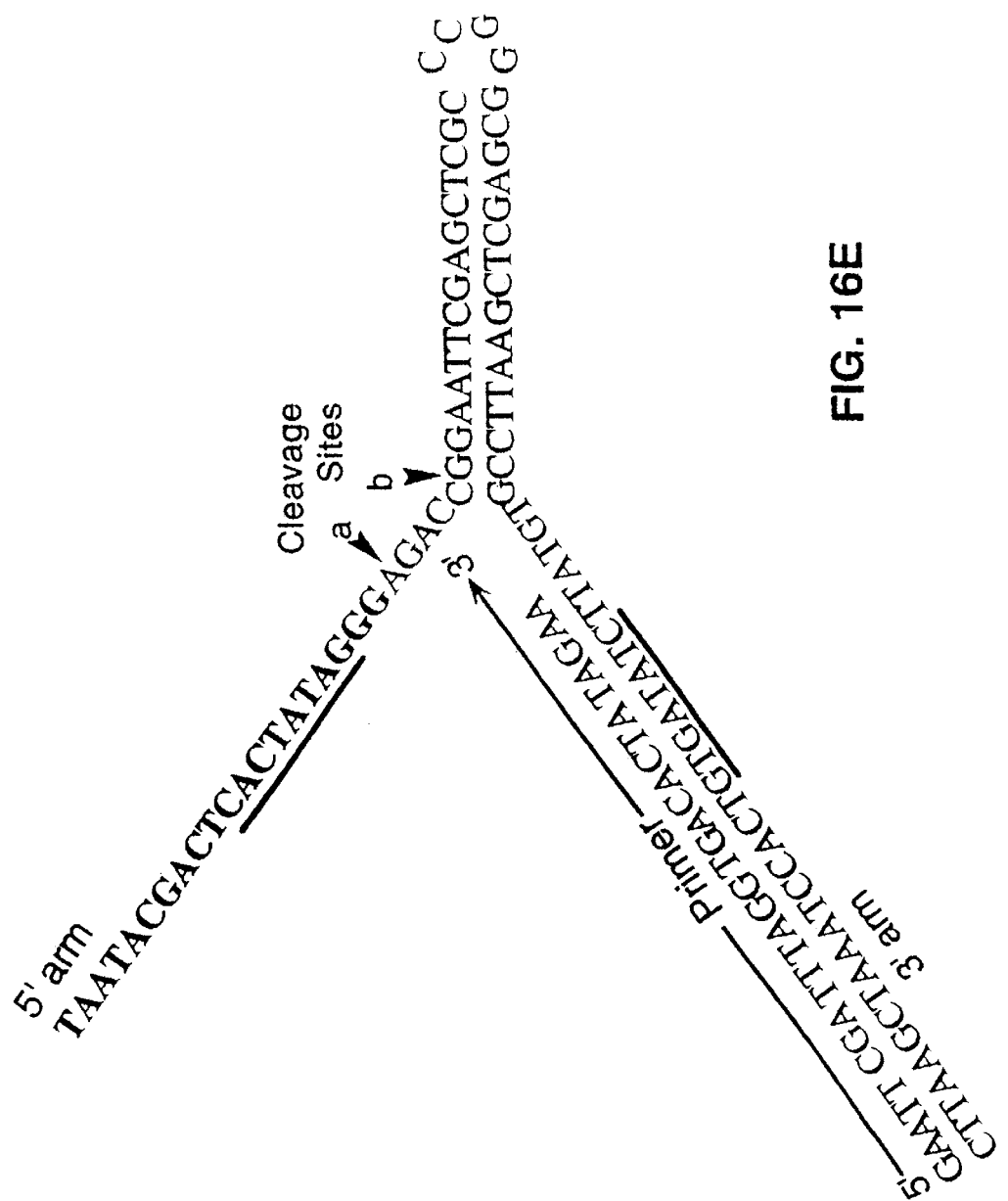

The cleavage structure may be made as a single hairpin molecule, with the 3' end of the target and the 5' end of the pilot joined as a loop as shown in FIG. 16E. A primer oligonucleotide complementary to the 3' arm is also required for these tests so that the enzyme's sensitivity to the presence of a primer may be tested.

Nucleic acids to be used to form test cleavage structures can be chemically synthesized, or can be generated by standard recombinant DNA techniques. By the latter method, the hairpin portion of the molecule can be created by inserting into a cloning vector duplicate copies of a short DNA segment, adjacent to each other but in opposing orientation. The double-stranded fragment encompassing this inverted repeat, and including enough flanking sequence to give short (about 20 nucleotides) unpaired 5' and 3' arms, can then be released from the vector by restriction enzyme digestion, or by PCR performed with an enzyme lacking a 5' exonuclease (e.g., the Stoffel fragment of Amplitaq™ DNA polymerase, Vent™ DNA polymerase).

The test DNA can be labeled on either end, or internally, with either a radioisotope, or with a non-isotopic tag. Whether the hairpin DNA is a synthetic single strand or a cloned double strand, the DNA is heated prior to use to melt all duplexes. When cooled on ice, the structure depicted in FIG. 16E is formed, and is stable for sufficient time to perform these assays.

To test for primer-directed cleavage (Reaction 1), a detectable quantity of the test molecule (typically 1–100 fmol of $^{32}$P-labeled hairpin molecule) and a 10 to 100-fold molar excess of primer are placed in a buffer known to be compatible with the test enzyme. For Reaction 2, where primer-directed cleavage is performed under condition which allow primer-independent cleavage, the same quantities of molecules are placed in a solution that is the same as the buffer used in Reaction 1 regarding pH, enzyme stabilizers (e.g., bovine serum albumin, nonionic detergents, gelatin) and reducing agents (e.g., dithiothreitol, 2-mercaptoethanol) but that replaces any monovalent cation salt with 20 mM KCl; 20 mM KCl is the demonstrated optimum for primer-independent cleavage. Buffers for enzymes, such as DNAPEcl, that usually operate in the absence of salt are not supplemented to achieve this concentration. To test for primer-independent cleavage (Reaction 3) the same quantity of the test molecule, but no primer, are combined under the same buffer conditions used for Reaction 2.

All three test reactions are then exposed to enough of the enzyme that the molar ratio of enzyme to test complex is approximately 1:1. The reactions are incubated at a range of temperatures up to, but not exceeding, the temperature allowed by either the enzyme stability or the complex stability, whichever is lower, up to 80° C. for enzymes from thermophiles, for a time sufficient to allow cleavage (10 to 60 minutes). The products of Reactions 1, 2 and 3 are resolved by denaturing polyacrylamide gel electrophoresis, and visualized by autoradiography or by a comparable method appropriate to the labeling system used. Additional labeling systems include chemiluminescence detection, silver or other stains, blotting and probing and the like. The presence of cleavage products is indicated by the presence of molecules which migrate at a lower molecular weight than does the uncleaved test structure. These cleavage products indicate that the candidate polymerase has structure-specific 5' nuclease activity.

To determine whether a modified DNA polymerase has substantially the same 5' nuclease activity as that of the native DNA polymerase, the results of the above-described tests are compared with the results obtained from these tests performed with the native DNA polymerase. By "substantially the same 5' nuclease activity" we mean that the modified polymerase and the native polymerase will both cleave test molecules in the same manner. It is not necessary that the modified polymerase cleave at the same rate as the native DNA polymerase.

Some enzymes or enzyme preparations may have other associated or contaminating activities that may be functional under the cleavage conditions described above and that may interfere with 5' nuclease detection. Reaction conditions can be modified in consideration of these other activities, to avoid destruction of the substrate, or other masking of the 5' nuclease cleavage and its products. For example, the DNA polymerase I of E. coli (Pol I), in addition to its polymerase and 5' nuclease activities, has a 3' exonuclease that can degrade DNA in a 3' to 5' direction. Consequently, when the molecule in FIG. 16E is exposed to this polymerase under the conditions described above, the 3' exonuclease quickly removes the unpaired 3' arm, destroying the bifurcated structure required of a substrate for the 5' exonuclease cleavage and no cleavage is detected. The true ability of Pol I to cleave the structure can be revealed if the 3' exonuclease is inhibited by a change of conditions (e.g., pH), mutation, or by addition of a competitor for the activity. Addition of 500 pmoles of a single-stranded competitor oligonucleotide, unrelated to the FIG. 16E structure, to the cleavage reaction with Pol I effectively inhibits the digestion of the 3' arm of the FIG. 16E structure without interfering with the 5' exonuclease release of the 5' arm. The concentration of the competitor is not critical, but should be high enough to occupy the 3' exonuclease for the duration of the reaction.

Similar destruction of the test molecule may be caused by contaminants in the candidate polymerase preparation. Several sets of the structure specific nuclease reactions may be performed to determine the purity of the candidate nuclease and to find the window between under and over exposure of the test molecule to the polymerase preparation being investigated.

The above described modified polymerases were tested for 5' nuclease activity as follows: Reaction 1 was performed in a buffer of 10 mM Tris-Cl, pH 8.5 at 20° C., 1.5 mM MgCl$_2$ and 50 mM KCl and in Reaction 2 the KCl concentration was reduced to 20 mM. In Reactions 1 and 2, 10 fmoles of the test substrate molecule shown in FIG. 16E were combined with 1 pmole of the indicated primer and 0.5 to 1.0 µl of extract containing the modified polymerase (prepared as described above). This mixture was then incubated for 10 minutes at 55° C. For all of the mutant polymerases tested these conditions were sufficient to give complete cleavage. When the molecule shown in FIG. 16E was labeled at the 5' end, the released 5' fragment, 25 nucleotides long, was conveniently resolved on a 20% polyacrylamide gel (19:1 cross-linked) with 7 M urea in a buffer containing 45 mM Tris-borate pH 8.3, 1.4 mM EDTA. Clones 4C–F and 5B exhibited structure-specific cleavage comparable to that of the unmodified DNA polymerase. Additionally, clones 4E, 4F and 4G have the added ability to cleave DNA in the absence of a 3' arm as discussed above. Representative cleavage reactions are shown in FIG. 17.

Figure 17:
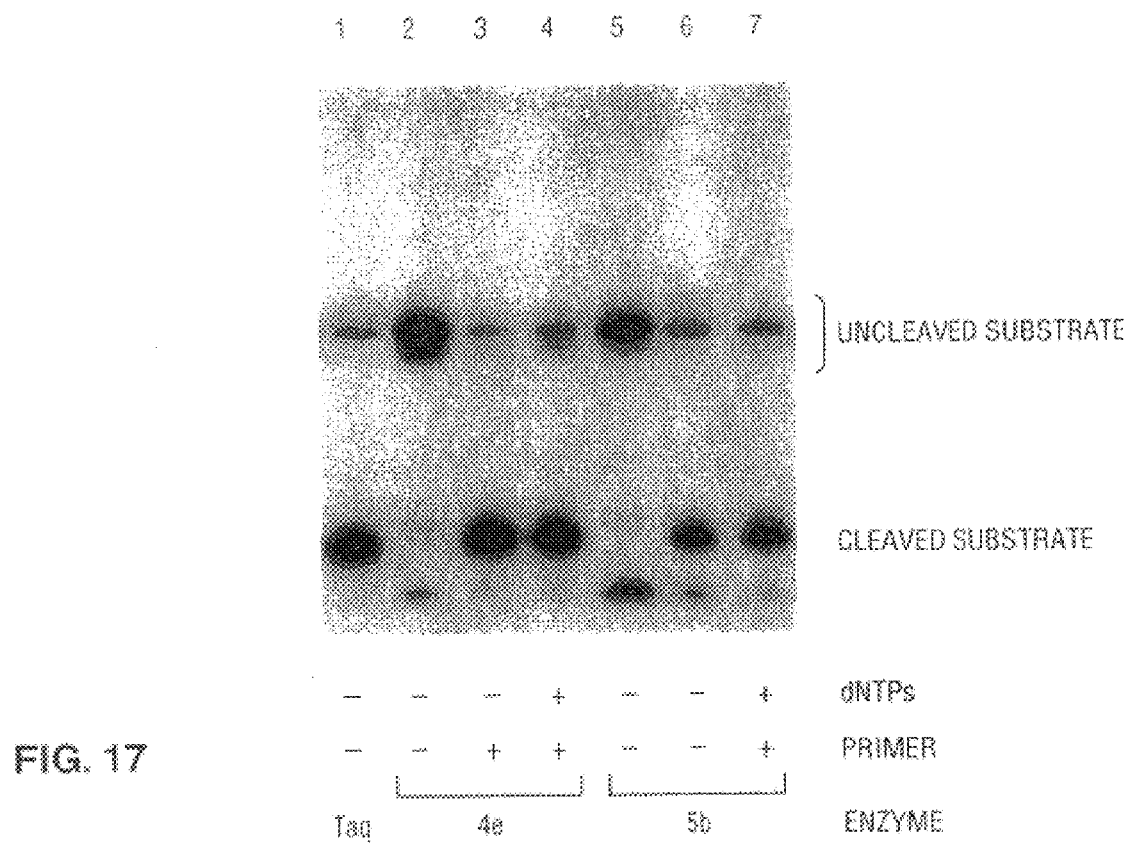
FIG. 17 is an autoradiogram of a gel showing the results of a cleavage reaction run with synthesis-deficient DNAPs.

For the reactions shown in FIG. 17, the mutant polymerase clones 4E (Taq mutant) and 5B (Tfl mutant) were examined for their ability to cleave the hairpin substrate molecule shown in FIG. 16E. The substrate molecule was labeled at the 5' terminus with $^{32}$P. 10 fmoles of heat-denatured, end-labeled substrate DNA and 0.5 units of DNAPTaq (lane 1) or 0.5 µl of 4e or 5b extract (FIG. 17, lanes 2–7, extract was prepared as described above) were mixed together in a buffer containing 10 mM Tris-Cl, pH 8.5, 50 mM KCl and 1.5 mM MgCl$_2$. The final reaction volume was 10 µl. Reactions shown in lanes 4 and 7 contain in addition 50 µM of each dNTP. Reactions shown in lanes 3, 4, 6 and 7 contain 0.2 µM of the primer oligonucleotide (complementary to the 3' arm of the substrate and shown in FIG. 16E). Reactions were incubated at 55° C. for 4 minutes. Reactions were stopped by the addition of 8 µl of 95% formamide containing 20 mM EDTA and 0.05% marker dyes per 10 µl reaction volume. Samples were then applied to 12% denaturing acrylamide gels. Following electrophoresis, the gels were autoradiographed. FIG. 17 shows that clones 4E and 5B exhibit cleavage activity similar to that of the native DNAPTaq. Note that some cleavage occurs in these reactions in the absence of the primer. When long hairpin structure, such as the one used here (FIG. 16E), are used in cleavage reactions performed in buffers containing 50 mM KCl a low level of primer-independent cleavage is seen. Higher concentrations of KCl suppress, but do not eliminate, this primer-independent cleavage under these conditions.

2. Assay For Synthetic Activity

The ability of the modified enzyme or proteolytic fragments is assayed by adding the modified enzyme to an assay system in which a primer is annealed to a template and DNA synthesis is catalyzed by the added enzyme. Many standard laboratory techniques employ such an assay. For example, nick translation and enzymatic sequencing involve extension of a primer along a DNA template by a polymerase molecule.

In a preferred assay for determining the synthetic activity of a modified enzyme an oligonucleotide primer is annealed to a single-stranded DNA template, e.g., bacteriophage M13 DNA, and the primer/template duplex is incubated in the presence of the modified polymerase in question, deoxynucleoside triphosphates (dNTPs) and the buffer and salts known to be appropriate for the unmodified or native enzyme. Detection of either primer extension (by denaturing gel electrophoresis) or dNTP incorporation (by acid precipitation or chromatography) is indicative of an active polymerase. A label, either isotopic or non-isotopic, is preferably included on either the primer or as a dNTP to facilitate detection of polymerization products. Synthetic activity is quantified as the amount of free nucleotide incorporated into the growing DNA chain and is expressed as amount incorporated per unit of time under specific reaction conditions.

Figure 18:
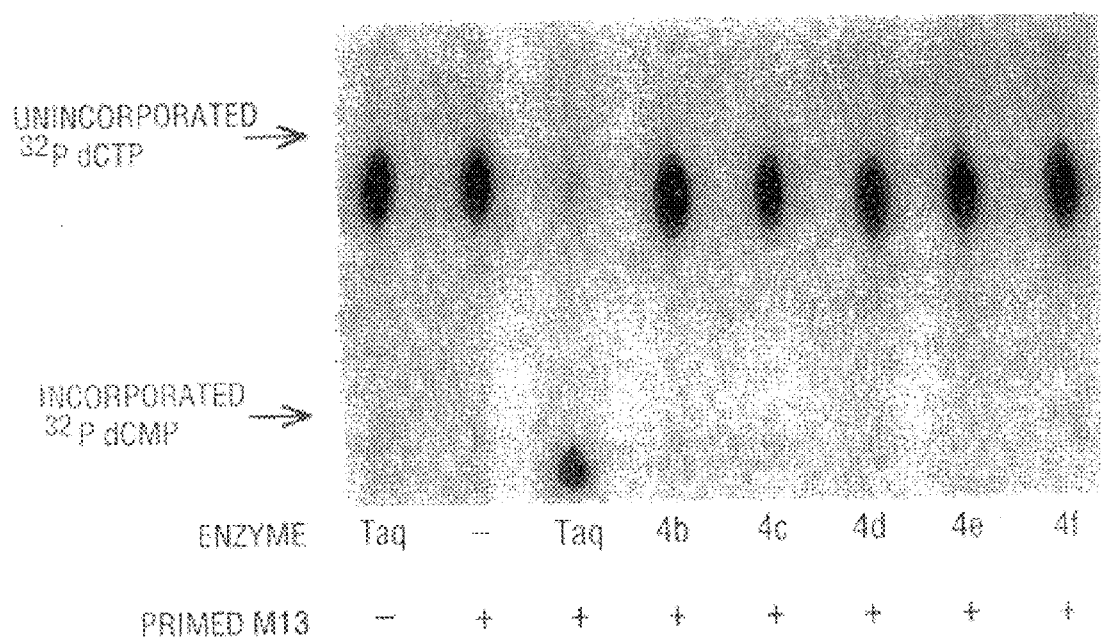
FIG. 18 is an autoradiogram of a PEI chromatogram resolving the products of an assay for synthetic activity in synthesis-deficient DNAPTaq clones.

Representative results of an assay for synthetic activity is shown in FIG. 18. The synthetic activity of the mutant DNAPTaq clones 4B–F was tested as follows: A master mixture of the following buffer was made: 1.2× PCR buffer (1× PCR buffer contains 50 mM KCl, 1.5 mM MgCl$_2$, 10 mM Tris-Cl, pH 8.5 and 0.05% each Tween 20 and Nonidet P40), 50 µM each of dGTP, dATP and dTTP, 5 µM dCTP and 0.125 µM α-$^{32}$P-dCTP at 600 Ci/mmol. Before adjusting this mixture to its final volume, it was divided into two equal aliquots. One received distilled water up to a volume of 50 µl to give the concentrations above. The other received 5 µg of single-stranded M13mp18 DNA (approximately 2.5 pmol or 0.05 µM final concentration) and 250 pmol of M13 sequencing primer (5 µM final concentration) and distilled water to a final volume of 50 µl. Each cocktail was warmed to 75° C. for 5 minutes and then cooled to room temperature. This allowed the primers to anneal to the DNA in the DNA-containing mixtures.

For each assay, 4 µl of the cocktail with the DNA was combined with 1 µl of the mutant polymerase, prepared as described, or 1 unit of DNAPTaq (Perkin Elmer) in 1 µl of dH$_2$O. A "no DNA" control was done in the presence of the DNAPTaq (FIG. 18, lane 1), and a "no enzyme" control was done using water in place of the enzyme (lane 2). Each reaction was mixed, then incubated at room temperature (approx. 22° C.) for 5 minutes, then at 55° C. for 2 minutes, then at 72° C. for 2 minutes. This step incubation was done to detect polymerization in any mutants that might have optimal temperatures lower than 72° C. After the final incubation, the tubes were spun briefly to collect any condensation and were placed on ice. One µl of each reaction was spotted at an origin 1.5 cm from the bottom edge of a polyethyleneimine (PEI) cellulose thin layer chromatography plate and allowed to dry. The chromatography plate was run in 0.75 M NaH$_2$PO$_4$, pH 3.5, until the buffer front had run approximately 9 cm from the origin. The plate was dried, wrapped in plastic wrap, marked with luminescent ink, and exposed to X-ray film. Incorporation was detected as counts that stuck where originally spotted, while the unincorporated nucleotides were carried by the salt solution from the origin.

Comparison of the locations of the counts with the two control lanes confirmed the lack of polymerization activity in the mutant preparations. Among the modified DNAPTaq clones, only clone 4B retains any residual synthetic activity as shown in FIG. 18.

EXAMPLE 3

Figure 19A:
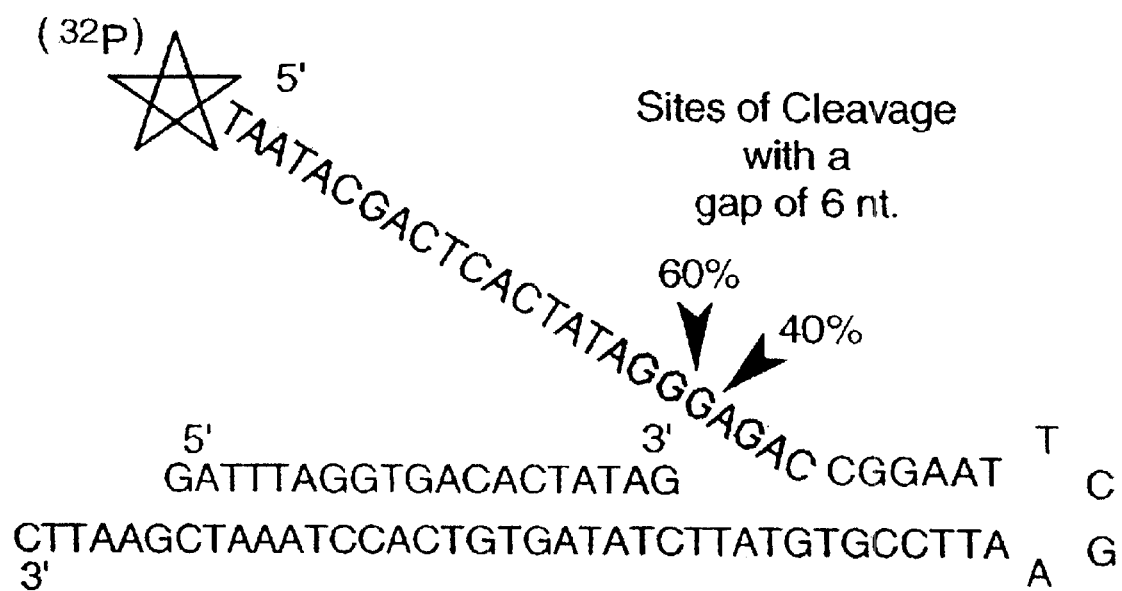
FIG. 19A depicts the substrate molecule used to test the ability of synthesis-deficient DNAPs to cleave short hairpin structures.

5' Nucleases Derived From Thermostable DNA Polymerases Can Cleave Short Hairpin Structures With Specificity The ability of the 5' nucleases to cleave hairpin structures to generate a cleaved hairpin structure suitable as a detection molecule was examined. The structure and sequence of the hairpin test molecule is shown in FIG. 19A (SEQ ID NO:15). The oligonucleotide (labeled "primer" in FIG. 19A, SEQ ID NO:22) is shown annealed to its complementary sequence on the 3' arm of the hairpin test molecule. The hairpin test molecule was single-end labeled with $^{32}$P using a labeled T7 promoter primer in a polymerase chain reaction. The label is present on the 5' arm of the hairpin test molecule and is represented by the star in FIG. 19A.

The cleavage reaction was performed by adding 10 fmoles of heat-denatured, end-labeled hairpin test molecule, 0.2 uM of the primer oligonucleotide (complementary to the 3' arm of the hairpin), 50 µM of each dNTP and 0.5 units of DNAPTaq (Perkin Elmer) or 0.5 µl of extract containing a 5' nuclease (prepared as described above) in a total volume of 10 µl in a buffer containing 10 mM Tris-Cl, pH 8.5, 50 mM KCl and 1.5 mM $MgCl_2$. Reactions shown in lanes 3, 5 and 7 were run in the absence of dNTPs.

Reactions were incubated at 55° C. for 4 minutes. Reactions were stopped at 55° C. by the addition of 8 µl of 95% formamide with 20 mM EDTA and 0.05% marker dyes per 10 µl reaction volume. Samples were not heated before loading onto denaturing polyacrylamide gels (10% polyacrylamide, 19:1 crosslinking, 7 M urea, 89 mM Tris-borate, pH 8.3, 2.8 mM EDTA). The samples were not heated to allow for the resolution of single-stranded and re-duplexed uncleaved hairpin molecules.

Figure 19B:
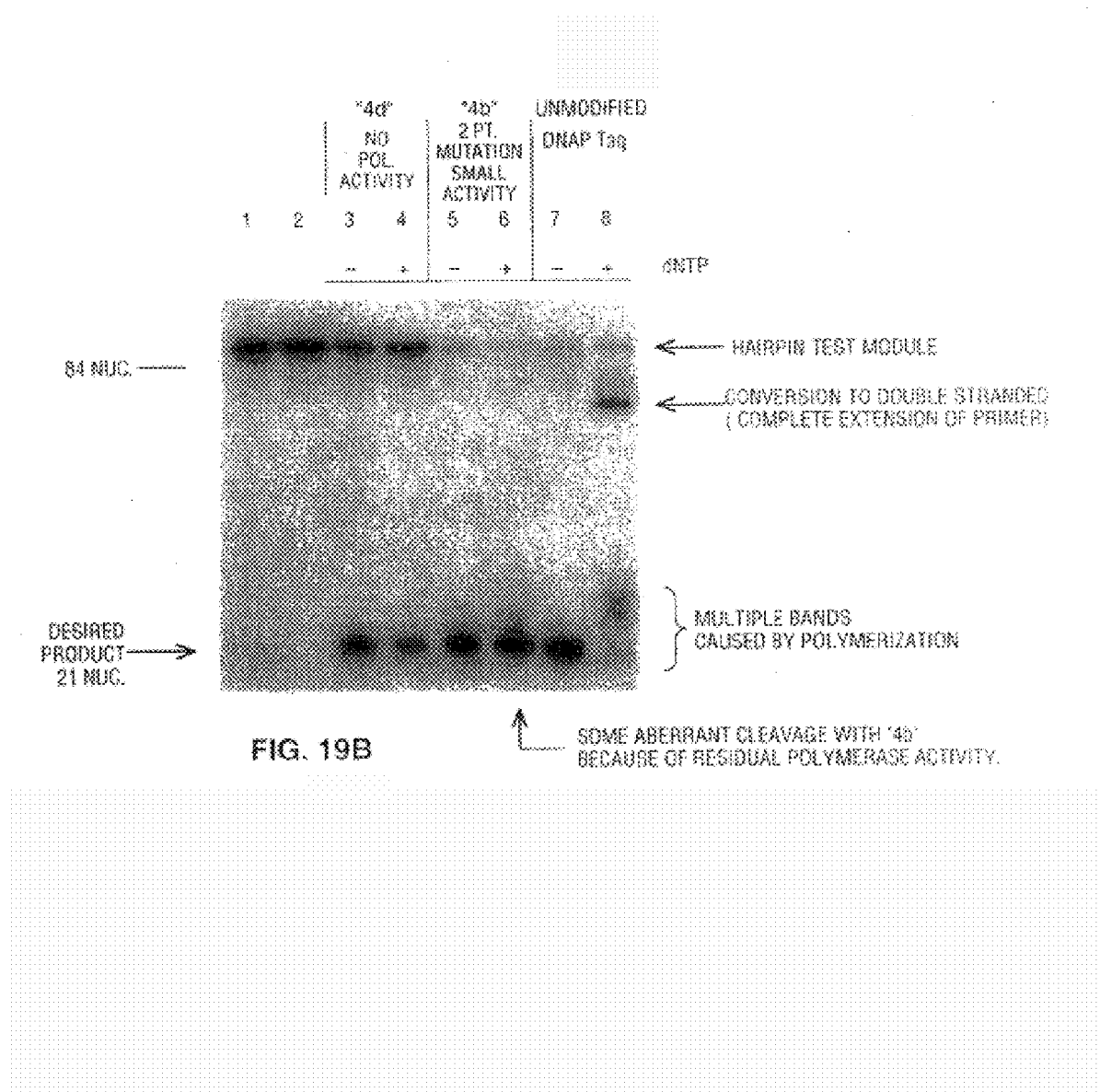
FIG. 19B shows an autoradiogram of a gel resolving the products of a cleavage reaction run using the substrate shown in FIG. 19A.

FIG. 19B shows that altered polymerases lacking any detectable synthetic activity cleave a hairpin structure when an oligonucleotide is annealed to the single-stranded 3' arm of the hairpin to yield a single species of cleaved product (FIG. 19B, lanes 3 and 4). 5' nucleases, such as clone 4D, shown in lanes 3 and 4, produce a single cleaved product even in the presence of dNTPs. 5' nucleases which retain a residual amount of synthetic activity (less than 1% of wild type activity) produce multiple cleavage products as the polymerase can extend the oligonucleotide annealed to the 3' arm of the hairpin thereby moving the site of cleavage (clone 4B, lanes 5 and 6). Native DNAPTaq produces even more species of cleavage products than do mutant polymerases retaining residual synthetic activity and additionally converts the hairpin structure to a double-stranded form in the presence of dNTPs due to the high level of synthetic activity in the native polymerase (FIG. 19B, lane 8).

EXAMPLE 4

Test Of The Trigger/Detection Assay

To test the ability of an oligonucleotide of the type released in the trigger reaction of the trigger/detection assay to be detected in the detection reaction of the assay, the two hairpin structures shown in FIG. 20A were synthesized using standard techniques. The two hairpins are termed the A-hairpin (SEQ ID NO:23) and the T-hairpin (SEQ ID NO:24). The predicted sites of cleavage in the presence of the appropriate annealed primers are indicated by the arrows. The A- and T-hairpins were designed to prevent intra-strand mis-folding by omitting most of the T residues in the A-hairpin and omitting most of the A residues in the T-hairpin. To avoid mis-priming and slippage, the hairpins were designed with local variations in the sequence motifs (e.g., spacing T residues one or two nucleotides apart or in pairs). The A- and T-hairpins can be annealed together to form a duplex which has appropriate ends for directional cloning in pUC-type vectors; restriction sites are located in the loop regions of the duplex and can be used to elongate the stem regions if desired.

The sequence of the test trigger oligonucleotide is shown in FIG. 20B; this oligonucleotide is termed the alpha primer (SEQ ID NO:25). The alpha primer is complementary to the 3' arm of the T-hairpin as shown in FIG. 20A. When the alpha primer is annealed to the T-hairpin, a cleavage structure is formed that is recognized by thermostable DNA polymerases. Cleavage of the T-hairpin liberates the 5' single-stranded arm of the T-hairpin, generating the tau primer (SEQ ID NO:26) and a cleaved T-hairpin (FIG. 20B; SEQ ID NO:27). The tau primer is complementary to the 3' arm of the A-hairpin as shown in FIG. 20A. Annealing of the tau primer to the A-hairpin generates another cleavage structure; cleavage of this second cleavage structure liberates the 5' single-stranded arm of the A-hairpin, generating another molecule of the alpha primer which then is annealed to another molecule of the T-hairpin. Thermocycling releases the primers so they can function in additional cleavage reactions. Multiple cycles of annealing and cleavage are carried out. The products of the cleavage reactions are primers and the shortened hairpin structures shown in FIG. 20C. The shortened or cleaved hairpin structures may be resolved from the uncleaved hairpins by electrophoresis on denaturing acrylamide gels.

The annealing and cleavage reactions are carried as follows: In a 50 µl reaction volume containing 10 mM Tris-Cl, pH 8.5, 1.0 $MgCl_2$, 75 mM KCl, 1 pmole of A-hairpin, 1 pmole T-hairpin, the alpha primer is added at equimolar amount relative to the hairpin structures (1 pmole) or at dilutions ranging from 10- to $10^6$-fold and 0.5 µl of extract containing a 5' nuclease (prepared as described above) are added. The predicted melting temperature for the alpha or trigger primer is 60° C. in the above buffer. Annealing is performed just below this predicted melting temperature at 55° C. Using a Perkin Elmer DNA Thermal Cycler, the reactions are annealed at 55° C. for 30 seconds. The temperature is then increased slowly over a five minute period to 72° C. to allow for cleavage. After cleavage, the reactions are rapidly brought to 55° C. (1° C. per second) to allow another cycle of annealing to occur. A range of cycles are performed (20, 40 and 60 cycles) and the reaction products are analyzed at each of these number of cycles. The number of cycles which indicates that the accumulation of cleaved hairpin products has not reached a plateau is then used for subsequent determinations when it is desirable to obtain a quantitative result.

Following the desired number of cycles, the reactions are stopped at 55° C. by the addition of 8 µl of 95% formamide with 20 mM EDTA and 0.05% marker dyes per 10 µl reaction volume. Samples are not heated before loading onto denaturing polyacrylamide gels (10% polyacrylamide, 19:1 crosslinking, 7 M urea, 89 mM tris-borate, pH 8.3, 2.8 mM EDTA). The samples were not heated to allow for the resolution of single-stranded and re-duplexed uncleaved hairpin molecules.

The hairpin molecules may be attached to separate solid support molecules, such as agarose, styrene or magnetic beads, via the 3' end of each hairpin. A spacer molecule may be placed between the 3' end of the hairpin and the bead if so desired. The advantage of attaching the hairpins to a solid support is that this prevents the hybridization of the A- and T-hairpins to one another during the cycles of melting and annealing. The A- and T-hairpins are complementary to one another (as shown in FIG. 20D) and if allowed to anneal to one another over their entire lengths this would reduce the amount of hairpins available for hybridization to the alpha and tau primers during the detection reaction.

The 5' nucleases of the present invention are used in this assay because they lack significant synthetic activity. The lack of synthetic activity results in the production of a single cleaved hairpin product (as shown in FIG. 19B, lane 4). Multiple cleavage products may be generated by 1) the presence of interfering synthetic activity (see FIG. 19B, lanes 6 and 8) or 2) the presence of primer-independent cleavage in the reaction. The presence of primer-independent cleavage is detected in the trigger/detection assay by the presence of different sized products at the fork of the cleavage structure. Primer-independent cleavage can be dampened or repressed, when present, by the use of uncleavable nucleotides in the fork region of the hairpin molecule. For example, thiolated nucleotides can be used to replace several nucleotides at the fork region to prevent primer-independent cleavage.

EXAMPLE 5

Cleavage Of Linear Nucleic Acid Substrates

Figure 22A:
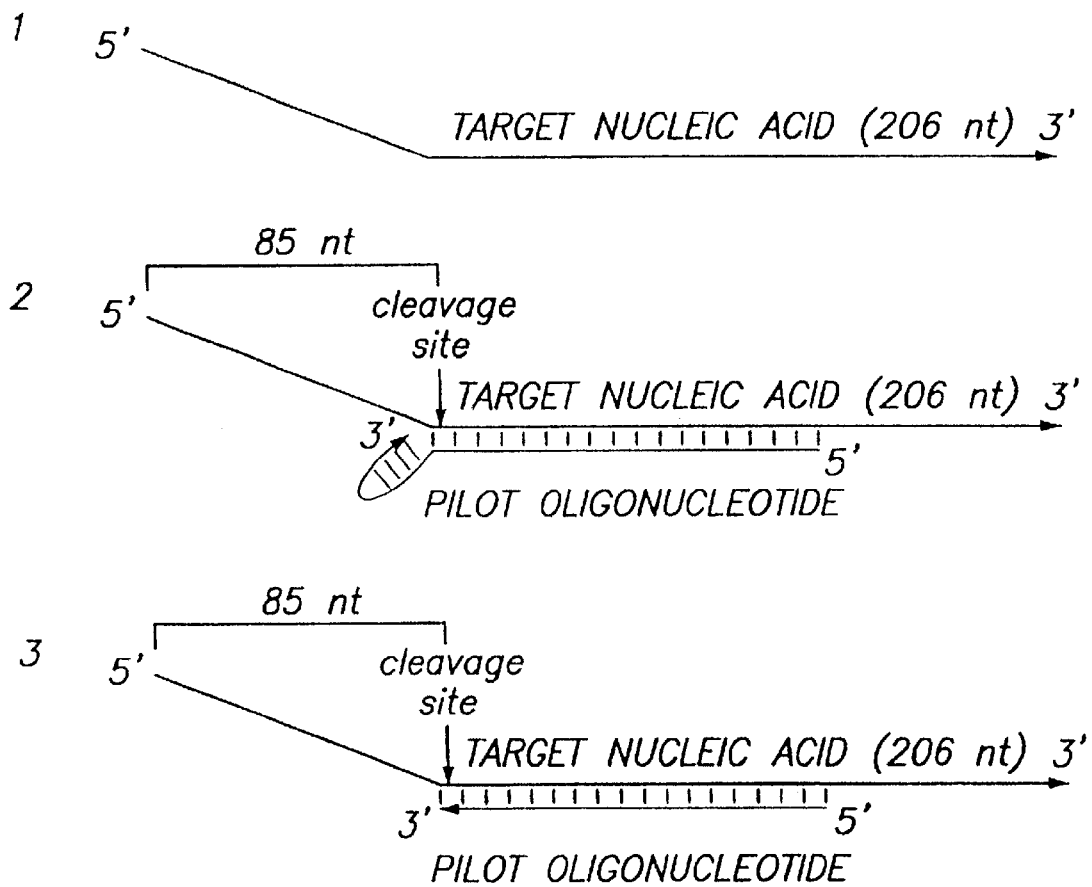

From the above, it should be clear that native (i.e., "wild type") thermostable DNA polymerases are capable of cleaving hairpin structures in a specific manner and that this discovery can be applied with success to a detection assay. In this example, the mutant DNAPs of the present invention are tested against three different cleavage structures shown in FIG. 22A. Structure 1 in FIG. 22A is simply single stranded 206-mer (the preparation and sequence information for which was discussed above). Structures 2 and 3 are duplexes; structure 2 is the same hairpin structure as shown in FIG. 12A (bottom), while structure 3 has the hairpin portion of structure 2 removed.

The cleavage reactions comprised 0.01 pmoles of the resulting substrate DNA, and 1 pmole of pilot oligonucleotide in a total volume of 10 µl of 10 mM Tris-Cl, pH 8.3. 100 mM KCl, 1 mM MgCl$_2$. Reactions were incubated for 30 minutes at 55° C., and stopped by the addition of 8 µl of 95% formamide with 20 mM EDTA and 0.05% marker dyes. Samples were heated to 75° C. for 2 minutes immediately before electrophoresis through a 10% polyacrylamide gel (19:1 cross link), with 7 M urea, in a buffer of 45 mM Tris-Borate, pH 8.3, 1.4 mM EDTA.

Figure 22B:
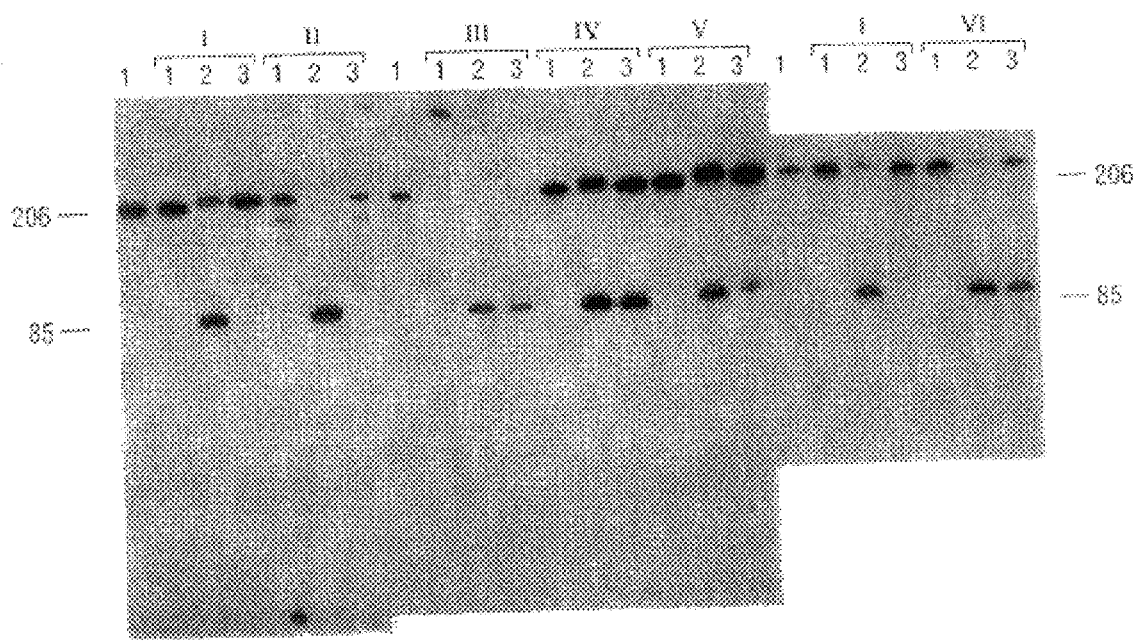

The results were visualized by autoradiography and are shown in FIG. 22B with the enzymes indicated as follows: I is native Taq DNAP; II is native Tfl DNAP; III is Cleavase® BX shown in FIG. 4E; IV is Cleavase® BB shown in FIG. 4F; V is the mutant shown in FIG. 5B; and VI is Cleavase® BN shown in FIG. 4G.

Structure 2 was used to "normalize" the comparison. For example, it was found that it took 50 ng of Taq DNAP and 300 ng of Cleavase® BN to give similar amounts of cleavage of Structure 2 in thirty (30) minutes. Under these conditions native Taq DNAP is unable to cleave Structure 3 to any significant degree. Native Tfl DNAP cleaves Structure 3 in a manner that creates multiple products.

By contrast, all of the mutants tested cleave the linear duplex of Structure 3. This finding indicates that this characteristic of the mutant DNA polymerases is consistent of thermostable polymerases across thermophilic species.

Figure 23:
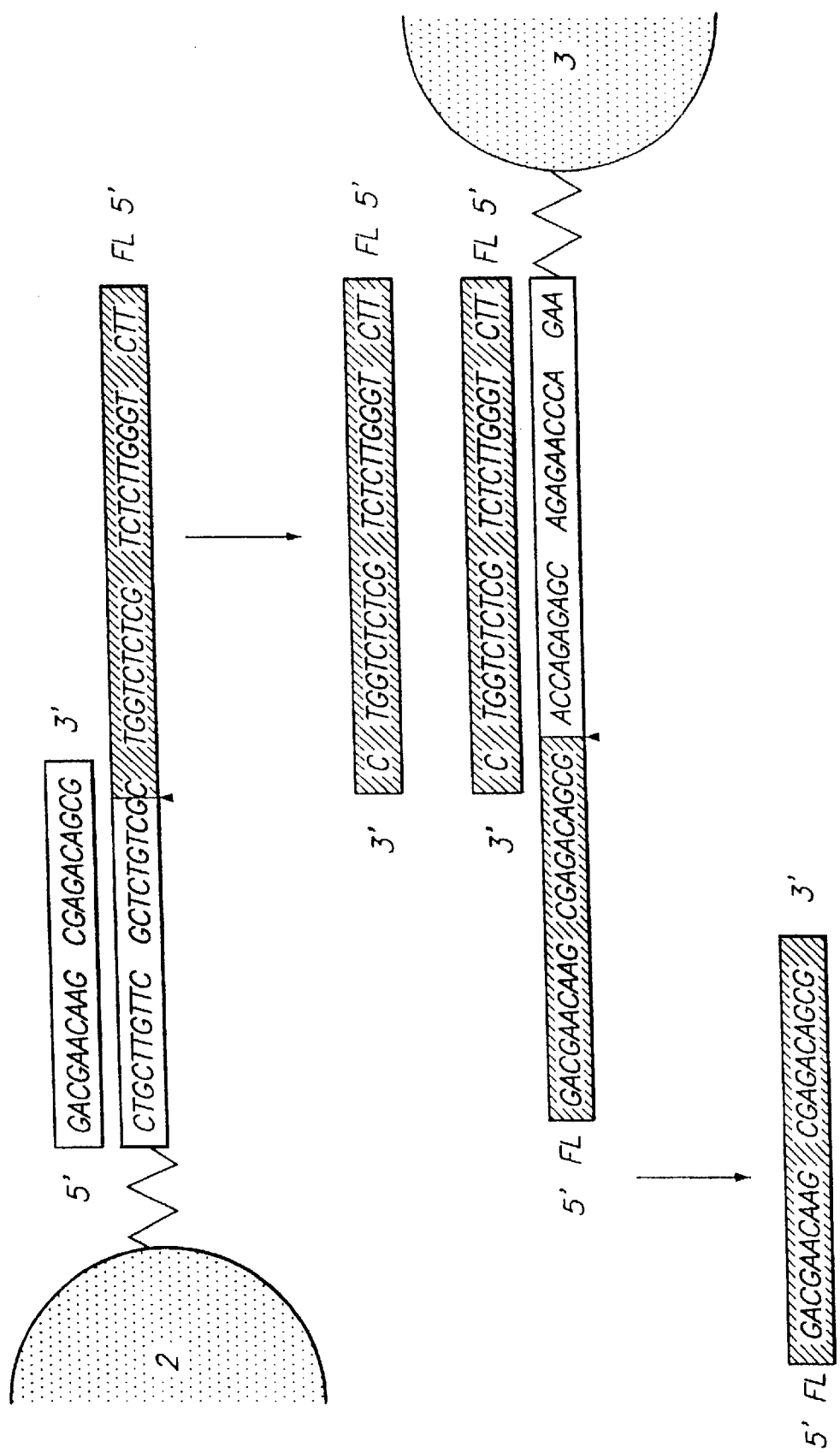
FIG. 23 provides a detailed schematic corresponding to one embodiment of the detection method of the present invention.

The finding described herein that the mutant DNA polymerases of the present invention are capable of cleaving linear duplex structures allows for application to a more straightforward assay design (FIG. 1A). FIG. 23 provides a more detailed schematic corresponding to the assay design of FIG. 1A.

The two 43-mers depicted in FIG. 23 were synthesized by standard methods. Each included a fluorescein on the 5' end for detection purposes and a biotin on the 3' end to allow attachment to streptavidin coated paramagnetic particles (the biotin-avidin attachment is indicated by the zig-zag line).

Before the trityl groups were removed, the oligonucleotides were purified by HPLC to remove truncated by-products of the synthesis reaction. Aliquots of each 43-mer were bound to M-280 Dynabeads (Dynal) at a density of 100 pmoles per mg of beads. Two (2) mgs of beads (200 µl) were washed twice in 1× wash/bind buffer (1 M NaCl, 5 mM Tris-Cl, pH 7.5, 0.5 mM EDTA) with 0.1% BSA, 200 µl per wash. The beads were magnetically sedimented between washes to allow supernatant removal. After the second wash, the beads were resuspended in 200 µl of 2× wash/bind buffer (2 M Na Cl, 10 mM Tris-Cl, pH 7.5 with 1 mM EDTA), and divided into two 100 µl aliquots. Each aliquot received 1 µl of a 100 µM solution of one of the two oligonucleotides. After mixing, the beads were incubated at room temperature for 60 minutes with occasional gentle mixing. The beads were then sedimented and analysis of the supernatants showed only trace amounts of unbound oligonucleotide, indicating successful binding. Each aliquot of beads was washed three times, 100 µl per wash, with 1× wash/bind buffer, then twice in a buffer of 10 mM Tris-Cl, pH 8.3 and 75 mM KCl. The beads were resuspended in a final volume of 100 µl of the Tris/KCl, for a concentration of 1 pmole of oligonucleotide bound to 10 µg of beads per µl of suspension. The beads were stored at 4° C. between uses.

The types of beads correspond to FIG. 1A. That is to say, type 2 beads contain the oligonucleotide (SEQ ID NO:33) comprising the complementary sequence (SEQ ID NO:34) for the alpha signal oligonucleotide (SEQ ID NO:35) as well as the beta signal oligonucleotide (SEQ ID NO:36) which when liberated is a 24-mer. This oligonucleotide has no "As" and is "T" rich. Type 3 beads contain the oligonucleotide (SEQ ID NO:37) comprising the complementary sequence (SEQ ID NO:38) for the beta signal oligonucleotide (SEQ ID NO:39) as well as the alpha signal oligonucleotide (SEQ ID NO:35) which when liberated is a 20-mer. This oligonucleotide has no "Ts" and is "A" rich.

Cleavage reactions comprised 1 µl of the indicated beads, 10 pmoles of unlabelled alpha signal oligonucleotide as "pilot" (if indicated) and 500 ng of Cleavase® BN in 20 µl of 75 mM KCl, 10 mM Tris-Cl, pH 8.3, 1.5 mM MgCl$_2$ and 10 µM CTAB. All components except the enzyme were assembled, overlaid with light mineral oil and warmed to 53° C. The reactions were initiated by the addition of prewarmed enzyme and incubated at that temperature for 30 minutes. Reactions were stopped at temperature by the addition of 16 µl of 95% formamide with 20 mM EDTA and 0.05% each of bromophenol blue and xylene cyanol. This addition stops the enzyme activity and, upon heating, disrupts the biotin-avidin link, releasing the majority (greater than 95%) of the oligonucleotides from the beads. Samples were heated to 75° C. for 2 minutes immediately before electrophoresis through a 10% polyacrylamide gel (19:1 cross link), with 7 M urea, in a buffer of 45 mM Tris-Borate, pH 8.3, 1.4 mM EDTA. Results were visualized by contact transfer of the resolved DNA to positively charged nylon membrane and probing of the blocked membrane with an anti-fluorescein antibody conjugated to alkaline phosphatase. After washing, the signal was developed by incubating the membrane in Western Blue (Promega) which deposits a purple precipitate where the antibody is bound.

Figure 24:
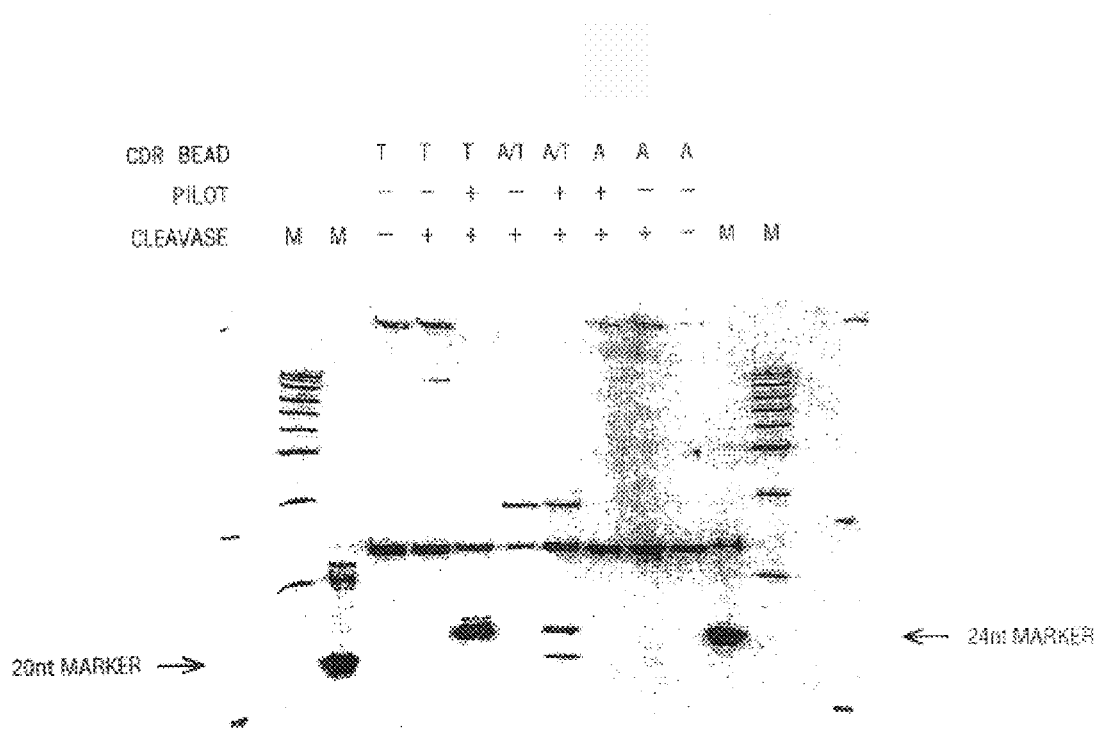
FIG. 24 shows the propagation of cleavage of the linear duplex nucleic acid structures of FIG. 23 by the 5' nucleases of the present invention.

FIG. 24 shows the propagation of cleavage of the linear duplex nucleic acid structures of FIG. 23 by the DNAP mutants of the present invention. The two center lanes contain both types of beads. As noted above, the beta signal oligonucleotide (SEQ ID NO:36) when liberated is a 24-mer and the alpha signal oligonucleotide (SEQ ID NO:35) when liberated is a 20-mer. The formation of the two lower bands corresponding to the 24-mer and 20-mer is clearly dependent on "pilot".

EXAMPLE 6

5' Exonucleolytic Cleavage ("Nibbling") By Thermostable DNAPs

It has been found that thermostable DNAPs, including those of the present invention, have a true 5' exonuclease capable of nibbling the 5' end of a linear duplex nucleic acid structures. In this example, the 206 base pair DNA duplex substrate is again employed (see above). In this case, it was produced by the use of one $^{32}$P-labeled primer and one unlabeled primer in a polymerase chain reaction. The cleavage reactions comprised 0.01 pmoles of heat-denatured, end-labeled substrate DNA (with the unlabeled strand also present), 5 pmoles of pilot oligonucleotide (see pilot oligonucleotides in FIG. 12A) and 0.5 units of DNAPTaq or 0.5μ of Cleavase® BB in the *E. coli* extract (see above), in a total volume of 10 μl of 10 mM Tris•Cl, pH 8.5, 50 mM KCl, 1.5 mM MgCl$_2$.

Figures 25A, 25B:
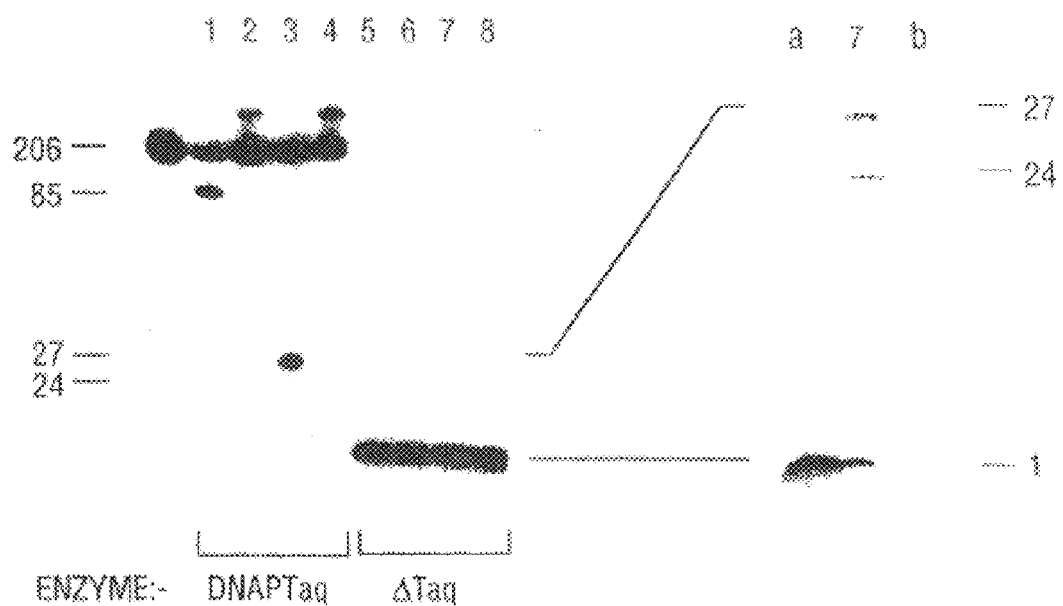
FIG. 25A shows the "nibbling" phenomenon detected with the DNAPs of the present invention.
FIG. 25B shows that the "nibbling" of FIG. 25A is 5' nucleolytic cleavage and not phosphatase cleavage.

Reactions were initiated at 65° C. by the addition of pre-warmed enzyme, then shifted to the final incubation temperature for 30 minutes. The results are shown in FIG. 25A. Samples in lanes 1–4 are the results with native Taq DNAP, while lanes 5–8 shown the results with Cleavase® BB. The reactions for lanes 1, 2, 5, and 6 were performed at 65° C. and reactions for lanes 3, 4, 7, and 8 were performed at 50° C. and all were stopped at temperature by the addition of 8 μl of 95% formamide with 20 mM EDTA and 0.05% marker dyes. Samples were heated to 75° C. for 2 minutes immediately before electrophoresis through a 10% acrylamide gel (19:1 cross-linked), with 7 M urea, in a buffer of 45 mM Tris•Borate, pH 8.3, 1.4 mM EDTA. The expected product in reactions 1, 2, 5, and 6 is 85 nucleotides long; in reactions 3 and 7, the expected product is 27 nucleotides long. Reactions 4 and 8 were performed without pilot, and should remain at 206 nucleotides. The faint band seen at 24 nucleotides is residual end-labeled primer from the PCR.

The surprising result is that Cleavase® BB under these conditions causes all of the label to appear in a very small species, suggesting the possibility that the enzyme completely hydrolyzed the substrate. To determine the composition of the fastest-migrating band seen in lanes 5–8 (reactions performed with the deletion mutant), samples of the 206 base pair duplex were treated with either T7 gene 6 exonuclease (USB) or with calf intestine alkaline phosphatase (Promega), according to manufacturers' instructions, to produce either labeled mononucleotide (lane a of FIG. 25B) or free $^{32}$P-labeled inorganic phosphate (lane b of FIG. 25B), respectively. These products, along with the products seen in lane 7 of panel A were resolved by brief electrophoresis through a 20% acrylamide gel (19:1 cross-link), with 7 M urea, in a buffer of 45 mM Tris•Borate, pH 8.3, 1.4 mM EDTA. Cleavase® BB is thus capable of converting the substrate to mononucleotides.

EXAMPLE 7

Nibbling Is Duplex Dependent

The nibbling by Cleavase® BB is duplex dependent. In this example, internally labeled, single strands of the 206-mer were produced by 15 cycles of primer extension incorporating α-$^{32}$P labeled dCTP combined with all four unlabeled dNTPs, using an unlabeled 206-bp fragment as a template. Single and double stranded products were resolved by electrophoresis through a non-denaturing 6% polyacrylamide gel (29:1 cross-link) in a buffer of 45 mM Tris•Borate, pH 8.3, 1.4 mM EDTA, visualized by autoradiography, excised from the gel, eluted by passive diffusion, and concentrated by ethanol precipitation.

Figure 26A:
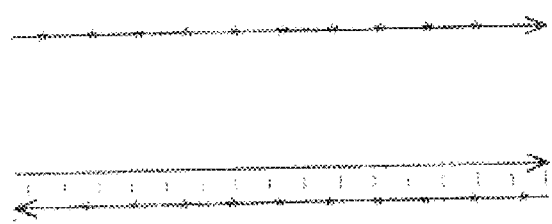
FIG. 26 demonstrates that the "nibbling" phenomenon is duplex dependent.
Figure 26B:
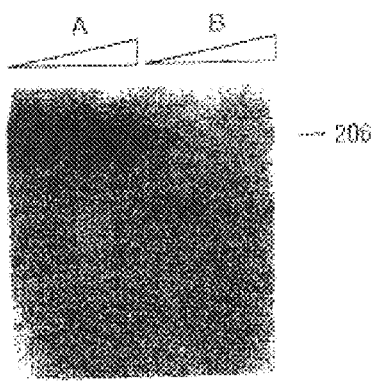

The cleavage reactions comprised 0.04 pmoles of substrate DNA, and 2 μl of Cleavase® BB (in an *E. coil* extract as described above) in a total volume of 40 μl of 10 mM Tris•Cl, pH 8.5, 50 mM KCl, 1.5 mM MgCl$_2$. Reactions were initiated by the addition of pre-warmed enzyme; 10 μl aliquots were removed at 5, 10, 20, and 30 minutes, and transferred to prepared tubes containing 8 μl of 95% formamide with 30 mM EDTA and 0.05% marker dyes. Samples were heated to 75° C. for 2 minutes immediately before electrophoresis through a 10% acrylamide gel (19:1 cross-linked), with 7 M urea, in a buffer of 45 mM Tris•Borate, pH 8.3, 1.4 mM EDTA. Results were visualized by autoradiography as shown in FIG. 26. Clearly, the cleavage by Cleavase® BB depends on a duplex structure; no cleavage of the single strand structure is detected whereas cleavage of the 206-mer duplex is complete.

EXAMPLE 8

Nibbling Can Be Target Directed

Figure 27:
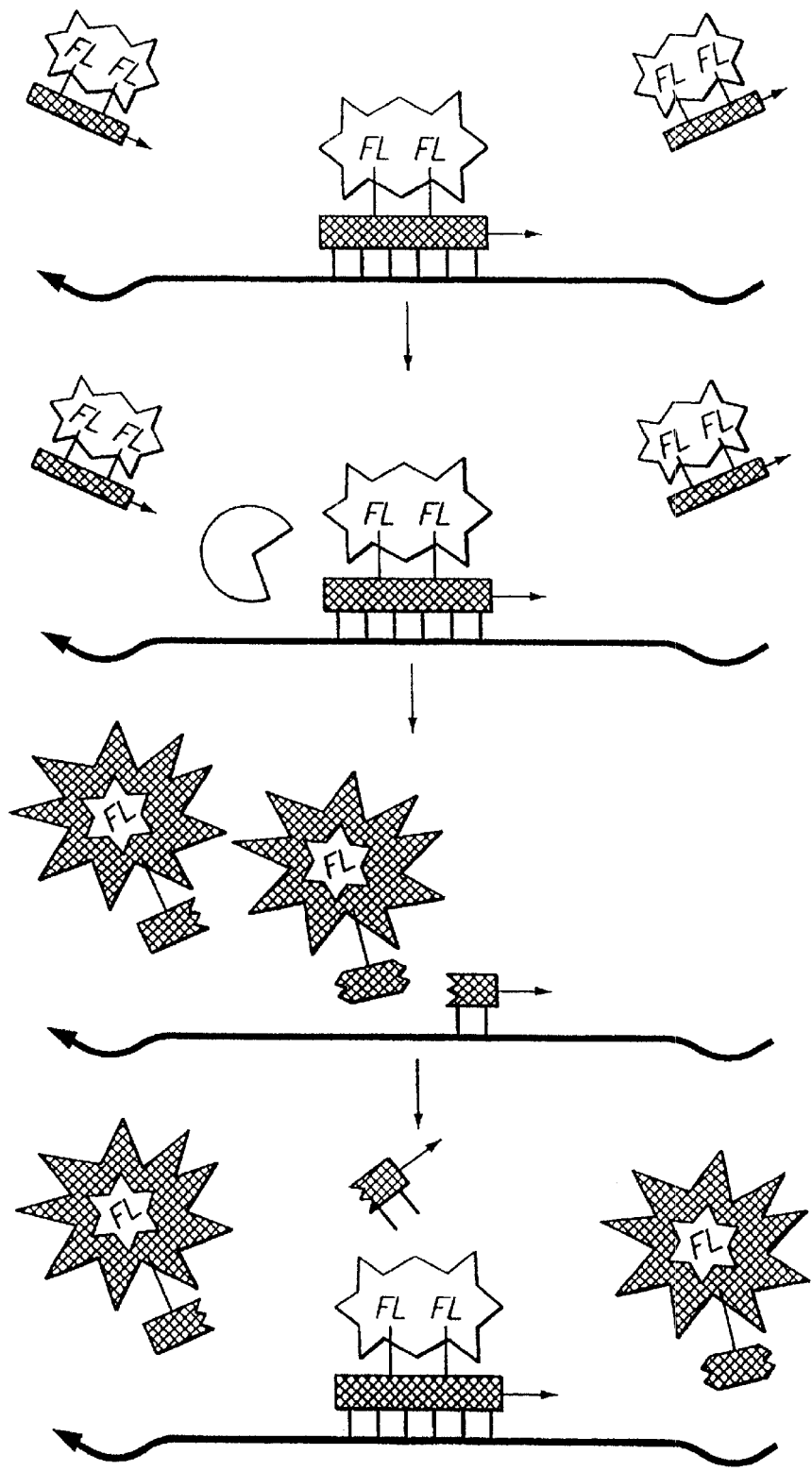
FIG. 27 is a schematic showing how "nibbling" can be employed in a detection assay.

The nibbling activity of the DNAPs of the present invention can be employed with success in a detection assay. One embodiment of such an assay is shown in FIG. 27. In this assay, a labeled oligonucleotide is employed that is specific for a target sequence. The oligonucleotide is in excess of the target so that hybridization is rapid. In this embodiment, the oligonucleotide contains two fluorescein labels whose proximity on the oligonucleotide causes their emission to be quenched. When the DNAP is permitted to nibble the oligonucleotide the labels separate and are detectable. The shortened duplex is destabilized and disassociates. Importantly, the target is now free to react with an intact labeled oligonucleotide. The reaction can continue until the desired level of detection is achieved. An analogous, although different, type of cycling assay has been described employing lambda exonuclease. See C. G. Copley and C. Boot, *BioTechniques* 13:888 (1992).

Figure 28A:
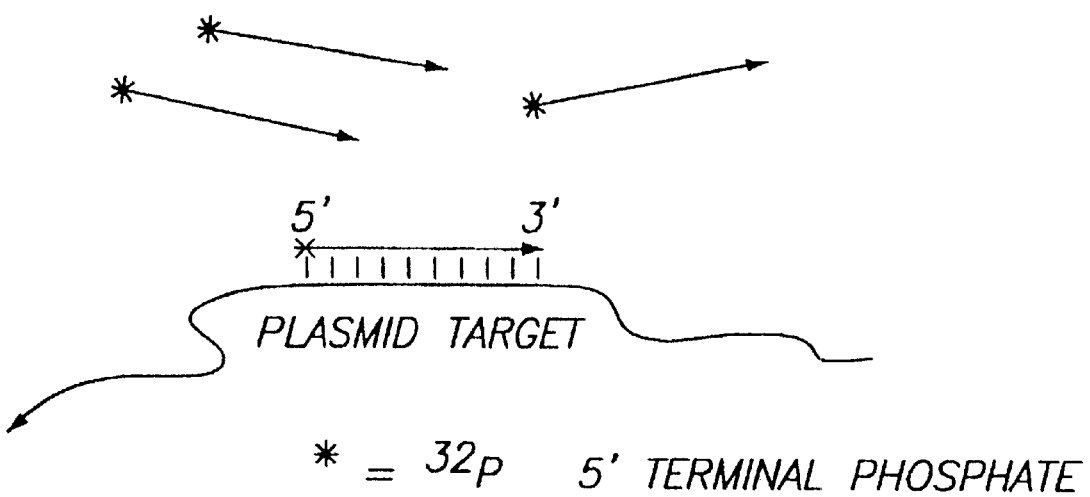
FIG. 28 demonstrates that "nibbling" can be target directed.

The success of such an assay depends on specificity. In other words, the oligonucleotide must hybridize to the specific target. It is also preferred that the assay be sensitive; the oligonucleotide ideally should be able to detect small amounts of target. FIG. 28A shows a 5'-end $^{32}$P-labelled primer bound to a plasmid target sequence. In this case, the plasmid was pUC19 (commercially available) which was heat denatured by boiling two (2) minutes and then quick chilling. The primer is a 21-mer (SEQ ID NO:39). The enzyme employed was Cleavase® BX (a dilution equivalent to 5×10$^{-3}$ μl extract) in 100 mM KCl, 10 mM Tris-Cl, pH 8.3, 2 mM MnCl$_2$. The reaction was performed at 55° C. for sixteen (16) hours with or without genomic background DNA (from chicken blood). The reaction was stopped by the addition of 8 μl of 95% formamide with 20 mM EDTA and marker dyes.

Figure 28B:
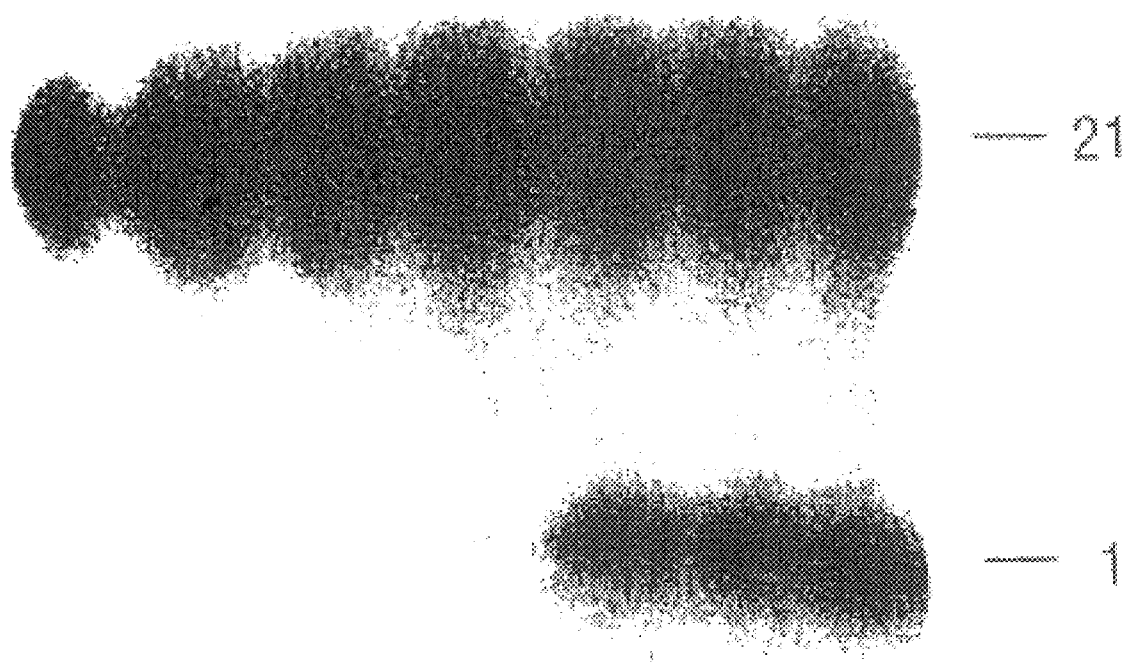

The products of the reaction were resolved by PAGE (10% polyacrylamide, 19:1 cross link, 1×TBE) as seen in FIG. 28B. Lane "M" contains the labeled 21-mer. Lanes 1–3 contain no specific target, although Lanes 2 and 3 contain 100 ng and 200 ng of genomic DNA, respectively. Lanes 4, 5 and 6 all contain specific target with either 0 ng, 100 ng or 200 ng of genomic DNA, respectively. It is clear that conversion to mononucleotides occurs in Lanes 4, 5 and 6 regardless of the presence or amount of background DNA. Thus the nibbling can be target directed and specific.

EXAMPLE 9

Cleavase® Purification

As noted above, expressed thermostable proteins (i.e., the 5' nucleases), were isolated by crude bacterial cell extracts. The precipitated *E. coli* proteins were then, along with other cell debris, removed by centrifugation. In this example, cells expressing the BN clone were cultured and collected (500 grams). For each gram (wet weight) of E. coli, 3 ml of lysis buffer (50 mM Tris-HCl, pH 8.0, 1 mM EDTA, 100 µM NaCl) was added. The cells were lysed with 200 µg/ml lysozyme at room temperature for 20 minutes. Thereafter deoxycholic acid was added to make a 0.2% final concentration and the mixture was incubated 15 minutes at room temperature.

The lysate was sonicated for approximately 6–8 minutes at 0° C. The precipitate was removed by centrifugation (39,000 g for 20 minutes). Polyethyleneimine was added (0.5%) to the supernatant and the mixture was incubated on ice for 15 minutes. The mixture was centrifuged (5,000 g for 15 minutes) and the supernatant was retained. This was heated for 30 minutes at 60° C. and then centrifuged again (5,000 g for 15 minutes) and the supernatant was again retained.

The supernatant was precipitated with 35% ammonium sulfate at 4° C. for 15 minutes. The mixture was then centrifuged (5,000 g for 15 minutes) and the supernatant was removed. The precipitate was then dissolved in 0.25 M KCl, 20 Tris pH 7.6, 0.2% Tween and 0.1 EDTA) and then dialyzed against Binding Buffer (8× Binding Buffer comprises: 4 mM imidazole, 4 M NaCl, 160 mM Tris-HCl, pH 7.9).

The solubilized protein is then purified on the $Ni^{++}$ column (Novagen). The Binding Buffer is allows to drain to the top of the column bed and load the column with the prepared extract. A flow rate of about 10 column volumes per hour is optimal for efficient purification. If the flow rate is too fast, more impurities will contaminate the eluted fraction.

The column is washed with 25 ml (10 volumes) of 1× Binding Buffer and then washed with 15 ml (6 volumes) of 1× Wash Buffer (8× Wash Buffer comprises: 480 mM imidazole. 4 M NaCl, 160 mM Tris-HCl, pH 7.9). The bound protein was eluted with 15 ml (6 volumes) of 1× Elute Buffer (4× Elute Buffer comprises: 4 mM imidazole, 2 M NaCl, 80 mM Tris-HCl, pH 7.9). Protein is then reprecipitated with 35% Ammonium Sulfate as above. The precipitate was then dissolved and dialyzed against: 20 mM Tris, 100 mM KCl, 1 mM EDTA). The solution was brought up to 0.1% each of Tween 20 and NP-40 and stored at 4° C.

EXAMPLE 10

The Use Of Various Divalent Cations In The Cleavage Reaction Influences The Nature Of The Resulting Cleavage Products In comparing the 5' nucleases generated by the modification and/or deletion of the C-terminal polymerization domain of Thermus aquaticus DNA polymerase (DNAPTaq), as diagrammed in FIGS. 4B–G, significant differences in the strength of the interactions of these proteins with the 3' end of primers located upstream of the cleavage site (as depicted in FIG. 6) were noted. In describing the cleavage of these structures by Pol I-type DNA polymerases (Example 1 and Lyamichev et al., Science 260:778 [1993]), it was observed that in the absence of a primer, the location of the junction between the double-stranded region and the single-stranded 5' and 3' arms determined the site of cleavage, but in the presence of a primer, the location of the 3' end of the primer became the determining factor for the site of cleavage. It was postulated that this affinity for the 3' end was in accord with the synthesizing function of the DNA polymerase.

Structure 2, shown in FIG. 22A, was used to test the effects of a 3' end proximal to the cleavage site in cleavage reactions comprising several different solutions [e.g., solutions containing different salts (KCl or NaCl), different divalent cations ($Mn^{2+}$ or $Mg^{2+}$), etc.] as well as the use of different temperatures for the cleavage reaction. When the reaction conditions were such that the binding of the enzyme (e.g., a DNAP comprising a 5' nuclease, a modified DNAP or a 5' nuclease) to the 3' end (of the pilot oligonucleotide) near the cleavage site was strong, the structure shown is cleaved at the site indicated in FIG. 22A. This cleavage releases the unpaired 5' arm and leaves a nick between the remaining portion of the target nucleic acid and the folded 3' end of the pilot oligonucleotide. In contrast, when the reaction conditions are such that the binding of the DNAP (comprising a 5' nuclease) to the 3' end was weak, the initial cleavage was as described above, but after the release of the 5' arm, the remaining duplex is digested by the exonuclease function of the DNAP.

One way of weakening the binding of the DNAP to the 3' end is to remove all or part of the domain to which at least some of this function has been attributed. Some of 5' nucleases created by deletion of the polymerization domain of DNAPTaq have enhanced true exonuclease function, as demonstrated in Ex. 6.

The affinity of these types of enzymes (i.e., 5' nucleases associated with or derived from DNAPs) for recessed 3' ends may also be affected by the identity of the divalent cation present in the cleavage reaction. It was demonstrated by Longley et al. (Longley et al., Nucl. Acids Res., 18:7317 [1990]) that the use of $MnCl_2$ in a reaction with DNAPTaq enabled the polymerase to remove nucleotides from the 5' end of a primer annealed to a template, albeit inefficiently. Similarly, by examination of the cleavage products generated using Structure 2 from FIG. 22A, as described above, in a reaction containing either DNAPTaq or the Cleavase® BB nuclease, it was observed that the substitution of $MnCl_2$ for $MgCl_2$ in the cleavage reaction resulted in the exonucleolytic "nibbling" of the duplex downstream of the initial cleavage site. While not limiting the invention to any particular mechanism, it is thought that the substitution of $MnCl_2$ for $MgCl_2$ in the cleavage reaction lessens the affinity of these enzymes for recessed 3' ends.

In all cases, the use of $MnCl_2$ enhances the 5' nuclease function, and in the case of the Cleavase® BB nuclease, a 50- to 100-fold stimulation of the 5' nuclease function is seen. Thus, while the exonuclease activity of these enzymes was demonstrated above in the presence of $MgCl_2$, the assays described below show a comparable amount of exonuclease activity using 50 to 100-fold less enzyme when $MnCl_2$ is used in place of $MgCl_2$. When these reduced amounts of enzyme are used in a reaction mixture containing $MgCl_2$, the nibbling or exonuclease activity is much less apparent than that seen in Examples 6–8.

Similar effects are observed in the performance of the nucleic acid detection assay described in Examples 11–18 below when reactions performed in the presence of either $MgCl_2$ or $MnCl_2$ are compared. In the presence of either divalent cation, the presence of the invader oligonucleotide (described below) forces the site of cleavage into the probe duplex, but in the presence of $MnCl_2$ the probe duplex can be further nibbled producing a ladder of products that are visible when a 3' end label is present on the probe oligonucleotide. When the invader oligonucleotide is omitted from a reaction containing $Mn^{2+}$, the probe is nibbled from the 5' end. $Mg^{2+}$-based reactions display minimal nibbling of the probe oligonucleotide. In any of these cases, the digestion of the probe is dependent upon the presence of the target nucleic acid. In the examples below, the ladder produced by the enhanced nibbling activity observed in the presence of $Mn^{2+}$ is used as a positive indicator that the probe oligonucleotide has hybridized to the target sequence.

EXAMPLE 11

Invasive 5' Endonucleolytic Cleavage By Thermostable 5' Nucleases In The Absence of Polymerization As described in the examples above, 5' nucleases cleave near the junction between single-stranded and base-paired regions in a bifurcated duplex, usually about one base pair into the base-paired region. In this example, it is shown that thermostable 5' nucleases, including those of the present invention (e.g., Cleavase® BN nuclease, Cleavase® A/G nuclease), have the ability to cleave a greater distance into the base paired region when provided with an upstream oligonucleotide bearing a 3' region that is homologous to a 5' region of the subject duplex, as shown in FIG. 30.

FIG. 30 shows a synthetic oligonucleotide which was designed to fold upon itself which consists of the following sequence: 5'-GTTCTCTGCTCTCTGGTCGCTGTCTCGC TTGTGAAACAAGCGAGACAGCGTGGTCTCTCG-3' (SEQ ID NO:40). This oligonucleotide is referred to as the "S-60 Hairpin." The 15 basepair hairpin formed by this oligonucleotide is further stabilized by a "tri-loop" sequence in the loop end (i.e., three nucleotides form the loop portion of the hairpin) [Hiraro, I. et al. (1994) Nucleic Acids Res. 22(4):576]. FIG. 30 also show the sequence of the P-15 oligonucleotide and the location of the region of complementarity shared by the P-15 and S-60 hairpin oligonucleotides. The sequence of the P-15 oligonucleotide is 5'-CGAGAGACCACGCTG-3' (SEQ ID NO:41). As discussed in detail below, the solid black arrowheads shown in FIG. 29 indicate the sites of cleavage of the S-60 hairpin in the absence of the P-15 oligonucleotide and the hollow arrow heads indicate the sites of cleavage in the presence of the P-15 oligonucleotide. The size of the arrow head indicates the relative utilization of a particular site.

Figure 31:
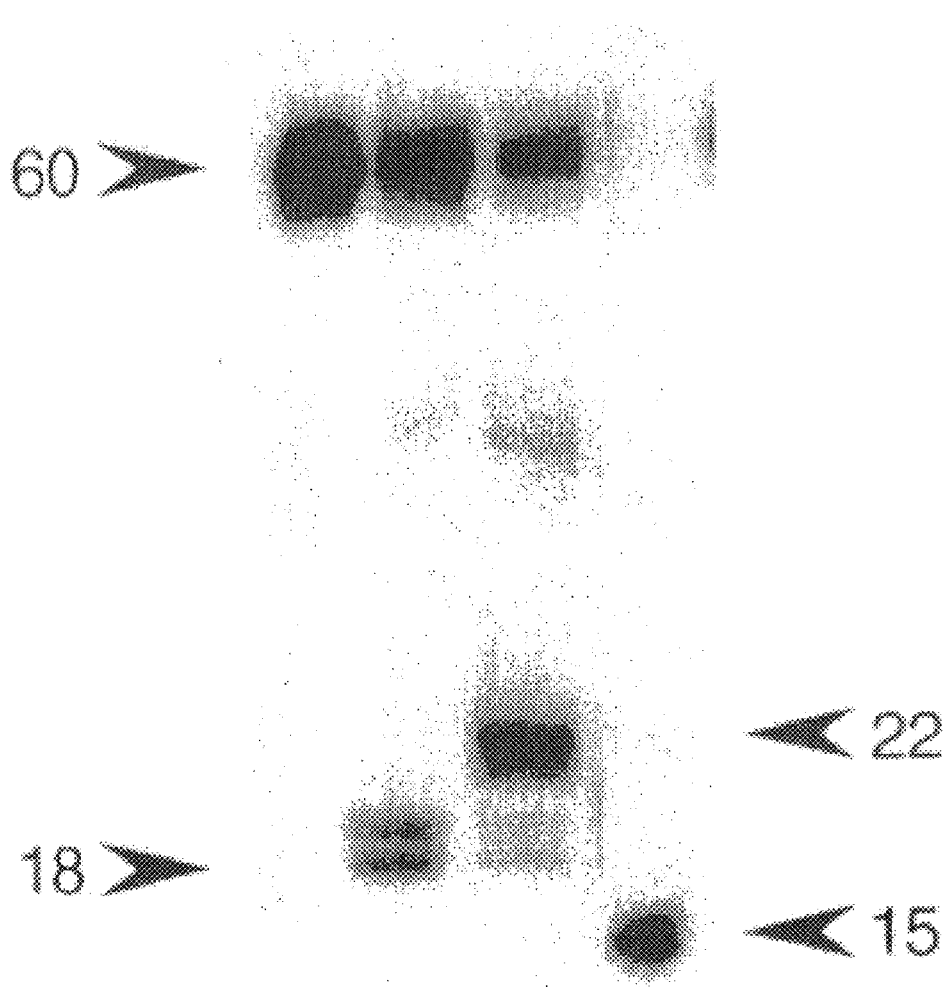
FIG. 31 is an autoradiogram of a gel showing the results of a cleavage reaction run using the S-60 hairpin in the presence or absence of the P-15 oligonucleotide.

The S-60 hairpin molecule was labeled on its 5' end with biotin for subsequent detection. The S-60 hairpin was incubated in the presence of a thermostable 5' nuclease in the presence or the absence of the P-15 oligonucleotide. The presence of the full duplex which can be formed by the S-60 hairpin is demonstrated by cleavage with the Cleavase® BN 5' nuclease, in a primer-independent fashion (i.e., in the absence of the P-15 oligonucleotide). The release of 18 and 19-nucleotide fragments from the 5' end of the S-60 hairpin molecule showed that the cleavage occurred near the junction between the single and double stranded regions when nothing is hybridized to the 3' arm of the S-60 hairpin (FIG. 31, lane 2).

The reactions shown in FIG. 31 were conducted as follows. Twenty fmole of the 5' biotin-labeled hairpin DNA (SEQ ID NO:40) was combined with 0.1 ng of Cleavase® BN enzyme and 1 µl of 100 mM MOPS (pH 7.5) containing 0.5% each of Tween-20 and NP-40 in a total volume of 9 µl. In the reaction shown in lane 1, the enzyme was omitted and the volume was made up by addition of distilled water (this served as the uncut or no enzyme control). The reaction shown in lane 3 of FIG. 31 also included 0.5 pmole of the P15 oligonucleotide (SEQ ID NO:41), which can hybridize to the unpaired 3' arm of the S-60 hairpin (SEQ ID NO:40), as diagrammed in FIG. 30.

The reactions were overlaid with a drop of mineral oil, heated to 95° C. for 15 seconds, then cooled to 37° C., and the reaction was started by the addition of 1 µl of 10 mM $MnCl_2$ to each tube. After 5 minutes, the reactions were stopped by the addition of 6 µl of 95% formamide containing 20 mM EDTA and 0.05% marker dyes. Samples were heated to 75° C. for 2 minutes immediately before electrophoresis through a 15% acrylamide gel (19:1 cross-linked), with 7 M urea, in a buffer of 45 mM Tris-Borate, pH 8.3, 1.4 mM EDTA.

After electrophoresis, the gel plates were separated allowing the gel to remain flat on one plate. A 0.2 mm-pore positively-charged nylon membrane (NYTRAN, Schleicher and Schuell, Keene, N.H.), pre-wetted in $H_2O$, was laid on top of the exposed gel. All air bubbles were removed. Two pieces of 3 MM filter paper (Whatman) were then placed on top of the membrane, the other glass plate was replaced, and the sandwich was clamped with binder clips. Transfer was allowed to proceed overnight. After transfer, the membrane was carefully peeled from the gel and allowed to air dry. After complete drying, the membrane was washed in 1.2× Sequenase Images Blocking Buffer (USB) using 0.3 ml of buffer/$cm^2$ of membrane. The wash was performed for 30 minutes at room temperature. A streptavidin-alkaline phosphatase conjugate (SAAP, USB) was added to a 1:4000 dilution directly to the blocking solution, and agitated for 15 minutes. The membrane was rinsed briefly with $H_2O$ and then washed three times for 5 minutes per wash using 0.5 ml/$cm^2$ of 1× SAAP buffer (100 mM Tris-HCl, pH 10, 50 mM NaCl) with 0.1% sodium dodecyl sulfate (SDS). The membrane was rinsed briefly with $H_2O$ between each wash. The membrane was then washed once in 1× SAAP buffer containing 1 mM $MgCl_2$ without SDS, drained thoroughly and placed in a plastic heat-sealable bag. Using a sterile pipet, 5 mls of CDP-Star™ (Tropix, Bedford, Mass.) chemiluminescent substrate for alkaline phosphatase were added to the bag and distributed over the entire membrane for 2–3 minutes. The CDP-Star™-treated membrane was exposed to XRP X-ray film (Kodak) for an initial exposure of 10 minutes.

The resulting autoradiograph is shown in FIG. 31. In FIG. 31, the lane labeled "M" contains the biotinylated P-15 oligonucleotide which served as a marker. The sizes (in nucleotides) of the uncleaved S-60 hairpin (60 nt; lane 1), the marker (15 nt; lane "M") and the cleavage products generated by cleavage of the S-60 hairpin in the presence (lane 3) or absence (lane 2) of the P-15 oligonucleotide are indicated.

Because the complementary regions of the S-60 hairpin are located on the same molecule, essentially no lag time should be needed to allow hybridization (i.e., to form the duplex region of the hairpin). This hairpin structure would be expected to form long before the enzyme could locate and cleave the molecule. As expected, cleavage in the absence of the primer oligonucleotide was at or near the junction between the duplex and single-stranded regions, releasing the unpaired 5' arm (FIG. 31, lane 2). The resulting cleavage products were 18 and 19 nucleotides in length.

It was expected that stability of the S-60 hairpin with the tri-loop would prevent the P-15 oligonucleotide from promoting cleavage in the "primer-directed" manner described in Ex. 1 above, because the 3' end of the "primer" would remain unpaired. Surprisingly, it was found that the enzyme seemed to mediate an "invasion" by the P-15 primer into the duplex region of the S-60 hairpin, as evidenced by the shifting of the cleavage site 3 to 4 basepairs further into the duplex region, releasing the larger products (22 and 21 nt.) observed in lane 3 of FIG. 31.

The precise sites of cleavage of the S-60 hairpin are diagrammed on the structure in FIG. 30, with the solid black arrowheads indicating the sites of cleavage in the absence of the P-15 oligonucleotide and the hollow arrow heads indicating the sites of cleavage in the presence of P-15.

These data show that the presence on the 3' arm of an oligonucleotide having some sequence homology with the first several bases of the similarly oriented strand of the downstream duplex can be a dominant factor in determining the site of cleavage by 5' nucleases. Because the oligonucleotide which shares some sequence homology with the first several bases of the similarly oriented strand of the downstream duplex appears to invade the duplex region of the hairpin, it is referred to as an "invader" oligonucleotide. As shown in the examples below, an invader oligonucleotide appears to invade (or displace) a region of duplexed nucleic acid regardless of whether the duplex region is present on the same molecule (i.e., a hairpin) or whether the duplex is formed between two separate nucleic acid strands.

EXAMPLE 12

The Invader Oligonucleotide Shifts The Site Of Cleavage In A Pre-Formed Probe/Target Duplex In Ex. 11 it was demonstrated that an invader oligonucleotide could shift the site at which a 5' nuclease cleaves a duplex region present on a hairpin molecule. In this example, the ability of an invader oligonucleotide to shift the site of cleavage within a duplex region formed between two separate strands of nucleic acid molecules was examined.

A single-stranded target DNA comprising the single-stranded circular M13mp19 molecule and a labeled (fluorescein) probe oligonucleotide were mixed in the presence of the reaction buffer containing salt (KCl) and divalent cations ($Mg^{2+}$ or $Mn^{2+}$) to promote duplex formation. The probe oligonucleotide refers to a labeled oligonucleotide which is complementary to a region along the target molecule (e.g., M13mp19). A second oligonucleotide (unlabelled) was added to the reaction after the probe and target had been allowed to anneal. The second oligonucleotide binds to a region of the target which is located downstream of the region to which the probe oligonucleotide binds. This second oligonucleotide contains sequences which are complementary to a second region of the target molecule. If the second oligonucleotide contains a region which is complementary to a portion of the sequences along the target to which the probe oligonucleotide also binds, this second oligonucleotide is referred to as an invader oligonucleotide (see FIG. 32c).

Figure 32A:
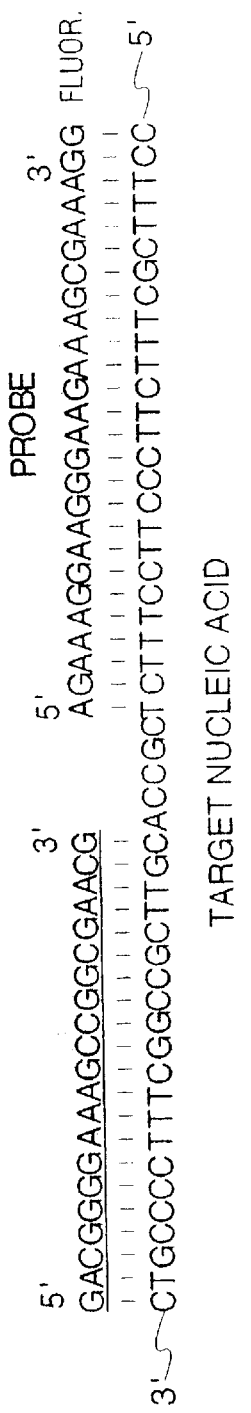
FIG. 32 provides a schematic showing three different arrangements of target-specific oligonucleotides and their hybridization to a target nucleic acid which also has a probe oligonucleotide annealed thereto.
Figure 32B:
Figure 32C:
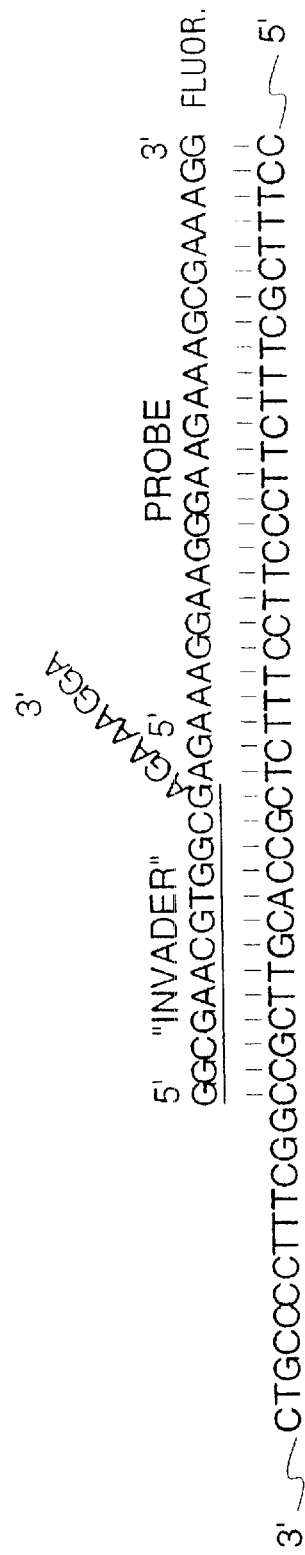

FIG. 32 depicts the annealing of two oligonucleotides to regions along the M13mp19 target molecule (bottom strand in all three structures shown). In FIG. 32 only a 52 nucleotide portion of the M13mp19 molecule is shown; this 52 nucleotide sequence is listed in SEQ ID NO:42. The probe oligonucleotide contains a fluorescein label at the 3' end; the sequence of the probe is 5'-AGAAAGGAAGGGAAGA AAGCGAAAGG-3' (SEQ ID NO:43). In FIG. 32, sequences comprising the second oligonucleotide, including the invader oligonucleotide are underlined. In FIG. 32a, the second oligonucleotide, which has the sequence 5'-GACGGGGAAAGCCGGCGA ACG-3' (SEQ ID NO:44), is complementary to a different and downstream region of the target molecule than is the probe oligonucleotide (labeled with fluorescein or "Fluor"); there is a gap between the second, upstream oligonucleotide and the probe for the structure shown in FIG. 32a. In FIG. 32b, the second, upstream oligonucleotide, which has the sequence 5'-GAAAGCCGGCGAACGTGGCG-3' (SEQ ID NO:45), is complementary to a different region of the target molecule than is the probe oligonucleotide, but in this case, the second oligonucleotide and the probe oligonucleotide abut one another (that is the 3' end of the second, upstream oligonucleotide is immediately adjacent to the 5' end of the probe such that no gap exists between these two oligonucleotides). In FIG. 32c, the second, upstream oligonucleotide (5'-GGCGAACGTGGCGAGAAAGGA-3' [SEQ ID NO:46]) and the probe oligonucleotide share a region of complementarity with the target molecule. Thus, the upstream oligonucleotide has a 3' arm which has a sequence identical to the first several bases of the downstream probe. In this situation, the upstream oligonucleotide is referred to as an "invader" oligonucleotide.

The effect of the presence of an invader oligonucleotide upon the pattern of cleavage in a probe/target duplex formed prior to the addition of the invader was examined. The invader oligonucleotide and the enzyme were added after the probe was allowed to anneal to the target and the position and extent of cleavage of the probe were examined to determine a) if the invader was able to shift the cleavage site to a specific internal region of the probe, and b), if the reaction could accumulate specific cleavage products over time, even in the absence of thermal cycling, polymerization, or exonuclease removal of the probe sequence.

The reactions were carried out as follows. Twenty μl each of two enzyme mixtures were prepared, containing 2 μl of Cleavase® A/G nuclease extract (prepared as described in Ex. 2), with or without 50 pmole of the invader oligonucleotide (SEQ ID NO:46), as indicated, per 4 μl of the mixture. For each of the eight reactions shown in FIG. 33, 150 fmole of M13mp19 single-stranded DNA (available from Life Technologies, Inc.) was combined with 5 pmoles of fluorescein labeled probe (SEQ ID NO:43), to create the structure shown in FIG. 31c, but without the invader oligonucleotide present (the probe/target mixture). One half (4 tubes) of the probe/target mixtures were combined with 1 μl of 100 mM MOPS, pH 7.5 with 0.5% each of Tween-20 and NP-40, 0.5 μl of 1 M KCl and 0.25 μl of 80 mM $MnCl_2$, and distilled water to a volume of 6 μl. The second set of probe/target mixtures were combined with 1 μl of 100 mM MOPS, pH 7.5 with 0.5% each of Tween-20 and NP-40, 0.5 μl of 1 M KCl and 0.25 μl of 80 mM $MgCl_2$. The second set of mixtures therefore contained $MgC_2$ in place of the $MnCl_2$ present in the first set of mixtures.

The mixtures (containing the probe/target with buffer, KCl and divalent cation) were covered with a drop of ChillOut® evaporation barrier (MJ Research) and were brought to 60° C. for 5 minutes to allow annealing. Four μl of the above enzyme mixtures without the invader oligonucleotide was added to reactions whose products are shown in lanes 1, 3, 5 and 7 of FIG. 33. Reactions whose products are shown lanes 2, 4, 6, and 8 of FIG. 33 received the same amount of enzyme mixed with the invader oligonucleotide (SEQ ID NO:46). Reactions 1, 2, 5 and 6 were incubated for 5 minutes at 60° C. and reactions 3, 4, 7 and 8 were incubated for 15 minutes at 60° C.

Figure 33:
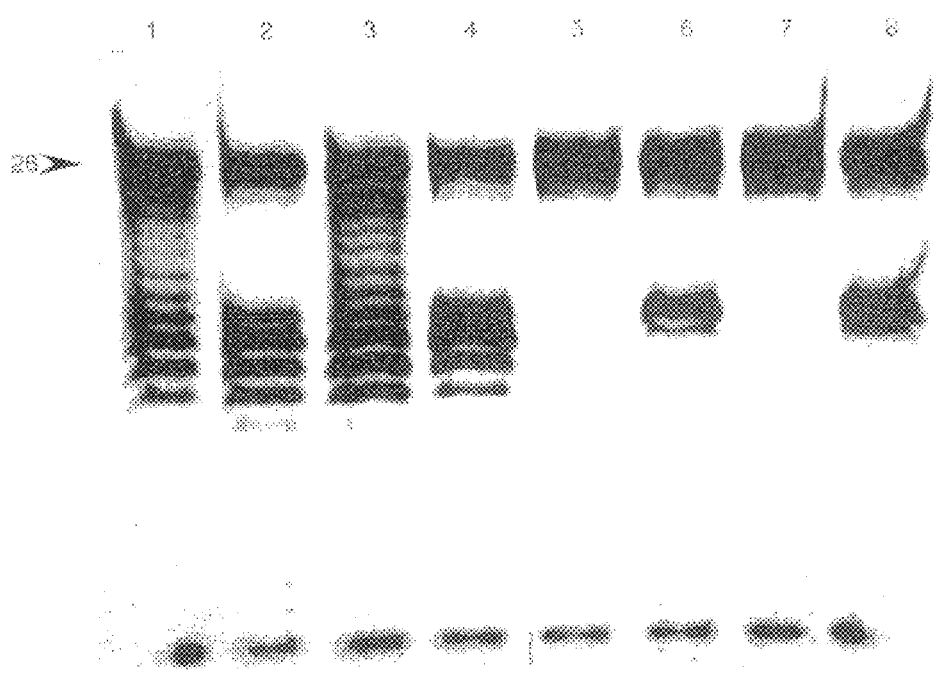
FIG. 33 is the image generated by a fluorescence imager showing that the presence of an invader oligonucleotide causes a shift in the site of cleavage in a probe/target duplex.

All reactions were stopped by the addition of 8 μl of 95% formamide with 20 mM EDTA and 0.05% marker dyes. Samples were heated to 90° C. for 1 minute immediately before electrophoresis through a 20% acrylamide gel (19:1 cross-linked), containing 7 M urea, in a buffer of 45 mM Tris-Borate, pH 8.3, 1.4 mM EDTA. Following electrophoresis, the reaction products and were visualized by the use of an Hitachi FMBIO fluorescence imager, the output of which is seen in FIG. 33. The very low molecular weight fluorescent material seen in all lanes at or near the salt front in FIG. 33 and other fluoro-imager figures is observed when fluorescently-labeled oligonucleotides are electrophoresed and imaged on a fluoro-imager. This material is not a product of the cleavage reaction.

The use of $MnCl_2$ in these reactions (lanes 1–4) stimulates the true exonuclease or "nibbling" activity of the Cleavase® enzyme, as described in Ex. 7, as is clearly seen in lanes 1 and 3 of FIG. 33. This nibbling of the probe oligonucleotide (SEQ ID NO:43) in the absence of invader oligonucleotide (SEQ ID NO:46) confirms that the probe oligonucleotide is forming a duplex with the target sequence. The ladder-like products produced by this nibbling reaction may be difficult to differentiate from degradation of the probe by nucleases that might be present in a clinical specimen. In contrast, introduction of the invader oligonucleotide (SEQ ID NO:46) caused a distinctive shift in the cleavage of the probe, pushing the site of cleavage 6 to 7 bases into the probe, confirming the annealing of both oligonucleotides. In presence of $MnCl_2$, the exonuclease "nibbling" may occur after the invader-directed cleavage event, until the residual duplex is destabilized and falls apart.

In a magnesium based cleavage reaction (lanes 5–8), the nibbling or true exonuclease function of the Cleavase® A/G is enzyme suppressed (but the endonucleolytic function of the enzyme is essentially unaltered), so the probe oligonucleotide is not degraded in the absence of the invader (FIG. 33, lanes 5 and 7). When the invader is added, it is clear that the invader oligonucleotide can promote a shift in the site of the endonucleolytic cleavage of the annealed probe. Comparison of the products of the 5 and 15 minute reactions with invader (lanes 6 and 8 in FIG. 33) shows that additional probe hybridizes to the target and is cleaved. The calculated melting temperature ($T_m$) of the portion of probe that is not invaded (i.e., nucleotides 9–26 of SEQ ID NO:43) is 56° C., so the observed turnover (as evidenced by the accumulation of cleavage products with increasing reaction time) suggests that the full length of the probe molecule, with a calculated $T_m$ of 76° C., is must be involved in the subsequent probe annealing events in this 60° C. reaction.

EXAMPLE 13

The Overlap Of The 3' Invader Oligonucleotide Sequence With The 5' Region Of The Probe Causes A Shift In The Site Of Cleavage In Ex. 12, the ability of an invader oligonucleotide to cause a shift in the site of cleavage of a probe annealed to a target molecule was demonstrated. In this example, experiments were conducted to examine whether the presence of an oligonucleotide upstream from the probe was sufficient to cause a shift in the cleavage site(s) along the probe or whether the presence of nucleotides on the 3' end of the invader oligonucleotide which have the same sequence as the first several nucleotides at the 5' end of the probe oligonucleotide were required to promote the shift in cleavage.

To examine this point, the products of cleavage obtained from three different arrangements of target-specific oligonucieotides are compared. A diagram of these oligonucleotides and the way in which they hybridize to a test nucleic acid, M13mp19, is shown in FIG. 32. In FIG. 32a, the 3' end of the upstream oligonucleotide (SEQ ID NO:45) is located upstream of the 5' end of the downstream "probe" oligonucleotide (SEQ ID NO:43) such that a region of the M13 target which is not paired to either oligonucleotide is present. In FIG. 32b, the sequence of the upstream oligonucleotide (SEQ ID NO:45) is immediately upstream of the probe (SEQ ID NO:43), having neither a gap nor an overlap between the sequences. FIG. 32c diagrams the arrangement of the substrates used in the assay of the present invention, showing that the upstream "invader" oligonucleotide (SEQ ID NO:46) has the same sequence on a portion of its 3' region as that present in the 5' region of the downstream probe (SEQ ID NO:43). That is to say, these regions will compete to hybridize to the same segment of the M13 target nucleic acid.

In these experiments, four enzyme mixtures were prepared as follows (planning 5 µl per digest): Mixture 1 contained 2.25 µl of Cleavase® A/G nuclease extract (prepared as described in Ex. 2) per 5 µl of mixture, in 20 mM MOPS, pH 7.5 with 0.1 % each of Tween 20 and NP-40, 4 mM $MnCl_2$ and 100 mM KCl. Mixture 2 contained 11.25 units of Taq DNA polymerase (Promega Corp., Madison, Wis.) per 5 µl of mixture in 20 mM MOPS, pH 7.5 with 0.1% each of Tween 20 and NP-40, 4 mM $MnCl_2$ and 100 mM KCl. Mixture 3 contained 2.25 µl of Cleavase® A/G nuclease extract per 5 µl of mixture in 20 mM Tris-HCl, pH 8.5, 4 mM $MgCl_2$ and 100 mM KCl. Mixture 4 contained 11.25 units of Taq DNA polymerase per 5 µl of mixture in 20 mM Tris-HCl, pH 8.5, 4 mM $MgCl_2$ and 100 mM KCl.

For each reaction, 50 fmole of M13mp19 single-stranded DNA (the target nucleic acid) was combined with 5 pmole of the probe oligonucleotide (SEQ ID NO:43 which contained a fluorescein label at the 3' end) and 50 pmole of one of the three upstream oligonucleotides diagrammed in FIG. 32 (i.e., one of SEQ ID NOS:44–46), in a total volume of 5 µl of distilled water. The reactions were overlaid with a drop of ChillOut™ evaporation barrier (MJ Research) and warmed to 62° C. The cleavage reactions were started by the addition of 5 µl of an enzyme mixture to each tube, and the reactions were incubated at 62° C. for 30 min. The reactions shown in lanes 1–3 of FIG. 34 received Mixture 1; reactions 4–6 received Mixture 2; reactions 7–9 received Mixture 3 and reactions 10–12 received Mixture 4.

After 30 minutes at 62° C., the reactions were stopped by the addition of 8 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA.

Figure 34:
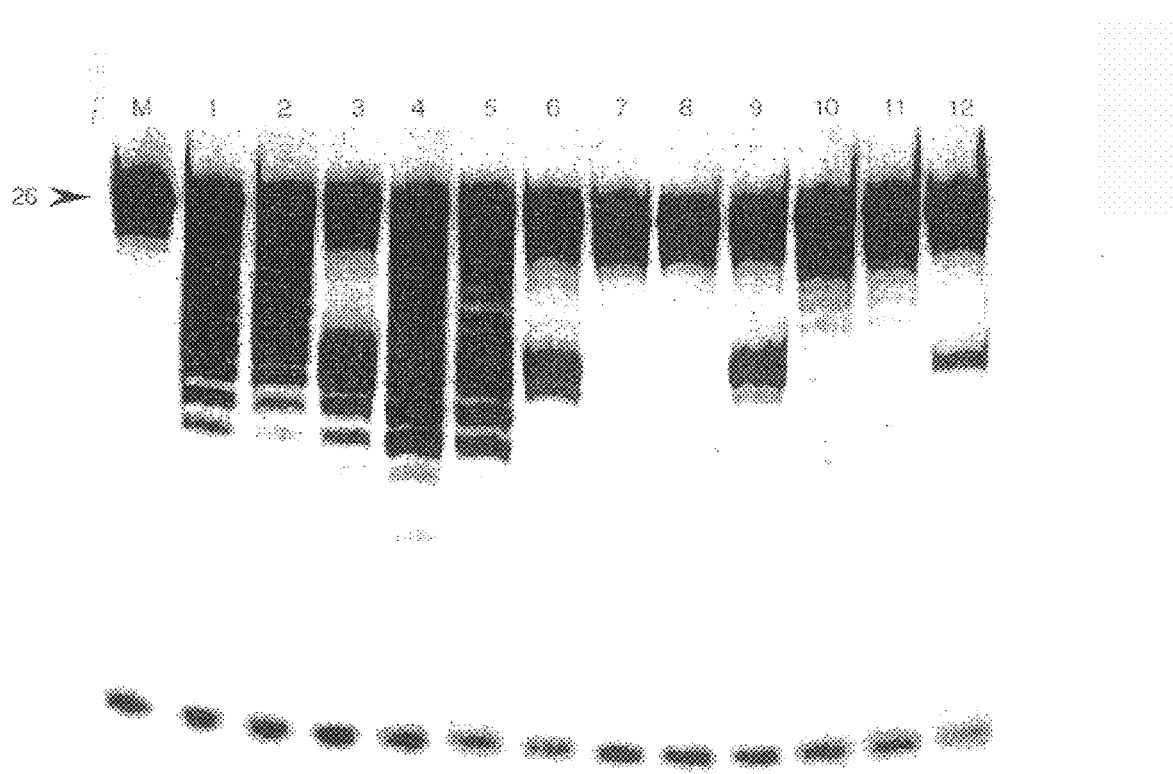
FIG. 34 is the image generated by a fluorescence imager showing the products of invader-directed cleavage assays run using the three target-specific oligonucleotides diagrammed in FIG. 32.

Following electrophoresis, the products of the reactions were visualized by the use of an Hitachi FMBIO fluorescence imager, the output of which is seen in FIG. 34. The reaction products shown in lanes 1, 4, 7 and 10 of FIG. 34 were from reactions which contained SEQ ID NO:44 as the upstream oligonucleotide (see FIG. 32a). The reaction products shown in lanes 2, 5, 8 and 11 of FIG. 34 were from reactions which contained SEQ ID NO:45 as the upstream oligonucleotide (see FIG. 32b). The reaction products shown in lanes 3, 6, 9 and 12 of FIG. 34 were from reactions which contained SEQ ID NO:46, the invader oligonucleotide, as the upstream oligonucleotide (see FIG. 32c).

Examination of the $Mn^{2+}$ based reactions using either Cleavase® A/G nuclease or DNAPTaq as the cleavage agent (lanes 1 through 3 and 4 through 6, respectively) shows that both enzymes have active exonuclease function in these buffer conditions. The use of a 3' label on the probe oligonucleotide allows the products of the nibbling activity to remain labeled, and therefore visible in this assay. The ladders seen in lanes 1, 2, 4 and 5 confirm that the probe hybridize to the target DNA as intended. These lanes also show that the location of the non-invasive oligonucleotides have little effect on the products generated. The uniform ladder created by these digests would be difficult to distinguish from a ladder causes by a contaminating nuclease, as one might find in a clinical specimen. In contrast, the products displayed in lanes 3 and 6, where an invader oligonucleotide was provided to direct the cleavage, show a very distinctive shift, so that the primary cleavage product is smaller than those seen in the non-invasive cleavage. This product is then subject to further nibbling in these conditions, as indicated by the shorter products in these lanes. These invader-directed cleavage products would be easily distinguished from a background of non-specific degradation of the probe oligonucleotide.

When $Mg^{2+}$ is used as the divalent cation the results are even more distinctive. In lanes 7, 8, 10 and 11 of FIG. 34, where the upstream oligonucleotides were not invasive, minimal nibbling is observed. The products in the DNAPTaq reactions show some accumulation of probe that has been shortened on the 5' end by one or two nucleotides consistent with previous examination of the action of this enzyme on nicked substrates (Longley et al., supra). When the upstream oligonucleotide is invasive, however, the appearance of the distinctively shifted probe band is seen. These data clearly indicated that it is the invasive 3' portion of the upstream oligonucleotide that is responsible for fixing the site of cleavage of the downstream probe.

Thus, the above results demonstrate that it is the presence of the free or initially non-annealed nucleotides at the 3' end of the invader oligonucleotide which mediate the shift in the cleavage site, not just the presence of an oligonucleotide annealed upstream of the probe. Nucleic acid detection assays which employ the use of an invader oligonucleotide are termed "invader-directed cleavage" assays.

EXAMPLE 14

Invader-Directed Cleavage Recognizes Single And Double Stranded Target Molecules In A Background Of Non-Target DNA Molecules For a nucleic acid detection method to be broadly useful, it must be able to detect a specific target in a sample that may contain large amounts of other DNA, e.g., bacterial or human chromosomal DNA. The ability of the invader directed cleavage assay to recognize and cleave either single- or double-stranded target molecules in the presence of large amounts of non-target DNA was examined. In these experiments a model target nucleic acid, M13, in either single or double stranded form (single-stranded M13mp18 is available from Life Technologies, Inc. and double-stranded M13mp19 is available from New England Biolabs), was combined with human genomic DNA (Novagen, Madison, Wis.) and then utilized in invader-directed cleavage reactions. Before the start of the cleavage reaction, the DNAs were heated to 95° C. for 15 minutes to completely denature the samples, as is standard practice in assays, such as polymerase chain reaction or enzymatic DNA sequencing, which involve solution hybridization of oligonucleotides to double-stranded target molecules.

Figure 35:
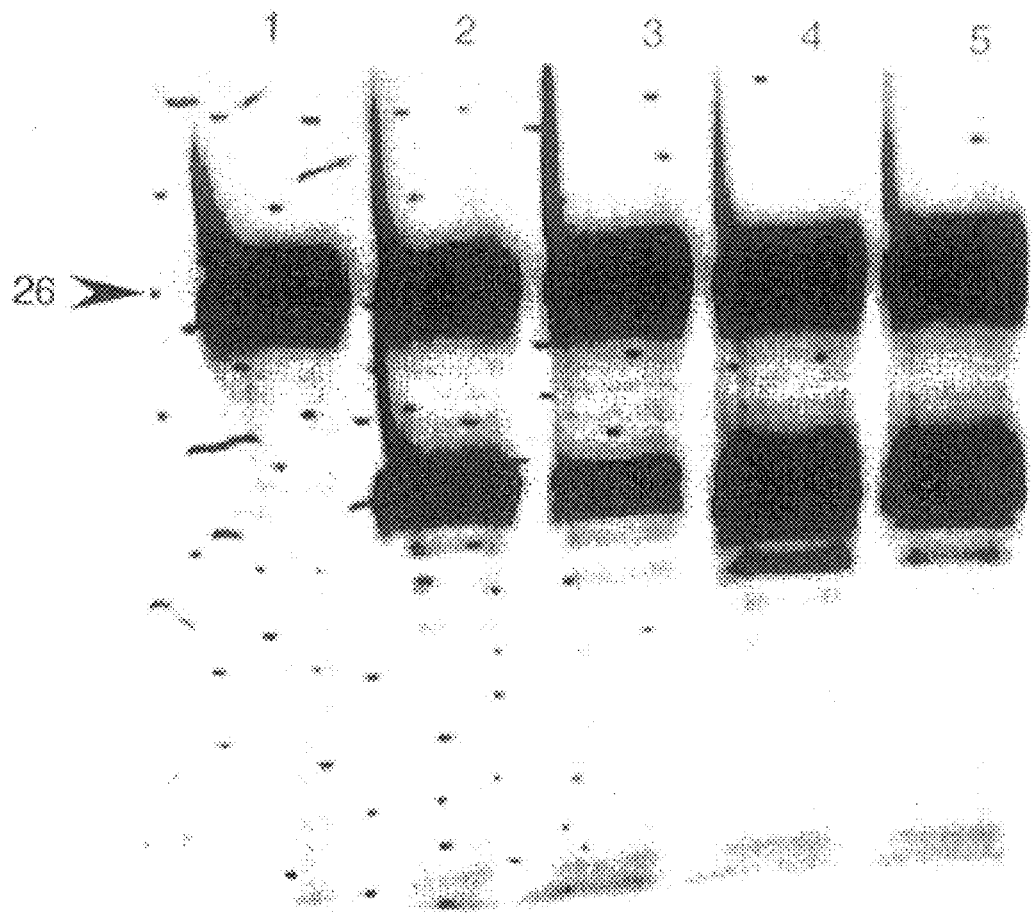
FIG. 35 is the image generated by a fluorescence imager showing the products of invader-directed cleavage assays run in the presence or absence of non-target nucleic acid molecules.

For each of the reactions shown in lanes 2–5 of FIG. 35, the target DNA (25 fmole of the ss DNA or 1 pmole of the ds DNA) was combined with 50 pmole of the invader oligonucleotide (SEQ ID NO:46); for the reaction shown in lane 1 the target DNA was omitted. Reactions 1, 3 and 5 also contained 470 ng of human genomic DNA. These mixtures were brought to a volume of 10 µl with distilled water, overlaid with a drop of ChillOut™ evaporation barrier (MJ Research), and brought to 95° C. for 15 minutes. After this incubation period, and still at 95° C., each tube received 10 µl of a mixture comprising 2.25 µl of Cleavase® A/G nuclease extract (prepared as described in Ex. 2) and 5 pmole of the probe oligonucleotide (SEQ ID NO:43), in 20 mM MOPS, pH 7.5 with 0.1% each of Tween 20 and NP-40, 4 mM $MnCl_2$ and 100 mM KCl. The reactions were brought to 62° C. for 15 minutes and stopped by the addition of 12 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager. The results are displayed in FIG. 35.

In FIG. 35, lane 1 contains the products of the reaction containing the probe (SEQ ID NO:43), the invader oligonucleotide (SEQ ID NO:46) and human genomic DNA. Examination of lane 1 shows that the probe and invader oligonucleotides are specific for the target sequence, and that the presence of genomic DNA does not cause any significant background cleavage.

In FIG. 35, lanes 2 and 3 contain reaction products from reactions containing the single-stranded target DNA (M13mpl18), the probe (SEQ ID NO:43) and the invader oligonucleotide (SEQ ID NO:46) in the absence or presence of human genomic DNA, respectively. Examination of lanes 2 and 3 demonstrate that the invader detection assay may be used to detect the presence of a specific sequence on a single-stranded target molecule in the presence or absence of a large excess of competitor DNA (human genomic DNA).

In FIG. 35, lanes 4 and 5 contain reaction products from reactions containing the double-stranded target DNA (M13mp19), the probe (SEQ ID NO:43) and the invader oligonucleotide (SEQ ID NO:46) in the absence or presence of human genomic DNA, respectively. Examination of lanes 4 and 5 show that double stranded target molecules are eminently suitable for invader-directed detection reactions. The success of this reaction using a short duplexed molecule, M13mp19, as the target in a background of a large excess of genomic DNA is especially noteworthy as it would be anticipated that the shorter and less complex M13 DNA strands would be expected to find their complementary strand more easily than would the strands of the more complex human genomic DNA. If the M13 DNA reannealed before the probe and/or invader oligonucleotides could bind to the target sequences along the M13 DNA, the cleavage reaction would be prevented. In addition, because the denatured genomic DNA would potentially contain regions complementary to the probe and/or invader oligonucleotides it was possible that the presence of the genomic DNA would inhibit the reaction by binding these oligonucleotides thereby preventing their hybridization to the M13 target. The above results demonstrate that these theoretical concerns are not a problem under the reaction conditions employed above.

In addition to demonstrating that the invader detection assay may be used to detect sequences present in a double-stranded target, these data also show that the presence of a large amount of non-target DNA (470 ng/20 µl reaction) does not lessen the specificity of the cleavage. While this amount of DNA does show some impact on the rate of product accumulation, probably by binding a portion of the enzyme, the nature of the target sequence, whether single- or double-stranded nucleic acid, does not limit the application of this assay.

EXAMPLE 15

Signal Accumulation In The Invader-Directed Cleavage Assay As A Function Of Target Concentration To investigate whether the invader-directed cleavage assay could be used to indicate the amount of target nucleic acid in a sample, the following experiment was performed. Cleavage reactions were assembled which contained an invader oligonucleotide (SEQ ID NO:46), a labeled probe (SEQ ID NO:43) and a target nucleic acid, M13mp19. A series of reactions, which contained smaller and smaller amounts of the M13 target DNA, was employed in order to examine whether the cleavage products would accumulate in a manner that reflected the amount of target DNA present in the reaction.

The reactions were conducted as follows. A master mix containing enzyme and buffer was assembled. Each 5 µl of the master mixture contained 25 ng of Cleavase® BN nuclease in 20 mM MOPS (pH 7.5) with 0.1% each of Tween 20 and NP-40, 4 mM $MnCl_2$ and 100 mM KCl. For each of the cleavage reactions shown in lanes 4–13 of FIG. 36, a DNA mixture was generated which contained 5 pmoles of the fluorescein-labeled probe oligonucleotide (SEQ ID NO:43), 50 pmoles of the invader oligonucleotide (SEQ ID NO:46) and 100, 50, 10, 5, 1, 0.5, 0.1, 0.05, 0.01 or 0.005 fmoles of single-stranded M13mp19, respectively, for every 5 µl of the DNA mixture. The DNA solutions were covered with a drop of ChillOut® evaporation barrier (MJ Research) and brought to 61° C. The cleavage reactions were started by the addition of 5 µl of the enzyme mixture to each of tubes (final reaction volume was 10 µl). After 30 minutes at 61° C., the reactions were terminated by the addition of 8 µl of 95% formamide with 20 mM EDTA and 0.05% marker dyes. Samples were heated to 90° C. for 1 minutes immediately before electrophoresis through a 20% denaturing acrylamide gel (19:1 cross-linked) with 7 M urea, in a buffer containing 45 mM Tris-Borate (pH 8.3), 1.4 mM EDTA. To provide reference (i.e., standards), 1.0, 0.1 and 0.01 pmole aliquots of fluorescein-labeled probe oligonucleotide (SEQ ID NO:43) were diluted with the above formamide solution to a final volume of 18 µl. These reference markers were loaded into lanes 1–3, respectively of the gel. The products of the cleavage reactions (as well as the reference standards) were visualized following electrophoresis by the use of a Hitachi FMBIO fluorescence imager. The results are displayed in FIG. 36.

Figure 36:
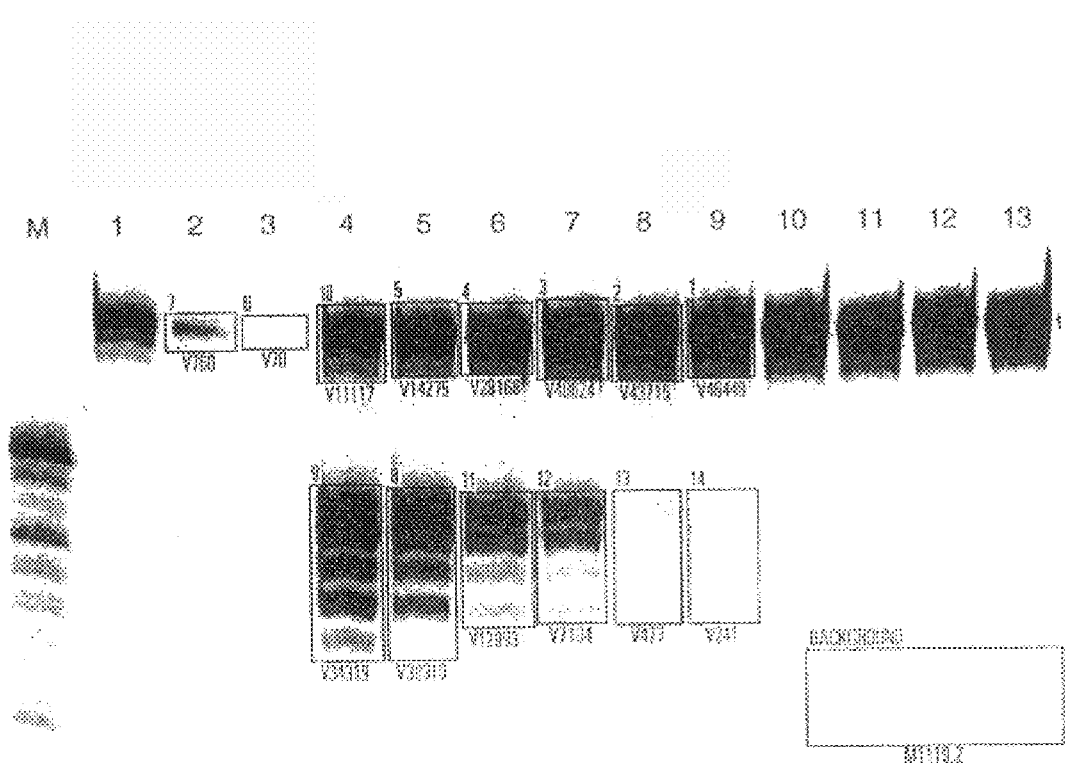
FIG. 36 is the image generated by a fluorescence imager showing the products of invader-directed cleavage assays run in the presence of decreasing amounts of target nucleic acid.

In FIG. 36, boxes appear around fluorescein-containing nucleic acid (i.e., the cleaved and uncleaved probe molecules) and the amount of fluorescein contained within each box is indicated under the box. The background fluorescence of the gel (see box labeled "background") was subtracted by the fluoro-imager to generate each value displayed under a box containing cleaved or uncleaved probe products (the boxes are numbered 1–14 at top left with a V followed by a number below the box). The lane marked "M" contains fluoresceinated oligonucleotides which served as markers.

The results shown in FIG. 36, demonstrate that the accumulation of cleaved probe molecules in a fixed-length incubation period reflects the amount of target DNA present in the reaction. The results also demonstrate that the cleaved probe products accumulate in excess of the copy number of the target. This is clearly demonstrated by comparing the results shown in lane 3, in which 10 fmole (0.01 pmole) of uncut probe are displayed with the results shown in 5, where the products which accumulated in response to the presence of 10 fmole of target DNA are displayed. These results show that the reaction can cleave hundreds of probe oligonucleotide molecules for each target molecule present, dramatically amplifying the target-specific signal generated in the invader-directed cleavage reaction.

EXAMPLE 16

Effect Of Saliva Extract On The Invader-Directed Cleavage Assay

For a nucleic acid detection method to be useful in a medical (i.e., a diagnostic) setting, it must not be inhibited by materials and contaminants likely to be found in a typical clinical specimen. To test the susceptibility of the invader-directed cleavage assay to various materials, including but not limited to nucleic acids, glycoproteins and carbohydrates, likely to be found in a clinical sample, a sample of human saliva was prepared in a manner consistent with practices in the clinical laboratory and the resulting saliva extract was added to the invader-directed cleavage assay. The effect of the saliva extract upon the inhibition of cleavage and upon the specificity of the cleavage reaction was examined.

One and one-half milliliters of human saliva were collected and extracted once with an equal volume of a mixture containing phenol:chloroform:isoamyl alcohol (25:24:1). The resulting mixture was centrifuged in a microcentrifuge to separate the aqueous and organic phases. The upper, aqueous phase was transferred to a fresh tube. One-tenth volumes of 3 M NaOAc were added and the contents of the tube were mixed. Two volumes of 100% ethyl alcohol were added to the mixture and the sample was mixed and incubated at room temperature for 15 minutes to allow a precipitate to form. The sample was centrifuged in a microcentrifuge at 13,000 rpm for 5 minutes and the supernatant was removed and discarded. A milky pellet was easily visible. The pellet was rinsed once with 70% ethanol, dried under vacuum and dissolved in 200 µl of 10 mM Tris-HCl, pH 8.0, 0.1 mM EDTA (this constitutes the saliva extract). Each µl of the saliva extract was equivalent to 7.5 µl of saliva. Analysis of the saliva extract by scanning ultraviolet spectrophotometry showed a peak absorbance at about 260 nm and indicated the presence of approximately 45 ng of total nucleic acid per µl of extract.

The effect of the presence of saliva extract upon the following enzymes was examined: Cleavase® BN nuclease, Cleavase® A/G nuclease and three different lots of DNAPTaq: AmpliTaq® (Perkin Elmer; a recombinant form of DNAPTaq), AmpliTaq® LD (Perkin-Elmer; a recombinant DNAPTaq preparation containing very low levels of DNA) and Taq DNA polymerase (Fisher). For each enzyme tested, an enzyme/probe mixture was made comprising the chosen amount of enzyme with 5 pmole of the probe oligonucleotide (SEQ ID NO:43) in 10 µl of 20 mM MOPS (pH 7.5) containing 0.1% each of Tween 20 and NP-40, 4 mM $MnCl_2$, 100 mM KCl and 100 µg/ml BSA. The following amounts of enzyme were used: 25 ng of Cleavase® BN prepared as described in Ex. 9; 2 µl of Cleavase® A/G nuclease extract prepared as described in Ex. 2; 2.25 µl (11.25 polymerase units) the following DNA polymerases: AmpliTaq® DNA polymerase (Perkin Elmer); AmpliTaq® DNA polymerase LD (low DNA; from Perkin Elmer); Taq DNA polymerase (Fisher Scientific).

Figure 37:
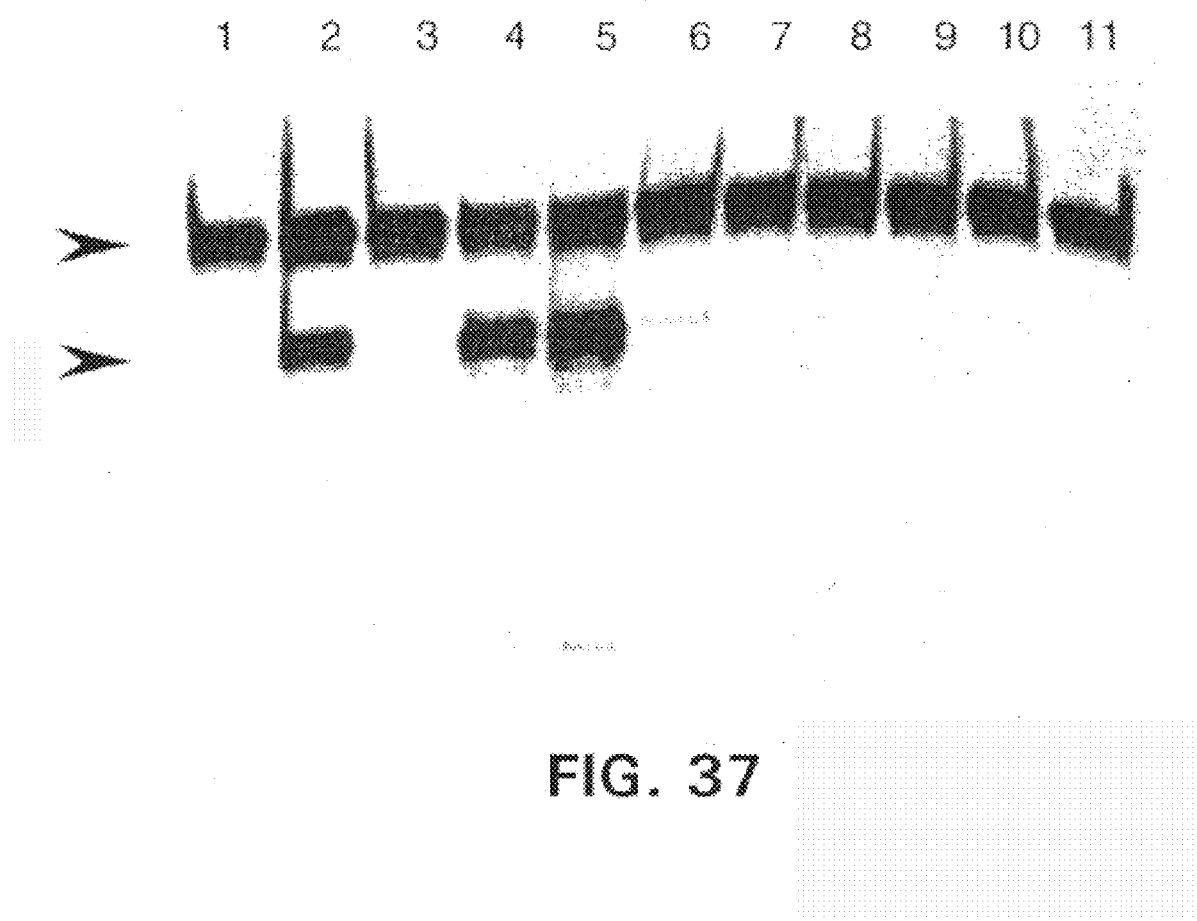
FIG. 37 is the image generated by a fluorescence imager showing the products of invader-directed cleavage assays run in the presence or absence of saliva extract using various thermostable 5' nucleases or DNA polymerases.

For each of the reactions shown in FIG. 37, except for that shown in lane 1, the target DNA (50 fmoles of single-stranded M13mp19 DNA) was combined with 50 pmole of the invader oligonucleotide (SEQ ID NO:46) and 5 pmole of the probe oligonucleotide (SEQ ID NO:43); target DNA was omitted in reaction 1 (lane 1). Reactions 1, 3, 5, 7, 9 and 11 included 1.5 μl of saliva extract. These mixtures were brought to a volume of 5 μl with distilled water, overlaid with a drop of ChillOut® evaporation barrier (MJ Research) and brought to 95° C. for 10 minutes. The cleavage reactions were then started by the addition of 5 μl of the desired enzyme/probe mixture; reactions 1, 4 and 5 received Cleavase® A/G nuclease. Reactions 2 and 3 received Cleavase® BN; reactions 6 and 7 received AmpliTaq®; reactions 8 and 9 received AmpliTaq® LD; and reactions 10 and 11 received Taq DNA Polymerase from Fisher Scientific.

The reactions were incubated at 63° C. for 30 minutes and were stopped by the addition of 6 μl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager, and the results are displayed in FIG. 37.

A pairwise comparison of the lanes shown in FIG. 37 without and with the saliva extract, treated with each of the enzymes, shows that the saliva extract has different effects on each of the enzymes. While the Cleavase® BN nuclease and the AmpliTaq® are significantly inhibited from cleaving in these conditions, the Cleavase® A/G nuclease and AmpliTaq® LD display little difference in the yield of cleaved probe. The preparation of Taq DNA polymerase from Fisher Scientific shows an intermediate response, with a partial reduction in the yield of cleaved product. From the standpoint of polymerization, the three DNAPTaq variants should be equivalent; these should be the same protein with the same amount of synthetic activity. It is possible that the differences observed could be due to variations in the amount of nuclease activity present in each preparation caused by different handling during purification, or by different purification protocols. In any case, quality control assays designed to assess polymerization activity in commercial DNAP preparations would be unlikely to reveal variation in the amount of nuclease activity present. If preparations of DNAPTaq were screened for full 5' nuclease activity (i.e., f the 5' nuclease activity was specifically quantitated), it is likely that the preparations would display sensitivities (to saliva extract) more in line with that observed using Cleavase® A/G nuclease, from which DNAPTaq differs by a very few amino acids.

It is worthy of note that even in the slowed reactions of Cleavase® BN and the DNAPTaq variants there is no noticeable increase in non-specific cleavage of the probe oligonucleotide due to inappropriate hybridization or saliva-borne nucleases.

EXAMPLE 17

Comparison Of Additional 5' Nucleases In The Invader-Directed Cleavage Assay

A number of eubacterial Type A DNA polymerases (i.e., Pol I type DNA polymerases) have been shown to function as structure specific endonucleases (Ex. 1 and Lyamichev et al., supra). In this example, it was demonstrated that the enzymes of this class can also be made to catalyze the invader-directed cleavage of the present invention, albeit not as efficiently as the Cleavase® enzymes.

Figure 38:
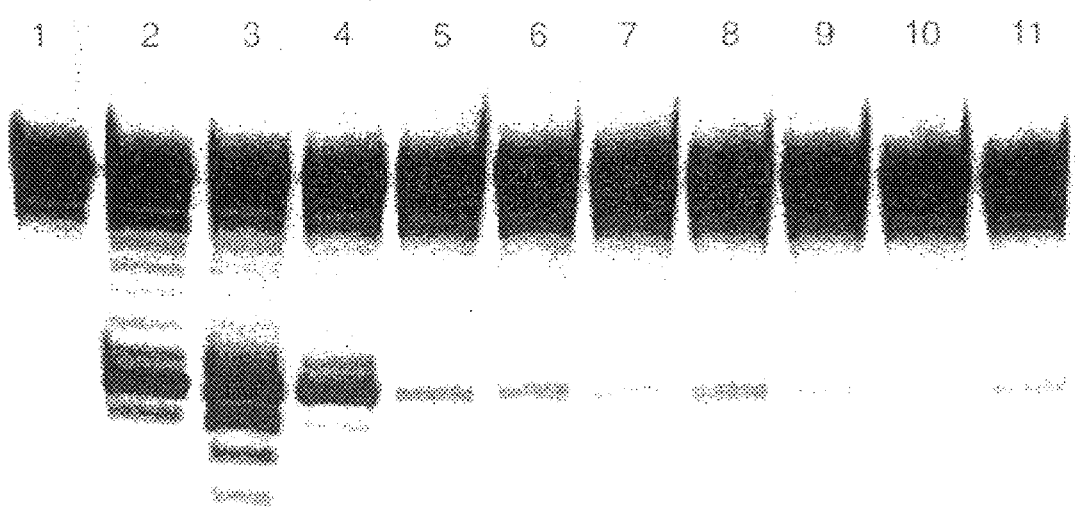
FIG. 38 is the image generated by a fluorescence imager showing the products of invader-directed cleavage assays run using various 5' nucleases.

Cleavase® BN nuclease and Cleavase® A/G nuclease were tested along side three different thermostable DNA polymerases: *Thermus aquaticus* DNA polymerase (Promega), *Thermus thermophilus* and *Thermus flavus* DNA polymerases (Epicentre). The enzyme mixtures used in the reactions shown in lanes 1–11 of FIG. 38 contained the following, each in a volume of 5 μl: Lane 1: 20 mM MOPS (pH 7.5) with 0.1% each of Tween 20 and NP-40, 4 mM $MnCl_2$, 100 mM KCl; Lane 2: 25 ng of Cleavase® BN nuclease in the same solution described for lane 1; Lane 3: 2.25 μl of Cleavase® A/G nuclease extract (prepared as described in Ex. 2), in the same solution described for lane 1; Lane 4: 2.25 μl of Cleavase® A/G nuclease extract in 20 mM Tris-Cl, (pH 8.5), 4 mM $MgCl_2$ and 100 mM KCl; Lane 5: 11.25 polymerase units of Taq DNA polymerase in the same buffer described for lane 4; Lane 6: 11.25 polymerase units of Tth DNA polymerase in the same buffer described for lane 1; Lane 7: 11.25 polymerase units of Tth DNA polymerase in a 2× concentration of the buffer supplied by the manufacturer, supplemented with 4 mM $MnCl_2$; Lane 8: 11.25 polymerase units of Tth DNA polymerase in a 2× concentration of the buffer supplied by the manufacturer, supplemented with 4 mM $MgCl_2$; Lane 9: 2.25 polymerase units of Tfl DNA polymerase in the same buffer described for lane 1; Lane 10: 2.25 polymerase units of Tfl polymerase in a 2× concentration of the buffer supplied by the manufacturer, supplemented with 4 mM $MnCl_2$; Lane 11: 2.25 polymerase units of Tfl DNA polymerase in a 2× concentration of the buffer supplied by the manufacturer, supplemented with 4 mM $MgCl_2$.

Sufficient target DNA, probe and invader for all 11 reactions was combined into a master mix. This mix contained 550 fmoles of single-stranded M13mp19 target DNA, 550 pmoles of the invader oligonucleotide (SEQ ID NO:46) and 55 pmoles of the probe oligonucleotide (SEQ ID NO:43), each as depicted in FIG. 32c, in 55 μl of distilled water. Five μl of the DNA mixture was dispensed into each of 11 labeled tubes and overlaid with a drop of ChillOut® evaporation barrier (MJ Research). The reactions were brought to 63° C. and cleavage was started by the addition of 5 μl of the appropriate enzyme mixture. The reaction mixtures were then incubated at 63° C. temperature for 15 minutes. The reactions were stopped by the addition of 8 μl of 95% formamide with 20 mM EDTA and 0.05% marker dyes. Samples were heated to 90° C. for 1 minute immediately before electrophoresis through a 20% acrylamide gel (19:1 cross-linked), with 7 M urea, in a buffer of 45 mM Tris-Borate (pH 8.3), 1.4 mM EDTA. Following electrophoresis, the products of the reactions were visualized by the use of an Hitachi FMBIO fluorescence imager, and the results are displayed in FIG. 38. Examination of the results shown in FIG. 38 demonstrates that all of the 5' nucleases tested have the ability to catalyze invader-directed cleavage in at least one of the buffer systems tested. Although not optimized here, these cleavage agents are suitable for use in the methods of the present invention.

EXAMPLE 18

The Invader-Directed Cleavage Assay Can Detect Single Base Differences In Target Nucleic Acid Sequences The ability of the invader-directed cleavage assay to detect single base mismatch mutations was examined. Two target nucleic acid sequences containing Cleavase® enzyme-resistant phosphorothioate backbones were chemically synthesized and purified by polyacrylamide gel electrophoresis. Targets comprising phosphorothioate backbones were used to prevent exonucleolytic nibbling of the target when duplexed with an oligonucleotide. A target oligonucleotide, which provides a target sequence that is completely complementary to the invader oligonucleotide (SEQ ID NO:46) and the probe oligonucleotide (SEQ ID NO:43), contained the following sequence: 5'-CCTTTC GCTTTCTTCCCTTCCTTTCTCGCCACGTTCGCCG GC-3' (SEQ ID NO:47). A second target sequence containing a single base change relative to SEQ ID NO:47 was synthesized: 5'-CCTTTCGCTCTCTTCCCTTCCTTTCTC GCCACGTTCGCCGGC-3 (SEQ ID NO:48; the single base change relative to SEQ ID NO:47 is shown using bold and underlined type). The consequent mismatch occurs within the "Z" region of the target as represented in FIG. 29.

To discriminate between two target sequences which differ by the presence of a single mismatch), invader-directed cleavage reactions were conducted using two different reaction temperatures (55° C. and 60° C.). Mixtures containing 200 fmoles of either SEQ ID NO:47 or SEQ ID NO:48, 3 pmoles of fluorescein-labeled probe oligonucleotide (SEQ ID NO:43), 7.7 pmoles of invader oligonucleotide (SEQ ID NO:46) and 2 μl of Cleavase® A/G nuclease extract (prepared as described in Ex. 2) in 9 μl of 10 mM MOPS (pH 7.4) with 50 mM KCl were assembled, covered with a drop of ChillOut® evaporation barrier (MJ Research) and brought to the appropriate reaction temperature. The cleavage reactions were initiated by the addition of 1 μl of 20 mM $MgCl_2$. After 30 minutes at either 55° C. or 60° C., 10 μl of 95% formamide with 20 mM EDTA and 0.05% marker dyes was added to stop the reactions. The reaction mixtures where then heated to 90° C. for one minute prior to loading 4 μl onto 20% denaturing polyacrylamide gels. The resolved reaction products were visualized using a Hitachi FMBIO fluorescence imager. The resulting image is shown in FIG. 39.

Figure 39:
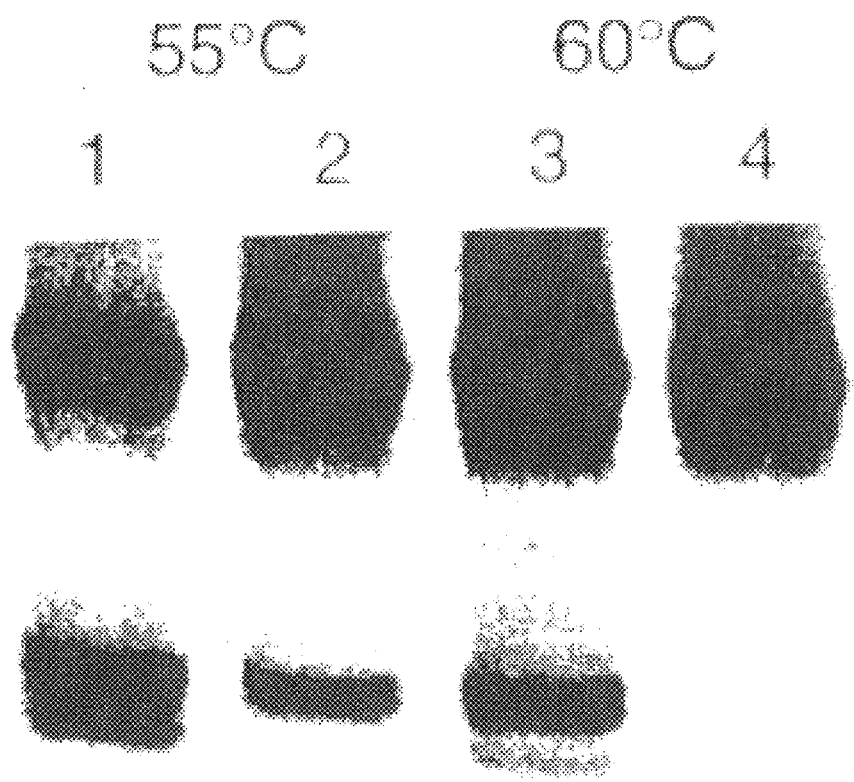
FIG. 39 is the image generated by a fluorescence imager showing the products of invader-directed cleavage assays run using two target nucleic acids which differ by a single basepair at two different reaction temperatures.

In FIG. 39, lanes 1 and 2 show the products from reactions conducted at 55° C.; lanes 3 and 4 show the products from reactions conducted at 60° C. Lanes 1 and 3 contained products from reactions containing SEQ ID NO:47 (perfect match to probe) as the target. Lanes 2 and 4 contained products from reactions containing SEQ ID NO:48 (single base mismatch with probe) as the target. The target that does not have a perfect hybridization match (i.e., complete complementarity) with the probe will not bind as strongly, i.e., the $T_m$ of that duplex will be lower than the $T_m$ of the same region if perfectly matched. The results presented here show that reaction conditions can be varied to either accommodate the mis-match (e.g., by lowering the temperature of the reaction) or to exclude the binding of the mismatched sequence (e.g., by raising the reaction temperature).

The results shown in FIG. 39 demonstrate that the specific cleavage event which occurs in invader-directed cleavage reactions can be eliminated by the presence of a single base mismatch between the probe oligonucleotide and the target sequence. Thus, reaction conditions can be chosen so as to exclude the hybridization of mismatched invader-directed cleavage probes thereby diminishing or even eliminating the cleavage of the probe. In an extension of this assay system, multiple cleavage probes, each possessing a separate reporter molecule (i.e., a unique label), could also be used in a single cleavage reaction, to simultaneously probe for two or more variants in the same target region. The products of such a reaction would allow not only the detection of mutations which exist within a target molecule, but would also allow a determination of the relative concentrations of each sequence (i.e., mutant and wild type or multiple different mutants) present within samples containing a mixture of target sequences. When provided in equal amounts, but in a vast excess (e.g., at least a 100-fold molar excess; typically at least 1 pmole of each probe oligonucleotide would be used when the target sequence was present at about 10 fmoles or less) over the target and used in optimized conditions. As discussed above, any differences in the relative amounts of the target variants will not affect the kinetics of hybridization, so the amounts of cleavage of each probe will reflect the relative amounts of each variant present in the reaction.

The results shown in the example clearly demonstrate that the invader-directed cleavage reaction can be used to detect single base difference between target nucleic acids.

EXAMPLE 19

The Invader-Directed Cleavage Reaction Is Insensitive To Large Changes In Reaction Conditions The results shown above demonstrated that the invader-directed cleavage reaction can be used for the detection of target nucleic acid sequences and that this assay can be used to detect single base difference between target nucleic acids. These results demonstrated that 5' nucleases (e.g., Cleavase® BN, Cleavase® A/G, DNAPTaq, DNAPTth, DNAPTfl) could be used in conjunction with a pair of overlapping oligonucleotides as an efficient way to recognize nucleic acid targets. In the experiments below it is demonstrated that invasive cleavage reaction is relatively insensitive to large changes in conditions thereby making the method suitable for practice in clinical laboratories.

The effects of varying the conditions of the cleavage reaction were examined for their effect(s) on the specificity of the invasive cleavage and the on the amount of signal accumulated in the course of the reaction. To compare variations in the cleavage reaction a "standard" invader cleavage reaction was first defined. In each instance, unless specifically stated to be otherwise, the indicated parameter of the reaction was varied, while the invariant aspects of a particular test were those of this standard reaction. The results of these tests are shown in FIGS. 42–51.

a) The Standard Invader-Directed Cleavage Reaction

The standard reaction was defined as comprising 1 fmole of M13mp18 single-stranded target DNA (New England Biolabs), 5 pmoles of the labeled probe oligonucleotide (SEQ ID NO:49), 10 pmole of the upstream invader oligonucleotide (SEQ ID NO:50) and 2 units of Cleavase® A/G in 10 μl of 10 mM MOPS, pH 7.5 with 100 mM KCl, 4 mM $MnCl_2$, and 0.05% each Tween-20 and Nonidet-P40. For each reaction, the buffers, salts and enzyme were combined in a volume of 5 μl; the DNAs (target and two oligonucleotides) were combined in 5 μl of $dH_2O$ and overlaid with a drop of ChillOut® evaporation barrier (MJ Research). When multiple reactions were performed with the same reaction constituents, these formulations were expanded proportionally.

Unless otherwise stated, the sample tubes with the DNA mixtures were warmed to 61° C., and the reactions were started by the addition of 5 μl of the enzyme mixture. After 20 minutes at this temperature, the reactions were stopped by the addition of 8 μl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager. In each case, the uncut probe material was visible as an intense black band or blob, usually in the top half of the panel, while the desired products of invader specific cleavage were visible as one or two narrower black bands, usually in the bottom half of the panel. Under some reaction conditions, particularly those with elevated salt concentrations, a secondary cleavage product is also visible (thus generating a doublet). Ladders of lighter gray bands generally indicate either exonuclease nibbling of the probe oligonucleotide or heat-induced, non-specific breakage of the probe.

FIG. 41 depicts the annealing of the probe and invader oligonucleotides to regions along the M13mp18 target molecule (the bottom strand). In FIG. 41 only a 52 nucleotide portion of the M13mp18 molecule is shown; this 52 nucleotide sequence is listed in SEQ ID NO:42 (this sequence is identical in both M13mp18 and M13mp19). The probe oligonucleotide (top strand) contains a Cy3 amidite label at the 5' end; the sequence of the probe is 5'-AGAAAGGAAGGGAAGAAAGCGAAA GGT-3' (SEQ ID NO:49. The bold type indicates the presence of a modified base (2'-O-CH$_3$). Cy3 amidite (Pharmacia) is a indodicarbocyanine dye amidite which can be incorporated at any position during the synthesis of oligonucleotides; Cy3 fluoresces in the yellow region (excitation and emission maximum of 554 and 568 nm, respectively). The invader oligonucleotide (middle strand) has the following sequence: 5'-GCCGGCGAACGTGGCGAGAAAGGA-3' (SEQ ID NO:50).

b) KCl Titration

Figure 42:
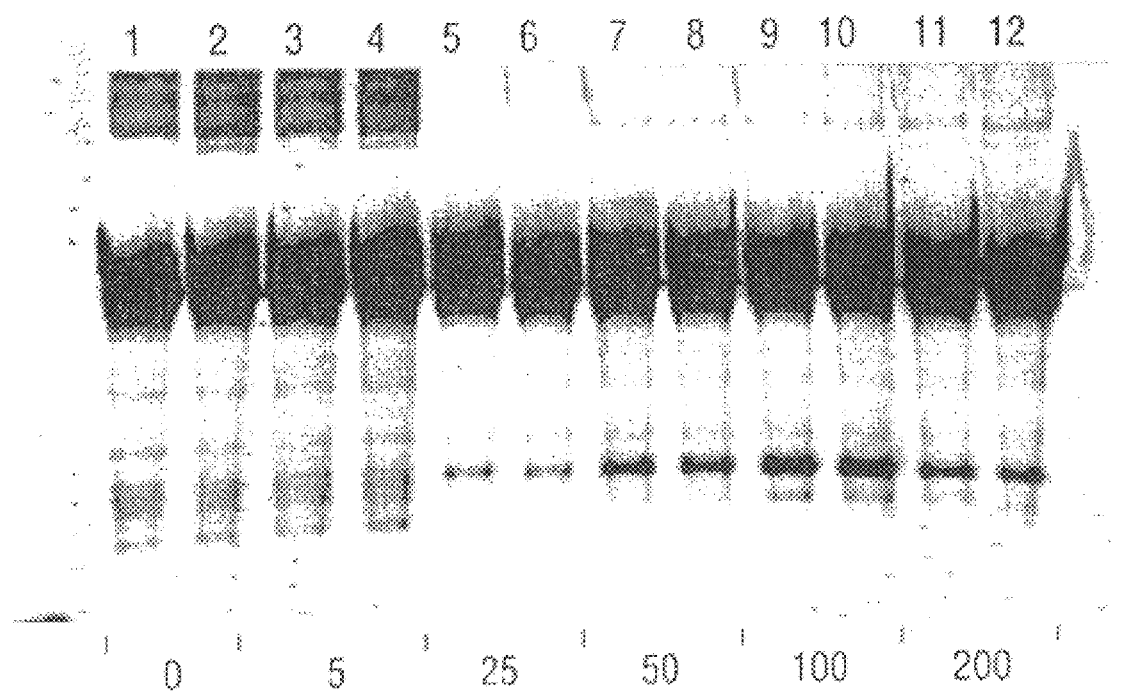
FIG. 42 is the image generated by a fluorescence imager showing the products of invader-directed cleavage assays run in the presence of increasing concentrations of KCl.

FIG. 42 shows the results of varying the KCl concentration in combination with the use of 2 mM MnCl$_2$, in an otherwise standard reaction. The reactions were performed in duplicate for confirmation of observations; the reactions shown in lanes 1 and 2 contained no added KCl, lanes 3 and 4 contained KCl at 5 mM, lanes 5 and 6 contained 25 mM KCl, lanes 7 and 8 contained 50 mM KCl, lanes 9 and 10 contained 100 mM KCl and lanes 11 and 12 contained 200 mM KCl. These results show that the inclusion of KCl allows the generation of a specific cleavage product. While the strongest signal is observed at the 100 mM KCl concentration, the specificity of signal in the other reactions with KCl at or above 25 mM indicates that concentrations in the full range (i.e., 25–200 mM) may be chosen if it is so desirable for any particular reaction conditions.

As shown in FIG. 42, the invader-directed cleavage reaction requires the presence of salt (e.g., KCl) for effective cleavage to occur. In other reactions, it has been found that KCl can inhibit the activity of certain Cleavase® enzymes when present at concentrations above about 25 mM (For example, in cleavage reactions using the S-60 oligonucleotide shown in FIG. 30, in the absence of primer, the Cleavase® BN enzyme loses approximately 50% of its activity in 50 mM KCl). Therefore, the use of alternative salts in the invader-directed cleavage reaction was examined. In these experiments, the potassium ion was replaced with either Na$^+$ or Li$^+$ or the chloride ion was replaced with glutamic acid. The replacement of KCl with alternative salts is described below in sections c–e.

c) NaCl Titration

Figure 43:
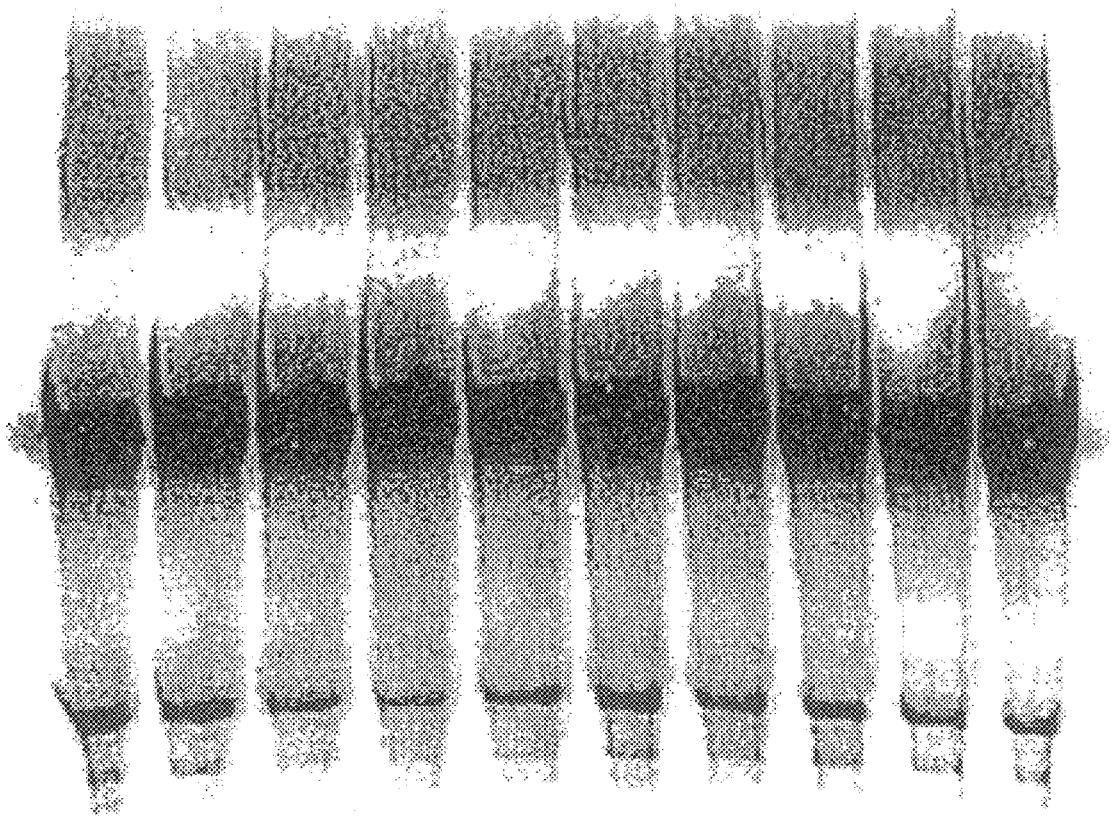
FIG. 43 is the image generated by a fluorescence imager showing the products of invader-directed cleavage assays run in the presence of increasing concentrations of NaCl.

FIG. 43 shows the results of using various concentrations of NaCl in place of KCl (lanes 3–10) in combination with the use 2 mM MnCl$_2$, in an otherwise standard reaction, in comparison to the effects seen with 100 mM KCl (lanes 1 and 2). The reactions analyzed in lanes 3 and 4 contained NaCl at 75 mM, lanes 5 and 6 contained 100 mM, lanes 7 and 8 contained 150 mM and lanes 9 and 10 contained 200 mM. These results show that NaCl can be used as a replacement for KCl in the invader-directed cleavage reaction (i.e., the presence of NaCl, like KCl, enhances product accumulation).

d) LiCl Titration

Figure 44:
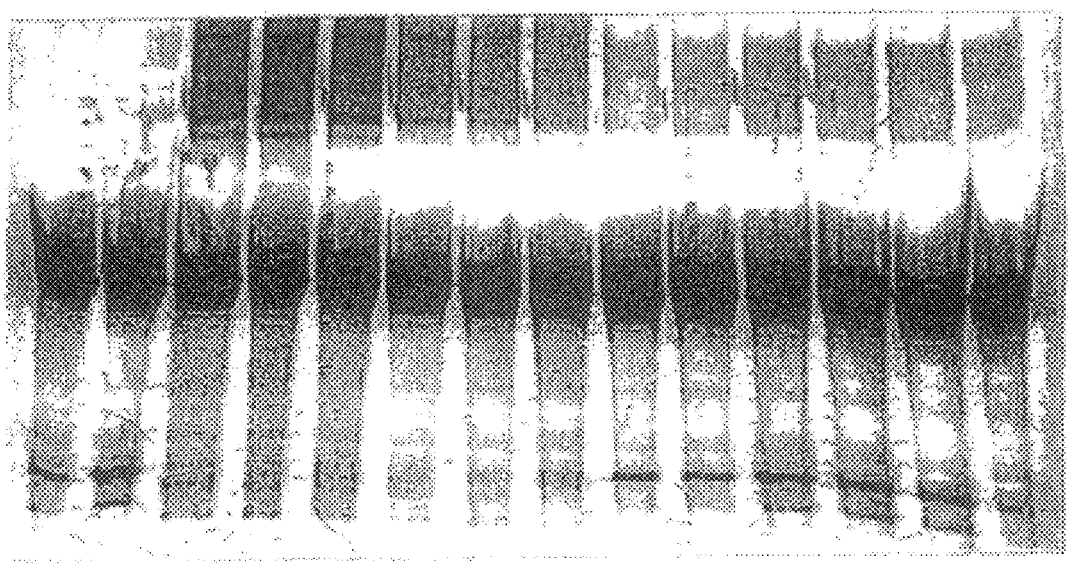
FIG. 44 is the image generated by a fluorescence imager showing the products of invader-directed cleavage assays run in the presence of increasing concentrations of LiCl.

FIG. 44 shows the results of using various concentrations of LiCl in place of KCl (lanes 3–14) in otherwise standard reactions, compared to the effects seen with 100 mM KCl (lanes 1 and 2). The reactions analyzed in lanes 3 and 4 contained LiCl at 25 mM, lanes 5 and 6 contained 50 mM, lanes 7 and 8 contained 75 mM, lanes 9 and 10 contained 100 mM, lanes 11 and 12 contained 150 mM and lanes 13 and 14 contained 200 mM. These results demonstrate that LiCl can be used as a suitable replacement for KCl in the invader-directed cleavage reaction (i.e., the presence of LiCl, like KCl, enhances product accumulation).

e) KGlu Titration

Figure 45:
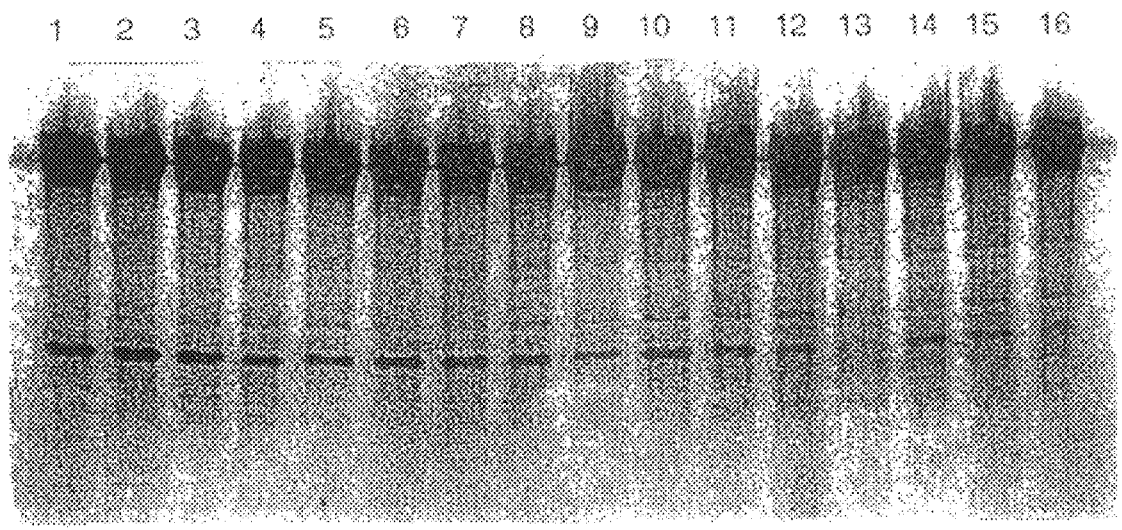
FIG. 45 is the image generated by a fluorescence imager showing the products of invader-directed cleavage assays run in the presence of increasing concentrations of KGlu.

FIG. 45 shows the results of using a glutamate salt of potassium (KGlu) in place of the more commonly used chloride salt (KCl) in reactions performed over a range of temperatures. KGlu has been shown to be a highly effective salt source for some enzymatic reactions, showing a broader range of concentrations which permit maximum enzymatic activity [Leirmo et al. (1987) Biochem. 26:2095]. The ability of KGlu to facilitate the annealing of the probe and invader oligonucleotides to the target nucleic acid was compared to that of LiCl. In these experiments, the reactions were run for 15 minutes, rather than the standard 20 minutes. The reaction analyzed in lane 1 contained 150 mM LiCl and was run at 65° C.; the reactions analyzed in lanes 2–4 contained 200 mM, 300 mM and 400 mM KGlu, respectively and were run at 65° C. The reactions analyzed in lanes 5–8 repeated the array of salt concentrations used in lanes 1–4, but were performed at 67° C.; lanes 9–12 show the same array run at 69° C. and lanes 13–16 show the same array run at 71° C. The results shown in FIG. 45 demonstrate that KGlu was very effective as a salt in the invasive cleavage reactions. In addition, these data show that the range of allowable KGlu concentrations was much greater than that of LiCl, with full activity apparent even at 400 mM KGlu.

f) MnCl$_2$ And MgCl$_2$ Titration And Ability To Replace MnCl$_2$ With MgCl$_2$ In some instances it may be desirable to perform the invasive cleavage reaction in the presence of Mg$^{2+}$, either in addition to, or in place of Mn$^{2+}$ as the necessary divalent cation required for activity of the enzyme employed. For example, some common methods of preparing DNA from bacterial cultures or tissues use MgCl$_2$ in solutions which are used to facilitate the collection of DNA by precipitation. In addition, elevated concentrations (i.e., greater than 5 mM) of divalent cation can be used to facilitate hybridization of nucleic acids, in the same way that the monovalent salts were used above, thereby enhancing the invasive cleavage reaction. In this experiment, the tolerance of the invasive cleavage reaction was examined for 1) the substitution of MgCl$_2$ for MnCl$_2$ and for the ability to produce specific product in the presence of increasing concentrations of MgCl$_2$ and MnCl$_2$.

Figure 46:
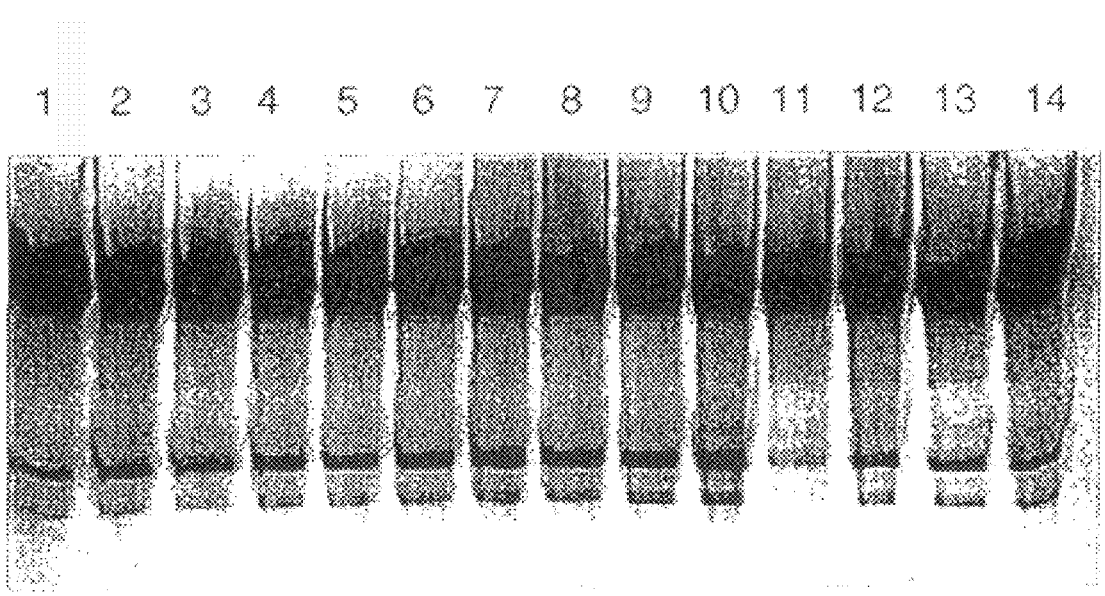
FIG. 46 is the image generated by a fluorescence imager showing the products of invader-directed cleavage assays run in the presence of increasing concentrations of $MnCl_2$ or $MgCl_2$.

FIG. 46 shows the results of either varying the concentration of MnCl$_2$ from 2 mM to 8 mM, replacing the MnCl$_2$ with MgCl$_2$ at 2 to 4 mM, or of using these components in combination in an otherwise standard reaction. The reactions analyzed in lanes 1 and 2 contained 2 mM each MnCl$_2$ and MgCl$_2$, lanes 3 and 4 contained 2 mM MnCl$_2$ only, lanes 5 and 6 contained 3 mM MnCl$_2$, lanes 7 and 8 contained 4 mM MnCl$_2$, lanes 9 and 10 contained 8 mM MnCl$_2$. The reactions analyzed in lanes 11 and 12 contained 2 mM MgCl$_2$ and lanes 13 and 14 contained 4 mM MgCl$_2$. These results show that both MnCl$_2$ and MgCl$_2$ can be used as the necessary divalent cation to enable the cleavage activity of the Cleavase® A/G enzyme in these reactions and that the invasive cleavage reaction can tolerate a broad range of concentrations of these components.

In addition to examining the effects of the salt environment on the rate of product accumulation in the invasive cleavage reaction, the use of reaction constituents shown to be effective in enhancing nucleic acid hybridization in either standard hybridization assays (e.g., blot hybridization) or in ligation reactions was examined. These components may act as volume excluders, increasing the effective concentration of the nucleic acids of interest and thereby enhancing hybridization, or they may act as charge-shielding agents to minimize repulsion between the highly charged backbones of the nucleic acids strands. The results of these experiments are described in sections g and h below.

g) Effect Of CTAB Addition

Figure 47:
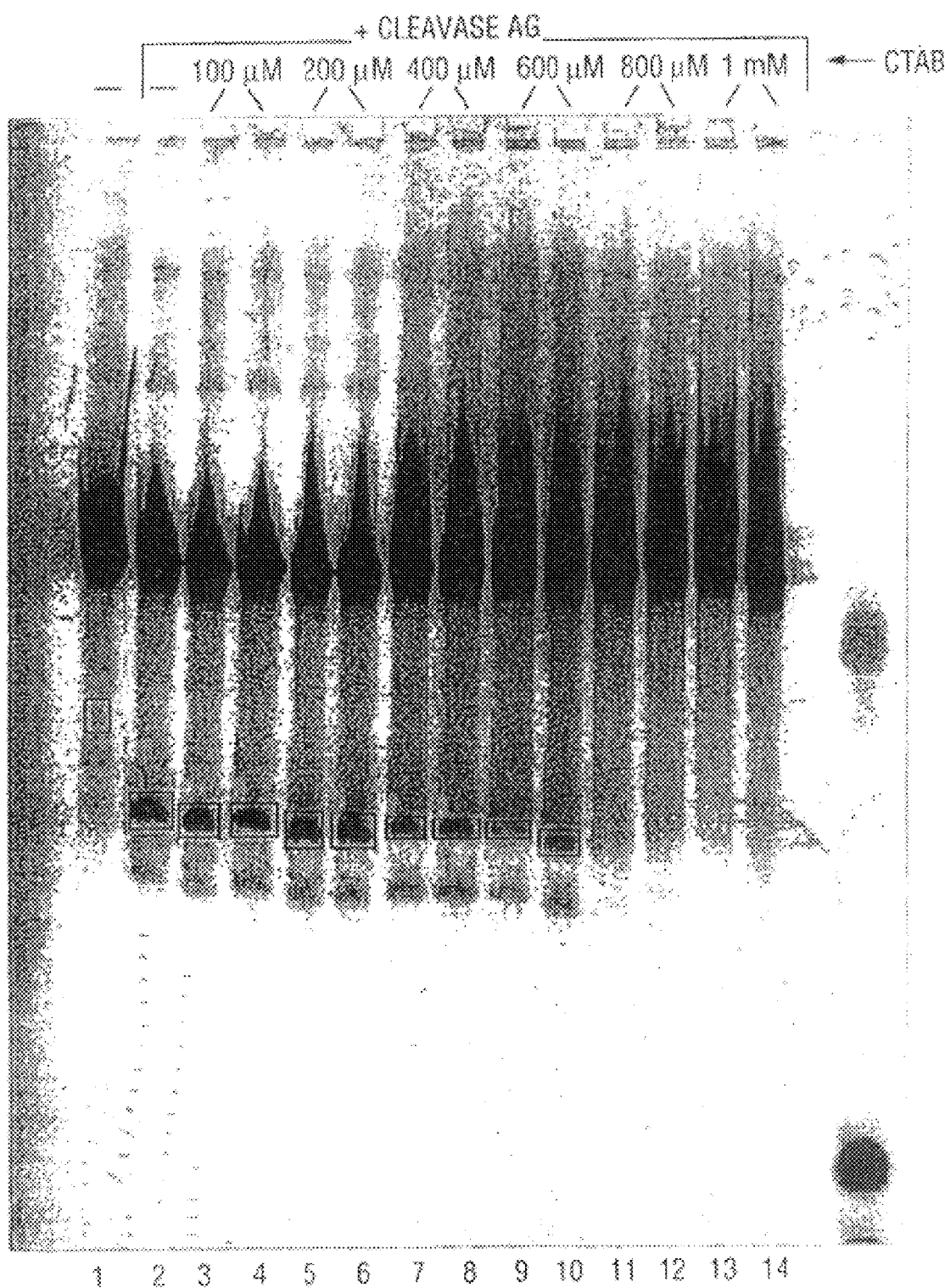
FIG. 47 is the image generated by a fluorescence imager showing the products of invader-directed cleavage assays run in the presence of increasing concentrations of CTAB.

The polycationic detergent cetyltrietheylammonium bromide (CTAB) has been shown to dramatically enhance hybridization of nucleic acids [Pontius and Berg (1991) Proc. Natl. Acad. Sci. USA 88:8237]. The data shown in FIG. 47 depicts the results of adding the detergent CTAB to invasive cleavage reactions in which 150 mM LiCl was used in place of the KCl in otherwise standard reactions. Lane 1 shows unreacted (i.e., uncut) probe, and the reaction shown in lane 1 is the LiCl-modified standard reaction without CTAB. The reactions analyzed in lanes 3 and 4 contained 100 μM CTAB, lanes 5 and 6 contained 200 μM CTAB, lanes 7 and 8 contained 400 μM CTAB, lanes 9 and 10 contained 600 μM CTAB, lanes 11 and 12 contained 800 μM CTAB and lanes 13 and 14 contained 1 mM CTAB. These results showed that the lower amounts of CTAB may have a very moderate enhancing effect under these reaction conditions, and the presence of CTAB in excess of about 500 μM was inhibitory to the accumulation of specific cleavage product.

h) Effect Of PEG Addition

Figure 48:
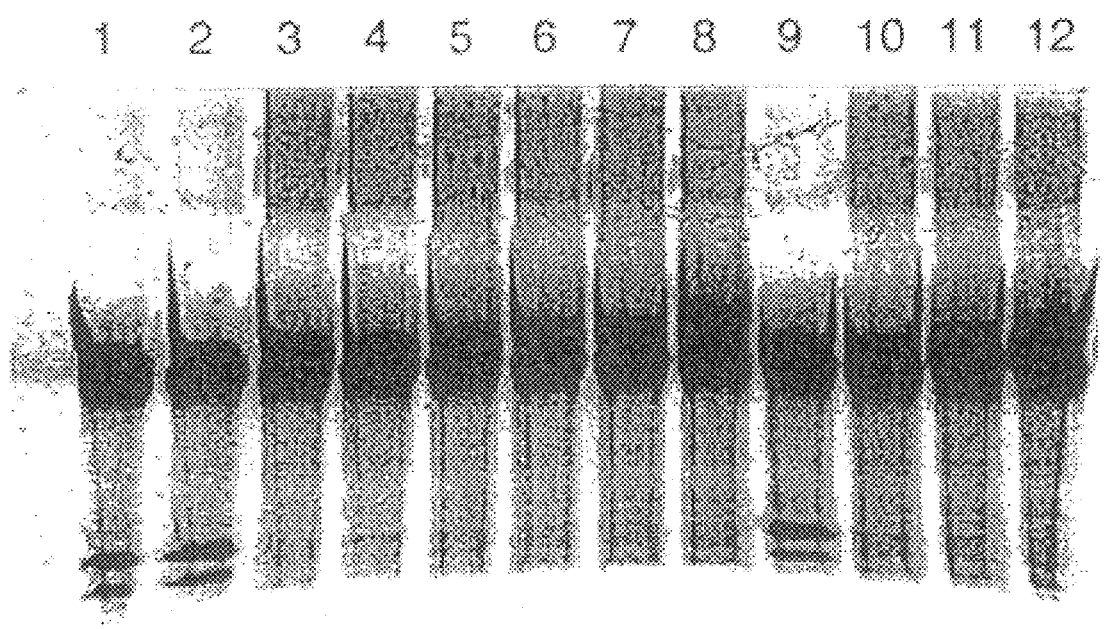
FIG. 48 is the image generated by a fluorescence imager showing the products of invader-directed cleavage assays run in the presence of increasing concentrations of PEG.

FIG. 48 shows the effect of adding polyethylene glycol (PEG) at various percentage (w/v) concentrations to otherwise standard reactions. The effects of increasing the reaction temperature of the PEG-containing reactions was also examined. The reactions assayed in lanes 1 and 2 were the standard conditions without PEG, lanes 3 and 4 contained 4% PEG, lanes 5 and 6 contained 8% PEG and lanes 7 and 8 contained 12% PEG. Each of the aforementioned reactions was performed at 61° C. The reactions analyzed in lanes 9, 10, 11 and 12 were performed at 65° C., and contained 0%, 4%, 8% and 12% PEG, respectively. These results show that at all percentages tested, and at both temperatures tested, the inclusion of PEG substantially eliminated the production of specific cleavage product.

In addition to the data presented above (i.e., effect of CTAB and PEG addition), the presence of 1× Denhardts in the reaction mixture was found to have no adverse effect upon the cleavage reaction [50× Denhardt's contains per 500 ml: 5 g Ficoll, 5 g polyvinylpyrrolidone, 5 g BSA]. In addition, the presence of each component of Denhardt's was examined individually (i.e., Ficoll alone, polyvinylpyrrolidone alone, BSA alone) for the effect upon the invader-directed cleavage reaction; no adverse effect was observed.

i) Effect Of The Addition Of Stabilizing Agents

Another approach to enhancing the output of the invasive cleavage reaction is to enhance the activity of the enzyme employed, either by increasing its stability in the reaction environment or by increasing its turnover rate. Without regard to the precise mechanism by which various agents operate in the invasive cleavage reaction, a number of agents commonly used to stabilize enzymes during prolonged storage were tested for the ability to enhance the accumulation of specific cleavage product in the invasive cleavage reaction.

Figure 49:
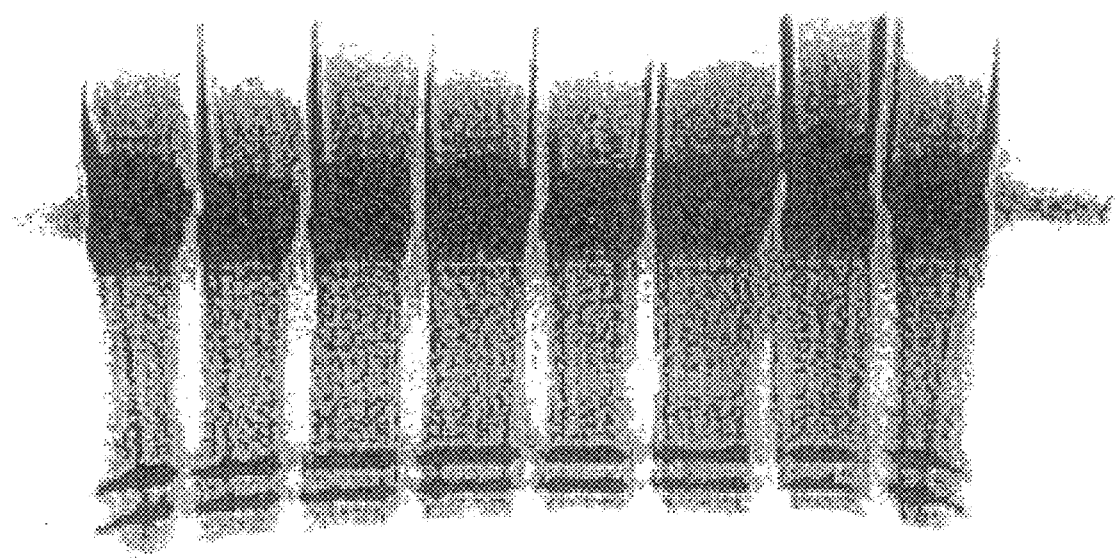
FIG. 49 is the image generated by a fluorescence imager showing the products of invader-directed cleavage assays run in the presence of glycerol, Tween-20 and/or Nonidet-P40.

FIG. 49 shows the effects of adding glycerol at 15% and of adding the detergents Tween-20 and Nonidet-P40 at 1.5%, alone or in combination, in otherwise standard reactions. The reaction analyzed in lane 1 was a standard reaction. The reaction analyzed in lane 2 contained 1.5% NP-40, lane 3 contained 1.5% Tween 20, lane 4 contained 15% glycerol. The reaction analyzed in lane 5 contained both Tween-20 and NP-40 added at the above concentrations, lane 6 contained both glycerol and NP-40, lane 7 contained both glycerol and Tween-20, and lane 8 contained all three agents. The results shown in FIG. 49 demonstrate that under these conditions these adducts had little or no effect on the accumulation of specific cleavage product.

Figure 50:
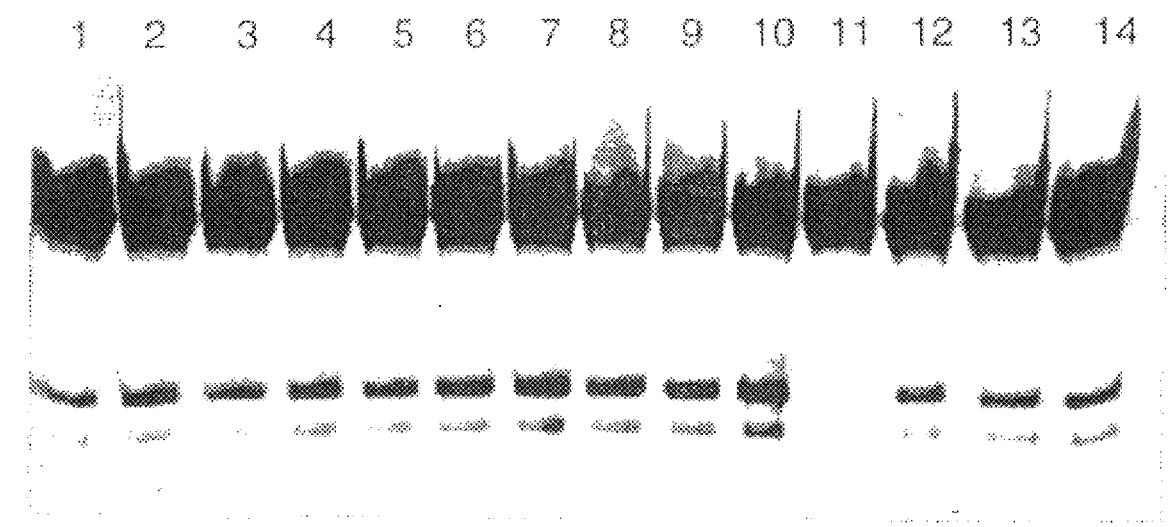
FIG. 50 is the image generated by a fluorescence imager showing the products of invader-directed cleavage assays run in the presence of increasing concentrations of gelatin in reactions containing or lacking KCl or LiCl.

FIG. 50 shows the effects of adding gelatin to reactions in which the salt identity and concentration were varied from the standard reaction. In addition, all of these reactions were performed at 65° C., instead of 61° C. The reactions assayed in lanes 1–4 lacked added KCl, and included 0.02%, 0.05%, 0.1% or 0.2% gelatin, respectively. Lanes 5, 6, 7 and 8 contained the same titration of gelatin, respectively, and included 100 mM KCl. Lanes 9, 10, 11 and 12, also had the same titration of gelatin, and additionally included 150 mM LiCl in place of KCl. Lanes 13 and 14 show reactions that did not include gelatin, but which contained either 100 mM KCl or 150 mM LiCl, respectively. The results shown in FIG. 50 demonstrated that in the absence of salt the gelatin had a moderately enhancing effect on the accumulation of specific cleavage product, but when either salt (KCl or LiCl) was added to reactions performed under these conditions, increasing amounts of gelatin reduced the product accumulation.

j) Effect Of Adding Large Amounts Of Non-Target Nucleic Acid

In detecting specific nucleic acid sequences within samples, it is important to determine if the presence of additional genetic material (i.e., non-target nucleic acids) will have a negative effect on the specificity of the assay. In this experiment, the effect of including large amounts of non-target nucleic acid, either DNA or RNA, on the specificity of the invasive cleavage reaction was examined. The data was examined for either an alteration in the expected site of cleavage, or for an increase in the nonspecific degradation of the probe oligonucleotide.

Figure 51:
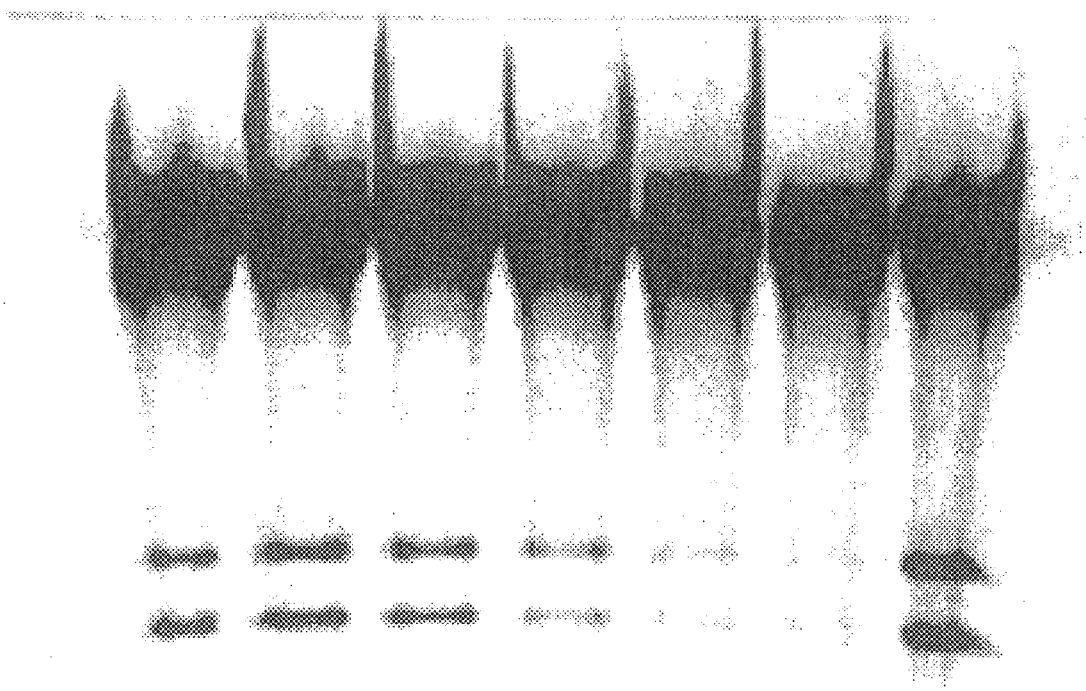
FIG. 51 is the image generated by a fluorescence imager showing the products of invader-directed cleavage assays run in the presence of increasing amounts of genomic DNA or tRNA.

FIG. 51 shows the effects of adding non-target nucleic acid (e.g., genomic DNA or tRNA) to an invasive cleavage reaction performed at 65° C., with 150 mM LiCl in place of the KCl in the standard reaction. The reactions assayed in lanes 1 and 2 contained 235 and 470 ng of genomic DNA, respectively. The reactions analyzed in lanes 3, 4, 5 and 6 contained 100 ng, 200 ng, 500 ng and 1 μg of tRNA, respectively. Lane 7 represents a control reaction which contained no added nucleic acid beyond the amounts used in the standard reaction. The results shown in FIG. 51 demonstrate that the inclusion of non-target nucleic acid in large amounts could visibly slow the accumulation of specific cleavage product (while not limiting the invention to any particular mechanism, it is thought that the additional nucleic acid competes for binding of the enzyme with the specific reaction components). In additional experiments it was found that the effect of adding large amounts of non-target nucleic acid can be compensated for by increasing the enzyme in the reaction. The data shown in FIG. 51 also demonstrate that a key feature of the invasive cleavage reaction, the specificity of the detection, was not compromised by the presence of large amounts of non-target nucleic acid.

In addition to the data presented above, invasive cleavage reactions were run with succinate buffer at pH 5.9 in place of the MOPS buffer used in the "standard" reaction; no adverse effects were observed.

The data shown in FIGS. 42–51 and described above demonstrate that the invasive cleavage reaction can be performed using a wide variety of reaction conditions and is therefore suitable for practice in clinical laboratories.

EXAMPLE 20

Detection of RNA Targets by Invader-Directed Cleavage

In addition to the clinical need to detect specific DNA sequences for infectious and genetic diseases, there is a need for technologies that can quantitatively detect target nucleic acids that are composed of RNA. For example, a number of viral agents, such as hepatitis C virus (HCV) and human immunodeficiency virus (HIV) have RNA genomic material, the quantitative detection of which can be used as a measure of viral load in a patient sample. Such information can be of critical diagnostic or prognostic value.

Hepatitis C virus (HCV) infection is the predominant cause of post-transfusion non-A, non-B (NANB) hepatitis around the world. In addition, HCV is the major etiologic agent of hepatocellular carcinoma (HCC) and chronic liver disease world wide. The genome of HCV is a small (9.4 kb) RNA molecule. In studies of transmission of HCV by blood transfusion it has been found the presence of HCV antibody, as measured in standard immunological tests, does not always correlate with the infectivity of the sample, while the presence of HCV RNA in a blood sample strongly correlates with infectivity. Conversely, serological tests may remain negative in immunosuppressed infected individuals, while HCV RNA may be easily detected [J. A. Cuthbert (1994) Clin. Microbiol. Rev. 7:505].

The need for and the value of developing a probe-based assay for the detection the HCV RNA is clear. The polymerase chain reaction has been used to detect HCV in clinical samples, but the problems associated with carry-over contamination of samples has been a concern. Direct detection of the viral RNA without the need to perform either reverse transcription or amplification would allow the elimination of several of the points at which existing assays may fail.

The genome of the positive-stranded RNA hepatitis C virus comprises several regions including 5' and 3' noncoding regions (i.e., 5' and 3' untranslated regions) and a polyprotein coding region which encodes the core protein (C), two envelope glycoproteins (E1 and E2/NS1) and six nonstructural glycoproteins (NS2–NS5b). Molecular biological analysis of the HCV genome has showed that some regions of the genome are very highly conserved between isolates, while other regions are fairly rapidly changeable. The 5' noncoding region (NCR) is the most highly conserved region in the HCV. These analyses have allowed these viruses to be divided into six basic genotype groups, and then further classified into over a dozen sub-types [the nomenclature and division of HCV genotypes is evolving; see Altamirano et al., *J. Infect. Dis.* 171:1034 (1995) for a recent classification scheme].

In order to develop a rapid and accurate method of detecting HCV present in infected individuals, the ability of the invader-directed cleavage reaction to detect HCV RNA was examined. Plasmids containing DNA derived from the conserved 5'-untranslated region of six different HCV RNA isolates were used to generate templates for in vitro transcription. The HCV sequences contained within these six plasmids represent genotypes 1 (four sub-types represented; 1a, 1b, 1c, and Δ1c), 2, and 3. The nomenclature of the HCV genotypes used herein is that of Simmonds et al. [as described in Altamirano et at., supra]. The Δ1c subtype was used in the model detection reaction described below.

a) Generation of Plasmids Containing HCV Sequences

Six DNA fragments derived from HCV were generated by RT-PCR using RNA extracted from serum samples of blood donors; these PCR fragments were a gift of Dr. M. Altamirano (University of British Columbia. Vancouver). These PCR fragments represent HCV sequences derived from HCV genotypes 1a, 1b, 1c, Δ1c, 2c and 3a.

The RNA extraction, reverse transcription and PCR were performed using standard techniques (Altamirano et al., supra). Briefly, RNA was extracted from 100 μl of serum using guanidine isothiocyanate, sodium lauryl sarkosate and phenol-chloroform [Inchauspe et al., *Hepatology* 14:595 (1991)]. Reverse transcription was performed according to the manufacturer's instructions using a GeneAmp rTth reverse transcriptase RNA PCR kit (Perkin-Elmer) in the presence of an external antisense primer, HCV342. The sequence of the HCV342 primer is 5'-GGTTTTTCTTTGAGG TTTAG-3' (SEQ ID NO:51). Following termination of the RT reaction, the sense primer HCV7 [5'-GCGACACTCCACCATAGAT-3' (SEQ ID NO:52)] and magnesium were added and a first PCR was performed. Aliquots of the first PCR products were used in a second (nested) PCR in the presence of primers HCV46 [5'-CTGTCTTCACGCAGAAAGC-3' (SEQ ID NO:53)] and HCV308 [5'-GCACGGTCTACGAGACCTC-3' (SEQ ID NO:54)]. The PCRs produced a 281 bp product which corresponds to a conserved 5' noncoding region (NCR) region of HCV between positions –284 and –4 of the HCV genome (Altamirano et al., supra).

The six 281 bp PCR fragments were used directly for cloning or they were subjected to an additional amplification step using a 50 μl PCR comprising approximately 100 fmoles of DNA, the HCV46 and HCV308 primers at 0.1 μM, 100 μM of all four dNTPs and 2.5 units of Taq DNA polymerase in a buffer containing 10 mM Tris-HCl, pH 8.3, 50 mM KCl, 1.5 mM MgCl$_2$ and 0.1% Tween 20. The PCRs were cycled 25 times at 96° C. for 45 sec., 55° C. for 45 sec. and 72° C. for 1 min. Two microliters of either the original DNA samples or the reamplified PCR products were used for cloning in the linear pT7Blue T-vector (Novagen, Madison, Wis.) according to manufacturer's protocol. After the PCR products were ligated to the pT7Blue T-vector, the ligation reaction mixture was used to transform competent JM109 cells (Promega). Clones containing the pT7Blue T-vector with an insert were selected by the presence of colonies having a white color on LB plates containing 40 μg/ml X-Gal, 40 μg/ml IPTG and 50 μg/ml ampicillin. Four colonies for each PCR sample were picked and grown overnight in 2 ml LB media containing 50 μg/ml carbenicillin. Plasmid DNA was isolated using the following alkaline miniprep protocol. Cells from 1.5 ml of the overnight culture were collected by centrifugation for 2 min. in a microcentrifuge (14K rpm), the supernatant was discarded and the cell pellet was resuspended in 50 μl TE buffer with 10 μg/ml RNAse A (Pharmacia). One hundred microliters of a solution containing 0.2 N NaOH, 1% SDS was added and the cells were lysed for 2 min. The lysate was gently mixed with 100 μl of 1.32 M potassium acetate, pH 4.8, and the mixture was centrifuged for 4 min. in a microcentrifuge (14K rpm); the pellet comprising cell debris was discarded. Plasmid DNA was precipitated from the supernatant with 200 μl ethanol and pelleted by centrifugation a microcentrifuge (14K rpm). The DNA pellet was air dried for 15 min. and was then redissolved in 50 μl TE buffer (10 mM Tris-HCl, pH 7.8, 1 mM EDTA).

b) Reamplification Of HCV Clones To Add The Phage T7 Promoter For Subsequent In Vitro Transcription To ensure that the RNA product of transcription had a discrete 3' end it was necessary to create linear transcription templates which stopped at the end of the HCV sequence. These fragments were conveniently produced using the PCR to reamplify the segment of the plasmid containing the phage promoter sequence and the HCV insert. For these studies, the clone of HCV type Δ1c was reamplified using a primer that hybridizes to the T7 promoter sequence: 5'-TAATACGACTCACTATAGGG-3' (SEQ ID NO:55; "the T7 promoter primer") (Novagen) in combination with the 3' terminal HCV-specific primer HCV308 (SEQ ID NO:54). For these reactions, 1 μl of plasmid DNA (approximately 10 to 100 ng) was reamplified in a 200 μl PCR using the T7 and HCV308 primers as described above with the exception that 30 cycles of amplification were employed. The resulting amplicon was 354 bp in length. After amplification the PCR mixture was transferred to a fresh 1.5 ml microcentrifuge tube, the mixture was brought to a final concentration of 2 M NH$_4$OAc, and the products were precipitated by the addition of one volume of 100% isopropanol. Following a 10 min. incubation at room temperature, the precipitates were collected by centrifugation, washed once with 80% ethanol and dried under vacuum. The collected material was dissolved in 100 μl nuclease-free distilled water (Promega).

Segments of RNA were produced from this amplicon by in vitro transcription using the RiboMAX™ Large Scale RNA Production System (Promega) in accordance with the manufacturer's instructions, using 5.3 μg of the amplicon described above in a 100 μl reaction. The transcription reaction was incubated for 3.75 hours, after which the DNA template was destroyed by the addition of 5–6 μl of RQ1 RNAse-free DNAse (1 unit/μl) according to the RiboMAX™ kit instructions. The reaction was extracted twice with phenol/chloroform/isoamyl alcohol (50:48:2) and the aqueous phase was transferred to a fresh microcentrifuge tube. The RNA was then collected by the addition of 10 μl of 3M NH$_4$OAc, pH 5.2 and 110 μl of 100% isopropanol. Following a 5 min. incubation at 4° C., the precipitate was collected by centrifugation, washed once with 80% ethanol and dried under vacuum. The sequence of the resulting RNA transcript (HCV1.1 transcript) is listed in SEQ ID NO:56.

c) Detection Of The HCV1.1 Transcript In The Invader-Directed Cleavage Assay

Detection of the HCV1.1 transcript was tested in the invader-directed cleavage assay using an HCV-specific probe oligonucleotide (5'-CCGGTCGTCCTGGCAAT XCC-3' [SEQ ID NO:57]); X indicates the presence of a fluorescein dye on an abasic linker) and an HCV-specific invader oligonucleotide (5'-GTTTATCCAAGAAAGGAC CCGGTC-3' [SEQ ID NO:58]) that causes a 6-nucleotide invasive cleavage of the probe.

Each 10 μl of reaction mixture comprised 5 pmole of the probe oligonucleotide (SEQ ID NO:57) and 10 pmole of the invader oligonucleotide (SEQ ID NO:58) in a buffer of 10 mM MOPS, pH 7.5 with 50 mM KCl, 4 mM MnCl$_2$, 0.05% each Tween-20 and Nonidet-P40 and 7.8 units RNasin® ribonuclease inhibitor (Promega). The cleavage agents employed were Cleavase® A/G (used at 5.3 ng/10 μl reaction) or DNAPTth (used at 5 polymerase units/10 μl reaction). The amount of RNA target was varied as indicated below. When RNAse treatment is indicated, the target RNAs were pre-treated with 10 μg of RNase A (Sigma) at 37° C. for 30 min. to demonstrate that the detection was specific for the RNA in the reaction and not due to the presence of any residual DNA template from the transcription reaction. RNase-treated aliquots of the HCV RNA were used directly without intervening purification.

For each reaction, the target RNAs were suspended in the reaction solutions as described above, but lacking the cleavage agent and the MnCl$_2$ for a final volume of 10 μl, with the invader and probe at the concentrations listed above. The reactions were warmed to 46° C. and the reactions were started by the addition of a mixture of the appropriate enzyme with MnCl$_2$. After incubation for 30 min. at 46° C., the reactions were stopped by the addition of 8 μl of 95% formamide, 10 mM EDTA and 0.02% methyl violet (methyl violet loading buffer). Samples were then resolved by electrophoresis through a 15% denaturing polyacrylamide gel (19:1 cross-linked), containing 7 M urea, in a buffer of 45 mM Tris-Borate, pH 8.3, 1.4 mM EDTA. Following electrophoresis, the labeled reaction products were visualized using the FMBIO-100 Image Analyzer (Hitachi), with the resulting imager scan shown in FIG. 52.

Figure 52:
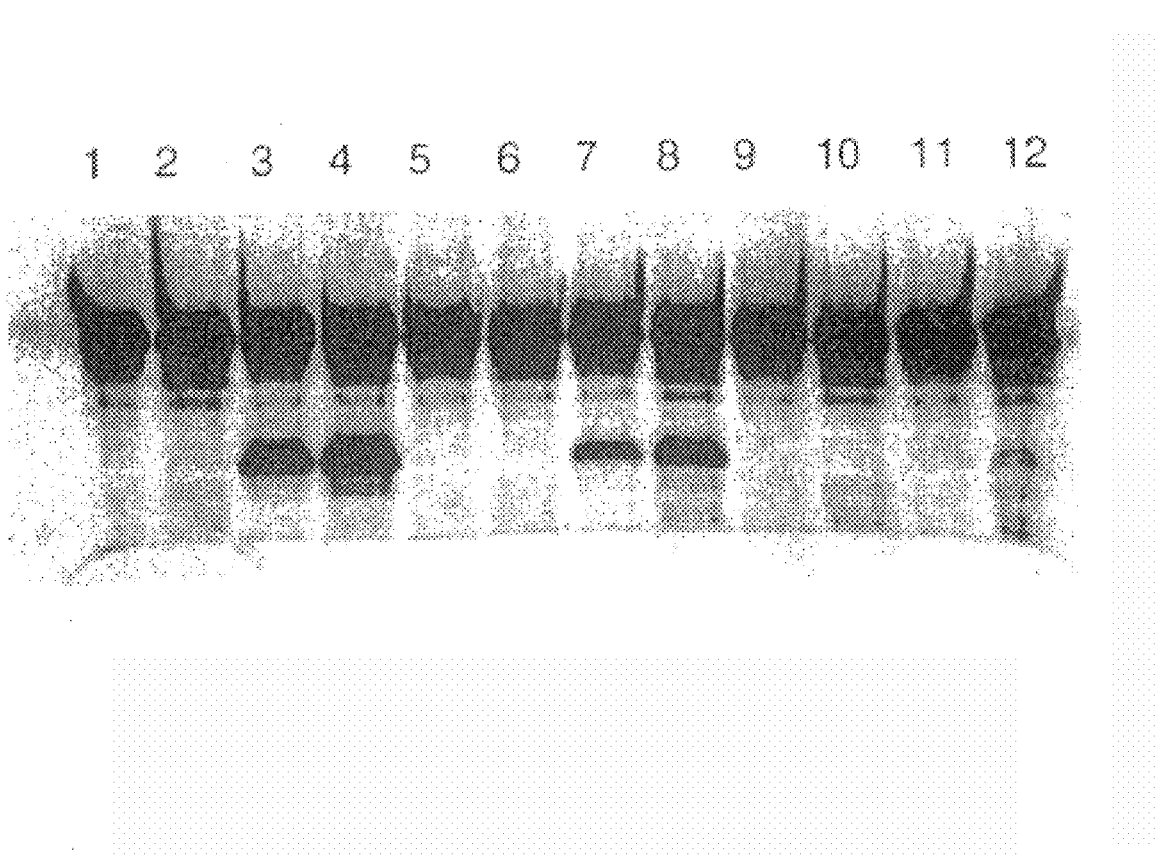
FIG. 52 is the image generated by a fluorescence imager showing the products of invader-directed cleavage assays run use a HCV RNA target.

In FIG. 52, the samples analyzed in lanes 1–4 contained 1 pmole of the RNA target, the reactions shown in lanes 5–8 contained 100 fmoles of the RNA target and the reactions shown in lanes 9–12 contained 10 fmoles of the RNA target. All odd-numbered lanes depict reactions performed using Cleavase® A/G enzyme and all even-numbered lanes depict reactions performed using DNAPTth. The reactions analyzed in lanes 1, 2, 5, 6, 9 and 10 contained RNA that had been pre-digested with RNase A. These data demonstrate that the invasive cleavage reaction efficiently detects RNA targets and further, the absence of any specific cleavage signal in the RNase-treated samples confirms that the specific cleavage product seen in the other lanes is dependent upon the presence of input RNA.

EXAMPLE 21

The Fate of the Target RNA in the Invader-Directed Cleavage Reaction

In this example, the fate of the RNA target in the invader-directed cleavage reaction was examined. As shown above in Ex. 1D, when RNAs are hybridized to DNA oligonucleotides, the 5' nucleases associated with DNA polymerases can be used to cleave the RNAs; such cleavage can be suppressed when the 5' arm is long or when it is highly structured [Lyamichev et al. (1993) Science 260:778 and U.S. Pat. No. 5,422,253, the disclosure of which is herein incorporated by reference]. In this experiment, the extent to which the RNA target would be cleaved by the cleavage agents when hybridized to the detection oligonucleotides (i.e., the probe and invader oligonucleotides) was examined using reactions similar to those described in Ex. 20, performed using fluorescein-labeled RNA as a target.

Transcription reactions were performed as described in Ex. 20 with the exception that 2% of the UTP in the reaction was replaced with fluorescein-12-UTP (Boehringer Mannheim) and 5.3 μg of the amplicon was used in a 100 μl reaction. The transcription reaction was incubated for 2.5 hours, after which the DNA template was destroyed by the addition of 5–6 μl of of RQ1 RNAse-free DNAse (1 unit/) according to the RiboMAXÔ kit instructions. The organic extraction was omitted and the RNA was collected by the addition of 10 μl of 3M NaOAc, pH 5.2 and 110 μl of 100% isopropanol. Following a 5 min. incubation at 4° C., the precipitate was collected by centrifugation, washed once with 80% ethanol and dried under vacuum. The resulting RNA was dissolved in 100 μl of nuclease-free water. 50% of the sample was purified by electrophoresis through a 8% denaturing polyacrylamide gel (19:1 cross-linked), containing 7 M urea, in a buffer of 45 mM Tris-Borate, pH 8.3, 1.4 mM EDTA. The gel slice containing the full-length material was excised and the RNA was eluted by soaking the slice overnight at 4° C. in 200 μl of 10 mM Tris-Cl, pH 8.0, 0.1 mM EDTA and 0.3 M NaOAc. The RNA was then precipitated by the addition of 2.5 volumes of 100% ethanol. After incubation at −20° C. for 30 min., the precipitates were recovered by centrifugation, washed once with 80% ethanol and dried under vacuum. The RNA was dissolved in 25 μl of nuclease-free water and then quantitated by UV absorbance at 260 nm.

Samples of the purified RNA target were incubated for 5 or 30 min. in reactions that duplicated the Cleavase® A/G and DNAPTth invader reactions described in Ex. 20 with the exception that the reactions lacked probe and invader oligonucleotides. Subsequent analysis of the products showed that the RNA was very stable, with a very slight background of non-specific degradation, appearing as a gray background in the gel lane. The background was not dependent on the presence of enzyme in the reaction.

Figure 53A:
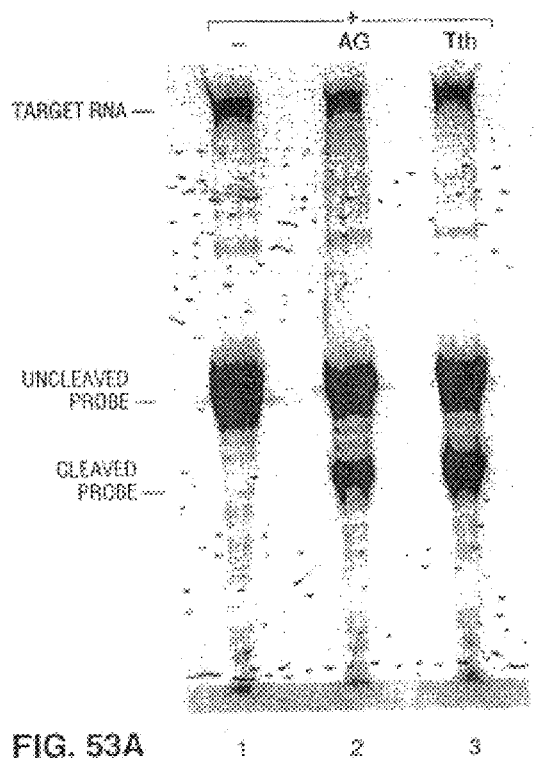
FIG. 53 is the image generated by a fluorescence imager showing the products of invader-directed cleavage assays run using a HCV RNA target and demonstrate the stability of RNA targets under invader-directed cleavage assay conditions.

Invader detection reactions using the purified RNA target were performed using the probe/invader pair described in Ex. 20 (SEQ ID NOS:57 and 58). Each reaction included 500 fmole of the target RNA, 5 pmoles of the fluorescein-labeled probe and 10 pmoles of the invader oligonucleotide in a buffer of 10 mM MOPS, pH 7.5 with 150 mM LiCl, 4 mM MnCl$_2$, 0.05% each Tween-20 and Nonidet-P40 and 39 units RNAsin® (Promega). These components were combined and warmed to 50° C. and the reactions were started by the addition of either 53 ng of Cleavase® A/G or 5 polymerase units of DNAPTth. The final reaction volume was 10 μl. After 5 min at 50° C., 5 μl aliquots of each reaction were removed to tubes containing 4 μl of 95% formamide, 10 mM EDTA and 0.02% methyl violet. The remaining aliquot received a drop of ChillOut® evaporation barrier and was incubated for an additional 25 min. These reactions were then stopped by the addition of 4 μl of the above formamide solution. The products of these reactions were resolved by electrophoresis through separate 20% denaturing polyacrylamide gels (19:1 cross-linked), containing 7 M urea, in a buffer of 45 mM Tris-Borate, pH 8.3, 1.4 mM EDTA. Following electrophoresis, the labeled reaction products were visualized using the FMBIO-100 Image Analyzer (Hitachi), with the resulting imager scans shown in FIGS. 53A (5 min reactions) and 53B (30 min. reactions).

Figure 53B:
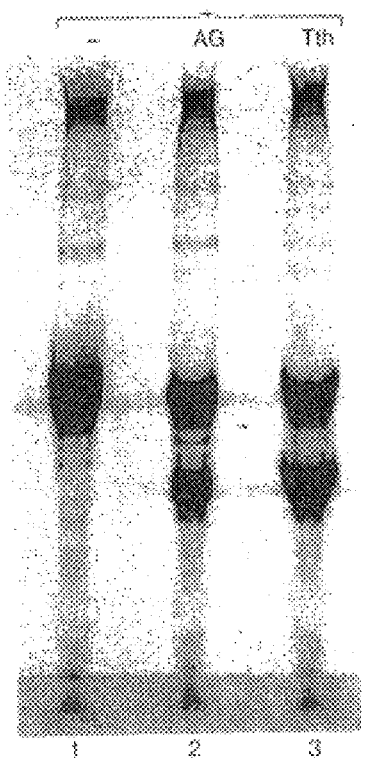

In FIG. 53 the target RNA is seen very near the top of each lane, while the labeled probe and its cleavage products are seen just below the middle of each panel. The FMBIO-100 Image Analyzer was used to quantitate the fluorescence signal in the probe bands. In each panel, lane 1 contains products from reactions performed in the absence of a cleavage agent, lane 2 contains products from reactions performed using Cleavase® A/G and lane 3 contains products from reactions performed using DNAPTth.

Quantitation of the fluorescence signal in the probe bands revealed that after a 5 min. incubation, 12% or 300 fmole of the probe was cleaved by the Cleavase® A/G and 29% or 700 fmole was cleaved by the DNAPTth. After a 30 min. incubation, Cleavase® A/G had cleaved 32% of the probe molecules and DNAPTth had cleaved 70% of the probe molecules. (The images shown in FIGS. 53A and 53B were printed with the intensity adjusted to show the small amount of background from the RNA degradation, so the bands containing strong signals are saturated and therefore these images do not accurately reflect the differences in measured fluorescence)

The data shown in FIG. 53 clearly shows that, under invasive cleavage conditions, RNA molecules are sufficiently stable to be detected as a target and that each RNA molecule can support many rounds of probe cleavage.

EXAMPLE 22

Titration of Target RNA in the Invader-Directed Cleavage Assay

One of the primary benefits of the invader-directed cleavage assay as a means for detection of the presence of specific target nucleic acids is the correlation between the amount of cleavage product generated in a set amount of time and the quantity of the nucleic acid of interest present in the reaction. The benefits of quantitative detection of RNA sequences was discussed in Ex. 20. In this example, we demonstrate the quantitative nature of the detection assay through the use of various amounts of target starting material. In addition to demonstrating the correlation between the amounts of input target and output cleavage product, these data graphically show the degree to which the RNA target can be recycled in this assay The RNA target used in these reactions was the fluorescein-labeled material described in Ex. 21 (i.e., SEQ ID NO:56). Because the efficiency of incorporation of the fluorescein-12-UTP by the T7 RNA polymerase was not known, the concentration of the RNA was determined by measurement of absorbance at 260 nm, not by fluorescence intensity. Each reaction comprised 5 pmoles of the fluorescein-labeled probe (SEQ ID NO:57) and 10 pmoles of the invader oligonucleotide (SEQ ID NO:58) in a buffer of 10 mM MOPS, pH 7.5 with 150 mM LiCl, 4 mM MnCl$_2$, 0.05% each Tween-20 and Nonidet-P40 and 39 units of RNAsin® (Promega). The amount of target RNA was varied from 1 to 100 fmoles, as indicated below. These components were combined, overlaid with ChillOut® evaporation barrier (MJ Research) and warmed to 50° C.; the reactions were started by the addition of either 53 ng of Cleavase® A/G or 5 polymerase units of DNAPTth, to a final reaction volume of 10 μl. After 30 minutes at 50° C., reactions were stopped by the addition of 8 μl of 95% formamide, 10 mM EDTA and 0.02% methyl violet. The unreacted markers in lanes 1 and 2 were diluted in the same total volume (18 μl). The samples were heated to 90° C. for 1 minute and 2.5 μl of each of these reactions were resolved by electrophoresis through a 20% denaturing polyacrylamide gel (19:1 cross link) with 7M urea in a buffer of 45 mM Tris-Borate, pH 8.3, 1.4 mM EDTA, and the labeled reaction products were visualized using the FMBIO-100 image Analyzer (Hitachi), with the resulting imager scans shown in FIG. 54.

Figure 54:
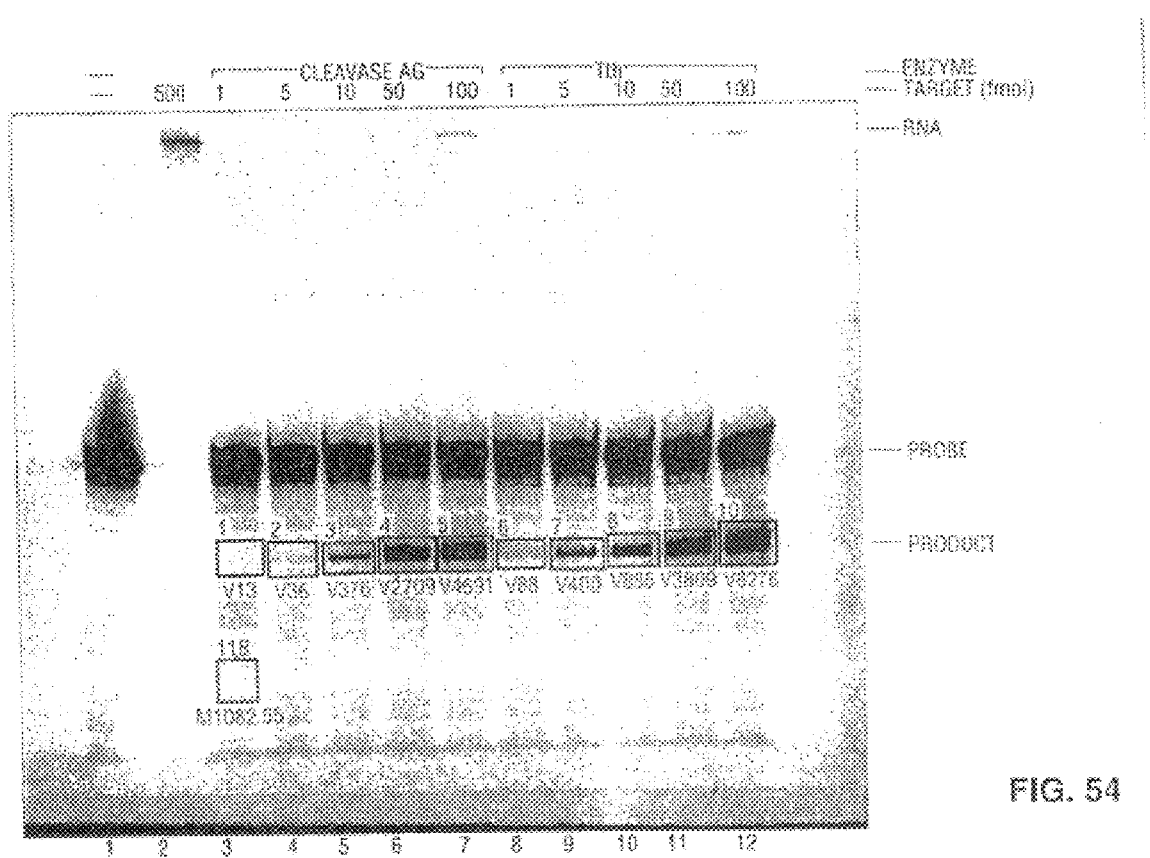
FIG. 54 is the image generated by a fluorescence imager showing the sensitivity of detection and the stability of RNA in invader-directed cleavage assays run using a HCV RNA target.

In FIG. 54, lanes 1 and 2 show 5 pmoles of uncut probe and 500 fmoles of untreated RNA, respectively. The probe is the very dark signal near the middle of the panel, while the RNA is the thin line near the top of the panel. These RNAs were transcribed with a 2% substitution of fluorescein-12-UTP for natural UTP in the transcription reaction. The resulting transcript contains 74 U residues, which would give an average of 1.5 fluorescein labels per molecule. With one tenth the molar amount of RNA loaded in lane 2, the signal in lane 2 should be approximately one seventh (0.15×) the fluorescence intensity of the probe in lane 1. Measurements indicated that the intensity was closer to one fortieth, indicating an efficiency of label incorporation of approximately 17%. Because the RNA concentration was verified by A260 measurement this does not alter the experimental observations below, but it should be noted that the signal from the RNA and the probes does not accurately reflect the relative amounts in the reactions.

The reactions analyzed in lanes 3 through 7 contained 1, 5, 10, 50 and 100 fmoles of target, respectively, with cleavage of the probe accomplished by Cleavase® A/G. The reactions analyzed in lanes 8 through 12 repeated the same array of target amounts, with cleavage of the probe accomplished by DNAPTth. The boxes seen surrounding the product bands show the area of the scan in which the fluorescence was measured for each reaction. The number of fluorescence units detected within each box is indicated below each box; background florescence was also measured.

It can be seen by comparing the detected fluorescence in each lane that the amount of product formed in these 30 minute reactions can be correlated to the amount of target material. The accumulation of product under these conditions is slightly enhanced when DNAPTth is used as the cleavage agent, but the correlation with the amount of target present remains. This demonstrates that the invader assay can be used as a means of measuring the amount of target RNA within a sample.

Comparison of the fluorescence intensity of the input RNA with that of the cleaved product shows that the invader-directed cleavage assay creates signal in excess of the amount of target, so that the signal visible as cleaved probe is far more intense than that representing the target RNA. This further confirms the results described in Ex. 20, in which it was demonstrated that each RNA molecule could be used many times.

EXAMPLE 23

Detection of DNA By Charge Reversal

The detection of specific targets is achieved in the invader-directed cleavage assay by the cleavage of the probe oligonucleotide. In addition to the methods described in the preceding examples, the cleaved probe may be separated from the uncleaved probe using the charge reversal technique described below. This novel separation technique is related to the observation that positively charged adducts can affect the electrophoretic behavior of small oligonucleotides because the charge of the adduct is significant relative to charge of the whole complex. Observations of aberrant mobility due to charged adducts have been reported in the literature, but in all cases found, the applications pursued by other scientists have involved making oligonucleotides larger by enzymatic extension. As the negatively charged nucleotides are added on, the positive influence of the adduct is reduced to insignificance. As a result, the effects of positively charged adducts have been dismissed and have received infinitesimal notice in the existing literature.

This observed effect is of particular utility in assays based on the cleavage of DNA molecules. When an oligonucleotide is shortened through the action of a Cleavase® enzyme or other cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer.

An additional benefit of this type of readout is that the absolute nature of the partition of products from substrates means that an abundance of uncleaved probe can be supplied to drive the hybridization step of the probe-based assay, yet the unconsumed probe can be subtracted from the result to reduce background.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which lack a 3' phosphate, and the products of thermal degradation, which retain a 3' phosphate (and thus two additional negative charges).

a) Characterization Of The Products Of Thermal Breakage Of DNA Oligonucleotides

Figure 55:
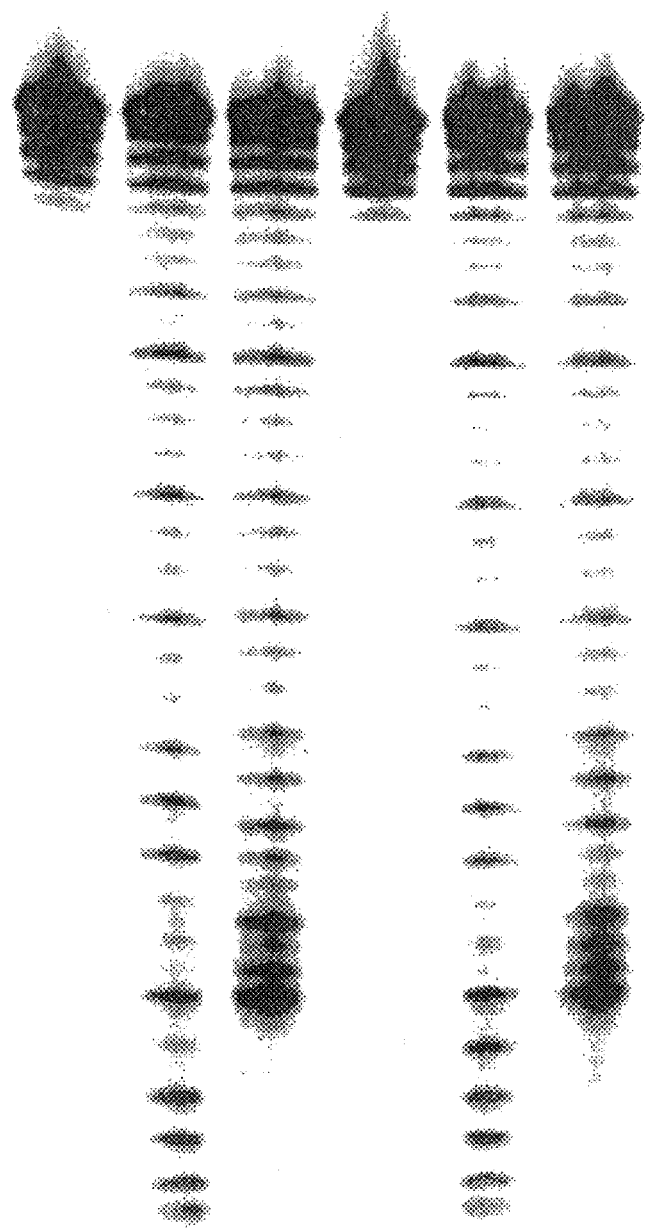
FIG. 55 is the image generated by a fluorescence imager showing thermal degradation of oligonucleotides containing or lacking a 3' phosphate group.

Thermal degradation of DNA probes results in high background which can obscure signals generated by specific enzymatic cleavage, decreasing the signal-to-noise ratio. To better understand the nature of DNA thermal degradation products, we incubated the 5' tetrachlorofluorescein (TET)-labeled oligonucleotides 78 (SEQ ID NO:59) and 79 (SEQ ID NO:60) (100 pmole each) in 50 µl 10 mM $NaCO_3$ (pH 10.6), 50 mM NaCl at 90° C. for 4 hours. To prevent evaporation of the samples, the reaction mixture was overlaid with 50 µl of ChillOut® 14 liquid wax (MJ Research). The reactions were then divided in two equal aliquots (A and B). Aliquot A was mixed with 25 µl of methyl violet loading buffer and Aliquot B was dephosphorylated by addition of 2.5 µl of 100 mM $MgCl_2$ and 1 µl of 1 unit/µl Calf Intestinal Alkaline Phosphatase (CIAP) (Promega), with incubation at 37° C. for 30 min. after which 20 µl of methyl violet loading buffer was added. One microliter of each sample was resolved by electrophoresis through a 12% polyacrylamide denaturing gel and imaged as described in Ex. 21; a 585 nm filter was used with the FMBIO Image Analyzer. The resulting imager scan is shown in FIG. 55. In FIG. 55, lanes 1–3 contain the TET-labeled oligonucleotide 78 and lanes 4–6 contain the TET-labeled oligonucleotides 79. Lanes 1 and 4 contain products of reactions which were not heat treated. Lanes 2 and 5 contain products from reactions which were heat treated and lanes 3 and 6 contain products from reactions which were heat treated and subjected to phosphatase treatment.

As shown in FIG. 55, heat treatment causes significant breakdown of the 5'-TET-labeled DNA, generating a ladder of degradation products (FIG. 55, lanes 2, 3, 5 and 6). Band intensities correlate with purine and pyrimidine base positioning in the oligonucleotide sequences, indicating that backbone hydrolysis may occur through formation of abasic intermediate products that have faster rates for purines then for pyrimidines (Lindahl and Karlström, Biochem., 12:5151 [1973]).

Dephosphorylation decreases the mobility of all products generated by the thermal degradation process, with the most pronounced effect observed for the shorter products (FIG. 55, lanes 3 and 6). This demonstrates that thermally degraded products possess a 3' end terminal phosphoryl group which can be removed by dephosphorylation with CIAP. Removal of the phosphoryl group decreases the overall negative charge by 2. Therefore, shorter products which have a small number of negative charges are influenced to a greater degree upon the removal of two charges. This leads to a larger mobility shift in the shorter products than that observed for the larger species.

Figure 58:
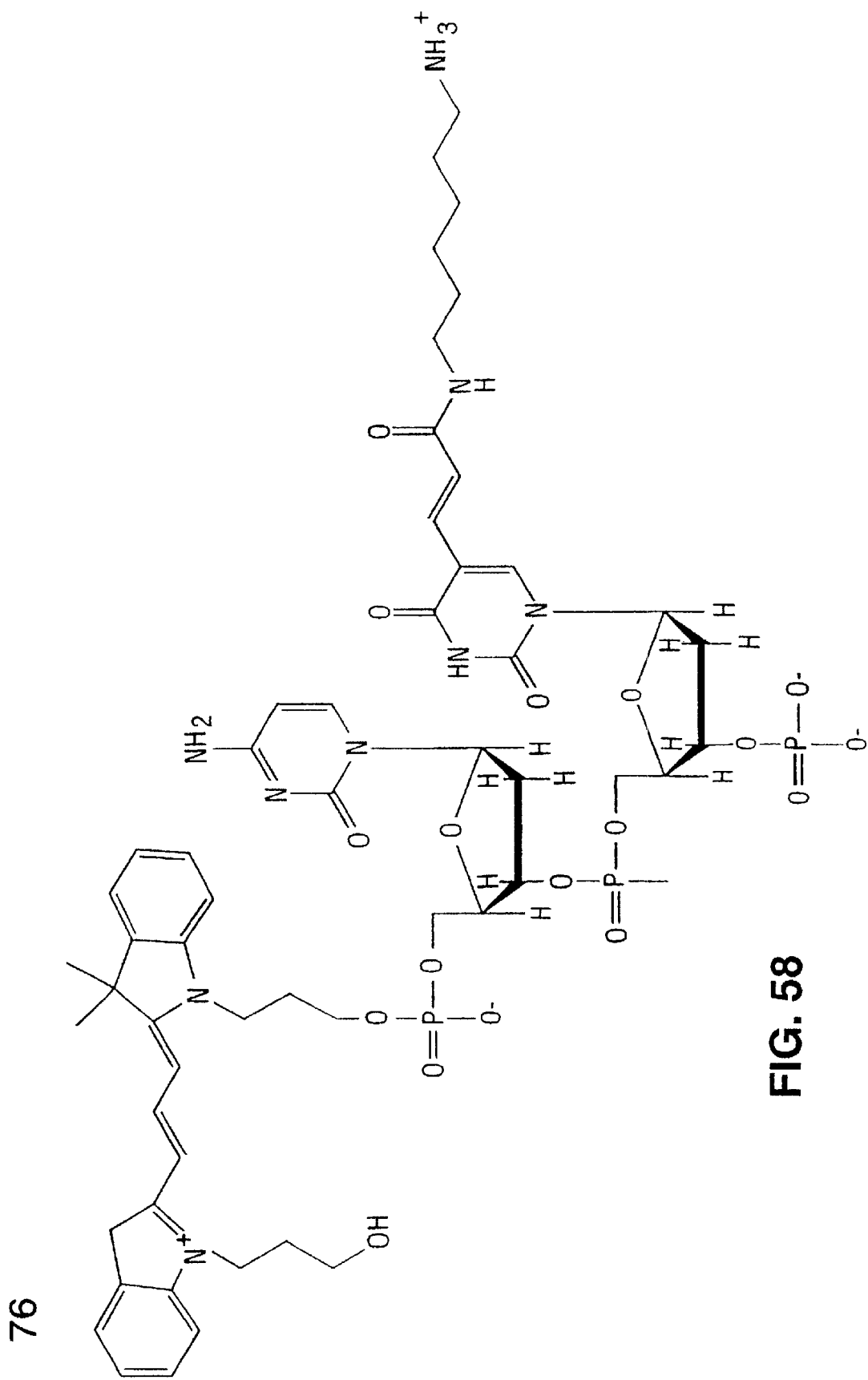
FIG. 58 depicts the structure of amino-modified oligonucleotide 76.

The fact that the majority of thermally degraded DNA products contain 3' end phosphate groups and Cleavase® enzyme-generated products do not allowed the development of simple isolation methods for products generated in the invader-directed cleavage assay. The extra two charges found in thermal breakdown products do not exist in the specific cleavage products. Therefore, if one designs assays that produce specific products which contain a net positive charge of one or two, then similar thermal breakdown products will either be negative or neutral. The difference can be used to isolate specific products by reverse charge methods as shown below.

b) Dephosphorylation Of Short Amino-Modified Oligonucleotides Can Reverse The Net Charge Of The Labeled Product To demonstrate how oligonucleotides can be transformed from net negative to net positively charged compounds, the four short amino-modified oligonucleotides labeled 70, 74, 75 and 76 and shown in FIGS. 56–58 were synthesized (FIG. 56 shows both oligonucleotides 70 and 74). All four modified oligonucleotides possess Cy-3 dyes positioned at the 5'-end which individually are positively charged under reaction and isolation conditions described in this example. Compounds 70 and 74 contain two amino modified thymidines that, under reaction conditions, display positively charged R—$NH_3^+$ groups attached at the C5 position through a $C_{10}$ or $C_6$ linker, respectively. Because compounds 70 and 74 are 3'-end phosphorylated, they consist of four negative charges and three positive charges. Compound 75 differs from 74 in that the internal $C_6$ amino modified thymidine phosphate in 74 is replaced by a thymidine methyl phosphonate. The phosphonate backbone is uncharged and so there are a total of three negative charges on compound 75. This gives compound 75 a net negative one charge. Compound 76 differs from 70 in that the internal amino modified thymidine is replaced by an internal cytosine phosphonate. The $pK_a$ of the N3 nitrogen of cytosine can be from 4 to 7. Thus, the net charges of this compound, can be from −1 to 0 depending on the pH of the solution. For the simplicity of analysis, each group is assigned a whole number of charges, although it is realized that, depending on the $pK_a$ of each chemical group and ambient pH, a real charge may differ from the whole number assigned. It is assumed that this difference is not significant over the range of pHs used in the enzymatic reactions studied here.

Dephosphorylation of these compounds, or the removal of the 3' end terminal phosphoryl group, results in elimination of two negative charges and generates products that have a net positive charge of one. In this experiment, the method of isoelectric focusing (IEF) was used to demonstrate a change from one negative to one positive net charge for the described substrates during dephosphorylation.

Substrates 70, 74, 75 and 76 were synthesized by standard phosphoramidite chemistries and deprotected for 24 hours at 22° C. in 14 M aqueous ammonium hydroxide solution, after which the solvent was removed in vacuo. The dried powders were resuspended in 200 μl of $H_2O$ and filtered through 0.2 μm filters. The concentration of the stock solutions was estimated by UV-absorbance at 261 nm of samples diluted 200-fold in $H_2O$ using a spectrophotometer (Spectronic Genesys 2, Milton Roy).

Dephosphorylation of compounds 70 and 74, 75 and 76 was accomplished by treating 10 μl of the crude stock solutions (ranging in concentration from approximately 0.5 to 2 mM) with 2 units of CIAP in 100 μl of CIAP buffer (Promega) at 37° C. for 1 hour. The reactions were then heated to 75° C. for 15 min. in order to inactivate the CIAP. For clarity, dephosphorylated compounds are designated 'dp'. For example, after dephosphorylation, substrate 70 becomes 70dp.

To prepare samples for IEF experiments, the concentration of the stock solutions of substrate and dephosphorylated product were adjusted to a uniform absorbance of $8.5 \times 10^{-3}$ at 532 nm by dilution with water. Two microliters of each sample were analyzed by IEF using a PhastSystem electrophoresis unit (Pharmacia) and PhastGel IEF 3–9 media (Pharmacia) according to the manufacturer's protocol. Separation was performed at 15° C. with the following program: pre-run; 2,000 V, 2.5 mA, 3.5 W, 75 Vh; load; 200 V, 2.5 mA, 3.5 W, 15 Vh; run; 2,000 V; 2.5 mA; 3.5 W, 130 Vh. After separation, samples were visualized by using the FMBIO Image Analyzer (Hitachi) fitted with a 585 nm filter. The resulting imager scan is shown in FIG. 59.

Figure 59:
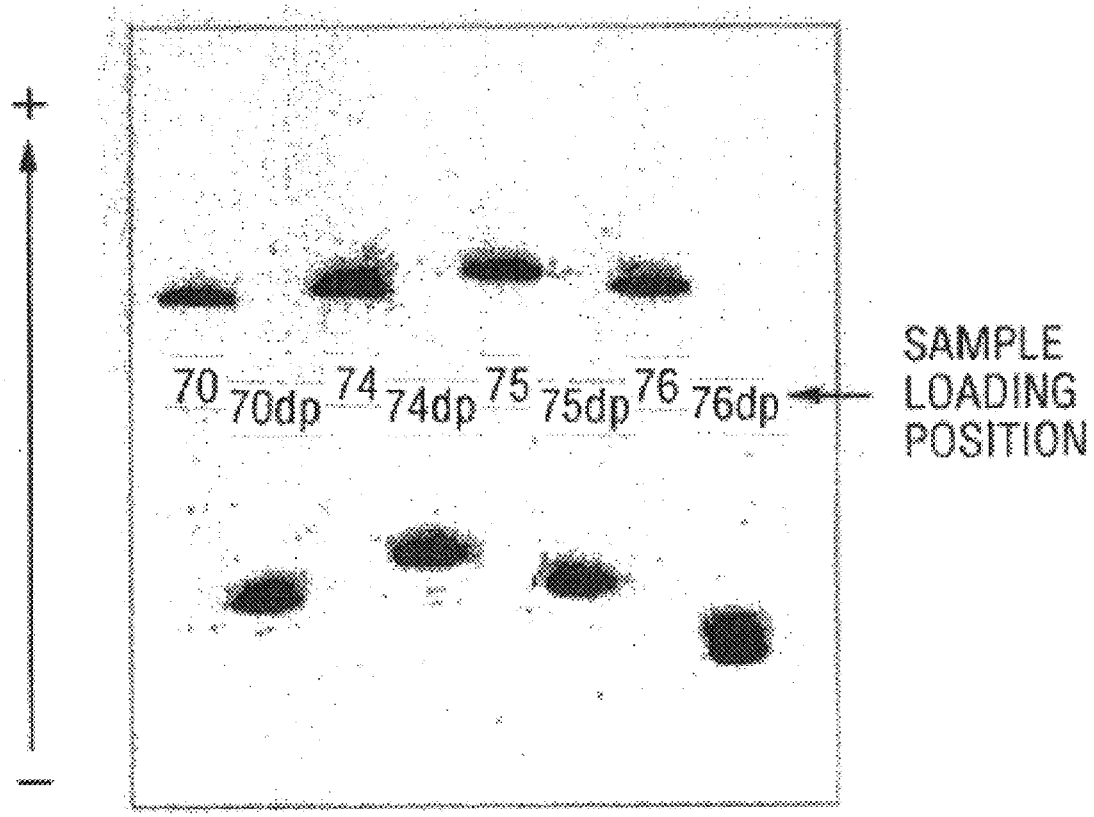
FIG. 59 is the image generated by a fluorescence imager scan of an IEF gel showing the migration of substrates 70, 70dp, 74, 74dp, 75, 75dp, 76 and 76dp.

FIG. 59 shows results of IEF separation of substrates 70, 74, 75 and 76 and their dephosphorylated products. The arrow labeled "Sample Loading Position" indicates a loading line, the '+' sign shows the position of the positive electrode and the '−' sign indicates the position of the negative electrode.

The results shown in FIG. 59 demonstrate that substrates 70, 74, 75 and 76 migrated toward the positive electrode, while the dephosphorylated products 70dp, 74dp, 75dp and 76dp migrated toward negative electrode. The observed differences in mobility direction was in accord with predicted net charge of the substrates (minus one) and the products (plus one). Small perturbations in the mobilities of the phosphorylated compounds indicate that the overall pIs vary. This was also true for the dephosphorylated compounds. The presence of the cytosine in 76dp, for instance, moved this compound further toward the negative electrode which was indicative of a higher overall pI relative to the other dephosphorylated compounds. It is important to note that additional positive charges can be obtained by using a combination of natural amino modified bases (70dp and 74dp) along with uncharged methylphosphonate bridges (products 75dp and 76dp).

The results shown above demonstrate that the removal of a single phosphate group can flip the net charge of an oligonucleotide to cause reversal in an electric field, allowing easy separation of products, and that the precise base composition of the oligonucleotides affect absolute mobility but not the charge-flipping effect.

EXAMPLE 24

Detection of Specific Cleavage Products in the Invader-Directed Cleavage Reaction by Charge Reversal In this example the ability to isolate products generated in the invader-directed cleavage assay from all other nucleic acids present in the reaction cocktail was demonstrated using charge reversal. This experiment utilized the following Cy3-labeled oligonucleotide: 5'-Cy3-AminoT-AminoT-CTTTTCACCAGCGAGACGGG-3' (SEQ ID NO:61; termed "oligonucleotide 61"). Oligonucleotide 61 was designed to release upon cleavage a net positively charged labeled product. To test whether or not a net positively charged 5'-end labeled product would be recognized by the Cleavase® enzymes in the invader-directed cleavage assay format, probe oligonucleotide 61 (SEQ ID NO:61) and invading oligonucleotide 67 (SEQ ID NO:62) were chemically synthesized on a DNA synthesizer (ABI 391) using standard phosphoramidite chemistries and reagents obtained from Glen Research (Sterling, Va.).

Each assay reaction comprised 100 fmoles of M13mp18 single stranded DNA, 10 pmoles each of the probe (SEQ ID NO:61) and invader (SEQ ID NO:62) oligonucleotides, and 20 units of Cleavase® A/G in a 10 µl solution of 10 mM MOPS, pH 7.4 with 100 mM KCl. Samples were overlaid with mineral oil to prevent evaporation. The samples were brought to either 50° C., 55° C., 60° C., or 65° C. and cleavage was initiated by the addition of 1 µl of 40 mM MnCl$_2$. Reactions were allowed to proceed for 25 minutes and then were terminated by the addition of 10 µl of 95% formamide containing 20 mM EDTA and 0.02% methyl violet. The negative control experiment lacked the target M13mp18 and was run at 60° C. Five microliters of each reaction were loaded into separate wells of a 20% denaturing polyacrylamide gel (cross-linked 29:1) with 8 M urea in a buffer containing 45 mM Tris-Borate (pH 8.3) and 1.4 mM EDTA. An electric field of 20 watts was applied for 30 minutes, with the electrodes oriented as indicated in FIG. 60B (i.e., in reverse orientation). The products of these reactions were visualized using the FMBIO fluorescence imager and the resulting imager scan is shown in FIG. 60B.

Figure 60A:
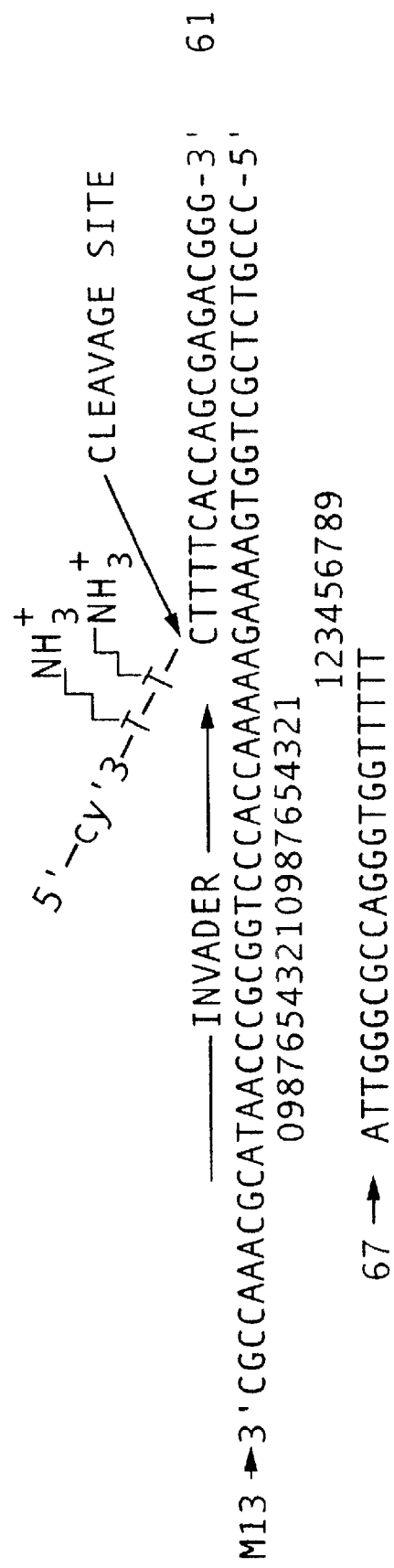
FIG. 60A provides a schematic showing an arrangement of a target-specific invader oligonucleotide (SEQ ID NO:61) and a target-specific probe oligonucleotide (SEQ ID NO:62) bearing a 5' Cy3 label along a target nucleic acid (SEQ ID NO:63).
Figure 60B:
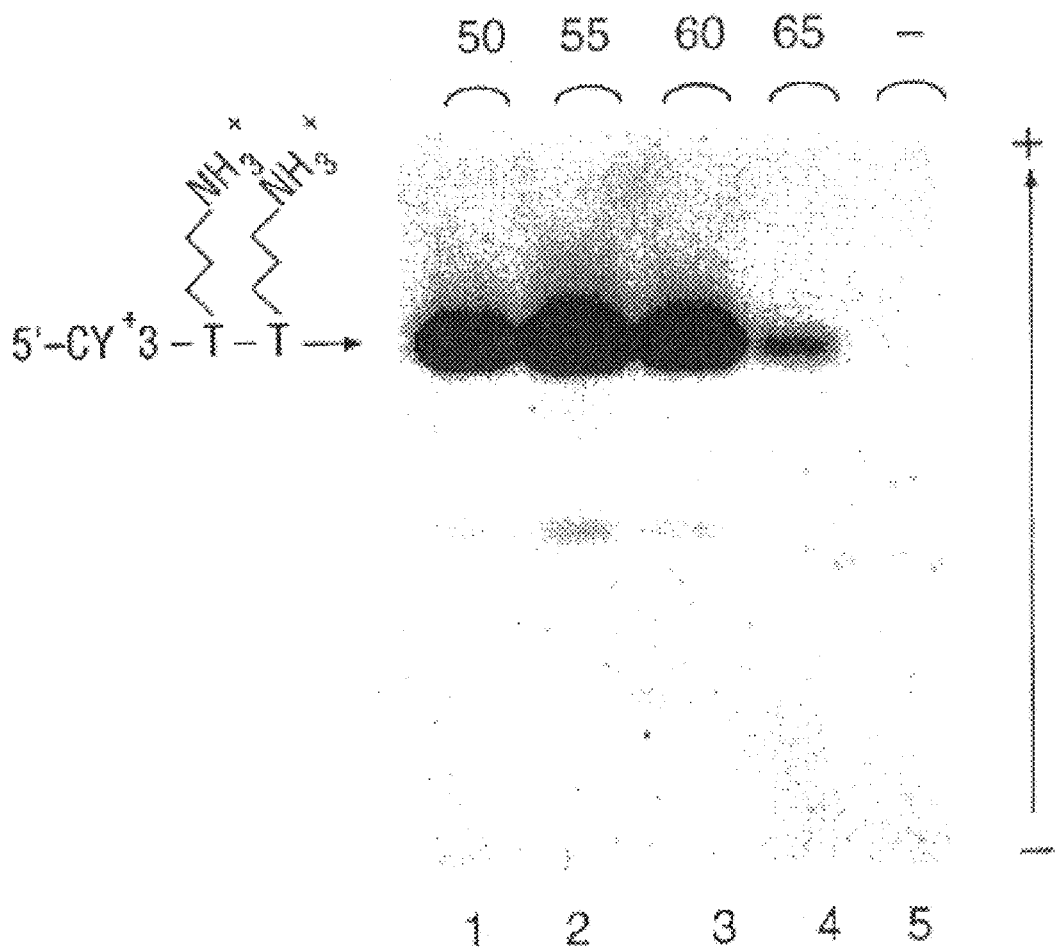
FIG. 60B is the image generated by a fluorescence imager showing the detection of specific cleavage products generated in an invasive cleavage assay using charge reversal (i.e., charge based separation of cleavage products).

FIG. 60A provides a schematic illustration showing an alignment of the invader (SEQ ID NO:61) and probe (SEQ ID NO:62) along the target M13mp18 DNA; only 53 bases of the M13mp18 sequence is shown (SEQ ID NO:63). The sequence of the invader oligonucleotide is displayed under the M13mp18 target and an arrow is used above the M13mp18 sequence to indicate the position of the invader relative to the probe and target. As shown in FIG. 60A, the invader and probe oligonucleotides share a 2 base region of overlap.

In FIG. 60B, lanes 1–6 contain reactions performed at 50° C., 55° C., 60° C., and 65° C., respectively; lane 5 contained the control reaction (lacking target). In FIG. 60B, the products of cleavage are seen as dark bands in the upper half of the panel; the faint lower band seen appears in proportion to the amount of primary product produced and, while not limiting the invention to a particular mechanism, may represent cleavage one nucleotide into the duplex. The uncleaved probe does not enter the gel and is thus not visible. The control lane showed no detectable signal over background (lane 5). As expected in an invasive cleavage reaction, the rate of accumulation of specific cleavage product was temperature-dependent. Using these particular oligonucleotides and target, the fastest rate of accumulation of product was observed at 55° C. (lane 2) and very little product observed at 65° C. (lane 4).

When incubated for extended periods at high temperature, DNA probes can break non-specifically (i.e., suffer thermal degradation) and the resulting fragments contribute an interfering background to the analysis. The products of such thermal breakdown are distributed from single-nucleotides up to the full length probe. In this experiment, the ability of charge based separation of cleavage products (i.e., charge reversal) would allow the sensitive separation of the specific products of target-dependent cleavage from probe fragments generated by thermal degradation was examined.

To test the sensitivity limit of this detection method, the target M13mp18 DNA was serially diluted ten fold over than range of 1 fmole to 1 amole. The invader and probe oligonucleotides were those described above (i.e., SEQ ID NOS:61 and 62). The invasive cleavage reactions were run as described above with the following modifications: the reactions were performed at 55° C., 250 mM or 100 mM KGlu was used in place of the 100 mM KCl and only 1 pmole of the invader oligonucleotide was added. The reactions were initiated as described above and allowed to progress for 12.5 hours. A negative control reaction which lacked added M13m18 target DNA was also run. The reactions were terminated by the addition of 10 µl of 95% formamide containing 20 mM EDTA and 0.02% methyl violet, and 5 µl of these mixtures were electrophoresed and visualized as described above. The resulting imager scan is shown in FIG. 61.

Figure 61:
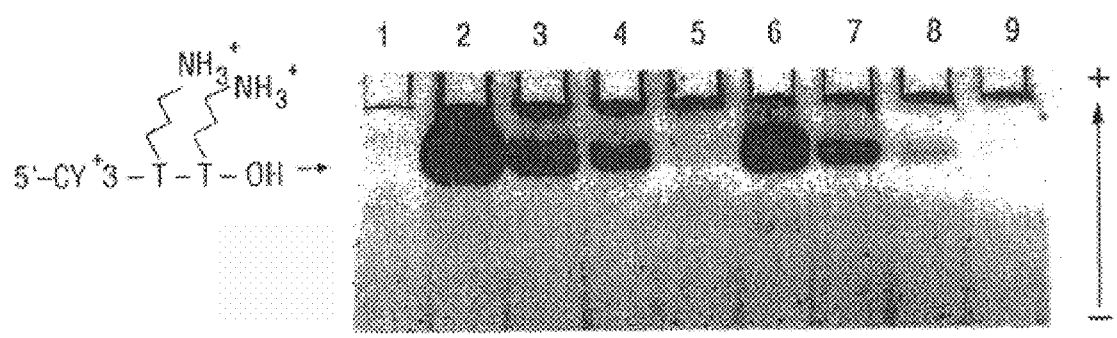
FIG. 61 is the image generated by a fluorescence imager which depicts the sensitivity of detection of specific cleavage products generated in an invasive cleavage assay using charge reversal.

In FIG. 61, lane 1 contains the negative control; lanes 2–5 contain reactions performed using 100 mM KGlu; lanes 6–9 contain reactions performed using 250 mM KGlu. The reactions resolved in lanes 2 and 6 contained 1 fmole of target DNA; those in lanes 3 and 7 contained 100 amole of target; those in lanes 4 and 8 contained 10 amole of target and those in lanes 5 and 9 contained 1 amole of target. The results shown in FIG. 61 demonstrate that the detection limit using charge reversal to detect the production of specific cleavage products in an invasive cleavage reaction is at or below 1 attomole or approximately $6.02 \times 10^5$ target molecules. No detectable signal was observed in the control lane, which indicates that non-specific hydrolysis or other breakdown products do not migrate in the same direction as enzyme-specific cleavage products. The excitation and emission maxima for Cy3 are 554 and 568, respectively, while the FMBIO Imager Analyzer excites at 532 and detects at 585. Therefore, the limit of detection of specific cleavage products can be improved by the use of more closely matched excitation source and detection filters.

EXAMPLE 25

Devices and Methods for the Separation and Detection of Charged Reaction Products This example is directed at methods and devices for isolating and concentrating specific reaction products produced by enzymatic reactions conducted in solution whereby the reactions generate charged products from either a charge neutral substrate or a substrate bearing the opposite charge borne by the specific reaction product. The methods and devices of this example allow isolation of, for example, the products generated by the invader-directed cleavage assay of the present invention.

The methods and devices of this example are based on the principle that when an electric field is applied to a solution of charged molecules, the migration of the molecules toward the electrode of the opposite charge occurs very rapidly. If a matrix or other inhibitory material is introduced between the charged molecules and the electrode of opposite charge such that this rapid migration is dramatically slowed, the first molecules to reach the matrix will be nearly stopped, thus allowing the lagging molecules to catch up. In this way a dispersed population of charged molecules in solution can be effectively concentrated into a smaller volume. By tagging the molecules with a detectable moiety (e.g., a fluorescent dye), detection is facilitated by both the concentration and the localization of the analytes. This example illustrates two embodiments of devices contemplated by the present invention; of course, variations of these devices will be apparent to those skilled in the art and are within the spirit and scope of the present invention.

Figure 62:
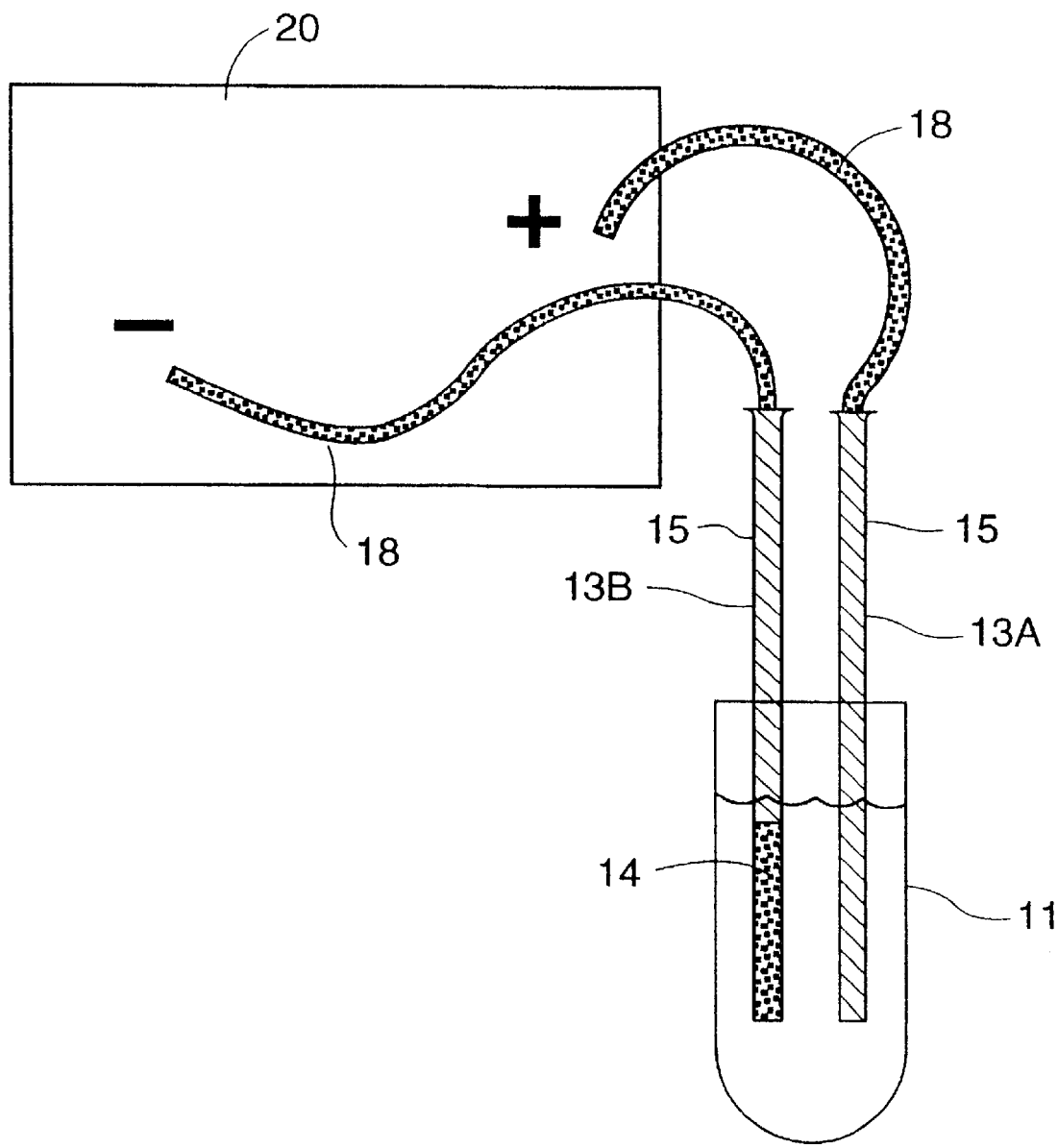
FIG. 62 depicts a first embodiment of a device for the charge-based separation of oligonucleotides.

FIG. 62 depicts one embodiment of a device for concentrating the positively-charged products generated using the methods of the present invention. As shown in FIG. 62, the device comprises a reaction tube (10) which contains the reaction solution (11). One end of each of two thin capillaries (or other tubes with a hollow core) (13A and 13B) are submerged in the reaction solution (11). The capillaries (13A and 13B) may be suspended in the reaction solution (11) such that they are not in contact with the reaction tube itself; one appropriate method of suspending the capillaries is to hold them in place with clamps (not shown). Alternatively, the capillaries may be suspended in the reaction solution (11) such that they are in contact with the reaction tube itself. Suitable capillaries include glass capillary tubes commonly available from scientific supply companies (e.g., Fisher Scientific or VWR Scientific) or from medical supply houses that carry materials for blood drawing and analysis. Though the present invention is not limited to capillaries of any particular inner diameter, tubes with inner diameters of up to about ⅛ inch (approximately 3 mm) are particularly preferred for use with the present invention; for example Kimble No. 73811-99 tubes (VWR Scientific) have an inner diameter of 1.1 mm and are a suitable type of capillary tube. Although the capillaries of the device are commonly composed of glass, any nonconductive tubular material, either rigid or flexible, that can contain either a conductive material or a trapping material is suitable for use in the present invention. One example of a suitable flexible tube is Tygon® clear plastic tubing (Part No. R3603; inner diameter=¹⁄₁₆ inch; outer diameter=⅛ inch).

As illustrated in FIG. 62, capillary 13A is connected to the positive electrode of a power supply (20) (e.g., a controllable power supply available through the laboratory suppliers listed above or through electronics supply houses like Radio Shack) and capillary 13B is connected to the negative electrode of the power supply (20). Capillary 13B is filled with a trapping material (14) capable of trapping the positively-charged reaction products by allowing minimal migration of products that have entered the trapping material (14). Suitable trapping materials include, but are not limited to, high percentage (e.g., about 20%) acrylamide polymerized in a high salt buffer (0.5 M or higher sodium acetate or similar salt); such a high percentage polyacrylamide matrix dramatically slows the migration of the positively-charged reaction products. Alternatively, the trapping material may comprise a solid, negatively-charged matrix, such as negatively-charged latex beads, that can bind the incoming positively-charged products. It should be noted that any amount of trapping material (14) capable of inhibiting any concentrating the positively-charged reaction products may be used. Thus, while the capillary 13B in FIG. 62 only contains trapping material in the lower, submerged portion of the tube, the trapping material (14) can be present in the entire capillary (13B); similarly, less trapping material (14) could be present than that shown in FIG. 62 because the positively-charged reaction products generally accumulate within a very small portion of the bottom of the capillary (13B). The amount of trapping material need only be sufficient to make contact with the reaction solution (11) and have the capacity to collect the reaction products. When capillary 13B is not completely filled with the trapping material, the remaining space is filled with any conductive material (15); suitable conductive materials are discussed below.

By comparison, the capillary (13A) connected to the positive electrode of the power supply 20 may be filled with any conductive material (15; indicated by the hatched lines in FIG. 62). This may be the sample reaction buffer (e.g., 10 mM MOPS, pH 7.5 with 150 mM LiCl, 4 mM $MnCl_2$), a standard electrophoresis buffer (e.g., 45 mM Tris-Borate, pH 8.3, 1.4 mM EDTA), or the reaction solution (11) itself. The conductive material (15) is frequently a liquid, but a semisolid material (e.g., a gel) or other suitable material might be easier to use and is within the scope of the present invention. Moreover, that trapping material used in the other capillary (i.e., capillary 13B) may also be used as the conductive material. Conversely, it should be noted that the same conductive material used in the capillary (13A) attached to the positive electrode may also be used in capillary 13B to fill the space above the region containing the trapping material (14) (see FIG. 62).

The top end of each of the capillaries (13A and 13B) is connected to the appropriate electrode of the power supply (20) by electrode wire (18) or other suitable material. Fine platinum wire (e.g., 0.1 to 0.4 mm, Aesar Johnson Matthey, Ward Hill, Mass.) is commonly used as conductive wire because it does not corrode under electrophoresis conditions. The electrode wire (18) can be attached to the capillaries (13A and 13B) by a nonconductive adhesive (not shown), such as the silicone adhesives that are commonly sold in hardware stores for sealing plumbing fixtures. If the capillaries are constructed of a flexible material, the electrode wire (18) can be secured with a small hose clamp or constricting wire (not shown) to compress the opening of the capillaries around the electrode wire. If the conducting material (15) is a gel, an electrode wire (18) can be embedded directly in the gel within the capillary.

The cleavage reaction is assembled in the reaction tube (10) and allowed to proceed therein as described in proceeding examples (e.g., Examples 22–23). Though not limited to any particular volume of reaction solution (11), a preferred volume is less than 10 ml and more preferably less than 0.1 ml. The volume need only be sufficient to permit contact with both capillaries. After the cleavage reaction is completed, an electric field is applied to the capillaries by turning on the power source (20). As a result, the positively-charged products generated in the course of the invader-directed cleavage reaction which employs an oligonucleotide, which when cleaved, generates a positively charged fragment (described in Ex. 23) but when uncleaved bears a net negative charge, migrate to the negative capillary, where their migration is slowed or stopped by the trapping material (14), and the negatively-charged uncut and thermally degraded probe molecules migrate toward the positive electrode. Through the use of this or a similar device, the positively-charged products of the invasive cleavage reaction are separated from the other material (i.e., uncut and thermally degraded probe) and concentrated from a large volume. Concentration of the product in a small amount of trapping material (14) allows for simplicity of detection, with a much higher signal-to-noise ratio than possible with detection in the original reaction volume. Because the concentrated product is labeled with a detectable moiety like a fluorescent dye, a commercially-available fluorescent plate reader (not shown) can be used to ascertain the amount of product. Suitable plate readers include both top and bottom laser readers. Capillary 13B can be positioned with the reaction tube (10) at any desired position so as to accommodate use with either a top or a bottom plate reading device.

Figure 63:
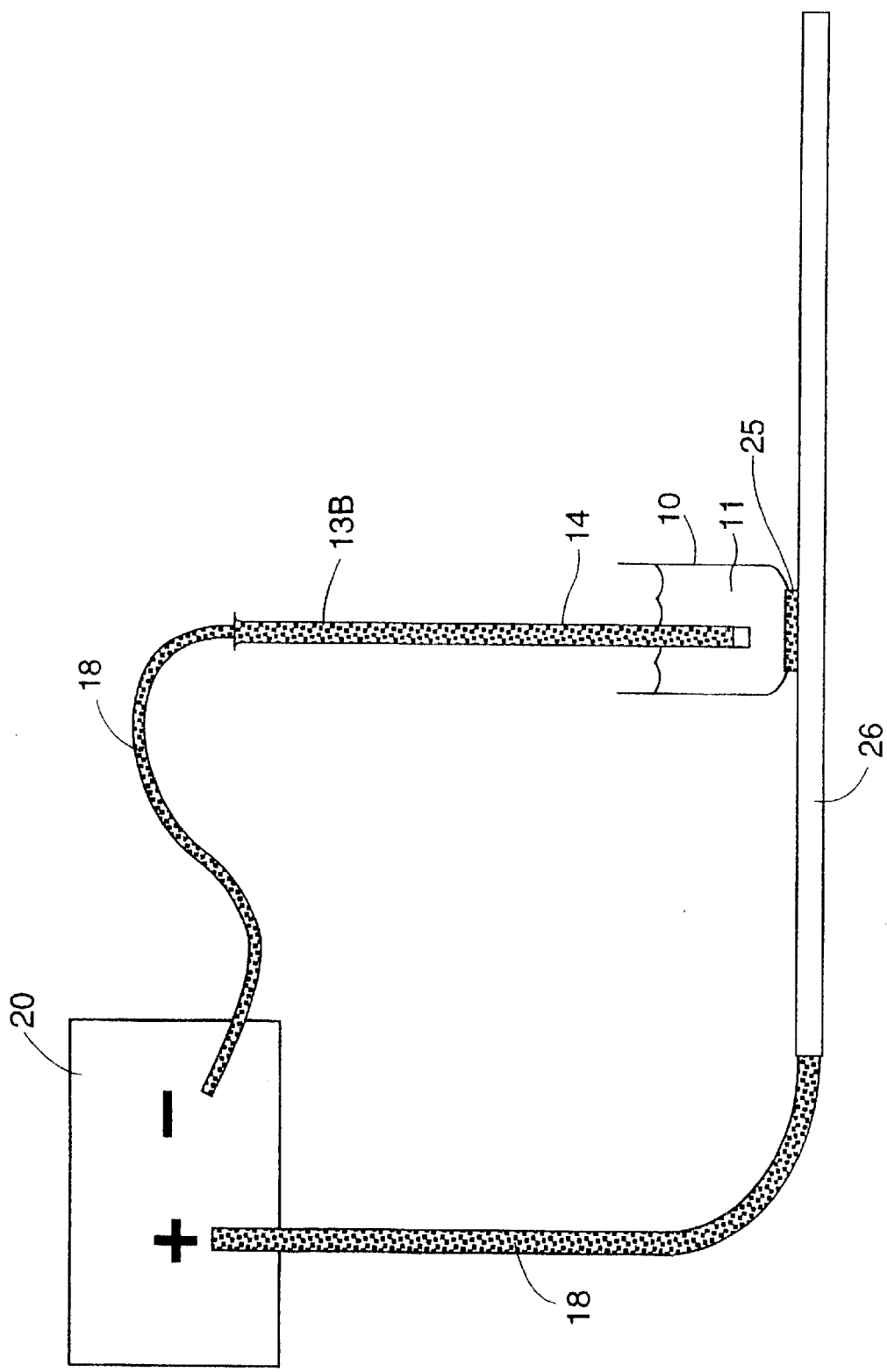
FIG. 63 depicts a second embodiment of a device for the charge-based separation of oligonucleotides.

In the alternative embodiment of the present invention depicted in FIG. 63, the procedure described above is accomplished by utilizing only a single capillary (13B). The capillary (13B) contains the trapping material (14) described above and is connected to an electrode wire (18), which in turn is attached to the negative electrode of a power supply (20). The reaction tube (10) has an electrode (25) embedded into its surface such that one surface of the electrode is exposed to the interior of the reaction tube (10) and another surface is exposed to the exterior of the reaction tube. The surface of the electrode (25) on the exterior of the reaction tube is in contact with a conductive surface (26) connected to the positive electrode of the power supply (20) through an electrode wire (18). Variations of the arrangement depicted in FIG. 63 are also contemplated by the present invention. For example, the electrode (25) may be in contact with the reaction solution (11) through the use of a small hole in the reaction tube (10); furthermore, the electrode wire (18) can be directly attached to the electrode wire (18), thereby eliminating the conductive surface (26).

As indicated in FIG. 63, the electrode (25) is embedded in the bottom of a reaction tube (10) such that one or more reaction tubes may be set on the conductive surface (26). This conductive surface could serve as a negative electrode for multiple reaction tubes; such a surface with appropriate contacts could be applied through the use of metal foils (e.g., copper or platinum, Aesar Johnson Matthey, Ward Hill, Mass.) in much the same way contacts are applied to circuit boards. Because such a surface contact would not be exposed to the reaction sample directly, less expensive metals, such as the copper could be used to make the electrical connections.

The above devices and methods are not limited to separation and concentration of positively charged oligonucleotides. As will be apparent to those skilled in the art, negatively charged reaction products may be separated from neutral or positively charged reactants using the above device and methods with the exception that capillary 13B is attached to the positive electrode of the power supply (20) and capillary 13A or alternatively, electrode 25, is attached to the negative electrode of the power supply (20).

EXAMPLE 26

Figure 64:
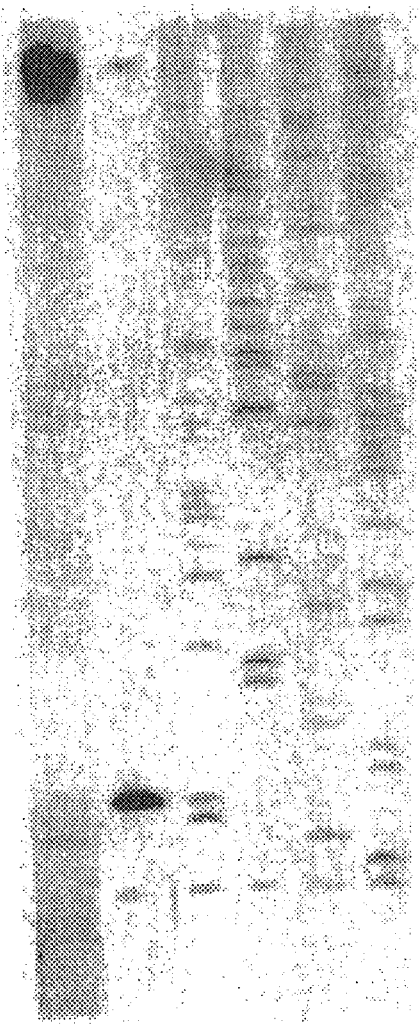
FIG. 64 shows an autoradiogram of a gel showing the results of cleavage reactions run in the presence or absence of a primer oligonucleotide; a sequencing ladder is shown as a size marker.

Primer-Directed and Primer Independent Cleavage Occur at the Same Site When the Primer Extends to the 3' Side of a Mismatched "Bubble" in the Downstream Duplex As discussed above in Ex. 1, the presence of a primer upstream of a bifurcated duplex can influence the site of cleavage, and the existence of a gap between the 3' end of the primer and the base of the duplex can cause a shift of the cleavage site up the unpaired 5' arm of the structure (see also Lyamichev et al., supra and U.S. Pat. No. 5,422,253). The resulting non-invasive shift of the cleavage site in response to a primer is demonstrated in FIGS. 9, 10 and 11, in which the primer used left a 4-nucleotide gap (relative to the base of the duplex). in FIGS. 9–11, all of the "primer-directed" cleavage reactions yielded a 21 nucleotide product, while the primer-independent cleavage reactions yielded a 25 nucleotide product. The site of cleavage obtained when the primer was extended to the base of the duplex, leaving no gap was examined. The results are shown in FIG. 64 (FIG. 64 is a reproduction of FIG. 2C in Lyamichev et al. These data were derived from the cleavage of the structure shown in FIG. 6, as described in Ex. 1. Unless otherwise specified, the cleavage reactions comprised 0.01 pmoles of heat-denatured, end-labeled hairpin DNA (with the unlabeled complementary strand also present), 1 pmole primer [complementary to the 3' arm shown in FIG. 6 and having the sequence: 5'-GAAT TCGATTAGGTGACACTATA-GAATACA (SEQ ID NO:64)] and 0.5 units of DNAPTaq (estimated to be 0.026 pmoles) in a total volume of 10 μl of 10 mM Tris-Cl, pH 8.5, and 1.5 mM $MgCl_2$ and 50 mM KCl. The primer was omitted from the reaction shown in the first lane of FIG. 64 and included in lane 2. These reactions were incubated at 55° C. for 10 minutes. Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes.

FIG. 64 is an autoradiogram that indicates the effects on the site of cleavage of a bifurcated duplex structure in the presence of a primer that extends to the base of the hairpin duplex. The size of the released cleavage product is shown to the left (i.e., 25 nucleotides). A dideoxynucleotide sequencing ladder of the cleavage substrate is shown on the right as a marker (lanes 3–6).

These data show that the presence of a primer that is adjacent to a downstream duplex (lane 2) produces cleavage at the same site as seen in reactions performed in the absence of the primer (lane 1) (see FIGS. 9A and B, 10B and 11A for additional comparisons). When the 3' terminal nucleotides of the upstream oligonucleotide can base pair to the template strand but are not homologous to the displaced strand in the region immediately upstream of the cleavage site (i.e., when the upstream oligonucleotide is opening up a "bubble" in the duplex), the site to which cleavage is apparently shifted is not wholly dependent on the presence of an upstream oligonucleotide.

As discussed above in the Background section and in Table 1, the requirement that two independent sequences be recognized in an assay provides a highly desirable level of specificity. In the invasive cleavage reactions of the present invention, the invader and probe oligonucleotides must hybridize to the target nucleic acid with the correct orientation and spacing to enable the production of the correct cleavage product. When the distinctive pattern of cleavage is not dependent on the successful alignment of both oligonucleotides in the detection system these advantages of independent recognition are lost.

EXAMPLE 27

Invasive Cleavage and Primer-Directed Cleavage When There Is Only Partial Homology in the "X" Overlap Region While not limiting the present invention to any particular mechanism, invasive cleavage occurs when the site of cleavage is shifted to a site within the duplex formed between the probe and the target nucleic acid in a manner that is dependent on the presence of an upstream oligonucleotide which shares a region of overlap with the downstream probe oligonucleotide. In some instances, the 5' region of the downstream oligonucleotide may not be completely complementary to the target nucleic acid. In these instances, cleavage of the probe may occur at an internal site within the probe even in the absence of an upstream oligonucleotide (in contrast to the base-by-base nibbling seen when a fully paired probe is used without an invader). Invasive cleavage is characterized by an apparent shifting of cleavage to a site within a downstream duplex that is dependent on the presence of the invader oligonucleotide.

A comparison between invasive cleavage and primer-directed cleavage may be illustrated by comparing the expected cleavage sites of a set of probe oligonucleotides having decreasing degrees of complementarity to the target strand in the 5' region of the probe (i.e., the region that overlaps with the invader). A simple test, similar to that performed on the hairpin substrate above (Ex. 25), can be performed to compare invasive cleavage with the non-invasive primer-directed cleavage described above. Such a set of test oligonucleotides is diagrammed in FIG. 65. The structures shown in FIG. 65 are grouped in pairs, labeled "a", "b", "c", and "d". Each pair has the same probe sequence annealed to the target strand (SEQ ID NO:65), but the top structure of each pair is drawn without an upstream oligonucleotide, while the bottom structure includes this oligonucleotide (SEQ ID NO:66). The sequences of the probes shown in FIGS. 64a–64d are listed in SEQ ID NOS:43, 67, 68 and 69, respectively. Probable sites of cleavage are indicated by the black arrowheads. (It is noted that the precise site of cleavage on each of these structures may vary depending on the choice of cleavage agent and other experimental variables. These particular sites are provided for illustrative purposes only.)

To conduct this test, the site of cleavage of each probe is determined both in the presence and the absence of the upstream oligonucleotide, in reaction conditions such as those described in Ex. 19. The products of each pair of reactions are then be compared to determine whether the fragment released from the 5' end of the probe increases in size when the upstream oligonucleotide is included in the reaction.

Figure 65A:
FIGS. 65a–d depict four pairs of oligonucleotides; in each pair shown, the upper arrangement of a probe annealed to a target nucleic acid lacks an upstream oligonucleotide and the lower arrangement contains an upstream oligonucleotide.

The arrangement shown in FIG. 65a, in which the probe molecule is completely complementary to the target strand, is similar to that shown in FIG. 32. Treatment of the top structure with the 5' nuclease of a DNA polymerase would cause exonucleolytic nibbling of the probe (i.e., in the absence of the upstream oligonucleotide). In contrast, inclusion of an invader oligonucleotide would cause a distinctive cleavage shift similar, to those observed in FIG. 33.

Figure 65B:
Figure 65C:

The arrangements shown in FIGS. 65b and 65c have some amount of unpaired sequence at the 5' terminus of the probe (3 and 5 bases, respectively). These small 5' arms are suitable cleavage substrate for the 5' nucleases and would be cleaved within 2 nucleotide's of the junction between the single stranded region and the duplex. In these arrangements, the 3' end of the upstream oligonucleotide shares identity with a portion of the 5' region of the probe which is complementary to the target sequence (that is the 3' end of the invader has to compete for binding to the target with a portion of the 5' end of the probe). Therefore, when the upstream oligonucleotide is included it is thought to mediate a shift in the site of cleavage into the downstream duplex (although the present invention is not limited to any particular mechanism of action), and this would, therefore, constitute invasive cleavage. If the extreme 5' nucleotides of the unpaired region of the probe were able to hybridize to the target strand, the cleavage site in the absence of the invader might change but the addition of the invader oligonucleotide would still shift the cleavage site to the proper position.

Figure 65D:

Finally, in the arrangement shown in FIG. 65d, the probe and upstream oligonucleotides share no significant regions of homology, and the presence of the upstream oligonucleotide would not compete for binding to the target with the probe. Cleavage of the structures shown in FIG. 64d would occur at the same site with or without the upstream oligonucleotide, and is thus would not constitute invasive cleavage.

By examining any upstream oligonucleotide/probe pair in this way, it can easily be determined whether the resulting cleavage is invasive or merely primer-directed. Such analysis is particularly useful when the probe is not fully complementary to the target nucleic acid, so that the expected result may not be obvious by simple inspection of the sequences.

EXAMPLE 28

Modified Cleavase® Enzymes

In order to develop nucleases having useful activities for the cleavage of nucleic acids the following modified nucleases were produced.

a) Cleavase® BN/thrombin Nuclease i) Cloning and Expression of Cleavase® BN/thrombin Nuclease Site-directed mutagenesis was used to introduce a protein sequence recognized by the protease thrombin into the region of the Cleavase® BN nuclease which is thought to form the helical arch of the protein through which the single-stranded DNA that is cleaved must presumably pass. Mutagenesis was carried out using the Transformer™ mutagenesis kit (Clonetech) according to manufacturer's protocol using the mutagenic oligonucleotide 5'-GGGAAAGTCCTCGCAGCCGCGCGGGACG AGCGTGGGGGCCCG (SEQ ID NO:100). After mutagenesis, the DNA was sequenced to verify the insertion of the thrombin cleavage site. The DNA sequence encoding the Cleavase® BN/thrombin nuclease is provided in SEQ ID NO:101; the amino acid sequence of Cleavase® BN/thrombin nuclease is provided in SEQ ID NO:102.

A large scale preparation of the thrombin mutant (i.e., Cleavase® BN/thrombin) was done using *E. coli* cells overexpressing the Cleavase® BN/thrombin nuclease as described in Ex. 28.

ii) Thrombin Cleavage of Cleavase® BN/thrombin

Six point four (6.4) mg of the purified Cleavase® BN/thrombin nuclease was digested with 0.4 U of thrombin (Novagen, Madison, Wis.) for 4 hours at 23° C. or 37° C. Complete digestion was verified by electrophoresis on a 15% SDS polyacrylamide gel followed by staining with Coomassie Brilliant Blue R. Wild-type Cleavase® BN nuclease was also digested with thrombin as a control. The resulting gel is shown in FIG. 72.

Figure 72:
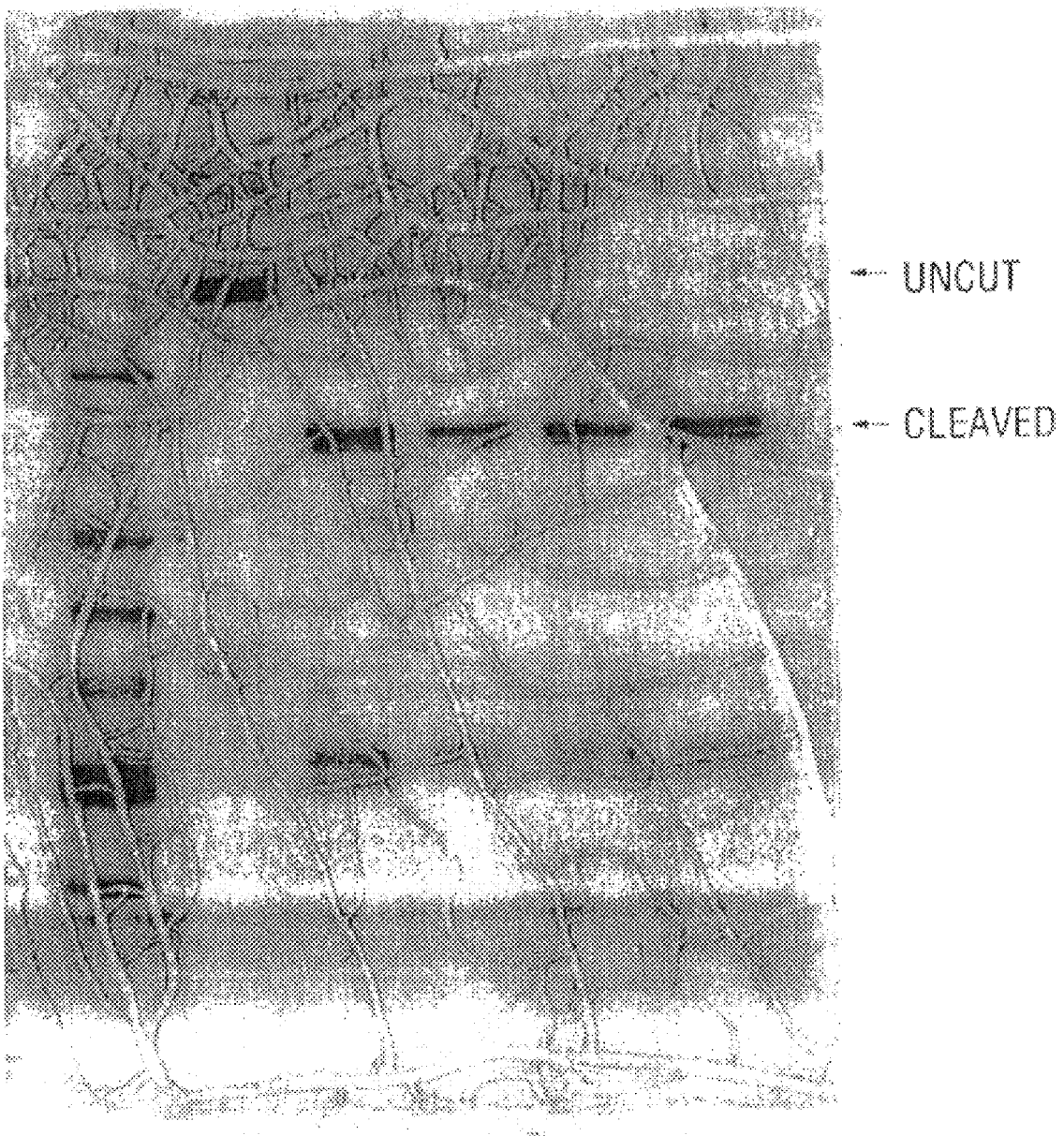
FIG. 72 shows a Coomassie stained SDS-PAGE gel showing the thrombin digestion of Cleavase® BN/thrombin.

In FIG. 72, lane 1 contains molecular weight markers (Low-Range Protein Molecular Weight Markers; Promega), lane 2 contains undigested Cleavase® BN/thrombin nuclease, lanes 3 and 4 contain Cleavase® BN/thrombin nuclease digested with thrombin at 23° C. for 2 and 4 hours, respectively, and lanes 5 and 6 contain Cleavase® BN/thrombin nuclease digested with thrombin at 37° C. for 2 and 4 hours, respectively. These results show that the Cleavase® BN/thrombin nuclease has an apparent molecular weight of 36.5 kilodaltons and demonstrate that Cleavase® BN/thrombin nuclease is efficiently cleaved by thrombin. In addition, the thrombin cleavage products have approximate molecular weights of 27 kilodaltons and 9 kilodaltons, the size expected based upon the position of the inserted thrombin site in the Cleavase® BN/thrombin nuclease.

To determine the level of hairpin cleavage activity in digested and undigested Cleavase® BN/thrombin nuclease, dilutions were made and used to cleave a test hairpin containing a 5' fluorescein label. Varying amounts of digested and undigested Cleavase® BN/thrombin nuclease were incubated with 5 µM oligonucleotide S-60 hairpin (SEQ ID NO:40; see FIG. 30) in 10 mM MOPS (pH 7.5), 0.05% Tween-20, 0.05% NP-40, and 1 mM $MnCl_2$ for 5 minutes at 60° C. The digested mixture was electrophoresed on a 20% acrylamide gel and visualized on a Hitachi FMBIO 100 fluorescence imager. The resulting image is shown in FIG. 73.

Figure 73:
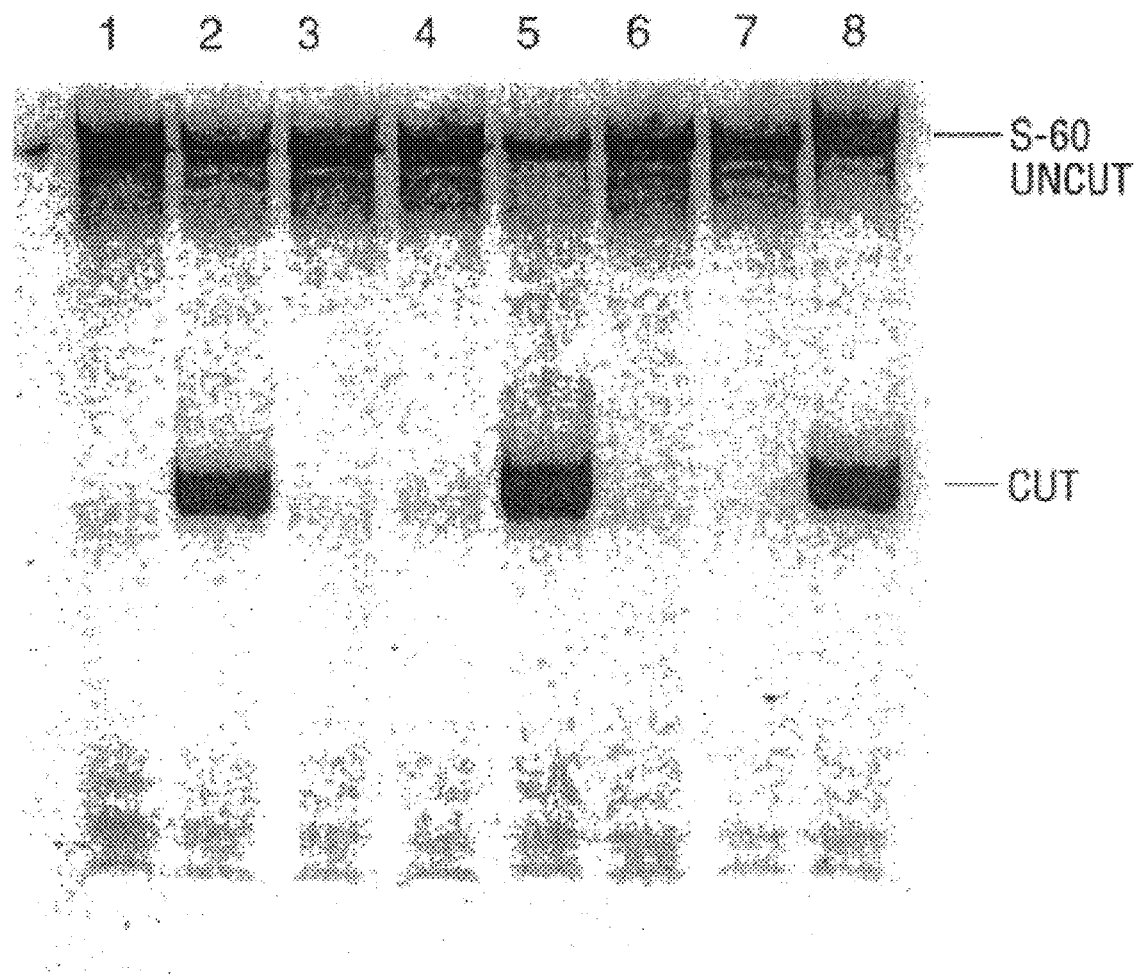
FIG. 73 is the image generated by a fluorescence imager showing the products produced by the cleavage of the S-60 hairpin using Cleavase® BN/thrombin (before and after thrombin digestion).

In FIG. 73, lane 1 contains the no enzyme control, lane 2 contains reaction products produced using 0.01 ng of Cleavase® BN nuclease, lanes 3, 4, and 5 contain reaction products produced using 0.01 ng, 0.04 ng, and 4 ng of undigested Cleavase® BN/thrombin nuclease, respectively, and lanes 6, 7, and 8 contain reaction products produced using 0.01 ng, 0.04 ng, and 4 ng of thrombin-digested Cleavase® BN/thrombin nuclease, respectively. The results shown in FIG. 73 demonstrated that the insertion of the thrombin cleavage site reduced cleavage activity about 200-fold (relative to the activity of Cleavase® BN nuclease), but that digestion with thrombin did not reduce the activity significantly.

M13 single-stranded DNA was used as a substrate for cleavage by Cleavase® BN nuclease and digested and undigested Cleavase® BN/thrombin nuclease. Seventy nanograms of single-stranded M13 DNA (New England Biolabs, Beverly, Mass.) was incubated in 10 mM MOPS, pH 7.5, 0.05% Tween-20, 0.05% NP-40, 1 mM $MgCl_2$ or 1 mM $MnCl_2$, with 8 ng of Cleavase® BN nuclease, undigested Cleavase® BN/thrombin nuclease, or digested Cleavase® BN/thrombin nuclease for 10 minutes at 50° C. Reaction mixtures were electrophoresed on a 0.8% agarose gel and then stained with a solution containing 0.5 µg/ml ethidium bromide (EtBr) to visualize DNA bands. A negative image of the EtBr-stained gel is shown in FIG. 74.

Figure 74:
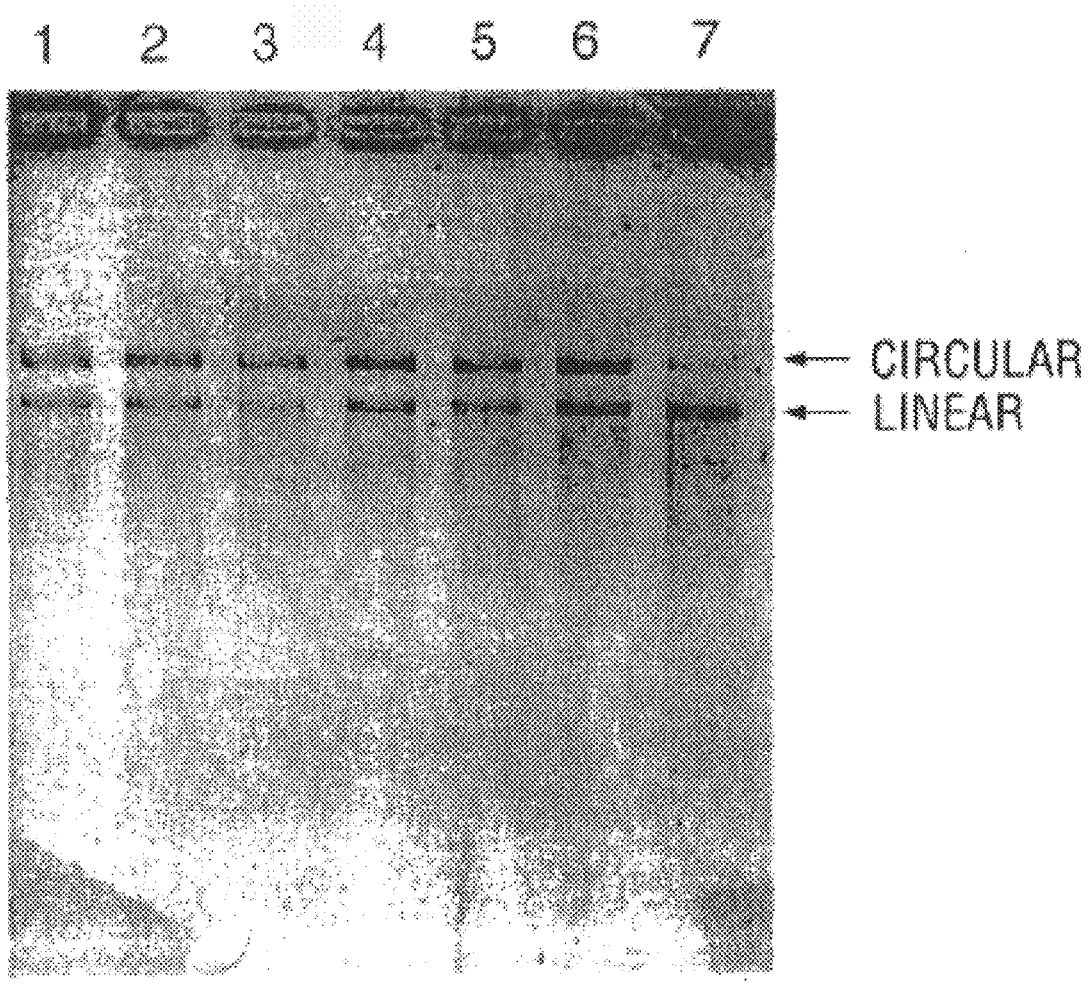
FIG. 74 is the image generated by a fluorescence imager showing the products produced by the cleavage of circular M13 DNA using Cleavase® BN/thrombin.

In FIG. 74, lane 1 contains the no enzyme control, lane 2 contains reaction products produced using Cleavase® BN nuclease and 1 mM $MgCl_2$, lane 3 contains reaction products produced using Cleavase® BN nuclease and 1 mM $MnCl_2$, lane 4 contains reaction products produced using undigested Cleavase® BN/thrombin nuclease and 1 mM $MgCl_2$, lane 5 contains reaction products produced using undigested Cleavase® BN/thrombin nuclease and 1 mM $MnCl_2$, lane 6 contains reaction products produced using thrombin-digested Cleavase® BN/thrombin nuclease and 1 mM $MgCl_2$, and lane 7 contains reaction products produced using thrombin-digested Cleavase® BN/thrombin nuclease and 1 mM $MnCl_2$. The results shown in FIG. 74 demonstrated that the Cleavase® BN/thrombin nuclease had an enhanced ability to cleave circular DNA (and thus a reduced requirement for the presence of a free 5' end) as compared to the Cleavase® BN nuclease.

It can be seen from these data that the helical arch of these proteins can be opened without destroying the enzyme or its ability to specifically recognize cleavage structures. The Cleavase® BN/thrombin mutant has an increased ability to cleave without reference to a 5' end, as discussed above. The ability to cleave such structures will allow the cleavage of long molecules, such as genomic DNA that, while often not circular, may present many desirable cleavage sites that are at a far removed from any available 5' end. Cleavage structures may be made at such sites either by folding of the strands (i.e., CFLP® cleavage) or by the introduction of structure-forming oligonucleotides (U.S. Pat. No. 5,422,253). 5' ends of nucleic acids can also be made unavailable because of binding of a substance too large to thread through the helical arch. Such binding moieties may include proteins such as streptavidin or antibodies, or solid supports such as beads or the walls of a reaction vessel. A cleavage enzyme with an opening in the loop of the helical arch will be able to cleave DNAs that are configured in this way, extending the number of ways in which reactions using such enzymes can be formatted.

b) Cleavase® DN Nuclease i) Construction and Expression of Cleavase® DN Nuclease A polymerization deficient mutant of Taq DNA polymerase, termed Cleavase® DN nuclease, was constructed. Cleavase® DN nuclease contains an asparagine residue in place of the wild-type aspartic acid residue at position 785 (D785N).

DNA encoding the Cleavase® DN nuclease was constructed from the gene encoding for Cleavase® A/G (mutTaq, Ex. 2) in two rounds of site-directed mutagenesis. First, the G at position 1397 and the G at position 2264 of the Cleavase® A/G gene (SEQ ID NO:21) were changed to A at each position to recreate a wild-type DNAPTaq gene. As a second round of mutagenesis, the wild type DNAPTaq gene was converted to the Cleavase® DN gene by changing the G at position 2356 to A. These manipulations were performed as follows. DNA encoding the Cleavase® A/G nuclease was recloned from pTTQ18 plasmid (Ex. 2) into the pTrc99A plasmid (Pharmacia) in a two step procedure. First, the pTrc99A vector was modified by removing the G at position 270 of the pTrc99A map, creating the pTrc99G cloning vector. To this end, pTrc99A plasmid DNA was cut with NcoI and the recessive 3' ends were filled-in using the Klenow fragment of E.coli polymerase I in the presence of all four dNTPs at 37° C. for 15 min. After inactivation of the Klenow fragment by incubation at 65° C. for 10 min, the plasmid DNA was cut with EcoRI, the ends were again filled-in using the Klenow fragment in the presence of all four dNTPs at 37° C. for 15 min. The Klenow fragment was then inactivated by incubation at 65° C. for 10 min. The plasmid DNA was ethanol precipitated, recircularized by ligation, and used to transform E.coli JM109 cells (Promega). Plasmid DNA was isolated from single colonies and deletion of the G at position 270 of the pTrc99A map was confirmed by DNA sequencing.

As a second step, DNA encoding the Cleavase® A/G nuclease was removed from the pTTQ18 plasmid using EcoRI and SalI and the DNA fragment carrying the Cleavase® A/G nuclease gene was separated on a 1% agarose gel and isolated with Geneclean II Kit (Bio 101, Vista, Calif.). The purified fragment was ligated into the pTrc99G vector which had been cut with EcoRI and SalI. The ligation mixture was used to transform competent E.coli JM109 cells (Promega). Plasmid DNA was isolated from single colonies and insertion of the Cleavase® A/G nuclease gene was confirmed by restriction analysis using EcoRI and SalI.

Plasmid DNA pTrcAG carrying the Cleavase® A/G nuclease gene cloned into the pTrc99A vector was purified from 200 ml of JM109 overnight culture using QIAGEN Plasmid Maxi kit (QIAGEN, Chatsworth, Calif.) according to manufacturer's protocol. pTrcAG plasmid DNA was mutagenized using two mutagenic primers, E465 (SEQ ID NO:103) (Integrated DNA Technologies, Iowa) and R754Q (SEQ ID NO:104) (Integrated DNA Technologies), and the selection primer Trans Oligonucleotide AlwNI/SpeI (Clontech, Palo Alto, Calif., catalog #6488-1) according to Transformer™ Site-Directed Mutagenesis Kit protocol (Clontech, Palo Alto, Calif.) to produce a restored wild-type DNAPTaq gene (pTrcWT).

pTrcWT plasmid DNA carrying the wild-type DNAPTaq gene cloned into the pTrc99A vector was purified from 200 ml of JM109 overnight culture using QIAGEN Plasmid Maxi kit (QIAGEN, Chatsworth, Calif.) according to manufacturer's protocol. pTrcWT was then mutagenized using the mutagenic primer D785N (SEQ ID NO:105) (Integrated DNA Technologies) and the selection primer Switch Oligonucleotide SpeI/AlwNI (Clontech, Palo Alto, Calif., catalog #6373-1) according to Transformer™ Site-Directed Mutagenesis Kit protocol (Clontech, Palo Alto, Calif.) to create a plasmid containing DNA encoding the Cleavase® DN nuclease. The DNA sequence encoding the Cleavase® DN nuclease is provided in SEQ ID NO:106; the amino acid sequence of Cleavase® DN nuclease is provided in SEQ ID NO:107.

A large scale preparation of the Cleavase® DN nuclease was done using E. coli cells overexpressing the Cleavase® DN nuclease as described in Ex. 29.

c) Cleavase® DA Nuclease and Cleavase® DV Nuclease

Two polymerization deficient mutants of Taq DNA polymerase, termed Cleavase® DA nuclease and Cleavase® DV nuclease, were constructed. The Cleavase® DA nuclease contains a alanine residue in place of the wild-type aspartic acid residue at position 610 (D785A). The Cleavase® DV nuclease contains a valine residue in place of the wild-type aspartic acid residue at position 610 (D610V).

i) Construction and Expression of the Cleavase® DA and Cleavase® DV Nucleases

To construct vectors encoding the Cleavase® DA and DV nucleases, the Cleavase® A/G nuclease gene contained within pTrcAG was mutagenized with two mutagenic primers, R754Q (SEQ ID NO:104) and D610AV (SEQ ID NO:128) and the selection primer Trans Oligonucleotide AlwNI/SpeI (Clontech, catalog #6488-1) according to the Transformer™ Site-Directed Mutagenesis Kit protocol (Clontech,) to create a plasmid containing DNA encoding the Cleavase® DA nuclease or Cleavase® DV nuclease. The D610AV oligonucleotide was synthesized to have a purine, A or G, at position 10 from the 5' end of the oligonucleotide. Following mutagenesis, plasmid DNA was isolated from single colonies and the type of mutation present, DA or DV, was determined by DNA sequencing. The DNA sequence encoding the Cleavase® DA nuclease is provided in SEQ ID NO:129; the amino acid sequence of Cleavase® DA nuclease is provided in SEQ ID NO:130. The DNA sequence encoding the Cleavase® DV nuclease is provided in SEQ ID NO:131; the amino acid sequence of Cleavase® DV nuclease is provided in SEQ ID NO:132.

Large scale preparations of the Cleavase® DA and Cleavase® DV nucleases was done using E. coli cells overexpressing the Cleavase® DA nuclease or the Cleavase® DV nuclease as described in Ex. 29.

d) Cleavase® Tth DN Nuclease i) Construction and Expression of Cleavase® TthDN Nuclease The DNA polymerase enzyme from the bacterial species Thermus thermophilus (Tth) was produced by cloning the gene for this protein into an expression vector and overproducing it in E. coli cells. Genomic DNA was prepared from 1 vial of dried Thermus thermophilus strain HB-8 from ATCC (ATCC #27634) as described in Ex. 29a. The DNA polymerase gene was amplified by PCR as described in Ex. 29b using the following primers: 5'-CACGAATTCCG AGGCGATGCTTCCGCTC-3' (SEQ ID NO:166) and 5'-TCGACGTCGACTAACCCTTGGCGGAAAGCC-3' (SEQ ID NO:167), as described in Ex. 29a.

The resulting PCR product was digested with EcoR I and SalI restriction endonucleases and inserted into EcoRI/Sal I digested plasmid vector pTrc99g (described in Example 27b) by ligation, as described in Example 27b, to create the plasmid pTrcTth-1. This Tth polymerase construct is missing a single nucleotide which was inadvertently omitted from the 5' oligonucleotide, resulting in the polymerase gene being out of frame. This mistake was corrected by mutagenesis of pTrcTth-1 as described in Example 27b using the following oligonucleotide: 5'-GCATCGCCTCGG AATTCATGGTC-3' (SEQ ID NO:168), to create the plasmid pTrcTth-2. The Tth DN construct was created by mutating the sequence encoding an aspartic acid at position 787 to a sequence encoding asparagine. Mutagenesis of pTrcTth-2 with the following oligonucleotide: 5'-CAGGA GGAGCTCGTTGTGGACCTGGA-3' (SEQ ID NO:169) as described in Example 27b, to create the plasmid pTrcTth-DN. The resulting polymerase-deficient nuclease, Cleavase® TthDN was expressed and purified as described in Ex. 29.

EXAMPLE 29

Cloning and Expression of Thermostable FEN-1 Endonucleases

Sequences encoding thermostable FEN-1 proteins derived from three Archaebacterial species were cloned and overexpressed in E. coli. This Example involved: a) Cloning and Expression of a FEN-1 Endonuclease from Methanococcus jannaschii; b) Cloning and Expression of a FEN-1 Endonuclease from Pyrococcus furiosus; c) Cloning and Expression of a FEN-1 Endonuclease from Pyrococcus woesei; d) Cloning and Expression of a FEN-1 Endonuclease from Archaeoglobus fulgidus; e) Cloning and Expression of a FEN-1 Endonuclease from Methanobacterium thermoautotrophicum; f) Large Scale Preparation of Recombinant Thermostable FEN-1 Proteins; and e) Activity Assays using FEN-1 endonucleases.

a) Cloning and Expression Of A FEN-1 Endonuclease From Methanococcus jannaschii

In this Example, DNA encoding the FEN-1 endonuclease from Methanococcus jannaschii (M. jannaschii) was isolated from M. jannaschii cells and inserted into a plasmid under the transcriptional control of an inducible promoter as follows. Genomic DNA was prepared from 1 vial of live M. jannaschii bacteria (DSMZ # 2661) with the DNA XTRAX kit (Gull), according to the manufacturer's protocol. The final DNA pellet was resuspended in 100 μl of TE (10 mM Tris HCl, pH 8.0, 1 mM EDTA). One microliter of the DNA solution was employed in a PCR using the Advantage™ cDNA PCR kit (Clonetech); the PCR was conducted according to manufacturer's recommendations. The 5'-end primer (SEQ ID NO:108) is complementary to the 5' end of the Mja FEN-1 open reading frame with a one base substitution to create an NcoI restriction site (a fragment of the *M. jannaschii* genome which contains the gene encoding *M. jannaschii* (Mja) FEN-1 is available from GenBank as accession # U67585). The 3'-end primer (SEQ ID NO:109) is complementary to a sequence about 15 base pairs downstream from the 3' end of the Mja FEN-1 open reading frame with 2 base substitutions to create a SalI restriction enzyme site. The sequences of the 5'-end and 3'-end primers are: 5'-GGGATACCATGGGAGTGCAGTTTGG-3' (SEQ ID NO:108) and 5'-GGTAAATTTTTCTCGTCGACATC CCAC-3' (SEQ ID NO:109), respectively. The PCR reaction resulted in the amplification (i.e., production) of a single major band about 1 kilobase in length. The open reading frame (ORF) encoding the Mja FEN-1 endonuclease is provided in SEQ ID NO:110; the amino acid sequence encoded by this ORF is provided in SEQ ID NO:111.

Following the PCR amplification, the entire reaction was electrophoresed on a 1.0% agarose gel and the major band was excised from the gel and purified using the Geneclean II kit (Bio101, Vista, Calif.) according to manufacturer's instructions. Approximately 1 μg of the gel-purified Mja FEN-1 PCR product was digested with NcoI and SalI. After digestion, the DNA was purified using the Geneclean II kit according to manufacturer's instructions. One microgram of the pTrc99a vector (Pharmacia) was digested with NcoI and SalI in preparation for ligation with the digested PCR product. One hundred nanograms of digested pTrc99a vector and 250 ng of digested Mja FEN-1 PCR product were combined and ligated to create pTrc99-MJFEN1. pTrc99-MJFEN1 was used to transform competent *E. coli* JM109 cells (Promega) using standard techniques.

b) Cloning and Expression Of A FEN-1 Endonuclease From *Pyrococcus furiosus*

DNA encoding the *Pyrococcus furiosus* (*P. furiosus*) FEN-1 endonuclease was obtained by PCR amplification using a plasmid containing DNA encoding the *P. furiosus* (Pfu) FEN-1 endonuclease (obtained from Dr. Frank Robb, Center of Marine Biotechnology, Baltimore, Md.). DNA sequences encoding a portion of the Pfu FEN-1 endonuclease can be obtained from GenBank (Accession Nos. AA113505 and W36094). The amplified Pfu FEN-1 gene was inserted into the pTrc99a expression vector (Pharmacia) to place the Pfu FEN-1 gene under the transcriptional control of the inducible trc promoter. The PCR amplification was conducted as follows. One hundred microliter reactions contained 50 mM Tris HCl, pH 9.0, 20 mM $(NH_4)_2SO_4$, 2 mM $MgCl_2$, 50 μM dNTPs, 50 pmole each primer, 1 U Tfl polymerase (Epicentre) and 1 ng of FEN-1 gene-containing plasmid DNA. The 5'-end primer (SEQ ID NO:112) is complementary to the 5' end of the Pfu FEN-1 open reading frame but with two substitutions to create an NcoI site and the 3'-end primer (SEQ ID NO:113) is complementary to a region located about 30 base pairs downstream of the FEN-1 open reading frame with two substitutions to create a PstI site. The sequences of the 5'-end and 3'-end primers are: 5'-GAGGTGATACCATGGGTGTCC-3' (SEQ ID NO:112) and 5'-GAAACTCTGCAGCGCGTCAG-3' (SEQ ID NO:113), respectively. The PCR reaction resulted in the amplification of a single major band about 1 kilobase in length. The open reading frame (ORF) encoding the Pfu FEN-1 endonuclease is provided in SEQ ID NO:114; the amino acid sequence encoded by this ORF is provided in SEQ ID NO:115.

Following the PCR amplification, the entire reaction was electrophoresed on a 1.0% agarose gel and the major band was excised from the gel and purified using the Geneclean II kit (Bio101, Vista, Calif.) according to manufacturer's instructions. Approximately 1 μg of gel purified Pfu FEN-1 PCR product was digested with NcoI and PstI. After digestion, the DNA was purified using the Geneclean II kit according to manufacturer's instructions. One microgram of the pTrc99a vector was digested with NcoI and PstI prior to ligation with the digested PCR product. One hundred nanograms of digested pTrc99a and 250 ng of digested Pfu FEN-1 PCR product were combined and ligated to create pTrc99-PFFEN 1. pTrc99-PFFEN1 was used to transform competent *E. coli* JM109 cells (Promega) using standard techniques.

c) Cloning and Expression Of A FEN-1 Endonuclease From *Pyrococcus woesei*

For the cloning of DNA encoding the *Pyrococcus woesei* (Pwo) FEN-1 endonuclease, DNA was prepared from lyophilized *P. woesei* bacteria (DSMZ # 3773) as described (Zwickl et al., J. Bact., 172:4329 [1990]) with several changes. Briefly, one vial of *P. woesei* bacteria was rehydrated and resuspended in 0.5 ml of LB (Luria broth). The cells were centrifuged at 14,000×g for 1 min and the cell pellet was resuspended in 0.45 ml of TE. Fifty microliters of 10% SDS was added and the mixture was incubated at RT for 5 min. The cell lysate was then extracted three time with 1:1 phenol:chloroform and three times with chloroform. Five hundred microliters of isopropanol was added to the extracted lysate and the DNA was pelleted by centrifugation at 14,000×g for 10 min. The DNA pellet was washed in 0.5 ml of 70% ethanol and the DNA was pelleted again by centrifugation at 14,000×g for 5 min. The DNA pellet was dried and resuspended in 100 μl of TE and used for PCR reactions without further purification.

To generate a *P. woesei* FEN-1 gene fragment for cloning into an expression vector, low stringency PCR was attempted with primers complementary to the ends of the *P. furiosus* FEN-1 gene open reading frame. The sequences of the 5'-end and 3'-end primers are 5'-GATACCATGGG TGTCCCAATTGGTG-3 (SEQ ID NO:116) and 5'-TCGA CGTCGACTTATCTCTTGAACCAACTTTCAAGGG (SEQ ID NO:117), respectively. The high level of sequence similarity of protein homologs (i.e., proteins other than FEN-1 proteins) from *P. furiosus* and *P. woesei* suggested that there was a high probability that the *P. woesei* FEN-1 gene could be amplified using primers containing sequences complementary to the *P. furiosus* FEN-1 gene. However, this approach was unsuccessful under several different PCR conditions.

The DNA sequence of FEN-1 genes from *P. furiosus* and *M. jannaschii* were aligned and blocks of sequence identity between the two genes were identified. These blocks were used to design internal primers (i.e., complementary to sequences located internal to the 5' and 3' ends of the ORF) for the FEN-1 gene that are complementary to the *P. furiosus* FEN-1 gene in those conserved regions. The sequences of the 5'- and 3'-internal primers are 5'-AGCGAGGGAGAGG CCCAAGC-3' (SEQ ID NO:118) and 5'-GCCTATGCC CTTTATTCCTCC-3' (SEQ ID NO:119), respectively. A PCR employing these internal primers was conducted using the Advantage™ PCR kit and resulted in production of a major band of ~300 bp.

Since the PCR with the internal primers was successful, reactions were attempted which contained mixtures of the internal (SEQ ID NOS:118 and 119) and external (SEQ ID NOS:116 and 117) primers. A reaction containing the 5'-end external primer (SEQ ID NO:116) and 3'-end internal primer (SEQ ID NO:119) resulted in the production of a 600 bp band and a reaction containing the 5'-end internal primer (SEQ ID NO:118) and 3'-end external primer (SEQ ID NO:117) resulted in the production of a 750 bp band. These overlapping DNA fragments were gel-purified and combined with the external primers (SEQ ID NOS:116 and 117) in a PCR reaction. This reaction generated a 1 kb DNA fragment containing the entire Pwo FEN-1 gene open reading frame. The resulting PCR product was gel-purified, digested, and ligated exactly as described above for the Mja FEN-1 gene PCR product. The resulting plasmid was termed pTrc99-PWFEN1. pTrc99-PWFEN1 was used to transform competent *E. coli* JM109 cells (Promega) using standard techniques.

d) Cloning and Expression Of A FEN-1 Endonuclease From *Archaeoglobus fulgidus*

The preliminary *Archaeoglobus fulgidus* (Afu) chromosome sequence of 2.2 million bases was downloaded from the TIGR (The Institute for Genomic Research) world wide web site, and imported into a software program (MacDNAsis), used to analyze and manipulate DNA and protein sequences. The unannotated sequence was translated into all 6 of the possible reading frames, each comprising approximately 726,000 amino acids. Each frame was searched individually for the presence of the amino acid sequence "VFDG" (valine, phenylalanine, aspartic acid, glycine), a sequence which is conserved in the FEN-1 family. The amino acid sequence was found in an open reading frame that contained other amino acid sequences conserved in the FEN-1 genes and which was approximately the same size as the other FEN-1 genes. The ORF DNA sequence is shown in SEQ ID NO:178, while the ORF protein sequence is shown in SEQ ID NO:179. Based on the position of this amino acid sequence within the reading frame, the DNA sequence encoding a putative FEN-1 gene was identified.

The sequence information was used to design oligonucleotide primers which were used for PCR amplification of the FEN-1-like sequence from *A. fulgidus* genomic DNA. Genomic DNA was prepared from *A. fulgidus* as described in Ex. 29a for *M. jannaschii*, except that one vial (approximately 5 ml of culture) of live *A. fulgidus* bacteria from DSMZ (DSMZ #4304) was used. One microliter of the genomic DNA was used for PCR reaction as described in Ex. 29a. The 5' end primer is complementary to the 5' end of the Afu FEN-1 gene except it has a 1 base pair substitution to create an Nco I site. The 3' end primer is complentary to the 3' end of the Afu FEN-1 gene downstream from the FEN-1 ORF except it contains a 2 base substitution to create a Sal I site. The sequences of the 5' and 3' end primers are 5'-CCGTCAACATTTACCATGGGTGCGGA-3' (SEQ ID NO:170) and 5'-CCGCCACCTCGTAGTCGACATCCT TTTCGTG (SEQ ID NO:171), respectively. Cloning, expression and purification of the Afu FEN-1 gene was done as described in Examples 29a and 29d.

e) Cloning and Expression Of A FEN-1 Endonuclease From *Methanobacterium thermoautotrophicum*

A tentative listing of all open reading frames of the *Methanobacterium thermoautotrophicum* (Mth) genome on the Genome Therapeutics world wide web page was searched for amino acid sequences conserved in the FEN-1 genes. The amino acid sequence "VFDG" (valine, phenylalanine, aspartic acid, glycine) was found in an open reading frame which also contained other conserved FEN-1 sequences. SEQ ID NO:180 provides the Mth FEN-1 ORF DNA sequence as indicated by Genome Therapeutics, while SEQ ID NO:181 provides the Mth FEN-1 ORF protein sequence as indicated by Genome Therapeutics. However, this open reading frame was 259 amino acids in length, as compared to the other archael FEN-1 genes, which are approximately 325 amino acids long. To determine the cause of this discrepancy, the DNA sequence for Mth FEN-1 was obtained in an identical manner as described above for Afu FEN-1.

Upon examination of the sequence, it was apparent that the open reading frame could be extended to 328 amino acids by deletion of a single base at about position 750 of the open reading frame. The additional amino sequence added by deleting one base is 39% identical to the same region of the *P. furiosus* FEN-1 gene. The DNA sequence of the putative Mth FEN-1 gene was used to design oligonucleotide primers complementary to the 5' and 3' ends of the gene. The 5' oligonucleotide is complementary to the 5' end of the Mth FEN-1 gene except that it contains 2 substitutions which create an NcoI site. The 3' oligonucleotide is complementary to the 3' end of the gene about 100 base pairs downstream of where it is believed that the true open reading frame ends. This region contains a natural PstI site. The sequences of the 5' and 3' oligonucleotides are 5'-GGGTGTTCCCATGGGAGTTAAACTCAGG-3' (SEQ ID NO:172) and 5'-CTGAATTCTGCAGAAAAAGGGG-3' (SEQ ID NO:173), respectively.

Genomic DNA was prepared from 1 vial of frozen *M. thermoautotrophicum* bacteria from ATCC (ATCC # 29096) as described in Ex. 29a. PCR, cloning, expression, and purification of Mth FEN-1 was done as described in Examples 29a and 29d, except PstI was used instead of SalI. Sequencing of the cloned Mth FEN-1 gene revealed the presence of additional "T" nucleotide when compared to the genome sequence published on the world wide web. This "T" residue at position 775 of the FEN-1 open reading frame causes a frame shift, creating the larger open reading frame that originally thought, based on comparison to the FEN genes from other organisms. SEQ ID NO: 182 provides the sequence of the Mth ORF DNA sequence of the present invention, while SEQ ID NO:183 provides the sequence of the Mth FEN-1 protein sequence of the present invention.

f) Large Scale Preparation of Recombinant Thermostable FEN-1 Proteins

The Mja, Pwo and Pfu FEN-1 proteins were purified by the following technique which is derived from a Taq DNA polymerase preparation protocol (Engelke et al., Anal. Biochem., 191:396 [1990]) as follows. *E. coli* cells (strain JM109) containing either pTrc99-PFFEN1, pTrc99-PWFEN1, or pTrc99-MJFEN1 were inoculated into 3 ml of LB (Luria Broth) containing 100 µg/ml ampicillin and grown for 16 hrs at 37° C. The entire overnight culture was inoculated into 200 ml or 350 ml of LB containing 100 µg/ml ampicillin and grown at 37° C. with vigorous shaking to an $A_{600}$ of 0.8. IPTG (1 M stock solution) was added to a final concentration of 1 mM and growth was continued for 16 hrs at 37° C.

The induced cells were pelleted and the cell pellet was weighed. An equal volume of 2× DG buffer (100 mM Tris-HCl, pH 7.6, 0.1 mM EDTA) was added and the pellet was resuspended by agitation. Fifty mg/ml lysozyme (Sigma) were added to 1 mg/ml final concentration and the cells were incubated at room temperature for 15 min. Deoxycholic acid (10% solution) was added dropwise to a final concentration of 0.2 % while vortexing. One volume of H₂O and 1 volume of 2× DG buffer was added and the resulting mixture was sonicated for 2 minutes on ice to reduce the viscosity of the mixture. After sonication, 3 M $(NH_4)_2SO_4$ was added to a final concentration of 0.2 M and the lysate was centrifuged at 14000×g for 20 min at 4° C. The supernatant was removed and incubated at 70° C. for 60 min at which time 10% polyethylimine (PEI) was added to 0.25%. After incubation on ice for 30 min., the mixture was centrifuged at 14,000×g for 20 min at 4° C. At this point, the supernatant was removed and the FEN-1 proteins was precipitated by the addition of $(NH_4)_2SO_4$ as follows.

For the Pwo and the Pfu FEN-1 preparations, the FEN-1 protein was precipitated by the addition of 2 volumes of 3 M $(NH_4)_2SO_4$. The mixture was incubated overnight at room temperature for 16 hrs and the protein was centrifuged at 14,000×g for 20 min at 4° C. The protein pellet was resuspended in 0.5 ml of Q buffer (50 mM Tris-HCl, pH 8.0, 0.1 mM EDTA, 0.1% Tween 20). For the Mja FEN-1 preparation, solid $(NH_4)_2SO_4$ was added to a final concentration of 3 M (~75% saturated), the mixture was incubated on ice for 30 min, and the protein was spun down and resuspended as described above.

Figure 75:
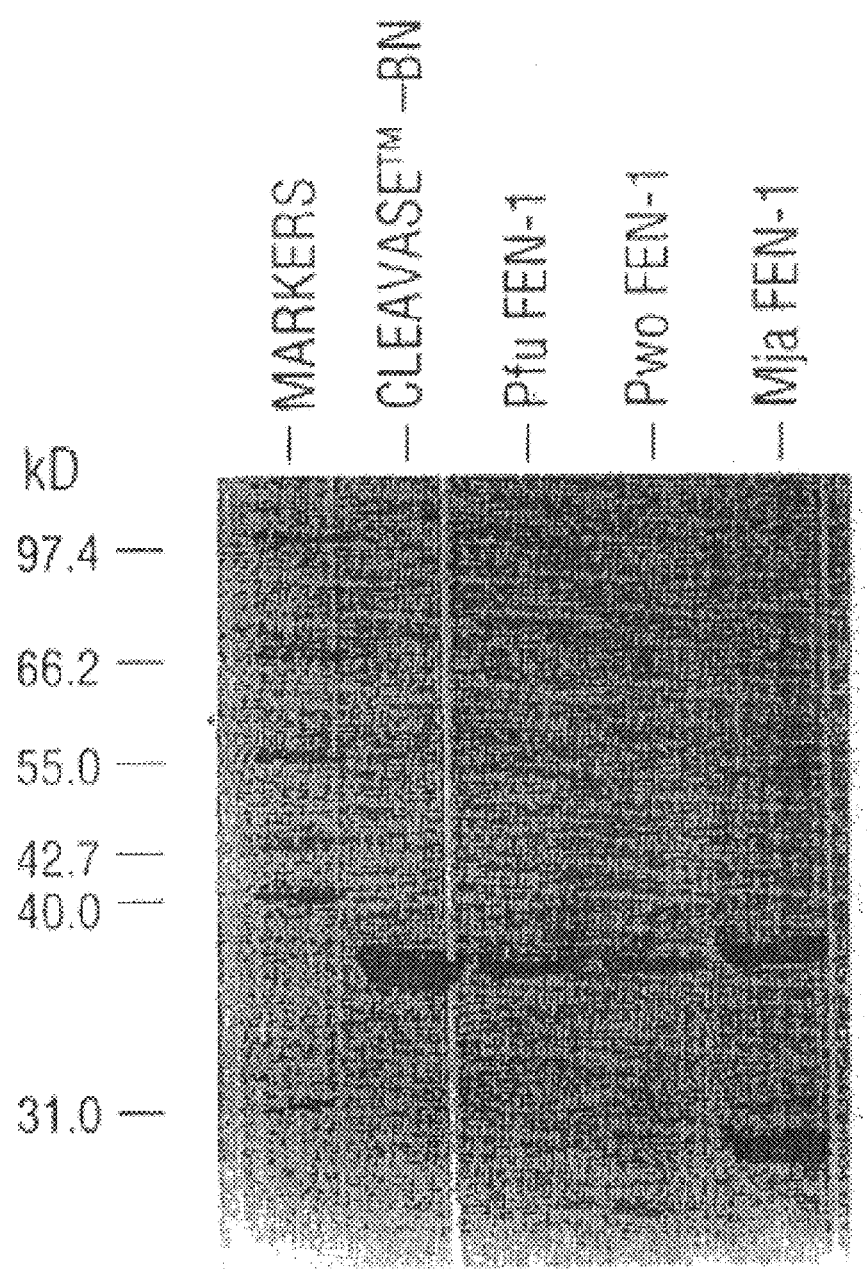
FIG. 75 is an SDS-PAGE gel showing the migration of purified Cleavase® BN nuclease, Pfu FEN-1, Pwo FEN-1 and Mja FEN-1.

The resuspended protein preparations were quantitated by determination of the $A_{279}$ and aliquots containing 2–4 µg of total protein were electrophoresed on a 10% SDS polyacrylamide gel (29:1 acrylamide: bis-acrylamide) and stained with Coomassie Brilliant Blue R; the results are shown in FIG. 75.

In FIG. 75, lane 1 contains molecular weight markers (Mid-Range Protein Molecular Weight Markers; Promega); the size of the marker proteins is indicated to the left of the gel. Lane 2 contains purified Cleavase® BN nuclease; lanes 3–5 contain extracts prepared from *E. coli* expressing the Pfu, Pwo and Mja FEN-1 nucleases, respectively. The calculated (i.e., using a translation of the DNA sequence encoding the nuclease) molecular weight of the Pfu FEN-1 nuclease is 38,714 daltons and the calculated molecular weight for the Mja FEN-1 nuclease is 37,503 Daltons. The Pwo and Pfu FEN-1 proteins co-migrated on the SDS-PAGE gel and therefore, the molecular weight of the Pwo FEN-1 nuclease was estimated to be 38.7 kDa.

e-g) Activity Assays Using FEN-1 Endonucleases i) Mixed Hairpin Assay

The Cleavase® BN nuclease has an approximately 60-fold greater affinity for a 12 base pair stem-loop structure than an 8 base pair stem-loop DNA structure. As a test for activity differences between the Cleavase® BN nuclease and the FEN-1 nucleases, a mixture of oligonucleotides having either a 8 or a 12 bp stem-loop (see FIG. 71 which depicts the S-33 and 11-8-0 oligonucleotides) was incubated with an extract prepared from *E. coli* cells overexpressing the Mja FEN-1 nuclease (prepared as described above). Reactions contained 0.05 µM of oligonucleotides S-33 (SEQ ID NO:120) and 11-8-0 (SEQ ID NO:121) (both oligonucleotides contained 5'-fluorescein labels), 10 mM MOPS, pH 7.5, 0.05% Tween-20, 0.05% NP-40, 1 mM $MnCl_2$. Reactions were heated to 90° C. for 10 seconds, cooled to 55° C., then 1 µl of crude extract (Mja FEN-1) or purified enzyme (Cleavase® BN nuclease) was added and the mixtures were incubated at 55° C. for 10 minutes; a no enzyme control was also run. The reactions were stopped by the addition of formamide/EDTA, the samples were electrophoresed on a denaturing 20% acrylamide gel and visualized on a Hitachi FMBIO 100 fluorescence imager. The resulting image is shown in FIG. 76.

Figure 76:
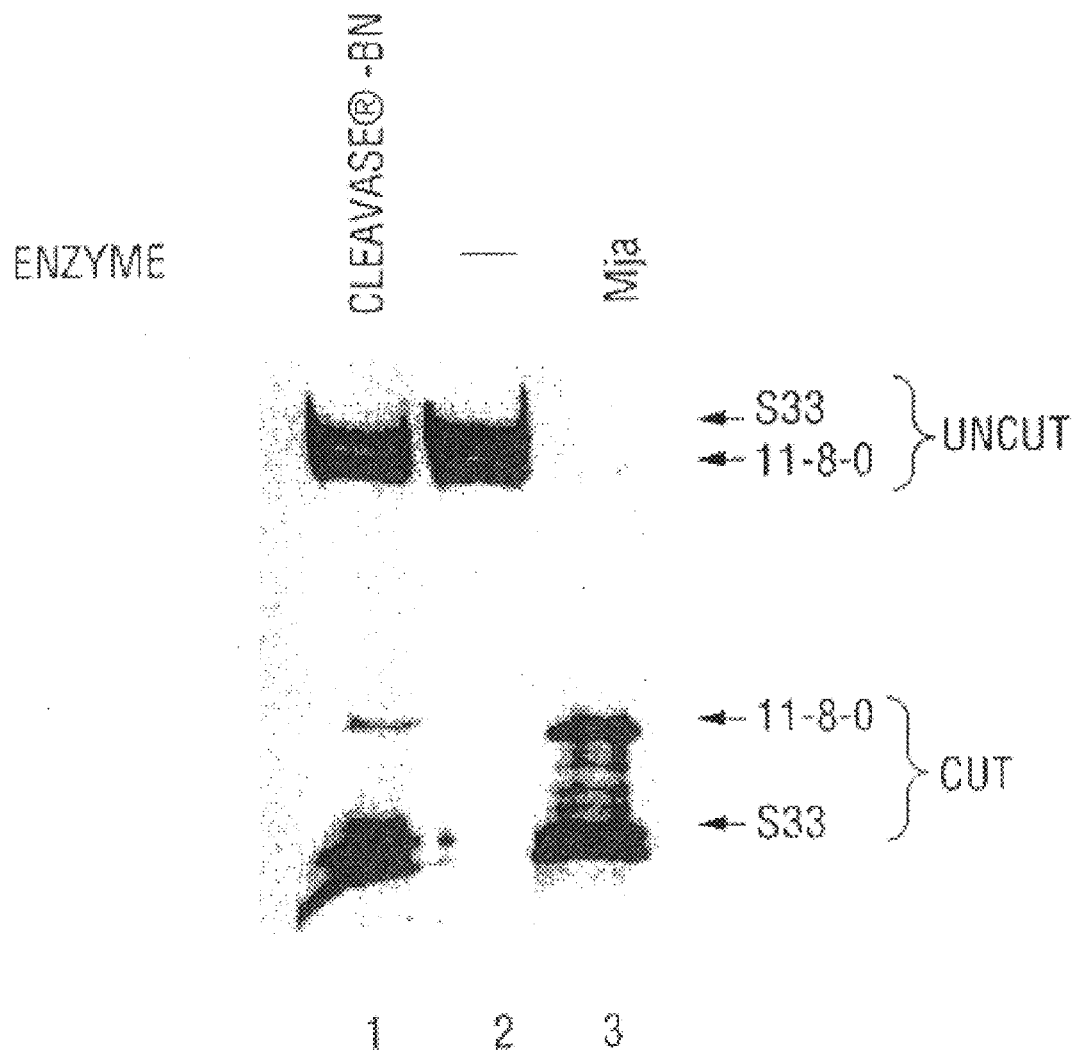
FIG. 76 is the image generated by a fluorescence imager showing the products produced by the cleavage of the S-33 and 11-8-0 oligonucleotides by Cleavase® BN and the Mja FEN-1 nucleases.
Figure 77:
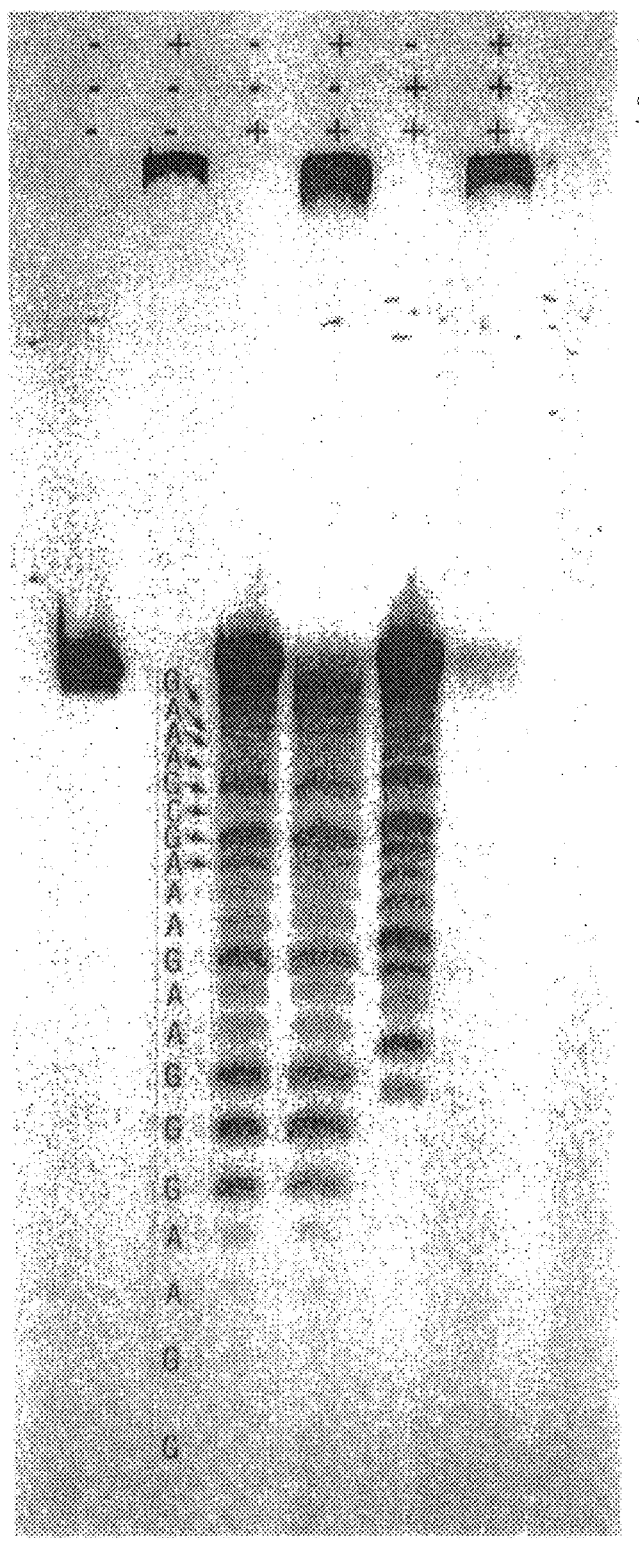
FIG. 77 is the image generated by a fluorescence imager showing the products produced by the incubation of an oligonucleotide either having or lacking a 3'-OH group with TdT.
Figure 78:
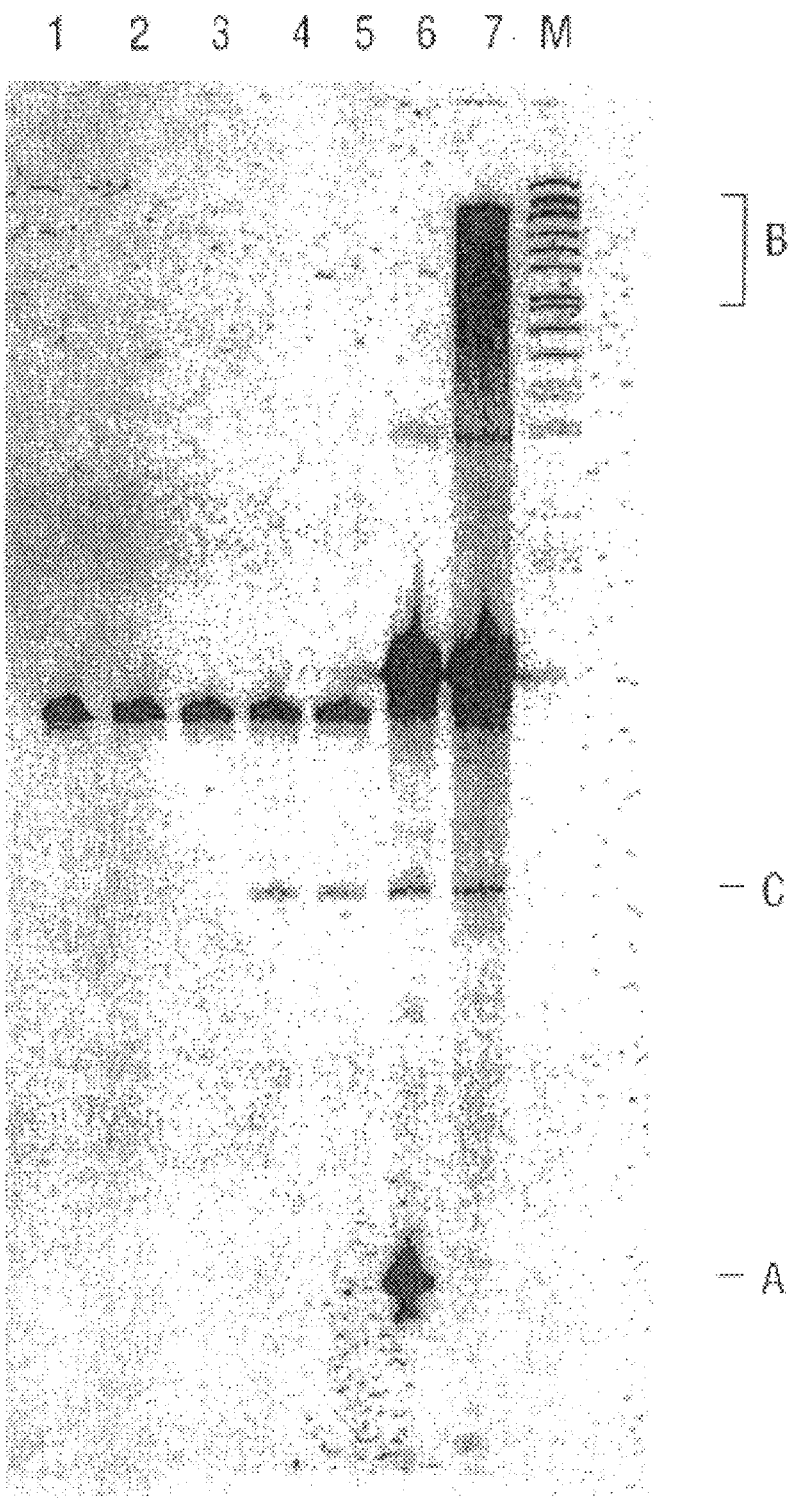
FIG. 78 is the image generated by a fluorescence imager showing the products produced the incubation of cleavage products with TdT.

In FIG. 76, lane 1 contains the reaction products generated by the Cleavase® BN nuclease, lane 2 contains the reaction products from the no enzyme control reaction and lane 3 contains the reaction products generated by the Mja FEN-1 nuclease. The data shown in FIG. 76 demonstrates that the Cleavase® BN nuclease strongly prefers the S33 structure (12 bp stem-loop) while the Mja FEN-1 nuclease cleaves structures having either an 8 or a 12 bp stem-loop with approximately the same efficiency. This shows that the Mja FEN-1 nuclease has a different substrate specificity than the Cleavase® BN nuclease, a useful feature for Invader™ assays or CFLP® analysis as discussed in the Description of the Invention.

EXAMPLE 30

Terminal Deoxynucleotidyl Transferase Selectively Extends the Products of Invader™-Directed Cleavage The majority of thermal degradation products of DNA probes will have a phosphate at the 3'-end. To investigate if the template-independent DNA polymerase, terminal deoxynucleotidyl transferase (TdT) can tail or polymerize the aforementioned 3'-end phosphates (i.e., add nucleotide triphosphates to the 3' end) the following experiment was performed.

To create a sample containing a large percentage of thermal degradation products, the 5' fluorescein-labeled oligonucleotide 34-078-01 (SEQ ID NO:73) (200 pmole) was incubated in 100 µl 10 mM $NaCO_3$ (pH 10.6), 50 mM NaCl at 95° C. for 13 hours. To prevent evaporation, the reaction mixture was overlaid with 60 µl ChillOut™4 liquid wax (MJ Research). The reaction mixture was then divided into two equal aliquots (A and B). Aliquot A was mixed with one-tenth volume 3M NaOAc followed by three volumes ethanol and stored at −20° C. Aliquot B was dephosphorylated by the addition of 0.5 µl of 1M $MgCl_2$ and 1 µl of 1 unit/µl Calf Intestine Alkaline Phosphatase (CIAP) (Promega), with incubation at 37° C. for 30 minutes. An equal volume of phenol:chloroform:isoamyl alcohol (24:24:1) was added to the sample followed by vortexing for one minute and then centrifugation 5 minutes at maximum speed in a microcentrifuge to separate the phases. The aqueous phase was removed to a new tube to which one-tenth volume 3M NaOAc, and three volumes ethanol was added followed by storage at −20° C. for 30 minutes. Both aliquots (A and B) were then centrifuged for 10 minutes at maximum speed in a microcentrifuge to pellet the DNA. The pellets were then washed two times each with 80% ethanol and then desiccated to dryness. The dried pellets were then dissolved in 70 µl ddH₂O each.

The TdT reactions were conducted as follows. Six mixes were assembled, all mixes contained 10 mM TrisOAc (pH 7.5), 10 mM MgOAc, 50 mM KCl, and 2 mM dATP. Mixes 1 and 2 contained one pmole of untreated 34-078-01 (SEQ ID NO:73), mixes 3 and 4 contained 2 µl of aliquot A (above), mixes 5 and 6 contained 2 µl of aliquot B (above). To each 9 µl of mixes 1,3 and 5, 1 µl ddH₂O was added, to each 9 µl of mixes 2, 4, and 6, 1 µl of 20 units/µl TdT (Promega) was added. The mixes were incubated at 37° C. for 1 hour and then the reaction was terminated by the addition of 5 µl 95% formamide with 10 mM EDTA and 0.05% marker dyes. Five microliters of each mixture was resolved by electrophoresis through a 20% denaturing acrylamide gel (19:1 cross-linked) with 7 M urea, in a buffer containing 45 mM Tris-Borate (pH 8.3), 1.4 mM EDTA, and imaged as described in Ex. 21; a 505 nm filter was used with the FMBIO Image Analyzer. The resulting imager scan is shown in FIG. 81.

Figure 81:
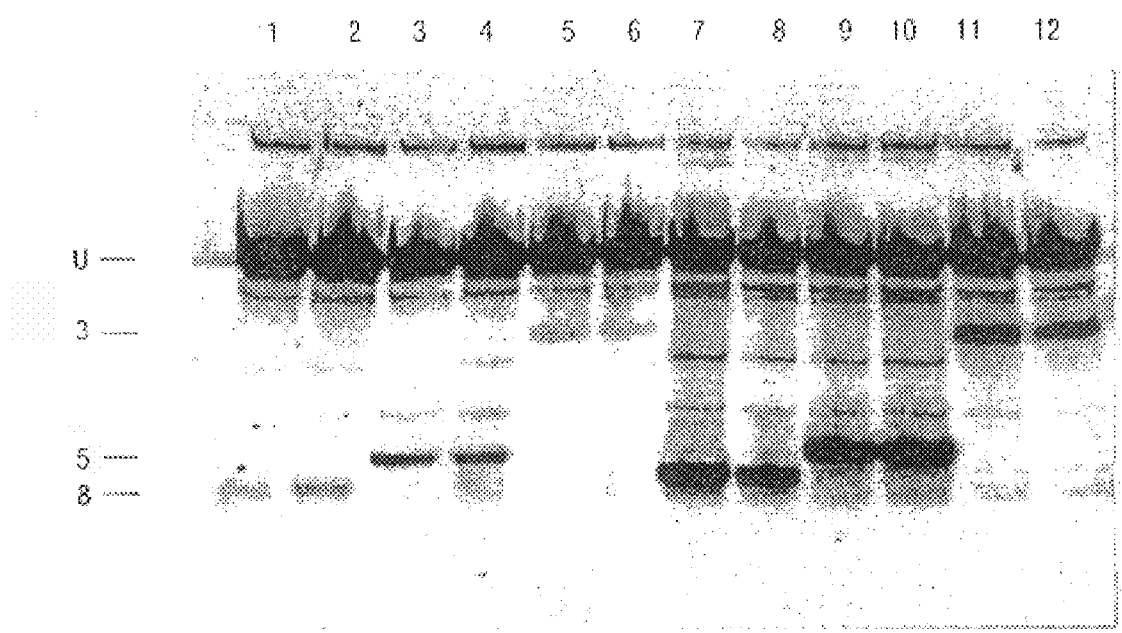
FIG. 81 is the image generated by a fluorescence imager showing the products produced using the Cleavase® A/G and Pfu FEN-1 nucleases and a Cy3-labeled probe.

In FIG. 81, lanes 1, 3 and 5 contain untreated 34-078-01 (SEQ ID NO:73), heat-degraded 34-078-01 (SEQ ID NO:73), and heat-degraded, dephosphorylated, 34-078-01 (SEQ ID NO:73), respectively incubated in the absence of TdT. Lanes 2, 4 and 6 contain, untreated 34-078-01 (SEQ ID NO:73), heat-degraded 34-078-01 (SEQ ID NO:73), and heat-degraded, dephosphorylated, 34-078-01 (SEQ ID NO:73), respectively incubated in the presence of TdT.

As shown in FIG. 81, lane 4, TdT was unable to extend thermal degradation products which contain a 3'-end phosphate group, and selectively extends molecules which have a 3'-end hydroxyl group.

EXAMPLE 31

Specific TdT Tailing of the Products of Invader™-Directed Cleavage With Subsequent Capture and Detection on Nitrocellulose Supports When TdT is used to extend the specific products of cleavage, one means of detecting the tailed products is to selectively capture the extension products on a solid support before visualization. This example demonstrates that the cleavage products can be selectively tailed by the use of TdT and deoxynucleotide triphosphates, and that the tailed products can be visualized by capture using a complementary oligonucleotide bound to a nitrocellulose support.

To extend the cleavage product produced in an Invader™-directed cleavage reaction, the following experiment was performed. Three reaction mixtures were assembled, each in a buffer of 10 mM MES (pH 6.5), 0.5%Tween-20, 0.5% NP-40. The first mixture contained 5 fmols of target DNA-M13mp18, 10 pmols of probe oligonucleotide 32-161-2 (SEQ ID NO:71; this probe oligonucleotide contains 3' ddC and a Cy3 amidite group near the 3' end), and 5 pmols of Invader™ oligonucleotide 32 161-1 (SEQ ID NO:70; this oligonucleotide contains a 3' ddC). The second mixture contained the probe and Invader™ oligonucleotides without target DNA. The third mixture was the same as the first mixture, and contained the same probe sequence, but with a 5' fluorescein label [oligonucleotide 32-161-4 (SEQ ID NO:72; this oligonucleotide contains a 3' ddC, 5' fluorescein label, and a Cy3 amidite group near the 3' end)], so that the Invader™-directed cleavage products could be detected before and after cleavage by fluorescence imaging. The probe only control sample contained 10 pmols of oligonucleotide 32-161-2 (SEQ ID NO:71). Each 3 µl of enzyme mix contained 5 ng of Cleavase® DN nuclease in 7.5 mM MgCl$_2$. The TdT mixture (per each 4 µl) contained: 10U of TdT (Promega), 1 mM CoCl$_2$, 50 mM KCl, and 100 µM of dTTP. The Invader™ cleavage reaction mixtures described above were assembled in thin wall tubes, and the reactions were initiated by the addition of 3 µl of Cleavase® DN enzyme mix. The reactions were incubated at 65° C. for 20 min. After cooling to 37° C., 4 µl of the TdT mix was added and the samples were incubated for 4 min at 37° C., Biotin-16-dUTP was then added to 100 µM and the samples were incubated for 50 min at 37° C. The reactions were terminated by the addition of 1 µl of 0.5 M EDTA.

To test the efficiency of tailing the products were run on an acrylamide gel. Four microliters of each reaction mixture was mixed with 2.6 µl of 95% formamide, 10 mM EDTA and 0.05% methyl violet and heated to 90° C. for 1 min, and 3 µl were loaded on a 20% denaturing acrylamide gel (19:1 cross-linked ) with 7 M urea, in buffer containing 45 mM Tris-Borate (pH 8.3), 1.4 mM EDTA. A marker [ΦX174-HinfI (fluorescein labeled)] also was loaded. After electrophoresis, the gel was analyzed using a FMBIO-100 Image Analyzer (Hitachi) equipped with a 505 nm filter. The resulting scan is shown in FIG. 82.

Figure 82:
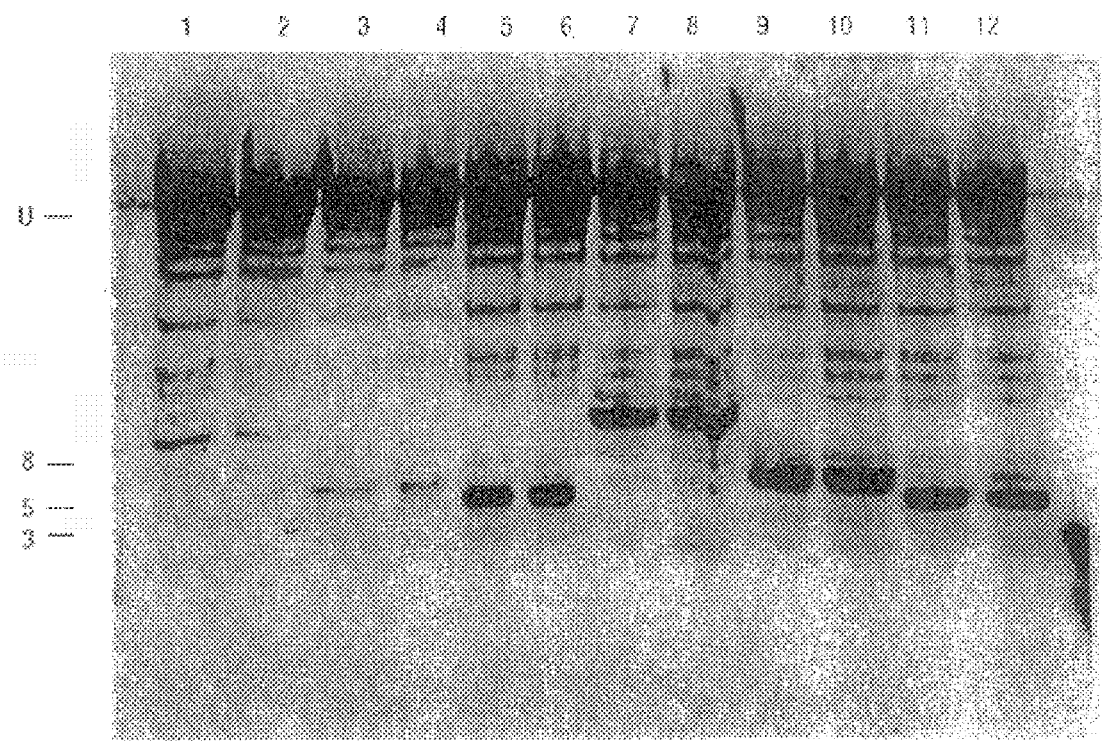
FIG. 82 is the image generated by a fluorescence imager showing the products produced using the Cleavase® A/G and Pfu FEN-1 nucleases and a TET-labeled probe.

In FIG. 82, lane 1 contained the probe 32-161-2 only, without any treatment. Lanes 2 and 3 contained the products of reactions run without target DNA, without or with subsequent TdT tailing, respectively. Lanes 4 and 5 contained the products of reactions run with target DNA, probe oligonucleotide 32-161-2 (SEQ ID NO:71) and Invader™ oligonucleotide 32-161-1 (SEQ ID NO:70), without or with subsequent TdT tailing, respectively. Lanes 6 and 7 show the products of reactions containing target DNA, probe oligonucleotide 32-161-4 (SEQ ID NO:72) and Invader™ oligonucleotide 32-161-1 (SEQ ID NO:70), without or with subsequent TdT tailing, respectively. Lane M contains the marker ΦX174-HinfI.

The reaction products in lanes 4 and 5 are the same as those seen in lanes 6 and 7, except that the absence of a 5' fluorescein on the probe prevents detection of the released 5' product (indicated as "A" near the bottom of the gel) or the TdT extended 5' product (indicated as "B", near the top of the gel). The Cy3-labeled 3' portion of the cleaved probe is visible in all of these reactions (indicated as "C", just below the center of the gel).

Figure 79:
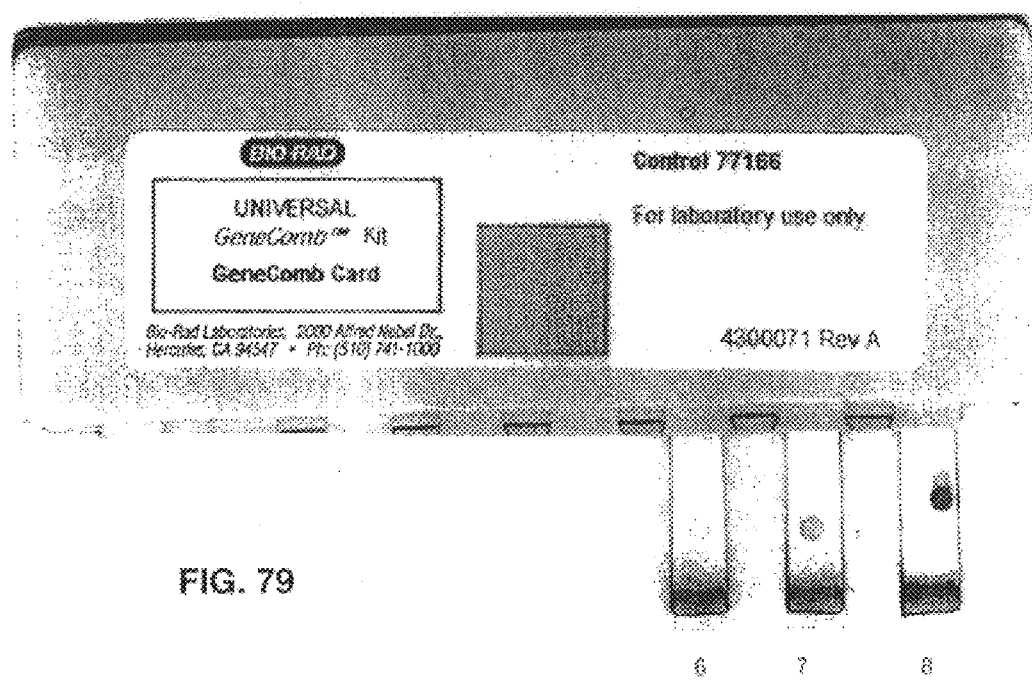
FIG. 79 is a photograph of a Universal GeneComb™ card showing the capture and detection of cleavage products on a nitrocellulose support.

To demonstrate detection of target-dependent Invader-directed cleavage products on a solid support, the reactions from lanes 3 and 5 were tested on the Universal GeneCombÔ® (Bio-Rad) which is a standard nitrocellulose matrix on a rigid nylon backing styled in a comb format, as depicted in FIG. 79. Following the manufacturer's protocol, with one modification: 10 µl of the Invader-directed cleavage reactions were used instead the recommended 10% of a PCR. To capture the cleavage products, 2.5 pmols of the capture oligonucleotide 59-28-1 (SEQ ID NO:133) were spotted on each tooth. The capture and visualization steps were conducted according to the manufacturer's directions. The results are shown in FIG. 79.

In FIG. 79, teeth numbered 6 and 7 show the capture results of reactions performed without and with target DNA present. Tooth 8 shows the kit positive control.

The darkness of the spot seen on tooth 7, when compared to tooth 6, clearly indicates that products of Invader™-directed cleavage assays may be specifically detected on solid supports. While the Universal GeneCombÔ® was used to demonstrate solid support capture in this instance, other support capture methods known to those skilled in the art would be equally suitable. For example, beads or the surfaces of reaction vessels may easily be coated with capture oligonucleotides so that they can then be used in this step. Alternatively, similar solid supports may easily be coated with streptavidin or antibodies for the capture of biotin- or hapten-tagged products of the cleavage/tailing reaction. In any of these embodiments, the products may be appropriately visualized by detecting the resulting fluorescence, chemiluminescence, calorimetric changes, radioactive emissions, optical density change or any other distinguishable feature of the product.

EXAMPLE 32

Comparison of the Effects of Invasion Length and 5' Label of the Probe on Invader™-Directed Cleavage by the Cleavase® A/G and Pfu FEN-1 Nucleases To investigate the effect of the length of invasion as well as the effect of the type of dye on ability of Pfu FEN-1 and the Cleavase® A/G nuclease to cleave 5' arms, the following experiment was performed. Three probes of similar sequences labeled with either fluorescein, TET, or Cy3, were assembled in reactions with three Invader™ oligonucleotides which created overlapping target hybridization regions of eight, five, and three bases along the target nucleic acid, M13mp18.

The reactions were conducted as follows. All conditions were performed in duplicate. Enzyme mixes for Pfu FEN-1 and the Cleavase® A/G nuclease were assembled. Each 2 µl of the Pfu FEN-1 mix contained 100 ng of Pfu FEN-1 (prepared as described in Ex. 28) and 7.5 mM $MgCl_2$. Each 2 µl of the Cleavase® A/G mix contained 5.3 ng of the Cleavase® A/G nuclease and 4.0 mM $MnCl_2$. Six master mixes containing buffer, M13mp18, and Invader™ oligonucleotides were assembled. Each 7 µl of mixes 1–3 contained 1 fmol M13mp18,d 10 pmoles Invader™ oligonucleotide (34-078-4 [SEQ ID NO:50], 24-181-2 [SEQ ID NO:76], or 24-181-1 [SEQ ID NO:75] in 10 mM MOPS (pH 7.5), 150 mM LiCl. Each 7 µl of mixes 4–6 contained 1 fmol of M13mp18, 10 pmoles of Invader™ oligonucleotide (34-078-4 [SEQ ID NO:50], 24-181-2 [SEQ ID NO:76], or 24-181-1 [SEQ ID NO:75]) in 10 mM Tris (pH 8.0). Mixtures 1–6 were then divided into three mixtures each, to which was added either the fluorescein-labeled probe (oligonucleotide 34-078-01; SEQ ID NO:73), the Cy3-labeled probe (oligonucleotide 43-20; SEQ ID NO:74) or the TET-labeled probe (oligonucleotide 90; SEQ ID NO:43 containing a 5' TET label). Each 7 µl of all mixtures contained 10 pmoles of corresponding probe. The DNA solutions described above were covered with 10 µl of ChillOut® evaporation barrier (MJ Research) and brought to 68° C.

Figure 80:
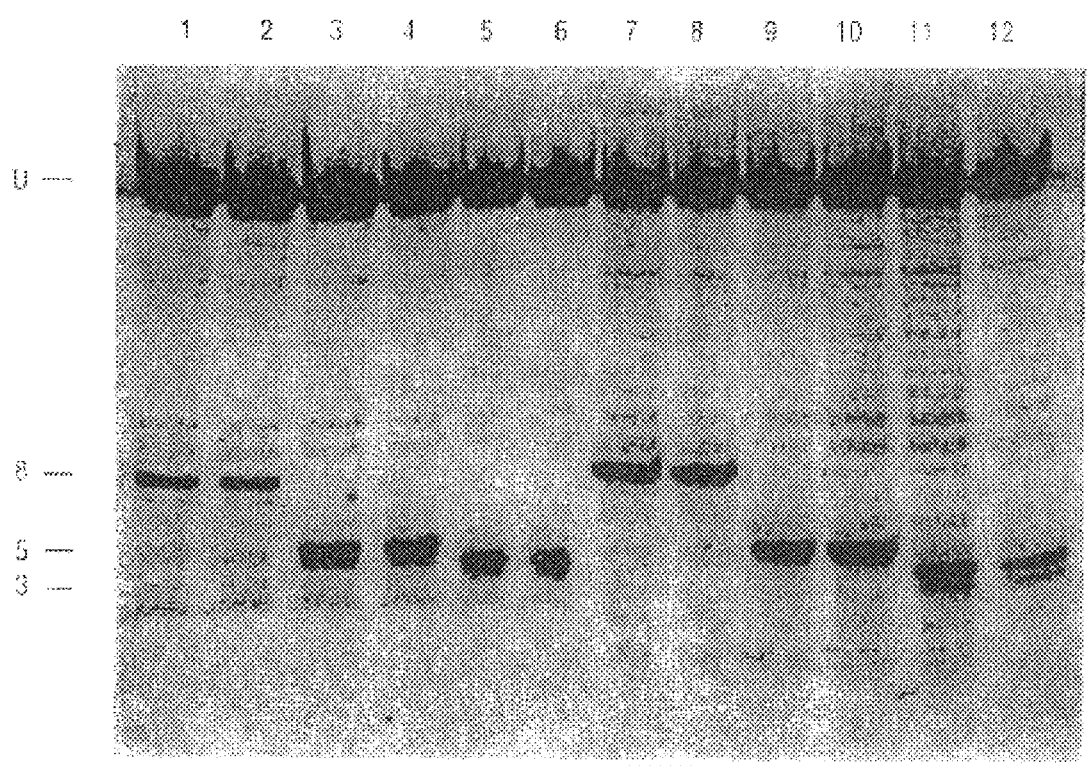
FIG. 80 is the image generated by a fluorescence imager showing the products produced using the Cleavase® A/G and Pfu FEN-1 nucleases and a fluorescein-labeled probe.

The reactions made from mixes 1–3 were started with 2 µl of the Cleavase® A/G nuclease mix, and the reactions made from mixes 4–6 were started with 2 µl of the Pfu FEN-1 mix. After 30 minutes at 68° C., the reactions were terminated by the addition of 8 µl of 95% formamide with 10 mM EDTA and 0.05% marker dyes. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA. The products of the cleavage reactions were visualized following electrophoresis by the use of a Hitachi FMBIO fluorescence imager. Results from the fluorescein-labeled probe are shown in FIG. 80, results from the Cy3-labeled probe in FIG. 81, and results from the TET-labeled probe in FIG. 82. In each of these figures the products of cleavage by Cleavase® A/G are shown in lanes 1–6 and the products of cleavage by Pfu FEN-1 are shown in lanes 7–12. In each in case the uncut material appears as a very dark band near the top of the gel, indicated by a "U" on the left. The products of cleavage directed by Invader oligonucleotides with 8, 5 or 3 bases of overlap (i.e., the "X" region was 8, 5, or 3 nt long) are shown in the first, second and third pair of lanes in each set, respectively and the released labeled 5' ends from these reactions are indicated by the numbers 8, 5, and 3 on the left. Note that in the cleavage reactions shown in FIG. 81 the presence of the positively charged Cy3 dye causes the shorter products to migrate more slowly than the larger products. These products do not contain any additional positive charges, e.g., amino modifications as used in Ex. 23, and thus still carry a net negative charge, and migrate towards the positive electrode in a standard electrophoresis run.

It can be seen from these data that the Cleavase® A/G and Pfu FEN-1 structure-specific nucleases respond differently to both dye identity and to the size of the piece to be cleaved from the probe. The Pfu FEN-1 nuclease showed much less variability in response to dye identity than did the Cleavase® A/G nuclease, showing that any dye would be suitable for use with this enzyme. In contrast, the amount of cleavage catalyzed by the Cleavase® A/G nuclease varied substantially with dye identity. Use of the fluorescein dye gave results very close to those seen with the Pfu FEN-1 nuclease, while the use of either Cy3 or TET gave dramatically reduced signal when compared to the Pfu FEN-1 reactions. The one exception to this was in the cleavage of the 3 nt product carrying a TET dye (lanes 5 and 6, FIG. 82), in which the Cleavase® A/G nuclease gave cleavage at the same rate as the Pfu FEN-1 nuclease. These data indicate that, while Cleavase® A/G may be used to cleave probes labeled with these other dyes, the Pfu FEN-1 nuclease is a preferred nuclease for cleavage of Cy3- and TET-labeled probes.

EXAMPLE 33

Examination of the Effects of a 5' Positive Charge on the Rate of Invasive Cleavage Using the Cleavase A/G or Pfu FEN-1 Nucleases To investigate whether the positive charges on 5' end of probe oligonucleotides containing a positively charged adduct(s) (i.e., charge reversal technology or CRT probes as described in Exs. 23 and 24) have an effect on the ability of the Cleavase® A/G or Pfu FEN-1 nucleases to cleave the 5' arm of the probe, the following experiment was performed.

Two probe oligonucleotides having the following sequences were utilized in Invader™ reactions: Probe 34-180-1: (N-Cy3)$T_{NH2}T_{NH2}$CCAGAGCCTAATTTGCC AGT(N-fluorescein)A, where N represents a spacer containing either the Cy3 or fluorescein group (SEQ ID NO:77) and Probe 34-180-2: 5'-(N-TET)TTCCAGAG CCTAATTTGCCAGT-(N-fluorescein)A, where N represents a spacer containing either the TET or fluorescein group (SEQ ID NO:78). Probe 34-180-1 has amino-modifiers on the two 5' end T residues and a Cy3 label on the 5' end, creating extra positive charges on the 5' end. Probe 34-180-2 has a TET label on the 5' end, with no extra positive charges. The fluorescein label on the 3' end of probe 34-180-1 enables the visualization of the 3' cleaved products and uncleaved probes together on an acrylamide gel run in the standard direction (i.e., with the DNA migrating toward the positive electrode). The 5' cleaved product of probe 34-180-1 has a net positive charge and will not migrate in the same direction as the uncleaved probe, and is thus visualized by resolution on a gel run in the opposite direction (i.e.; with this DNA migrating toward the negative electrode).

The cleavage reactions were conducted as follows. All conditions were performed in duplicate. Enzyme mixes for the Pfu FEN-1 and Cleavase® A/G nucleases were assembled. Each 2 µl of the Pfu FEN-1 mix contained 100 ng of Pfu FEN-1 (prepared as described in Ex. 28) and 7.5 mM $MgCl_2$. Each 2 µl of the Cleavase® A/G nuclease mix contained 26.5 ng of Cleavase® A/G nuclease and 4.0 mM $MnCl_2$. Four master mixes containing buffer, M13mp18, and Invader™ oligonucleotides were assembled. Each 7 µl of mix 1 contained 5 fmol M13mp18, 10 pmoles Invader™ oligonucleotide 123 (SEQ ID NO:79) in 10 mM HEPES (pH 7.2). Each 7 µl of mix 2 contained 1 fmol M13mp18, 10 pmoles Invader™ oligonucleotide 123 in 10 mM HEPES (pH 7.2). Each 7 µl of mix 3 contained 5 fmol M13mp18, 10 pmoles Invader™ oligonucleotide 123 in 10 mM HEPES (pH 7.2), 250 mM KGlu. Each 7 µl of mix 4 contained 1 fmol M13mp18, 10 pmoles Invader™ oligonucleotide 123 in 10 mM HEPES (pH 7.2), 250 mM KGlu. For every 7 µl of each mix, 10 pmoles of either probe 34-180-1 (SEQ ID NO:77) or probe 34-180-2 (SEQ ID NO:78) was added. The DNA solutions described above were covered with 10 µl of ChillOut® evaporation barrier (MJ Research) and brought to 65° C. The reactions made from mixes 1–2 were started by the addition of 2 µl of the Pfu FEN-1 mix, and the reactions made from mixes 3–4 were started by the addition of 2 µl of the Cleavase® A/G nuclease mix. After 30 minutes at 65° C., the reactions were terminated by the addition of 8 µl of 95% formamide containing 10 mM EDTA. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA and a 20% native acrylamide gel (29:1 cross-linked) in a buffer containing 45 mM Tris-Borate (pH 8.3), 1.4 mM EDTA.

Figure 83A:
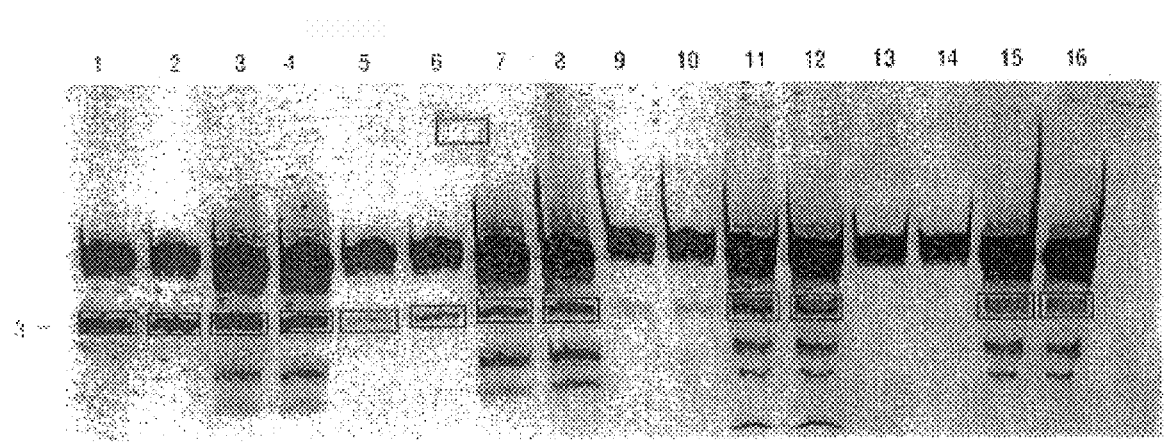
FIGS. 83A and 83B are images generated by a fluorescence imager showing the products produced using the Cleavase® A/G and Pfu FEN-1 nucleases and probes having or lacking a 5' positive charge; the gel shown in FIG. 83A was run in the standard direction and the gel shown in FIG. 84B was run in the reverse direction.
Figure 83B:
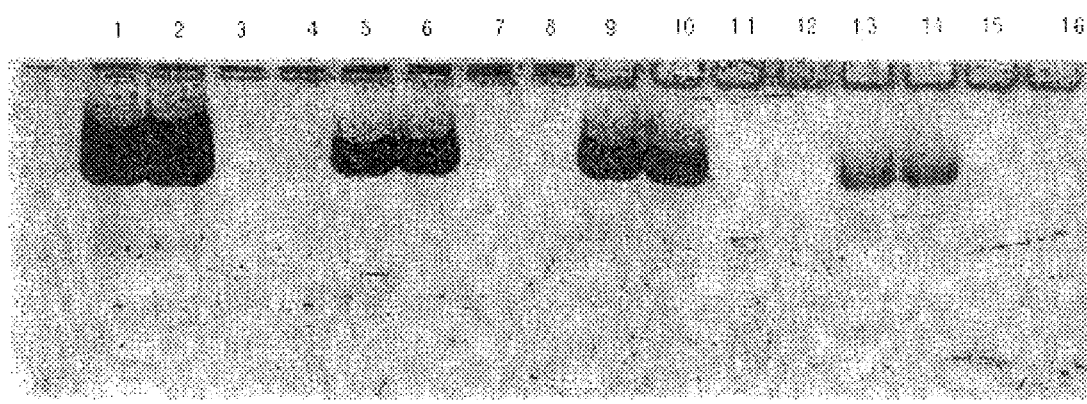

The products of the cleavage reactions were visualized following electrophoresis by the use of a Hitachi FMBIO fluorescence imager. The resulting images are shown in FIG. 83. FIG. 83A shows the denaturing gel which was run in the standard electrophoresis direction, and FIG. 83B shows the native gel which was run in the reverse direction. The reaction products produced by Pfu FEN-1 and Cleavase® A/G nucleases are shown in lanes 1–8 and 9–16, respectively. The products from the 5 fmol M13mp18 and 1 fmol M13mp18 reactions are shown in lanes 1–4, 9–12 (5 fmol) and 5–8, 13–16 (1 fmol). Probe 34-180-1 is in lanes 1–2, 5–6, 9–10, 13–14 and probe 34-180-2 is in lanes 3–4, 7–8, 11–12, 15–16.

The fluorescein-labeled 3' end fragments from all cleavage reactions are shown in FIG. 83A, indicated by a "3'" mark at the left. The 3 nt 5' TET-labeled products are not visible in this figure, while the 5° Cy3-labeled products are shown in FIG. 83B.

The 3' end bands in FIG. 83A can be used to compare the rates of cleavage by the different enzymes in the presence of the different 5' end labels. It can be seen from this band that regardless of the amount of target nucleic acid present, both the Pfu FEN-1 and the Cleavase® A/G nucleases show more product from the 5' TET-labeled probe. With the Pfu FEN-1 nuclease this preference is modest, with only an approximately 25 to 40% increase in signal. In the case of the Cleavase® A/G nuclease, however, there is a strong preference for the 5' TET label. Therefore, although when the charge reversal method is used to resolve the products, a substantial amount of product is observed from the Cleavase® A/G nuclease-catalyzed reactions, the Pfu FEN-1 nuclease is a preferred enzyme for cleavage of Cy3-labeled probes.

EXAMPLE 33

Figure 84:
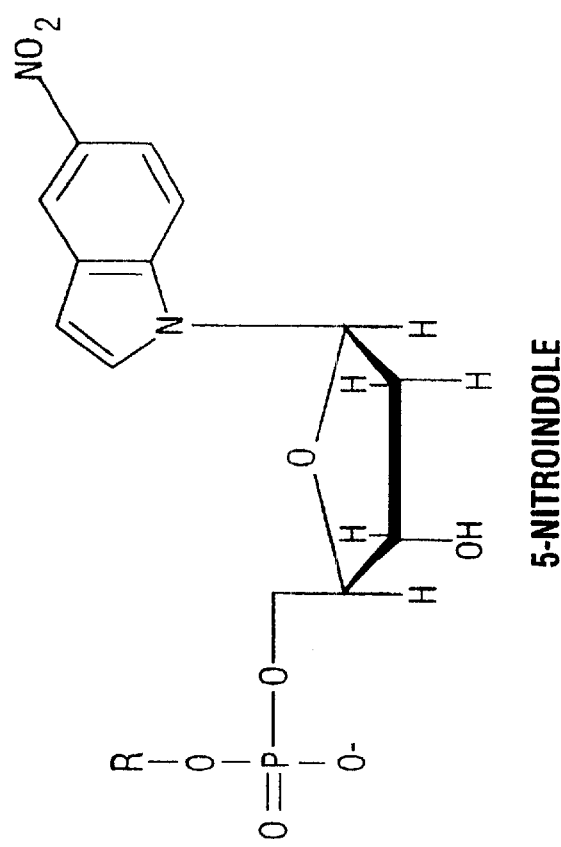
FIG. 84 shows the structure of 3-nitropyrrole and 5-nitroindole.
Figure 84:
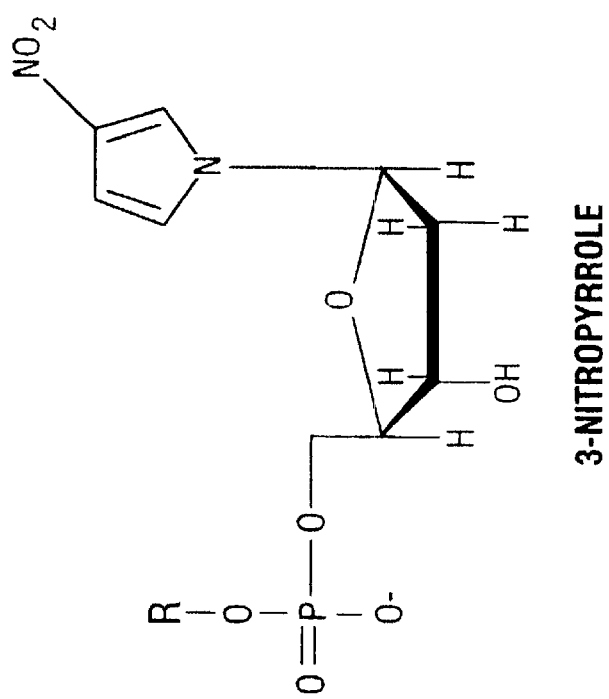

The Use of Universal Bases in the Detection of Mismatches by Invader™-Directed Cleavage The term "degenerate base" refers to a base on a nucleotide that does not hydrogen bond in a standard "Watson-Crick" fashion to a specific base complement, i.e., A to T and G to C. For example, the inosine base can be made to pair via one or two hydrogen bonds to all of the natural bases (the "wobble" effect) and thus is called degenerate. Alternatively, a degenerate base may not pair at all; this type of base has been referred to as a "universal" base because it can be placed opposite any nucleotide in a duplex and, while it cannot contribute stability by base-pairing, it does not actively destabilize by crowding the opposite base. Duplexes using these universal bases are stabilized by stacking interactions only. Two examples of universal bases, 3-nitropyrrole and 5-nitroindole, are shown in FIG. 84. In hybridization, placement of a 3-nitropyrrole three bases from a mismatch position enhances the differential recognition of one base mismatches. The enhanced discrimination seems to come from the destabilizing effect of the unnatural base (i.e., an altered $T_m$ in close proximity to the mismatch). To test this same principle as a way of sensitively detecting mismatches using the Invader™-directed cleavage assay, Invader™ oligonucleotides were designed using the universal bases shown in FIG. 84, in the presence or absence of a natural mismatch. In these experiments, the use of single nitropyrrole bases or pairs of nitroindole bases that flank the site of the mismatch were examined.

Figure 85:
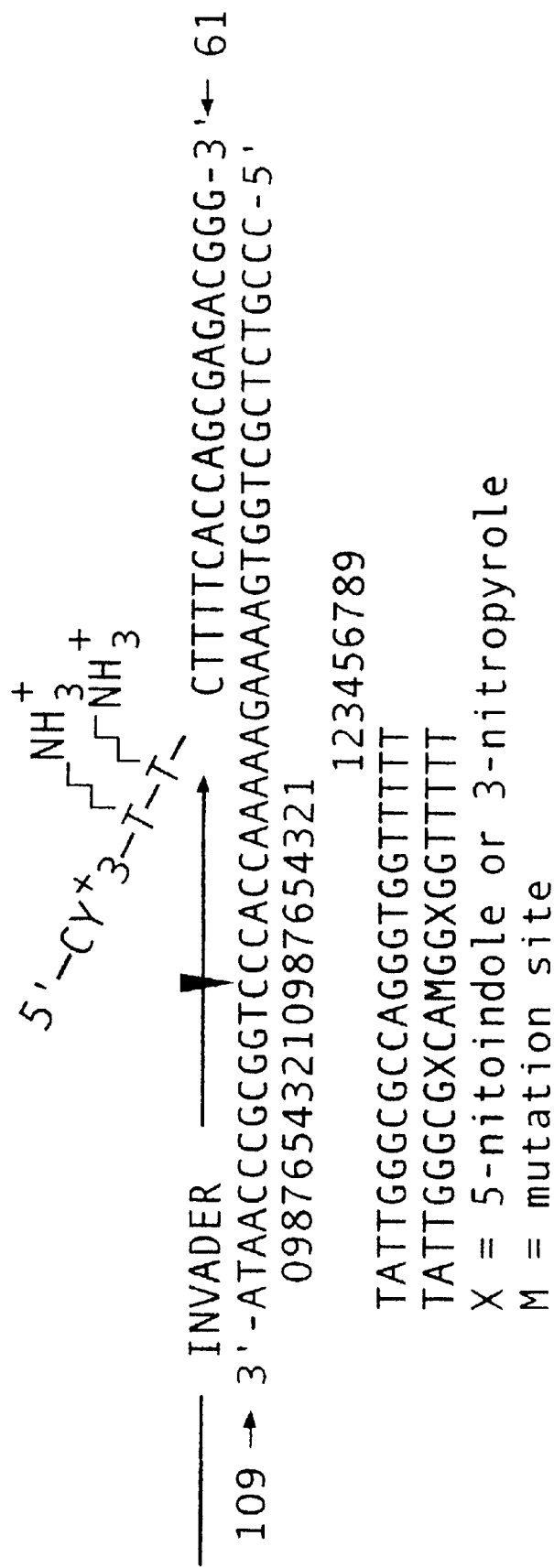
FIG. 85 shows the sequence of oligonucleotides 109, 61 and 67 (SEQ ID NOS:83, 61 and 62) annealed into a cleavage structure as well as the sequence of oligonucleotide 67 (SEQ ID NO:62) and a composite of SEQ ID NOS:84–88.

The target, probe and Invader™ oligonucleotides used in these assays are shown in FIG. 85. A 43 nucleotide oligonucleotide (oligonucleotide 109; SEQ ID NO:83) was used as the target. The probe oligonucleotide (oligonucleotide 61; SEQ ID NO:61) releases a net positively charged labeled product upon cleavage. In FIG. 85, the Invader™ oligonucleotide is shown schematically above the target oligonucleotide as an arrow; the large arrowhead indicates the location of the mismatch between the Invader™ oligonucleotides and the target. Under the target oligonucleotide, the completely complementary, all natural (i.e., no universal bases) Invader™ oligonucleotide (oligonucleotide 67; SEQ ID NO:62) and a composite of Invader™ oligonucleotides containing universal bases ("X") on either side of the mismatch ("M") are shown. The following Invader™ oligonucleotides were employed: oligonucleotide 114 (SEQ ID NO:86) which contains a single nt mismatch; oligonucleotide 115 (SEQ ID NO:87) which contains two 5-nitroindole bases and no mismatch; oligonucleotide 116 (SEQ ID NO:88) which contains two 5-nitroindole bases and a single nt mismatch; oligonucleotide 112 (SEQ ID NO:84) which contains one 3-nitropyrrole base and no mismatch; oligonucleotide 113 (SEQ ID NO:85) which contains one 5-nitropyrrole base and a single nt mismatch; and oligonucleotide 67 (SEQ ID NO:62) which is completely complementary to the target.

Figure 86A:
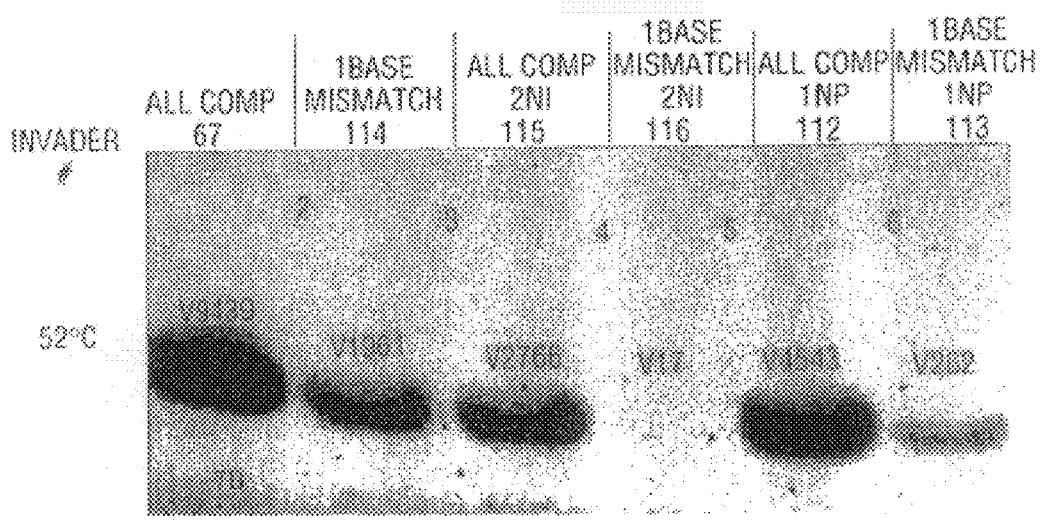
FIGS. 86A–C show images generated by a fluorescence imager showing the products produced in an Invader™-directed cleavage assay performed at various temperatures using a miniprobe which is either completely complementary to the target or contains a single mismatch with the target.
Figure 86B:
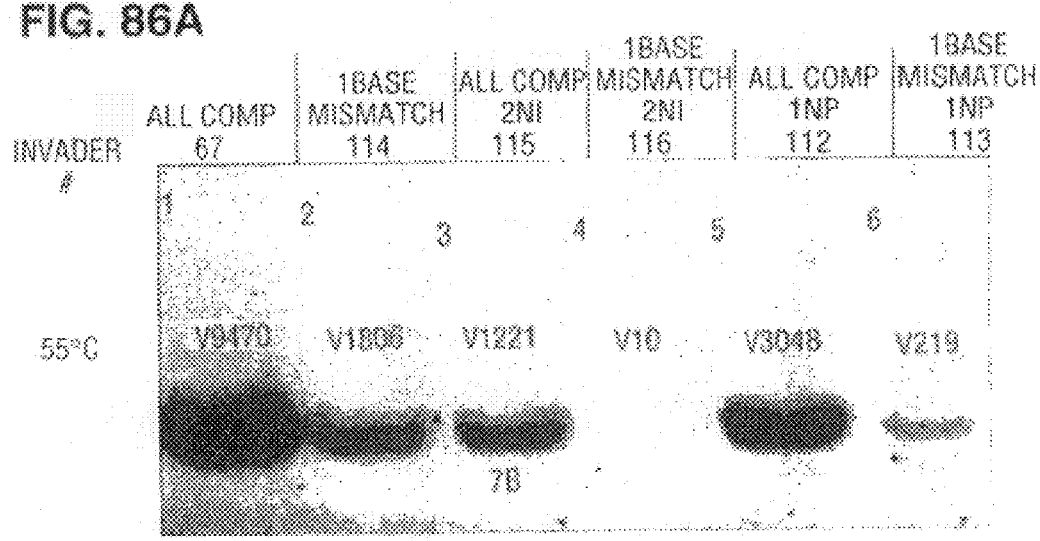
Figure 86C:
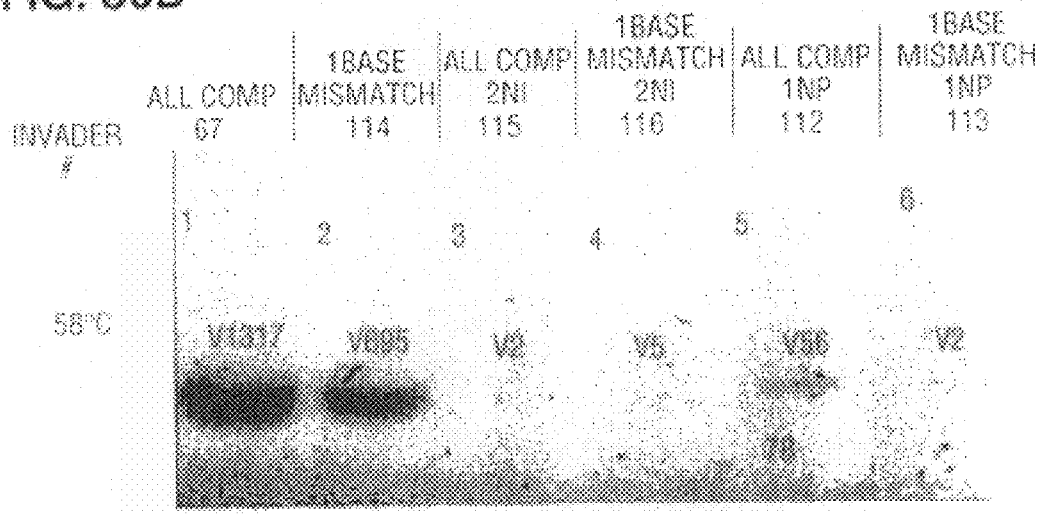

The Invader™-directed cleavage reactions were carried out in 10 µl of 10 mM MOPS (pH 7.2), 100 mM KCl, containing 1 µM of the appropriate invading oligonucleotide (oligonucleotides 67, 112–116), 10 nM synthetic target 109, 1 µM Cy-3 labeled probe 61 and 2 units of Cleavase® DV (prepared as described in Ex. 27). The reactions were overlaid with Chill-Out® liquid wax, brought to the appropriate reaction temperature, 52° C., 55° C., or 58° C. and initiated with the addition of 1 µl of 40 mM $MnCl_2$. Reactions were allowed to proceed for 1 hour and were stopped by the addition of 10 µl formamide. One fourth of the total volume of each reaction was loaded onto 20% non-denaturing polyacrylamide gels which were electrophoresed in the reverse direction. The products were visualized using an Hitachi FMBIO-100 fluorescent scanner using a 585 nm filter. The resulting images are shown in FIGS. 86A–C. In each panel, lanes 1–6 contain reactions products from reactions using Invader™ oligonucleotide 67, 114, 115, 116, 112 and 113, respectively. Reactions run at 52° C., 55° C. and 58° C. are shown in Panels A, B and C, respectively.

These data show that two flanking 5-nitroindoles display a significantly greater differentiation then does the one 3-nitropyrrole system, or the all natural base hybridization, and this increased sensitivity is not temperature dependent.

This demonstrates that the use of universal bases is a useful means of sensitively detecting single base mismatches between the target nucleic acid and the complex of detection oligonucleotides of the present invention.

EXAMPLE 35

Detection of Point Mutations in the Human Ras Oncogene Using a Miniprobe

Figure 87:
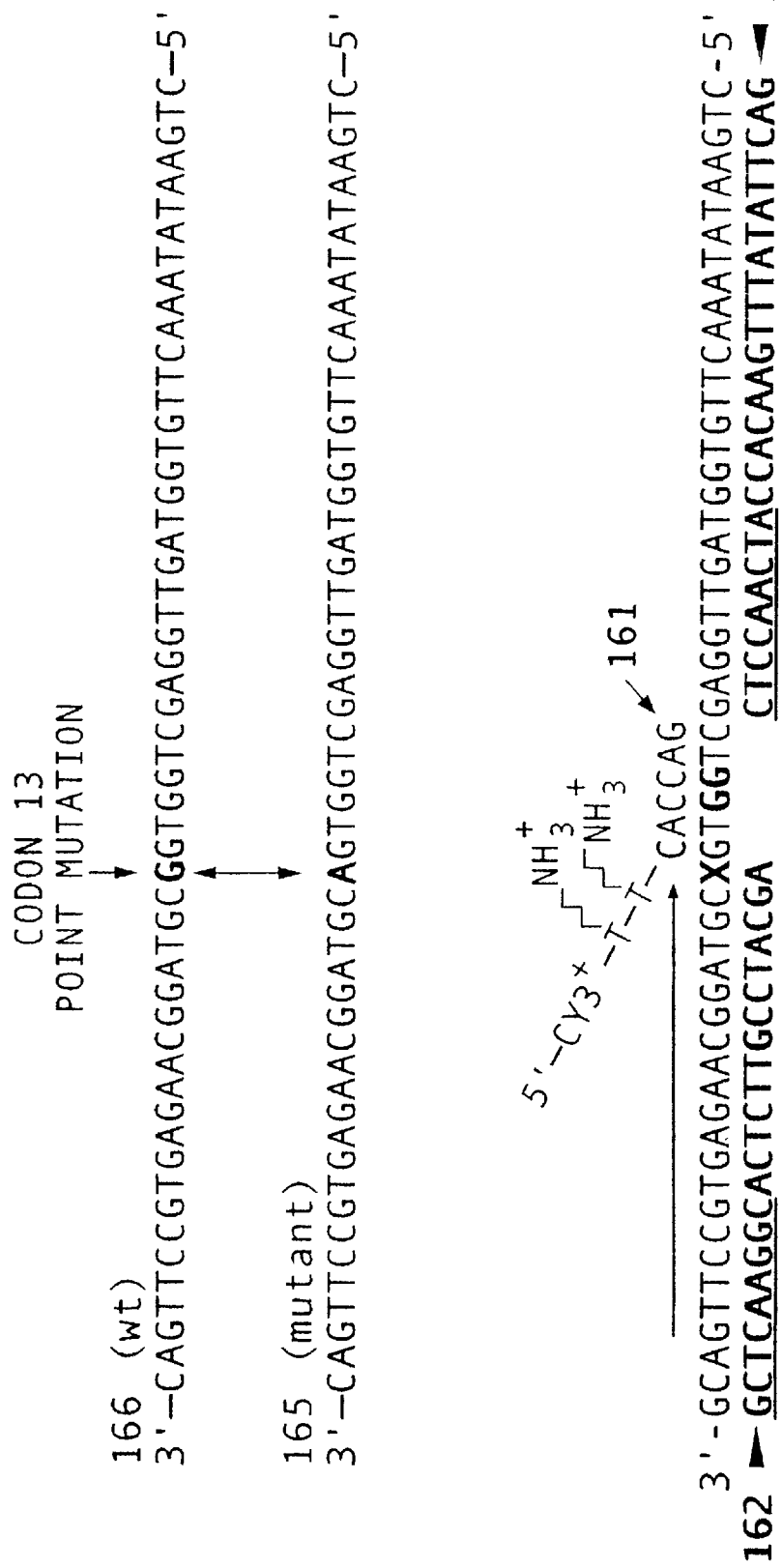
FIG. 87 shows the sequence of oligonucleotides 166 (SEQ ID NO:93), 165 (SEQ ID NO:92), 161 (SEQ ID NO:89), 162 (SEQ ID NO:90) and 164 (SEQ ID NO:91) as well as a cleavage structure.

It is demonstrated herein that very short probes can be used for sensitive detection of target nucleic acid sequences (Ex. 37). In this example, it is demonstrated that the short probes work very poorly when mismatched to the target, and thus can be used to distinguish a given nucleic acid sequence from a close relative with only a single base difference. To test this system synthetic human ras oncogene target sequences were created that varied from each other at one position. Oligonucleotide 166 (SEQ ID NO:93) provided the wild-type ras target sequence. Oligonucleotide 165 (SEQ ID NO:92) provided the mutant ras target sequence. The sequence of these oligonucleotides are shown in FIG. 87, and the site of the sequence variation in the site corresponding to codon 13 of the ras gene is indicated. The Invader™ oligonucleotide (oligonucleotide 162) has the sequence: 5'-$G_S C_S T_S C_S A_S A_S G_S G_S C_S$ACTCTTGCCTACGA-3' (SEQ ID NO:90), where the "S" indicates thiol linkages [i.e., these are 2'-deoxynucleotide-5'-O-(1-thiomonophates)]. The miniprobe (oligonucleotide 161) has the sequence: 5'-(N-Cy3) $T_{NH2}T_{NH2}$CACCAG-3' (SEQ ID NO:89) and is designed to detect the mutant ras target sequence (i.e., it is completely complementary to oligonucleotide 165). The stacker oligonucleotide (oligonucleotide 164) has the sequence: 5'-$C_S T_S C_S C_S A_S A_S C_S T_S A_S$CCAC AAGTTTATATTCAG-3' (SEQ ID NO:91). A schematic showing the assembly of these oligonucleotides into a cleavage structure is depicted in FIG. 87.

Each cleavage reaction contained 100 nM of both the invading (oligonucleotide 162) and stacking (oligonucleotide 164) oligonucleotides, 10 μM Cy3-labeled probe (oligonucleotide 161) and 100 pM of either oligonucleotide 165 or oligonucleotide 166 (target DNA) in 10 μl of 10 mM HEPES (pH 7.2), 250 mM KGlu, 4 mM $MnCl_2$. The DNA mixtures were overlaid with mineral oil, heated to 90° C. for 15 sec then brought to a reaction temperature of 47°, 50°, 53° or 56° C. Reactions were initiated by the addition of 1 μl of 100 ng/μl Pfu FEN-1. Reactions were allowed to proceed for 3 hours and stopped by the addition of 10 μl formamide. One fourth of the total volume of each reaction was loaded onto a 20% non-denaturing polyacrylamide gel which was electrophoresed in the reverse direction. The gel was scanned using an Hitachi FMBIO-100 fluorescent scanner fitted with a 585 nm filter, and the resulting image is shown in FIG. 88.

Figure 88:
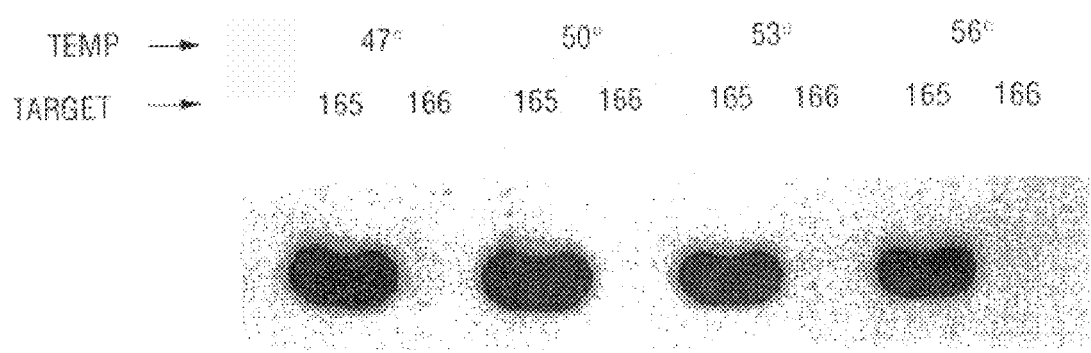
FIGS. 88 shows the image generated by a fluorescence imager showing the products produced in an Invader™-directed cleavage assay performed using ras gene sequences as the target.

In FIG. 88, for each reaction temperature tested, the products from reactions containing either the mutant ras target sequence (oligonucleotide 165) or the wild-type (oligonucleotide 166) are shown.

These data demonstrate that the miniprobe can be used to sensitively discriminate between sequences that differ by a single nucleotide. The miniprobe was cleaved to produce a strong signal in the presence of the mutant target sequence, but little or no miniprobe was cleaved in the presence of the wild-type target sequence. Furthermore, the discrimination between closely related targets is effective over a temperature range of at least 10° C., which is a much broader range of temperature than can usually be tolerated when the selection is based on hybridization alone (e.g., hybridization with ASOs). This suggests that the enzyme may be a factor in the discrimination, with the perfectly matched miniprobe being the preferred substrate when compared to the mismatched miniprobe. Thus, this system provides sensitive and specific detection of target nucleic acid sequences.

EXAMPLE 36

Effects of 3' End Identity on Site of Cleavage of a Model Oligonucleotide Structure As described in the examples above, structure-specific nucleases cleave near the junction between single-stranded and base-paired regions in a bifurcated duplex, usually about one base pair into the base-paired region. It was shown in Ex. 11 that thermostable 5' nucleases, including those of the present invention (e.g., Cleavase® BN nuclease, Cleavase® A/G nuclease), have the ability to cleave a greater distance into the base paired region when provided with an upstream oligonucleotide bearing a 3' region that is homologous to a 5' region of the subject duplex, as shown in FIG. 30. It has also been determined that the 3' terminal nucleotide of the invader oligonucleotide may be unpaired to the target nucleic acid, and still shift cleavage the same distance into the down stream duplex as when paired. It is shown in this example that it is the base component of the nucleotide, not the sugar or phosphate, that that is necessary to shift cleavage.

FIGS. 89A and B shows a synthetic oligonucleotide which was designed to fold upon itself which consists of the following sequence: 5'-GTTCTCTGCTCTCTGGTCGCT GTCTCGCTTGTGAAACAAGCGAGACAGCGTGGTC TCTCG-3' (SEQ ID NO:40). This oligonucleotide is referred to as the "S-60 Hairpin." The 15 basepair hairpin formed by this oligonucleotide is further stabilized by a "tri-loop" sequence in the loop end (i.e., three nucleotides form the loop portion of the hairpin) (Hiraro et al., Nucleic Acids Res. 22(4): 576 [1949]). FIG. 89B shows the sequence of the P-15 oligonucleotide (SEQ ID NO:41) and the location of the region of complementarity shared by the P-15 and S-60 hairpin oligonucleotides. In addition to the P-15 oligonucleotide shown, cleavage was also tested in the presence of the P-14 oligonucleotide (SEQ ID NO:122) (P-14 is one base shorter on the 3' end as compared to P-15), the P-14 with an abasic sugar (P-14d; SEQ ID NO:80) and the P14 with an abasic sugar with a 3' phosphate (P-14dp; SEQ ID NO:81). A P-15 oligonucleotide with a 3' phosphate, P-15p (SEQ ID NO:82) was also examined. The black arrows shown in FIG. 89 indicate the sites of cleavage of the S-60 hairpin in the absence (top structure; A) or presence (bottom structure; B) of the P-15 oligonucleotide.

The S-60 hairpin molecule was labeled on its 5' end with fluorescein for subsequent detection. The S-60 hairpin was incubated in the presence of a thermostable 5' nuclease in the presence or the absence of the P-15 oligonucleotide. The presence of the full duplex which can be formed by the S-60 hairpin is demonstrated by cleavage with the Cleavase® BN 5' nuclease, in a primer-independent fashion (i.e., in the absence of the P-15 oligonucleotide). The release of 18 and 19-nucleotide fragments from the 5' end of the S-60 hairpin molecule showed that the cleavage occurred near the junction between the single and double stranded regions when nothing is hybridized to the 3' arm of the S-60 hairpin (FIG. 31, lane 2).

Figure 89C:
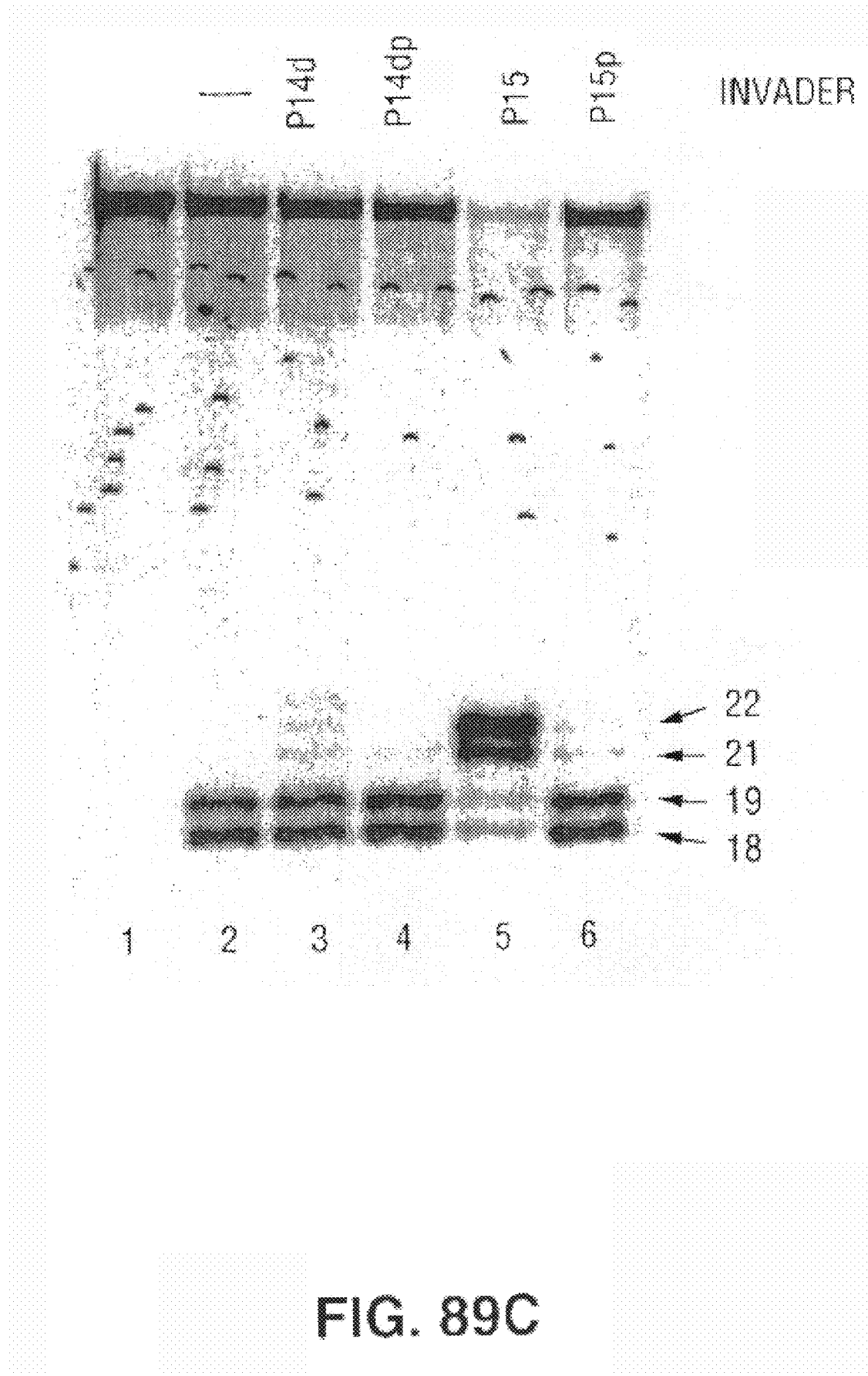

The reactions shown in FIG. 89C were conducted in 10 μl 1× CFLP buffer with 1 mM $MnCl_2$ and 50 mM K-Glutamate, in the presence of 0.02 μM S-60, 0.5 μM Invader™ oligonucleotide and 0.01 ng per μl Cleavase® BN nuclease. Reactions were incubated at 40° C. for 5 minutes and stopped by the addition of 8 μl of stop buffer (95% formamide, 20 mM EDTA, 0.02% methyl violet). Samples were heated to 75° C. for 2 min immediately before electrophoresis through a 15% acrylamide gel (19:1 cross-linked), with 7 M urea, in a buffer of 45 mM Tris-Borate, pH 8.3, 1.4 mM EDTA. Gels were then analyzed with a FMBIO-100 Image Analyzer (Hitachi) equipped with 505 nm filter. The resulting image is shown in FIG. 89C.

In FIG. 89C lane 1 contains products from the no enzyme control; lane 2 contains products from a reaction run in the absence of an Invader™ oligonucleotide; lanes 3–6 contain products from reactions run the presence of the P-14d, P-14dp, P-15 and P-15p Invader™ oligonucleotides, respectively.

From the data shown in FIG. 89C, it can be seen that the use of the P-15 Invader™ oligonucleotide produces a shift in the cleavage site, while the P14 Invader™ oligonucleotide with either a ribose (P14d) or a phosphorylated ribose (P14dp) did not This indicates that the 15th residue of the Invader™ oligonucleotide must have the base group attached to promote the shift in cleavage. Interestingly, the addition of phosphate to the 3' end of the P15 oligonucleotide apparently reversed the shifting of cleavage site. The cleavage in this lane may in fact be cleavage in the absence of an Invader™ oligonucleotide as is seen in lane 2. In experiments with 5' dye-labeled Invader™ oligonucleotides with 3' phosphate groups these oligonucleotides have been severely retarded in gel migration, suggesting that either the enzyme or another constituent of the reaction (e.g., BSA) is able to bind the 3' phosphate irrespective of the rest of the cleavage structure. If the Invader™ oligonucleotides are indeed being sequestered away from the cleavage structure, the resulting cleavage of the S-60 hairpin would occur in a "primer-independent" fashion, and would thus not be shifted.

In addition to the study cited above, the effects of other substituents on the 3' ends of the Invader™ oligonucleotides were investigated in the presence of several different enzymes, and in the presence of either Mn++ or Mg++. The effects of these 3' end modifications on the generation of cleaved product are summarized in the following table. All of modifications were made during standard oligonucleotide synthesis by the use of controlled pore glass (CPG) synthesis columns with the listed chemical moiety provided on the support as the synthesis starting residue. All of these CPG materials were obtained from Glen Research Corp. (Sterling, Va.).

Figure 90:
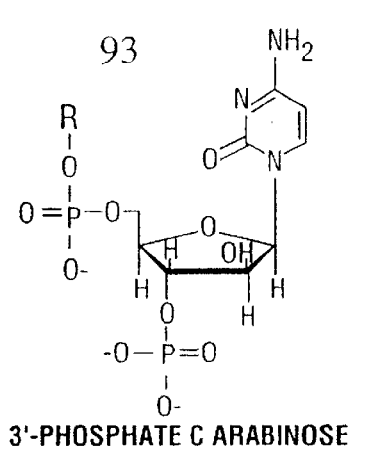
FIG. 90 shows the structure of various 3' end substituents.
Figure 90:
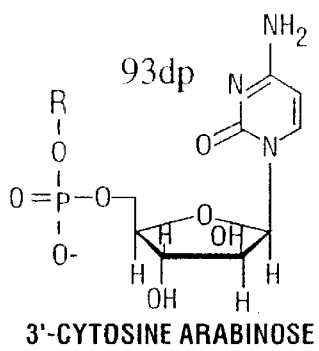
Figure 90:
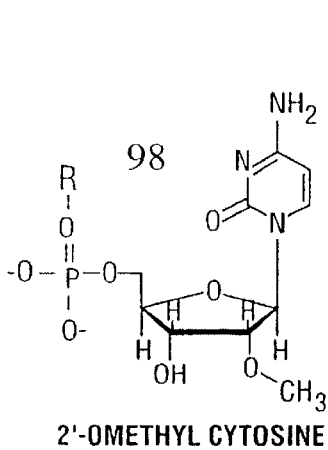
Figure 90:
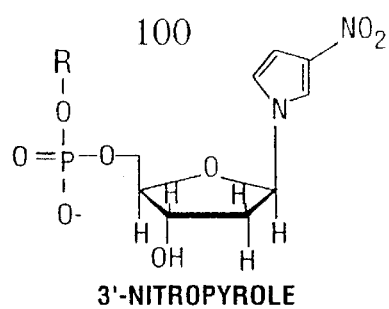
Figure 90:
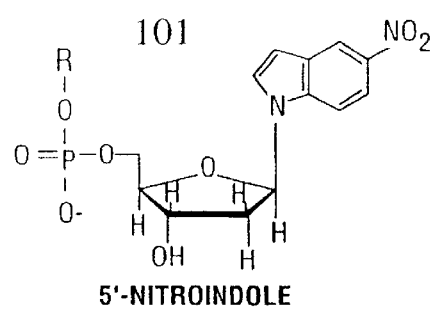
Figure 90:
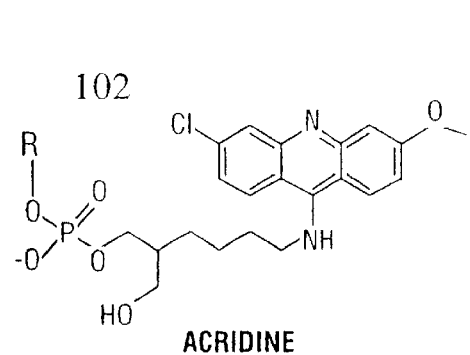
Figure 90:
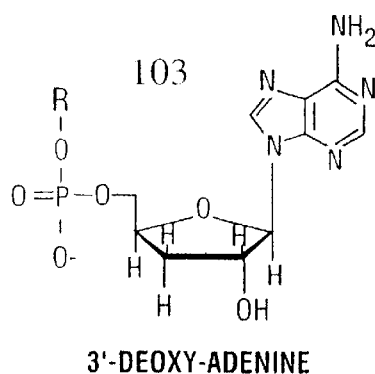

FIG. 90 provides the structures for the 3' end substituents used in these experiments.

TABLE 2

Modification Studies at 3' End of Invader Oligonucleotide

| 3'-End Modification | Extension by Terminal Transferase | Effect on Invader Rxn. (as invader) Enzyme: Condition | Effect |
|---|---|---|---|
| 3' phosphate Glen part #20-2900-42 | no | A:5 | inhibits reaction, no detectable activity |
| 3' acridine Glen part #20-2973-42 | yes, poorly | A:5 | decrease in activity, <10% |
| | | B:5 | decrease in activity, <10% |
| | | B:4 | decrease in activity, <10% |
| | | C:1 | decrease in activity, <10% |
| | | C:2 | decrease in activity, ~20% |
| | | C:4 | decrease in activity, ~50% |
| | | C:3 | decrease in activity, <5% |
| 3' carboxylate Glen part #20-4090-42 | no | A:1 | decrease in activity, ~50% activity shift in cleavage site |
| | | C:3 | reduces rate, <10% activity |
| 3' nitropyrrole Glen part #20-2143-42 | yes | A:5 | increase in activity, ~2X |
| 3' nitroindole Glen part #20-2144-42 | yes | A:5 | decrease in activity, ~33% activity |
| 3' arabinose Glen part #10-4010-90 | yes | A:5 | decrease in activity, ~50% activity |
| 3'dideoxyUTP-fluorescein | no | A:5 | decrease in activity, ~40% activity |
| 3'-3' linkage Glen part #20-0002-01 | no | A:1 | equivalent cleavage activity shift in cleavage site |
| | | C:3 | decrease in activity, ~25% activity |
| 3' glyceryl Glen part #20-2902-42 | yes, very poorly | C:3 | decrease in activity, ~30% activity loss of specificity of cleavage (2 sites) |
| 3' amino modifier C7 Glen part #20-2957-42 | yes | C:3 | decrease in activity, ~30% activity loss of specificity, multiple sites |
| 3'deoxy, 2'OH Glen part #20-2104-42 | yes, very poorly | A:5 | decrease in activity, <20% activity |
| | | B:5 | decrease in activity, <20% activity |
| | | B:3 | decrease in activity, <20% activity |
| | | C:1 | equivalent activity |
| | | C:2 | equivalent activity |
| | | C:4 | ? increase in activity |
| | | C:3 | decrease in activity, ~40% activity |

Enzymes
A Cleavase ® DV nuclease
B Cleavase ® BN nuclease
C Pfu FEN-1
Condition
1 4 mM MnCl$_2$, 150 mM LiCl
2 4 mM MnCl$_2$, 50 mM KCl
3 7.5 mM MgCl$_2$, no monovalent
4 4 mM MgCl$_2$, 50 mM KCl
5 10 mM MgOAc, 50 mM KCl It can be seen from these data that many different modifications can be used on the 3' end of the Invader™ oligonucleotide without detriment. In various embodiments of the present invention, such 3' end modifications may be used to block, facilitate, or otherwise alter the hybridization characteristics of the Invader™ oligonucleotide, (e.g., to increase discrimination against mismatches, or to increase tolerance of mismatches, or to tighten the association between the Invader™ oligonucleotide and the target nucleic acid). Some substituents may be used to alter the behavior of the enzyme in recognizing and cleaving within the assembled complex.

Altered 3' ends may also be used to prevent extension of the Invader™ oligonucleotide by either template-dependent or template-independent nucleic acid polymerases. The use of otherwise unmodified dideoxynucleotides (i.e., without attached dyes or other moieties) are a particularly preferred means of blocking extension of Invader™ oligonucleotides, because they do not decrease cleavage activity, and they are absolutely unextendable.

EXAMPLE 37

Effect of Probe Concentration, Temperature and a Stacker Oligonucleotide on the Cleavage of Miniprobes by Invader™-Directed Cleavage The stacker oligonucleotides employed to form cleavage structures may serve two purposes in the detection of a nucleic acid target using a miniprobe. The stacker oligonucleotide may help stabilize the interaction of the miniprobe with the target nucleic acid, leading to greater accumulation of cleaved probe. In addition, the presence of this oligonucleotide in the complex elongates the duplex downstream of the cleavage site, which may enhance the cleavage activity of some of the enzymes of the present invention. An example of different preferences for the length of this duplex by different structure-specific nucleases is seen in the comparison of the Cleavase® BN nuclease and the Mja FEN-1 nuclease cleavage of 8 bp and 12 bp duplex regions in FIG. 76. Increased affinity of the enzyme for the cleavage structure also results in increased accumulation of cleaved probe during reactions done for a set amount of time.

The amount of miniprobe binding to the target is also affected by the concentration of the miniprobe in the reaction mixture. Even when a miniprobe is only marginally likely to hybridize (e.g., when the reaction is performed at temperatures in excess of the expected melting temperature of the probe/target duplex), the amount of probe on the target at any given time can be increased by using high concentrations of the miniprobe.

The need for a stacker oligonucleotide to enhance cleavage of the miniprobe was examined at both low and high probe concentrations. The reactions were carried out in 10 μl of 10 mM HEPES (pH 7.2), 250 mM KGlu, 4 mM MnCl$_2$, containing 100 nM of both the invading (oligonucleotide 135; SEQ ID NO:98) and stacking oligonucleotides (oligonucleotide 147; SEQ ID NO:134) and 100 pM ssM13 DNA. The reactions were overlaid with mineral oil, heated to 90° C. for 15 sec then brought to the reaction temperature. Reactions were performed at 35°, 40°, 45°, 50°, 55°, 60°, and 65° C. The cleavage reactions were initiated by the addition of 1 μl of 100 ng/μl Pfu FEN-1 and 1 μl of varying concentrations of Cy-3 labeled 142 miniprobe oligonucleotide (SEQ ID NO:97). Reactions were allowed to proceed for 1 hour and stopped by the addition of 10 μl formaldehyde. One fourth of the total volume of each reaction was loaded onto 20% non-denaturing polyacrylamide gels which were electrophoresed in the reverse direction. Gels were visualized using an Hitachi FMBIO-100 fluorescent scanner using a 585 nm filter. The fluorescence in each product band was measured and the graph shown in FIG. 91 was created using a Microsoft Excel spreadsheet.

Figure 91:
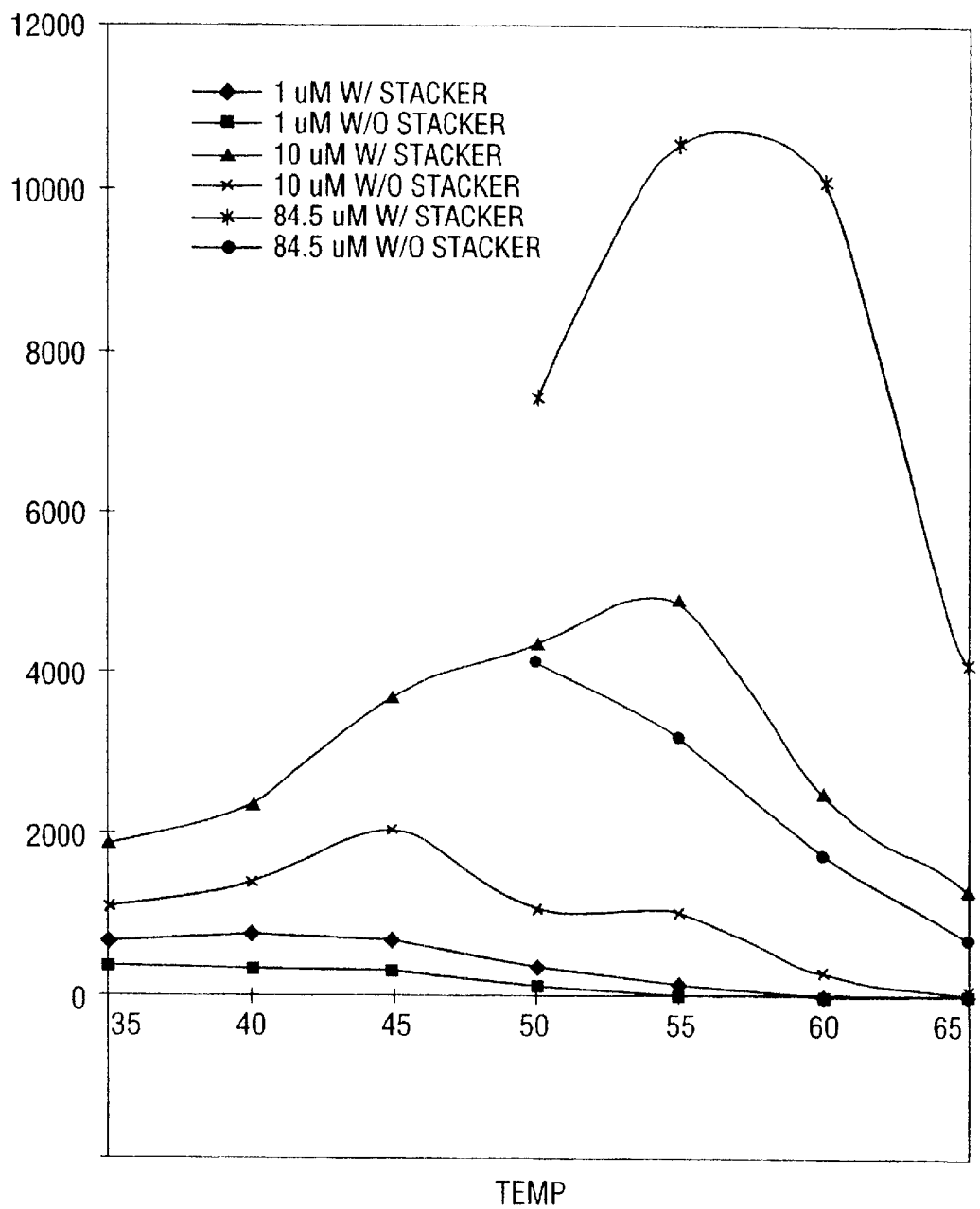
FIG. 91 is a composite graph showing the effect of probe concentration, temperature and a stacker oligonucleotide on the cleavage of miniprobes.

The data summarized in FIG. 91 showed that the concentration of the miniprobe had a significant effect on the final measure of product, showing dramatic increases as the concentration was raised. Increases in the concentration of the miniprobe also shifted the optimum reaction temperature upward. It is known in the art that the concentration of the complementary strands in a hybridization will affect the apparent T$_m$ of the duplex formed between them. More significantly to the methods and compositions of the present invention is the fact that the presence of the stacker oligonucleotide has a profound influence on the cleavage rate of the miniprobe at all probe concentrations. At each of the probe concentrations the presence of the stacker as much as doubled the signal from the cleavage product. This demonstrated the utility of using the stacker oligonucleotide in combination with the miniprobes described herein.

EXAMPLE 38

The Presence of a Mismatch in the Invader™ Oligonucleotide Decreases the Cleavage Activity of the Cleavase® A/G Nuclease In any nucleic acid detection assay it is of additional benefit if the assay can be made to sensitively detect minor differences between related nucleic acids. In the following experiment, model cleavage substrates were used that were identical except for the presence or absence of a mismatch near the 3' end of the Invader™ oligonucleotide when hybridized to the model target nucleic acid. The effect of a mismatch in this region on the accumulation of cleaved probe was then assessed.

Figure 92:
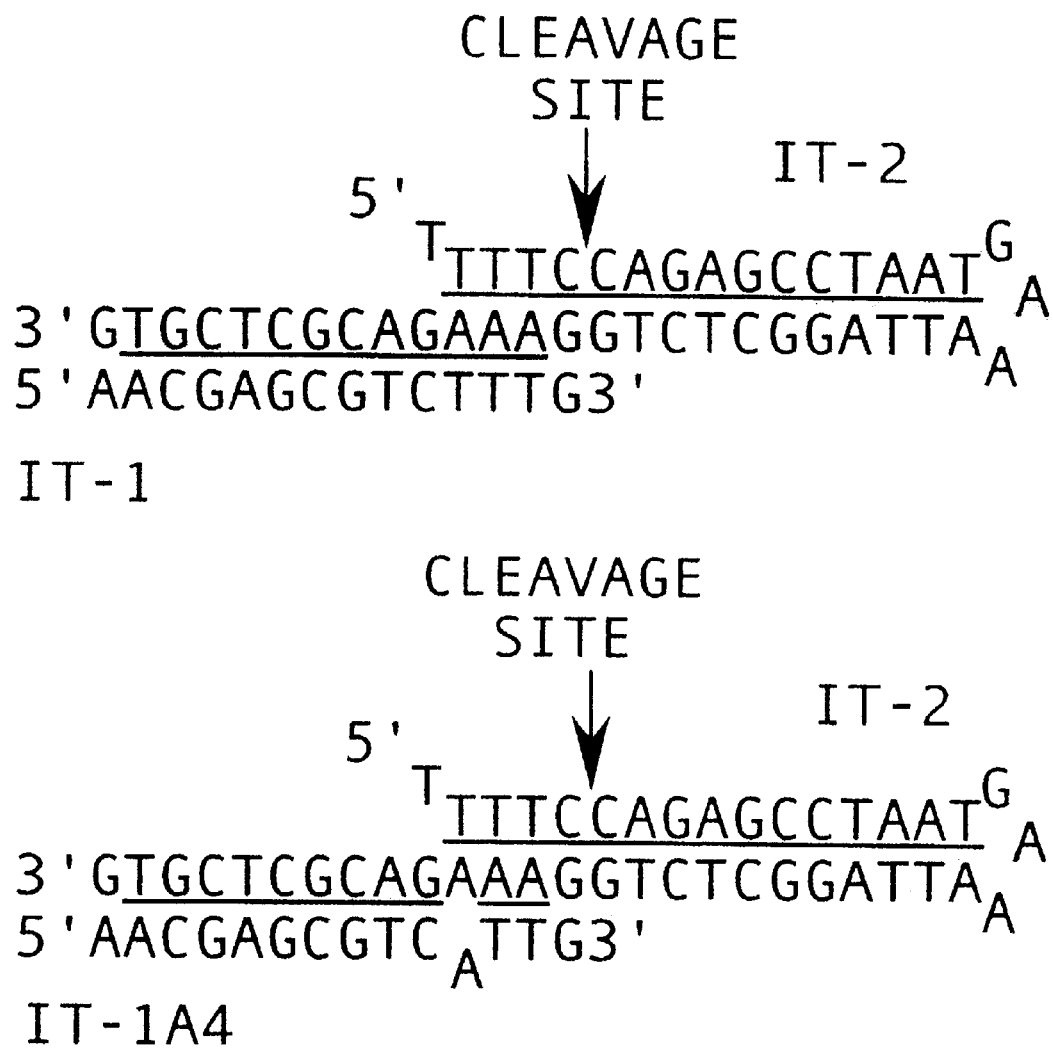
FIG. 92 shows the sequence of the IT-2 oligonucleotide (SEQ ID NO:123; shown in a folded configuration) as well as the sequence of the IT-1 (SEQ ID NO:124) and IT-IA4 (SEQ ID NO:125) oligonucleotides.

To demonstrate the effect of the presence of a mismatch in the Invader™ oligonucleotide on the ability of the Cleavase®b A/G nuclease to cleave the probe oligonucleotide in an Invader™ assay the following experiment was conducted. Cleavage of the test oligonucleotide IT-2 (SEQ ID NO:123) in the presence of Invader™ oligonucleotides IT-1 (SEQ ID NO:124) and IT-1A4 (SEQ ID NO:125). Oligonucleotide IT-1 is fully complementary to the 3' arm of IT-2, whereas oligonucleotide IT-1A4 has a T->A substitution at position 4 from the 3' end that results in an A/A mismatch in the Invader™-target duplex. Both the matched and mismatched Invader™ oligonucleotides would be expected to hybridize at the temperature at which the following reaction was performed. FIG. 92 provides a schematic showing IT-1 annealed to the folded IT-2 structure and showing IT-1A4 annealed to the folded IT-2 structure.

The reactions were conducted as follows. Test oligonucleotide IT-2 (0.1 μM), labeled at the 5' end with fluorescein (Integrated DNA Technologies), was incubated with 0.26 ng/μl Cleavase® AG in 10 μl of CFLP® buffer with 4 mM MgCl$_2$, in the presence of 1 μM IT-1 or IT-1A4 at 40° C. for 10 min; a no enzyme control was also run. Samples were overlaid with 15 μl Chill-Out® liquid wax to prevent evaporation. Reactions were stopped by addition of 4 μl stop buffer (95% formamide, 20 mM EDTA, 0.02% methyl violet). The cleavage products were separated on a 20% denaturing polyacrylamide gel and analyzed with the FMBIO-100 Image Analyzer (Hitachi) equipped with 505 nm filter. The resulting image is shown in FIG. 93.

Figure 93:
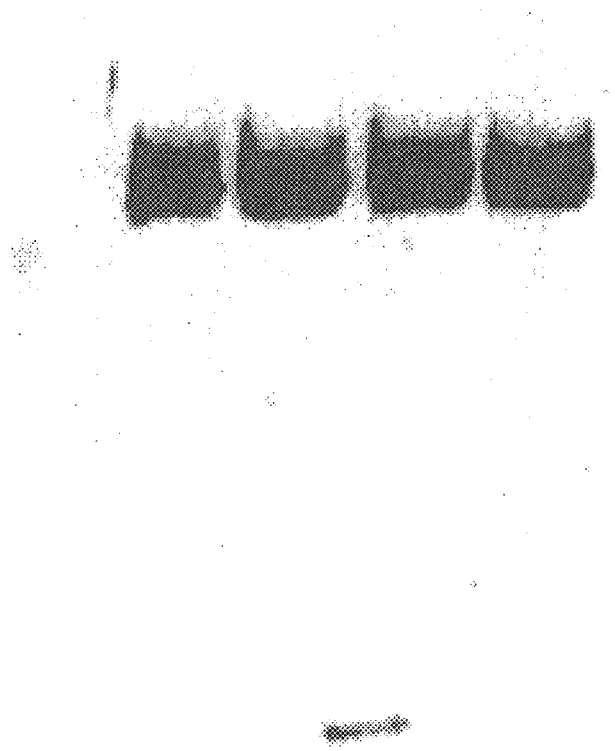
FIG. 93 shows the image generated by a fluorescence imager showing the products produced cleavage of the oligonucleotides shown in FIG. 92 by Cleavase® A/G nuclease.

In FIG. 93, lane 1 contains reaction products from the no enzyme control and shows the migration of the uncut IT-2 oligonucleotide; lanes 2–4 contain products from reactions containing no Invader™ oligonucleotide, the IT-1 Invader™ oligonucleotide and the IT-1A4 Invader™ oligonucleotide, respectively.

These data show that cleavage is markedly reduced by the presence of the mismatch, even under conditions in which the mismatch would not be expected to disrupt hybridization. This demonstrates that the invader oligonucleotide binding region is one of the regions within the complex in which can be used for mismatch detection, as revealed by a drop in the cleavage rate.

EXAMPLE 39

Comparison of the Activity of the Pfu FEN-1 and Mja FEN-1 Nucleases in the Invader™ Reaction To compare the activity of the Pfu FEN-1 and the Mja FEN-1 nucleases in Invader™ reaction the following experiment was performed. A test oligonucleotide IT3 (SEQ ID NO:126) that forms an Invader-Target hairpin structure and probe oligonucleotide PR1 (SEQ ID NO:127) labeled at the 5' end with fluorescein (Integrated DNA Technologies) were employed in Invader™ assays using either the Pfu FEN-1 or the Mja FEN-1 nucleases.

Figure 94:
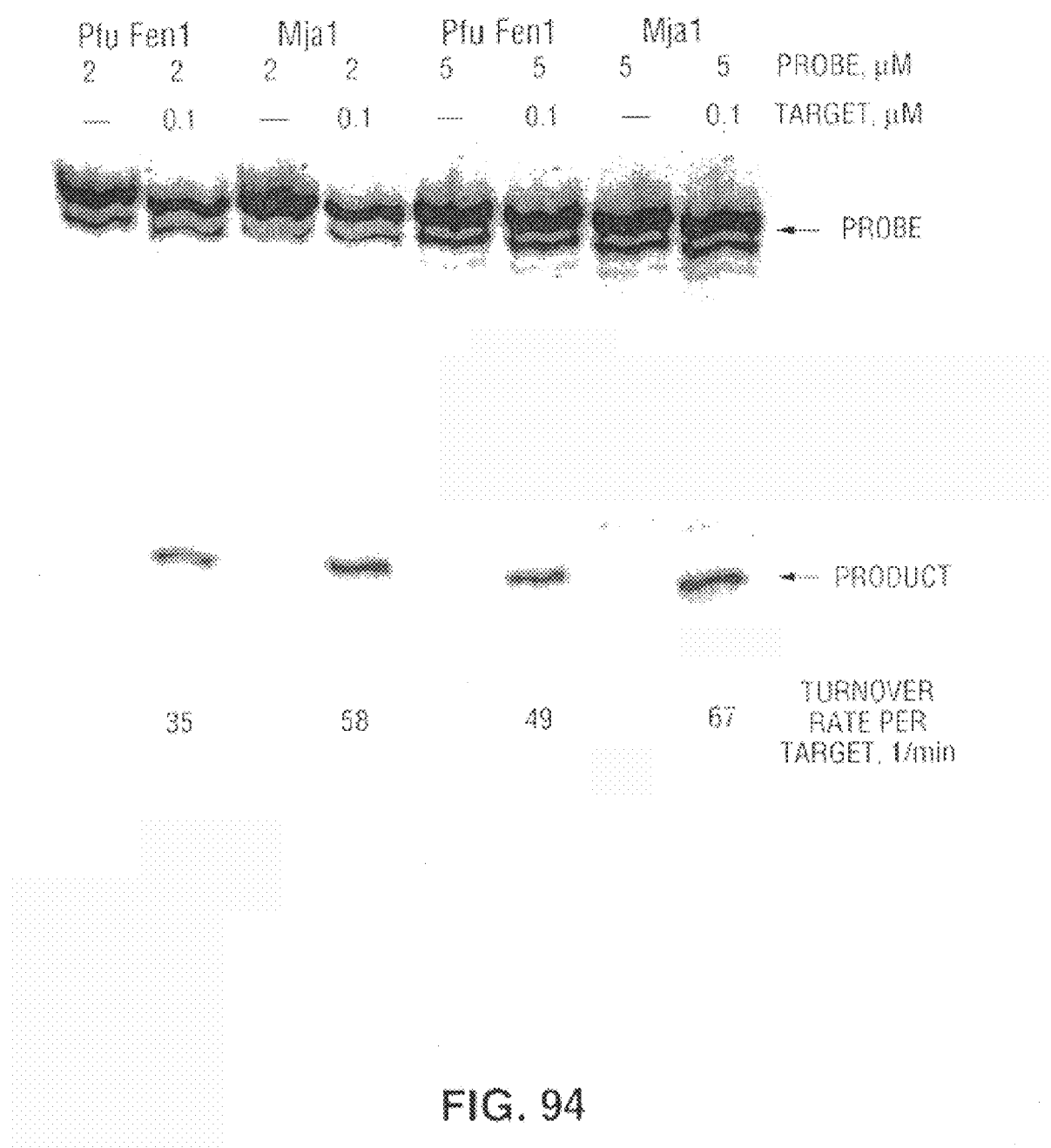
FIG. 94 shows the image generated by a fluorescence imager which provides a comparison of the rates of cleavage by the Pfu FEN-1 and Mja FEN-1 nucleases.

The assays were conducted as follows. Pfu FEN-1 (13 ng/µl) and Mja FEN-1 (10 ng/µl) (prepared as described in Ex. 28) were incubated with the IT3 (0.1 nM) and PR1 (2 and 5 µM) oligonucleotides in 10 µL CFLP® buffer, 4 mM $MgCl_2$, 20 mg/ml tRNA at 55° C. for 41 min. Samples were overlaid with 15 µl Chill-Out® evaporation barrier to prevent evaporation. Reactions were stopped by addition of 70 µl stop buffer (95% formamide, 20 mM EDTA, 0.02% methyl violet). Reaction products (1 µl) were separated on a 20% denaturing polyacrylamide gel, visualized using a fluorescence imager and the bands corresponding to the probe and the product were quantitated. The resulting image is shown in FIG. 94. In FIG. 94, the turnover rate per target per minute is shown below the image for each nuclease at each concentration of probe and target tested.

It was demonstrated in Ex. 33 that the use of the Pfu FEN-1 structure-specific nuclease in the Invader™-directed cleavage reaction resulted in a faster rate of product accumulation than did the use of the Cleavase® A/CG. The data presented here demonstrates that the use of Mja FEN-1 nuclease with the fluorescein labeled probe further increases the amount of product generated by an average of about 50%, demonstrating that, in addition to the Pfu FEN-1 nuclease, the Mja FEN-1 nuclease is a preferred structure-specific nuclease for the detection of nucleic acid targets by the method of the present invention.

EXAMPLE 40

Detection of RNA Target Nucleic Acids Using Miniprobe and Stacker Oligonucleotides In addition to the detection of the M13 DNA target material described above, a miniprobe/stacker system was designed to detect the HCV-derived RNA sequences described in Ex. 20. A probe of intermediate length, either a long mid-range or a short standard probe, was also tested. The miniprobe used (oligonucleotide 42-168-1) has the sequence: 5'-TET-CCGGTCGTCCTGG-3' (SEQ ID NO:95), the stacker oligonucleotide used (oligonucleotide 32-085) with this miniprobe has the sequence: 5'-CAATTCCGGTG TACTACCGGTTCC-3' (SEQ ID NO:96). The slightly longer probe, used without a stacker (oligonucleotide 42-088), has the sequence: 5'-TET-CCGGTCGTCCTGGCAA-3' (SEQ ID NO:94). The Invader™ oligonucleotide used with both probes has the sequence: 5'-GTTTATCCAAGAAAGGACCCGGTC-3' (SEQ ID NO:58). The reactions included 50 fmole of target RNA, 10 pmole of the Invader™ oligonucleotide and 5 pmole of the miniprobe oligonucleotide in 10 µl of buffer containing 10 mM MES, pH 6.5 with 150 mM LiCl, 4 mM $MnCl_2$, 0.05% each Tween-20 and NP-40, and 39 units of RNAsin (Promega Corp., Madison, Wis.). When used, 10 pmoles of the stacker oligonucleotide was added. These components were combined, overlaid with ChillOut® evaporation barrier (MJ Research), and warmed to 50° C; the reactions were started by the addition of 5 polymerase units of DNAPTth, to a final reaction volume of 10 µl. After 30 minutes at 50° C., reactions were stopped by the addition of 8 µl of 95% formamide, 10 mM EDTA and 0.02% methyl violet. The samples were heated to 90° C. for 1 minute and 2.5 µl of each of these reactions were resolved by electrophoresis through a 20% denaturing polyacrylamide (19:1 cross link) with 7M urea in a buffer of 45 mM Tris-Borate, pH 8.3, 1.4 mM EDTA, and the labeled reaction products were visualized using the FMBIO-100 Image Analyzer (Hitachi). The resulting image is shown in FIG. 95.

Figure 95:
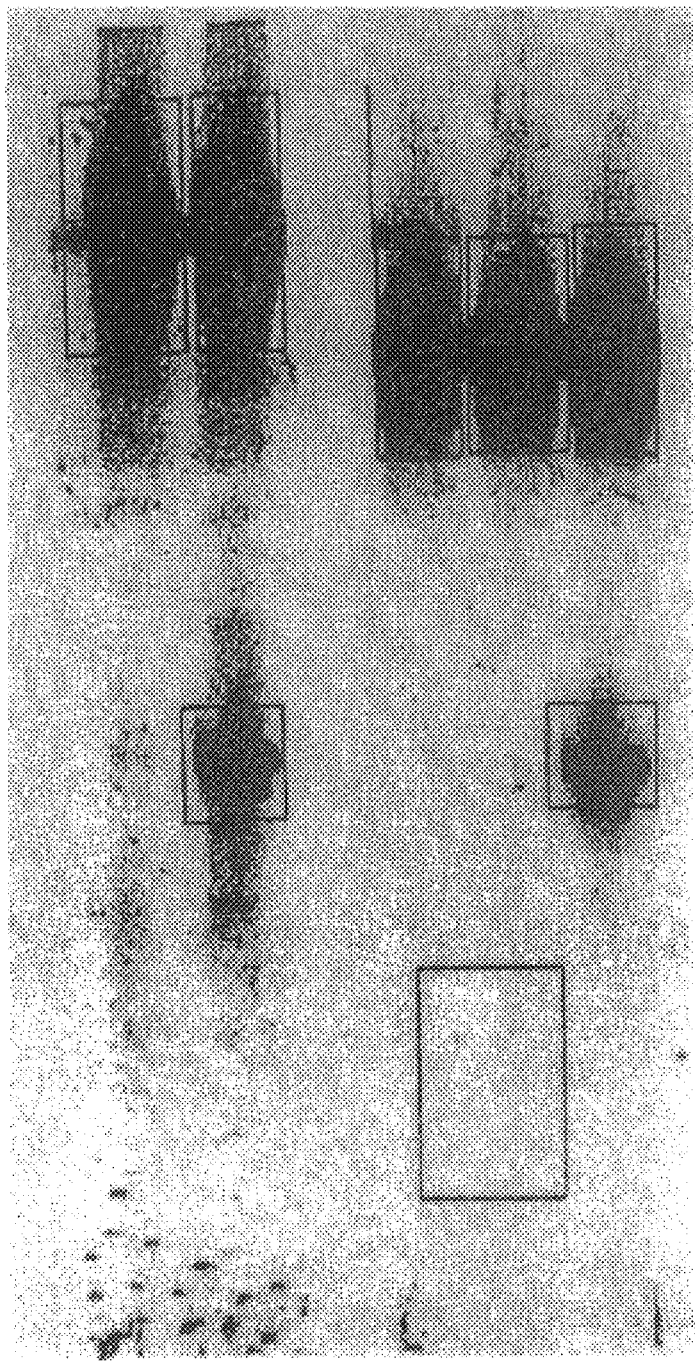
FIG. 95 shows the image generated by a fluorescence imager which depicts the detection of RNA targets using a miniprobe and stacker oligonucleotides.

In FIG. 95, lanes 1 and 2 show the products of reactions containing the HCV Invader™ oligonucleotide and the longer probe (oligonucleotide 42-088), without and with the target RNA present, respectively. Lanes 3, 4, and 5 show the products of reactions containing the Invader™ oligonucleotide and the shorter probe (oligonucleotide 42-168-1). Lane 3 is a control reaction without target RNA present, while lanes 4 and 5 have the target, but are without or with the stacker oligonucleotide, respectively.

Under these conditions the slightly longer (16 nt) probe oligonucleotide was cleaved quite easily without the help of a stacker oligonucleotide. In contrast, the shorter probe (13 nt) required the presence of the stacker oligonucleotide to produce detectable levels of cleavage. These data show that the miniprobe system of target detection by Invader™-directed cleavage is equally applicable to the detection of RNA and DNA targets. In addition, the comparison of the cleavage performance of longer and shorter probes in the absence of a stacker oligonucleotide give one example of the distinction between the performance of the miniprobe/stacker system and the performance of the mid-range and long probes in the detection of nucleic acid targets.

EXAMPLE 41

Construction of Chimerical Structure Specific Nucleases

FIG. 70 provides an alignment of the amino acid sequences of several structure-specific nucleases including several each of the FEN-1, XPG and RAD type nucleases. The numbers to the left of each line of sequence refers to the amino acid residue number; portions of the amino acid sequence of some of these proteins were not shown in order to maximize the alignment between proteins. Dashes represent gaps introduced to maximize alignment. From this alignment, it can be seen that the proteins can be roughly divided into blocks of conservation, which may also represent functional regions of the proteins. While not intended as a limitation on the chimeric nucleases of the present invention, these blocks of conservation may be used to select junction sites for the creation of such chimeric proteins.

Figure 96:
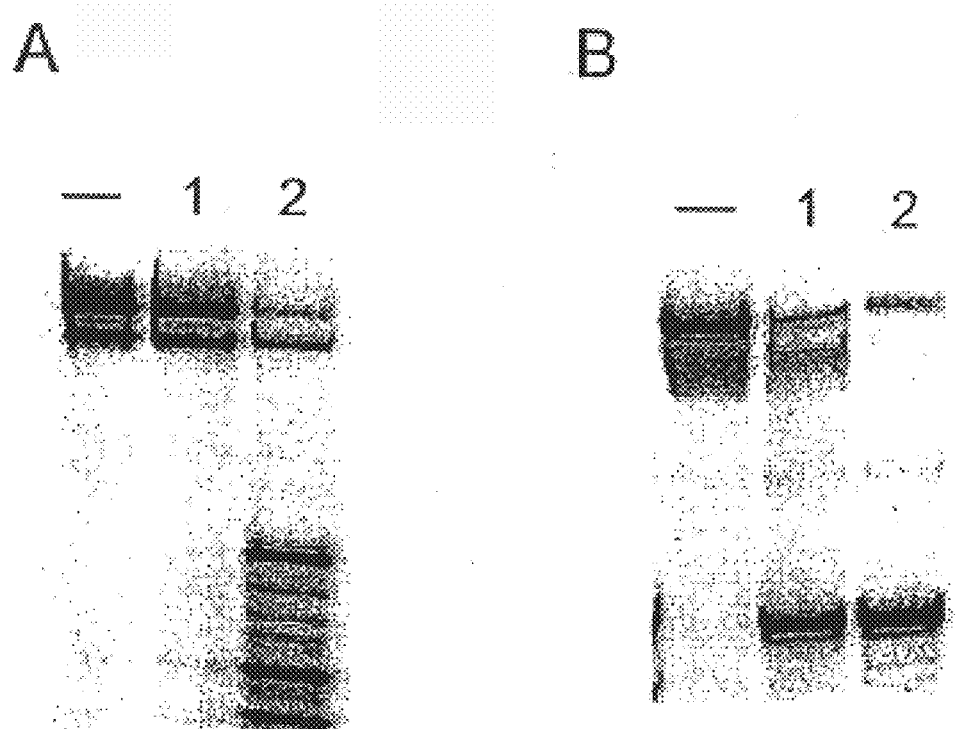
FIG. 96A shows the image generated by a fluorescence imager comparing the products produced by cleavage of a mixture of the oligonucleotides shown in FIG. 71 by either Pfu FEN-1 (A) or Mja FEN-1 (B).
FIG. 96B shows the image generated by a fluorescence imager comparing the products produced by cleavage of the oligonucleotides shown in FIG. 30 by either Pfu FEN-1 (A) or Mja FEN-1 (B).

The *Methanococcus jannaschii* FEN-1 protein (MJAFEN1.PRO), the *Pyrococcus furiosus* FEN-1 protein (PFUFEN1.PRO) are shown in the alignment in FIG. 70. These two natural genes were used to demonstrate the creation of chimeric nucleases having different activities than either of the parent nucleases. As known to those of skill in the art, appropriately sited restriction cleavage and ligation would also be a suitable means of creating the nucleases of the present invention. The activities of the parent nucleases on two types of cleavage structures, namely folded structures (See e.g. FIG. 71), and invasive structures (See e.g., FIG. 30) are demonstrated in the data shown in FIGS. 96A and 96B, respectively. These test molecules were digested as described in Ex. 29e. Lanes marked with "1" show cleavage by Pfu FEN-1, while lanes marked with "2" indicate cleavage by Maj FEN-1.

In this example, PCR was used to construct complete coding sequences for the chimeric proteins. This is a small subset of the possible combinations. It would also be within common practice in the art to design primers to allow the combination of any fragment of a gene for a nuclease with one or more other nuclease gene fragments, to create further examples of the chimeric nucleases of the present invention. The present invention provides methods, including an activity test, so that the activity of any such chimeric nuclease not explicitly described herein may be determined and characterized. Thus, it is intended that the present invention encompass any chimeric nuclease meeting the requirements of chimeric nucleases, as determined by methods such as the test methods described herein.

Figure 97:
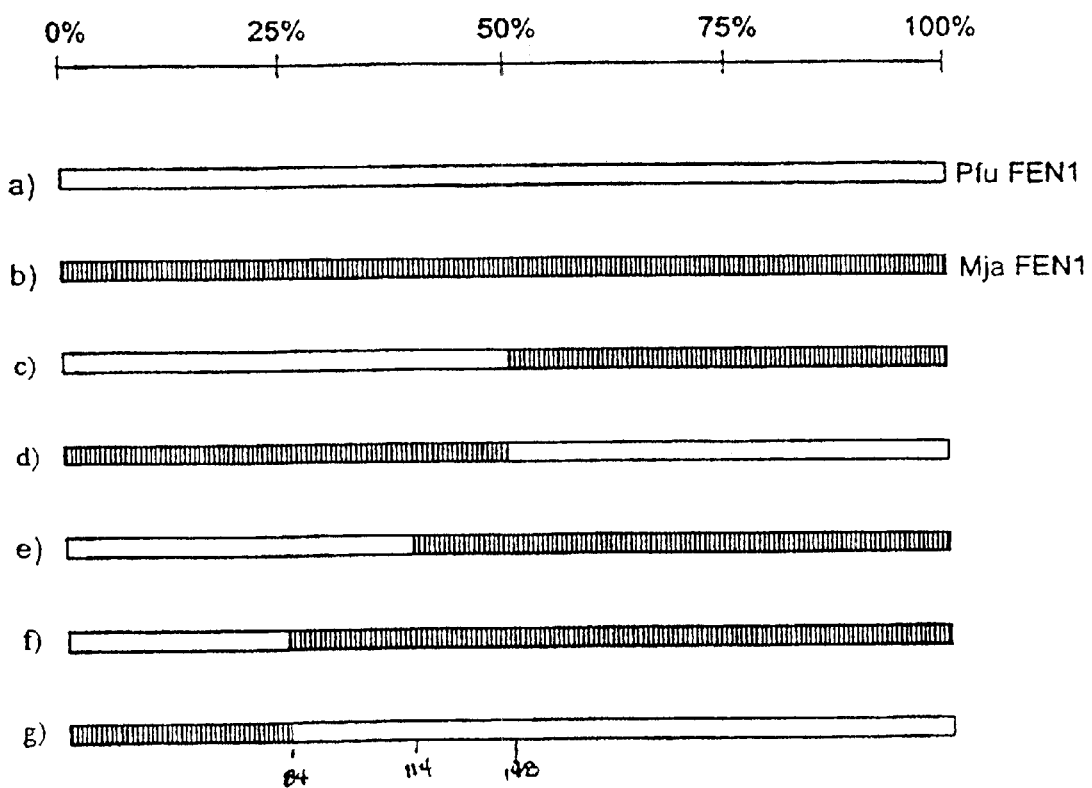
FIG. 97 shows a schematic diagram of the portions of the Pfu FEN-1 and Mja FEN-1 proteins combined to create chimeric nucleases.

To make chimeric nucleases from the *M. jannaschii* and *P. furiosus* 5' nuclease genes, homologous parts were PCR amplified using sets of external and internal primers as shown in FIG. 97. In the next step, 5' portions from one gene and a 3' portions from the other gene were joined in pairs by recombinant PCR, such that each combination created a different full size chimerical gene. The resulting coding regions were cloned into the pTrc99A vector and expressed to produce chimerical nucleases. The specific details of construction of each of the chimeric genes shown in FIG. 97 are described below.

a) Construction of chimerical 5' nuclease with *M. jannaschii* N-terminal portion and *P. furiosus* C-terminal portion with a junction point at codon 84 (FIG. 97g).

A fragment of the pTrc99A vector carrying the *M. jannaschii* 5' nuclease gene was PCR amplified with TrcFwd (SEQ ID NO:135) and 025-141-02 (SEQ ID NO:136) primers (5 pmole each) in a 50 µl reaction using the Advantage™ cDNA PCR kit (Clonetech), for 30 cycles (92° C., 30 s; 55° C., 1 min; 72° C. 1 min) to make an N-terminus-encoding gene fragment (SEQ ID NO:137). The TrcRev (SEQ ID NO:138) and 025-141-01 (SEQ ID NO:139) primers were used to amplify a fragment of the pTrc99A vector carrying the *P. furiosus* gene to produce a C-terminus encoding gene fragment (SEQ ID NO:140). The PCR products were cleaned with the High Pure PCR Product Purification kit (Boehringer Mannheim, Germany) as described in the manufacturer's protocol and eluted in 100 µl water.

The 025-141-02 (SEQ ID NO:136) primer and the 025-141-01 (SEQ ID NO:139) primer are complementary to each other, so that the PCR fragments created above had the corresponding regions of complementarity on one end. When these fragments are combined in an amplification reaction, the region of complementarity allows the parts to hybridize to each other, to be filled in with the DNA polymerase, and then to be amplified using the outer primer pair, TrcFwd (SEQ ID NO:135) and TrcRev (SEQ ID NO:138) in this case, to form one fragment (SEQ ID NO:141). Five pmole of each outer primer was then placed in 50 µl PCR reaction using the Advantage™ cDNA PCR kit (Clonetech) as described above. The full length PCR product (SEQ ID NO:141) including the chimerical coding region (positions 45–1067 of SEQ ID:141) was separated in 1% agarose gel by standard procedures and isolated using the Geneclean II Kit (Bio 101, Vista, Calif.) The isolated fragment was then cut with NcoI and PstI restriction enzymes and cloned in pTrc99A vector.

b) Construction of chimerical 5' nuclease with *P. furiosus* N-terminal portion and *M.jannaschii* C-terminal portion with a junction point at codon 84 (FIG. 97f).

A fragment of the pTrc99A vector carrying the *P. furiosus* 5' nuclease gene was PCR amplified with TrcFwd (SEQ ID NO:135) and 025-141-02 (SEQ ID NO:136) primers (5 pmole each) as described above to make an N-terminus-encoding gene fragment (SEQ ID NO:142). The TrcRev (SEQ ID NO:138) and 025-141-01 (SEQ ID NO:139) primers were used to amplify a fragment of the pTrc99A vector carrying the *M. jannaschii* gene to produce a C-terminus encoding gene fragment (SEQ ID NO:143). The fragments were purified and combined in a PCR, as described above to form one fragment (SEQ ID NO:144), containing the entire chimerical gene (positions 45-1025 of SEQ ID NO:144). This chimerical gene was cut with NcoI and PstI, and cloned into pTrc99A vector as described in a) above.

c) Construction of chimerical 5' nuclease with *P. furiosus* N-terminal portiono and *M.jannaschii* C-terminal portion with a junction point at codon 114 (FIG. 97e).

A fragment of the pTrcPfuHis plasmid was PCR amplified with TrcFwd (SEQ ID NO:135) and 025-164-04 (SEQ ID NO:146) primers (5 pmole each), as described above to make an N-terminus-encoding gene fragment (SEQ ID NO:145). The pTrcPfuHis plasmid was constructed by modifying pTrc99-PFFFEN1 (described in Ex. 28), by adding a histidine tail to facilitate purification. To add this histidine tail, standard primer directed mutagenesis methods were used to insert the coding sequence for six histidine residues between the last amino acid codon of the pTrc99-PFFFEN1 coding region and the stop codon. The resulting plasmid was termed pTrcPfuHis.

The 159-006-01 (SEQ ID NO:148) and 025-164-07 (SEQ ID NO:149) primers were used as described in section a) above, to amplify a fragment of the pTrcMjaHis plasmid to produce a C-terminus encoding gene fragment (SEQ ID NO:147). The pTrcMjaHis plasmid was constructed by modifying pTrc99-MJFEN1 (described in Ex. 28), by adding a histidine tail to facilitate purification. To add this histidine tail, standard PCR mutagenesis methods were used to insert the coding sequence for six histidine residues between the last amino acid codon of the pTrc99-MJFEN1 coding region and the stop codon. The resulting plasmid was termed pTrcMjaHis. The fragments were purified, and combined by PCR amplification with TrcFwd (SEQ ID NO:135) and 159-006-01 (SEQ ID NO:148) primers in one fragment (SEQ ID NO:150) containing the chimerical gene (positions 45-1043). This chimerical gene was cut with NcoI and PstI, and cloned into pTrc99A vector as described in a), above.

d) Construction of chimerical 5' nuclease with *M. jannaschii* N-terminal portion and *P. furiosus* C-terminal portion with a junction point at codon 148 (FIG. 97d).

A fragment of the pTrc99A vector carrying the *M.jannaschii* 5' nuclease gene was PCR amplified with TrcFwd (SEQ ID NO:135) and 025-119-05 (SEQ ID NO:152) primers, as described above, to make an N-terminus-encoding gene fragment (SEQ ID NO:151). The TrcRev (SEQ ID NO:138) and 025-119-04 (SEQ ID NO:154) primers were used to amplify a fragment of the pTrc99A vector carrying the *P. furiosus* gene to produce a C-terminus encoding gene fragment (SEQ ID NO:153). The fragments were purified as described above and combined by PCR amplification with the TrcFwd (SEQ ID NO:135) and TrcRev (SEQ ID NO:138) primers into one fragment (SEQ ID NO:155) containing the chimerical gene (positions 45-1067). This chimerical gene was cut with NcoI and PstI, and cloned into pTrc99A vector as described in a), above.

e) Construction of chimerical 5' nuclease with *P. furiosus* N-terminal portion and *M.jannaschii* C-terminal portion art with a junction point at codon 148 (FIG. 97c).

A fragment of the pTrcPfuHis plasmid was PCR amplified with TrcFwd (SEQ ID NO:135) and 025-119-05 (SEQ ID NO:152) primers as described above to make an N-terminus-encoding gene fragment (SEQ ID NO:156). The TrcRev (SEQ ID NO:138) and 025-119-04 (SEQ ID NO:154) primers were used to amplify a fragment of the pTrcMjaHis plasmid to produce a C-terminus encoding gene fragment (SEQ ID NO:157). The fragments were purified as described above and combined by PCR amplification with TrcFwd (SEQ ID NO:135) and TrcRev (SEQ ID NO:138) primers in one fragment (SEQ ID NO:158) containing the chimerical gene (positions 45-1025). This chimerical gene was cut with NcoI and PstI, and cloned into pTrc99A vector as described in a), above.

f) Expression and Purification of Chimeras.

All of the chimerical enzymes described above except *P. furiosus-M. jannaschii* construct containing a junction point at the codon 114 (i.e., Example 41c) were purified as described for Taq DN. The *P. furiosus-M. jannaschii* codon 114 chimera with His-tag was purified as described for the 5' nuclease domain BN of Taq Pol I.

g) Activity Characterization of Natural and Chimerical Structure-Specific Nuclease.

All of the chimerical enzymes produced as described above were characterized. In one assay, the enzymes were tested using a mixture of long and short hairpin substrates in the assay system described in Example 29e.

Figure 98A:
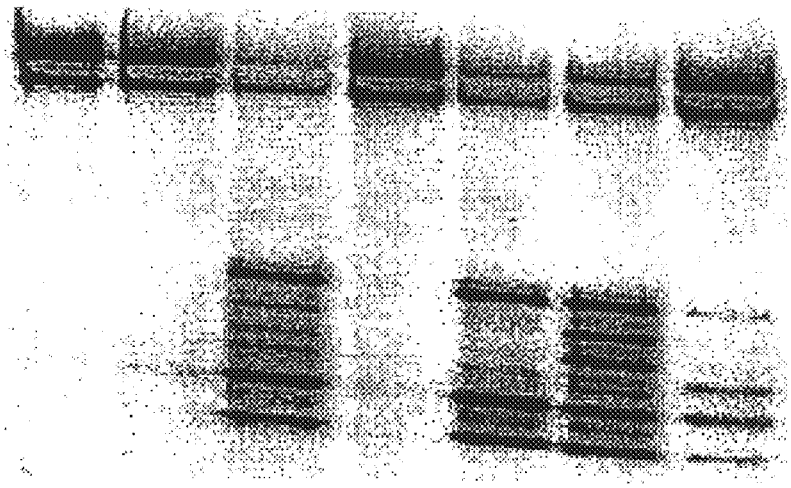
FIG. 98A shows the image generated by a fluorescence imager comparing the products produced by cleavage of a mixture of the oligonucleotides shown in FIG. 71 by Pfu FEN-1 (A), Mja FEN-1 (B) or the chimeric nucleases diagrammed in FIG. 97.

In these tests, reactions were done using 50 ng of each enzyme for 2 min., at 50° C. The results of the analysis are shown in FIG. 98A. In this Figure, the lanes marked "1" and "2" in FIG. 98A, indicate reactions with the Pfu and Maj parent enzymes, respectively. The remaining uncut hairpin molecules are visible as two bands at the top of each lane. Each chimeric enzyme tested is represented by reference in FIG. 97. For example, the lane marked "97f" shows the cleavage of these test molecules by the chimerical 5' nuclease with the *P. furiosus* N-terminus and the *M. jannaschii* C-terminus joined at codon 84. The various products of cleavage are seen in the lower portion of each lane. These data show that the chimerical nucleases may display cleavage activities (i.e., substrate specificities) like either parent (e.g., 97c and parent Pfu FEN-1 show little cleavage in this test) or distinct from either parent (i.e., different product profiles).

Figure 98B:
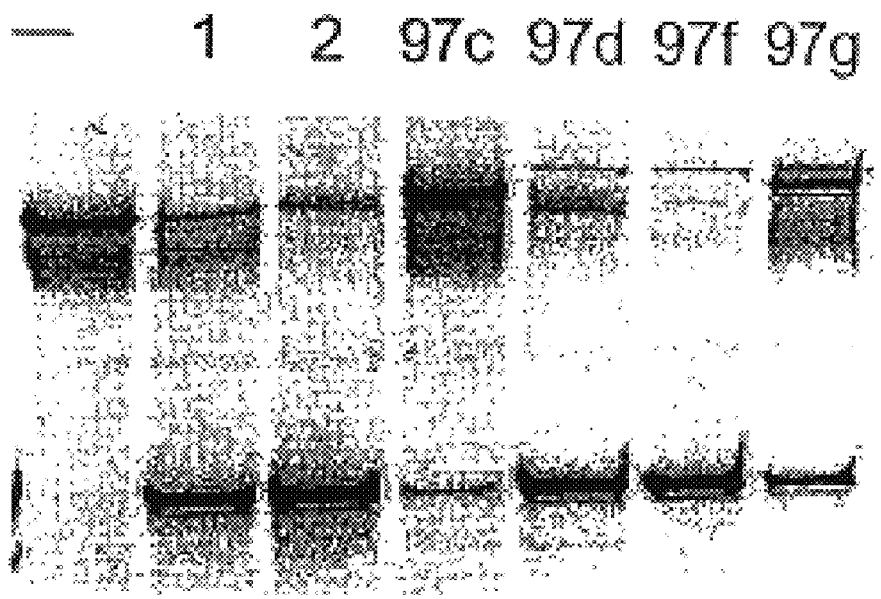
FIG. 98B shows the image generated by a fluorescence imager comparing the products produced by cleavage of the oligonucleotides shown in FIG. 30 by Pfu FEN-1 (A), Mja FEN-1 (B) or the chimeric nucleases diagrammed in FIG. 97.

Similarly, the chimerical enzymes were examined for invasive cleavage activity using the S-60 structure and the P15 oligonucleotide depicted in FIG. 30, as described in Ex. 11. The results are shown in FIG. 98B. The uncleaved labeled P15 oligonucleotide appears in the upper portion of each lane, while the labeled product of cleavage appears in the lower portion.

These results indicate that chimerical enzymes are different in activity and specificity from the original (i.e., wild-type) *M. jannaschii* and *P. furiosus* 5' nucleases.

EXAMPLE 42

Comparison of Digestion of Folded Cleavage Structures With Chimeric Nucleases

CFLP™ analysis was applied to a PCR amplified segment derived from *E. coli* 16S rRNA genes. Although bacterial 16S rRNA genes vary throughout the phylogenetic tree, these genes contain segments that are conserved at the species, genus or kingdom level. These features have been exploited to generate primers containing consensus sequences which flank regions of variability. In prokaryotes, the ribosomal RNA genes are present in 2 to 10 copies, with an average of 7 copies in Escherichia strains. Any PCR amplification produces a mixed population of these genes and is in essence a "multiplex" PCR from that strain. CFLP™ analysis represents a composite pattern from the slightly varied rRNA genes within that organism, such that no one particular rRNA sequence is directly responsible for the entire "bar code." As a representative example of an amplicon as described below from the *E. coli* 16s *E. coli* rrsE gene is provided (SEQ ID NO:165). Despite the variable nature of these genes, amplification by PCR can be performed between conserved regions of the rRNA genes, so prior knowledge of the entire collection of rRNA sequences for any microbe of interest is not required (See e.g., Brow et al., J. Clin. Microbiol., 34:3129 [1996]).

In this Example, the 1638 (5'-AGAGTTTGATCC TGGCTCAG-3')(SEQ ID NO:174)/TET-1659 (5'-CTGCTGCCTCCCGTAGGAGT-3')(SEQ ID NO:175) primer pair was used to amplify an approximately 350 bp fragment of rrsE from genomic DNA derived from *E. coli* O157: H7 (ATCC #43895). The PCR reactions contained 10 mM Tris-HCl (pH 8.3 at 25° C.), 50 mM KCl, 1.5 mM $MgCl_2$, 0.001% w/v gelatin. 60 $\mu$M each of dGTP, dATP, dTTP, and dCTP, 1 $\mu$M of each primer, 25 ng of genomic DNA, and 2.5 units AmpliTaq DNA polymerase, LD in a volume of 100 $\mu$l. Control reactions that contained no input bacterial genomic DNA were also run to examine the amount of 16S rRNA product produced due to contaminants in the DNA polymerase preparations. The reactions were subjected to 30 cycles of 95° C. for 30 sec; 60° C. for 1 min; 72° C. for 30 sec; after the last cycle the tubes were cooled to 4° C.

After thermal cycling, the PCR mixtures were treated with *E. coli* exonuclease I (Exo I, Amersham) to remove single-stranded partial amplicons and primers. One unit of ExoI was added directly to each PCR mixture, and the samples were incubated at 37° C. for 20 minutes. Then, the nuclease was inactivated by heating to 70° C. for 15 min. The reaction mixtures were brought to 2 M $NH_4OAc$, and the DNAs were precipitated by the addition of 1 volume of 100% ethanol.

Cleavage reactions comprising 1 $\mu$l of TET-labeled PCR products (approximately 100 fmoles) in a total volume of 10 $\mu$l containing 1× CFLP™ buffer (10 mM MOPS, pH 7.5; 0.5% each Tween 20 and NP-40) and 0.2 mM $MnCl_2$, were then conducted. All components except the enzyme were assembled in a volume of 9 $\mu$l. The reactions were heated to 95° C. for 15 sec., cooled to 55° C., and the cleavage reactions were started by the addition of 50 ng of enzyme. After 2 minutes at 55° C., the reactions were stopped by the addition of 6 $\mu$l of a solution containing 95% formamide, 10 mM EDTA and 0.02% methyl violet.

Figure 99:
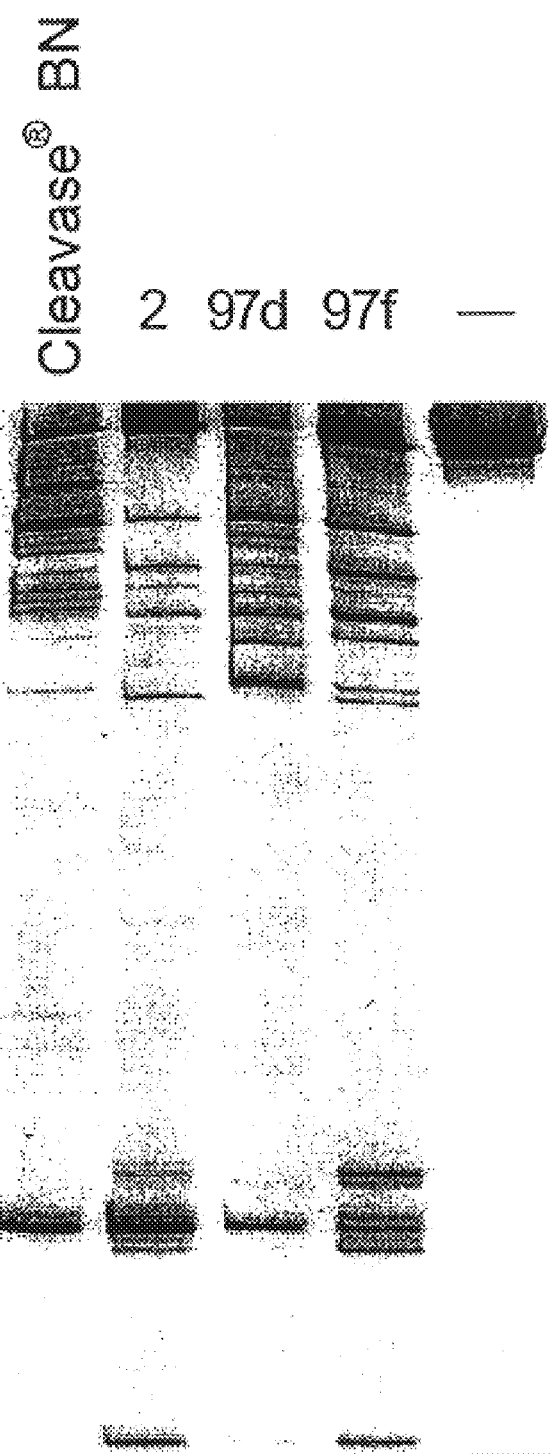
FIG. 99 shows the image generated by a fluorescence imager comparing the products produced by cleavage of folded cleavage structures by Pfu FEN-1 (A), Mja FEN-1 (B) or the chimeric nucleases diagrammed in FIG. 97.
Figure 100A:
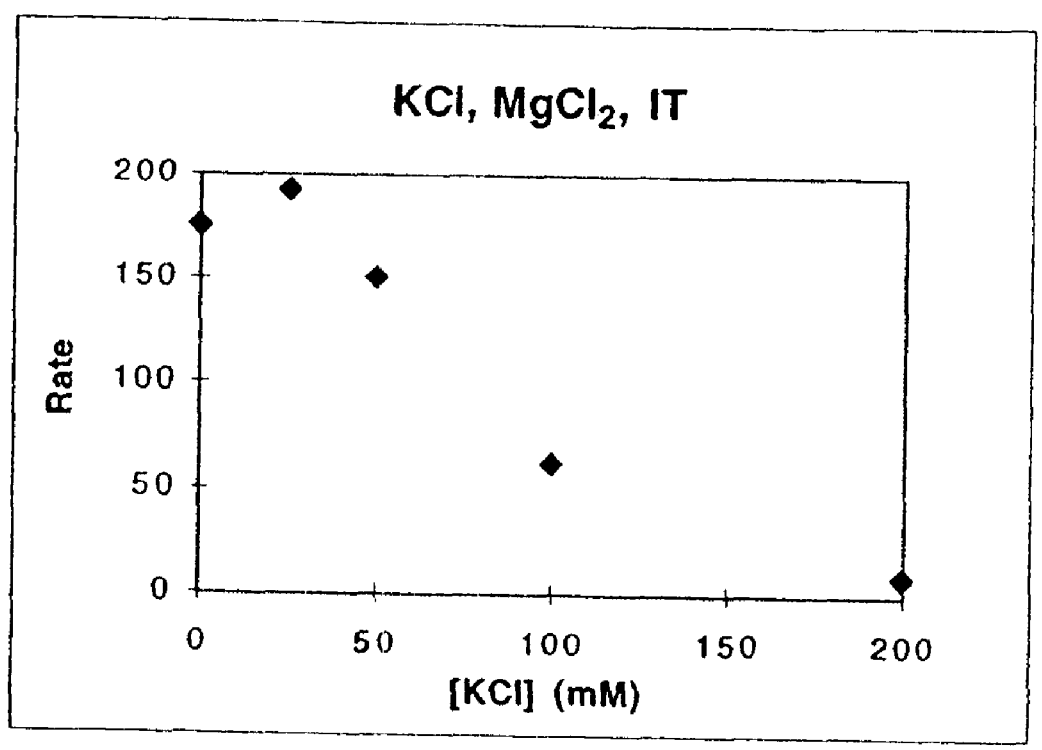
FIGS. 100A–J shows the results of various assays used to determine the activity of Cleavase BN under various conditions.
Figure 100B:
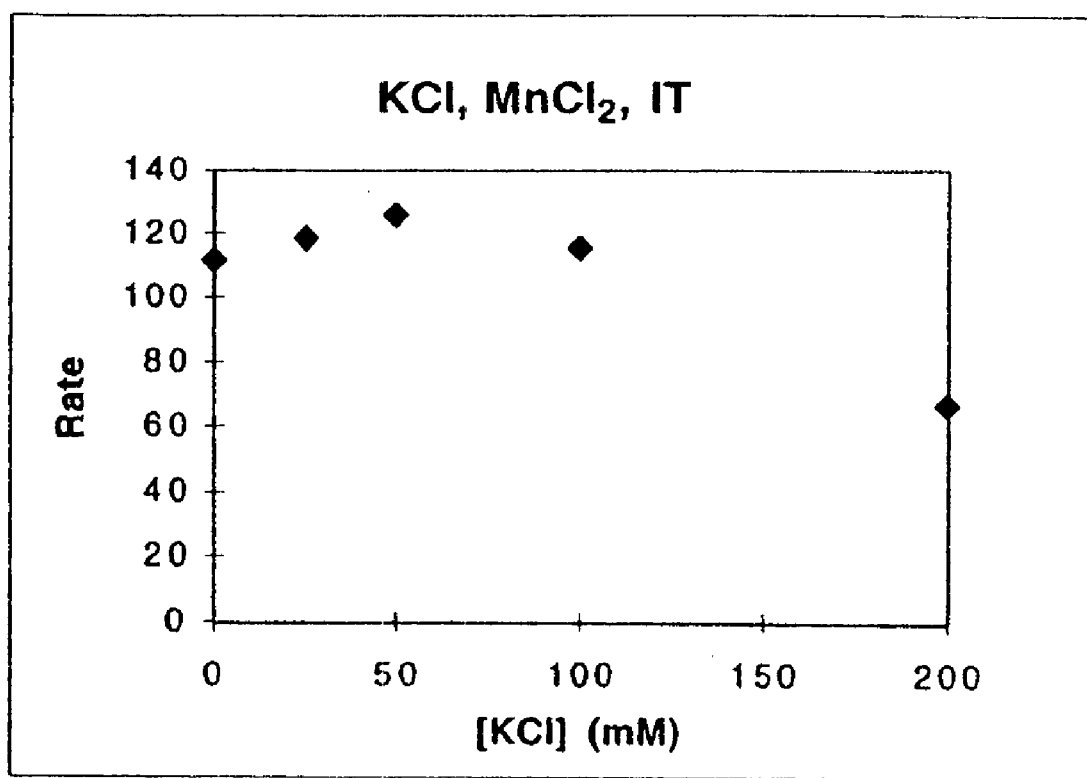
Figure 100C:
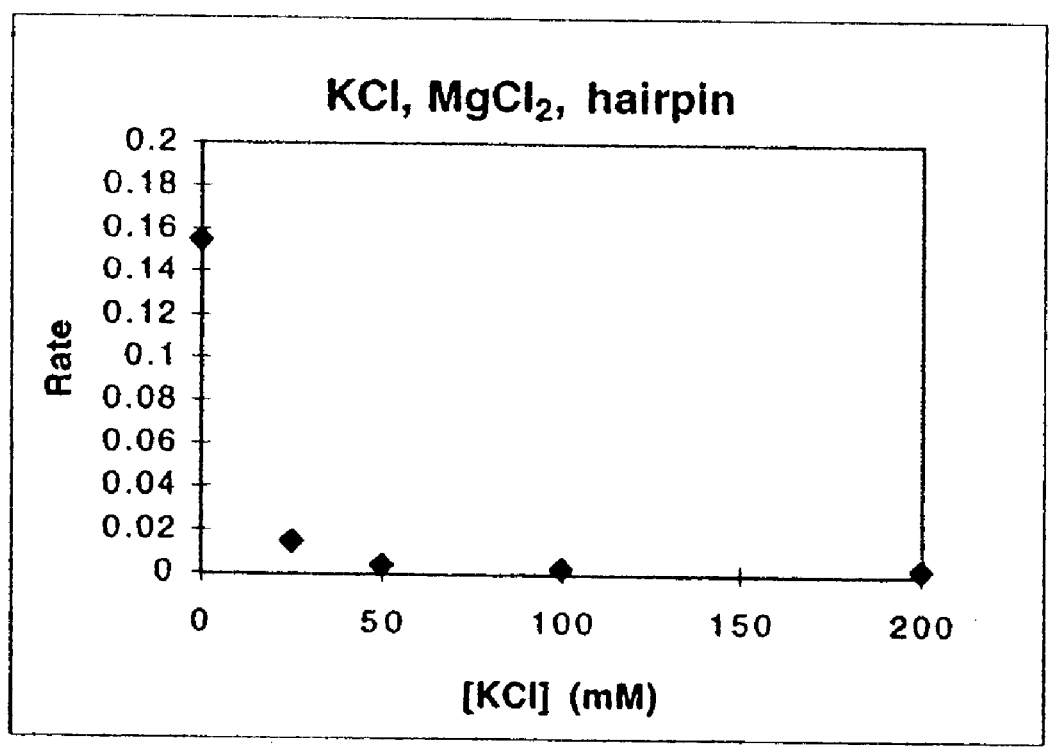
Figure 100D:
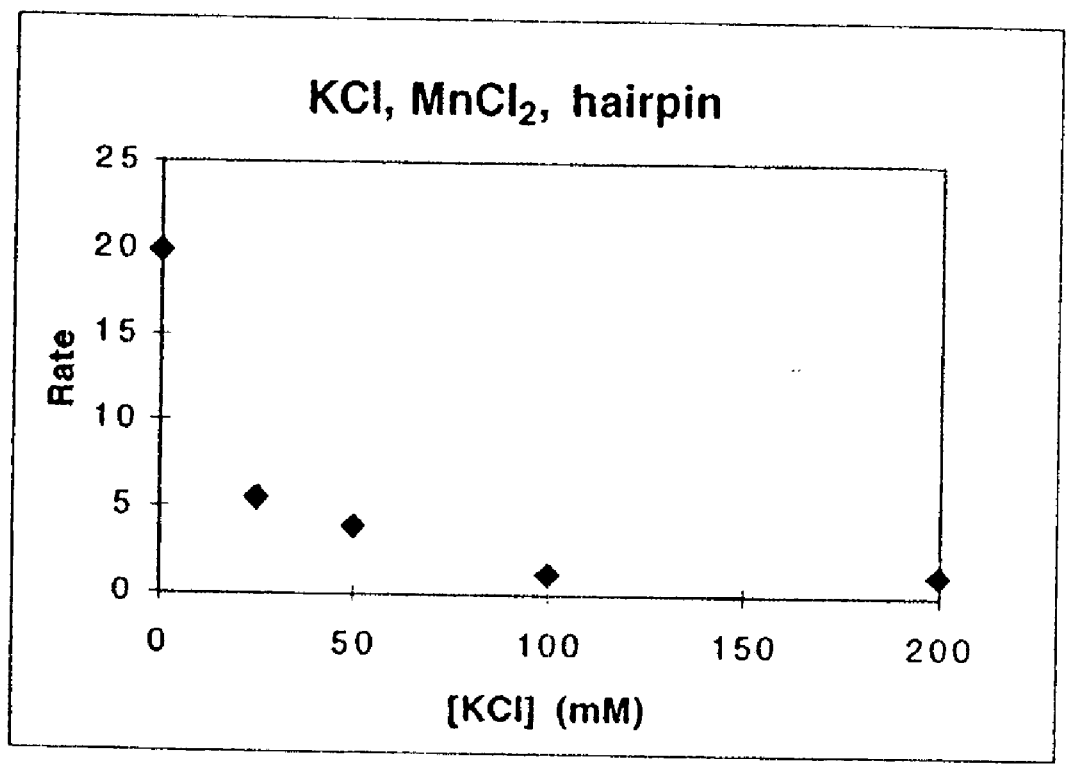
Figure 100E:
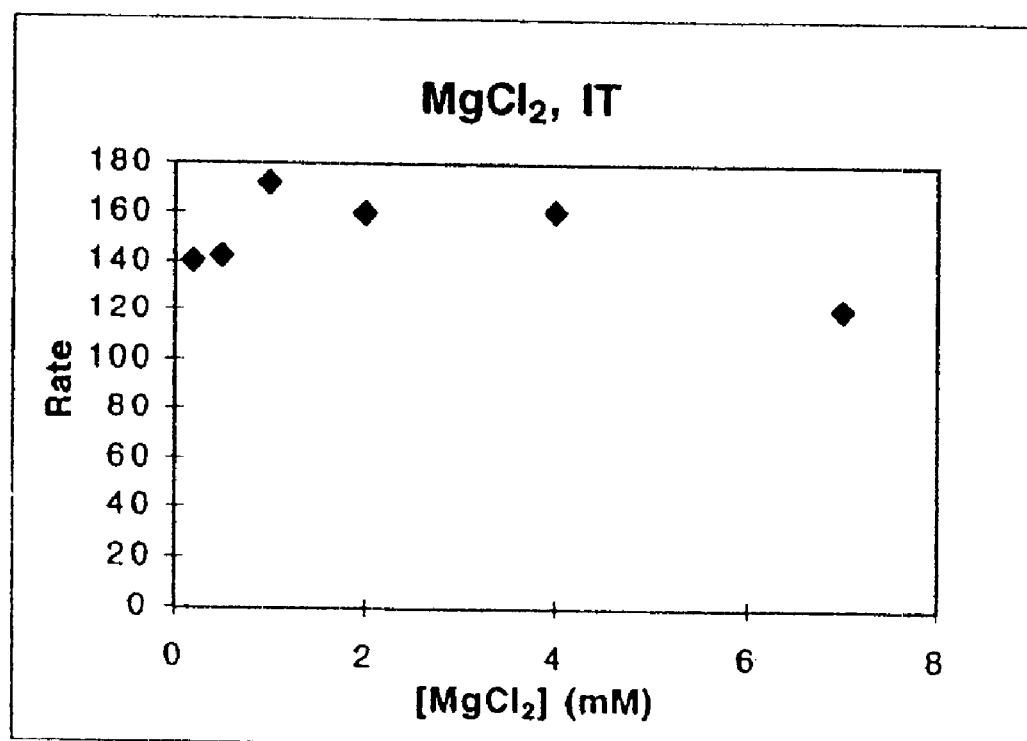
Figure 100F:
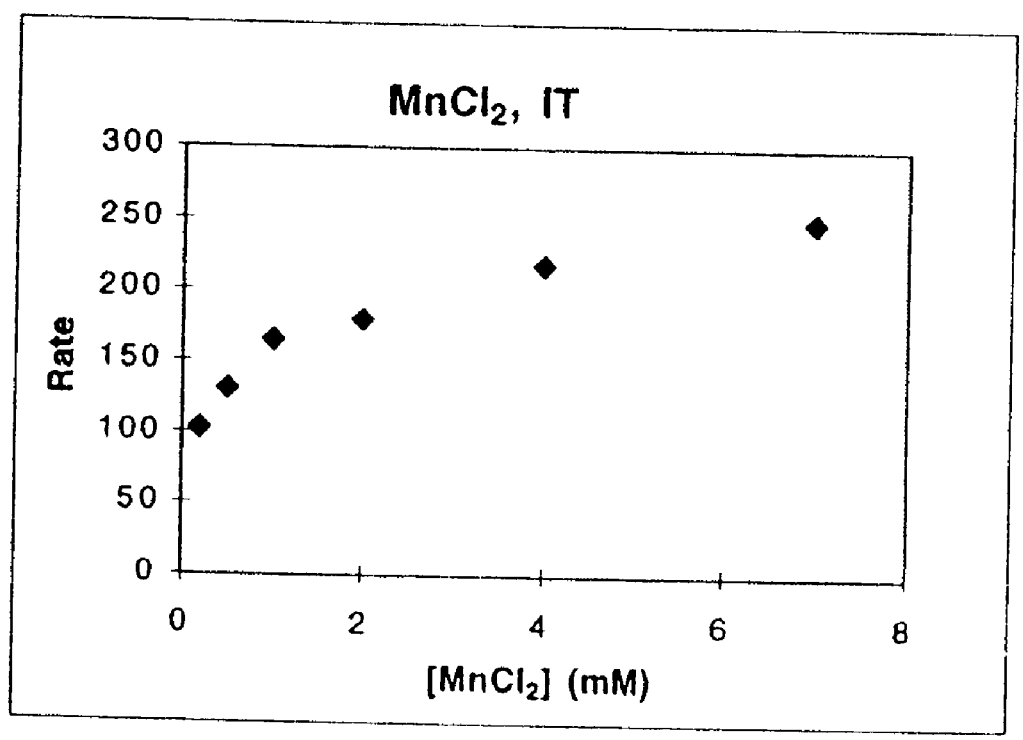
Figure 100G:
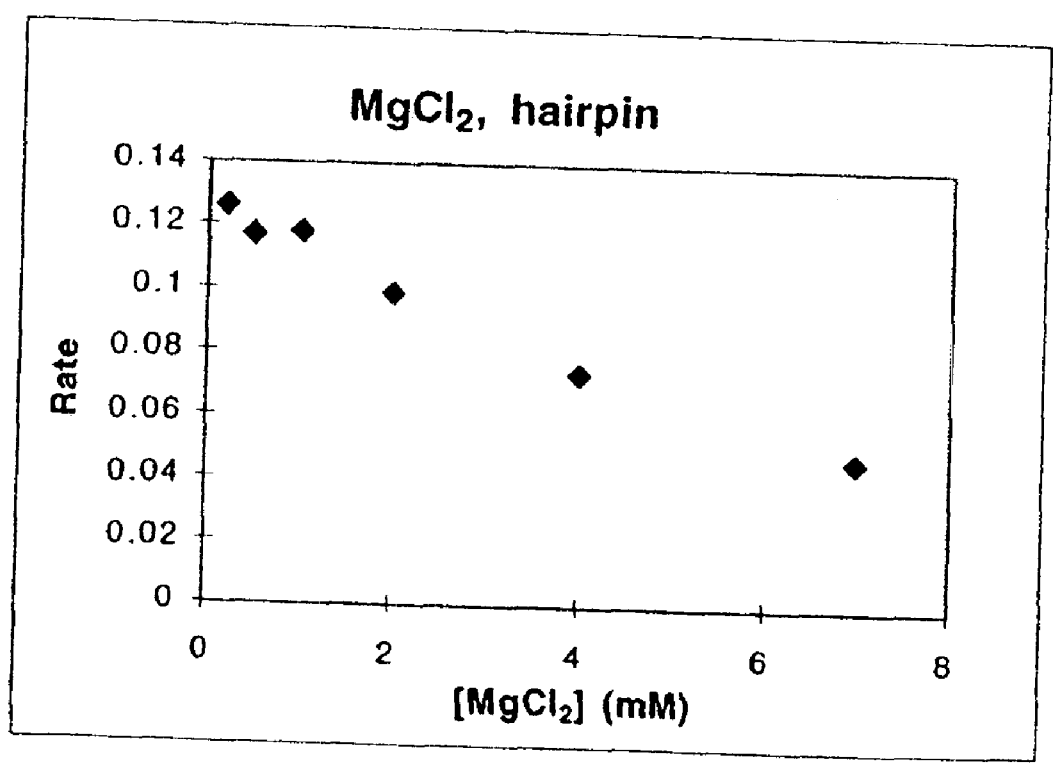
Figure 100H:
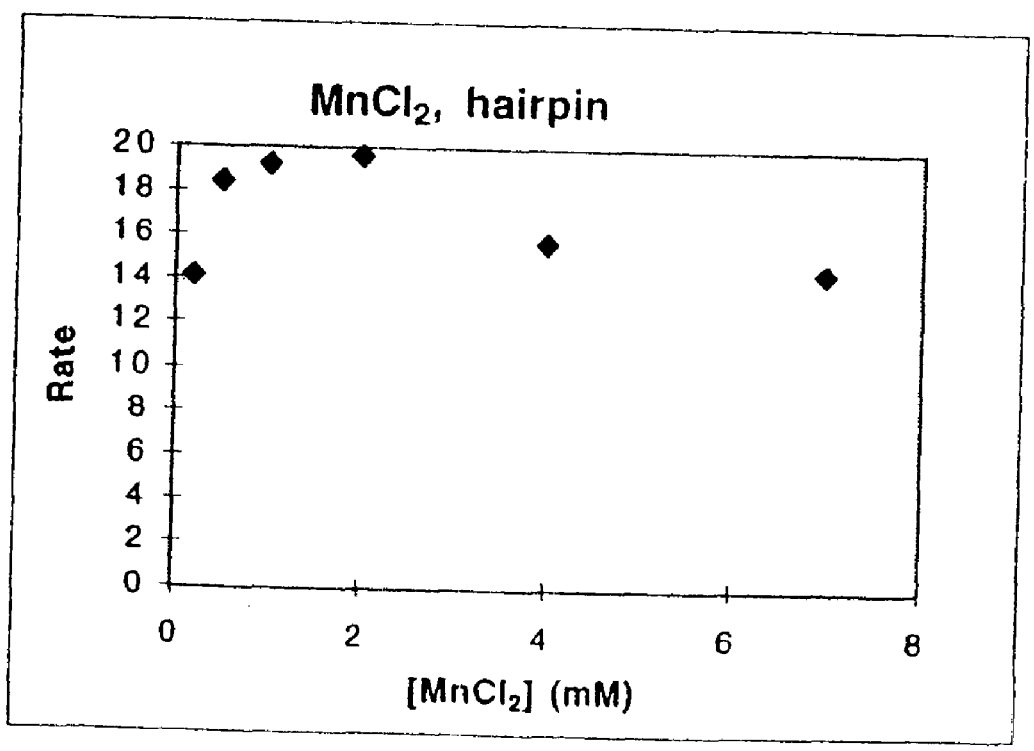
Figure 100I:
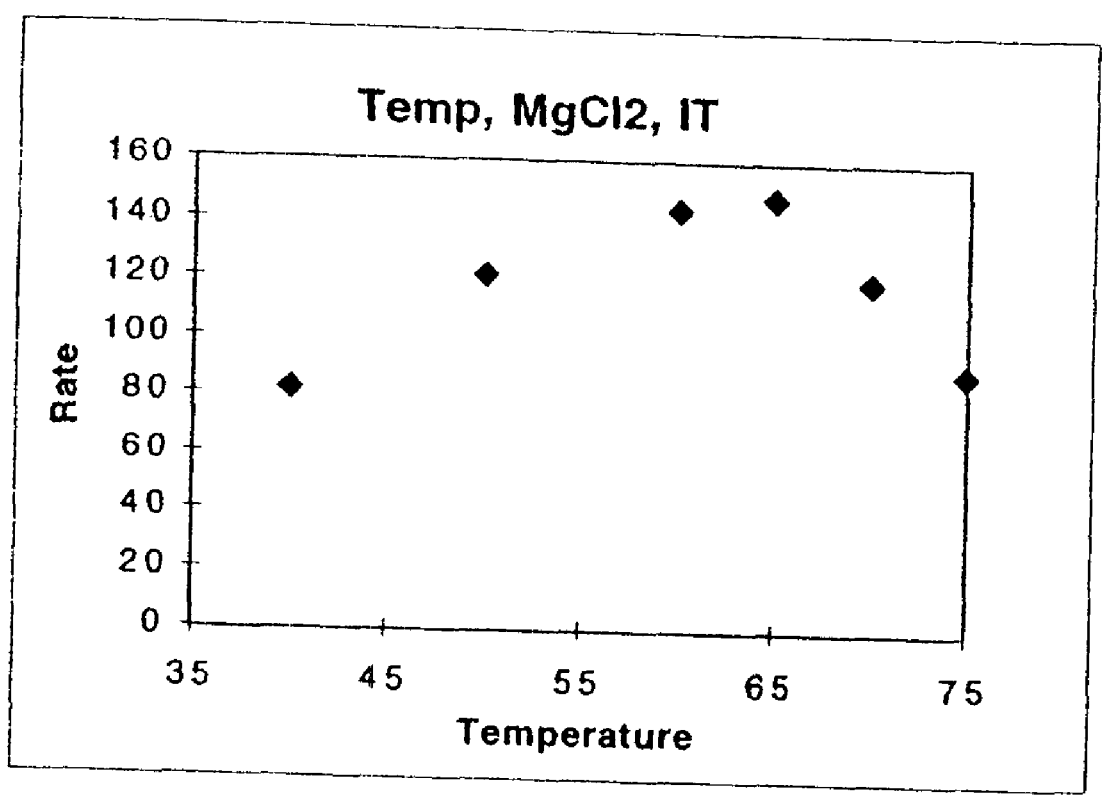
Figure 100J:
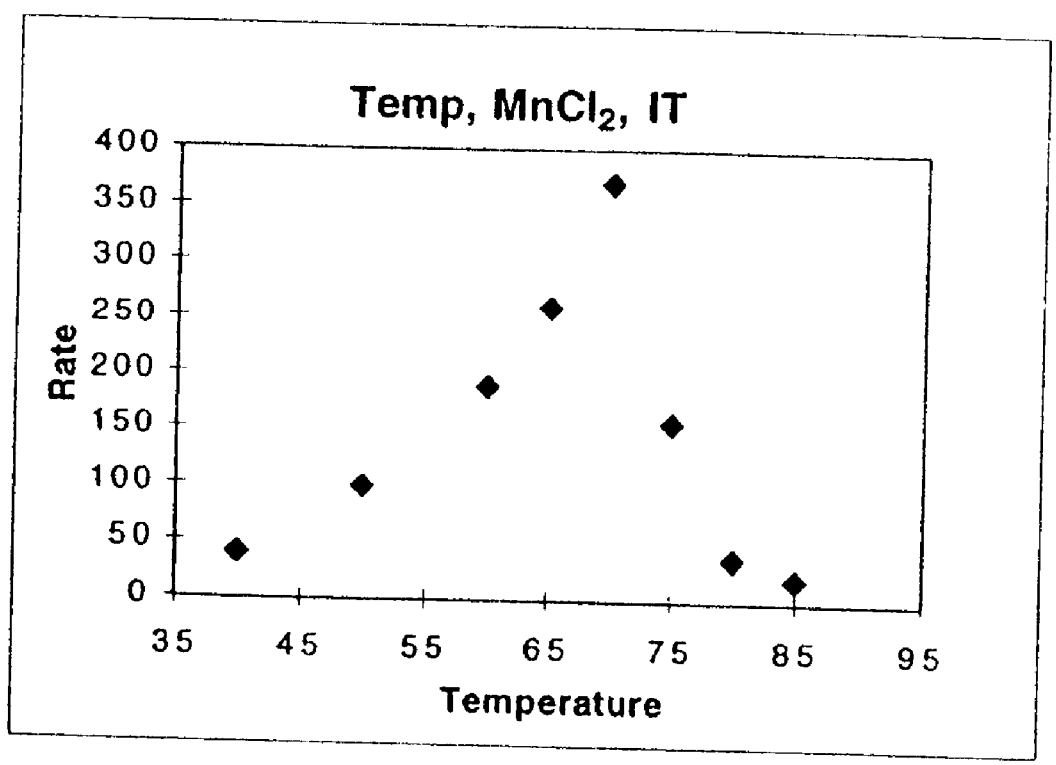
Figure 101A:
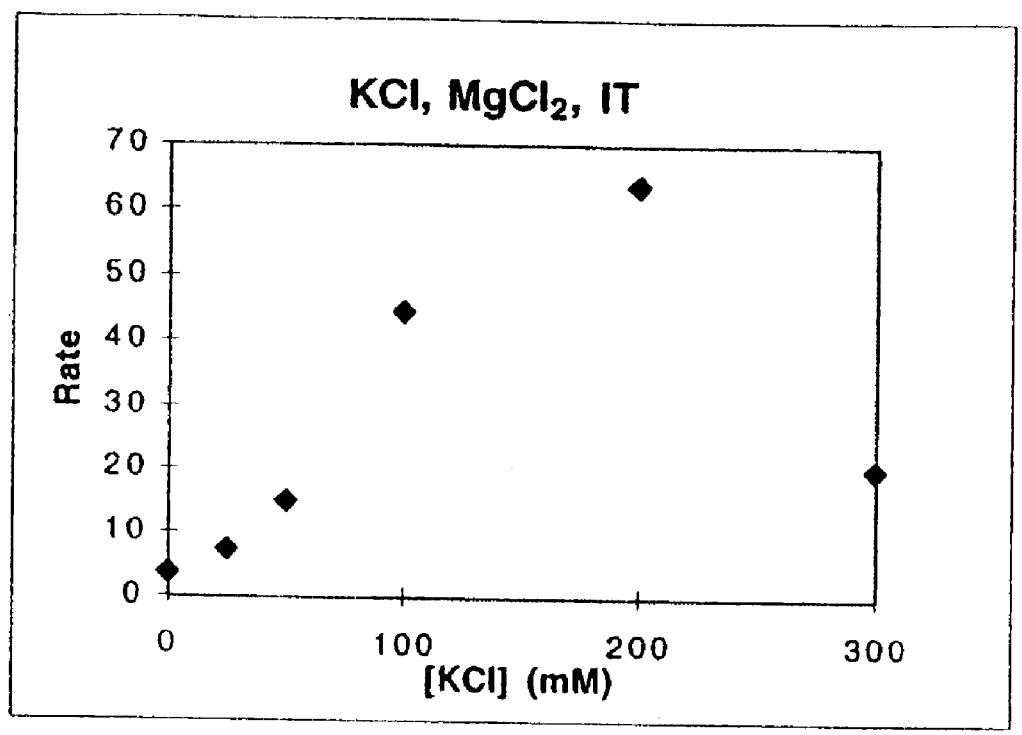
FIGS. 101A–B, D–F, and H–J show the results of various assays used to determine the activity of TaqDN under various conditions.
Figure 101B:
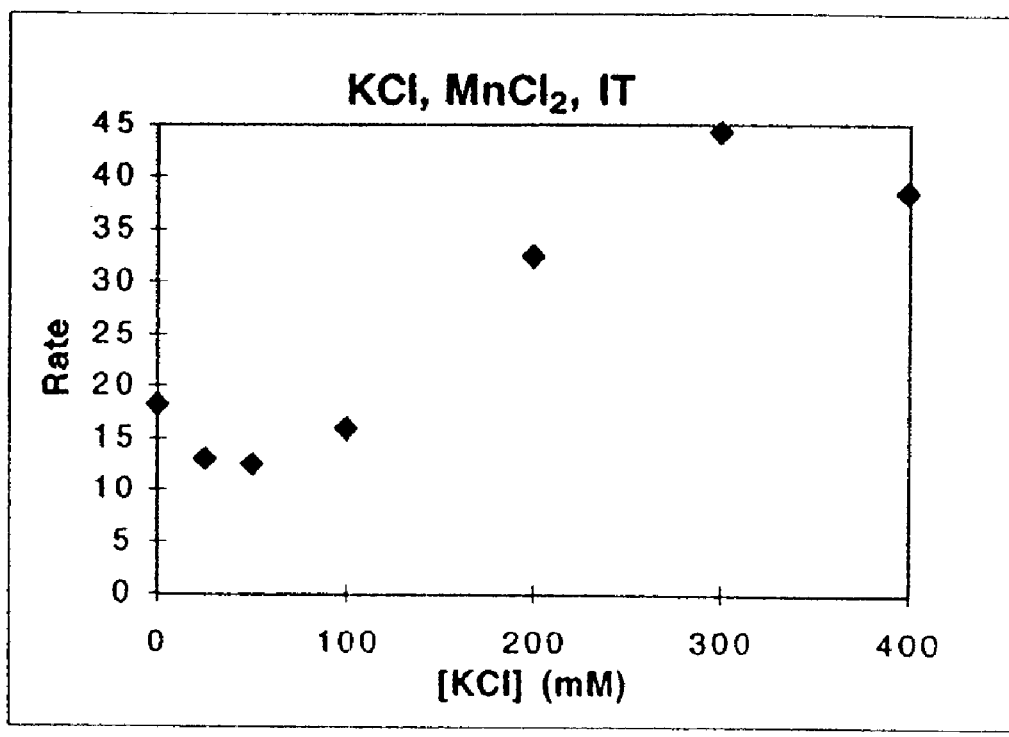
Figure 101D:
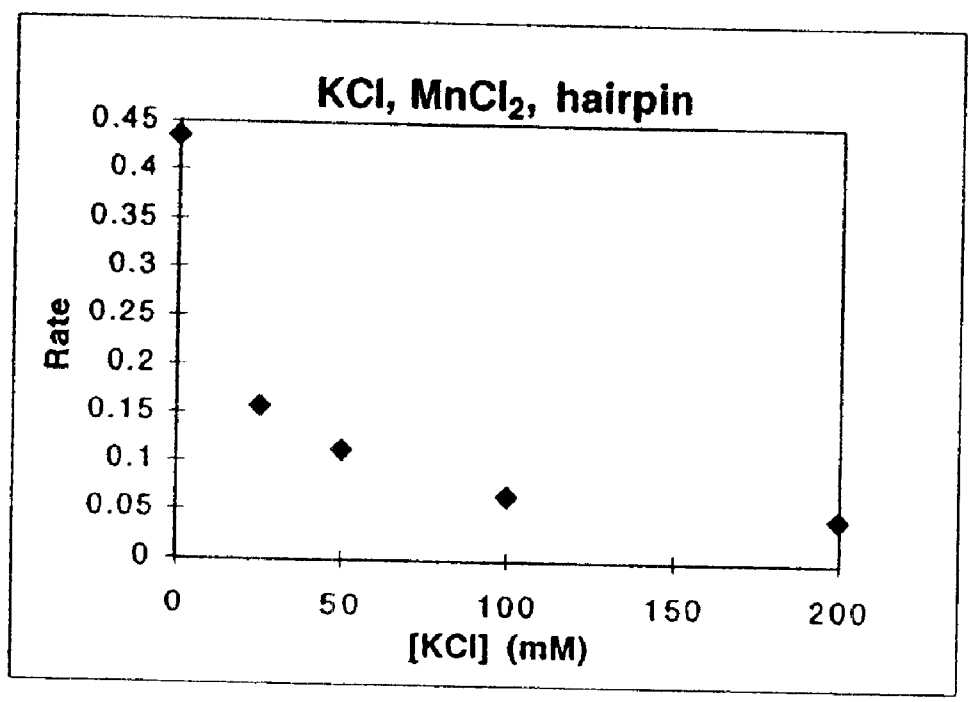
Figure 101E:
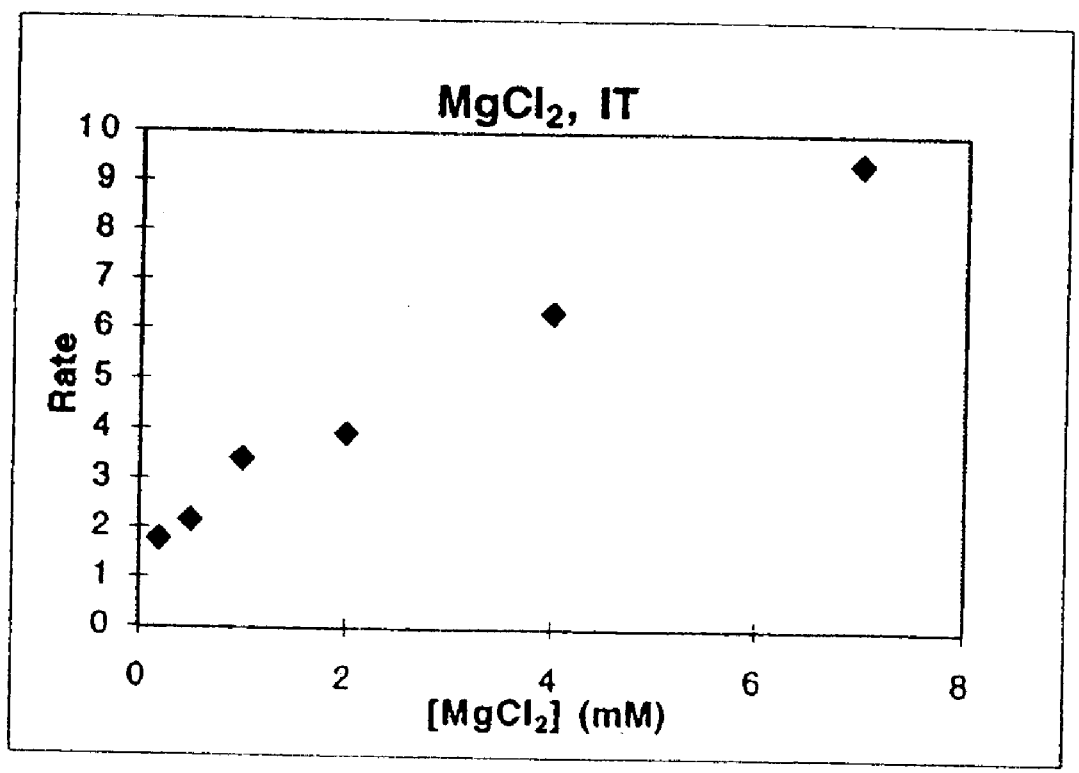
Figure 101F:
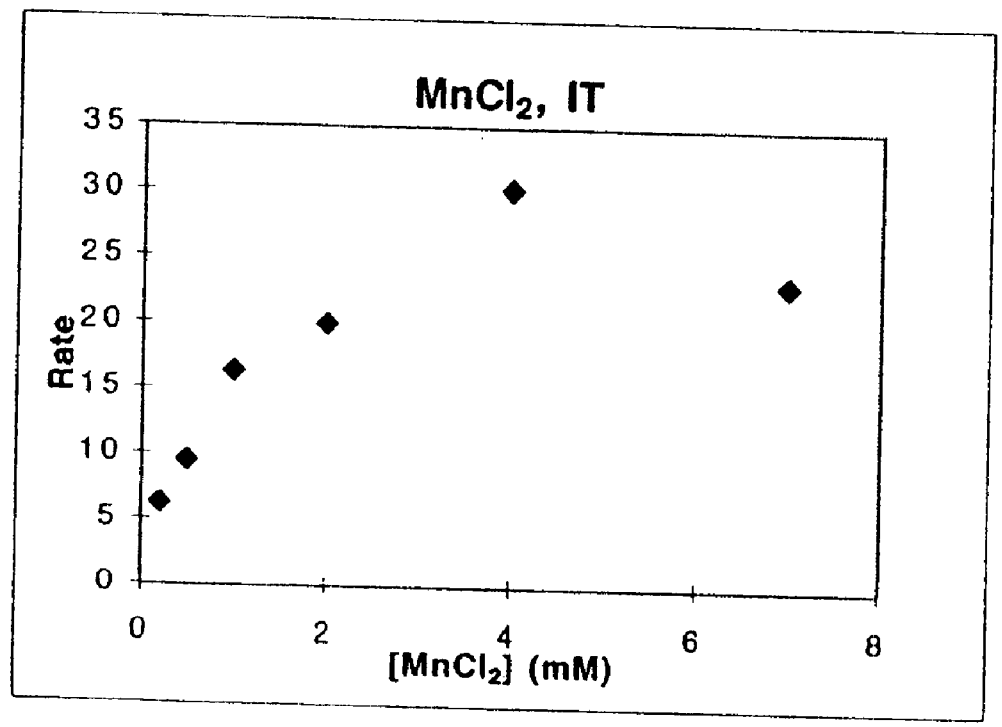
Figure 101H:
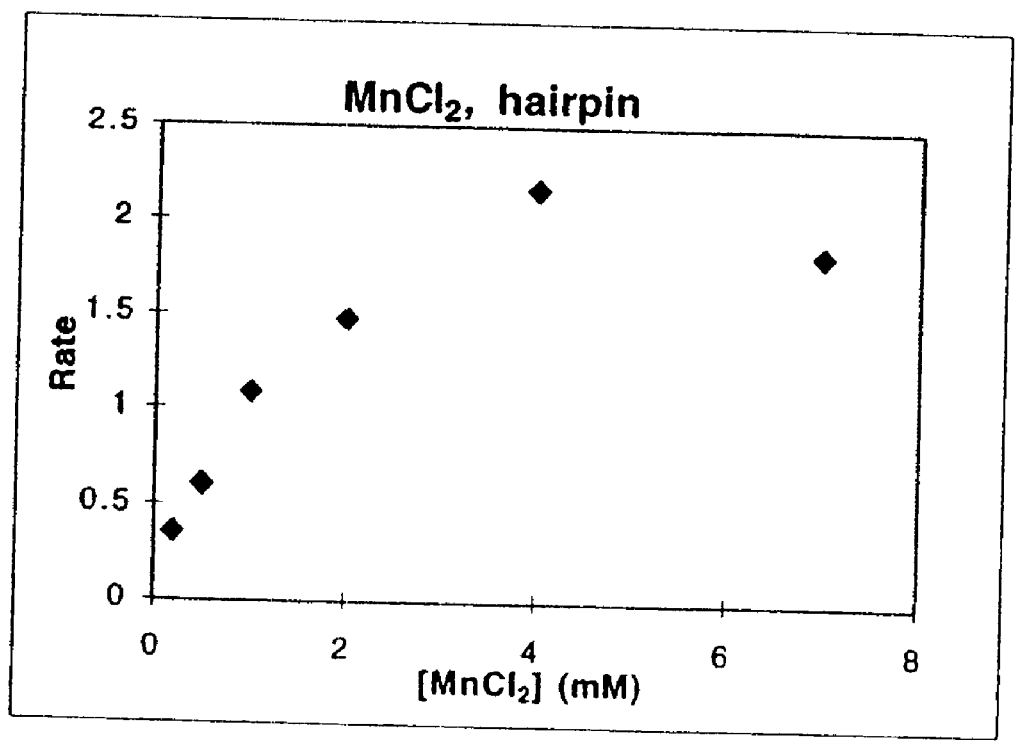
Figure 101I:
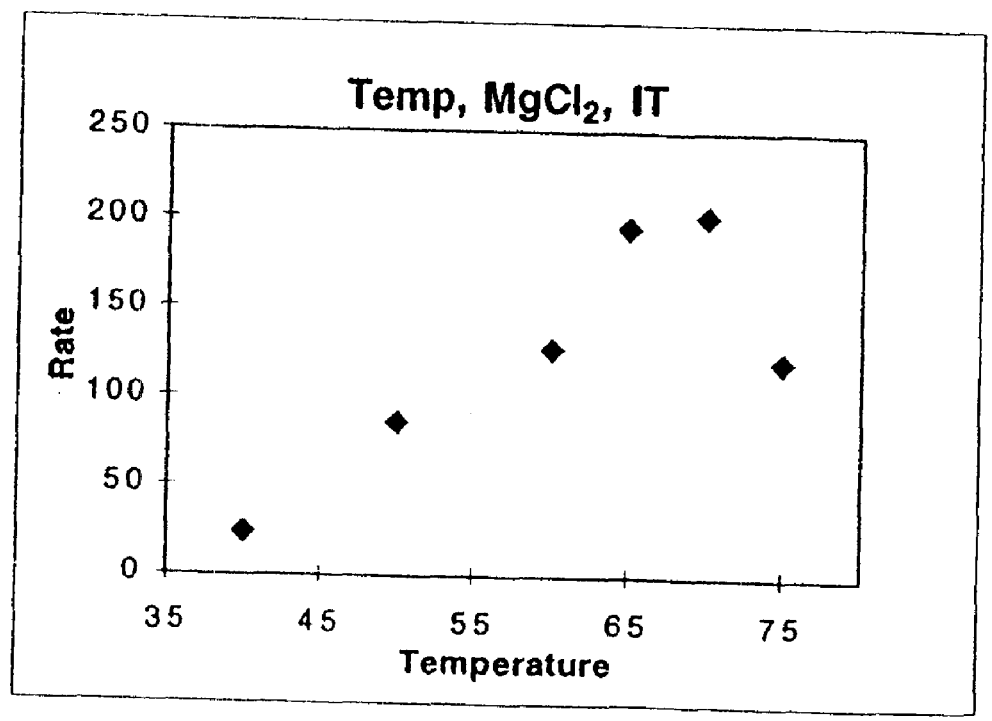
Figure 101J:
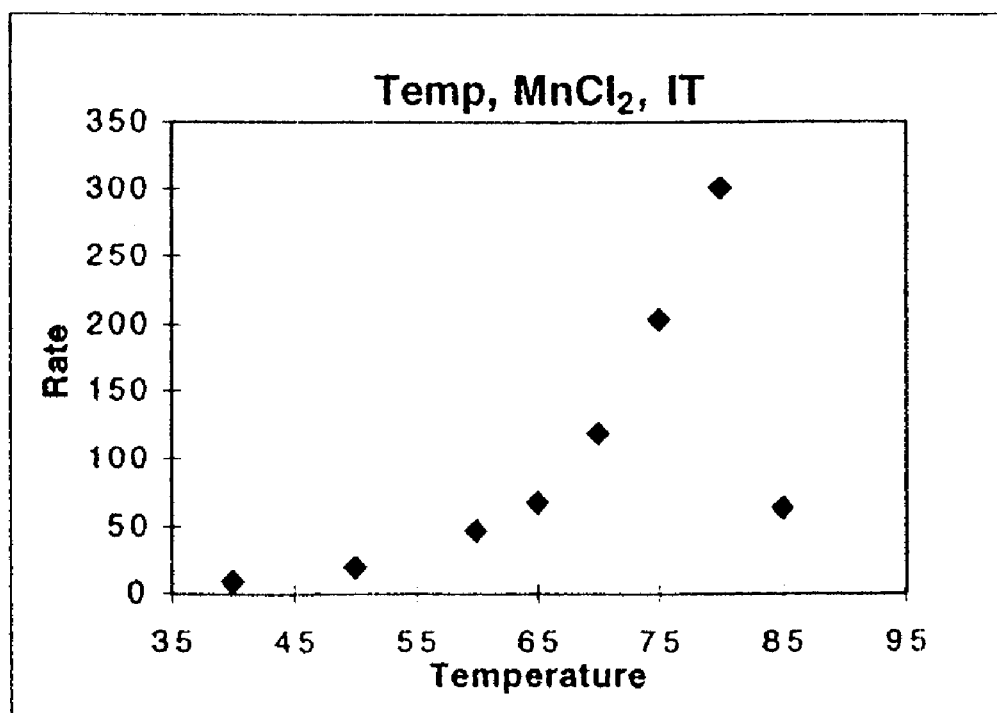
Figure 102A:
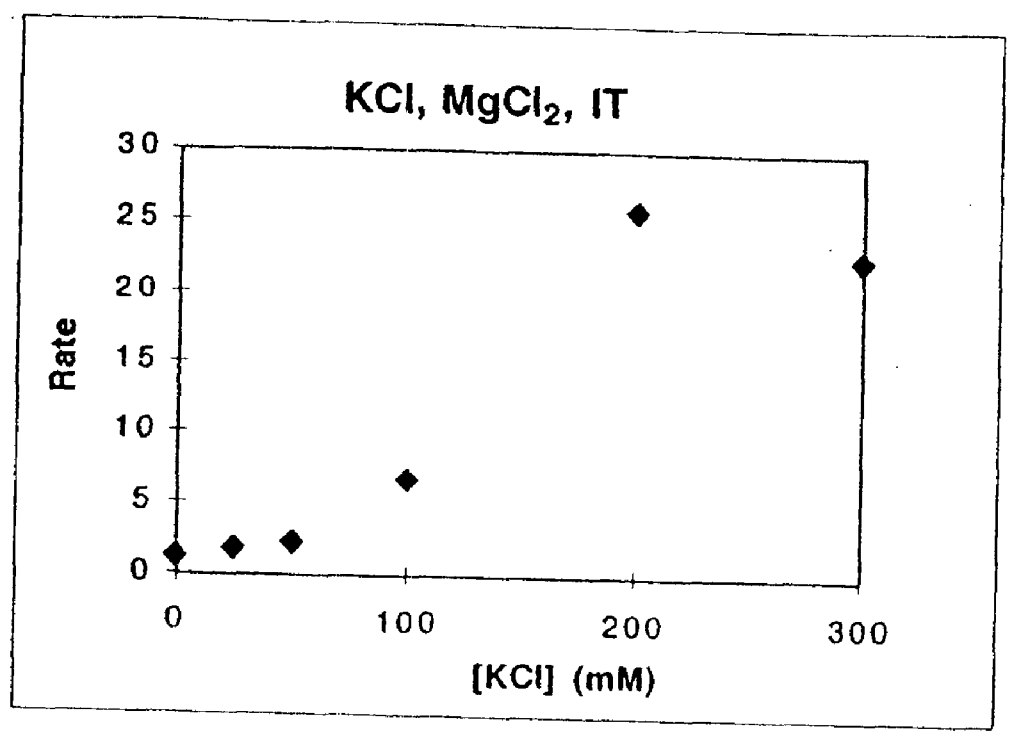
FIGS. 102A–B, D–F, H–J show the results of various assays used to determine the activity of TthDN under various conditions.
Figure 102B:
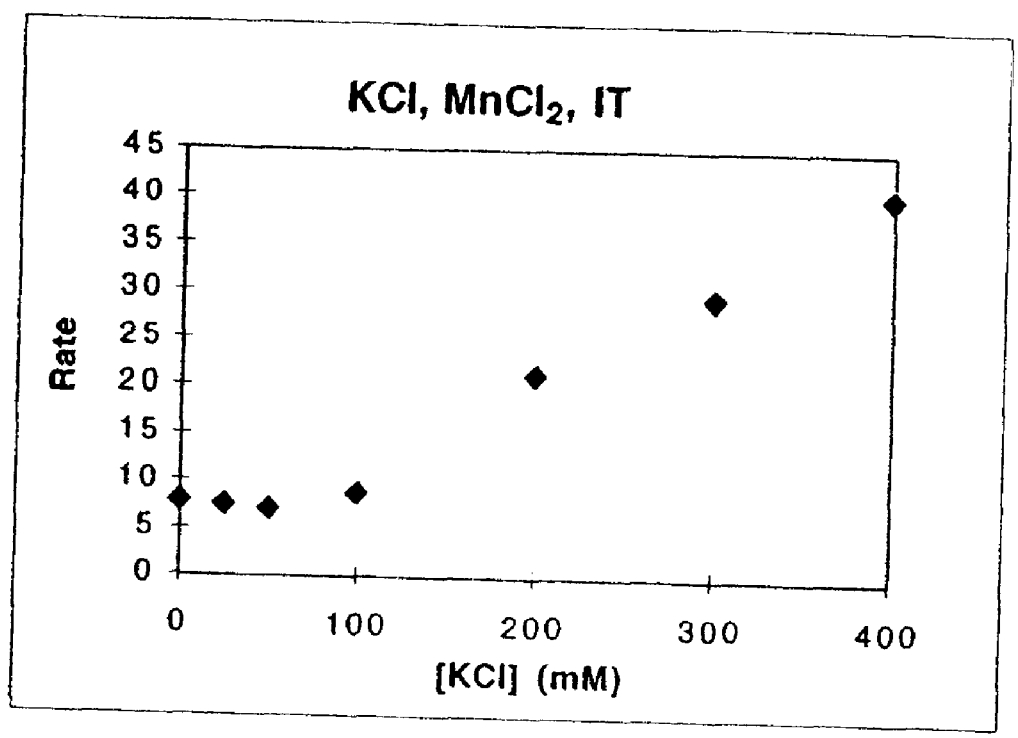
Figure 102D:
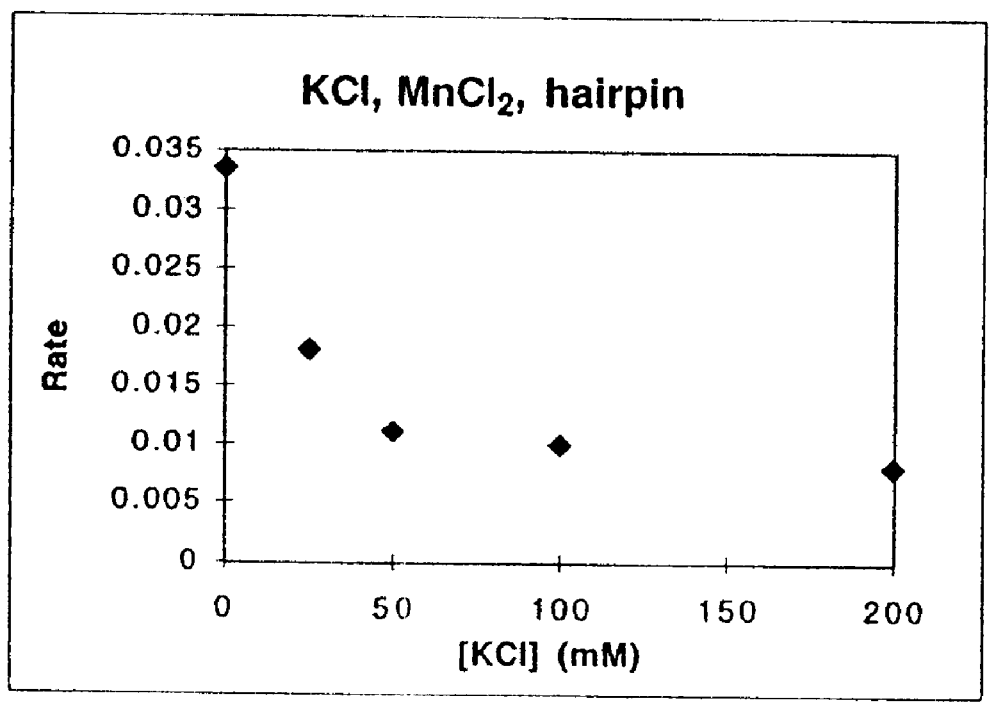
Figure 102E:
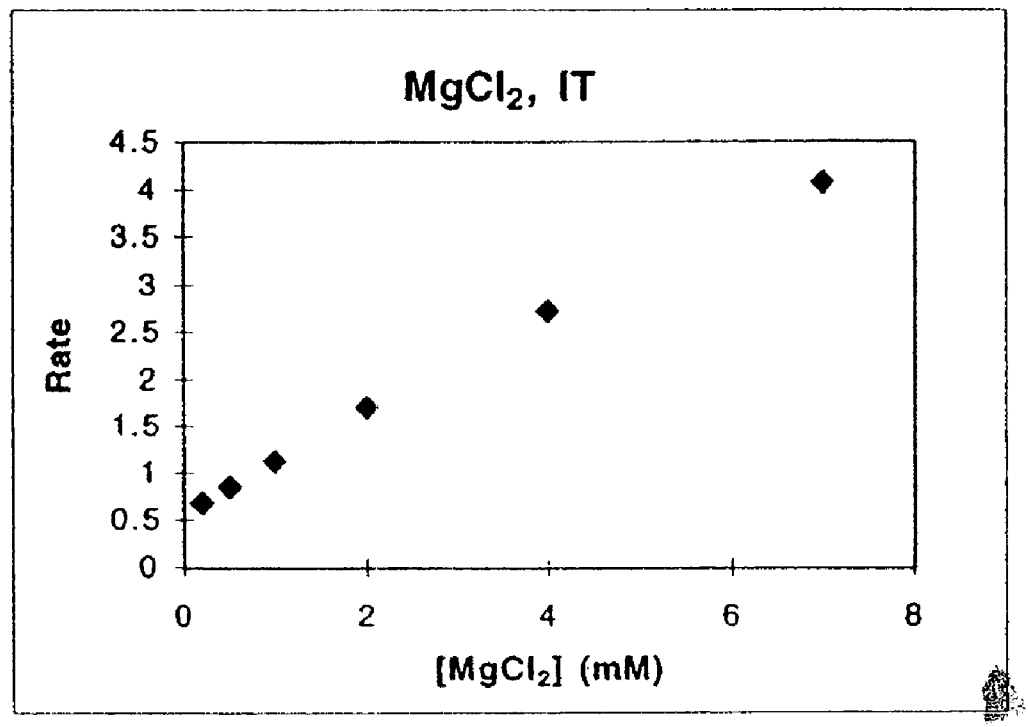
Figure 102F:
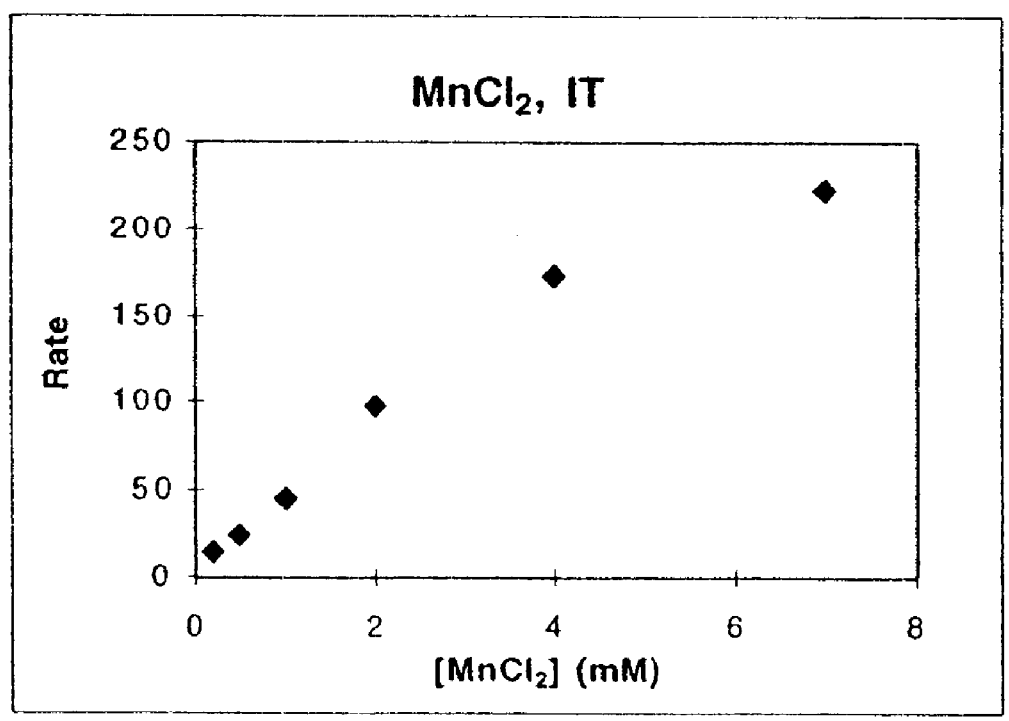
Figure 102H:
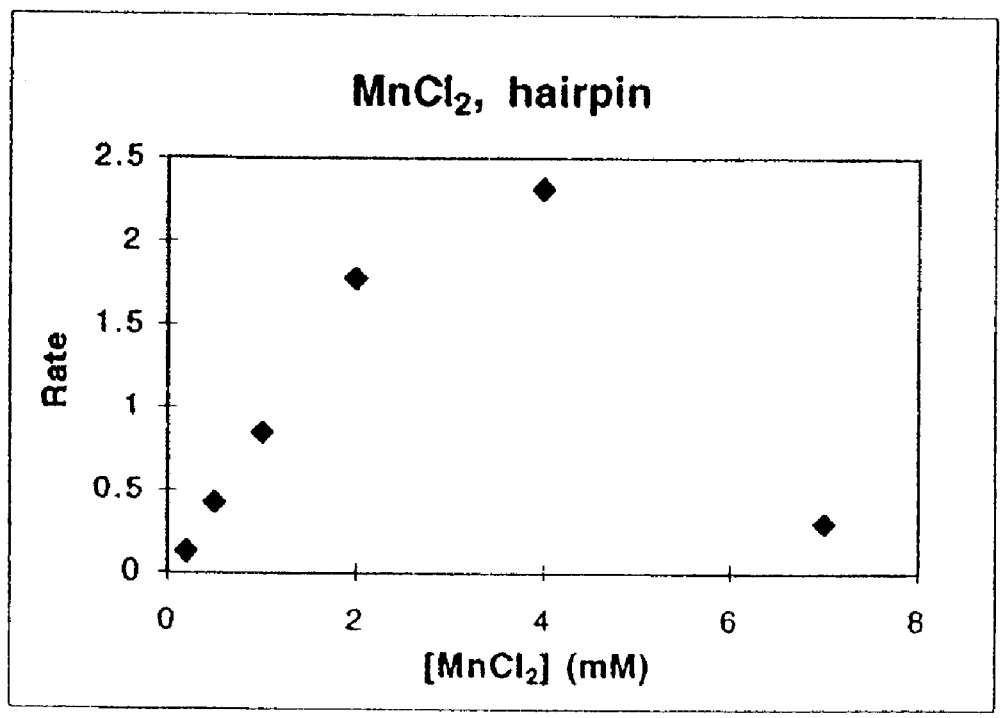
Figure 102I:
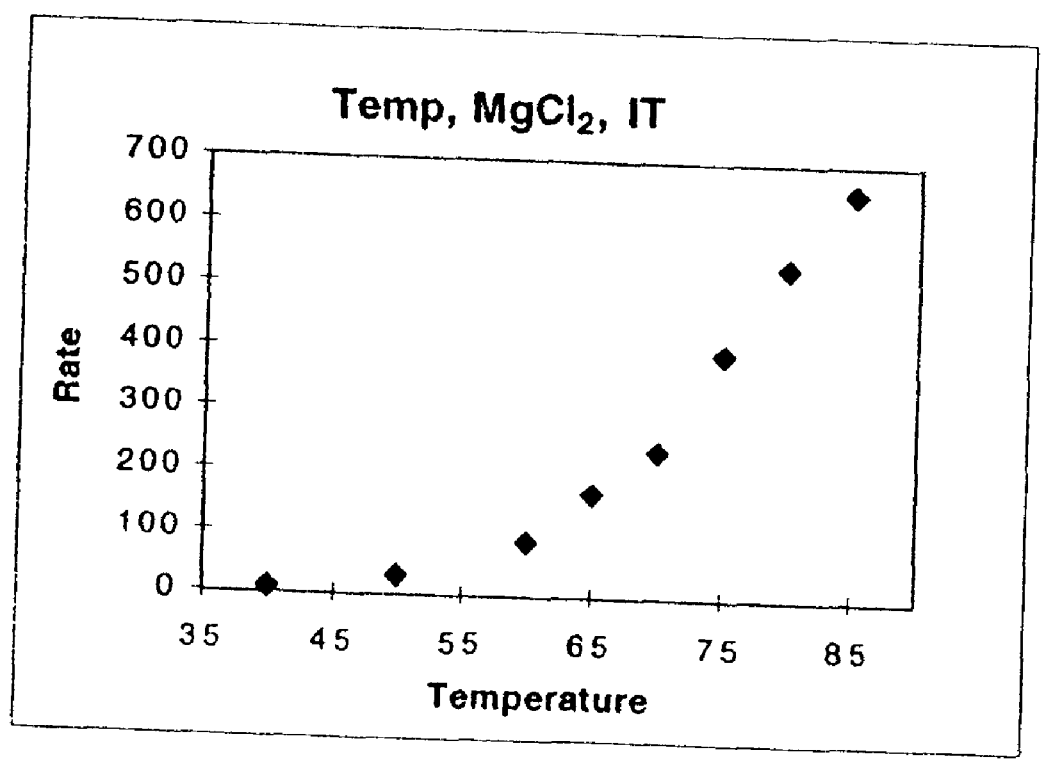
Figure 102J:
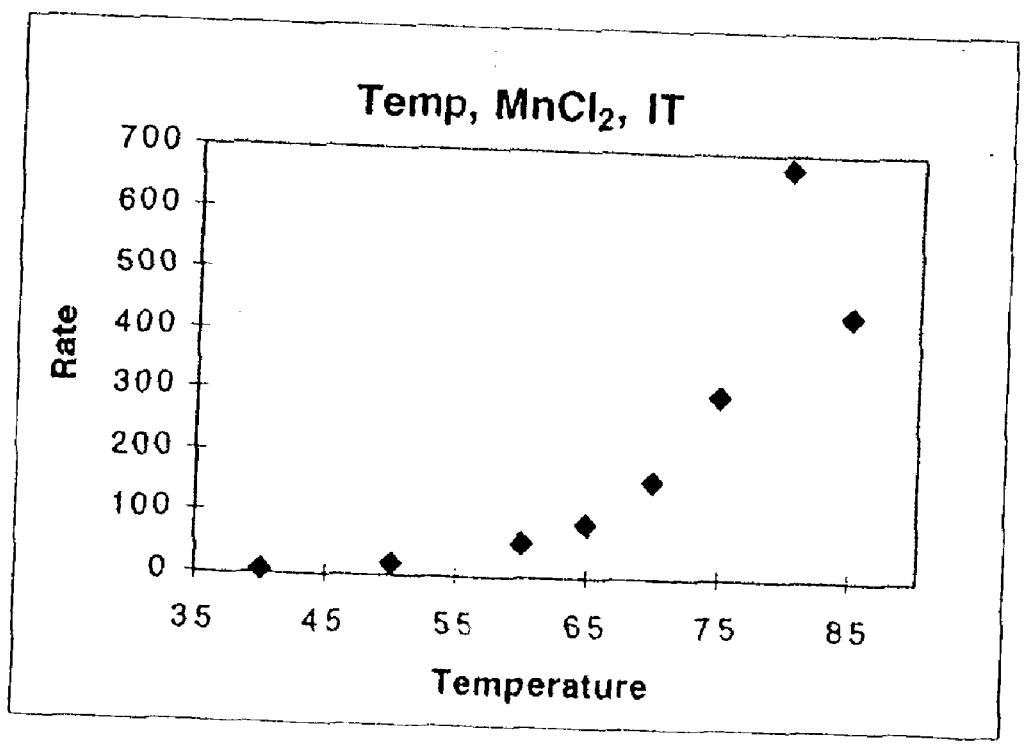
Figure 103A:
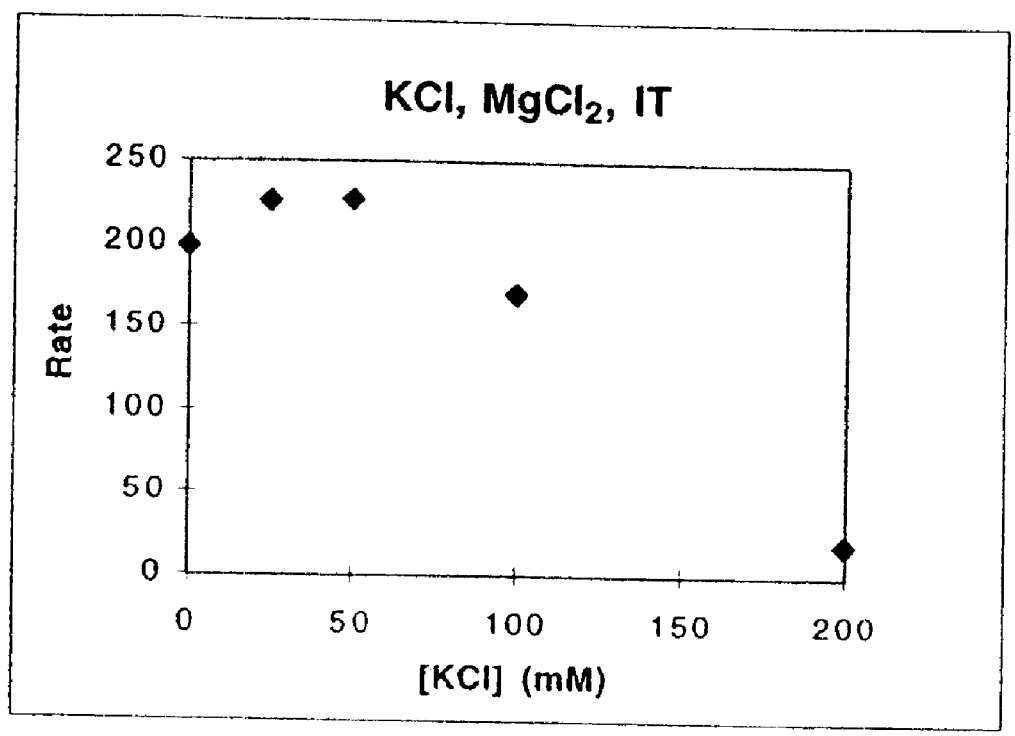
FIGS. 103A–B, D–F, and H–J show the results of various assays used to determine the activity of Pfu FEN-1 under various conditions.
Figure 103B:
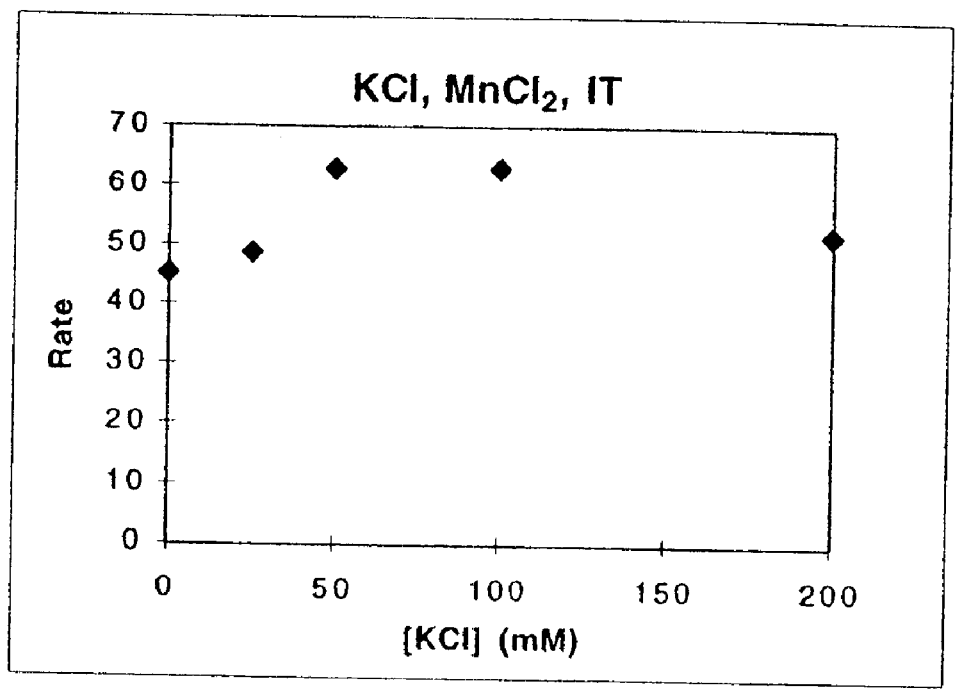
Figure 103D:
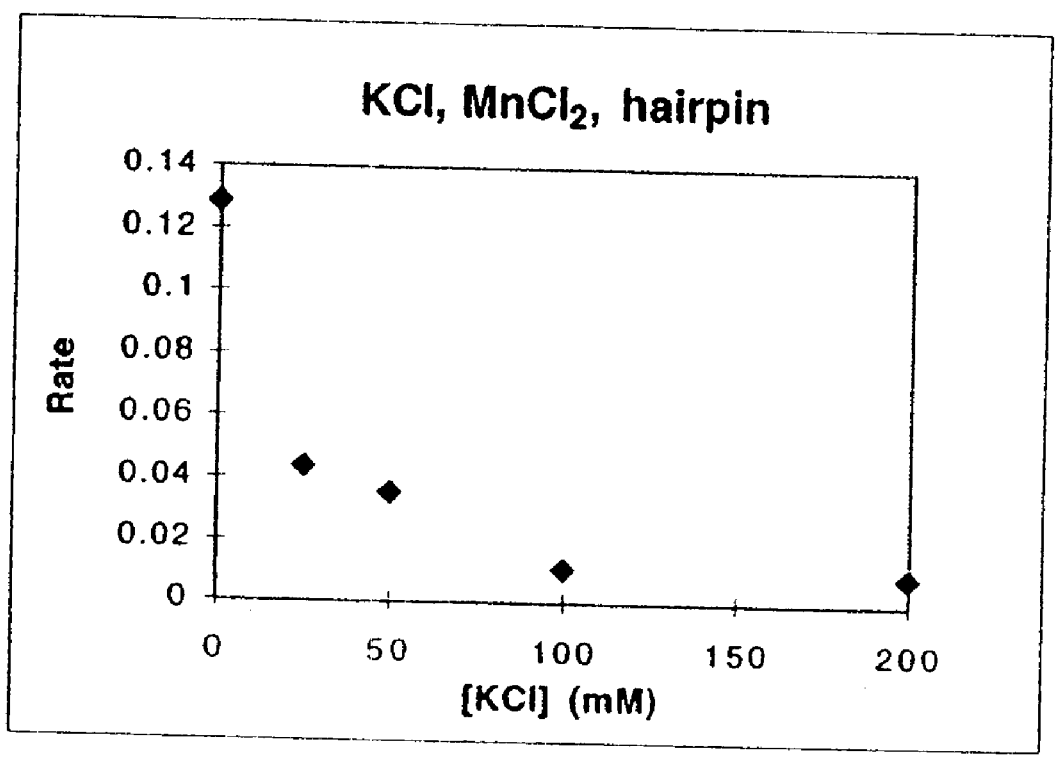
Figure 103E:
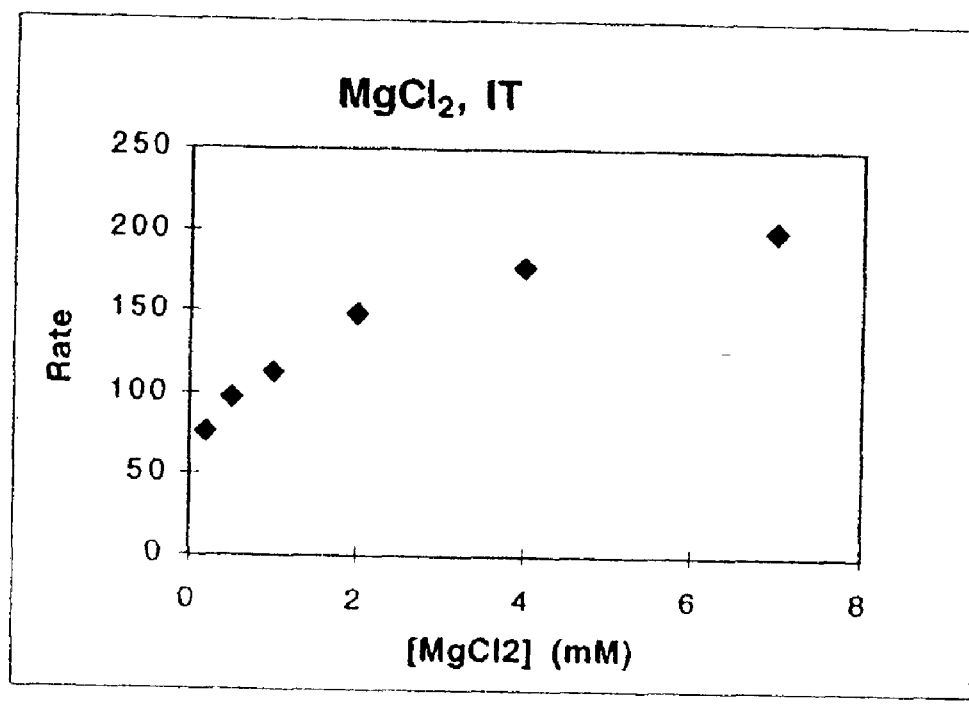
Figure 103F:
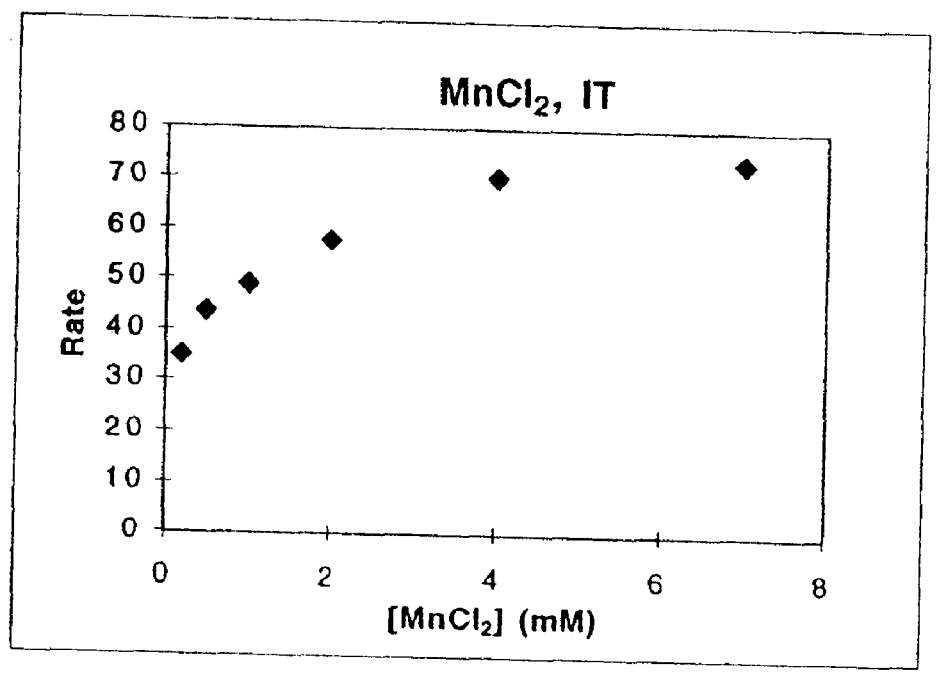
Figure 103H:
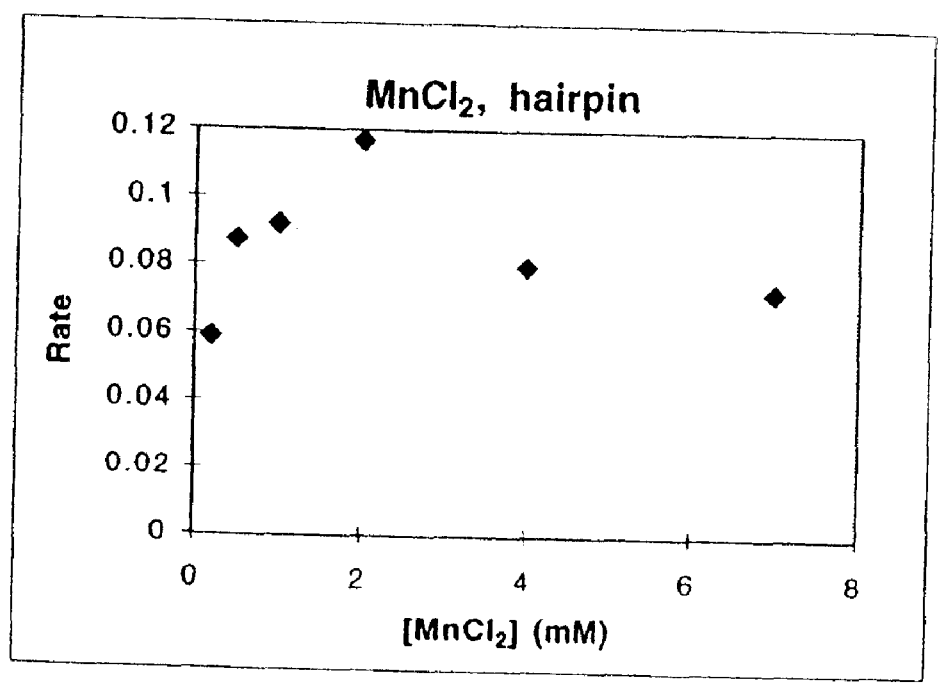
Figure 103I:
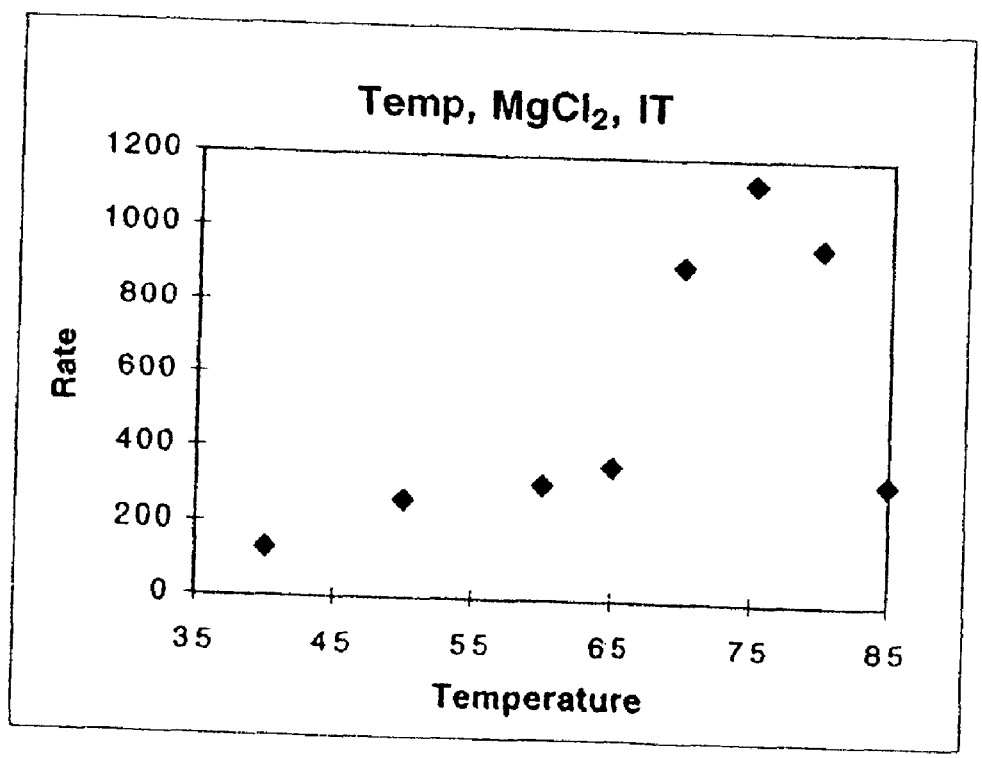
Figure 103J:
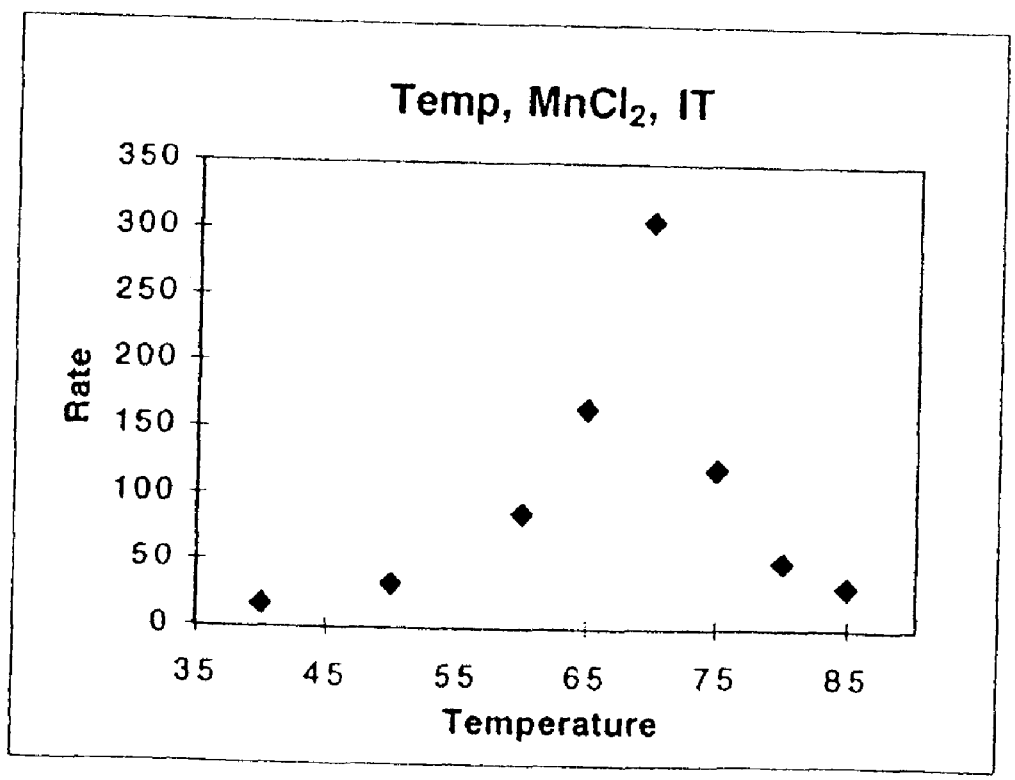
Figure 104A:
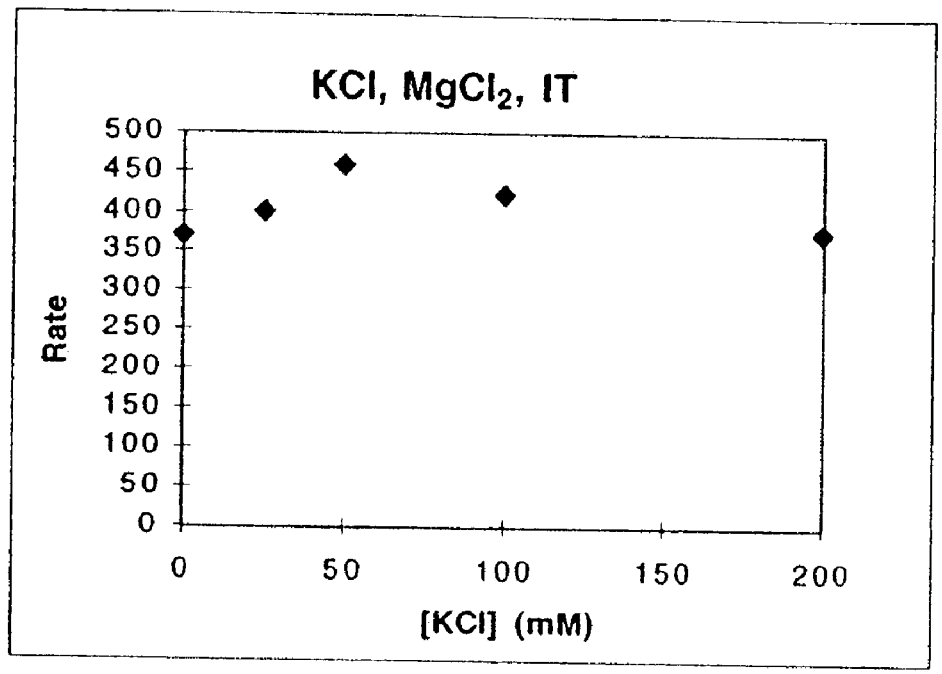
FIGS. 104A–J show the results of various assays used to determine the activity of Mja FEN-1 under various conditions.
Figure 104B:
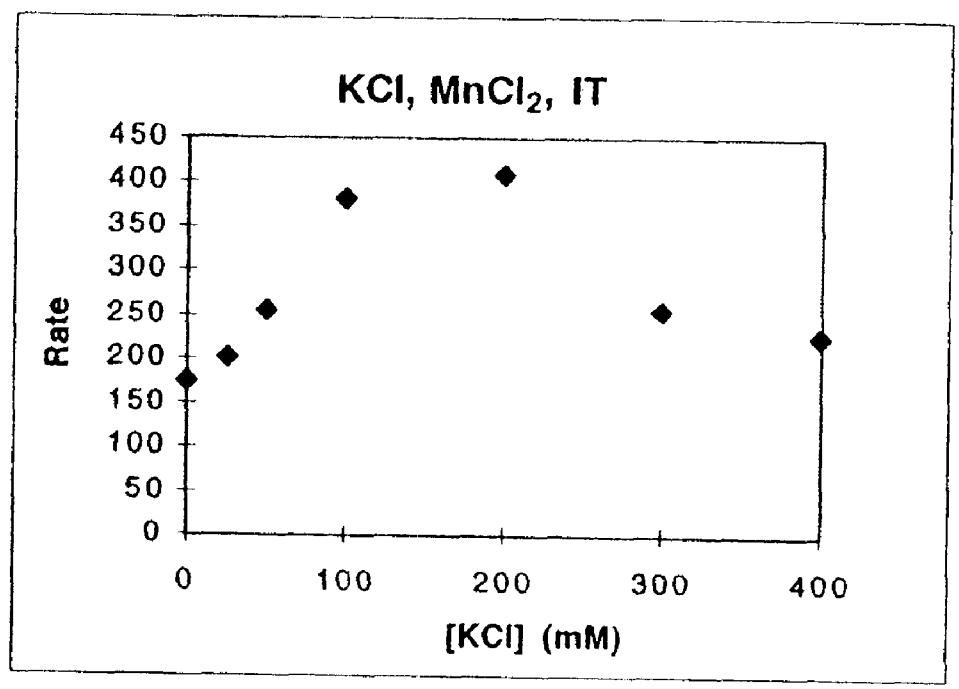
Figure 104C:
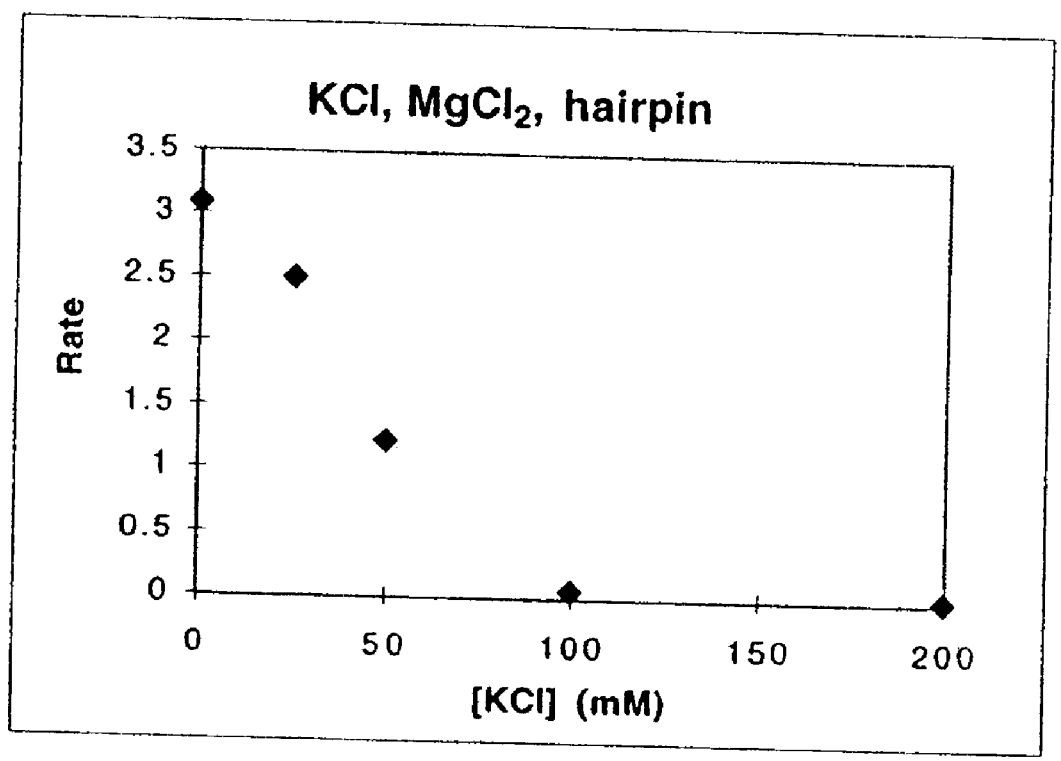
Figure 104D:
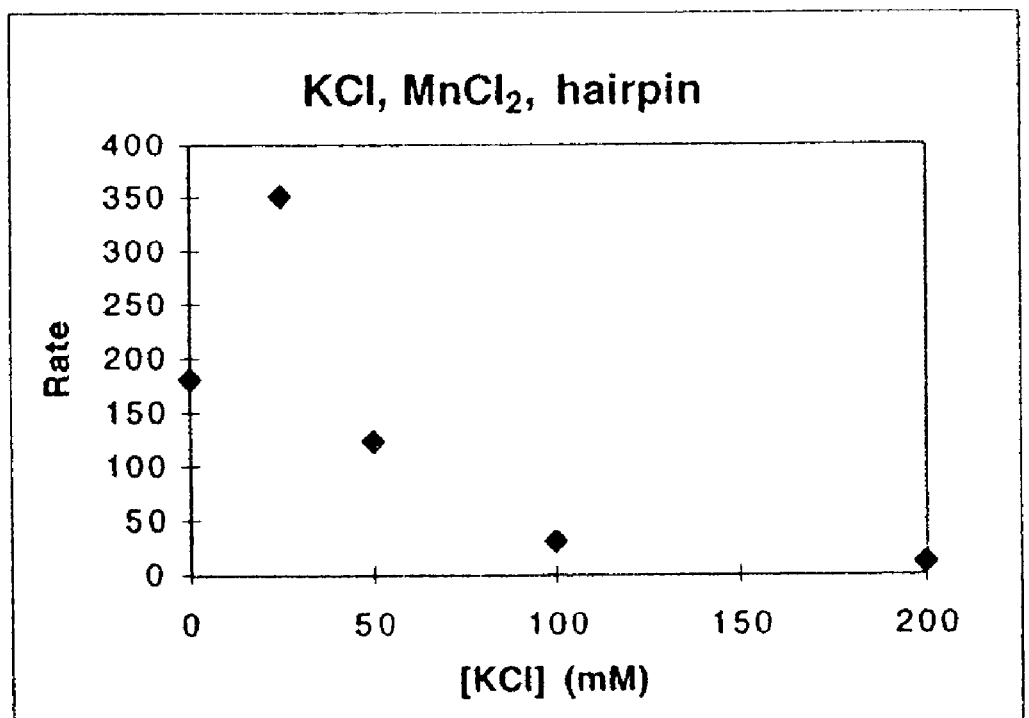
Figure 104E:
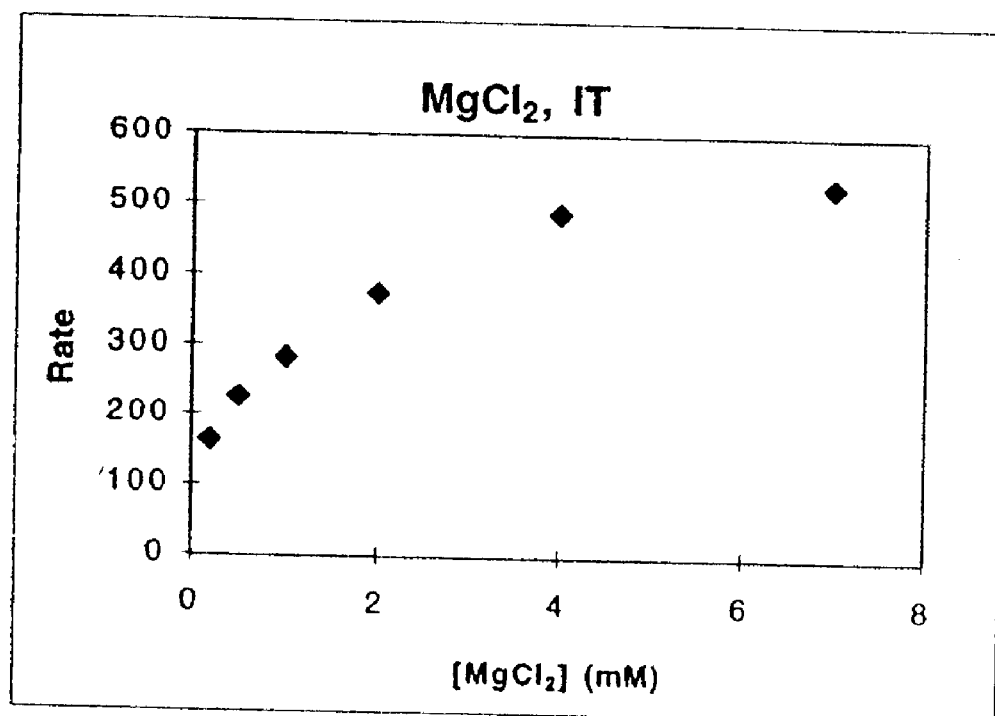
Figure 104F:
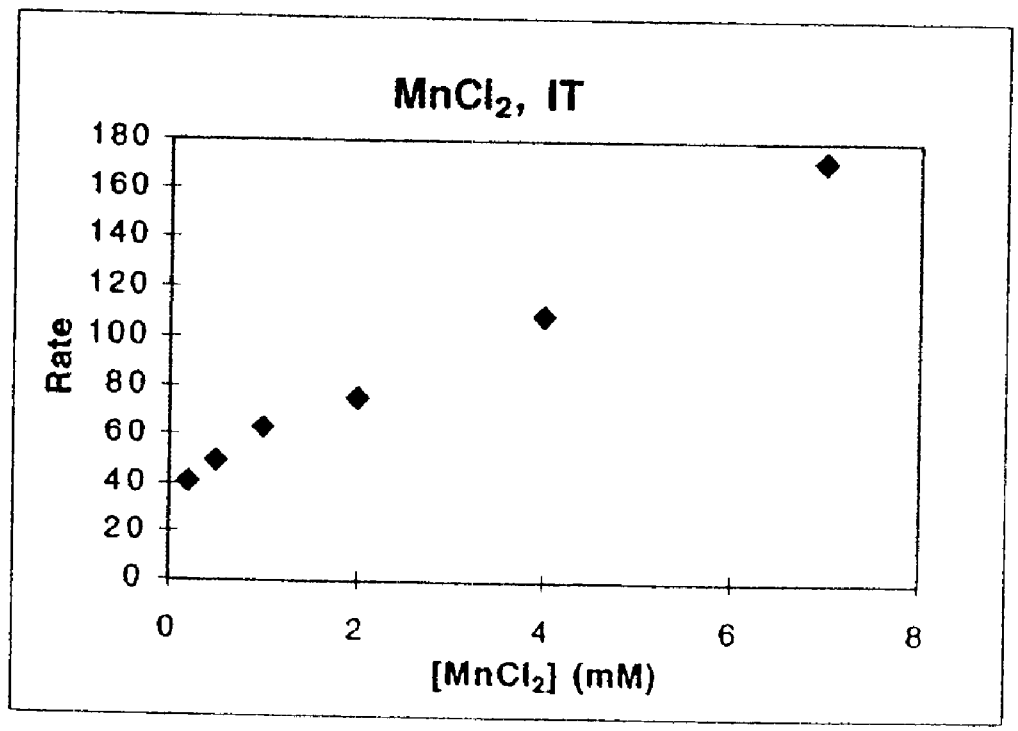
Figure 104G:
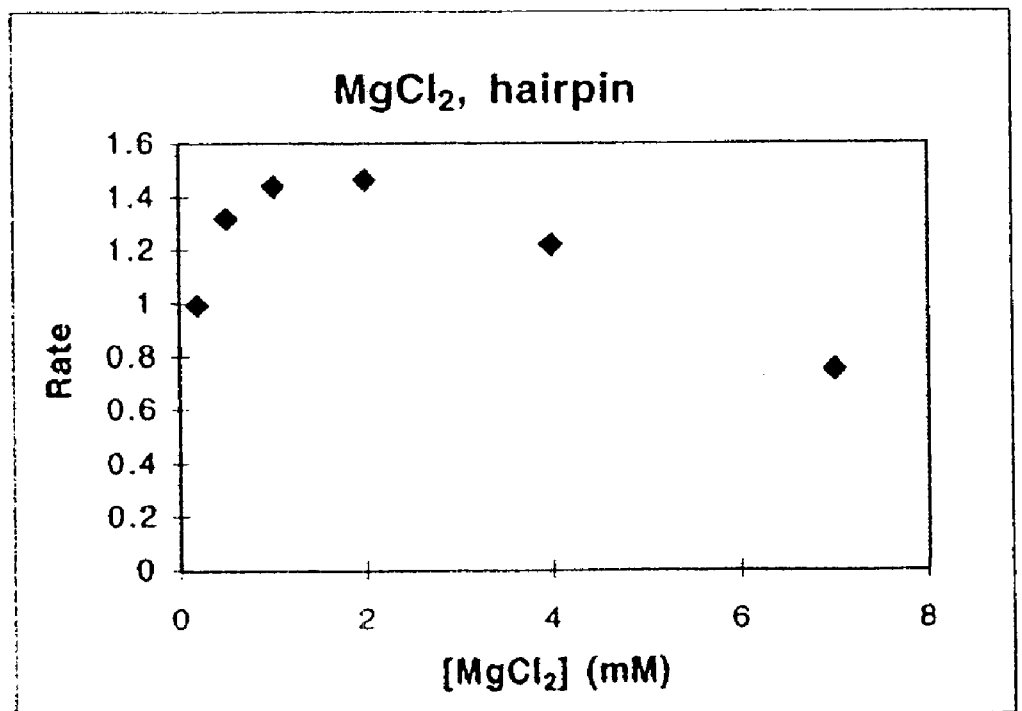
Figure 104H:
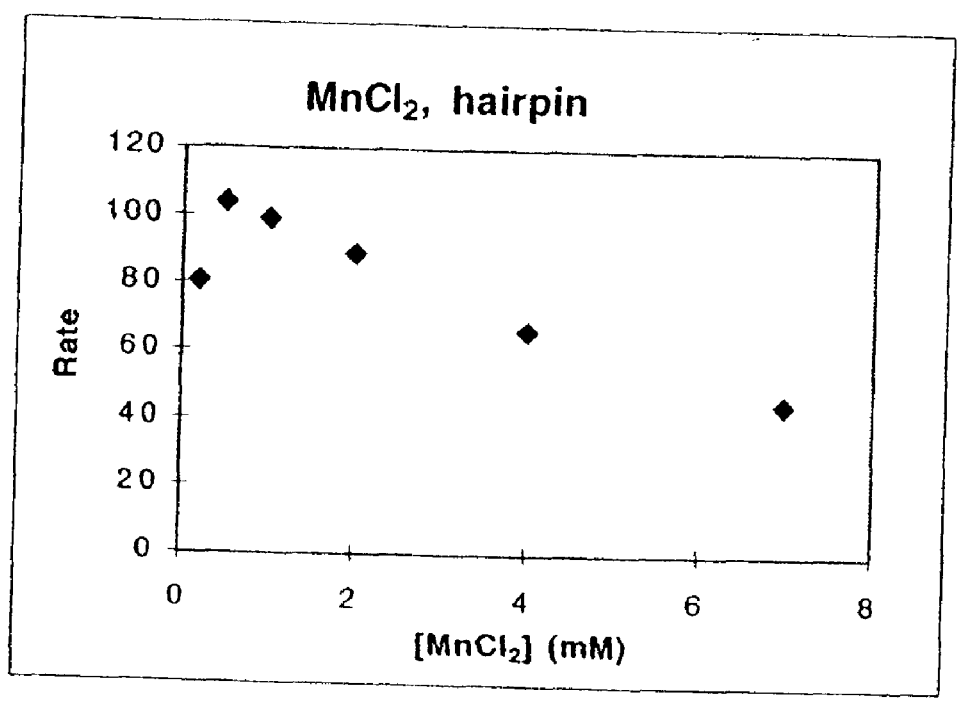
Figure 104I:
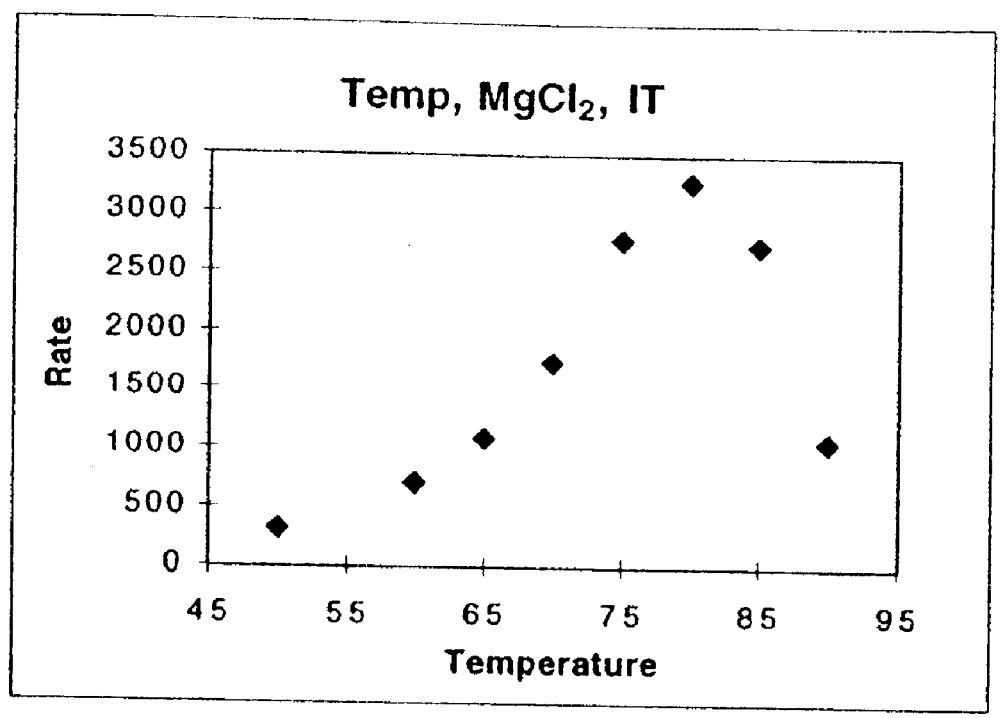
Figure 104J:
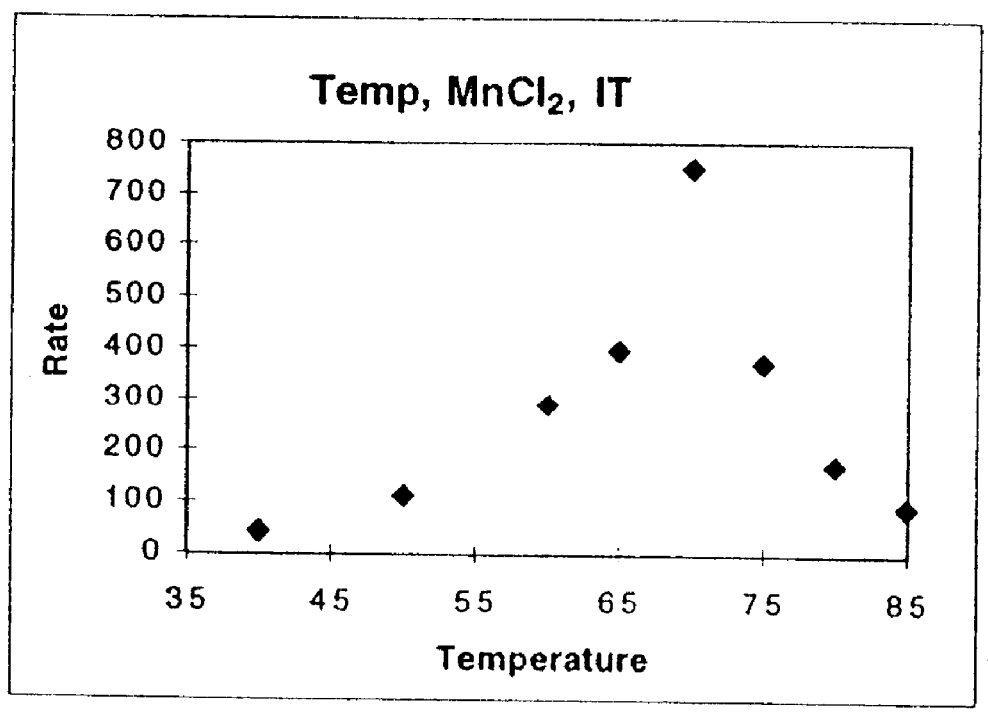
Figure 105A:
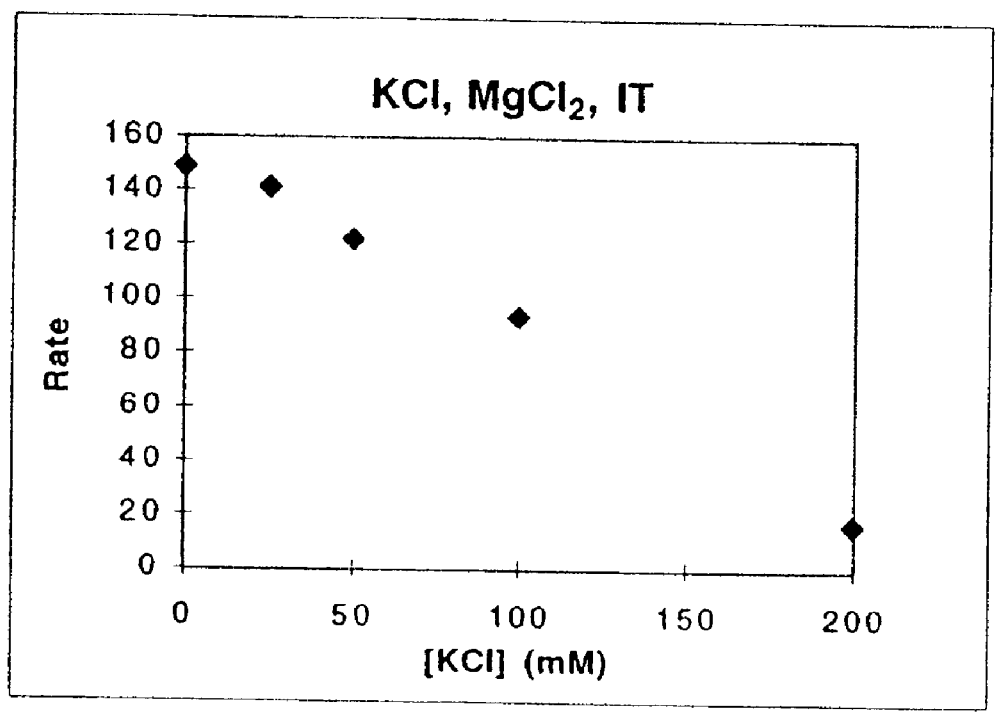
FIGS. 105A–B, D–F, and H–J show the results of various assays used to determine the activity of Afu FEN-1 under various conditions.
Figure 105B:
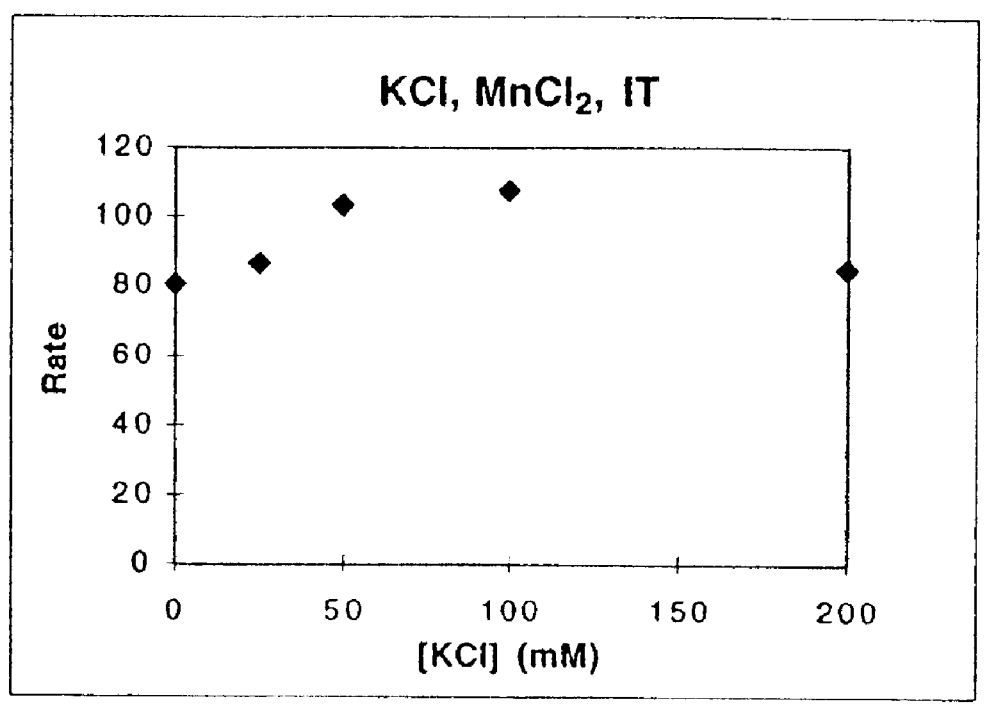
Figure 105D:
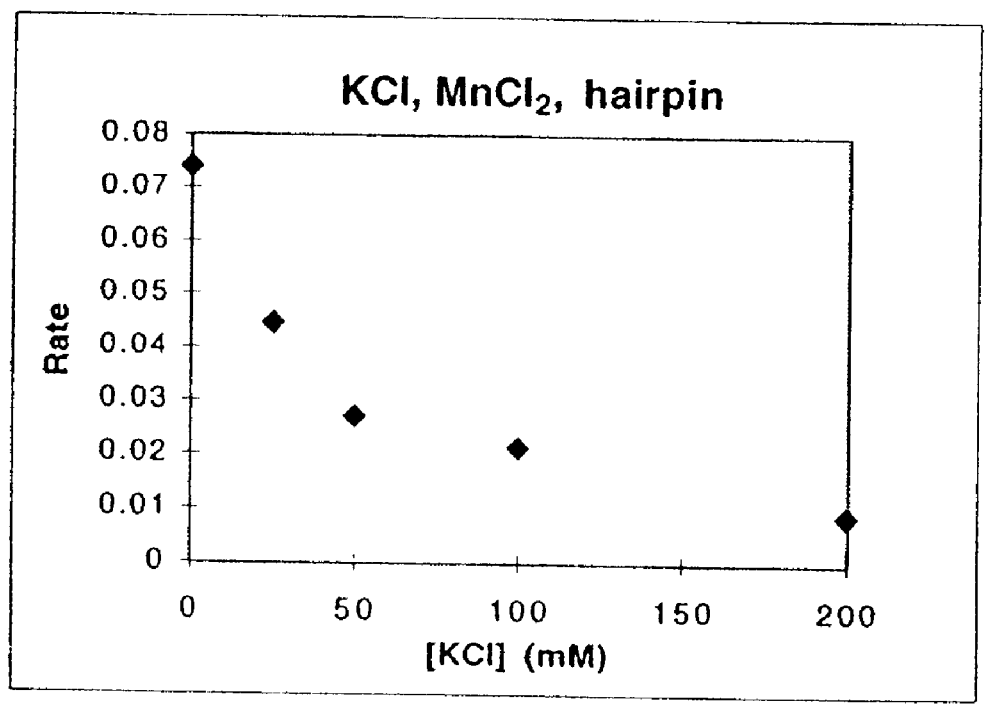
Figure 105E:
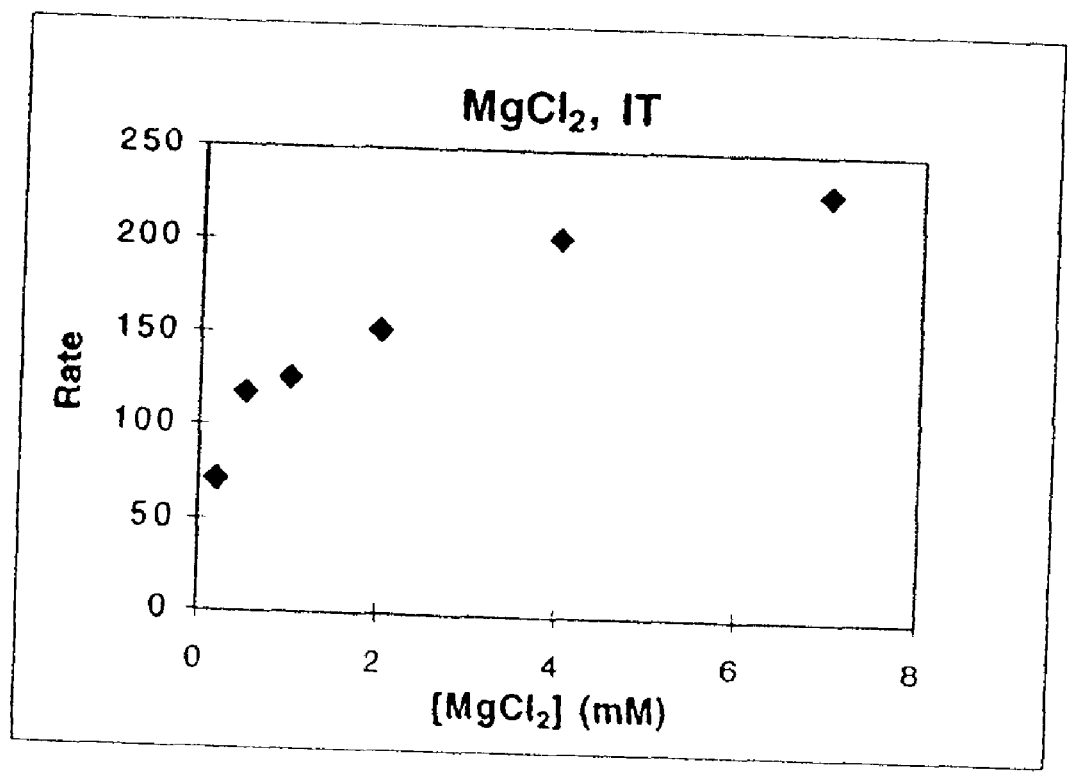
Figure 105F:
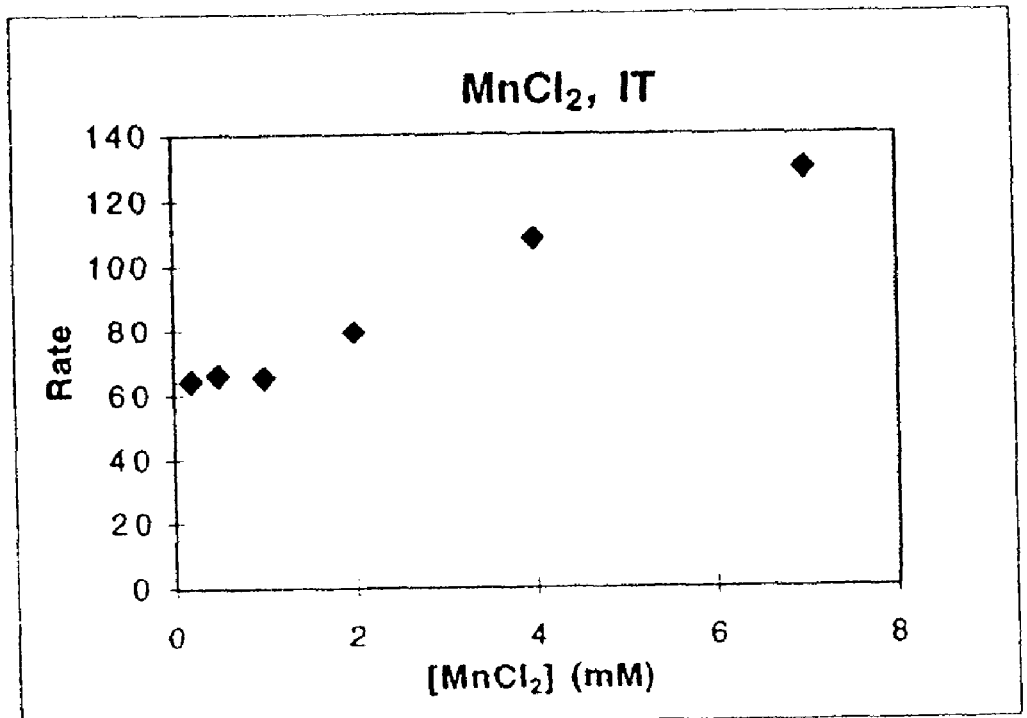
Figure 105H:
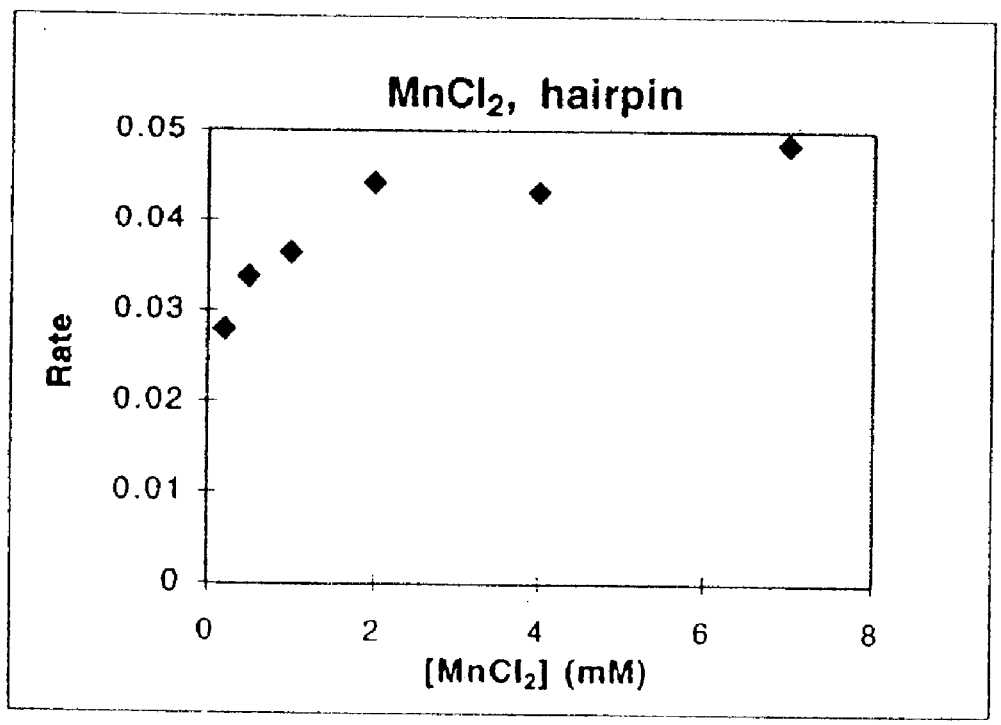
Figure 105I:
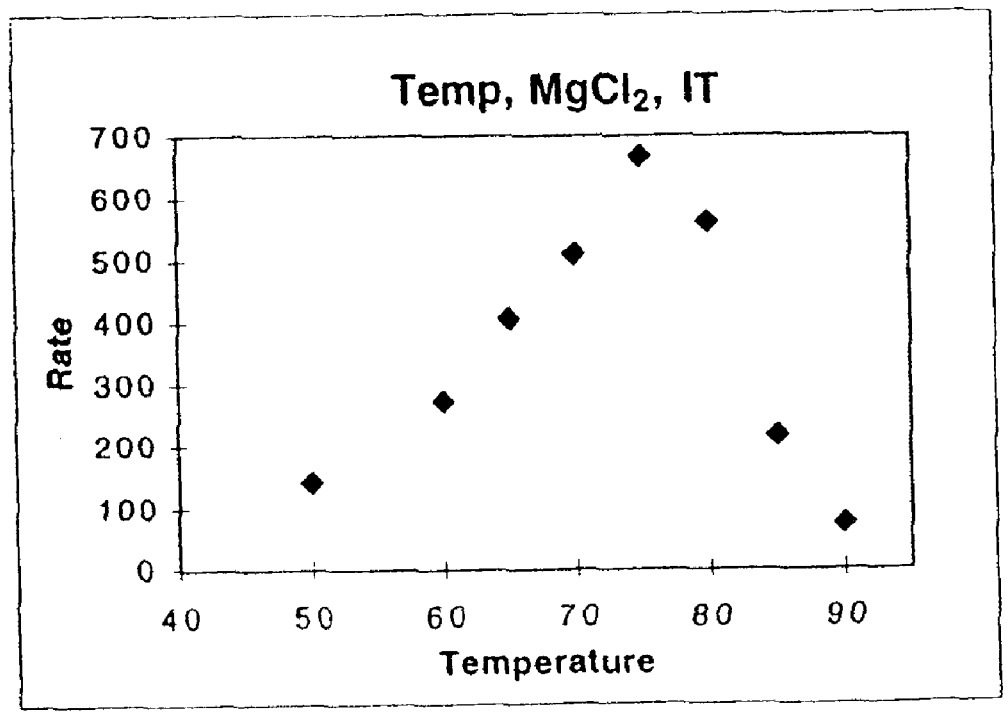
Figure 105J:
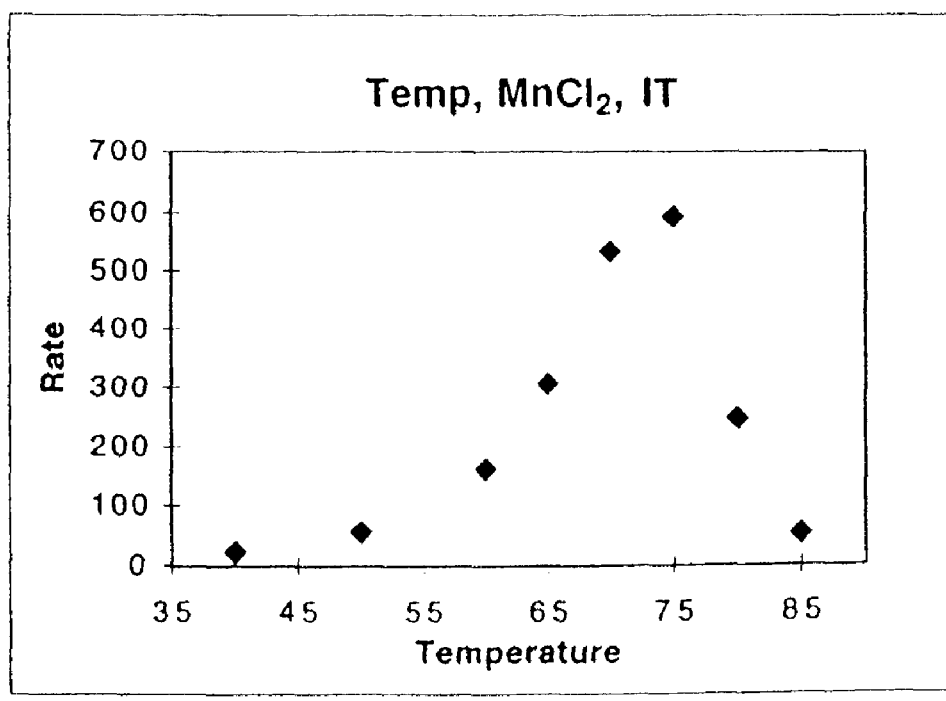
Figure 106A:
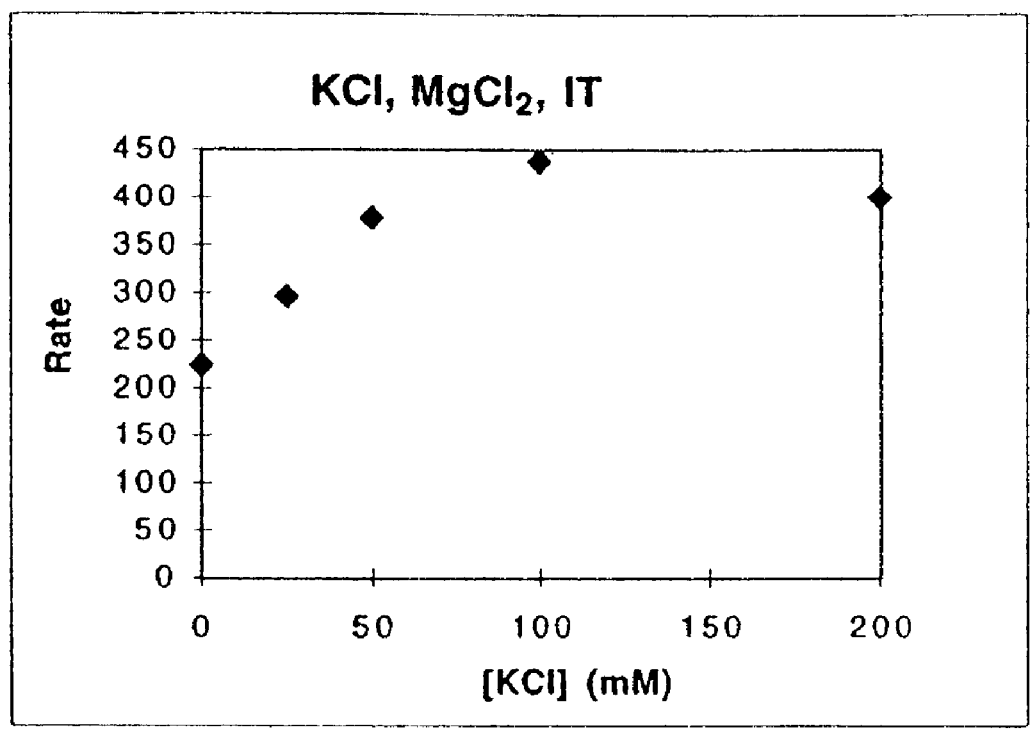
FIGS. 106A–J show the results of various assays used to determine the activity of Mth FEN-1 under various conditions.
Figure 106B:
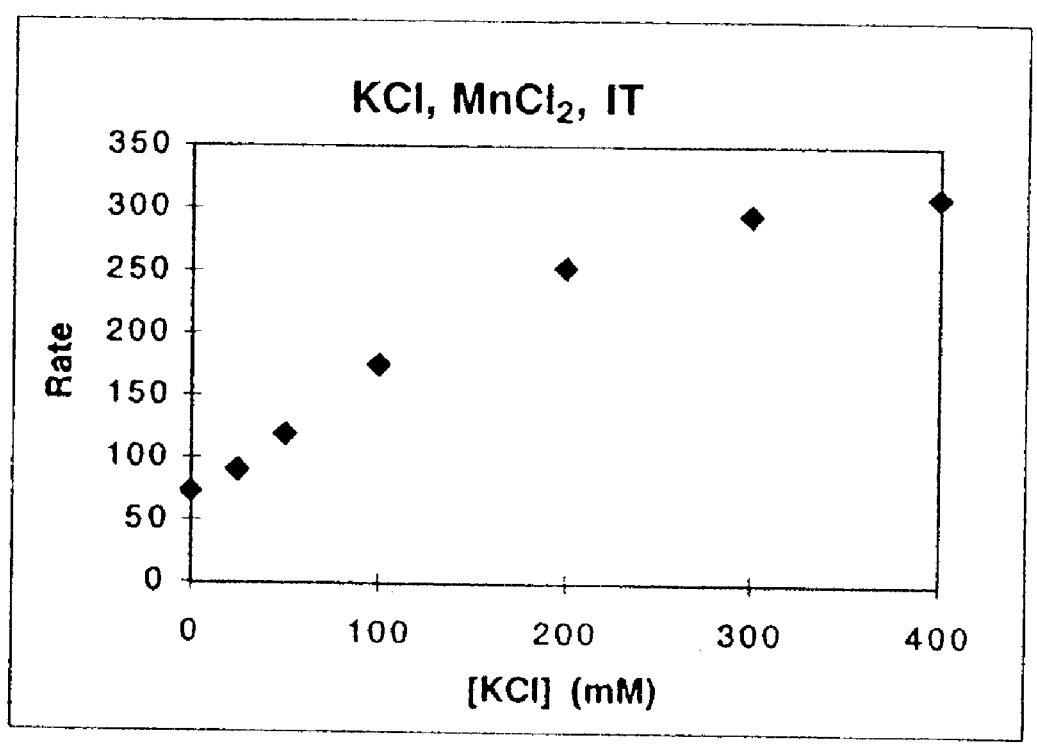
Figure 106C:
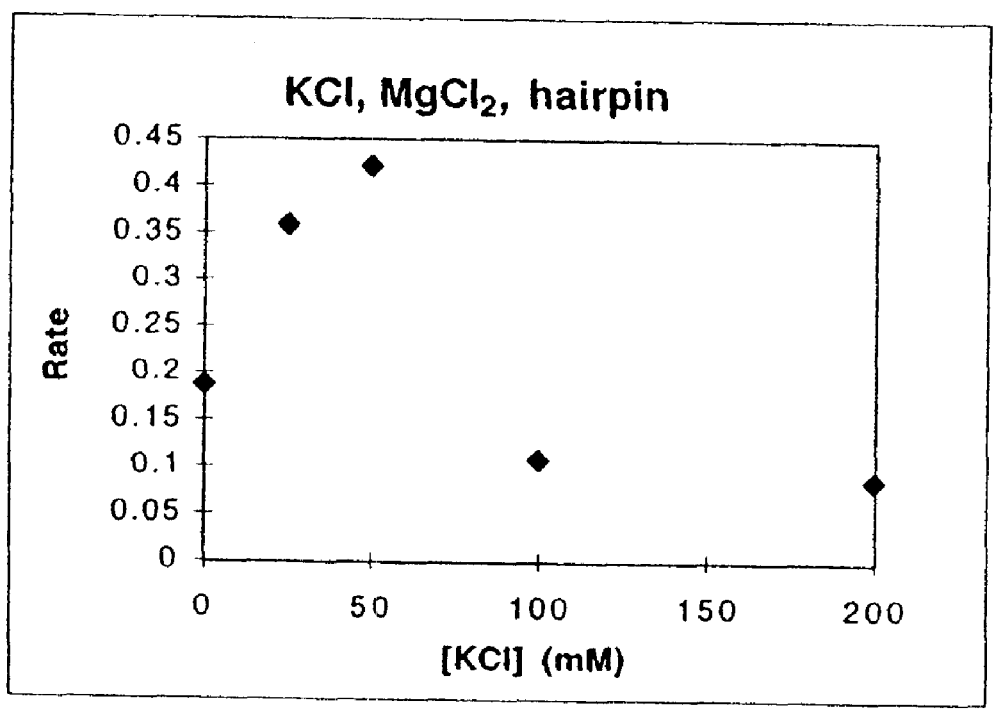
Figure 106D:
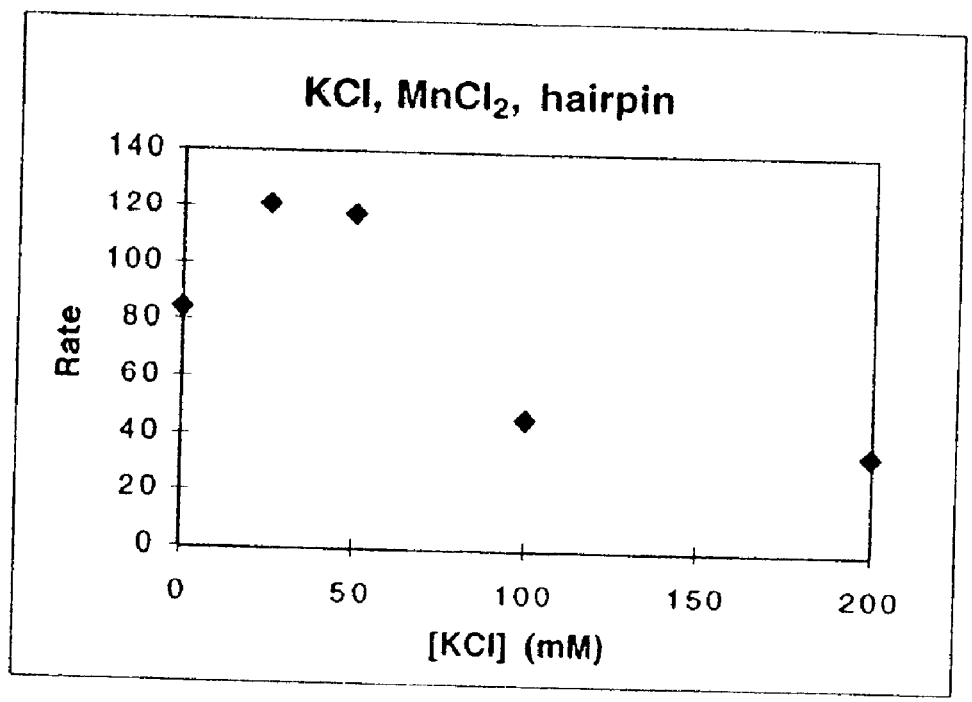
Figure 106E:
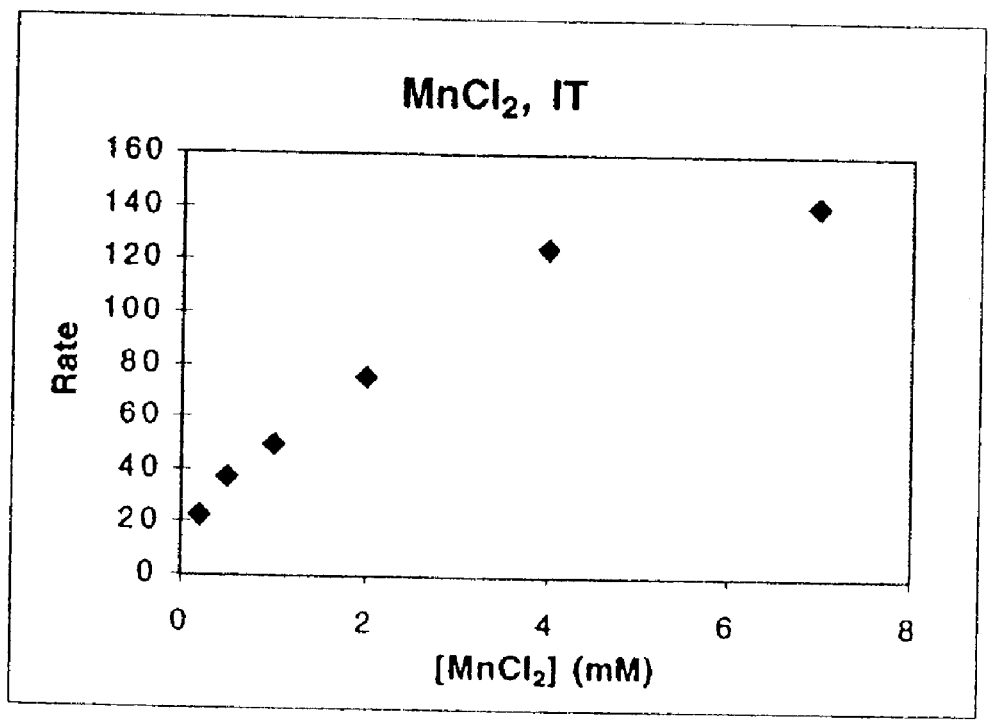
Figure 106F:
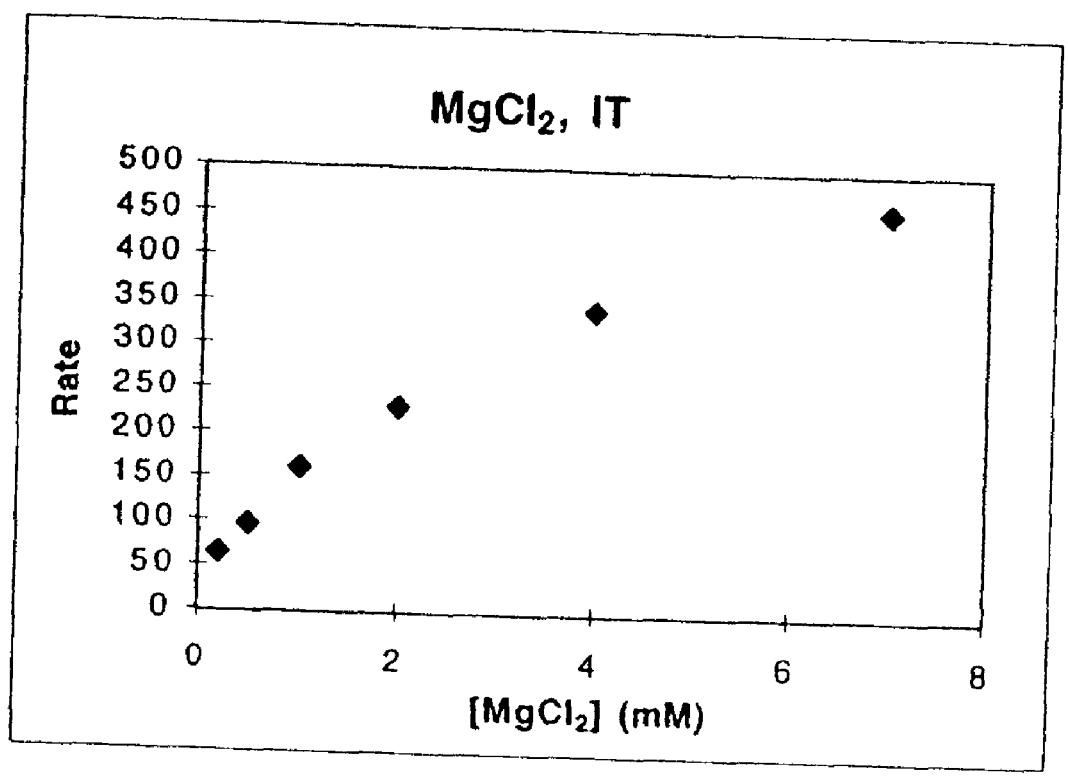
Figure 106G:
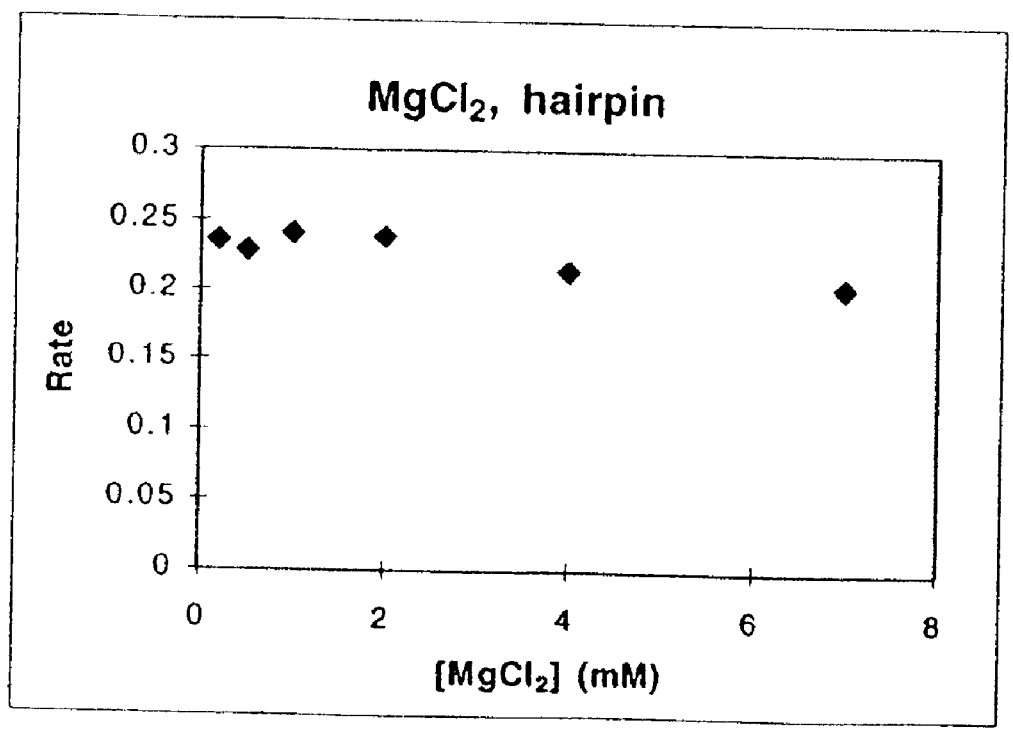
Figure 106H:
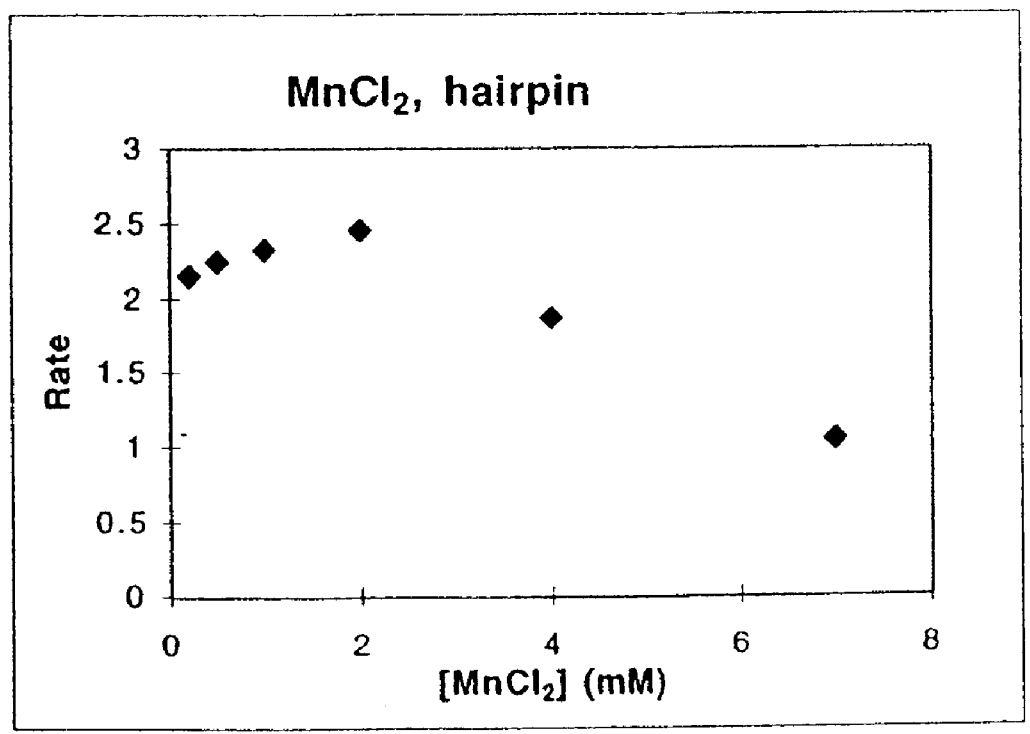
Figure 106I:
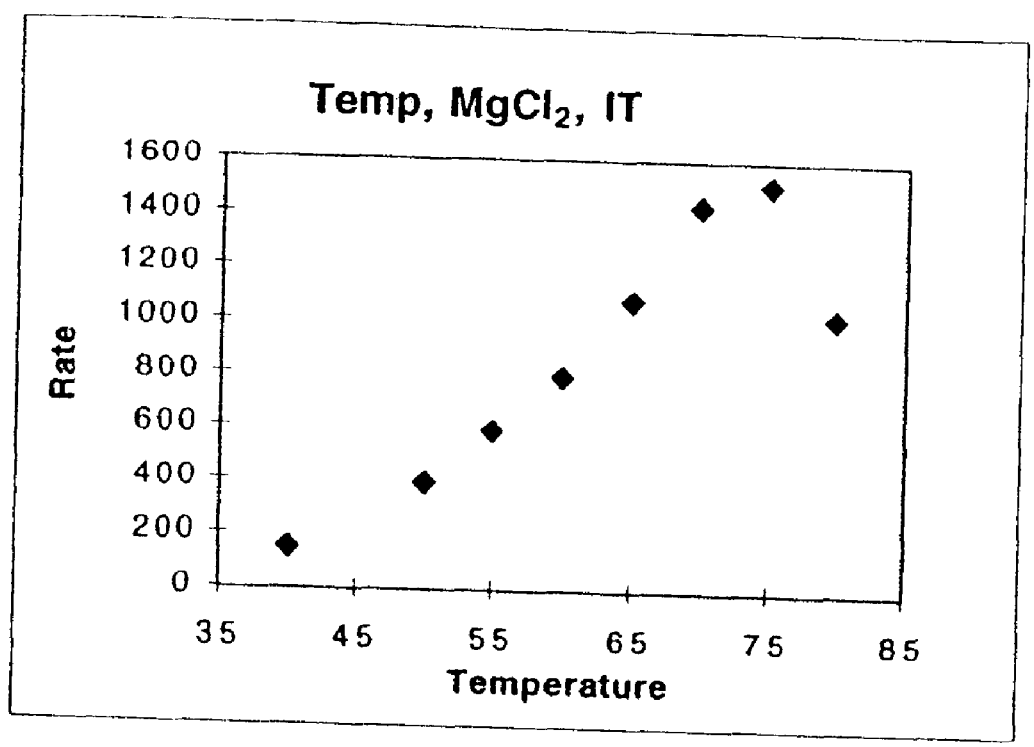
Figure 106J:
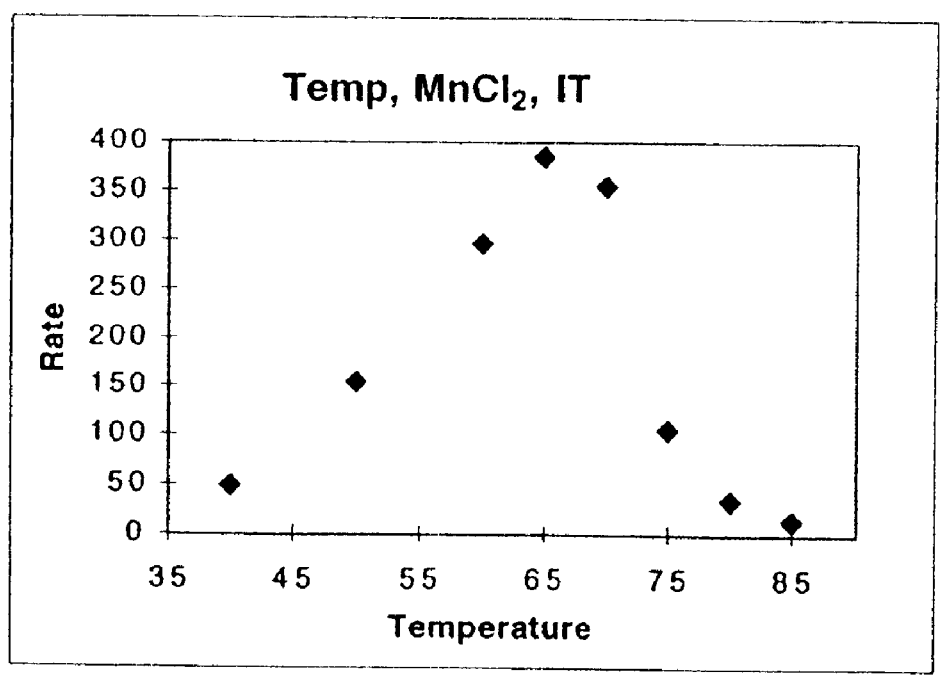

Reaction mixtures were heated at 85° C. for 2 min, and were then resolved by electrophoresis through a 10% denaturing polyacrylamide gel (19:1 cross link) with 7M urea in a buffer of 45 mM Tris-Borate, pH 8.3, 1.4 mM EDTA, and were visualized using the FMBIO-100 Image Analyzer (Hitachi). The resulting scanned image is shown in FIG. 99. In this Figure, the enzymes used in each digest are indicated at the top of each lane. Cleavase® BN is described in Ex. 2. Lane 2 shows the results of digestion with the Mja FEN-1 parent nuclease, while digests with the chimerical nucleases are indicated by reference to the diagrams in FIG. 97. These data show that the use of each of these nucleases under identical reaction conditions (i.e., conditions in which the DNA assumes similar folded structures) can produce distinct pattern differences, indicating differences in the specificities of the enzymes. Thus, each enzyme can provide additional information about the folded structure assumed by a nucleic acid of interest, thereby allowing more accurate comparisons of molecules for identification, genotyping, and/or mutation detection.

These data show that the activities of these enzymes may vary substantially in similar reaction situations. The performance of an optimization panel for an unknown enzyme can help in selection of the optimal enzyme and conditions for a given application. For example, in the invasive cleavage reactions it is often desirable to choose a combination of nuclease and conditions that perform invasive cleavage, but that do not exhibit activity in the absence of the invader oligonucleotide (i.e., do not cut a hairpin type substrate). The optimization panel allows selection of conditions that do not favor hairpin cleavage, such as the use of the Pfu FEN-1 enzyme in a $MgCl_2$-containing solution. Conversely, hairpin cleavage is desirable for CFLP-type cleavage, so it is contemplated that reaction conditions be screened accordingly for strength in this activity.

EXAMPLE 43

Characterization of Performance of Structure-Specific Nucleases

Two substrates were used to determine the optimal conditions for seven enzymes, Afu, Pfu, Mth and Mja FEN-1s, Cleavase® BN, Taq DN and Tth DN. As shown in FIG. 107 Panel A, Substrate 25-65-1 (5'-Fluorescein-TTTTCGCTGTCTCGCTGAAAGCGAGACAGCGTTT-3'; SEQ ID NO:176) is a stem-loop structure with a 5' arm labeled at its 5' end with fluorescein. As shown in FIG. 107 Panel B, substrate 25-184-5 (Invader-like "IT" test substrate") (5'-Fluorescein-TTTTCGCTGTCTCGCTG AAAGCGAGACAGCGAAAGACGCTCGTGAAACGA GCGTCTTTG-3'; SEQ ID NO:177) is a substrate with an upstream primer adjacent to the 5' fluoroscein labled arm; this mimics an invader oligo and target ("IT"). Standard reactions contained 2 µM labeled substrate, 10 mM MOPS, pH7.5, 0.05% TWEEN 20, 0.05% NP-40, 20 µg/ml tRNA (Sigma # R-5636) and 2 mM $MgCl_2$ or 2 mM $MnCl_2$. Ten µl reactions were heated to 90° C. for 15 seconds in the absence of enzyme and divalent cation, after which the reactions were cooled to room temperature and enzyme was added. Reactions were heated to 50° C. for 20 seconds and divalent cation was then added to start the reaction. The incubation time varied from 1 minute to 1 hour depending on the particular enzyme/substrate combination. Reaction times were adjusted so that less than 25% of the substrate was cleaved during the incubation. Reactions were stopped with the addition of 10 µl of 95% formamide, 20 mM EDTA, methyl violet. One µl of each reaction was electrophoresed on a 20% denaturing acrylamide gel and then scanned on an FMBIO 100 scanner (Hitachi).

Divalent cation titrations varied $MgCl_2$ or $MnCl_2$ from 0.25 mM to 7 mM under otherwise standard conditions. Salt titrations varied KCl from 0 mM to 200 mM or 400 mM for salt tolerant enzymes under otherwise standard conditions. For temperature titrations, reactions with Cleavase® BN and the FEN-1 enzymes contained 50 mM KCl and 4 mM $MgCl_2$ or $MnCl_2$. Temperature titrations with Taq DN and Tth DN contained 200 mM KCl and 4 mM $MgCl_2$ or $MnCl_2$. Temperature was varied from 40° C. to 85° C. in 5 or 10 degree increments depending on the particular enzyme used.

The results are shown in FIGS. 100–106. FIG. 100 shows the results for Cleavase® BN, while FIG. 101 shows the results for Taq DN, FIG. 102 shows the results for Tth DN, FIG. 103 shows the results for Pfu FEN-, FIG. 104 shows the results for Mja FEN-, FIG. 105 shows the results for Afu FEN-1, and FIG. 106 shows the results for Mth FEN-1. In each of the Panels within these Figures, the activity of the enzyme is defined as cleavages per molecule of enzyme per minute. Panels marked "IT" refer to cleavage of the 25-184-5 structure (SEQ ID NO:177; FIG. 107B), which mimics an invader oligo/target DNA structure, while Panels marked with "hairpin" refer to cleavage of the 25-65-1 structure (SEQ ID NO:176; FIG. 107A), which indicates activity on folded cleavage structures.

In each of these Figures, Panel A shows the results from reactions containing 2 mM $MgCl_2$ and the IT substrate as described in the text, with KCl varied as indicated; Panel B shows the results from reactions containing 2 mM $MnCl_2$ and the IT substrate as described in the text, with KCl varied as indicated; Panel C shows the results from reactions containing 2 mM $MgCl_2$ and the hairpin substrate as described in the text, with KCl varied as indicated; Panel D shows the results from reactions containing 2 mM $MnCl_2$ and the hairpin substrate as described in the text, with KCl varied as indicated; Panel E shows the results from reactions containing the IT substrate as described in the text, with $MgCl_2$ varied as indicated; Panel F shows the results from reactions containing the IT substrate as described in the text, with $MnCl_2$ varied as indicated; Panel G shows the results from reactions containing the hairpin substrate as described in the text, with $MgCl_2$ varied as indicated; Panel H shows the results from reactions containing the hairpin substrate as described in the text, with $MnCl_2$ varied as indicated; Panel I shows the results from reactions containing the IT substrate, 4 mM $MgCl_2$, and 50 mM KCl (Afu FEN-1, Pfu FEN-1, Mja FEN-1, Mth FEN-1, and Cleavase® FN) or 200 mM KCl (Taq DN and Tth DN) as described in the text, with the temperature varied as indicated; and Panel J shows the results from reactions containing the IT substrate, 4 mM $MnCl_2$, and 50 mM KCl (Afu FEN-1, Pfu FEN-1, Mja FEN-1, Mth FEN-1, and Cleavase® BN) or 200 mM KCl (Taq DN and Tth DN) as described in the text, with the temperature varied as indicated. It is noted that some of these Figures (e.g., 101, 102, 103, and 105) do not show each of the above-named panels A–J.

From the above it is clear that the invention provides reagents and methods to permit the detection and characterization of nucleic acid sequences and variations in nucleic acid sequences. The Invader™-directed cleavage reaction of the present invention provides an ideal direct detection method that combines the advantages of the direct detection assays (e.g., easy quantification and minimal risk of carry-over contamination) with the specificity provided by a dual or tri oligonucleotide hybridization assay.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A composition comprising an isolated thermostable structure-specific nuclease having an amino acid sequence consisting of SEQ ID NO:179.

2. The composition of claim 1, wherein said nuclease is encoded by a DNA sequence consisting of SEQ ID NO:178.

3. A composition comprising a purified FEN-1 endonuclease comprising an *Archaeoglobus fulgidus* FEN-1 endonuclease.

4. The composition of claim 3, wherein said endonuclease comprises an amino acid sequence comprising SEQ ID NO:179.

5. The composition of claim 4, wherein said endonuclease is encoded by a DNA sequence comprising SEQ ID NO:178.

6. A kit comprising the endonuclease of claim 3.

7. A mixture comprising: i) a first structure-specific nuclease, wherein said first nuclease comprises a purified FEN-1 endonuclease; and ii) a purified second structure-specific nuclease.

8. The mixture of claim 7, wherein said first structure-specific nuclease comprises an archaeal FEN-1 endonuclease.

9. The mixture of claim 7, wherein said second structure-specific nuclease comprises an archaeal FEN-1 endonuclease.

10. The mixture of claim 7, wherein said first structure-specific nuclease comprises an Archaeoglobus fulgidus FEN-1 endonuclease.

11. The mixture of claim 10, wherein said Archaeoglobus fulgidus FEN-1 endonuclease comprises SEQ ID NO:179.

12. The mixture of claim 7, wherein said second structure-specific nuclease comprises an Archaeoglobus fulgidus FEN-1 endonuclease.

13. The mixture of claim 12, wherein said Archaeoglobus fulgidus FEN-1 endonuclease comprises SEQ ID NO:179.

14. The mixture of claim 7, wherein said second structure-specific nuclease comprises a polymerase.

15. The mixture of claim 14, wherein said polymerase comprises a DNA polymerase.

16. The mixture of claim 15, wherein said DNA polymerase comprises a thermostable DNA polymerase.

17. The mixture of claim 7, wherein said second structure-specific nuclease comprises a 5' nuclease derived from a DNA polymerase altered in amino acid sequence such that it exhibits reduced DNA synthetic activity from that of the wild-type DNA polymerase but retains substantially the same 5' nuclease activity of the wild-type DNA polymerase.

18. The mixture of claim 17, wherein said 5' nuclease comprises a thermostable 5' nuclease.

19. The mixture of claim 7, wherein said second structure-specific nuclease is selected from the group consisting of CLEAVASE BN enzyme, CLEAVASE DA enzyme, CLEAVASE DN enzyme, CLEAVASE DV enzyme, CLEAVASE BN/thrombin enzyme, CLEAVASE TThDN enzyme, Thermus aquaticus DNA polymerase, Thermus thermophilus DNA polymerase, Escherichia coli Exo III, and Saccharomyces cerevisiae Rad1/Rad10 complex.

20. A nucleic acid treatment kit, comprising:
a) a purified Archaeoglobus fulgidus FEN-1 endonuclease; and
b) a solution containing manganese.

21. The kit of claim 26, wherein said Archaeoglobus fulgidus FEN-1 endonuclease comprises SEQ ID NO:179.

22. The kit of claim 20, further comprising a second structure-specific nuclease.

23. The kit of claim 22, wherein said second structure-specific nuclease comprises a polymerase.

24. The kit of claim 23, wherein said polymerase comprises a DNA polymerase.

25. The kit of claim 24, wherein said DNA polymerase comprises a thermostable DNA polymerase.

26. The kit of claim 22, wherein said second structure-specific nuclease comprises a 5' nuclease derived from a DNA polymerase altered in amino acid sequence such that it exhibits reduced DNA synthetic activity from that of the wild-type DNA polymerase but retains substantially the same 5' nuclease activity of the wild-type DNA polymerase.

27. The kit of claim 26, wherein said 5' nuclease comprises a thermostable 5' nuclease.

28. The kit of claim 22, wherein a portion of the amino acid sequence of said second structure-specific nuclease is homologous to a portion of an amino acid sequence of a thermostable DNA polymerase derived from a eubacterial thermophile of the genus Thermus.

29. The kit of claim 28, wherein said thermophile is selected from the group consisting of Thermus aquaticus, Thermus flavus, and Thermus thermophilus.

30. The kit of claim 22, wherein said second structure-specific nuclease is selected from the group consisting of CLEAVASE BN enzyme, CLEAVASE DA enzyme, CLEAVASE DN enzyme, CLEAVASE DV enzyme, CLEAVASE BN/thrombin enzyme, CLEAVASE TThDN enzyme, Thermus aquaticus DNA polymerase, Thermus thermophilus DNA polymerase, Escherichia coli Exo III, and Saccharomyces cerevisiae Rad1/Rad10 complex.

31. The kit of claim 20, further comprising a nucleic acid comprising a folded structure.

32. The kit of claim 31, further comprising one or more reagents for the detection of a cleavage product generated from said nucleic acid.

33. A nucleic acid treatment kit comprising:
a) a composition comprising purified FEN-1 endonuclease;
b) a first oligonucleotide comprising a 5' portion complementary to a first portion of a target nucleic acid; and
c) a second oligonucleotide comprising: a 5' portion complementary to a second portion of said target nucleic acid downstream of and contiguous to said first portion; and a 3' portion.

34. The kit of claim 33, wherein said 3' portion of said second oligonucleotide comprises a 3' terminal nucleotide not complementary to said target nucleic acid.

35. The kit of claim 33, wherein said 3' portion of said second oligonucleotide consists of a single nucleotide not complementary to said target nucleic acid.

36. The kit of claim 33, further comprising a solid support.

37. The kit of claim 36, wherein said first oligonucleotide is attached to said solid support.

38. The kit of claim 36, wherein said second oligonucleotide is attached to said solid support.

39. The kit of claim 33, further comprising a buffer solution.

40. The kit of claim 39, wherein said buffer solution comprises a source of divalent cations.

41. The kit of claim 40, wherein said divalent cation comprises $Mn^{2+}$.

42. The kit of claim 33, further comprising a third oligonucleotide complementary to a third portion of said target nucleic acid upstream of said first portion of said first target nucleic acid.

43. The kit of claim 33, further comprising one or more target nucleic acids.

44. The kit of claim 40, wherein said divalent cation comprises $Mg^{2+}$.

45. The kit of claim 33, wherein said purified FEN-1 endonuclease comprises an Archaeoglobus fulgidus FEN-1 endonuclease.

46. The kit of claim 45, wherein said Archaeoglobus fulgidus FEN-1 endonuclease comprises SEQ ID NO:179.

47. The kit of claim 33, wherein said purified FEN-1 endonuclease comprises an archaeal FEN-1 endonuclease.

* * * * *

SEQUENCE LISTING

<160> NUMBER OF SEQ ID NOS: 188

<210> SEQ ID NO 1
<211> LENGTH: 2506
<212> TYPE: DNA
<213> ORGANISM: Thermus aquaticus

<400> SEQUENCE: 1

| | | | | |
|---|---|---|---|---|
| atgagggga | tgctgcccct | ctttgagccc | aagggccggg | tcctcctggt ggacggccac | 60 |
| cacctggcct | accgcaccgg | ccacgccctg | aagggcctca | ccaccagccg ggggagccg | 120 |
| gtgcaggcgg | tctacggctt | cgccaagagc | ctcctcaagg | ccctcaagga ggacgggga | 180 |
| gcggtgatcg | tggtctttga | cgccaaggcc | cctccttcc | gccacgaggc ctacggggg | 240 |
| tacaaggcgg | gccgggcccc | cacgccggag | gactttcccc | ggcaactcgc cctcatcaag | 300 |
| gagctggtgg | acctcctggg | gctggcgcgc | ctcgaggtcc | cgggctacga ggcggacgac | 360 |
| gtcctggcca | gctggccaa | gaaggcgaa | aaggaggct | acgaggtccg catcctcacc | 420 |
| gccgacaaag | acctttacca | gctcctttcc | gaccgcatcc | acgtcctcca ccccgagggg | 480 |
| tacctcatca | ccccggcctg | gctttgggaa | agtacggcc | tgaggcccga ccagtgggcc | 540 |
| gactaccggg | ccctgaccgg | ggacgagtcc | gacaaccttc | cgggggtcaa gggcatcggg | 600 |
| gagaagacgg | cgaggaagct | tctggaggag | tgggggagcc | tggaagccct cctcaagaac | 660 |
| ctggaccggc | tgaagcccgc | catccggag | aagatcctgg | cccacatgga cgatctgaag | 720 |
| ctctcctggg | acctgccaa | ggtgcgcacc | gacctgcccc | tggaggtgga cttcgccaaa | 780 |
| aggcggggagc | ccgaccggga | gaggcttagg | gcctttctgg | agaggcttga gtttggcagc | 840 |
| ctcctccacg | agttcggcct | tctggaaagc | cccaaggccc | tggaggaggc ccctggccc | 900 |
| cgccggaag | gggccttcgt | gggctttgtg | ctttcccgca | aggagcccat gtgggccgat | 960 |
| cttctggccc | tggccgccgc | caggggggc | cgggtccacc | gggcccccga gccttataaa | 1020 |
| gcccctcaggg | acctgaagga | ggcgcggggg | cttctcgcca | agacctgag cgttctggcc | 1080 |
| ctgagggaag | gccttggcct | cccgcccggc | gacgaccca | tgctcctcgc ctacctcctg | 1140 |
| gaccctccca | acaccacccc | cgaggggtg | gccggcgct | acgggggga gtggacggag | 1200 |
| gaggcggggg | agcgggccgc | cctttccgag | aggctcttcg | ccaacctgtg ggggaggctt | 1260 |
| gagggggagg | agaggctcct | ttggctttac | cgggaggtgg | agaggccct ttccgctgtc | 1320 |
| ctggcccaca | tggaggccac | gggggtgcgc | ctggacgtgg | cctatctcag ggccttgtcc | 1380 |
| ctggaggtgg | ccgaggagat | cgcccgcctc | gaggccgagg | tcttccgcct ggccggccac | 1440 |
| cccttcaacc | tcaactcccg | ggaccagctg | gaaagggtcc | tctttgacga gctagggctt | 1500 |
| cccgccatcg | gcaagacgga | gaagaccggc | aagcgctcca | ccagcgccgc cgtcctggag | 1560 |
| gccctccgcg | aggcccaccc | catcgtggag | aagatcctgc | agtaccggga gctcaccaag | 1620 |
| ctgaagagca | cctacattga | ccccttgccg | gacctcatcc | accccaggac gggccgcctc | 1680 |
| cacacccgct | tcaaccagac | ggccacggcc | acgggcaggc | taagtagctc cgatcccaac | 1740 |
| ctccagaaca | tccccgtccg | caccccgctt | gggcagagga | tccgccggc cttcatcgcc | 1800 |
| gaggagggt | ggctattggt | ggccctggac | tatagccaga | tagagctcag ggtgctggcc | 1860 |
| cacctctccg | gcgacgagaa | cctgatccgg | gtcttccagg | aggggcggga catccacacg | 1920 |
| gagaccgcca | gctggatgtt | cggcgtcccc | cggaggccg | tggaccccct gatgcgccgg | 1980 |
| gcggccaaga | ccatcaactt | cggggtcctc | tacggcatgt | cggcccaccg cctctcccag | 2040 |

```
gagctagcca tcccttacga ggaggcccag gccttcattg agcgctactt tcagagcttc    2100
cccaaggtgc gggcctggat tgagaagacc ctggaggagg caggaggcg gggtacgtg     2160 gagaccctct tcggccgccg ccgctacgtg ccagacctag aggcccggt gaagagcgtg    2220 cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agaggggcgga ggccgtggcc    2400 cggctggcca aggaggtcat ggaggggtg tatcccctgg ccgtgcccct ggaggtggag     2460
gtggggatag gggaggactg gctctccgcc aaggagtgat accacc                   2506

<210> SEQ ID NO 2
<211> LENGTH: 2496
<212> TYPE: DNA
<213> ORGANISM: thermus flavus

<400> SEQUENCE: 2
atggcgatgc ttcccctctt tgagcccaaa ggccgcgtgc tcctggtgga cggccaccac      60
ctggcctacc gcaccttctt tgccctcaag ggcctcacca ccagccgcgg cgaacccgtt     120
caggcggtct acggcttcgc caaaagcctc ctcaaggccc tgaaggagga cggggacgtg     180
gtggtggtgg tcttttgacgc caaggccccc tccttccgcc acgaggccta cgaggcctac     240
aaggcgggcc gggccccccac cccggaggac tttccccggc agctggccct catcaaggag     300
ttggtggacc tcctaggcct tgtgcggctg gaggttcccg gctttgaggc ggacgacgtg      360
ctggccaccc tggccaagcg ggcggaaaag gaggggtacg aggtgcgcat cctcactgcc      420
gaccgcgacc tctaccagct cctttcggag cgcatcgcca tcctccaccc tgagggtac      480 ctgatcaccc cggcgtggct ttacgagaag tacggcctgc gcccgagca gtgggtggac      540 taccgggccc tggcggggga cccctcggat aacatccccg gggtgaaggg catcggggag     600
aagaccgccc agaggctcat ccgcgagtgg gggagcctgg aaaacctctt ccagcacctg      660
gaccaggtga agcctccctt gcgggagaag ctccaggcgg catggaggc cctggccctt      720 tcccggaagc tttcccaggt gcacactgac ctgcccctgg aggtggactt cgggaggcgc      780
cgcacaccca acctggaggg tctgcgggct tttttggagc ggttggagtt tggaagcctc      840
ctccacgagt tcggcctcct ggaggggcg aaggcggcag aggaggcccc ctggcccct      900 ccggaagggg cttttttggg cttttccttt tcccgtcccg agcccatgtg ggccgagctt      960
ctggccctgg ctggggcgtg ggaggggcgc ctccatcggg cacaagaccc ccttaggggc     1020
ctgagggacc ttaaggggt gcggggaatc ctggccaagg acctggcggt tttggccctg     1080
cgggagggcc tggacctctt cccagaggac gacccccatgc tcctggccta ccttctggac    1140
ccctccaaca ccacccctga gggggtggcc cggcgttacg ggggggagtg gacggaggat     1200
gcgggggaga gggccctcct ggccgagcgc tcttccagaa ccctaaagga gcgccttaag     1260
ggagaagaac gcctgcttg gctttacgag gagtggagaa gccgcttc ccgggtgttg       1320 gcccggatgg aggccacggg ggtccggctg gacgtggcct acctccaggc cctctccctg     1380
gaggtggagg cggaggtgcg ccagctggag gaggaggtct ccgcctggc cggccacccc     1440 ttcaacctca actcccgcga ccagctggag cgggtgctct ttgacgagct gggcctgcct     1500
gccatcggca agacggagaa gacgggaaa cgctccacca gcgctgccgt gctgaggcc      1560 ctgcgagagg cccaccccat cgtggaccgc atcctgcagt accgggagct caccaagctc     1620
```

-continued

```
aagaacacct acatagaccc cctgcccgcc ctggtccacc ccaagaccgg ccggctccac    1680
acccgcttca accagacggc caccgccacg ggcaggcttt ccagctccga ccccaacctg    1740
cagaacatcc ccgtgcgcac ccctctgggc cagcgcatcc gccgagcctt cgtggccgag    1800
gagggctggg tgctggtggt cttggactac agccagattg agcttcgggt cctggcccac    1860
ctctccgggg acgagaacct gatccgggtc tttcaggagg ggagggacat ccacacccag    1920
accgccagct ggatgttcgg cgtttccccc gaagggtag accctctgat gcgccgggcg    1980
gccaagacca tcaacttcgg ggtgctctac ggcatgtccg cccaccgcct ctccggggag    2040 cttccatcc cctacgagga ggcggtggcc ttcattgagc gctacttcca gagctacccc    2100
aaggtgcggg cctggattga ggggaccctc gaggagggcc gccggcgggg gtatgtggag    2160
accctcttcg gccgccggcg ctatgtgccc gacctcaacg cccgggtgaa gagcgtgcgc    2220
gaggcggcgg agcgcatggc cttcaacatg ccggtccagg gcaccgccgc cgacctcatg    2280
aagctggcca tggtgcggct tttcccccgg cttcaggaac tgggggcgag gatgcttttg    2340
caggtgcacg acgagctggt cctcgaggcc ccaaggacc gggcggagag ggtagccgct    2400
ttggccaagg aggtcatgga gggggtctgg ccctgcagg tgcccctgga ggtggaggtg    2460
ggcctggggg aggactggct ctccgccaag gagtag                              2496
```

<210> SEQ ID NO 3
<211> LENGTH: 2504
<212> TYPE: DNA
<213> ORGANISM: Thermus thermophilus

<400> SEQUENCE: 3

```
atggaggcga tgcttccgct cttgaaccc aaaggccggg tcctcctggt ggacggccac      60
cacctggcct accgcacctt cttcgccctg aagggcctca ccacgagccg ggcgaaccg     120 gtgcaggcg tctacggctt cgccaagagc ctcctcaagg ccctgaagga ggacgggtac    180
aaggccgtct tcgtggtctt tgacgccaag gcccctcct ccgccacga ggcctacgag     240 gcctacaagg cggggagggc cccgaccccc gaggacttcc ccggcagct cgccctcatc    300 aaggagctgg tggacctcct ggggtttacc cgcctcgagg tccccggcta cgaggcggac    360
gacgttctcg ccaccctggc caagaaggcg gaaaaggagg ggtacgaggt gcgcatcctc    420
accgccgacc gcgacctcta ccaactcgtc tccgaccgcg tcgccgtcct ccaccccgag    480
ggccacctca tcaccccgga gtggcttttgg gagaagtacg gcctcaggcc ggagcagtgg   540
gtggacttcc gcgccctcgt ggggggaccc tccgacaacc tccccgggggt caagggcatc   600 ggggagaaga ccgccctcaa gctcctcaag gagtggggaa gctggaaaa cctcctcaag    660 aacctggacc gggtaaagcc agaaaacgtc cgggagaaga tcaaggccca cctggaagac    720
ctcaggctct ccttggagct ctccggggtg cgcaccgacc tcccctgga ggtggacctc     780 gcccaggggc gggagcccga ccgggagggg cttagggcct tcctggagag ctggagttc     840 ggcagcctcc tccacgagtt cggcctcctg gaggccccg ccccctgga ggaggccccc    900 tggccccgc cggaagggc cttcgtgggc ttcgtcctct cccgccccga gcccatgtgg     960
gcggagctta aagccctggc cgcctgcagg acggccgggg tgcaccgggc agcagacccc   1020 ttggcgggc taaaggacct caaggaggtc cggggcctcc tcgccaagga cctcgccgtc    1080
ttggcctcga gggaggggct agacctcgtg cccggggacg accccatgct cctcgcctac    1140
ctcctggacc cctccaacac cacccccgag ggggtggcgc ggcgctacgg gggggagtgg    1200
acggaggacg ccgcccaccg ggccctcctc tcggagaggc tccatcggaa cctccttaag    1260
```

-continued

```
cgcctcgagg gggaggagaa gctcctttgg ctctaccacg aggtggaaaa gcccctctcc    1320
cgggtcctgg cccacatgga ggccaccggg gtacggctgg acgtggccta ccttcaggcc    1380
ctttccctgg agcttgcgga ggagatccgc cgcctcgagg aggaggtctt ccgcttggcg    1440
ggccacccct caacctcaa ctcccgggac cagctggaaa gggtgctctt tgacgagctt    1500
aggcttcccg cctggggaa gacgcaaaag acaggcaagc gctccaccag cgccgcggtg    1560
ctggaggccc tacgggaggc ccacccatc gtggagaaga tcctccagca ccgggagctc    1620
accaagctca agaacaccta cgtggacccc ctcccaagcc tcgtccaccc gaggacgggc    1680
cgcctccaca cccgcttcaa ccagacggcc acggccacgg ggaggcttag tagctccgac    1740
cccaacctgc agaacatccc cgtccgcacc cccttgggcc agaggatccg ccgggccttc    1800
gtggccgagg cgggttgggc gttggtggcc ctggactata gccagataga gctccgcgtc    1860
ctcgccacc tctccgggga cgaaaacctg atcagggtct tccaggaggg gaaggacatc    1920
cacacccaga ccgcaagctg gatgttcggc gtccccccgg aggccgtgga cccctgatg    1980
cgccgggcgg ccaagacggt gaacttcggc gtcctctacg gcatgtccgc ccataggctc    2040
tcccaggagc ttgccatccc ctacgaggag gcggtggcct ttatagaggc tacttccaaa    2100
gcttccccaa ggtgcgggcc tggatagaaa agaccctgga ggaggggagg aagcggggct    2160
acgtggaaac cctcttcgga agaaggcgct acgtgcccga cctcaacgcc cgggtgaaga    2220
gcgtcaggga ggccgcggag cgcatggcct tcaacatgcc cgtccagggc accgccgccg    2280
acctcatgaa gctcgccatg gtgaagctct ccccccgcct ccgggagatg ggggcccgca    2340
tgctcctcca ggtccacgac gagctcctcc tggaggcccc caagcgcgg gccgaggagg    2400
tggcggcttt ggccaaggag gccatggaga aggcctatcc cctcgccgtg cccctggagg    2460
tggaggtggg gatgggggag gactggcttt ccgccaaggg ttag                    2504
```

<210> SEQ ID NO 4
<211> LENGTH: 832
<212> TYPE: PRT
<213> ORGANISM: Thermus aquaticus

<400> SEQUENCE: 4

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
```

-continued

```
                145                 150                 155                 160
Tyr Leu Ile Thr Pro Ala Trp Leu Trp Glu Lys Tyr Gly Leu Arg Pro
                    165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
        435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
```

-continued

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 5
<211> LENGTH: 831
<212> TYPE: PRT
<213> ORGANISM: thermus flavus

<400> SEQUENCE: 5

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
                20                  25                  30

Thr Thr Ser Arg Gly Glu Pro Val Gln Ala Val Tyr Gly Phe Ala Lys
            35                  40                  45

Ser Leu Leu Lys Ala Leu Lys Glu Asp Gly Asp Val Val Val Val Val
        50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
            100                 105                 110

Pro Gly Phe Glu Ala Asp Asp Val Leu Ala Thr Leu Ala Lys Arg Ala

-continued

```
            115                 120                 125
Glu Lys Glu Gly Tyr Glu Val Arg Ile Leu Thr Ala Asp Arg Asp Leu
    130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
            195                 200                 205

Glu Trp Gly Ser Leu Glu Asn Leu Phe Gln His Leu Asp Gln Val Lys
    210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Thr Pro Asn Leu Glu Gly Leu Arg Ala Phe Leu
            260                 265                 270

Glu Arg Leu Glu Phe Gly Ser Leu Leu His Glu Phe Gly Leu Leu Glu
    275                 280                 285

Gly Pro Lys Ala Ala Glu Glu Ala Pro Trp Pro Pro Glu Gly Ala
290                 295                 300

Phe Leu Gly Phe Ser Phe Ser Arg Pro Glu Pro Met Trp Ala Glu Leu
305                 310                 315                 320

Leu Ala Leu Ala Gly Ala Trp Glu Gly Arg Leu His Arg Ala Gln Asp
                325                 330                 335

Pro Leu Arg Gly Leu Arg Asp Leu Lys Gly Val Arg Gly Ile Leu Ala
            340                 345                 350

Lys Asp Leu Ala Val Leu Ala Leu Arg Glu Gly Leu Asp Leu Phe Pro
            355                 360                 365

Glu Asp Asp Pro Met Leu Leu Ala Tyr Leu Leu Asp Pro Ser Asn Thr
    370                 375                 380

Thr Pro Glu Gly Val Ala Arg Arg Tyr Gly Gly Glu Trp Thr Glu Asp
385                 390                 395                 400

Ala Gly Glu Arg Ala Leu Leu Ala Glu Arg Leu Phe Gln Thr Leu Lys
                405                 410                 415

Glu Arg Leu Lys Gly Glu Glu Arg Leu Leu Trp Leu Tyr Glu Glu Val
            420                 425                 430

Glu Lys Pro Leu Ser Arg Val Leu Ala Arg Met Glu Ala Thr Gly Val
            435                 440                 445

Arg Leu Asp Val Ala Tyr Leu Gln Ala Leu Ser Leu Glu Val Glu Ala
450                 455                 460

Glu Val Arg Gln Leu Glu Glu Val Phe Arg Leu Ala Gly His Pro
465                 470                 475                 480

Phe Asn Leu Asn Ser Arg Asp Gln Leu Glu Arg Val Leu Phe Asp Glu
                485                 490                 495

Leu Gly Leu Pro Ala Ile Gly Lys Thr Glu Lys Thr Gly Lys Arg Ser
            500                 505                 510

Thr Ser Ala Ala Val Leu Glu Ala Leu Arg Glu Ala His Pro Ile Val
            515                 520                 525

Asp Arg Ile Leu Gln Tyr Arg Glu Leu Thr Lys Leu Lys Asn Thr Tyr
    530                 535                 540
```

-continued

```
Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
            580                 585                 590

Ile Arg Arg Ala Phe Val Ala Glu Glu Gly Trp Val Leu Val Val Leu
        595                 600                 605

Asp Tyr Ser Gln Ile Glu Leu Arg Val Leu Ala His Leu Ser Gly Asp
    610                 615                 620

Glu Asn Leu Ile Arg Val Phe Gln Glu Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
                660                 665                 670

Ser Ala His Arg Leu Ser Gly Glu Leu Ser Ile Pro Tyr Glu Glu Ala
            675                 680                 685

Val Ala Phe Ile Glu Arg Tyr Phe Gln Ser Tyr Pro Lys Val Arg Ala
        690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
                740                 745                 750

Gln Gly Thr Ala Ala Asp Leu Met Lys Leu Ala Met Val Arg Leu Phe
            755                 760                 765

Pro Arg Leu Gln Glu Leu Gly Ala Arg Met Leu Leu Gln Val His Asp
        770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Glu Asp Trp Leu Ser Ala Lys Glu
                820                 825                 830

<210> SEQ ID NO 6
<211> LENGTH: 834
<212> TYPE: PRT
<213> ORGANISM: Thermus thermophilus

<400> SEQUENCE: 6

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
```

-continued

```
                        85                  90                  95
Leu Ala Leu Ile Lys Glu Leu Val Asp Leu Leu Gly Phe Thr Arg Leu
                100                 105                 110
Glu Val Pro Gly Tyr Glu Ala Asp Val Leu Ala Thr Leu Ala Lys
            115                 120                 125
Lys Ala Glu Lys Glu Gly Tyr Glu Val Arg Ile Leu Thr Ala Asp Arg
            130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
            195                 200                 205
Leu Lys Glu Trp Gly Ser Leu Glu Asn Leu Leu Lys Asn Leu Asp Arg
210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
            275                 280                 285
Leu Leu Glu Ala Pro Ala Pro Leu Glu Glu Ala Pro Trp Pro Pro Pro
        290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
            340                 345                 350
Leu Leu Ala Lys Asp Leu Ala Val Leu Ala Ser Arg Glu Gly Leu Asp
            355                 360                 365
Leu Val Pro Gly Asp Asp Pro Met Leu Leu Ala Tyr Leu Leu Asp Pro
        370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Glu Gly Glu Glu Lys Leu Leu Trp Leu Tyr
            420                 425                 430
His Glu Val Glu Lys Pro Leu Ser Arg Val Leu Ala His Met Glu Ala
            435                 440                 445
Thr Gly Val Arg Leu Asp Val Ala Tyr Leu Gln Ala Leu Ser Leu Glu
        450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
```

-continued

```
Lys Arg Ser Thr Ser Ala Ala Val Leu Glu Ala Leu Arg Glu Ala His
            515                 520                 525
Pro Ile Val Glu Lys Ile Leu Gln His Arg Glu Leu Thr Lys Leu Lys
        530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
        595                 600                 605
Val Ala Leu Asp Tyr Ser Gln Ile Glu Leu Arg Val Leu Ala His Leu
610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Phe Gly Val Leu
            660                 665                 670
Tyr Gly Met Ser Ala His Arg Leu Ser Gln Glu Leu Ala Ile Pro Tyr
        675                 680                 685
Glu Glu Ala Val Ala Phe Ile Glu Arg Tyr Phe Gln Ser Phe Pro Lys
690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln
770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly

<210> SEQ ID NO 7
<211> LENGTH: 2502
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(5)
<223> OTHER INFORMATION: The n at these positions can be a, c, t or g.
<221> NAME/KEY: misc_feature
<222> LOCATION: (181)..(182)
<223> OTHER INFORMATION: The n at these positions can be a, c, t or g.
<221> NAME/KEY: misc_feature
<222> LOCATION: (190)
<223> OTHER INFORMATION: The n at this position can be a, c, t or g.
```

-continued

```
<221> NAME/KEY: misc_feature
<222> LOCATION: (366)
<223> OTHER INFORMATION: The n at this position can be a, c, t or g.
<221> NAME/KEY: misc_feature
<222> LOCATION: (617)
<223> OTHER INFORMATION: The n at this position can be a, c, t or g.
<221> NAME/KEY: misc_feature
<222> LOCATION: (628)
<223> OTHER INFORMATION: The n at this position can be a, c, t or g.
<221> NAME/KEY: misc_feature
<222> LOCATION: (685)
<223> OTHER INFORMATION: The n a this position can be a, c, t or g.
<221> NAME/KEY: misc_feature
<222> LOCATION: (714)
<223> OTHER INFORMATION: The n at this position can be a, c, t or g.
<221> NAME/KEY: misc_feature
<222> LOCATION: (722)
<223> OTHER INFORMATION: The n at this position can be a, c, t or g.
<221> NAME/KEY: misc_feature
<222> LOCATION: (738)
<223> OTHER INFORMATION: The n at this position can be a, c, t or g.
<221> NAME/KEY: misc_feature
<222> LOCATION: (784)
<223> OTHER INFORMATION: The n at this position can be a, c, t or g.
<221> NAME/KEY: misc_feature
<222> LOCATION: (1022)
<223> OTHER INFORMATION: The n at this position can be a, c, t or g.
<221> NAME/KEY: misc_feature
<222> LOCATION: (1029)
<223> OTHER INFORMATION: The n at this position can be a, c, t or g.
<221> NAME/KEY: misc_feature
<222> LOCATION: (1038)
<223> OTHER INFORMATION: The n at this position can be a, c, t or g.
<221> NAME/KEY: misc_feature
<222> LOCATION: (1053)
<223> OTHER INFORMATION: The n at this position can be a, c, t or g.
<221> NAME/KEY: misc_feature
<222> LOCATION: (1098)
<223> OTHER INFORMATION: The n at this position can be a, c, t or g.
<221> NAME/KEY: misc_feature
<222> LOCATION: (1105)
<223> OTHER INFORMATION: The n at this position can be a, c, t or g.
<221> NAME/KEY: misc_feature
<222> LOCATION: (1206)
<223> OTHER INFORMATION: The n at this position can be a, c, t or g.
<221> NAME/KEY: misc_feature
<222> LOCATION: (1227)
<223> OTHER INFORMATION: The n at this position can be a, c, t or g.
<221> NAME/KEY: misc_feature
<222> LOCATION: (1244)
<223> OTHER INFORMATION: The n at this position can be a, c, t or g.
<221> NAME/KEY: misc_feature
<222> LOCATION: (1251)..(1253)
<223> OTHER INFORMATION: The n at these positions can be a, c, t or g.
<221> NAME/KEY: misc_feature
<222> LOCATION: (1350)
<223> OTHER INFORMATION: The n at this position can be a, c, t or g.
<221> NAME/KEY: misc_feature
<222> LOCATION: (1380)
<223> OTHER INFORMATION: The n at this position can be a, c, t or g.
<221> NAME/KEY: misc_feature
<222> LOCATION: (1497)
<223> OTHER INFORMATION: The n at this positon can be a, c, t or g.
<221> NAME/KEY: misc_feature
<222> LOCATION: (1530)
<223> OTHER INFORMATION: The n at this position can be a, c, t or g.
<221> NAME/KEY: misc_feature
<222> LOCATION: (1569)
<223> OTHER INFORMATION: The n at this position can be a, c, t or g.
<221> NAME/KEY: misc_feature
<222> LOCATION: (1572)
<223> OTHER INFORMATION: The n at this position can be a, c, t or g.
<221> NAME/KEY: misc_feature
<222> LOCATION: (1641)
<223> OTHER INFORMATION: The n at this position can be a, c, t or g.
<221> NAME/KEY: misc_feature
<222> LOCATION: (1653)
<223> OTHER INFORMATION: The n at this position can be a, c, t or g.
<221> NAME/KEY: misc_feature
```

```
<222> LOCATION: (1655)
<223> OTHER INFORMATION: The n at this position can be a, c, t or g.
<221> NAME/KEY: misc_feature
<222> LOCATION: (1770)
<223> OTHER INFORMATION: The n at this position can be a, c, t or g.
<221> NAME/KEY: misc_feature
<222> LOCATION: (1812)
<223> OTHER INFORMATION: The n at this position can be a, c, t or g.
<221> NAME/KEY: misc_feature
<222> LOCATION: (2319)
<223> OTHER INFORMATION: The n at this position can be a, c, t or g.
<221> NAME/KEY: misc_feature
<222> LOCATION: (2346)
<223> OTHER INFORMATION: The n at this position can be a, c, t or g.
<221> NAME/KEY: misc_feature
<222> LOCATION: (2396)
<223> OTHER INFORMATION: The n at this position can be a, c, t or g.

<400> SEQUENCE: 7
atgnnggcga tgcttcccct ctttgagccc aaaggccggg tcctcctggt ggacggccac      60
cacctggcct accgcacctt cttcgccctg aagggcctca ccaccagccg gggcgaaccg     120
gtgcaggcgg tctacggctt cgccaagagc ctcctcaagg ccctgaagga ggacggggac     180
nnggcggtgn tcgtggtctt tgacgccaag gccccctcct tccgccacga ggcctacgag     240
gcctacaagg cgggccgggc ccccacccccg gaggactttc ccggcagct cgccctcatc     300
aaggagctgg tggacctcct ggggcttgcg cgcctcgagt ccccggcta cgaggcggac     360
gacgtnctgg ccaccctggc caagaaggcg aaaaggagg ggtacgaggt gcgcatcctc     420
accgccgacc gcgacctcta ccagctcctt tccgaccgca tcgccgtcct ccaccccgag     480
gggtacctca tcaccccggc gtggctttgg gagaagtacg gcctgaggcc ggagcagtgg     540
gtggactacc gggccctggc gggggacccc tccgacaacc tccccggggt caagggcatc     600
ggggagaaga ccgcccngaa gctcctcnag gagtggggga gcctggaaaa cctcctcaag     660
aacctggacc gggtgaagcc cgccntccgg gagaagatcc aggcccacat ggangacctg     720
angctctcct gggagctntc ccaggtgcgc accgacctgc ccctggaggt ggacttcgcc     780
aagnggcggg agcccgaccg ggaggggctt agggcctttc tggagaggct ggagtttggc     840
agcctcctcc acgagttcgg cctcctggag ggccccaagg ccctggagga ggcccccctgg     900
ccccgccga aggggccctt cgtgggcttt gtcctttccc gccccgagcc catgtgggcc     960
gagcttctgg ccctggccgc cgccagggag ggccgggtcc accgggcacc agaccccttt    1020
angggcctna gggacctnaa ggaggtgcgc ggnctcctcg ccaaggacct ggccgttttg    1080
gccctgaggg agggcctnga cctcntgccc ggggacgacc ccatgctcct cgcctacctc    1140
ctggacccct ccaacaccac ccccgagggg gtggcccggc gctacggggg ggagtggacg    1200
gaggangcgg gggagcgggc cctcctntcc gagaggctct tccngaacct nnngcagcgc    1260
cttgagggg aggagaggct cctttggctt taccaggagg tggagaagcc cctttcccgg    1320
gtcctggccc acatggaggc cacggggtn cggctggacg tggcctacct ccaggccctn    1380
tccctggagg tggcggagga gatccgccgc ctcgaggagg aggtcttccg cctgccggc    1440
cacccttca acctcaactc ccgggaccag ctggaaaggg tgctctttga cgagctnggg    1500
cttcccgcca tcggcaagac ggagaagacn ggcaagcgct ccaccagcgc cgccgtgctg    1560
gaggccctnc gngaggccca ccccatcgtg gagaagatcc tgcagtaccg ggagctcacc    1620
aagctcaaga acacctacat ngaccccctg ccngncctcg tccacccag acgggccgc    1680
ctccacaccc gcttcaacca gacggccacg gccacggca ggcttagtag ctccgacccc    1740
aacctgcaga acatccccgt ccgcaccccn ctgggccaga ggatccgccg ggccttcgtg    1800
```

```
gccgaggagg gntgggtgtt ggtggccctg gactatagcc agatagagct ccgggtcctg    1860
gcccacctct ccggggacga gaacctgatc cgggtcttcc aggaggggag ggacatccac    1920
acccagaccg ccagctggat gttcggcgtc ccccggagg ccgtggaccc cctgatgcgc     1980
cgggcggcca agaccatcaa cttcggggtc ctctacggca tgtccgccca ccgcctctcc    2040
caggagcttg ccatcccta cgaggaggcg gtggccttca ttgagcgcta cttccagagc    2100
ttccccaagg tgcgggcctg gattgagaag accctggagg agggcaggag gcggggggtac   2160 gtggagaccc tcttcggccg ccggcgctac gtgcccgacc tcaacgcccg ggtgaagagc    2220
gtgcgggagg cggcggagcg catggccttc aacatgcccg tccagggcac cgccgccgac    2280
ctcatgaagc tggccatggt gaagctcttc ccccggctnc aggaaatggg ggccaggatg    2340
ctcctncagg tccacgacga gctggtcctc gaggccccca agagcgggc ggaggnggtg     2400 gccgctttgg ccaaggaggt catggagggg gtctatcccc tggccgtgcc cctggaggtg    2460
gaggtgggga tgggggagga ctggctctcc gccaaggagt ag                       2502
```

<210> SEQ ID NO 8
<211> LENGTH: 833
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (2)
<223> OTHER INFORMATION: Xaa at this position can be any amino acid.
<221> NAME/KEY: SITE
<222> LOCATION: (63)
<223> OTHER INFORMATION: Xaa at this position can be any amino acid.
<221> NAME/KEY: SITE
<222> LOCATION: (109)
<223> OTHER INFORMATION: Xaa at this position can be any amino acid.
<221> NAME/KEY: SITE
<222> LOCATION: (186)
<223> OTHER INFORMATION: Xaa at this position can be any amino acid.
<221> NAME/KEY: SITE
<222> LOCATION: (205)
<223> OTHER INFORMATION: Xaa at this position can be any amino acid.
<221> NAME/KEY: SITE
<222> LOCATION: (209)
<223> OTHER INFORMATION: Xaa at this position can be any amino acid.
<221> NAME/KEY: SITE
<222> LOCATION: (227)..(228)
<223> OTHER INFORMATION: Xaa at these positions can be any amino acid.
<221> NAME/KEY: SITE
<222> LOCATION: (233)
<223> OTHER INFORMATION: Xaa at this position can be any amino acid.
<221> NAME/KEY: SITE
<222> LOCATION: (240)
<223> OTHER INFORMATION: Xaa at this position can be any amino acid.
<221> NAME/KEY: SITE
<222> LOCATION: (243)..(244)
<223> OTHER INFORMATION: Xaa at these positions can be any amino acid.
<221> NAME/KEY: SITE
<222> LOCATION: (247)
<223> OTHER INFORMATION: Xaa at this position can be any amino acid.
<221> NAME/KEY: SITE
<222> LOCATION: (260)
<223> OTHER INFORMATION: Xaa at this position can be any amino acid.
<221> NAME/KEY: SITE
<222> LOCATION: (290)
<223> OTHER INFORMATION: Xaa at this position can be any amino acid.
<221> NAME/KEY: SITE
<222> LOCATION: (329)
<223> OTHER INFORMATION: Xaa at this positioncan be any amino acid.
<221> NAME/KEY: SITE
<222> LOCATION: (336)
<223> OTHER INFORMATION: Xaa at this position can be any amino acid.
<221> NAME/KEY: SITE
<222> LOCATION: (340)

```
<223> OTHER INFORMATION: Xaa at this position can be any amino acid.
<221> NAME/KEY: SITE
<222> LOCATION: (368)
<223> OTHER INFORMATION: Xaa at this position can be any amino acid.
<221> NAME/KEY: SITE
<222> LOCATION: (414)
<223> OTHER INFORMATION: Xaa at this position can be any amino acid.
<221> NAME/KEY: SITE
<222> LOCATION: (417)..(418)
<223> OTHER INFORMATION: Xaa at these positions can be any amino acid.
<221> NAME/KEY: SITE
<222> LOCATION: (431)
<223> OTHER INFORMATION: Xaa at this position can be any amino acid.
<221> NAME/KEY: SITE
<222> LOCATION: (551)
<223> OTHER INFORMATION: Xaa at this position can be any amino acid.
<221> NAME/KEY: SITE
<222> LOCATION: (605)
<223> OTHER INFORMATION: Xaa at this position can be any amino acid.
<221> NAME/KEY: SITE
<222> LOCATION: (773)
<223> OTHER INFORMATION: Xaa at this position can be any amino acid.
<221> NAME/KEY: SITE
<222> LOCATION: (794)
<223> OTHER INFORMATION: Xaa at this position can be any amino acid.
<221> NAME/KEY: SITE
<222> LOCATION: (798)
<223> OTHER INFORMATION: Xaa at this position can be any amino acid.
<221> NAME/KEY: SITE
<222> LOCATION: (823)
<223> OTHER INFORMATION: Xaa at this position can be any amino acid.
<221> NAME/KEY: SITE
<222> LOCATION: (833)
<223> OTHER INFORMATION: Xaa at this position can be any amino acid.

<400> SEQUENCE: 8

Met Xaa Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Xaa Val
     50                  55                  60

Val Phe Asp Ala Lys Ala Pro Ser Phe Arg His Glu Ala Tyr Glu Ala
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Xaa Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ala Val Leu His Pro Glu Gly
145                 150                 155                 160

Tyr Leu Ile Thr Pro Ala Trp Leu Trp Glu Lys Tyr Gly Leu Arg Pro
                165                 170                 175

Glu Gln Trp Val Asp Tyr Arg Ala Leu Xaa Gly Asp Pro Ser Asp Asn
            180                 185                 190

Leu Pro Gly Val Lys Gly Ile Gly Glu Lys Thr Ala Xaa Lys Leu Leu
        195                 200                 205

Xaa Glu Trp Gly Ser Leu Glu Asn Leu Leu Lys Asn Leu Asp Arg Val
    210                 215                 220
```

-continued

```
Lys Pro Xaa Xaa Arg Glu Lys Ile Xaa Ala His Met Glu Asp Leu Xaa
225                 230                 235                 240

Leu Ser Xaa Xaa Leu Ser Xaa Val Arg Thr Asp Leu Pro Leu Glu Val
            245                 250                 255

Asp Phe Ala Xaa Arg Arg Glu Pro Asp Arg Glu Gly Leu Arg Ala Phe
            260                 265                 270

Leu Glu Arg Leu Glu Phe Gly Ser Leu Leu His Glu Phe Gly Leu Leu
        275                 280                 285

Glu Xaa Pro Lys Ala Leu Glu Ala Pro Trp Pro Pro Glu Gly
    290                 295                 300

Ala Phe Val Gly Phe Val Leu Ser Arg Pro Glu Pro Met Trp Ala Glu
305                 310                 315                 320

Leu Leu Ala Leu Ala Ala Arg Xaa Gly Arg Val His Arg Ala Xaa
                325                 330                 335

Asp Pro Leu Xaa Gly Leu Arg Asp Leu Lys Glu Val Arg Gly Leu Leu
            340                 345                 350

Ala Lys Asp Leu Ala Val Leu Ala Leu Arg Glu Gly Leu Asp Leu Xaa
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Asp Ala Gly Glu Arg Ala Leu Leu Ser Glu Arg Leu Phe Xaa Asn Leu
                405                 410                 415

Xaa Xaa Arg Leu Glu Gly Glu Arg Leu Leu Trp Leu Tyr Xaa Glu
            420                 425                 430

Val Glu Lys Pro Leu Ser Arg Val Leu Ala His Met Glu Ala Thr Gly
        435                 440                 445

Val Arg Leu Asp Val Ala Tyr Leu Gln Ala Leu Ser Leu Glu Val Ala
    450                 455                 460

Glu Glu Ile Arg Arg Leu Glu Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Asn Thr
    530                 535                 540

Tyr Ile Asp Pro Leu Pro Xaa Leu Val His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Val Ala Glu Glu Gly Trp Xaa Leu Val Ala
    595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Gln Thr Ala Ser Trp Met Phe Gly Val Pro Pro Glu Ala Val Asp Pro
```

```
        645                 650                 655
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Val Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Asn Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Xaa Glu Met Gly Ala Arg Met Leu Leu Gln Val His
    770                 775                 780

Asp Glu Leu Val Leu Glu Ala Pro Lys Xaa Arg Ala Glu Xaa Val Ala
785                 790                 795                 800

Ala Leu Ala Lys Glu Val Met Glu Gly Val Tyr Pro Leu Ala Val Pro
                805                 810                 815

Leu Glu Val Glu Val Gly Xaa Gly Glu Asp Trp Leu Ser Ala Lys Glu
            820                 825                 830

Xaa
```

```
<210> SEQ ID NO 9
<211> LENGTH: 1647
<212> TYPE: DNA
<213> ORGANISM: Artificial Sequence
<220> FEATURE:
<223> OTHER INFORMATION: Description of Artificial Sequence:  Synthetic

<400> SEQUENCE: 9
atgaattcgg ggatgctgcc cctctttgag cccaagggcc gggtcctcct ggtggacggc      60
caccacctgg cctaccgcac cttccacgcc ctgaagggcc tcaccaccag ccggggggag     120
ccggtgcagg cggtctacgg cttcgccaag agcctcctca aggccctcaa ggaggacggg     180
gacgcggtga tcgtggtctt tgacgccaag gcccctcct ccgccacga ggcctacggg     240 gggtacaagg cgggccgggc ccccacgccg gaggactttc cccggcaact cgccctcatc     300
aaggagctgg tggacctcct ggggctggcg cgctcgagg tcccgggcta cgaggcggac     360
gacgtcctgg ccagcctggc caagaaggcg aaaaaggagg gctacgaggt ccgcatcctc     420
accgccgaca agaccttta ccagctcctt tccgaccgca tccacgtcct ccaccccgag     480
gggtacctca tcaccccggc ctggcttttgg gaaaagtacg gcctgaggcc cgaccagtgg     540
gccgactacc gggccctgac cggggacgag tccgacaacc ttcccggggt caagggcatc     600
ggggagaaga cggcgaggaa gcttctggag gagtggggga gcctggaagc cctcctcaag     660
aacctggacc ggctgaagcc cgccatccgg gagaagatcc tggcccacat ggacgatctg     720
aagctctcct gggacctggc caaggtgcgc accgacctgc cctgaggt ggacttcgcc     780 aaaaggcggg agcccgaccg ggagaggctt agggccttc tggagaggct tgagtttggc     840
agcctcctcc acgagttcgg ccttctggaa agccccaagg ccctgaagga ggccccctgg     900 ccccgccgg aaggggcctt cgtgggcttt gtgctttccc gcaaggagcc catgtgggcc     960
```

```
gatcttctgg ccctggccgc cgccaggggg ggccgggtcc accggccccc cgagccttat    1020
aaagccctca gggacctgaa ggaggcgcgg gggcttctcg ccaaagacct gagcgttctg    1080
gccctgaggg aaggccttgg cctcccgccc ggcgacgacc ccatgctcct cgcctacctc    1140 ctggacccctt ccaacaccac ccccgagggg gtggcccggc gctacggcgg ggagtggacg    1200
gaggaggcgg gggagcgggc cgcccttttcc gagaggctct tcgccaacct gtggggggagg    1260 cttgagggggg aggagaggct cctttggctt taccgggagg tggagaggcc cctttccgct    1320
gtcctggccc acatggaggc cacgggggtg cgcctggacg tggcctatct cagggccttg    1380
tccctggagg tggccgggga gatcgcccgc ctcgaggccg aggtcttccg cctggccggc    1440 cacccctttca acctcaactc ccgggaccag ctggaaaggg tcctctttga cgagctaggg    1500
cttcccgcca tcggcaagac ggagaagacc ggcaagcgct ccaccagcgc cgccgtcctg    1560 gaggcccctcc gcgaggccca ccccatcgtg gagaagatcc tgcaggcatg caagcttggc    1620
actggccgtc gttttacaac gtcgtga                                        1647

<210> SEQ ID NO 10
<211> LENGTH: 2088
<212> TYPE: DNA
<213> ORGANISM: Artificial Sequence
<220> FEATURE:
<223> OTHER INFORMATION: Description of Artificial Sequence:   Synthetic

<400> SEQUENCE: 10
atgaattcgg ggatgctgcc cctctttgag cccaagggcc gggtcctcct ggtggacggc      60
caccacctgg cctaccgcac cttccacgcc ctgaagggcc tcaccaccag ccggggggag     120
ccggtgcagg cggtctacgg cttcgccaag agcctcctca aggccctcaa ggaggacggg     180
gacgcggtga tcgtggtctt tgacgccaag gcccctcct ccgccacga ggcctacggg       240 gggtacaagg cgggccgggc ccccacgcgc gaggactttc cccggcaact cgccctcatc     300
aaggagctgg tggacctcct ggggctggcg cgcctcgagg tcccgggcta cgaggcggac     360
gacgtcctgg ccagcctggc caagaaggcg gaaaaggagg gctacgaggt ccgcatcctc     420
accgccgaca agacctttta ccagctcctt tccgaccgca tccacgtcct ccaccccgag     480
gggtacctca tcacccccggc ctggcttttgg gaaaagtacg gcctgaggcc cgaccagtgg     540
gccgactacc gggccctgac cggggacgag tccgacaacc ttcccgggggt caagggcatc     600 ggggagaaga cggcgaggaa gcttctggag gagtgggggga gcctggaagc cctcctcaag     660
aacctggacc ggctgaagcc cgccatccgg gagaagatcc tggcccacat ggacgatctg     720
aagctctcct gggacctggc caaggtgcgc accgacctgc ccctggaggt ggacttcgcc     780
aaaaggcggg agcccgaccg ggagaggctt agggcctttc tggagaggct tgagtttggc     840
agcctcctcc acgagttcgg ccttctggaa agccccaagg ccctggagga ggcccccctgg     900 ccccgccgg aagggggcctt cgtgggcttt gtgctttccc gcaaggagcc catgtgggcc     960
gatcttctgg ccctggccgc cgccaggggg ggccgggtcc accggccccc cgagccttat    1020
aaagccctca gggacctgaa ggaggcgcgg gggcttctcg ccaaagacct gagcgttctg    1080
gccctgaggg aaggccttgg cctcccgccc ggcgacgacc ccatgctcct cgcctacctc    1140 ctggacccctt ccaacaccac ccccgagggg gtggcccggc gctacggcgg ggagtggacg    1200
gaggaggcgg gggagcgggc cgcccttttcc gagaggctct tcgccaacct gtggggggagg    1260 cttgagggggg aggagaggct cctttggctt taccgggagg tggagaggcc cctttccgct    1320
gtcctggccc acatggaggc cacgggggtg cgcctggacg tggcctatct cagggccttg    1380
```

```
tccctggagg tggccgggga gatcgcccgc ctcgaggccg aggtcttccg cctggccggc    1440
caccccttca acctcaactc ccgggaccag ctggaaaggg tcctctttga cgagctaggg    1500
cttcccgcca tcggcaagac ggagaagacc ggcaagcgct ccaccagcgc cgccgtcctg    1560
gaggccctcc gcgaggccca ccccatcgtg gagaagatcc tgcagtaccg ggagctcacc    1620
aagctgaaga gcacctacat tgaccccttg ccggacctca tccacccag  acgggccgc    1680 ctccacaccc gcttcaacca gacggccacg gccacgggca ggctaagtag ctccgatccc    1740
aacctccaga acatccccgt ccgcacccg  cttgggcaga ggatccgccg ggccttcatc    1800
gccgaggagg ggtggctatt ggtggccctg gactatagcc agatagagct cagggtgctg    1860
gcccacctct ccggcgacga gaacctgatc cgggtcttcc aggaggggcg ggacatccac    1920
acggagaccg ccagctggat gttcggcgtc ccccgggagg ccgtggaccc cctgatgcgc    1980
cgggcggcca agaccatcaa cttcgggtc  ctctacggca tgtcggccca ccgcctctcc    2040
caggagctag ctagccatcc cttacgagga ggcccaggcc ttcattga               2088

<210> SEQ ID NO 11
<211> LENGTH: 962
<212> TYPE: DNA
<213> ORGANISM: Artificial Sequence
<220> FEATURE:
<223> OTHER INFORMATION: Description of Artificial Sequence:  Synthetic

<400> SEQUENCE: 11
atgaattcgg ggatgctgcc cctctttgag cccaagggcc gggtcctcct ggtggacggc      60
caccacctgg cctaccgcac cttccacgcc ctgaagggcc tcaccaccag ccgggggag     120 ccggtgcagg cggtctacgg cttcgccaag agcctcctca aggccctcaa ggaggacggg     180
gacgcggtga tcgtggtctt tgacgccaag gccccctcct ccgccacga ggcctacggg     240 gggtacaagg cgggccgggc ccccacgccg gaggactttc cccggcaact cgccctcatc     300
aaggagctgg tggacctcct ggggctggcg cgcctcgagg tccgggcta cgaggcggac     360 gacgtcctgg ccagcctggc caagaaggcg gaaaaggagg gctacgaggt ccgcatcctc     420
accgccgaca agaccttta ccagcttctt tccgaccgca tccacgtcct ccaccccgag     480
gggtacctca tcacccccgc ctggcttggg gaaaagtacg gcctgaggcc cgaccagtgg     540
gccgactacc gggccctgac cggggacgag tccgacaacc ttcccgggt  caagggcatc     600 ggggagaaga cggcgaggaa gcttctggag gagtggggga cctggaagc  cctcctcaag     660 aacctggacc ggctgaagcc cgccatccgg gagaagatcc tggcccacat ggacgatctg     720
aagctctcct gggacctggc caaggtgcgc accgacctgc cctggaggt  ggacttcgcc     780 aaaaggcggg agcccgaccg ggagaggctt agggcctttc tggagaggct tgagtttggc     840
agcctcctcc acgagttcgg ccttctggaa agccccaagt catggagggg gtgtatcccc     900
tggccgtgcc cctggaggtg gaggtgggga tagggga gga ctggctctcc gccaaggagt     960
ga                                                                    962

<210> SEQ ID NO 12
<211> LENGTH: 1600
<212> TYPE: DNA
<213> ORGANISM: Artificial Sequence
<220> FEATURE:
<223> OTHER INFORMATION: Description of Artificial Sequence:  Synthetic

<400> SEQUENCE: 12
```

-continued

```
atggaattcg gggatgctgc ccctctttga gcccaagggc cgggtcctcc tggtggacgg      60
ccaccacctg gcctaccgca ccttccacgc cctgaagggc ctcaccacca gccgggggga     120
gccggtgcag gcggtctacg gcttcgccaa gagcctcctc aaggccctca aggaggacgg     180
ggacgcggtg atcgtggtct tgacgccaa ggcccctcc ttccgccacg aggcctacgg      240
ggggtacaag gcggccgggc ccccacgcc ggaggacttt ccccggcaac tcgccctcat     300
caaggagctg gtggacctcc tggggctggc gcgcctcgag gtcccgggct acgaggcgga     360
cgacgtcctg gccagcctgg ccaagaaggc ggaaaaggag ggctacgagg tccgcatcct     420
caccgccgac aaagaccttt accagctcct ttccgaccgc atccacgtcc tccaccccga     480
ggggtacctc atcaccccgg cctggctttg ggaaaagtac ggcctgaggc ccgaccagtg     540
ggccgactac cgggccctga ccggggacga gtccgacaac cttcccgggg tcaagggcat     600
cggggagaag acggcgagga agcttctgga ggagtggggg agcctggaag ccctcctcaa     660
gaacctggac cggctgaagc ccgccatccg ggagaagatc ctggcccaca tggacgatct     720
gaagctctcc tgggacctgg ccaaggtgcg caccgacctg cccctggagg tggacttcgc     780
caaaaggcgg gagcccgacc gggagaggct tagggccttt ctggagaggc ttgagtttgg     840
cagcctcctc cacgagttcg gccttctgga agcccccaag atccgccggg ccttcatcgc     900
cgaggagggg tggctattgg tggccctgga ctatagccag atagagctca gggtgctggc     960
ccacctctcc ggcgacgaga acctgatccg ggtcttccag gagggcgggg acatccacac    1020
ggagaccgcc agctggatgt tcggcgtccc ccgggaggcc gtggacccc tgatgcgccg     1080 ggcggccaag accatcaact tcggggtcct ctacggcatg tcggcccacc gcctctccca    1140
ggagctagcc atcccttacg aggaggccca ggccttcatt gagcgctact ttcagagctt    1200 cccccaaggtg cgggcctgga ttgagaagac cctggaggag ggcaggaggc ggggtacgt    1260 ggagaccctc ttcggccgcc gccgctacgt gccagaccta gaggcccggg tgaagagcgt    1320
gcgggaggcg gccgagcgca tggccttcaa catgcccgtc cggggcaccg ccgccgacct    1380
catgaagctg gctatggtga agctcttccc caggctggag gaaatggggg ccaggatgct    1440
ccttcaggtc cacgacgagc tggtcctcga ggccccaaaa gagagggcgg aggccgtggc    1500
ccggctggcc aaggaggtca tggaggggt gtatcccctg gccgtgcccc tggaggtgga    1560
ggtggggata ggggaggact ggctctccgc caaggagtga                           1600
```

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 13

```
cacgaattcg gggatgctgc ccctctttga gcccaa                                36
```

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 14

```
gtgagatcta tcactccttg gcggagagcc agtc                                  34
```

<210> SEQ ID NO 15
<211> LENGTH: 91
<212> TYPE: DNA
<213> ORGANISM: Artificial Sequence
<220> FEATURE:
<223> OTHER INFORMATION: Description of Artificial Sequence: Synthetic

<400> SEQUENCE: 15
taatacgact cactataggg agaccggaat tcgagctcgc ccgggcgagc tcgaattccg    60
tgtattctat agtgtcacct aaatcgaatt c                                  91

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
taatacgact cactataggg                                               20

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 17
gaattcgatt taggtgacac tatagaa                                       27

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 18
gtaatcatgg tcatagctgg tagcttgcta c                                  31

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 19
ggatcctcta gagtcgacct gcaggcatgc ctaccttggt ag                      42

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 20
ggatcctcta gagtcgacct gcaggcatgc                                    30

<210> SEQ ID NO 21
<211> LENGTH: 2502
<212> TYPE: DNA
<213> ORGANISM: Artificial Sequence
<220> FEATURE:

<223> OTHER INFORMATION: Description of Artificial Sequence: Synthetic

<400> SEQUENCE: 21

| | | | | | |
|---|---|---|---|---|---|
| atgaattcgg | ggatgctgcc | cctctttgag | cccaagggcc | gggtcctcct | ggtggacggc | 60 |
| caccacctgg | cctaccgcac | cttccacgcc | ctgaagggcc | tcaccaccag | ccggggggag | 120 |
| ccggtgcagg | cggtctacgg | cttcgccaag | agcctcctca | aggccctcaa | ggaggacggg | 180 |
| gacgcggtga | tcgtggtctt | tgacgccaag | gcccctcct | tccgccacga | ggcctacggg | 240 |
| gggtacaagg | cgggccgggc | ccccacgccg | gaggactttc | cccggcaact | cgccctcatc | 300 |
| aaggagctgg | tggacctcct | ggggctggcg | cgcctcgagg | tcccgggcta | cgaggcggac | 360 |
| gacgtcctgg | ccagcctggc | caagaaggcg | gaaaaggagg | gctacgaggt | ccgcatcctc | 420 |
| accgccgaca | aagaccttta | ccagctcctt | tccgaccgca | tccacgtcct | ccaccccgag | 480 |
| gggtacctca | tcaccccggc | ctggctttgg | gaaaagtacg | gcctgaggcc | cgaccagtgg | 540 |
| gccgactacc | gggccctgac | cggggacgag | tccgacaacc | ttcccggggt | caagggcatc | 600 |
| ggggagaaga | cggcgaggaa | gcttctggag | gagtggggga | gcctggaagc | cctcctcaag | 660 |
| aacctggacc | ggctgaagcc | cgccatccgg | gagaagatcc | tggcccacat | ggacgatctg | 720 |
| aagctctcct | gggacctggc | caaggtgcgc | accgacctgc | cctggaggt | ggacttcgcc | 780 |
| aaaaggcggg | agcccgaccg | ggagaggctt | agggcctttc | tggagaggct | tgagtttggc | 840 |
| agcctcctcc | acgagttcgg | ccttctggaa | agccccaagg | ccctggagga | ggcccctgg | 900 |
| cccccgccgg | aagggccctt | cgtgggcttt | gtgctttccc | gcaaggagcc | catgtgggcc | 960 |
| gatcttctgg | ccctggccgc | cgccaggggg | ggccgggtcc | accgggcccc | cgagccttat | 1020 |
| aaagccctca | gggacctgaa | ggaggcgcgg | gggcttctcg | ccaaagacct | gagcgttctg | 1080 |
| gccctgaggg | aaggccttgg | cctcccgccc | ggcgacgacc | ccatgctcct | cgcctacctc | 1140 |
| ctggaccctt | ccaacaccac | ccccgagggg | gtggcccggc | gctacggcgg | ggagtggacg | 1200 |
| gaggaggcgg | gggagcgggc | cgccctttcc | gagaggctct | cgccaacct | gtgggggagg | 1260 |
| cttgagggg | aggagaggct | cctttggctt | taccgggagt | ggagaggcc | cctttccgct | 1320 |
| gtcctggccc | acatggaggc | cacggggtg | cgcctggacg | tggcctatct | cagggccttg | 1380 |
| tccctggagt | ggccggggga | gatcgcccgc | ctcgaggccg | aggtcttccg | cctgccggc | 1440 |
| caccccttca | acctcaactc | ccgggaccag | ctggaaaggg | tcctctttga | cgagctaggg | 1500 |
| cttcccgcca | tcggcaagac | ggagaagacc | ggcaagcgct | ccaccagcgc | cgccgtcctg | 1560 |
| gaggccctcc | gcgaggccca | cccatcgtg | gagaagatcc | tgcagtaccg | ggagctcacc | 1620 |
| aagctgaaga | gcacctacat | tgacccccttg | ccggacctca | tccacccag | gacgggccgc | 1680 |
| ctccacaccc | gcttcaacca | gacggccacg | gccacgggca | ggctaagtag | ctccgatccc | 1740 |
| aacctccaga | acatccccgt | ccgcacccc | cttgggcaga | ggatccgccg | ggccttcatc | 1800 |
| gccgaggagg | ggtggctatt | ggtggccctg | gactatagcc | agatagagct | cagggtgctg | 1860 |
| gcccacctct | ccgcgacga | gaacctgatc | cgggtcttcc | aggagggcg | ggacatccac | 1920 |
| acggagaccg | ccagctggat | gttcggcgtc | cccgggag | ccgtggaccc | cctgatgcgc | 1980 |
| cgggcggcca | agaccatcaa | cttcgggtc | ctctacggca | tgtcggccca | ccgcctctcc | 2040 |
| caggagctag | ccatcccta | cgaggaggcc | caggccttca | ttgagcgcta | ctttcagagc | 2100 |
| ttccccaagg | tgcgggcctg | gattgagaag | accctggagg | agggcaggag | gcgggggtac | 2160 |
| gtggagaccc | tcttcggccg | ccgccgctac | gtgccagacc | tagaggcccg | ggtgaagagc | 2220 |
| gtgcgggagg | cggccgagcg | catggccttc | aacatgcccg | tccggggcac | cgccgccgac | 2280 | ctcatgaagc tggctatggt gaagctcttc cccaggctgg aggaaatggg ggccaggatg    2340 ctccttcagg tccacgacga gctggtcctc gaggccccaa aagagagggc ggaggccgtg    2400 gcccggctgg ccaaggaggt catggagggg gtgtatcccc tggccgtgcc cctggaggtg    2460 gaggtgggga tagggagga ctggctctcc gccaaggagt ga                        2502

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 22
gatttaggtg acactatag                                                 19

<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic

<400> SEQUENCE: 23
cggacgaaca agcgagacag cgacacaggt accacatggt acaagaggca agagagacga    60
cacagcagaa ac                                                        72

<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: Synthetic

<400> SEQUENCE: 24
gtttctgctg tgtcgtctct cttgcctctt gtaccatgtg gtacctgtgt cgctgtctcg    60
cttgttcgtc                                                           70

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
gacgaacaag cgagacagcg                                                20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 26
gtttctgctg tgtcgtctct cttg                                           24

<210> SEQ ID NO 27
<211> LENGTH: 46
<212> TYPE: DNA
<213> ORGANISM: Artificial Sequence
<220> FEATURE:

<223> OTHER INFORMATION: Description of Artificial Sequence: Synthetic

<400> SEQUENCE: 27
cctcttgtac catgtggtac ctgtgtcgct gtctcgcttg ttcgtc    46

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic

<400> SEQUENCE: 28
acacaggtac cacatggtac aagaggcaag agagacgaca cagcagaaac    50

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 29

Met Ala Ser Met Thr Gly Gly Gln Gln Met Gly Arg Ile Asn Ser
 1               5                  10                  15

<210> SEQ ID NO 30
<211> LENGTH: 969
<212> TYPE: DNA
<213> ORGANISM: Artificial Sequence
<220> FEATURE:
<223> OTHER INFORMATION: Description of Artificial Sequence: Synthetic

<400> SEQUENCE: 30
atggctagca tgactggtgg acagcaaatg ggtcggatca attcggggat gctgcccctc    60
tttgagccca agggccgggt cctcctggtg gacggccacc acctggccta ccgcaccttc    120
cacgccctga agggcctcac caccagccgg ggggagccgg tgcaggcggt ctacggcttc    180
gccaagagcc tcctcaaggc cctcaaggag gacggggacg cggtgatcgt ggtctttgac    240
gccaaggccc cctccttccg ccacgaggcc tacgggggt acaaggcggg ccgggccccc    300
acgccggagg actttccccg gcaactcgcc ctcatcaagg agctggtgga cctcctgggg    360
ctggcgcgcc tcgaggtccc gggctacgag gcggacgacg tcctggccag cctggccaag    420
aaggcggaaa aggagggcta cgaggtccgc atcctcaccg ccgacaaaga cctttaccag    480
cttctttccg accgcatcca cgtcctccac cccgaggggt acctcatcac cccggcctgg    540
ctttgggaaa agtacggcct gaggcccgac cagtgggccg actaccggc cctgaccggg    600
gacgagtccg acaaccttcc cggggtcaag ggcatcgggg agaagacggc gaggaagctt    660
ctggaggagt gggggagcct ggaagccctc ctcaagaacc tggaccggct gaagcccgcc    720
atccgggaga agatcctggc ccacatggac gatctgaagc tctcctggga cctggccaag    780
gtgcgcaccg acctgcccct ggaggtggac ttcgccaaaa ggcggagcc cgaccgggag    840
aggcttaggg cctttctgga gaggcttgag tttggcagcc tcctccacga gttcggcctt    900
ctggaaagcc ccaagtcatg gagggggtgt atccctggc cgtgccctg gaggtggagg    960
tggggatag                                                            969

<210> SEQ ID NO 31
<211> LENGTH: 948
<212> TYPE: DNA

<213> ORGANISM: Artificial Sequence
<220> FEATURE:
<223> OTHER INFORMATION: Description of Artificial Sequence: Synthetic

<400> SEQUENCE: 31

| | | | | | |
|---|---|---|---|---|---|
| atggctagca | tgactggtgg | acagcaaatg | gtcggatca | attcgggat | gctgcccctc | 60 |
| tttgagccca | agggccgggt | cctcctggtg | acggccacc | acctggccta | ccgcaccttc | 120 |
| cacgccctga | agggcctcac | caccagccgg | ggggagccgg | tgcaggcggt | ctacggcttc | 180 |
| gccaagagcc | tcctcaaggc | cctcaaggag | acggggacg | cggtgatcgt | ggtcttttgac | 240 |
| gccaaggccc | cctccttccg | ccacgaggcc | tacgggggggt | acaaggcggg | ccgggcccccc | 300 |
| acgccgagg | actttccccg | gcaactcgcc | ctcatcaagg | agctggtgga | cctcctgggg | 360 |
| ctggcgcgcc | tcgaggtccc | gggctacgag | gcggacgacg | tcctggccag | cctggccaag | 420 |
| aaggcggaaa | aggagggcta | cgaggtccgc | atcctcaccg | ccgacaaaga | cctttaccag | 480 |
| cttctttccg | accgcatcca | cgtcctccac | cccgaggggt | acctcatcac | cccggcctgg | 540 |
| ctttgggaaa | agtacggcct | gaggcccgac | cagtgggccg | actaccgggc | cctgaccggg | 600 |
| gacgagtccg | acaaccttcc | cggggtcaag | ggcatcgggg | agaagacggc | gaggaagctt | 660 |
| ctggaggagt | gggggagcct | ggaagccctc | ctcaagaacc | tggaccggct | gaagcccgcc | 720 |
| atccgggaga | agatcctggc | ccacatggac | gatctgaagc | tctcctggga | cctggccaag | 780 |
| gtgcgcaccg | acctgcccct | ggaggtggac | ttcgccaaaa | ggcgggagcc | cgaccgggag | 840 |
| aggcttaggg | cctttctgga | gaggcttgag | tttggcagcc | tcctccacga | gttcggcctt | 900 |
| ctggaaagcc | ccaaggccgc | actcgagcac | caccaccacc | accactga | | 948 |

<210> SEQ ID NO 32
<211> LENGTH: 206
<212> TYPE: DNA
<213> ORGANISM: Artificial Sequence
<220> FEATURE:
<223> OTHER INFORMATION: Description of Artificial Sequence: Synthetic

<400> SEQUENCE: 32

| | | | | | |
|---|---|---|---|---|---|
| cgccagggtt | ttcccagtca | cgacgttgta | aaacgacggc | cagtgaattg | taatacgact | 60 |
| cactataggg | cgaattcgag | ctcggtaccc | ggggatcctc | tagagtcgac | ctgcaggcat | 120 |
| gcaagcttga | gtattctata | gtgtcaccta | aatagcttgg | cgtaatcatg | gtcatagctg | 180 |
| tttcctgtgt | gaaattgtta | tccgct | | | | 206 |

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 33
ttctgggttc tctgctctct ggtcgctgtc tcgcttgttc gtc    43

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 34
gctgtctcgc ttgttcgtc    19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 35
gacgaacaag cgagacagcg                                       20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 36
ttctgggttc tctgctctct ggtc                                  24

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 37
gacgaacaag cgagacagcg accagagagc agagaaccca gaa             43

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 38
accagagagc agagaaccca gaa                                   23

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 39
aacagctatg accatgatta c                                     21

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic

<400> SEQUENCE: 40
gttctctgct ctctggtcgc tgtctcgctt gtgaaacaag cgagacagcg tggtctctcg    60

<210> SEQ ID NO 41
<211> LENGTH: 15
<212> TYPE: DNA
<213> ORGANISM: Artificial Sequence
<220> FEATURE:

<223> OTHER INFORMATION: Description of Artificial Sequence: Synthetic

<400> SEQUENCE: 41
cgagagacca cgctg                                                            15

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: Synthetic

<400> SEQUENCE: 42
cctttcgctt tcttcccttc ctttctcgcc acgttcgccg gctttccccg tc                   52

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 43
agaaaggaag ggaagaaagc gaaagg                                                26

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 44
gacggggaaa gccggcgaac g                                                     21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
gaaagccggc gaacgtggcg                                                       20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 46
ggcgaacgtg gcgagaaagg a                                                     21

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 47
cctttcgctt tcttcccttc ctttctcgcc acgttcgccg gc                              42

```
<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 48
cctttcgctc tcttcccttc ctttctcgcc acgttcgccg gc                           42

<210> SEQ ID NO 49
<211> LENGTH: 27
<212> TYPE: DNA
<213> ORGANISM: Artificial Sequence
<220> FEATURE:
<221> NAME/KEY: misc_feature
<222> LOCATION: (8)
<223> OTHER INFORMATION: The A residue at this position is
      2'-O-methyladenosine.
<223> OTHER INFORMATION: Description of Artificial Sequence: Synthetic

<400> SEQUENCE: 49
agaaaggaag ggaagaaagc gaaaggt                                            27

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 50
gccggcgaac gtggcgagaa agga                                               24

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 51 ggttttttctt tgaggtttag                                                   20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 52
gcgacactcc accatagat                                                     19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 53
ctgtcttcac gcagaaagc                                                     19

<210> SEQ ID NO 54
<211> LENGTH: 19
<212> TYPE: DNA
```

<213> ORGANISM: Artificial Sequence
<220> FEATURE:
<223> OTHER INFORMATION: Description of Artificial Sequence: Synthetic

<400> SEQUENCE: 54
gcacggtcta cgagacctc                                                19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 55
taatacgact cactataggg                                               20

<210> SEQ ID NO 56
<211> LENGTH: 337
<212> TYPE: DNA
<213> ORGANISM: Artificial Sequence
<220> FEATURE:
<223> OTHER INFORMATION: Description of Artificial Sequence: Synthetic

<400> SEQUENCE: 56
gggaaagcuu gcaugccugc aggucgacuc uagaggaucu acuagucaua uggauucugu    60
cuucacgcag aaagcgucug gccauggcgu uaguaugagu gucgugcagc cuccaggacc   120
cccccucccg ggagaggcau aguggucugc ggaaccggug aguacaccgg aauugccagg   180
acgaccgggu ccuuucuugg auaaacccgc ucaaugccug gagauuuggg cgugccccg    240 caagacugcu agccgaguag uguugggucg cgaaaggccu ugugguacug ccugauaggg   300
ugccugcgag ugccccggga ggucucguag accgugc                           337

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (17)
<223> OTHER INFORMATION: The T at this position is linked to a
      fluorescein dye on an abasic linker.

<400> SEQUENCE: 57
ccggtcgtcc tggcaatcc                                                19

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 58
gtttatccaa gaaaggaccc ggtc                                          24

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 59
cagggtgaag ggaagaagaa agcgaaaggt                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 60 caggggggaag ggaagaagaa agcgaaaggt                                   30

<210> SEQ ID NO 61
<211> LENGTH: 22
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: The T residues at positions 1 and 2 are amino
      modified T residues.
<223> OTHER INFORMATION: Description of Artificial Sequence: Synthetic

<400> SEQUENCE: 61
ttcttttcac cagcgagacg gg                                            22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 62
attgggcgcc agggtggttt tt                                            22

<210> SEQ ID NO 63
<211> LENGTH: 53
<212> TYPE: DNA
<213> ORGANISM: Artificial Sequence
<220> FEATURE:
<223> OTHER INFORMATION: Description of Artificial Sequence: Synthetic

<400> SEQUENCE: 63
cccgtctcgc tggtgaaaag aaaaaccacc ctggcgccca atacgcaaac cgc          53

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 64
gaattcgatt taggtgacac tatagaatac a                                  31

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 65
cctttcgctt tcttcccttc ctttctcgcc acgttcgccg gc                      42

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 66
gccggcgaac gtggcgagaa agga                                           24

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 67
cagaaggaag ggaagaaagc gaaagg                                         26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 68 caggggaag ggaagaaagc gaaagg                                          26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 69
cagggtacag ggaagaaagc gaaagg                                         26

<210> SEQ ID NO 70
<211> LENGTH: 24
<212> TYPE: DNA
<213> ORGANISM: Artificial Sequence
<220> FEATURE:
<221> NAME/KEY: misc_feature
<222> LOCATION: (24)
<223> OTHER INFORMATION: The residue at this position is a
      dideoxycytidine.
<223> OTHER INFORMATION: Description of Artificial Sequence:
      Synthetic

<400> SEQUENCE: 70
gccggcgaac gtggcgagaa aggc                                           24

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (26)
<223> OTHER INFORMATION: The G at this position is linked to a spacer
      bearing a Cy3 amidite group.
<221> NAME/KEY: misc_feature
<222> LOCATION: (27)
<223> OTHER INFORMATION: The residue at this position is a

```
          dideoxycytidine.

<400> SEQUENCE: 71
agaaaggaag ggaagaaagc gaaaggc                                          27

<210> SEQ ID NO 72
<211> LENGTH: 27
<212> TYPE: DNA
<213> ORGANISM: Artificial Sequence
<220> FEATURE:
<221> NAME/KEY: misc_feature
<222> LOCATION: (1)
<223> OTHER INFORMATION: The A at this position is linked to a  spacer
      containing a fluorescein label.
<221> NAME/KEY: misc_feature
<222> LOCATION: (26)
<223> OTHER INFORMATION: The G at this position is linked to a spacer
      bearing a Cy3 amidite group.
<221> NAME/KEY: misc_feature
<222> LOCATION: (27)
<223> OTHER INFORMATION: The residue at this position is a
      dideoxycytidine.
<223> OTHER INFORMATION: Description of Artificial Sequence:  Synthetic

<400> SEQUENCE: 72
agaaaggaag ggaagaaagc gaaaggc                                          27

<210> SEQ ID NO 73
<211> LENGTH: 26
<212> TYPE: DNA
<213> ORGANISM: Artificial Sequence
<220> FEATURE:
<221> NAME/KEY: misc_feature
<222> LOCATION: (1)
<223> OTHER INFORMATION: The A at this position is linked to a  spacer
      containing a fluorescein label.
<223> OTHER INFORMATION: Description of Artificial Sequence:  Synthetic

<400> SEQUENCE: 73
agaaaggaag ggaagaaagc gaaagg                                           26

<210> SEQ ID NO 74
<211> LENGTH: 27
<212> TYPE: DNA
<213> ORGANISM: Artificial Sequence
<220> FEATURE:
<221> NAME/KEY: misc_feature
<222> LOCATION: (1)
<223> OTHER INFORMATION: The A at this position is linked to a spacer
      bearing a Cy3 amidite group.
<221> NAME/KEY: misc_feature
<222> LOCATION: (26)
<223> OTHER INFORMATION: The G at this position is linked to a  spacer
      bearing a biotin group.
<223> OTHER INFORMATION: Description of Artificial Sequence:  Synthetic

<400> SEQUENCE: 74
agaaaggaag ggaagaaagc gaaaggt                                          27

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:  Synthetic

<400> SEQUENCE: 75
ggaaagccgg cgaacgtggc gaga                                             24
```

```
<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 76
ggaaagccgg cgaacgtggc gagaaa                                          26

<210> SEQ ID NO 77
<211> LENGTH: 23
<212> TYPE: DNA
<213> ORGANISM: Artificial Sequence
<220> FEATURE:
<221> NAME/KEY: misc_feature
<222> LOCATION: (1)
<223> OTHER INFORMATION: The T at this position is linked to a spacer
      bearing a Cy3 amidite group.
<221> NAME/KEY: misc_feature
<222> LOCATION: (1)..(2)
<223> OTHER INFORMATION: The residues at these positions have an amino
      group added.
<221> NAME/KEY: misc_feature
<222> LOCATION: (22)
<223> OTHER INFORMATION: The T at this position is linked to a spacer
      containing a fluorescein label.
<223> OTHER INFORMATION: Description of Artificial Sequence: Synthetic

<400> SEQUENCE: 77
ttccagagcc taatttgcca gta                                             23

<210> SEQ ID NO 78
<211> LENGTH: 23
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position has a 5' TET-label.
<221> NAME/KEY: misc_feature
<222> LOCATION: (22)
<223> OTHER INFORMATION: The T at this position is linked to a spacer
      containing a fluorescein label.
<223> OTHER INFORMATION: Description of Artificial Sequence: Synthetic

<400> SEQUENCE: 78
ttccagagcc taatttgcca gta                                             23

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 79
cttaccaacg ctaacgagcg tcttg                                           25

<210> SEQ ID NO 80
<211> LENGTH: 14
<212> TYPE: DNA
<213> ORGANISM: Artificial Sequence
<220> FEATURE:
<221> NAME/KEY: misc_feature
<222> LOCATION: (14)
<223> OTHER INFORMATION: The residue at this positions contain an abasic
      ribose.
<223> OTHER INFORMATION: Description of Artificial Sequence: Synthetic

<400> SEQUENCE: 80
```
cgagagacca cgct                                                          14

<210> SEQ ID NO 81
<211> LENGTH: 14
<212> TYPE: DNA
<213> ORGANISM: Artificial Sequence
<220> FEATURE:
<221> NAME/KEY: misc_feature
<222> LOCATION: (14)
<223> OTHER INFORMATION: The residue at this position contains an abasic
      ribose with a 3' phosphate group.
<223> OTHER INFORMATION: Description of Artificial Sequence: Synthetic

<400> SEQUENCE: 81
cgagagacca cgct                                                          14

<210> SEQ ID NO 82
<211> LENGTH: 15
<212> TYPE: DNA
<213> ORGANISM: Artificial Sequence
<220> FEATURE:
<221> NAME/KEY: misc_feature
<222> LOCATION: (15)
<223> OTHER INFORMATION: The residue at this position contains a 3'
      phosphate group.
<223> OTHER INFORMATION: Description of Artificial Sequence: Synthetic

<400> SEQUENCE: 82
cgagagacca cgctg                                                         15

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 83
cccgtctcgc tggtgaaaag aaaaaccacc ctggcgccca ata                          43

<210> SEQ ID NO 84
<211> LENGTH: 22
<212> TYPE: DNA
<213> ORGANISM: Artificial Sequence
<220> FEATURE:
<221> NAME/KEY: misc_feature
<222> LOCATION: (15)
<223> OTHER INFORMATION: The G at this position is linked to a
      3-nitropyrrole.
<223> OTHER INFORMATION: Description of Artificial Sequence: Synthetic

<400> SEQUENCE: 84
tattgggcgc caggggttt tt                                                  22

<210> SEQ ID NO 85
<211> LENGTH: 22
<212> TYPE: DNA
<213> ORGANISM: Artificial Sequence
<220> FEATURE:
<221> NAME/KEY: misc_feature
<222> LOCATION: (15)
<223> OTHER INFORMATION: The G at this position is linked to a
      3-nitropyrrole group.
<223> OTHER INFORMATION: Description of Artificial Sequence: Synthetic

<400> SEQUENCE: 85
tattgggcgc catggggttt tt                                                 22

```
<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence:  Synthetic

<400> SEQUENCE: 86
tattgggcgc catggtggtt ttt                                            23

<210> SEQ ID NO 87
<211> LENGTH: 21
<212> TYPE: DNA
<213> ORGANISM: Artificial Sequence
<220> FEATURE:
<221> NAME/KEY: misc_feature
<222> LOCATION: (9)
<223> OTHER INFORMATION: The G at this position is linked to a
      5-nitroindole.
<221> NAME/KEY: misc_feature
<222> LOCATION: (14)
<223> OTHER INFORMATION: The G at this position is linked to a
      5-nitroindole.
<223> OTHER INFORMATION: Description of Artificial Sequence:  Synthetic

<400> SEQUENCE: 87
tattgggcgc aggggttttt t                                              21

<210> SEQ ID NO 88
<211> LENGTH: 21
<212> TYPE: DNA
<213> ORGANISM: Artificial Sequence
<220> FEATURE:
<221> NAME/KEY: misc_feature
<222> LOCATION: (9)
<223> OTHER INFORMATION: The G at this position is linked to a
      5-nitroindole.
<221> NAME/KEY: misc_feature
<222> LOCATION: (14)
<223> OTHER INFORMATION: The G at this position is linked to a
      5-nitroindole.
<223> OTHER INFORMATION: Description of Artificial Sequence:  Synthetic

<400> SEQUENCE: 88
tattgggcgc atggggtttt t                                              21

<210> SEQ ID NO 89
<211> LENGTH: 8
<212> TYPE: DNA
<213> ORGANISM: Artificial Sequence
<220> FEATURE:
<221> NAME/KEY: misc_feature
<222> LOCATION: (1)
<223> OTHER INFORMATION: The T at this position is linked to a spacer
      bearing a Cy3 amidite label.
<221> NAME/KEY: misc_feature
<222> LOCATION: (2)..(3)
<223> OTHER INFORMATION: The residues at these positions have an amino
      group added.
<223> OTHER INFORMATION: Description of Artificial Sequence:  Synthetic

<400> SEQUENCE: 89 ttcaccag                                                              8

<210> SEQ ID NO 90
<211> LENGTH: 23
<212> TYPE: DNA
<213> ORGANISM: Artificial Sequence
<220> FEATURE:
<221> NAME/KEY: misc_feature
```

```
<222> LOCATION: (1)
<223> OTHER INFORMATION: The residue at this position is a
      2'deoxyguanosine 5'-O-(1-Thiomonophosphate).
<221> NAME/KEY: misc_feature
<222> LOCATION: (2)
<223> OTHER INFORMATION: The residue at this position is a
      2'deoxycytosine 5'-O-(1-Thiomonophosphate).
<221> NAME/KEY: misc_feature
<222> LOCATION: (3)
<223> OTHER INFORMATION: The residue at this position is a
      2'deoxythymidine 5'-O-(1-Thiomonophosphate).
<221> NAME/KEY: misc_feature
<222> LOCATION: (4)
<223> OTHER INFORMATION: The residue at this position is a
      2'deoxycytosine 5'-O-(1-Thiomonophosphate).
<221> NAME/KEY: misc_feature
<222> LOCATION: (5)..(6)
<223> OTHER INFORMATION: The residues at these positions are
      2'deoxyadenosine 5'-O-(1-Thiomonophosphate).
<221> NAME/KEY: misc_feature
<222> LOCATION: (7)..(8)
<223> OTHER INFORMATION: The residues at these positions are
      2'deoxyguanosine 5'-O-(1-Thiomonophosphate)
<221> NAME/KEY: misc_feature
<222> LOCATION: (9)
<223> OTHER INFORMATION: The residue at this position is a
      2'deoxycytosine 5'-O-(1-Thiomonophosphate).
<223> OTHER INFORMATION: Description of Artificial Sequence:  Synthetic

<400> SEQUENCE: 90
gctcaaggca ctcttgccta cga                                          23

<210> SEQ ID NO 91
<211> LENGTH: 27
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position is a
      2'deoxycytosine 5'-O-(1-Thiomonophosphate).
<221> NAME/KEY: misc_feature
<222> LOCATION: (2)
<223> OTHER INFORMATION: The residue at this position is a
      2'deoxythymidine 5'-O-(1-Thiomonophosphate).
<221> NAME/KEY: misc_feature
<222> LOCATION: (3)..(4)
<223> OTHER INFORMATION: The residues at these positions are a
      2'deoxycytosine 5'-O-(1-Thiomonophosphate).
<221> NAME/KEY: misc_feature
<222> LOCATION: (5)..(6)
<223> OTHER INFORMATION: The residues at these positions are a
      2'deoxyadenosine 5'-O-(1-Thiomonophosphate).
<221> NAME/KEY: misc_feature
<222> LOCATION: (7)
<223> OTHER INFORMATION: The residue at this position is a
      2'deoxycytosine 5'-O-(1-Thiomonophosphate).
<221> NAME/KEY: misc_feature
<222> LOCATION: (8)
<223> OTHER INFORMATION: The residue at this position is a
      2'deoxythymidine 5'-O-(1-Thiomonophosphate).
<221> NAME/KEY: misc_feature
<222> LOCATION: (9)
<223> OTHER INFORMATION: The residue at this position is a
      2'deoxyadenosine 5'-O-(1-Thiomonophosphate).
<223> OTHER INFORMATION: Description of Artificial Sequence:
      Synthetic

<400> SEQUENCE: 91
ctccaactac cacaagttta tattcag                                      27

<210> SEQ ID NO 92
<211> LENGTH: 56
<212> TYPE: DNA
<213> ORGANISM: Artificial Sequence
```

```
<220> FEATURE:
<221> NAME/KEY: misc_feature
<222> LOCATION: (1)
<223> OTHER INFORMATION: The residue at this position is a
      2'deoxycytosine 5'-O-(1-Thiomonophosphate).
<221> NAME/KEY: misc_feature
<222> LOCATION: (2)
<223> OTHER INFORMATION: The residue at this position is a
      2'deoxythymidine 5'-O-(1-Thiomonophosphate).
<221> NAME/KEY: misc_feature
<222> LOCATION: (3)
<223> OTHER INFORMATION: The residue at this position is a
      2'deoxyguanosine 5'-O-(1-Thiomonophosphate).
<221> NAME/KEY: misc_feature
<222> LOCATION: (4)..(5)
<223> OTHER INFORMATION: The residues at these positions are a
      2'deoxyadenosine 5'-O-(1-Thiomonophosphate).
<221> NAME/KEY: misc_feature
<222> LOCATION: (6)
<223> OTHER INFORMATION: The residue at this position is a
      2'deoxythymidine 5'-O-(1-Thiomonophosphate).
<221> NAME/KEY: misc_feature
<222> LOCATION: (7)
<223> OTHER INFORMATION: The residue at this position is a
      2'deoxyadenosine 5'-O-(1-Thiomonophosphate).
<221> NAME/KEY: misc_feature
<222> LOCATION: (8)
<223> OTHER INFORMATION: The residue at this position is a
      2'deoxythymidine 5'-O-(1-Thiomonophosphate).
<221> NAME/KEY: misc_feature
<222> LOCATION: (9)..(10)
<223> OTHER INFORMATION: The residues at these positions are a
      2'deoxyadenosine 5'-O-(1-Thiomonophosphate).
<223> OTHER INFORMATION: Description of Artificial Sequence:
      Synthetic

<400> SEQUENCE: 92
ctgaatataa acttgtggta gttggagctg gtgacgtagg caagagtgcc ttgacg         56

<210> SEQ ID NO 93
<211> LENGTH: 56
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position is a
      2'deoxycytosine 5'-O-(1-Thiomonophosphate).
<221> NAME/KEY: misc_feature
<222> LOCATION: (2)
<223> OTHER INFORMATION: The residue at this position is a
      2'deoxythymidine 5'-O-(1-Thiomonophosphate).
<221> NAME/KEY: misc_feature
<222> LOCATION: (3)
<223> OTHER INFORMATION: The residue at this position is a
      2'deoxyguanosine 5'-O-(1-Thiomonophosphate).
<221> NAME/KEY: misc_feature
<222> LOCATION: (4)..(5)
<223> OTHER INFORMATION: The residues at these positions are a
      2'deoxyadenosine 5'-O-(1-Thiomonophosphate).
<221> NAME/KEY: misc_feature
<222> LOCATION: (6)
<223> OTHER INFORMATION: The residue at this position is a
      2'deoxythymidine 5'-O-(1-Thiomonophosphate).
<221> NAME/KEY: misc_feature
<222> LOCATION: (7)
<223> OTHER INFORMATION: The residue at this position is a
      2'deoxyadenosine 5'-O-(1-Thiomonophosphate).
<221> NAME/KEY: misc_feature
<222> LOCATION: (8)
<223> OTHER INFORMATION: The residue at this position is a
      2'deoxythymidine 5'-O-(1-Thiomonophosphate).
<221> NAME/KEY: misc_feature
<222> LOCATION: (9)..(10)
<223> OTHER INFORMATION: The residues at these positions are a
      2'deoxyadenosine 5'-O-(1-Thiomonophosphate).
<223> OTHER INFORMATION: Description of Artificial Sequence:
```

Synthetic

<400> SEQUENCE: 93
ctgaatataa acttgtggta gttggagctg gtgccgtagg caagagtgcc ttgacg    56

<210> SEQ ID NO 94
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position has a TET label.
<223> OTHER INFORMATION: Description of Artificial Sequence: Synthetic

<400> SEQUENCE: 94
ccggtcgtcc tggcaa    16

<210> SEQ ID NO 95
<211> LENGTH: 13
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position has a TET label.
<223> OTHER INFORMATION: Description of Artificial Sequence: Synthetic

<400> SEQUENCE: 95
ccggtcgtcc tgg    13

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 96
caattccggt gtactcaccg gttcc    25

<210> SEQ ID NO 97
<211> LENGTH: 8
<212> TYPE: DNA
<213> ORGANISM: Artificial Sequence
<220> FEATURE:
<221> NAME/KEY: misc_feature
<222> LOCATION: (1)
<223> OTHER INFORMATION: The T at this position is linked to a spacer
    bearing a Cy3 amidite label.
<221> NAME/KEY: misc_feature
<222> LOCATION: (2)..(3)
<223> OTHER INFORMATION: The residues at these positions have an amino
    group added.
<223> OTHER INFORMATION: Description of Artificial Sequence: Synthetic

<400> SEQUENCE: 97 ttccagag    8

<210> SEQ ID NO 98
<211> LENGTH: 30
<212> TYPE: DNA
<213> ORGANISM: Artificial Sequence
<220> FEATURE:
<221> NAME/KEY: misc_feature
<222> LOCATION: (1)
<223> OTHER INFORMATION: The residue at this position is a
    2'deoxyguanosine 5'-O-(1-Thiomonophosphate).
<221> NAME/KEY: misc_feature

```
<222> LOCATION: (2)
<223> OTHER INFORMATION: The residue at this position is a
      2'deoxythymidine 5'-O-(1-Thiomonophosphate).
<221> NAME/KEY: misc_feature
<222> LOCATION: (3)..(4)
<223> OTHER INFORMATION: The residues at these positions are a
      2'deoxyadenosine 5'-O-(1-Thiomonophosphate).
<221> NAME/KEY: misc_feature
<222> LOCATION: (5)
<223> OTHER INFORMATION: The residue at this position is a
      2'deoxythymidine 5'-O-(1-Thiomonophosphate).
<221> NAME/KEY: misc_feature
<222> LOCATION: (6)
<223> OTHER INFORMATION: The residue at this position is a
      2'deoxycytosine 5'-O-(1-Thiomonophosphate).
<221> NAME/KEY: misc_feature
<222> LOCATION: (7)..(8)
<223> OTHER INFORMATION: The residues at these positions are a
      2'deoxythymidine 5'-O-(1-Thiomonophosphate).
<221> NAME/KEY: misc_feature
<222> LOCATION: (9)
<223> OTHER INFORMATION: The residue at this position is a
      2'deoxyadenosine 5'-O-(1-Thiomonophosphate).
<221> NAME/KEY: misc_feature
<222> LOCATION: (10)
<223> OTHER INFORMATION: The residue at this position is a
      2'deoxycytosine 5'-O-(1-Thiomonophosphate).
<223> OTHER INFORMATION: Description of Artificial Sequence:
      Synthetic

<400> SEQUENCE: 98
gtaatcttac caacgctaac gagcgtcttg                                30

<210> SEQ ID NO 99
<211> LENGTH: 30
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: The residues at these positions are a
      2'deoxycytosine 5'-O-(1-Thiomonophosphate).
<221> NAME/KEY: misc_feature
<222> LOCATION: (3)
<223> OTHER INFORMATION: The residue at this position is a
      2'deoxythymidine 5'-O-(1-Thiomonophosphate).
<221> NAME/KEY: misc_feature
<222> LOCATION: (4)..(5)
<223> OTHER INFORMATION: The residues at these positions are a
      2'deoxyadenosine 5'-O-(1-Thiomonophosphate).
<221> NAME/KEY: misc_feature
<222> LOCATION: (6)..(8)
<223> OTHER INFORMATION: The residues at these positions are a
      2'deoxythymidine 5'-O-(1-Thiomonophosphate).
<221> NAME/KEY: misc_feature
<222> LOCATION: (9)
<223> OTHER INFORMATION: The residue at this position is a
      2'deoxyguanosine 5'-O-(1-Thiomonophosphate).
<221> NAME/KEY: misc_feature
<222> LOCATION: (10)
<223> OTHER INFORMATION: The residue at this position is a
      2'deoxycytosine 5'-O-(1-Thiomonophosphate).
<223> OTHER INFORMATION: Description of Artificial Sequence:
      Synthetic

<400> SEQUENCE: 99
cctaatttgc cagttacaaa ataaacagcc                                30

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence:  Synthetic
```

<400> SEQUENCE: 100
gggaaagtcc tcggagccgc gcgggacgag cgtgggggcc cg    42

<210> SEQ ID NO 101
<211> LENGTH: 963
<212> TYPE: DNA
<213> ORGANISM: Artificial Sequence
<220> FEATURE:
<223> OTHER INFORMATION: Description of Artificial Sequence: Synthetic
<221> NAME/KEY: CDS
<222> LOCATION: (1)..(960)

<400> SEQUENCE: 101

| atg | gct | agc | atg | act | ggt | gga | cag | caa | atg | ggt | cgg | atc | aat | tcg | ggg | 48 |
| Met | Ala | Ser | Met | Thr | Gly | Gly | Gln | Gln | Met | Gly | Arg | Ile | Asn | Ser | Gly | |
| 1 | | | | 5 | | | | | 10 | | | | | 15 | | |

| atg | ctg | ccc | ctc | ttt | gag | ccc | aag | ggc | cgg | gtc | ctg | ctg | gtg | gac | ggc | 96 |
| Met | Leu | Pro | Leu | Phe | Glu | Pro | Lys | Gly | Arg | Val | Leu | Leu | Val | Asp | Gly | |
| | | | 20 | | | | | 25 | | | | | 30 | | | |

| cac | cac | ctg | gcc | tac | cgc | acc | ttc | cac | gcc | ctg | aag | ggc | ctc | acc | acc | 144 |
| His | His | Leu | Ala | Tyr | Arg | Thr | Phe | His | Ala | Leu | Lys | Gly | Leu | Thr | Thr | |
| | | 35 | | | | | 40 | | | | | 45 | | | | |

| agc | cgg | ggg | gag | ccg | gtg | cag | gcg | gtc | tac | ggc | ttc | gcc | aag | agc | ctc | 192 |
| Ser | Arg | Gly | Glu | Pro | Val | Gln | Ala | Val | Tyr | Gly | Phe | Ala | Lys | Ser | Leu | |
| 50 | | | | | 55 | | | | | 60 | | | | | | |

| ctc | aag | gcc | ctc | aag | gag | gac | ggg | gac | gcg | gtg | atc | gtg | gtg | ttt | gac | 240 |
| Leu | Lys | Ala | Leu | Lys | Glu | Asp | Gly | Asp | Ala | Val | Ile | Val | Val | Phe | Asp | |
| 65 | | | | 70 | | | | | 75 | | | | | 80 | | |

| gcc | aag | gcc | ccc | tcc | ttc | cgc | cac | gag | gcc | tac | ggg | ggg | tac | aag | gcg | 288 |
| Ala | Lys | Ala | Pro | Ser | Phe | Arg | His | Glu | Ala | Tyr | Gly | Gly | Tyr | Lys | Ala | |
| | | | | 85 | | | | | 90 | | | | | 95 | | |

| ggc | cgg | gcc | ccc | acg | ctc | gtc | ccg | cgc | ggc | tcc | gag | gac | ttt | ccc | cgg | 336 |
| Gly | Arg | Ala | Pro | Thr | Leu | Val | Pro | Arg | Gly | Ser | Glu | Asp | Phe | Pro | Arg | |
| | | | 100 | | | | | 105 | | | | | 110 | | | |

| caa | ctc | gcc | ctc | atc | aag | gag | ctg | gtg | gac | ctc | ctg | ggg | ctg | gcg | cgc | 384 |
| Gln | Leu | Ala | Leu | Ile | Lys | Glu | Leu | Val | Asp | Leu | Leu | Gly | Leu | Ala | Arg | |
| | | 115 | | | | | 120 | | | | | 125 | | | | |

| ctc | gag | gtc | ccg | ggc | tac | gag | gcg | gac | gac | gtc | ctg | gcc | agc | ctg | gcc | 432 |
| Leu | Glu | Val | Pro | Gly | Tyr | Glu | Ala | Asp | Asp | Val | Leu | Ala | Ser | Leu | Ala | |
| | 130 | | | | | 135 | | | | | 140 | | | | | |

| aag | aag | gcg | gaa | aag | gag | ggc | tac | gag | gtc | cgc | atc | ctc | acc | gcc | gac | 480 |
| Lys | Lys | Ala | Glu | Lys | Glu | Gly | Tyr | Glu | Val | Arg | Ile | Leu | Thr | Ala | Asp | |
| 145 | | | | | 150 | | | | | 155 | | | | | 160 | |

| aaa | gac | ctt | tac | cag | ctc | ctt | tcc | gac | cgc | atc | cac | gtc | ctc | cac | ccc | 528 |
| Lys | Asp | Leu | Tyr | Gln | Leu | Leu | Ser | Asp | Arg | Ile | His | Val | Leu | His | Pro | |
| | | | | 165 | | | | | 170 | | | | | 175 | | |

| gag | ggg | tac | ctc | atc | acc | ccg | gcc | tgg | ctt | tgg | gaa | aag | tac | ggc | ctg | 576 |
| Glu | Gly | Tyr | Leu | Ile | Thr | Pro | Ala | Trp | Leu | Trp | Glu | Lys | Tyr | Gly | Leu | |
| | | | 180 | | | | | 185 | | | | | 190 | | | |

| agg | ccc | gac | cag | tgg | gcc | gac | tac | cgg | gcc | ctg | acc | ggg | gac | gag | tcc | 624 |
| Arg | Pro | Asp | Gln | Trp | Ala | Asp | Tyr | Arg | Ala | Leu | Thr | Gly | Asp | Glu | Ser | |
| | | | 195 | | | | | 200 | | | | | 205 | | | |

| gac | aac | ctt | ccc | ggg | gtc | aag | ggc | atc | ggg | gag | aag | acg | gcg | agg | aag | 672 |
| Asp | Asn | Leu | Pro | Gly | Val | Lys | Gly | Ile | Gly | Glu | Lys | Thr | Ala | Arg | Lys | |
| | 210 | | | | | 215 | | | | | 220 | | | | | |

| ctt | ctg | gag | gag | tgg | ggg | agc | ctg | gaa | gcc | ctc | ctc | aag | aac | ctg | gac | 720 |
| Leu | Leu | Glu | Glu | Trp | Gly | Ser | Leu | Glu | Ala | Leu | Leu | Lys | Asn | Leu | Asp | |
| 225 | | | | | 230 | | | | | 235 | | | | | 240 | |

| cgg | ctg | aag | ccc | gcc | atc | cgg | gag | aag | atc | ctg | gcc | cac | atg | gac | gat | 768 |
| Arg | Leu | Lys | Pro | Ala | Ile | Arg | Glu | Lys | Ile | Leu | Ala | His | Met | Asp | Asp | |
| | | | | 245 | | | | | 250 | | | | | 255 | | |

-continued

```
ctg aag ctc tcc tgg gac ctg gcc aag gtg cgc acc gac ctg ccc ctg    816
Leu Lys Leu Ser Trp Asp Leu Ala Lys Val Arg Thr Asp Leu Pro Leu
        260                 265                 270 gag gtg gac ttc gcc aaa agg cgg gag ccc gac cgg gag agg ctt agg    864
Glu Val Asp Phe Ala Lys Arg Arg Glu Pro Asp Arg Glu Arg Leu Arg
            275                 280                 285 gcc ttt ctg gag agg ctt gag ttt ggc agc ctc ctc cac gag ttc ggc    912
Ala Phe Leu Glu Arg Leu Glu Phe Gly Ser Leu Leu His Glu Phe Gly
290                 295                 300 ctt ctg gaa agc ccc aag gcc gca ctc gag cac cac cac cac cac cac    960
Leu Leu Glu Ser Pro Lys Ala Ala Leu Glu His His His His His His
305                 310                 315                 320 tga                                                                963
```

<210> SEQ ID NO 102
<211> LENGTH: 320
<212> TYPE: PRT
<213> ORGANISM: Artificial Sequence
<220> FEATURE:
<223> OTHER INFORMATION: Description of Artificial Sequence: Synthetic

<400> SEQUENCE: 102

```
Met Ala Ser Met Thr Gly Gly Gln Gln Met Gly Arg Ile Asn Ser Gly
1               5                   10                  15

Met Leu Pro Leu Phe Glu Pro Lys Gly Arg Val Leu Leu Val Asp Gly
            20                  25                  30

His His Leu Ala Tyr Arg Thr Phe His Ala Leu Lys Gly Leu Thr Thr
        35                  40                  45

Ser Arg Gly Glu Pro Val Gln Ala Val Tyr Gly Phe Ala Lys Ser Leu
    50                  55                  60

Leu Lys Ala Leu Lys Glu Asp Gly Asp Ala Val Ile Val Val Phe Asp
65                  70                  75                  80

Ala Lys Ala Pro Ser Phe Arg His Glu Ala Tyr Gly Gly Tyr Lys Ala
                85                  90                  95

Gly Arg Ala Pro Thr Leu Val Pro Arg Gly Ser Glu Asp Phe Pro Arg
            100                 105                 110

Gln Leu Ala Leu Ile Lys Glu Leu Val Asp Leu Leu Gly Leu Ala Arg
        115                 120                 125

Leu Glu Val Pro Gly Tyr Glu Ala Asp Asp Val Leu Ala Ser Leu Ala
    130                 135                 140

Lys Lys Ala Glu Lys Glu Gly Tyr Glu Val Arg Ile Leu Thr Ala Asp
145                 150                 155                 160

Lys Asp Leu Tyr Gln Leu Leu Ser Asp Arg Ile His Val Leu His Pro
                165                 170                 175

Glu Gly Tyr Leu Ile Thr Pro Ala Trp Leu Trp Glu Lys Tyr Gly Leu
            180                 185                 190

Arg Pro Asp Gln Trp Ala Asp Tyr Arg Ala Leu Thr Gly Asp Glu Ser
        195                 200                 205

Asp Asn Leu Pro Gly Val Lys Gly Ile Gly Glu Lys Thr Ala Arg Lys
    210                 215                 220

Leu Leu Glu Glu Trp Gly Ser Leu Glu Ala Leu Leu Lys Asn Leu Asp
225                 230                 235                 240

Arg Leu Lys Pro Ala Ile Arg Glu Lys Ile Leu Ala His Met Asp Asp
                245                 250                 255

Leu Lys Leu Ser Trp Asp Leu Ala Lys Val Arg Thr Asp Leu Pro Leu
            260                 265                 270
```

```
Glu Val Asp Phe Ala Lys Arg Arg Glu Pro Asp Arg Glu Arg Leu Arg
            275                 280                 285

Ala Phe Leu Glu Arg Leu Glu Phe Gly Ser Leu Leu His Glu Phe Gly
        290                 295                 300

Leu Leu Glu Ser Pro Lys Ala Ala Leu Glu His His His His His His
305                 310                 315                 320

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 103
cgatctcctc ggccacctcc                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 104
ggcggtgccc tggacgggca                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 105
ccagctcgtt gtggacctga                                              20

<210> SEQ ID NO 106
<211> LENGTH: 2505
<212> TYPE: DNA
<213> ORGANISM: Artificial Sequence
<220> FEATURE:
<221> NAME/KEY: CDS
<222> LOCATION: (1)..(2499)
<223> OTHER INFORMATION: Description of Artificial Sequence: Synthetic

<400> SEQUENCE: 106 atg aat tcg ggg atg ctg ccc ctc ttt gag ccc aag ggc cgg gtc ctc      48
Met Asn Ser Gly Met Leu Pro Leu Phe Glu Pro Lys Gly Arg Val Leu
  1               5                  10                  15 ctg gtg gac ggc cac cac ctg gcc tac cgc acc ttc cac gcc ctg aag      96
Leu Val Asp Gly His His Leu Ala Tyr Arg Thr Phe His Ala Leu Lys
             20                  25                  30 ggc ctc acc acc agc cgg ggg gag ccg gtg cag gcg gtc tac ggc ttc     144
Gly Leu Thr Thr Ser Arg Gly Glu Pro Val Gln Ala Val Tyr Gly Phe
         35                  40                  45 gcc aag agc ctc ctc aag gcc ctc aag gag gac ggg gac gcg gtg atc     192
Ala Lys Ser Leu Leu Lys Ala Leu Lys Glu Asp Gly Asp Ala Val Ile
     50                  55                  60 gtg gtc ttt gac gcc aag gcc ccc tcc ttc cgc cac gag gcc tac ggg     240
Val Val Phe Asp Ala Lys Ala Pro Ser Phe Arg His Glu Ala Tyr Gly
 65                  70                  75                  80 ggg tac aag gcg ggc cgg gcc ccc acg ccg gag gac ttt ccc cgg caa     288
```

```
                Gly Tyr Lys Ala Gly Arg Ala Pro Thr Pro Glu Asp Phe Pro Arg Gln
                             85                  90                  95 ctc gcc ctc atc aag gag ctg gtg gac ctc ctg ggg ctg gcg cgc ctc        336
Leu Ala Leu Ile Lys Glu Leu Val Asp Leu Leu Gly Leu Ala Arg Leu
            100                 105                 110 gag gtc ccg ggc tac gag gcg gac gac gtc ctg gcc agc ctg gcc aag        384
Glu Val Pro Gly Tyr Glu Ala Asp Asp Val Leu Ala Ser Leu Ala Lys
        115                 120                 125 aag gcg gaa aag gag ggc tac gag gtc cgc atc ctc acc gcc gac aaa        432
Lys Ala Glu Lys Glu Gly Tyr Glu Val Arg Ile Leu Thr Ala Asp Lys
    130                 135                 140 gac ctt tac cag ctc ctt tcc gac cgc atc cac gtc ctc cac ccc gag        480
Asp Leu Tyr Gln Leu Leu Ser Asp Arg Ile His Val Leu His Pro Glu
145                 150                 155                 160 ggg tac ctc atc acc ccg gcc tgg ctt tgg gaa aag tac ggc ctg agg        528
Gly Tyr Leu Ile Thr Pro Ala Trp Leu Trp Glu Lys Tyr Gly Leu Arg
                165                 170                 175 ccc gac cag tgg gcc gac tac cgg gcc ctg acc ggg gac gag tcc gac        576
Pro Asp Gln Trp Ala Asp Tyr Arg Ala Leu Thr Gly Asp Glu Ser Asp
            180                 185                 190 aac ctt ccc ggg gtc aag ggc atc ggg gag aag acg gcg agg aag ctt        624
Asn Leu Pro Gly Val Lys Gly Ile Gly Glu Lys Thr Ala Arg Lys Leu
        195                 200                 205 ctg gag gag tgg ggg agc ctg gaa gcc ctc ctc aag aac ctg gac cgg        672
Leu Glu Glu Trp Gly Ser Leu Glu Ala Leu Leu Lys Asn Leu Asp Arg
    210                 215                 220 ctg aag ccc gcc atc cgg gag aag atc ctg gcc cac atg gac gat ctg        720
Leu Lys Pro Ala Ile Arg Glu Lys Ile Leu Ala His Met Asp Asp Leu
225                 230                 235                 240 aag ctc tcc tgg gac ctg gcc aag gtg cgc acc gac ctg ccc ctg gag        768
Lys Leu Ser Trp Asp Leu Ala Lys Val Arg Thr Asp Leu Pro Leu Glu
                245                 250                 255 gtg gac ttc gcc aaa agg cgg gag ccc gac cgg gag agg ctt agg gcc        816
Val Asp Phe Ala Lys Arg Arg Glu Pro Asp Arg Glu Arg Leu Arg Ala
            260                 265                 270 ttt ctg gag agg ctt gag ttt ggc agc ctc ctc cac gag ttc ggc ctt        864
Phe Leu Glu Arg Leu Glu Phe Gly Ser Leu Leu His Glu Phe Gly Leu
        275                 280                 285 ctg gaa agc ccc aag gcc ctg gag gag gcc ccc tgg ccc ccg ccg gaa        912
Leu Glu Ser Pro Lys Ala Leu Glu Glu Ala Pro Trp Pro Pro Pro Glu
    290                 295                 300 ggg gcc ttc gtg ggc ttt gtg ctt tcc cgc aag gag ccc atg tgg gcc        960
Gly Ala Phe Val Gly Phe Val Leu Ser Arg Lys Glu Pro Met Trp Ala
305                 310                 315                 320 gat ctt ctg gcc ctg gcc gcc gcc agg ggg ggc cgg gtc cac cgg gcc       1008
Asp Leu Leu Ala Leu Ala Ala Ala Arg Gly Gly Arg Val His Arg Ala
                325                 330                 335 ccc gag cct tat aaa gcc ctc agg gac ctg aag gag gcg cgg ggg ctt       1056
Pro Glu Pro Tyr Lys Ala Leu Arg Asp Leu Lys Glu Ala Arg Gly Leu
            340                 345                 350 ctc gcc aaa gac ctg agc gtt ctg gcc ctg agg gaa ggc ctt ggc ctc       1104
Leu Ala Lys Asp Leu Ser Val Leu Ala Leu Arg Glu Gly Leu Gly Leu
        355                 360                 365 ccg ccc ggc gac gac ccc atg ctc ctc gcc tac ctc ctg gac cct tcc       1152
Pro Pro Gly Asp Asp Pro Met Leu Leu Ala Tyr Leu Leu Asp Pro Ser
    370                 375                 380 aac acc acc ccc gag ggg gtg gcc cgg cgc tac ggc ggg gag tgg acg       1200
Asn Thr Thr Pro Glu Gly Val Ala Arg Arg Tyr Gly Gly Glu Trp Thr
385                 390                 395                 400
```

```
gag gag gcg ggg gag cgg gcc gcc ctt tcc gag agg ctc ttc gcc aac     1248
Glu Glu Ala Gly Glu Arg Ala Ala Leu Ser Glu Arg Leu Phe Ala Asn
                    405                 410                 415 ctg tgg ggg agg ctt gag ggg gag gag agg ctc ctt tgg ctt tac cgg     1296
Leu Trp Gly Arg Leu Glu Gly Glu Glu Arg Leu Leu Trp Leu Tyr Arg
                420                 425                 430 gag gtg gag agg ccc ctt tcc gct gtc ctg gcc cac atg gag gcc acg     1344
Glu Val Glu Arg Pro Leu Ser Ala Val Leu Ala His Met Glu Ala Thr
            435                 440                 445 ggg gtg cgc ctg gac gtg gcc tat ctc agg gcc ttg tcc ctg gag gtg     1392
Gly Val Arg Leu Asp Val Ala Tyr Leu Arg Ala Leu Ser Leu Glu Val
        450                 455                 460 gcc gag gag atc gcc cgc ctc gag gcc gag gtc ttc cgc ctg gcc ggc     1440
Ala Glu Glu Ile Ala Arg Leu Glu Ala Glu Val Phe Arg Leu Ala Gly
465                 470                 475                 480 cac ccc ttc aac ctc aac tcc cgg gac cag ctg gaa agg gtc ctc ttt     1488
His Pro Phe Asn Leu Asn Ser Arg Asp Gln Leu Glu Arg Val Leu Phe
                485                 490                 495 gac gag cta ggg ctt ccc gcc atc ggc aag acg gag aag acc ggc aag     1536
Asp Glu Leu Gly Leu Pro Ala Ile Gly Lys Thr Glu Lys Thr Gly Lys
                500                 505                 510 cgc tcc acc agc gcc gcc gtc ctg gag gcc ctc cgc gag gcc cac ccc     1584
Arg Ser Thr Ser Ala Ala Val Leu Glu Ala Leu Arg Glu Ala His Pro
            515                 520                 525 atc gtg gag aag atc ctg cag tac cgg gag ctc acc aag ctg aag agc     1632
Ile Val Glu Lys Ile Leu Gln Tyr Arg Glu Leu Thr Lys Leu Lys Ser
        530                 535                 540 acc tac att gac ccc ttg ccg gac ctc atc cac ccc agg acg ggc cgc     1680
Thr Tyr Ile Asp Pro Leu Pro Asp Leu Ile His Pro Arg Thr Gly Arg
545                 550                 555                 560 ctc cac acc cgc ttc aac cag acg gcc acg gcc acg ggc agg cta agt     1728
Leu His Thr Arg Phe Asn Gln Thr Ala Thr Ala Thr Gly Arg Leu Ser
                565                 570                 575 agc tcc gat ccc aac ctc cag aac atc ccc gtc cgc acc ccg ctt ggg     1776
Ser Ser Asp Pro Asn Leu Gln Asn Ile Pro Val Arg Thr Pro Leu Gly
                580                 585                 590 cag agg atc cgc cgg gcc ttc atc gcc gag gag ggg tgg cta ttg gtg     1824
Gln Arg Ile Arg Arg Ala Phe Ile Ala Glu Glu Gly Trp Leu Leu Val
            595                 600                 605 gcc ctg gac tat agc cag ata gag ctc agg gtg ctg gcc cac ctc tcc     1872
Ala Leu Asp Tyr Ser Gln Ile Glu Leu Arg Val Leu Ala His Leu Ser
        610                 615                 620 ggc gac gag aac ctg atc cgg gtc ttc cag gag ggg cgg gac atc cac     1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac     1968
Thr Glu Thr Ala Ser Trp Met Phe Gly Val Pro Arg Glu Ala Val Asp
                645                 650                 655 ccc ctg atg cgc cgg gcg gcc aag acc atc aac ttc ggg gtc ctc tac     2016
Pro Leu Met Arg Arg Ala Ala Lys Thr Ile Asn Phe Gly Val Leu Tyr
                660                 665                 670 ggc atg tcg gcc cac cgc ctc tcc cag gag cta gcc atc cct tac gag     2064
Gly Met Ser Ala His Arg Leu Ser Gln Glu Leu Ala Ile Pro Tyr Glu
            675                 680                 685 gag gcc cag gcc ttc att gag cgc tac ttt cag agc ttc ccc aag gtg     2112
Glu Ala Gln Ala Phe Ile Glu Arg Tyr Phe Gln Ser Phe Pro Lys Val
        690                 695                 700 cgg gcc tgg att gag aag acc ctg gag gag ggc agg agg cgg ggg tac     2160
Arg Ala Trp Ile Glu Lys Thr Leu Glu Glu Gly Arg Arg Arg Gly Tyr
705                 710                 715                 720
```

-continued

```
gtg gag acc ctc ttc ggc cgc cgc cgc tac gtg cca gac cta gag gcc    2208
Val Glu Thr Leu Phe Gly Arg Arg Arg Tyr Val Pro Asp Leu Glu Ala
                725                 730                 735 cgg gtg aag agc gtg cgg gag gcg gcc gag cgc atg gcc ttc aac atg    2256
Arg Val Lys Ser Val Arg Glu Ala Ala Glu Arg Met Ala Phe Asn Met
            740                 745                 750 ccc gtc cag ggc acc gcc gcc gac ctc atg aag ctg gct atg gtg aag    2304
Pro Val Gln Gly Thr Ala Ala Asp Leu Met Lys Leu Ala Met Val Lys
        755                 760                 765 ctc ttc ccc agg ctg gag gaa atg ggg gcc agg atg ctc ctt cag gtc    2352
Leu Phe Pro Arg Leu Glu Glu Met Gly Ala Arg Met Leu Leu Gln Val
    770                 775                 780 cac aac gag ctg gtc ctc gag gcc cca aaa gag agg gcg gag gcc gtg    2400
His Asn Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg    2448
Ala Arg Leu Ala Lys Glu Val Met Glu Gly Val Tyr Pro Leu Ala Val
                805                 810                 815 ccc ctg gag gtg gag gtg ggg ata ggg gag gac tgg ctc tcc gcc aag    2496
Pro Leu Glu Val Glu Val Gly Ile Gly Glu Asp Trp Leu Ser Ala Lys
            820                 825                 830 gag tgatag                                                         2505
Glu
```

<210> SEQ ID NO 107
<211> LENGTH: 833
<212> TYPE: PRT
<213> ORGANISM: Artificial Sequence
<220> FEATURE:
<223> OTHER INFORMATION: Description of Artificial Sequence: Synthetic

<400> SEQUENCE: 107

```
Met Asn Ser Gly Met Leu Pro Leu Phe Glu Pro Lys Gly Arg Val Leu
  1               5                  10                  15

Leu Val Asp Gly His His Leu Ala Tyr Arg Thr Phe His Ala Leu Lys
             20                  25                  30

Gly Leu Thr Thr Ser Arg Gly Glu Pro Val Gln Ala Val Tyr Gly Phe
         35                  40                  45

Ala Lys Ser Leu Leu Lys Ala Leu Lys Glu Asp Gly Asp Ala Val Ile
     50                  55                  60

Val Val Phe Asp Ala Lys Ala Pro Ser Phe Arg His Glu Ala Tyr Gly
 65                  70                  75                  80

Gly Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Leu Ala Arg Leu
            100                 105                 110

Glu Val Pro Gly Tyr Glu Ala Asp Asp Val Leu Ala Ser Leu Ala Lys
        115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
```

-continued

```
            195                 200                 205
Leu Glu Glu Trp Gly Ser Leu Glu Ala Leu Leu Lys Asn Leu Asp Arg
            210                 215                 220
Leu Lys Pro Ala Ile Arg Glu Lys Ile Leu Ala His Met Asp Asp Leu
225                 230                 235                 240
Lys Leu Ser Trp Asp Leu Ala Lys Val Arg Thr Asp Leu Pro Leu Glu
            245                 250                 255
Val Asp Phe Ala Lys Arg Arg Glu Pro Asp Arg Glu Arg Leu Arg Ala
            260                 265                 270
Phe Leu Glu Arg Leu Glu Phe Gly Ser Leu Leu His Glu Phe Gly Leu
            275                 280                 285
Leu Glu Ser Pro Lys Ala Leu Glu Glu Ala Pro Trp Pro Pro Pro Glu
            290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Gly Arg Val His Arg Ala
            325                 330                 335
Pro Glu Pro Tyr Lys Ala Leu Arg Asp Leu Lys Glu Ala Arg Gly Leu
            340                 345                 350
Leu Ala Lys Asp Leu Ser Val Leu Ala Leu Arg Glu Gly Leu Gly Leu
            355                 360                 365
Pro Pro Gly Asp Asp Pro Met Leu Leu Ala Tyr Leu Leu Asp Pro Ser
370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
            405                 410                 415
Leu Trp Gly Arg Leu Glu Gly Glu Arg Leu Leu Trp Leu Tyr Arg
            420                 425                 430
Glu Val Glu Arg Pro Leu Ser Ala Val Leu Ala His Met Glu Ala Thr
            435                 440                 445
Gly Val Arg Leu Asp Val Ala Tyr Leu Arg Ala Leu Ser Leu Glu Val
            450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
            485                 490                 495
Asp Glu Leu Gly Leu Pro Ala Ile Gly Lys Thr Glu Lys Thr Gly Lys
            500                 505                 510
Arg Ser Thr Ser Ala Ala Val Leu Glu Ala Leu Arg Glu Ala His Pro
            515                 520                 525
Ile Val Glu Lys Ile Leu Gln Tyr Arg Glu Leu Thr Lys Leu Lys Ser
            530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
            565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Glu Gly Trp Leu Leu Val
            595                 600                 605
Ala Leu Asp Tyr Ser Gln Ile Glu Leu Arg Val Leu Ala His Leu Ser
610                 615                 620
```

Gly Asp Glu Asn Leu Ile Arg Val Phe Gln Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
    690                 695                 700

Arg Ala Trp Ile Glu Lys Thr Leu Glu Glu Gly Arg Arg Arg Gly Tyr
705                 710                 715                 720

Val Glu Thr Leu Phe Gly Arg Arg Tyr Val Pro Asp Leu Glu Ala
                725                 730                 735

Arg Val Lys Ser Val Arg Glu Ala Ala Glu Arg Met Ala Phe Asn Met
                740                 745                 750

Pro Val Gln Gly Thr Ala Ala Asp Leu Met Lys Leu Ala Met Val Lys
            755                 760                 765

Leu Phe Pro Arg Leu Glu Glu Met Gly Ala Arg Met Leu Leu Gln Val
770                 775                 780

His Asn Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 108
gggataccat gggagtgcag tttgg                                          25

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 109
ggtaaatttt tctcgtcgac atcccac                                        27

<210> SEQ ID NO 110
<211> LENGTH: 981
<212> TYPE: DNA
<213> ORGANISM: Methanococcus jannaschii
<220> FEATURE:
<221> NAME/KEY: CDS
<222> LOCATION: (1)..(978)

<400> SEQUENCE: 110 atg gga gtg cag ttt ggt gat ttt att cca aaa aat att atc tcc ttt    48
Met Gly Val Gln Phe Gly Asp Phe Ile Pro Lys Asn Ile Ile Ser Phe

```
       1               5                   10                  15
gaa gat tta aaa ggg aaa aaa gta gct att gat gga atg aat gca tta      96
Glu Asp Leu Lys Gly Lys Lys Val Ala Ile Asp Gly Met Asn Ala Leu
                20                  25                  30 tat cag ttt tta aca tct ata cgt ttg aga gat ggt tct cca ttg aga     144
Tyr Gln Phe Leu Thr Ser Ile Arg Leu Arg Asp Gly Ser Pro Leu Arg
            35                  40                  45 aat aga aaa gga gag ata acc tca gca tat aac gga gtt ttt tat aaa     192
Asn Arg Lys Gly Glu Ile Thr Ser Ala Tyr Asn Gly Val Phe Tyr Lys
        50                  55                  60 acc ata cat ttg tta gag aat gat ata act cca atc tgg gtt ttt gat     240
Thr Ile His Leu Leu Glu Asn Asp Ile Thr Pro Ile Trp Val Phe Asp
65                  70                  75                  80 ggt gag cca cca aag tta aag gag aaa aca agg aaa gtt agg aga gag     288
Gly Glu Pro Pro Lys Leu Lys Glu Lys Thr Arg Lys Val Arg Arg Glu
                85                  90                  95 atg aaa gag aaa gct gaa ctt aag atg aaa gag gca att aaa aag gag     336
Met Lys Glu Lys Ala Glu Leu Lys Met Lys Glu Ala Ile Lys Lys Glu
            100                 105                 110 gat ttt gaa gaa gct gct aag tat gca aag agg gtt agc tat cta act     384
Asp Phe Glu Glu Ala Ala Lys Tyr Ala Lys Arg Val Ser Tyr Leu Thr
        115                 120                 125 ccg aaa atg gtt gaa aac tgc aaa tat ttg tta agt ttg atg ggc att     432
Pro Lys Met Val Glu Asn Cys Lys Tyr Leu Leu Ser Leu Met Gly Ile
130                 135                 140 ccg tat gtt gaa gct ccc tct gag gga gag gca caa gca agc tat atg     480
Pro Tyr Val Glu Ala Pro Ser Glu Gly Glu Ala Gln Ala Ser Tyr Met
145                 150                 155                 160 gca aag aag gga gat gtt tgg gca gtt gta agt caa gat tat gat gcc     528
Ala Lys Lys Gly Asp Val Trp Ala Val Val Ser Gln Asp Tyr Asp Ala
                165                 170                 175 ttg tta tat gga gct ccg aga gtt gtt aga aat tta aca act aca aag     576
Leu Leu Tyr Gly Ala Pro Arg Val Val Arg Asn Leu Thr Thr Thr Lys
            180                 185                 190 gag atg cca gaa ctt att gaa tta aat gag gtt tta gag gat tta aga     624
Glu Met Pro Glu Leu Ile Glu Leu Asn Glu Val Leu Glu Asp Leu Arg
        195                 200                 205 att tct ttg gat gat ttg ata gat ata gcc ata ttt atg gga act gac     672
Ile Ser Leu Asp Asp Leu Ile Asp Ile Ala Ile Phe Met Gly Thr Asp
    210                 215                 220 tat aat cca gga gga gtt aaa gga ata gga ttt aaa agg gct tat gaa     720
Tyr Asn Pro Gly Gly Val Lys Gly Ile Gly Phe Lys Arg Ala Tyr Glu
225                 230                 235                 240 ttg gtt aga agt ggt gta gct aag gat gtt ttg aaa aaa gag gtt gaa     768
Leu Val Arg Ser Gly Val Ala Lys Asp Val Leu Lys Lys Glu Val Glu
                245                 250                 255 tac tac gat gag att aag agg ata ttt aaa gag cca aag gtt acc gat     816
Tyr Tyr Asp Glu Ile Lys Arg Ile Phe Lys Glu Pro Lys Val Thr Asp
            260                 265                 270 aac tat tca tta agc cta aaa ttg cca gat aaa gag gga att ata aaa     864
Asn Tyr Ser Leu Ser Leu Lys Leu Pro Asp Lys Glu Gly Ile Ile Lys
        275                 280                 285 ttc tta gtt gat gaa aat gac ttt aat tat gat agg gtt aaa aag cat     912
Phe Leu Val Asp Glu Asn Asp Phe Asn Tyr Asp Arg Val Lys Lys His
    290                 295                 300 gtt gat aaa ctc tat aac tta att gca aac aaa act aag caa aaa aca     960
Val Asp Lys Leu Tyr Asn Leu Ile Ala Asn Lys Thr Lys Gln Lys Thr
305                 310                 315                 320 tta gat gca tgg ttt aaa taa                                         981
```

```
Leu Asp Ala Trp Phe Lys
            325

<210> SEQ ID NO 111
<211> LENGTH: 326
<212> TYPE: PRT
<213> ORGANISM: Methanococcus jannaschii

<400> SEQUENCE: 111

Met Gly Val Gln Phe Gly Asp Phe Ile Pro Lys Asn Ile Ile Ser Phe
  1               5                  10                  15

Glu Asp Leu Lys Gly Lys Val Ala Ile Asp Gly Met Asn Ala Leu
                 20                  25                  30

Tyr Gln Phe Leu Thr Ser Ile Arg Leu Arg Asp Gly Ser Pro Leu Arg
                 35                  40                  45

Asn Arg Lys Gly Glu Ile Thr Ser Ala Tyr Asn Gly Val Phe Tyr Lys
 50                  55                  60

Thr Ile His Leu Leu Glu Asn Asp Ile Thr Pro Ile Trp Val Phe Asp
 65                  70                  75                  80

Gly Glu Pro Pro Lys Leu Lys Glu Lys Thr Arg Lys Val Arg Arg Glu
                 85                  90                  95

Met Lys Glu Lys Ala Glu Leu Lys Met Lys Glu Ala Ile Lys Lys Glu
                100                 105                 110

Asp Phe Glu Glu Ala Ala Lys Tyr Ala Lys Arg Val Ser Tyr Leu Thr
                115                 120                 125

Pro Lys Met Val Glu Asn Cys Lys Tyr Leu Leu Ser Leu Met Gly Ile
            130                 135                 140

Pro Tyr Val Glu Ala Pro Ser Glu Gly Glu Ala Gln Ala Ser Tyr Met
145                 150                 155                 160

Ala Lys Lys Gly Asp Val Trp Ala Val Val Ser Gln Asp Tyr Asp Ala
                165                 170                 175

Leu Leu Tyr Gly Ala Pro Arg Val Val Arg Asn Leu Thr Thr Thr Lys
                180                 185                 190

Glu Met Pro Glu Leu Ile Glu Leu Asn Glu Val Leu Glu Asp Leu Arg
                195                 200                 205

Ile Ser Leu Asp Asp Leu Ile Asp Ile Ala Ile Phe Met Gly Thr Asp
            210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Lys Glu Val Glu
                245                 250                 255

Tyr Tyr Asp Glu Ile Lys Arg Ile Phe Lys Glu Pro Lys Val Thr Asp
                260                 265                 270

Asn Tyr Ser Leu Ser Leu Lys Leu Pro Asp Lys Glu Gly Ile Ile Lys
            275                 280                 285

Phe Leu Val Asp Glu Asn Asp Phe Asn Tyr Asp Arg Val Lys Lys His
290                 295                 300

Val Asp Lys Leu Tyr Asn Leu Ile Ala Asn Lys Thr Lys Gln Lys Thr
305                 310                 315                 320

Leu Asp Ala Trp Phe Lys
            325

<210> SEQ ID NO 112
<211> LENGTH: 21
<212> TYPE: DNA
<213> ORGANISM: Artificial Sequence
```

```
<220> FEATURE:
<223> OTHER INFORMATION: Description of Artificial Sequence: Synthetic

<400> SEQUENCE: 112
gaggtgatac catgggtgtc c                                              21

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 113
gaaactctgc agcgcgtcag                                                20

<210> SEQ ID NO 114
<211> LENGTH: 1023
<212> TYPE: DNA
<213> ORGANISM: Pyrococcus furiosus
<220> FEATURE:
<221> NAME/KEY: CDS
<222> LOCATION: (1)..(1020)

<400> SEQUENCE: 114 atg ggt gtc cca att ggt gag att ata cca aga aaa gaa att gag tta      48
Met Gly Val Pro Ile Gly Glu Ile Ile Pro Arg Lys Glu Ile Glu Leu
 1               5                  10                  15 gaa aac cta tac ggg aaa aaa atc gca atc gac gct ctt aat gca atc      96
Glu Asn Leu Tyr Gly Lys Lys Ile Ala Ile Asp Ala Leu Asn Ala Ile
            20                  25                  30 tac caa ttt ttg tcc aca ata aga cag aaa gat gga act cca ctt atg     144
Tyr Gln Phe Leu Ser Thr Ile Arg Gln Lys Asp Gly Thr Pro Leu Met
        35                  40                  45 gat tca aag ggt aga ata acc tcc cac cta agc ggg ctc ttt tac agg     192
Asp Ser Lys Gly Arg Ile Thr Ser His Leu Ser Gly Leu Phe Tyr Arg
    50                  55                  60 aca ata aac cta atg gag gct gga ata aaa cct gtg tat gtt ttt gat     240
Thr Ile Asn Leu Met Glu Ala Gly Ile Lys Pro Val Tyr Val Phe Asp
65                  70                  75                  80 gga gaa cct cca gaa ttc aaa aag aaa gag ctc gaa aaa aga aga gaa     288
Gly Glu Pro Pro Glu Phe Lys Lys Lys Glu Leu Glu Lys Arg Arg Glu
                85                  90                  95 gcg aga gag gaa gct gaa gaa aag tgg aga gaa gca ctt gaa aaa gga     336
Ala Arg Glu Glu Ala Glu Glu Lys Trp Arg Glu Ala Leu Glu Lys Gly
            100                 105                 110 gag ata gag gaa gca aga aaa tat gcc caa aga gca acc agg gta aat     384
Glu Ile Glu Glu Ala Arg Lys Tyr Ala Gln Arg Ala Thr Arg Val Asn
        115                 120                 125 gaa atg ctc atc gag gat gca aaa aaa ctc tta gag ctt atg gga att     432
Glu Met Leu Ile Glu Asp Ala Lys Lys Leu Leu Glu Leu Met Gly Ile
    130                 135                 140 cct ata gtt caa gca cct agc gag gga gag gcc caa gct gca tat atg     480
Pro Ile Val Gln Ala Pro Ser Glu Gly Glu Ala Gln Ala Ala Tyr Met
145                 150                 155                 160 gcc gca aag ggg agc gtg tat gca tcg gct agt caa gat tac gat tcc     528
Ala Ala Lys Gly Ser Val Tyr Ala Ser Ala Ser Gln Asp Tyr Asp Ser
                165                 170                 175 cta ctt ttt gga gct cca aga ctt gtt aga aac tta aca ata aca gga     576
Leu Leu Phe Gly Ala Pro Arg Leu Val Arg Asn Leu Thr Ile Thr Gly
            180                 185                 190 aaa aga aag ttg cct ggg aaa aat gtc tac gtc gag ata aag ccc gag     624
```

```
Lys Arg Lys Leu Pro Gly Lys Asn Val Tyr Val Glu Ile Lys Pro Glu
            195                 200                 205 ttg ata att ttg gag gaa gta ctc aag gaa tta aag cta aca aga gaa      672
Leu Ile Ile Leu Glu Glu Val Leu Lys Glu Leu Lys Leu Thr Arg Glu
210                 215                 220 aag ctc att gaa cta gca atc ctc gtt gga aca gac tac aac cca gga      720
Lys Leu Ile Glu Leu Ala Ile Leu Val Gly Thr Asp Tyr Asn Pro Gly
225                 230                 235                 240 gga ata aag ggc ata ggc ctt aaa aaa gct tta gag att gtt aga cac      768
Gly Ile Lys Gly Ile Gly Leu Lys Lys Ala Leu Glu Ile Val Arg His
            245                 250                 255 tca aaa gat ccg cta gca aag ttc caa aag caa agc gat gtg gat tta      816
Ser Lys Asp Pro Leu Ala Lys Phe Gln Lys Gln Ser Asp Val Asp Leu
            260                 265                 270 tat gca ata aaa gag ttc ttc cta aac cca cca gtc aca gat aac tac      864
Tyr Ala Ile Lys Glu Phe Phe Leu Asn Pro Pro Val Thr Asp Asn Tyr
        275                 280                 285 aat tta gtg tgg aga gat ccc gac gaa gag gga ata cta aag ttc tta      912
Asn Leu Val Trp Arg Asp Pro Asp Glu Glu Gly Ile Leu Lys Phe Leu
290                 295                 300 tgt gac gag cat gac ttt agt gag gaa aga gta aag aat gga tta gag      960
Cys Asp Glu His Asp Phe Ser Glu Glu Arg Val Lys Asn Gly Leu Glu
305                 310                 315                 320 agg ctt aag aag gca atc aaa agt gga aaa caa tca acc ctt gaa agt     1008
Arg Leu Lys Lys Ala Ile Lys Ser Gly Lys Gln Ser Thr Leu Glu Ser
                325                 330                 335 tgg ttc aag aga taa                                                  1023
Trp Phe Lys Arg
            340

<210> SEQ ID NO 115
<211> LENGTH: 340
<212> TYPE: PRT
<213> ORGANISM: Pyrococcus furiosus

<400> SEQUENCE: 115

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Lys Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Lys Glu Leu Glu Lys Arg Arg Glu
                85                  90                  95

Ala Arg Glu Glu Ala Glu Lys Trp Arg Glu Ala Leu Glu Lys Gly
            100                 105                 110

Glu Ile Glu Glu Ala Arg Lys Tyr Ala Gln Arg Ala Thr Arg Val Asn
        115                 120                 125

Glu Met Leu Ile Glu Asp Ala Lys Lys Leu Leu Glu Leu Met Gly Ile
    130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175
```

```
Leu Leu Phe Gly Ala Pro Arg Leu Val Arg Asn Leu Thr Ile Thr Gly
                180                 185                 190
Lys Arg Lys Leu Pro Gly Lys Asn Val Tyr Val Glu Ile Lys Pro Glu
            195                 200                 205
Leu Ile Ile Leu Glu Glu Val Leu Lys Glu Leu Lys Leu Thr Arg Glu
        210                 215                 220
Lys Leu Ile Glu Leu Ala Ile Leu Val Gly Thr Asp Tyr Asn Pro Gly
225                 230                 235                 240
Gly Ile Lys Gly Ile Gly Leu Lys Lys Ala Leu Glu Ile Val Arg His
                245                 250                 255
Ser Lys Asp Pro Leu Ala Lys Phe Gln Lys Gln Ser Asp Val Asp Leu
            260                 265                 270
Tyr Ala Ile Lys Glu Phe Phe Leu Asn Pro Pro Val Thr Asp Asn Tyr
        275                 280                 285
Asn Leu Val Trp Arg Asp Pro Asp Glu Glu Gly Ile Leu Lys Phe Leu
            290                 295                 300
Cys Asp Glu His Asp Phe Ser Glu Glu Arg Val Lys Asn Gly Leu Glu
305                 310                 315                 320
Arg Leu Lys Lys Ala Ile Lys Ser Gly Lys Gln Ser Thr Leu Glu Ser
                325                 330                 335
Trp Phe Lys Arg
            340

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 116
gataccatgg gtgtcccaat tggtg                                        25

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 117
tcgacgtcga cttatctctt gaaccaactt tcaaggg                           37

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 118
agcgagggag aggcccaagc                                              20

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 119
```

```
gcctatgccc tttattcctc c                                              21

<210> SEQ ID NO 120
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 120
tggtcgctgt ctcgctgaaa gcgagacagc gtg                                 33

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 121
tgctctctgg tcgctgtctg aaagacagcg                                     30

<210> SEQ ID NO 122
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 122
cgagagacca cgct                                                      14

<210> SEQ ID NO 123
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 123
ttttccagag cctaatgaaa ttaggctctg gaaagacgct cgtg                     44

<210> SEQ ID NO 124
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 124
aacgagcgtc tttg                                                      14

<210> SEQ ID NO 125
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 125
aacgagcgtc attg                                                      14

<210> SEQ ID NO 126
<211> LENGTH: 51
<212> TYPE: DNA
```

<213> ORGANISM: Artificial Sequence
<220> FEATURE:
<223> OTHER INFORMATION: Description of Artificial Sequence: Synthetic

<400> SEQUENCE: 126 tttttttta attaggctct ggaaagacgc tcgtgaaacg agcgtctttg d          51

<210> SEQ ID NO 127
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 127
ttttccagag cctaatg          17

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 128
tggctatagr ccagggccac          20

<210> SEQ ID NO 129
<211> LENGTH: 2505
<212> TYPE: DNA
<213> ORGANISM: Artificial Sequence
<220> FEATURE:
<221> NAME/KEY: CDS
<222> LOCATION: (1)..(2499)
<223> OTHER INFORMATION: Description of Artificial Sequence: Synthetic

<400> SEQUENCE: 129

| atg | aat | tcg | ggg | atg | ctg | ccc | ctc | ttt | gag | ccc | aag | ggc | cgg | gtc | ctc | 48 |
| Met | Asn | Ser | Gly | Met | Leu | Pro | Leu | Phe | Glu | Pro | Lys | Gly | Arg | Val | Leu | |
| 1 | | | | 5 | | | | | 10 | | | | | 15 | | |

| ctg | gtg | gac | ggc | cac | cac | ctg | gcc | tac | cgc | acc | ttc | cac | gcc | ctg | aag | 96 |
| Leu | Val | Asp | Gly | His | His | Leu | Ala | Tyr | Arg | Thr | Phe | His | Ala | Leu | Lys | |
| | | | 20 | | | | | 25 | | | | | 30 | | | |

| ggc | ctc | acc | acc | agc | cgg | ggg | gag | ccg | gtg | cag | gcg | gtc | tac | ggc | ttc | 144 |
| Gly | Leu | Thr | Thr | Ser | Arg | Gly | Glu | Pro | Val | Gln | Ala | Val | Tyr | Gly | Phe | |
| | 35 | | | | | 40 | | | | | 45 | | | | | |

| gcc | aag | agc | ctc | ctc | aag | gcc | ctc | aag | gag | gac | ggg | gac | gcg | gtg | atc | 192 |
| Ala | Lys | Ser | Leu | Leu | Lys | Ala | Leu | Lys | Glu | Asp | Gly | Asp | Ala | Val | Ile | |
| 50 | | | | | 55 | | | | | 60 | | | | | | |

| gtg | gtc | ttt | gac | gcc | aag | gcc | ccc | tcc | ttc | cgc | cac | gag | gcc | tac | ggg | 240 |
| Val | Val | Phe | Asp | Ala | Lys | Ala | Pro | Ser | Phe | Arg | His | Glu | Ala | Tyr | Gly | |
| 65 | | | | 70 | | | | | 75 | | | | | 80 | | |

| ggg | tac | aag | gcg | ggc | cgg | gcc | ccc | acg | ccg | gag | gac | ttt | ccc | cgg | caa | 288 |
| Gly | Tyr | Lys | Ala | Gly | Arg | Ala | Pro | Thr | Pro | Glu | Asp | Phe | Pro | Arg | Gln | |
| | | | | 85 | | | | | 90 | | | | | 95 | | |

| ctc | gcc | ctc | atc | aag | gag | ctg | gtg | gac | ctc | ggg | ctg | gcg | cgc | ctc | | 336 |
| Leu | Ala | Leu | Ile | Lys | Glu | Leu | Val | Asp | Leu | Gly | Leu | Ala | Arg | Leu | | |
| | | | 100 | | | | | 105 | | | | | 110 | | | |

| gag | gtc | ccg | ggc | tac | gag | gcg | gac | gac | gtc | ctg | gcc | agc | ctg | gcc | aag | 384 |
| Glu | Val | Pro | Gly | Tyr | Glu | Ala | Asp | Asp | Val | Leu | Ala | Ser | Leu | Ala | Lys | |
| | | 115 | | | | | 120 | | | | | 125 | | | | |

| aag | gcg | gaa | aag | gag | ggc | tac | gag | gtc | cgc | atc | ctc | acc | gcc | gac | aaa | 432 |
| Lys | Ala | Glu | Lys | Glu | Gly | Tyr | Glu | Val | Arg | Ile | Leu | Thr | Ala | Asp | Lys | |
| | 130 | | | | | 135 | | | | | 140 | | | | | |

```
gac ctt tac cag ctc ctt tcc gac cgc atc cac gtc ctc cac ccc gag    480
Asp Leu Tyr Gln Leu Leu Ser Asp Arg Ile His Val Leu His Pro Glu
145                 150                 155                 160 ggg tac ctc atc acc ccg gcc tgg ctt tgg gaa aag tac ggc ctg agg    528
Gly Tyr Leu Ile Thr Pro Ala Trp Leu Trp Glu Lys Tyr Gly Leu Arg
                165                 170                 175 ccc gac cag tgg gcc gac tac cgg gcc ctg acc ggg gac gag tcc gac    576
Pro Asp Gln Trp Ala Asp Tyr Arg Ala Leu Thr Gly Asp Glu Ser Asp
            180                 185                 190 aac ctt ccc ggg gtc aag ggc atc ggg gag aag acg gcg agg aag ctt    624
Asn Leu Pro Gly Val Lys Gly Ile Gly Glu Lys Thr Ala Arg Lys Leu
        195                 200                 205 ctg gag gag tgg ggg agc ctg gaa gcc ctc ctc aag aac ctg gac cgg    672
Leu Glu Glu Trp Gly Ser Leu Glu Ala Leu Leu Lys Asn Leu Asp Arg
    210                 215                 220 ctg aag ccc gcc atc cgg gag aag atc ctg gcc cac atg gac gat ctg    720
Leu Lys Pro Ala Ile Arg Glu Lys Ile Leu Ala His Met Asp Asp Leu
225                 230                 235                 240 aag ctc tcc tgg gac ctg gcc aag gtg cgc acc gac ctg ccc ctg gag    768
Lys Leu Ser Trp Asp Leu Ala Lys Val Arg Thr Asp Leu Pro Leu Glu
                245                 250                 255 gtg gac ttc gcc aaa agg cgg gag ccc gac cgg gag agg ctt agg gcc    816
Val Asp Phe Ala Lys Arg Arg Glu Pro Asp Arg Glu Arg Leu Arg Ala
            260                 265                 270 ttt ctg gag agg ctt gag ttt ggc agc ctc ctc cac gag ttc ggc ctt    864
Phe Leu Glu Arg Leu Glu Phe Gly Ser Leu Leu His Glu Phe Gly Leu
        275                 280                 285 ctg gaa agc ccc aag gcc ctg gag gag gcc ccc tgg ccc ccg ccg gaa    912
Leu Glu Ser Pro Lys Ala Leu Glu Glu Ala Pro Trp Pro Pro Pro Glu
    290                 295                 300 ggg gcc ttc gtg ggc ttt gtg ctt tcc cgc aag gag ccc atg tgg gcc    960
Gly Ala Phe Val Gly Phe Val Leu Ser Arg Lys Glu Pro Met Trp Ala
305                 310                 315                 320 gat ctt ctg gcc ctg gcc gcc gcc agg ggg ggc cgg gtc cac cgg gcc   1008
Asp Leu Leu Ala Leu Ala Ala Ala Arg Gly Gly Arg Val His Arg Ala
                325                 330                 335 ccc gag cct tat aaa gcc ctc agg gac ctg aag gag gcg cgg ggg ctt   1056
Pro Glu Pro Tyr Lys Ala Leu Arg Asp Leu Lys Glu Ala Arg Gly Leu
            340                 345                 350 ctc gcc aaa gac ctg agc gtt ctg gcc ctg agg gaa ggc ctt ggc ctc   1104
Leu Ala Lys Asp Leu Ser Val Leu Ala Leu Arg Glu Gly Leu Gly Leu
        355                 360                 365 ccg ccc ggc gac gac ccc atg ctc ctc gcc tac ctc ctg gac cct tcc   1152
Pro Pro Gly Asp Asp Pro Met Leu Leu Ala Tyr Leu Leu Asp Pro Ser
    370                 375                 380 aac acc acc ccc gag ggg gtg gcc cgg cgc tac ggc ggg gag tgg acg   1200
Asn Thr Thr Pro Glu Gly Val Ala Arg Arg Tyr Gly Gly Glu Trp Thr
385                 390                 395                 400 gag gag gcg ggg gag cgg gcc gcc ctt tcc gag agg ctc ttc gcc aac   1248
Glu Glu Ala Gly Glu Arg Ala Ala Leu Ser Glu Arg Leu Phe Ala Asn
                405                 410                 415 ctg tgg ggg agg ctt gag ggg gag gag agg ctc ctt tgg ctt tac cgg   1296
Leu Trp Gly Arg Leu Glu Gly Glu Glu Arg Leu Leu Trp Leu Tyr Arg
            420                 425                 430 gag gtg gag agg ccc ctt tcc gct gtc ctg gcc cac atg gag gcc acg   1344
Glu Val Glu Arg Pro Leu Ser Ala Val Leu Ala His Met Glu Ala Thr
        435                 440                 445 ggg gtg cgc ctg gac gtg gcc tat ctc agg gcc ttg tcc ctg gag gtg   1392
Gly Val Arg Leu Asp Val Ala Tyr Leu Arg Ala Leu Ser Leu Glu Val
```

-continued

```
            450                 455                 460
gcc ggg gag atc gcc cgc ctc gag gcc gag gtc ttc cgc ctg gcc ggc      1440
Ala Gly Glu Ile Ala Arg Leu Glu Ala Glu Val Phe Arg Leu Ala Gly
465                 470                 475                 480 cac ccc ttc aac ctc aac tcc cgg gac cag ctg gaa agg gtc ctc ttt      1488
His Pro Phe Asn Leu Asn Ser Arg Asp Gln Leu Glu Arg Val Leu Phe
                    485                 490                 495 gac gag cta ggg ctt ccc gcc atc ggc aag acg gag aag acc ggc aag      1536
Asp Glu Leu Gly Leu Pro Ala Ile Gly Lys Thr Glu Lys Thr Gly Lys
                500                 505                 510 cgc tcc acc agc gcc gcc gtc ctg gag gcc ctc cgc gag gcc cac ccc      1584
Arg Ser Thr Ser Ala Ala Val Leu Glu Ala Leu Arg Glu Ala His Pro
            515                 520                 525 atc gtg gag aag atc ctg cag tac cgg gag ctc acc aag ctg aag agc      1632
Ile Val Glu Lys Ile Leu Gln Tyr Arg Glu Leu Thr Lys Leu Lys Ser
530                 535                 540 acc tac att gac ccc ttg ccg gac ctc atc cac ccc agg acg ggc cgc      1680
Thr Tyr Ile Asp Pro Leu Pro Asp Leu Ile His Pro Arg Thr Gly Arg
545                 550                 555                 560 ctc cac acc cgc ttc aac cag acg gcc acg gcc acg ggc agg cta agt      1728
Leu His Thr Arg Phe Asn Gln Thr Ala Thr Ala Thr Gly Arg Leu Ser
                    565                 570                 575 agc tcc gat ccc aac ctc cag aac atc ccc gtc cgc acc ccg ctt ggg      1776
Ser Ser Asp Pro Asn Leu Gln Asn Ile Pro Val Arg Thr Pro Leu Gly
                580                 585                 590 cag agg atc cgc cgg gcc ttc atc gcc gag gag ggg tgg cta ttg gtg      1824
Gln Arg Ile Arg Arg Ala Phe Ile Ala Glu Glu Gly Trp Leu Leu Val
            595                 600                 605 gcc ctg gcc tat agc cag ata gag ctc agg gtg ctg gcc cac ctc tcc      1872
Ala Leu Ala Tyr Ser Gln Ile Glu Leu Arg Val Leu Ala His Leu Ser
610                 615                 620 ggc gac gag aac ctg atc cgg gtc ttc cag gag ggg cgg gac atc cac      1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac      1968
Thr Glu Thr Ala Ser Trp Met Phe Gly Val Pro Arg Glu Ala Val Asp
                    645                 650                 655 ccc ctg atg cgc cgg gcg gcc aag acc atc aac ttc ggg gtc ctc tac      2016
Pro Leu Met Arg Arg Ala Ala Lys Thr Ile Asn Phe Gly Val Leu Tyr
                660                 665                 670 ggc atg tcg gcc cac cgc ctc tcc cag gag cta gcc atc cct tac gag      2064
Gly Met Ser Ala His Arg Leu Ser Gln Glu Leu Ala Ile Pro Tyr Glu
            675                 680                 685 gag gcc cag gcc ttc att gag cgc tac ttt cag agc ttc ccc aag gtg      2112
Glu Ala Gln Ala Phe Ile Glu Arg Tyr Phe Gln Ser Phe Pro Lys Val
690                 695                 700 cgg gcc tgg att gag aag acc ctg gag gag ggc agg agg cgg ggg tac      2160
Arg Ala Trp Ile Glu Lys Thr Leu Glu Glu Gly Arg Arg Arg Gly Tyr
705                 710                 715                 720 gtg gag acc ctc ttc ggc cgc cgc cgc tac gtg cca gac cta gag gcc      2208
Val Glu Thr Leu Phe Gly Arg Arg Arg Tyr Val Pro Asp Leu Glu Ala
                    725                 730                 735 cgg gtg aag agc gtg cgg gag gcg gcc gag cgc atg gcc ttc aac atg      2256
Arg Val Lys Ser Val Arg Glu Ala Ala Glu Arg Met Ala Phe Asn Met
                740                 745                 750 ccc gtc cag ggc acc gcc gcc gac ctc atg aag ctg gct atg gtg aag      2304
Pro Val Gln Gly Thr Ala Ala Asp Leu Met Lys Leu Ala Met Val Lys
            755                 760                 765 ctc ttc ccc agg ctg gag gaa atg ggg gcc agg atg ctc ctt cag gtc      2352
```

```
Leu Phe Pro Arg Leu Glu Glu Met Gly Ala Arg Met Leu Leu Gln Val
            770                 775                 780 cac gac gag ctg gtc ctc gag gcc cca aaa gag agg gcg gag gcc gtg        2400
His Asp Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg        2448
Ala Arg Leu Ala Lys Glu Val Met Glu Gly Val Tyr Pro Leu Ala Val
                805                 810                 815 ccc ctg gag gtg gag gtg ggg ata ggg gag gac tgg ctc tcc gcc aag        2496
Pro Leu Glu Val Glu Val Gly Ile Gly Glu Asp Trp Leu Ser Ala Lys
            820                 825                 830 gag tgatag                                                              2505
Glu <210> SEQ ID NO 130
<211> LENGTH: 833
<212> TYPE: PRT
<213> ORGANISM: Artificial Sequence
<220> FEATURE:
<223> OTHER INFORMATION: Description of Artificial Sequence: Synthetic

<400> SEQUENCE: 130

Met Asn Ser Gly Met Leu Pro Leu Phe Glu Pro Lys Gly Arg Val Leu
  1               5                  10                  15

Leu Val Asp Gly His His Leu Ala Tyr Arg Thr Phe His Ala Leu Lys
             20                  25                  30

Gly Leu Thr Thr Ser Arg Gly Glu Pro Val Gln Ala Val Tyr Gly Phe
         35                  40                  45

Ala Lys Ser Leu Leu Lys Ala Leu Lys Glu Asp Gly Asp Ala Val Ile
     50                  55                  60

Val Val Phe Asp Ala Lys Ala Pro Ser Phe Arg His Glu Ala Tyr Gly
 65                  70                  75                  80

Gly Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Leu Ala Arg Leu
            100                 105                 110

Glu Val Pro Gly Tyr Glu Ala Asp Asp Val Leu Ala Ser Leu Ala Lys
        115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270
```

-continued

```
Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
        290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
                340                 345                 350

Leu Ala Lys Asp Leu Ser Val Leu Ala Leu Arg Glu Gly Leu Gly Leu
                355                 360                 365

Pro Pro Gly Asp Asp Pro Met Leu Leu Ala Tyr Leu Leu Asp Pro Ser
        370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Arg Leu Leu Trp Leu Tyr Arg
                420                 425                 430

Glu Val Glu Arg Pro Leu Ser Ala Val Leu Ala His Met Glu Ala Thr
                435                 440                 445

Gly Val Arg Leu Asp Val Ala Tyr Leu Arg Ala Leu Ser Leu Glu Val
        450                 455                 460

Ala Gly Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
                500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
        530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
                580                 585                 590

Gln Arg Ile Arg Arg Ala Phe Ile Ala Glu Glu Gly Trp Leu Leu Val
        595                 600                 605

Ala Leu Ala Tyr Ser Gln Ile Glu Leu Arg Val Leu Ala His Leu Ser
        610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
                660                 665                 670

Gly Met Ser Ala His Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
```

```
                        690                 695                 700
Arg Ala Trp Ile Glu Lys Thr Leu Glu Glu Gly Arg Arg Gly Tyr
705                 710                 715                 720

Val Glu Thr Leu Phe Gly Arg Arg Tyr Val Pro Asp Leu Glu Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Glu Glu Met Gly Ala Arg Met Leu Leu Gln Val
    770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu
```

<210> SEQ ID NO 131
<211> LENGTH: 2505
<212> TYPE: DNA
<213> ORGANISM: Artificial Sequence
<220> FEATURE:
<221> NAME/KEY: CDS
<222> LOCATION: (1)..(2499)
<223> OTHER INFORMATION: Description of Artificial Sequence: Synthetic

<400> SEQUENCE: 131

```
atg aat tcg ggg atg ctg ccc ctc ttt gag ccc aag ggc cgg gtc ctc        48
Met Asn Ser Gly Met Leu Pro Leu Phe Glu Pro Lys Gly Arg Val Leu
 1               5                  10                  15 ctg gtg gac ggc cac cac ctg gcc tac cgc acc ttc cac gcc ctg aag        96
Leu Val Asp Gly His His Leu Ala Tyr Arg Thr Phe His Ala Leu Lys
            20                  25                  30 ggc ctc acc acc agc cgg ggg gag ccg gtg cag gcg gtc tac ggc ttc       144
Gly Leu Thr Thr Ser Arg Gly Glu Pro Val Gln Ala Val Tyr Gly Phe
        35                  40                  45 gcc aag agc ctc ctc aag gcc ctc aag gag gac ggg gac gcg gtg atc       192
Ala Lys Ser Leu Leu Lys Ala Leu Lys Glu Asp Gly Asp Ala Val Ile
    50                  55                  60 gtg gtc ttt gac gcc aag gcc ccc tcc ttc cgc cac gag gcc tac ggg       240
Val Val Phe Asp Ala Lys Ala Pro Ser Phe Arg His Glu Ala Tyr Gly
65                  70                  75                  80 ggg tac aag gcg ggc cgg gcc ccc acg ccg gag gac ttt ccc cgg caa       288
Gly Tyr Lys Ala Gly Arg Ala Pro Thr Pro Glu Asp Phe Pro Arg Gln
                85                  90                  95 ctc gcc ctc atc aag gag ctg gtg gac ctc ctg ggg ctg gcg cgc ctc       336
Leu Ala Leu Ile Lys Glu Leu Val Asp Leu Leu Gly Leu Ala Arg Leu
            100                 105                 110 gag gtc ccg ggc tac gag gcg gac gac gtc ctg gcc agc ctg gcc aag       384
Glu Val Pro Gly Tyr Glu Ala Asp Asp Val Leu Ala Ser Leu Ala Lys
        115                 120                 125 aag gcg gaa aag gag ggc tac gag gtc cgc atc ctc acc gcc gac aaa       432
Lys Ala Glu Lys Glu Gly Tyr Glu Val Arg Ile Leu Thr Ala Asp Lys
    130                 135                 140 gac ctt tac cag ctc ctt tcc gac cgc atc cac gtc ctc cac ccc gag       480
Asp Leu Tyr Gln Leu Leu Ser Asp Arg Ile His Val Leu His Pro Glu
145                 150                 155                 160
```

```
ggg tac ctc atc acc ccg gcc tgg ctt tgg gaa aag tac ggc ctg agg      528
Gly Tyr Leu Ile Thr Pro Ala Trp Leu Trp Glu Lys Tyr Gly Leu Arg
            165                 170                 175 ccc gac cag tgg gcc gac tac cgg gcc ctg acc ggg gac gag tcc gac      576
Pro Asp Gln Trp Ala Asp Tyr Arg Ala Leu Thr Gly Asp Glu Ser Asp
            180                 185                 190 aac ctt ccc ggg gtc aag ggc atc ggg gag aag acg gcg agg aag ctt      624
Asn Leu Pro Gly Val Lys Gly Ile Gly Glu Lys Thr Ala Arg Lys Leu
            195                 200                 205 ctg gag gag tgg ggg agc ctg gaa gcc ctc ctc aag aac ctg gac cgg      672
Leu Glu Glu Trp Gly Ser Leu Glu Ala Leu Leu Lys Asn Leu Asp Arg
        210                 215                 220 ctg aag ccc gcc atc cgg gag aag atc ctg gcc cac atg gac gat ctg      720
Leu Lys Pro Ala Ile Arg Glu Lys Ile Leu Ala His Met Asp Asp Leu
225                 230                 235                 240 aag ctc tcc tgg gac ctg gcc aag gtg cgc acc gac ctg ccc ctg gag      768
Lys Leu Ser Trp Asp Leu Ala Lys Val Arg Thr Asp Leu Pro Leu Glu
                245                 250                 255 gtg gac ttc gcc aaa agg cgg gag ccc gac cgg gag agg ctt agg gcc      816
Val Asp Phe Ala Lys Arg Arg Glu Pro Asp Arg Glu Arg Leu Arg Ala
            260                 265                 270 ttt ctg gag agg ctt gag ttt ggc agc ctc ctc cac gag ttc ggc ctt      864
Phe Leu Glu Arg Leu Glu Phe Gly Ser Leu Leu His Glu Phe Gly Leu
        275                 280                 285 ctg gaa agc ccc aag gcc ctg gag gag gcc ccc tgg ccc cgg ccg gaa      912
Leu Glu Ser Pro Lys Ala Leu Glu Glu Ala Pro Trp Pro Pro Pro Glu
    290                 295                 300 ggg gcc ttc gtg ggc ttt gtg ctt tcc cgc aag gag ccc atg tgg gcc      960
Gly Ala Phe Val Gly Phe Val Leu Ser Arg Lys Glu Pro Met Trp Ala
305                 310                 315                 320 gat ctt ctg gcc ctg gcc gcc gcc agg ggg ggc cgg gtc cac cgg gcc     1008
Asp Leu Leu Ala Leu Ala Ala Ala Arg Gly Gly Arg Val His Arg Ala
                325                 330                 335 ccc gag cct tat aaa gcc ctc agg gac ctg aag gag gcg cgg ggg ctt     1056
Pro Glu Pro Tyr Lys Ala Leu Arg Asp Leu Lys Glu Ala Arg Gly Leu
            340                 345                 350 ctc gcc aaa gac ctg agc gtt ctg gcc ctg agg gaa ggc ctt ggc ctc     1104
Leu Ala Lys Asp Leu Ser Val Leu Ala Leu Arg Glu Gly Leu Gly Leu
        355                 360                 365 ccg ccc ggc gac gac ccc atg ctc ctc gcc tac ctc ctg gac cct tcc     1152
Pro Pro Gly Asp Asp Pro Met Leu Leu Ala Tyr Leu Leu Asp Pro Ser
    370                 375                 380 aac acc acc ccc gag ggg gtg gcc cgg cgc tac ggc ggg gag tgg acg     1200
Asn Thr Thr Pro Glu Gly Val Ala Arg Arg Tyr Gly Gly Glu Trp Thr
385                 390                 395                 400 gag gag gcg ggg gag cgg gcc gcc ctt tcc gag agg ctc ttc gcc aac     1248
Glu Glu Ala Gly Glu Arg Ala Ala Leu Ser Glu Arg Leu Phe Ala Asn
                405                 410                 415 ctg tgg ggg agg ctt gag ggg gag gag agg ctc ctt tgg ctt tac cgg     1296
Leu Trp Gly Arg Leu Glu Gly Glu Glu Arg Leu Leu Trp Leu Tyr Arg
            420                 425                 430 gag gtg gag agg ccc ctt tcc gct gtc ctg gcc cac atg gag gcc acg     1344
Glu Val Glu Arg Pro Leu Ser Ala Val Leu Ala His Met Glu Ala Thr
        435                 440                 445 ggg gtg cgc ctg gac gtg gcc tat ctc agg gcc ttg tcc ctg gag gtg     1392
Gly Val Arg Leu Asp Val Ala Tyr Leu Arg Ala Leu Ser Leu Glu Val
    450                 455                 460 gcc ggg gag atc gcc cgc ctc gag gcc gag gtc ttc cgc ctg gcc ggc     1440
Ala Gly Glu Ile Ala Arg Leu Glu Ala Glu Val Phe Arg Leu Ala Gly
```

```
                465                 470                 475                 480
cac ccc ttc aac ctc aac tcc cgg gac cag ctg gaa agg gtc ctc ttt        1488
His Pro Phe Asn Leu Asn Ser Arg Asp Gln Leu Glu Arg Val Leu Phe
                        485                 490                 495 gac gag cta ggg ctt ccc gcc atc ggc aag acg gag aag acc ggc aag        1536
Asp Glu Leu Gly Leu Pro Ala Ile Gly Lys Thr Glu Lys Thr Gly Lys
                500                 505                 510 cgc tcc acc agc gcc gcc gtc ctg gag gcc ctc cgc gag gcc cac ccc        1584
Arg Ser Thr Ser Ala Ala Val Leu Glu Ala Leu Arg Glu Ala His Pro
            515                 520                 525 atc gtg gag aag atc ctg cag tac cgg gag ctc acc aag ctg aag agc        1632
Ile Val Glu Lys Ile Leu Gln Tyr Arg Glu Leu Thr Lys Leu Lys Ser
        530                 535                 540 acc tac att gac ccc ttg ccg gac ctc atc cac ccc agg acg ggc cgc        1680
Thr Tyr Ile Asp Pro Leu Pro Asp Leu Ile His Pro Arg Thr Gly Arg
545                 550                 555                 560 ctc cac acc cgc ttc aac cag acg gcc acg gcc acg ggc agg cta agt        1728
Leu His Thr Arg Phe Asn Gln Thr Ala Thr Ala Thr Gly Arg Leu Ser
                565                 570                 575 agc tcc gat ccc aac ctc cag aac atc ccc gtc cgc acc ccg ctt ggg        1776
Ser Ser Asp Pro Asn Leu Gln Asn Ile Pro Val Arg Thr Pro Leu Gly
            580                 585                 590 cag agg atc cgc cgg gcc ttc atc gcc gag gag ggg tgg cta ttg gtg        1824
Gln Arg Ile Arg Arg Ala Phe Ile Ala Glu Glu Gly Trp Leu Leu Val
        595                 600                 605 gcc ctg gtc tat agc cag ata gag ctc agg gtg ctg gcc cac ctc tcc        1872
Ala Leu Val Tyr Ser Gln Ile Glu Leu Arg Val Leu Ala His Leu Ser
610                 615                 620 ggc gac gag aac ctg atc cgg gtc ttc cag gag ggg cgg gac atc cac        1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac        1968
Thr Glu Thr Ala Ser Trp Met Phe Gly Val Pro Arg Glu Ala Val Asp
                645                 650                 655 ccc ctg atg cgc cgg gcg gcc aag acc atc aac ttc ggg gtc ctc tac        2016
Pro Leu Met Arg Arg Ala Ala Lys Thr Ile Asn Phe Gly Val Leu Tyr
            660                 665                 670 ggc atg tcg gcc cac cgc ctc tcc cag gag cta gcc atc cct tac gag        2064
Gly Met Ser Ala His Arg Leu Ser Gln Glu Leu Ala Ile Pro Tyr Glu
        675                 680                 685 gag gcc cag gcc ttc att gag cgc tac ttt cag agc ttc ccc aag gtg        2112
Glu Ala Gln Ala Phe Ile Glu Arg Tyr Phe Gln Ser Phe Pro Lys Val
    690                 695                 700 cgg gcc tgg att gag aag acc ctg gag gag ggc agg agg cgg ggg tac        2160
Arg Ala Trp Ile Glu Lys Thr Leu Glu Glu Gly Arg Arg Arg Gly Tyr
705                 710                 715                 720 gtg gag acc ctc ttc ggc cgc cgc cgc tac gtg cca gac cta gag gcc        2208
Val Glu Thr Leu Phe Gly Arg Arg Arg Tyr Val Pro Asp Leu Glu Ala
                725                 730                 735 cgg gtg aag agc gtg cgg gag gcg gcc gag cgc atg gcc ttc aac atg        2256
Arg Val Lys Ser Val Arg Glu Ala Ala Glu Arg Met Ala Phe Asn Met
            740                 745                 750 ccc gtc cag ggc acc gcc gcc gac ctc atg aag ctg gct atg gtg aag        2304
Pro Val Gln Gly Thr Ala Ala Asp Leu Met Lys Leu Ala Met Val Lys
        755                 760                 765 ctc ttc ccc agg ctg gag gaa atg ggg gcc agg atg ctc ctt cag gtc        2352
Leu Phe Pro Arg Leu Glu Glu Met Gly Ala Arg Met Leu Leu Gln Val
    770                 775                 780 cac gac gag ctg gtc ctc gag gcc cca aaa gag agg gcg gag gcc gtg        2400
```

-continued

```
His Asp Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg    2448
Ala Arg Leu Ala Lys Glu Val Met Glu Gly Val Tyr Pro Leu Ala Val
            805                 810                 815 ccc ctg gag gtg gag gtg ggg ata ggg gag gac tgg ctc tcc gcc aag    2496
Pro Leu Glu Val Glu Val Gly Ile Gly Glu Asp Trp Leu Ser Ala Lys
        820                 825                 830 gag tgatag                                                          2505
Glu

<210> SEQ ID NO 132
<211> LENGTH: 833
<212> TYPE: PRT
<213> ORGANISM: Artificial Sequence
<220> FEATURE:
<223> OTHER INFORMATION: Description of Artificial Sequence: Synthetic

<400> SEQUENCE: 132

Met Asn Ser Gly Met Leu Pro Leu Phe Glu Pro Lys Gly Arg Val Leu
 1               5                  10                  15

Leu Val Asp Gly His His Leu Ala Tyr Arg Thr Phe His Ala Leu Lys
            20                  25                  30

Gly Leu Thr Thr Ser Arg Gly Glu Pro Val Gln Ala Val Tyr Gly Phe
        35                  40                  45

Ala Lys Ser Leu Leu Lys Ala Leu Lys Glu Asp Gly Asp Ala Val Ile
    50                  55                  60

Val Val Phe Asp Ala Lys Ala Pro Ser Phe Arg His Glu Ala Tyr Gly
65                  70                  75                  80

Gly Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Leu Ala Arg Leu
            100                 105                 110

Glu Val Pro Gly Tyr Glu Ala Asp Asp Val Leu Ala Ser Leu Ala Lys
        115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
```

-continued

```
                    290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Arg Val His Arg Ala
                325                 330                 335
Pro Glu Pro Tyr Lys Ala Leu Arg Asp Leu Lys Glu Ala Arg Gly Leu
                340                 345                 350
Leu Ala Lys Asp Leu Ser Val Leu Ala Leu Arg Glu Gly Leu Gly Leu
                355                 360                 365
Pro Pro Gly Asp Asp Pro Met Leu Leu Ala Tyr Leu Leu Asp Pro Ser
370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Arg Leu Leu Trp Leu Tyr Arg
                420                 425                 430
Glu Val Glu Arg Pro Leu Ser Ala Val Leu Ala His Met Glu Ala Thr
                435                 440                 445
Gly Val Arg Leu Asp Val Ala Tyr Leu Arg Ala Leu Ser Leu Glu Val
                450                 455                 460
Ala Gly Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
                500                 505                 510
Arg Ser Thr Ser Ala Ala Val Leu Glu Ala Leu Arg Glu Ala His Pro
                515                 520                 525
Ile Val Glu Lys Ile Leu Gln Tyr Arg Glu Leu Thr Lys Leu Lys Ser
                530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Ile Ala Glu Glu Gly Trp Leu Leu Val
                595                 600                 605
Ala Leu Val Tyr Ser Gln Ile Glu Leu Arg Val Leu Ala His Leu Ser
                610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
                660                 665                 670
Gly Met Ser Ala His Arg Leu Ser Gln Glu Leu Ala Ile Pro Tyr Glu
                675                 680                 685
Glu Ala Gln Ala Phe Ile Glu Arg Tyr Phe Gln Ser Phe Pro Lys Val
                690                 695                 700
Arg Ala Trp Ile Glu Lys Thr Leu Glu Glu Gly Arg Arg Arg Gly Tyr
705                 710                 715                 720
```

```
Val Glu Thr Leu Phe Gly Arg Arg Arg Tyr Val Pro Asp Leu Glu Ala
            725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Phe Pro Arg Leu Glu Glu Met Gly Ala Arg Met Leu Leu Gln Val
    770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence:  Synthetic

<400> SEQUENCE: 133
aaaattcctt tctctttgcc ctttgcttcc                                      30

<210> SEQ ID NO 134
<211> LENGTH: 31
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: The residues at these positions are a
      2'deoxycytosine 5'-O-(1-Thiomonophosphate).
<221> NAME/KEY: misc_feature
<222> LOCATION: (3)
<223> OTHER INFORMATION: The residue at this position is a
      2'deoxythymidine 5'-O-(1-Thiomonophosphate).
<221> NAME/KEY: misc_feature
<222> LOCATION: (4)..(5)
<223> OTHER INFORMATION: The residues at these positions are a
      2'deoxyadenosine 5'-O-(1-Thiomonophosphate).
<221> NAME/KEY: misc_feature
<222> LOCATION: (6)..(8)
<223> OTHER INFORMATION: The residues at these positions are a
      2'deoxythymidine 5'-O-(1-Thiomonophosphate).
<221> NAME/KEY: misc_feature
<222> LOCATION: (9)
<223> OTHER INFORMATION: The residue at this position is a
      2'deoxyguanosine 5'-O-(1-Thiomonophosphate).
<221> NAME/KEY: misc_feature
<222> LOCATION: (10)
<223> OTHER INFORMATION: The residue at this position is a
      2'deoxycytosine 5'-O-(1-Thiomonophosphate).
<223> OTHER INFORMATION: Description of Artificial Sequence:
      Synthetic

<400> SEQUENCE: 134
cctaatttgc cagttacaaa ataaacagcc c                                    31

<210> SEQ ID NO 135
<211> LENGTH: 17
<212> TYPE: DNA
<213> ORGANISM: Artificial Sequence
<220> FEATURE:
```

```
<223> OTHER INFORMATION: Description of Artificial Sequence: Synthetic

<400> SEQUENCE: 135
tgtggaattg tgagcgg                                                      17

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 136
tggaggctct ccatcaaaaa c                                                 21

<210> SEQ ID NO 137
<211> LENGTH: 296
<212> TYPE: DNA
<213> ORGANISM: Artificial Sequence
<220> FEATURE:
<223> OTHER INFORMATION: Description of Artificial Sequence: Synthetic

<400> SEQUENCE: 137
tgtggaattg tgagcggata acaatttcac acaggaaaca gaccatggga gtgcagtttg      60
gtgattttat tccaaaaaat attatctcct ttgaagattt aaaagggaaa aaagtagcta     120
ttgatggaat gaatgcatta tatcagtttt taacatctat acgtttgaga gatggttctc     180
cattgagaaa tagaaaagga gagataacct cagcatataa cggagttttt tataaaacca     240
tacatttgtt agagaatgat ataactccaa tctgggtttt tgatggagag cctcca         296

<210> SEQ ID NO 138
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 138
taatctgtat caggctg                                                      17

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 139
gtttttgatg gagagcctcc a                                                 21

<210> SEQ ID NO 140
<211> LENGTH: 889
<212> TYPE: DNA
<213> ORGANISM: Artificial Sequence
<220> FEATURE:
<223> OTHER INFORMATION: Description of Artificial Sequence: Synthetic

<400> SEQUENCE: 140
gtttttgatg gagagcctcc agaattcaaa agaaagagc tcgaaaaaag aagagaagcg       60
agagaggaag ctgaagaaaa gtggagagaa gcacttgaaa aaggagagat agaggaagca     120
agaaaatatg cccaaagagc aaccagggta aatgaaatgc tcatcgagga tgcaaaaaaa     180
ctcttagagc ttatgggaat tcctatagtt caagcaccta gcgagggaga ggcccaagct     240
```

```
gcatatatgg ccgcaaaggg gagcgtgtat gcatcggcta gtcaagatta cgattccta      300 cttttttggag ctccaagact tgttagaaac ttaacaataa caggaaaaag aaagttgcct    360
gggaaaaatg tctacgtcga gataaagccc gagttgataa ttttggagga agtactcaag    420
gaattaaagc taacaagaga aaagctcatt gaactagcaa tcctcgttgg aacagactac    480
aacccaggag gaataaaggg cataggcctt aaaaaagctt tagagattgt tagacactca    540
aaagatccgc tagcaaagtt ccaaaagcaa agcgatgtgg atttatatgc aataaaagag    600
ttcttcctaa acccaccagt cacagataac tacaatttag tgtggagaga tcccgacgaa    660
gagggaatac taaagttctt atgtgacgag catgactttta gtgaggaaag agtaaagaat    720
ggattagaga ggcttaagaa ggcaatcaaa agtggaaaac aatcaaccct tgaaagttgg    780
ttcaagagat aaccttaaag tctattgcaa tgttatactg acgcgctgca ggcatgcaag    840
cttggctgtt ttggcggatg agaagagatt ttcagcctga tacagatta               889
```

```
<210> SEQ ID NO 141
<211> LENGTH: 1164
<212> TYPE: DNA
<213> ORGANISM: Artificial Sequence
<220> FEATURE:
<223> OTHER INFORMATION: Description of Artificial Sequence: Synthetic

<400> SEQUENCE: 141
tgtggaattg tgagcggata acaatttcac acaggaaaca gaccatggga gtgcagtttg      60
gtgattttat tccaaaaaat attatctcct ttgaagattt aaaagggaaa aaagtagcta    120
ttgatggaat gaatgcatta tatcagtttt taacatctat acgtttgaga gatggttctc    180
cattgagaaa tagaaaagga gagataaacct cagcatataa cggagttttt tataaaacca    240
tacatttgtt agagaatgat ataactccaa tctgggtttt tgatggagag cctccagaat    300
tcaaaaagaa agagctcgaa aaaagaagag aagcgagaga ggaagctgaa gaaaagtgga    360
gagaagcact tgaaaaagga gagatagagg aagcaagaaa atatgcccaa agagcaacca    420
gggtaaatga aatgctcatc gaggatgcaa aaaaactctt agagcttatg ggaattccta    480
tagttcaagc acctagcgag ggagaggccc aagctgcata tatggccgca aaggggagcg    540
tgtatgcatc ggctagtcaa gattacgatt ccctactttt tggagctcca agacttgtta    600
gaaacttaac aataacagga aaagaaagt gcctgggaa aaatgtctac gtcgagataa    660
agcccgagtt gataattttg gaggaagtac tcaaggaatt aaagctaaca agagaaaagc    720
tcattgaact agcaatcctc gttggaacag actacaaccc aggaggaata aagggcatag    780
gccttaaaaa agctttagag attgttagac actcaaaaga tccgctagca aagttccaaa    840
agcaaagcga tgtggattta tatgcaataa aagagttctt cctaaaccca ccagtcacag    900
ataactacaa tttagtgtgg agatcccg acgaagaggg aatactaaag ttcttatgtg    960
acgagcatga ctttagtgag gaaagagtaa agaatggatt agagaggctt aagaaggcaa    1020
tcaaaagtgg aaaacaatca acccttgaaa gttggttcaa gagataacct taaagtctat   1080
tgcaatgtta tactgacgcg ctgcaggcat gcaagcttgg ctgttttggc ggatgagaga   1140
agattttcag cctgatacag atta                                          1164
```

```
<210> SEQ ID NO 142
<211> LENGTH: 296
<212> TYPE: DNA
<213> ORGANISM: Artificial Sequence
<220> FEATURE:
```

<223> OTHER INFORMATION: Description of Artificial Sequence: Synthetic

<400> SEQUENCE: 142

| | | | | | |
|---|---|---|---|---|---|
| tgtggaattg | tgagcggata | acaatttcac | acaggaaaca | gaccatgggt | gtcccaattg | 60 |
| gtgagattat | accaagaaaa | gaattgagt | tagaaaacct | atacgggaaa | aaaatcgcaa | 120 |
| tcgacgctct | taatgcaatc | taccaatttt | tgtccacaat | aagacagaaa | gatgaactc | 180 |
| cacttatgga | ttcaaagggt | agaataacct | cccacctaag | cgggctcttt | tacaggacaa | 240 |
| taaacctaat | ggaggctgga | ataaaacctg | tgtatgtttt | tgatggagag | cctcca | 296 |

<210> SEQ ID NO 143
<211> LENGTH: 840
<212> TYPE: DNA
<213> ORGANISM: Artificial Sequence
<220> FEATURE:
<223> OTHER INFORMATION: Description of Artificial Sequence: Synthetic

<400> SEQUENCE: 143

| | | | | | |
|---|---|---|---|---|---|
| gtttttgatg | gagagcctcc | aaagttaaag | gagaaaacaa | ggaaagttag | gagagagatg | 60 |
| aaagagaaag | ctgaacttaa | gatgaaagag | gcaattaaaa | aggaggattt | tgaagaagct | 120 |
| gctaagtatg | caaagagggt | tagctatcta | actccgaaaa | tggttgaaaa | ctgcaaatat | 180 |
| ttgttaagtt | tgatgggcat | tccgtatgtt | gaagctccct | ctgagggaga | ggcacaagca | 240 |
| agctatatgg | caaagaaggg | agatgtttgg | gcagttgtaa | gtcaagatta | tgatgccttg | 300 |
| ttatatggag | ctccgagagt | tgttagaaat | ttaacaacta | caaaggagat | gccagaactt | 360 |
| attgaattaa | atgaggtttt | agaggattta | agaatttctt | tggatgattt | gatagatata | 420 |
| gccatattta | tgggaactga | ctataatcca | ggaggagtta | aggaataggg | atttaaaagg | 480 |
| gcttatgaat | tggttagaag | tggtgtagct | aaggatgttt | tgaaaaaaga | ggttgaatac | 540 |
| tacgatgaga | ttaagaggat | atttaaagag | ccaaaggtta | ccgataacta | ttcattaagc | 600 |
| ctaaaattgc | cagataaaga | gggaattata | aaattcttag | ttgatgaaaa | tgactttaat | 660 |
| tatgataggt | taaaaagca | tgttgataaa | ctctataact | taattgcaaa | caaaactaag | 720 |
| caaaaaacat | tagatgcatg | gtttaaataa | tttatataat | tttgtgggat | gtcgacctgc | 780 |
| aggcatgcaa | gcttggctgt | tttggcggat | gagagaagat | tttcagcctg | atacagatta | 840 |

<210> SEQ ID NO 144
<211> LENGTH: 1115
<212> TYPE: DNA
<213> ORGANISM: Artificial Sequence
<220> FEATURE:
<223> OTHER INFORMATION: Description of Artificial Sequence: Synthetic

<400> SEQUENCE: 144

| | | | | | |
|---|---|---|---|---|---|
| tgtggaattg | tgagcggata | acaatttcac | acaggaaaca | gaccatgggt | gtcccaattg | 60 |
| gtgagattat | accaagaaaa | gaattgagt | tagaaaacct | atacgggaaa | aaaatcgcaa | 120 |
| tcgacgctct | taatgcaatc | taccaatttt | tgtccacaat | aagacagaaa | gatgaactc | 180 |
| cacttatgga | ttcaaagggt | agaataacct | cccacctaag | cgggctcttt | tacaggacaa | 240 |
| taaacctaat | ggaggctgga | ataaaacctg | tgtatgtttt | tgatggagag | cctccaaagt | 300 |
| taaaggagaa | aacaaggaaa | gttaggagag | agatgaaaga | gaaagctgaa | cttaagatga | 360 |
| aagaggcaat | taaaaaggag | gattttgaag | aagctgctaa | gtatgcaaag | agggttagct | 420 |
| atctaactcc | gaaaatggtt | gaaaactgca | aatatttgtt | aagtttgatg | ggcattccgt | 480 |
| atgttgaagc | tccctctgag | ggagaggcac | aagcaagcta | tatggcaaag | aagggagatg | 540 |

```
tttgggcagt tgtaagtcaa gattatgatg ccttgttata tggagctccg agagttgtta    600
gaaatttaac aactacaaag gagatgccag aacttattga attaaatgag gttttagagg    660
atttaagaat ttctttggat gatttgatag atatagccat atttatggga actgactata    720
atccaggagg agttaaagga ataggattta aaagggctta tgaattggtt agaagtggtg    780
tagctaagga tgttttgaaa aaagaggttg aatactacga tgagattaag aggatatta    840 aagagccaaa ggttaccgat aactattcat taagcctaaa attgccagat aaagagggaa    900
ttataaaatt cttagttgat gaaatgact ttaattatga tagggttaaa aagcatgttg    960
ataaactcta taacttaatt gcaaacaaaa ctaagcaaaa acattagat gcatggttta    1020 aataatttat ataattttgt gggatgtcga cctgcaggca tgcaagcttg gctgttttgg   1080
cggatgagag aagattttca gcctgataca gatta                              1115

<210> SEQ ID NO 145
<211> LENGTH: 386
<212> TYPE: DNA
<213> ORGANISM: Artificial Sequence
<220> FEATURE:
<223> OTHER INFORMATION: Description of Artificial Sequence:  Synthetic

<400> SEQUENCE: 145
tgtggaattg tgagcggata acaatttcac acaggaaaca gaccatgggt gtcccaattg     60
gtgagattat accaagaaaa gaattgagt tagaaaacct atcgggaaa aaaatcgcaa     120 tcgacgctct taatgcaatc taccaatttt tgtccacaat aagacagaaa gatggaactc    180
cacttatgga ttcaaagggt agaataacct cccacctaag cgggctcttt tacaggacaa    240
taaacctaat ggaggctgga ataaaacctg tgtatgtttt tgatggagaa cctccagaat    300
tcaaaaagaa agagctcgaa aaagaagag aagcgagaga ggaagctgaa gaaaagtgga    360
gagaagcact tgaaaaagga gagata                                         386

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence:  Synthetic

<400> SEQUENCE: 146
tacttagcag cttcttctat ctctcctttt tca                                  33

<210> SEQ ID NO 147
<211> LENGTH: 668
<212> TYPE: DNA
<213> ORGANISM: Artificial Sequence
<220> FEATURE:
<223> OTHER INFORMATION: Description of Artificial Sequence:  Synthetic

<400> SEQUENCE: 147
gaagaagctg ctaagtatgc aaagagggtt agctatctaa ctccgaaaat ggttgaaaac     60
tgcaaatatt tgttaagttt gatgggcatt ccgtatgttg aagctccctc tgagggagag    120
gcacaagcaa gctatatggc aaagaaggga gatgtttggg cagttgtaag tcaagattat    180
gatgccttgt tatatggagc tccgagagtt gttagaaatt taacaactac aaaggagatg    240
ccagaactta ttgaattaaa tgaggtttta gaggatttaa gaatttcttt ggatgatttg    300
atagatatag ccatatttat gggaactgac tataatccag gaggagttaa aggaatagga    360
```

```
tttaaaaggg cttatgaatt ggttagaagt ggtgtagcta aggatgtttt gaaaaaagag      420
gttgaatact acgatgagat taagaggata tttaaagagc caaaggttac cgataactat      480
tcattaagcc taaaattgcc agataaagag ggaattataa aattcttagt tgatgaaaat      540
gactttaatt atgatagggt taaaaagcat gttgataaac tctataactt aattgcaaac      600
aaaactaagc aaaaaacatt agatgcatgg tttaaacacc accaccacca ccactaactg      660
cagcggta                                                              668

<210> SEQ ID NO 148
<211> LENGTH: 53
<212> TYPE: DNA
<213> ORGANISM: Artificial Sequence
<220> FEATURE:
<223> OTHER INFORMATION: Description of Artificial Sequence:  Synthetic

<400> SEQUENCE: 148
taccgctgca gttagtggtg gtggtggtgg tgtttaaacc atgcatctaa tgt             53

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 149
gaagaagctg ctaagta                                                     17

<210> SEQ ID NO 150
<211> LENGTH: 1054
<212> TYPE: DNA
<213> ORGANISM: Artificial Sequence
<220> FEATURE:
<223> OTHER INFORMATION: Description of Artificial Sequence:  Synthetic

<400> SEQUENCE: 150
tgtggaattg tgagcggata acaatttcac acaggaaaca gaccatgggt gtcccaattg       60
gtgagattat accaagaaaa gaaattgagt tagaaaacct atacgggaaa aaaatcgcaa      120
tcgacgctct taatgcaatc taccaatttt tgtccacaat aagacagaaa gatggaactc      180
cacttatgga ttcaaagggt agaataacct cccacctaag cgggctcttt tacaggacaa      240
taaacctaat ggaggctgga ataaaacctg tgtatgtttt tgatggagaa cctccagaat      300
tcaaaaagaa agagctcgaa aaaagaagag aagcgagaga ggaagctgaa gaaaagtgga      360
gagaagcact tgaaaaagga gagatagaag aagctgctaa gtatgcaaag agggttagct      420
atctaactcc gaaaatggtt gaaaactgca atatttgtt aagtttgatg ggcattccgt      480
atgttgaagc tccctctgag ggagaggcac aagcaagcta tatggcaaag aagggagatg      540
tttgggcagt tgtaagtcaa gattatgatg ccttgttata tggagctccg agagttgtta      600
gaaatttaac aactacaaag gagatgccag aacttattga attaaatgag gttttagagg      660
atttaagaat ttcttttggat gatttgatag atatagccat atttatggga actgactata      720
atccaggagg agttaaagga ataggattta aaagggctta tgaattggtt agaagtggtg      780
tagctaagga tgttttgaaa aaagaggttg aatactacga tgagattaag aggatatttta      840 aagagccaaa ggttaccgat aactattcat taagcctaaa attgccagat aaagagggaa      900
ttataaaatt cttagttgat gaaaatgact ttaattatga tagggttaaa aagcatgttg      960
ataaactcta taacttaatt gcaaacaaaa ctaagcaaaa aacattagat gcatggttta     1020
```

```
aacaccacca ccaccaccac taactgcagc ggta                                  1054

<210> SEQ ID NO 151
<211> LENGTH: 514
<212> TYPE: DNA
<213> ORGANISM: Artificial Sequence
<220> FEATURE:
<223> OTHER INFORMATION: Description of Artificial Sequence:  Synthetic

<400> SEQUENCE: 151
tgtggaattg tgagcggata acaatttcac acaggaaaca gaccatggga gtgcagtttg       60
gtgattttat tccaaaaaat attatctcct ttgaagattt aaaagggaaa aaagtagcta      120
ttgatggaat gaatgcatta tatcagtttt taacatctat acgtttgaga gatggttctc      180
cattgagaaa tagaaaagga gagataacct cagcatataa cggagttttt tataaaacca      240
tacatttgtt agagaatgat ataactccaa tctgggtttt tgatggtgag ccaccaaagt      300
taaaggagaa aacaaggaaa gttaggagag agatgaaaga gaaagctgaa cttaagatga      360
aagaggcaat taaaaggag gattttgaag aagctgctaa gtatgcaaag agggttagct      420
atctaactcc gaaaatggtt gaaaactgca aatatttgtt aagtttgatg ggcattccgt      480
atgttgaagc tccctctgag ggagaggccc aagc                                  514

<210> SEQ ID NO 152
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 152
gcttgggcct ctccctc                                                      17

<210> SEQ ID NO 153
<211> LENGTH: 667
<212> TYPE: DNA
<213> ORGANISM: Artificial Sequence
<220> FEATURE:
<223> OTHER INFORMATION: Description of Artificial Sequence:  Synthetic

<400> SEQUENCE: 153
gagggagagg cccaagctgc atatatggcc gcaaagggga gcgtgtatgc atcggctagt       60
caagattacg attccctact ttttggagct ccaagacttg ttagaaactt aacaataaca      120
ggaaaaagaa agttgcctgg gaaaaatgtc tacgtcgaga taaagcccga gttgataatt      180
ttggaggaag tactcaagga attaaagcta acaagagaaa agctcattga actagcaatc      240
ctcgttggaa cagactacaa cccaggagga ataaagggca taggccttaa aaaagcttta      300
gagattgtta gacactcaaa agatccgcta gcaaagttcc aaaagcaaag cgatgtggat      360
ttatatgcaa taaaagagtt cttcctaaac ccaccagtca cagataacta caatttagtg      420
tggagagatc ccgacgaaga gggaatacta aagttcttat gtgacgagca tgactttagt      480
gaggaaagag taaagaatgg attagagagg cttaagaagg caatcaaaag tggaaaacaa      540
tcaacccttg aaagttggtt caagagataa ccttaaagtc tattgcaatg ttatactgac      600
gcgctgcagg catgcaagct tggctgtttt ggcggatgag agaagatttt cagcctgata      660
cagatta                                                                667

<210> SEQ ID NO 154
```

```
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 154
gagggagagg cccaagc                                                      17

<210> SEQ ID NO 155
<211> LENGTH: 1164
<212> TYPE: DNA
<213> ORGANISM: Artificial Sequence
<220> FEATURE:
<223> OTHER INFORMATION: Description of Artificial Sequence: Synthetic

<400> SEQUENCE: 155
tgtggaattg tgagcggata acaatttcac acaggaaaca gaccatggga gtgcagtttg      60
gtgattttat tccaaaaaat attatctcct ttgaagattt aaaagggaaa aaagtagcta     120
ttgatggaat gaatgcatta tatcagtttt taacatctat acgtttgaga gatggttctc     180
cattgagaaa tagaaaagga gagataacct cagcatataa cggagttttt tataaaacca     240
tacatttgtt agagaatgat ataactccaa tctgggtttt tgatggtgag ccaccaaagt     300 taaggagaa acaaggaaa gttaggagag agatgaaaga gaaagctgaa cttaagatga      360
aagaggcaat taaaaaggag gattttgaag aagctgctaa gtatgcaaag agggttagct     420
atctaactcc gaaaatggtt gaaaactgca atatttgtt aagtttgatg ggcattccgt      480
atgttgaagc tccctctgag ggagaggccc aagctgcata tatggccgca aaggggagcg     540
tgtatgcatc ggctagtcaa gattacgatt ccctactttt tggagctcca agacttgtta     600
gaaacttaac aataacagga aaagaaagt tgcctgggaa aaatgtctac gtcgagataa      660
agcccgagtt gataattttg gaggaagtac tcaaggaatt aaagctaaca agagaaaagc     720
tcattgaact agcaatcctc gttggaacag actacaaccc aggaggaata aagggcatag     780
gccttaaaaa agctttagag attgttagac actcaaaaga tccgctagca aagttccaaa     840
agcaaagcga tgtggattta tatgcaataa aagagttctt cctaaaccca ccagtcacag     900
ataactacaa tttagtgtgg agagatcccg acgaagaggg aatactaaag ttcttatgtg     960
acgagcatga ctttagtgag gaaagagtaa agaatggatt agagaggctt aagaaggcaa    1020
tcaaaagtgg aaaacaatca acccttgaaa gttggttcaa gagataacct taaagtctat    1080
tgcaatgtta tactgacgcg ctgcaggcat gcaagcttgg ctgttttggc ggatgagaga    1140
agattttcag cctgatacag atta                                           1164

<210> SEQ ID NO 156
<211> LENGTH: 514
<212> TYPE: DNA
<213> ORGANISM: Artificial Sequence
<220> FEATURE:
<223> OTHER INFORMATION: Description of Artificial Sequence: Synthetic

<400> SEQUENCE: 156
tgtggaattg tgagcggata acaatttcac acaggaaaca gaccatgggt gtcccaattg      60
gtgagattat accaagaaaa gaattgagt tagaaaacct atacgggaaa aaaatcgcaa     120
tcgacgctct taatgcaatc taccaatttt tgtccacaat aagacagaaa gatggaactc     180
cacttatgga ttcaaagggt agaataacct cccacctaag cgggctcttt tacaggacaa     240
taaacctaat ggaggctgga ataaaacctg tgtatgtttt tgatggagaa cctccagaat     300
```

```
tcaaaaagaa agagctcgaa aaaagaagag aagcgagaga ggaagctgaa gaaaagtgga      360
gagaagcact tgaaaaagga gagatagagg aagcaagaaa atatgcccaa agagcaacca      420
gggtaaatga aatgctcatc gaggatgcaa aaaaactctt agagcttatg ggaattccta      480
tagttcaagc acctagcgag ggagaggccc aagc                                 514
```

<210> SEQ ID NO 157
<211> LENGTH: 618
<212> TYPE: DNA
<213> ORGANISM: Artificial Sequence
<220> FEATURE:
<223> OTHER INFORMATION: Description of Artificial Sequence: Synthetic

<400> SEQUENCE: 157

```
gagggagagg cccaagcaag ctatatggca agaagggag atgtttgggc agttgtaagt       60
caagattatg atgccttgtt atatggagct ccgagagttg ttagaaattt aacaactaca     120
aaggagatgc cagaacttat tgaattaaat gaggttttag aggatttaag aatttctttg     180
gatgatttga tagatatagc catatttatg gaactgact ataatccagg aggagttaaa     240
ggaataggat ttaaaagggc ttatgaattg gttagaagtg gtgtagctaa ggatgttttg     300 aaaaagagg ttgaatacta cgatgagatt aagaggatat ttaaagagcc aaaggttacc     360
gataactatt cattaagcct aaaattgcca gataaagagg gaattataaa attcttagtt     420
gatgaaaatg actttaatta tgatagggtt aaaaagcatg ttgataaact ctataactta     480
attgcaaaca aaactaagca aaaaacatta gatgcatggt ttaaataatt tatataattt     540
tgtgggatgt cgacctgcag gcatgcaagc ttggctgttt tggcggatga gagaagattt     600
tcagcctgat acagatta                                                   618
```

<210> SEQ ID NO 158
<211> LENGTH: 1115
<212> TYPE: DNA
<213> ORGANISM: Artificial Sequence
<220> FEATURE:
<223> OTHER INFORMATION: Description of Artificial Sequence: Synthetic

<400> SEQUENCE: 158

```
tgtggaattg tgagcggata caatttcac acaggaaaca gaccatgggt gtcccaattg       60
gtgagattat accaagaaaa gaaattgagt tagaaaacct atacgggaaa aaaatcgcaa     120
tcgacgctct taatgcaatc taccaatttt tgtccacaat aagacagaaa gatggaactc     180
cacttatgga ttcaaagggt agaataacct cccacctaag cgggctcttt tacaggacaa     240
taaacctaat ggaggctgga ataaaacctg tgtatgtttt tgatggagaa cctccagaat     300
tcaaaaagaa agagctcgaa aaagaagag aagcgagaga ggaagctgaa gaaaagtgga     360
gagaagcact tgaaaaagga gagatagagg aagcaagaaa atatgcccaa agagcaacca     420
gggtaaatga aatgctcatc gaggatgcaa aaaaactctt agagcttatg ggaattccta     480
tagttcaagc acctagcgag ggagaggccc aagcaagcta tatggcaaag aagggagatg     540
tttgggcagt tgtaagtcaa gattatgatg ccttgttata tggagctccg agagttgtta     600
gaaatttaac aactacaaag gagatgccag aacttattga attaaatgag gttttagagg     660
atttaagaat ttcttggat gatttgatag atatagccat atttatggga actgactata     720
atccaggagg agttaaagga ataggattta aaagggctta tgaattggtt agaagtggtg     780
tagctaagga tgttttgaaa aaagaggttg aatactacga tgagattaag aggatattta     840
```

```
aagagccaaa ggttaccgat aactattcat taagcctaaa attgccagat aaagagggaa      900
ttataaaatt cttagttgat gaaaatgact ttaattatga tagggttaaa aagcatgttg      960
ataaactcta taacttaatt gcaaacaaaa ctaagcaaaa acattagat gcatggttta      1020 aataatttat ataattttgt gggatgtcga cctgcaggca tgcaagcttg gctgttttgg     1080
cggatgagag aagattttca gcctgataca gatta                                 1115

<210> SEQ ID NO 159
<211> LENGTH: 2505
<212> TYPE: DNA
<213> ORGANISM: Artificial Sequence
<220> FEATURE:
<223> OTHER INFORMATION: Description of Artificial Sequence:  Synthetic

<400> SEQUENCE: 159
atggaggcga tgcttccgct ctttgaaccc aaaggccggg tcctcctggt ggacggccac       60
cacctggcct accgcacctt cttcgccctg aagggcctca ccacgagccg ggcgaaccg      120 gtgcaggcgg tctacggctt cgccaagagc ctcctcaagg ccctgaagga ggacgggtac     180
aaggccgtct tcgtggtctt tgacgccaag gcccctcct tccgccacga ggcctacgag      240
gcctacaagg cggggagggc cccgaccccc gaggacttcc cccggcagct cgccctcatc     300
aaggagctgg tggacctcct ggggtttacc cgcctcgagg tccccggcta cgaggcggac     360
gacgttctcg ccaccctggc caagaaggcg gaaaaggagg ggtacgaggt gcgcatcctc     420
accgccgacc gcgacctcta ccaactcgtc tccgaccgcg tcgccgtcct ccaccccgag     480
ggccacctca tccccggga gtggctttgg gagaagtacg gcctcaggcc ggagcagtgg     540
gtggacttcc gcgccctcgt gggggacccc tccgacaacc tccccgggt caaggggcatc     600 ggggagaaga ccgcccctcaa gctcctcaag gagtggggaa gcctggaaaa cctcctcaag     660
aacctggacc gggtaaagcc agaaaacgtc gggagaaga tcaaggccca cctggaagac     720
ctcaggctct ccttggagct ctcccgggtg cgcaccgacc tccccctgga ggtggacctc     780 gcccagggc gggagcccga ccgggagggg cttaggcct tcctggagag gctggagttc     840
ggcagcctcc tccacgagtt cggcctcctg gaggccccg cccccctgga ggaggccccc     900 tggccccgc cggaagggc cttcgtgggc ttcgtcctct cccgcccgga gcccatgtgg     960
gcggagctta agccctggc cgcctgcagg gacggccggg tgcaccgggc agcagacccc    1020 ttggcgggc taaaggacct caaggaggtc cggggcctcc tcgccaagga cctcgccgtc    1080
ttggcctcga gggagggct agacctcgtg cccggggacg accccatgct cctcgcctac    1140
ctcctggacc cctccaacac cacccccgag ggggtggcgc ggcgctacgg ggggagtgg    1200 acggaggacg ccgcccaccg ggccctcctc tcggagaggc tccatcggaa cctccttaag    1260
cgcctcgagg gggaggagaa gctcctttgg ctctaccacg aggtggaaaa gcccctctcc    1320
cgggtcctgg cccacatgga ggccaccggg gtacggcggg acgtggccta ccttcaggcc    1380
ctttccctgg agcttgcgga ggagatccgc cgctcgagg aggaggtctt ccgcttggcg    1440
ggccacccct tcaacctcaa ctcccgggac cagctggaaa gggtgctctt tgacgagctt    1500
aggcttcccg ccttggggaa gacgcaaaag acaggcaagc gctccaccag cgccgcggtg    1560
ctggaggccc tacggaggc ccaccccatc gtggagaaga tcctccagca ccgggagctc    1620
accaagctca agaacaccta cgtggacccc ctcccaagcc tcgtccaccc gaggacgggc    1680
cgcctccaca cccgcttcaa ccagacgcc acggccacgg ggaggcttag tagctccgac    1740
cccaacctgc agaacatccc cgtccgcacc cccttgggcc agaggatccg ccgggccttc    1800
```

```
gtggccgagg cgggttgggc gttggtggcc ctggactata gccagataga gctccgcgtc    1860
ctcgcccacc tctccgggga cgaaaacctg atcagggtct tccaggaggg aaggacatc    1920 cacacccaga ccgcaagctg gatgttcggc gtccccccgg aggccgtgga cccctgatg    1980 cgccgggcgg ccaagacggt gaacttcggc gtcctctacg gcatgtccgc cataggctc    2040 tcccaggagc ttgccatccc ctacgaggag gcggtggcct ttatagagcg ctacttccaa    2100
agcttcccca aggtgcgggc ctggatagaa aagaccctgg aggaggggag gaagcggggc    2160
tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
gacctcatga agctcgccat ggtgaagctc ttcccccgcc tccgggagat gggggcccgc    2340
atgctcctcc aggtccacga cgagctcctc ctggaggccc ccaagcgcg gccgaggag    2400 gtggcggctt tggccaagga ggccatggag aaggcctatc ccctcgccgt gcccctggag    2460
gtggaggtgg ggatggggga ggactggctt tccgccaagg gttag                    2505
```

<210> SEQ ID NO 160
<211> LENGTH: 834
<212> TYPE: PRT
<213> ORGANISM: Artificial Sequence
<220> FEATURE:
<223> OTHER INFORMATION: Description of Artificial Sequence: Synthetic

<400> SEQUENCE: 160

```
Met Glu Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
                 20                  25                  30

Leu Thr Thr Ser Arg Gly Glu Pro Val Gln Ala Val Tyr Gly Phe Ala
             35                  40                  45

Lys Ser Leu Leu Lys Ala Leu Lys Glu Asp Gly Tyr Lys Ala Val Phe
         50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240
```

-continued

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Arg Asp Val Ala Tyr Leu Gln Ala Leu Ser Leu Glu
            450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
            645                 650                 655

-continued

```
Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly
```

<210> SEQ ID NO 161
<211> LENGTH: 2511
<212> TYPE: DNA
<213> ORGANISM: Artificial Sequence
<220> FEATURE:
<223> OTHER INFORMATION: Description of Artificial Sequence: Synthetic

<400> SEQUENCE: 161

```
atgaattccg aggcgatgct tccgctcttt gaacccaaag gccgggtcct cctggtggac      60
ggccaccacc tggcctaccg caccttcttc gccctgaagg gcctcaccac gagccggggc     120
gaaccggtgc aggcggtcta cggcttcgcc aagagcctcc tcaaggccct gaaggaggac     180
gggtacaagg ccgtcttcgt ggtctttgac gccaaggccc cctccttccg ccacgaggcc     240
tacgaggcct acaaggcggg gagggccccg accccgagg acttccccg gcagctcgcc      300
ctcatcaagg agctggtgga cctcctgggg tttacccgcc tcgaggtccc cggctacgag     360
gcggacgacg ttctcgccac cctggccaag aaggcgaaa aggagggta cgaggtgcgc      420
atcctcaccg ccgaccgcga cctctaccaa ctcgtctccg accgcgtcgc cgtcctccac     480
cccgagggcc acctcatcac cccggagtgg ctttgggaga gtacggcct caggccggag      540
cagtgggtgg acttccgcgc cctcgtgggg gaccccccg acaacctccc cggggtcaag      600
ggcatcgggg agaagaccgc cctcaagctc tcaaggagt ggggaagcct ggaaaacctc      660
ctcaagaacc tggaccgggt aaagccagaa acgtccggg agaagatcaa ggcccacctg      720
gaagacctca ggctctcctt ggagctctcc cgggtgcgca ccgacctccc cctggaggtg      780
gacctcgccc aggggcggga gcccgaccgg gaggggctta gggccttcct ggagaggctg      840
gagttcggca gcctcctcca cgagttcggc ctcctggagg ccccgccc cctggaggag      900
gccccctggc cccgccgga aggggccttc gtgggcttcg tcctctcccg ccccgagccc      960
atgtgggcgg agcttaaagc cctggccgcc tgcagggacg gccgggtgca ccgggcagca    1020
```

```
gacccCttgg cggggctaaa ggacctcaag gaggtccggg gcctcctcgc caaggacctc   1080
gccgtcttgg cctcgaggga ggggctagac ctcgtgcccg ggacgaccc  catgctcctc   1140 gcctacctcc tggacccctc caacaccacc cccgaggggg tggcgcggcg ctacgggggg   1200
gagtggacgg aggacgccgc ccaccgggcc ctcctctcgg agaggctcca tcggaacctc   1260
cttaagcgcc tcgaggggga ggagaagctc ctttggctct accacgaggt ggaaaagccc   1320
ctctcccggg tcctggccca catggaggcc accggggtac ggcgggacgt ggcctacctt   1380
caggcccttt ccctggagct tgcggaggag atccgccgcc tcgaggagga ggtcttccgc   1440
ttggcgggcc acccCttcaa cctcaactcc cgggaccagc tggaaagggt gctctttgac   1500
gagcttaggc ttcccgcctt ggggaagacg caaaagacag gcaagcgctc caccagcgcc   1560
gcggtgctgg aggcCctacg ggaggccCac cccatcgtgg agaagatcct ccagcaccgg   1620
gagctcacca agctcaagaa cacctacgtg gaccccctcc caagcctcgt ccacccgagg   1680
acgggccgcc tccacacccg cttcaaccag acggccacgc cacggggag  gcttagtagc   1740 tccgacccca acctgcagaa catccccgtc cgcacccccT tgggccagag gatccgccgg   1800
gccttcgtgg ccgaggcggg ttgggcgttg gtggccctgg actatagcca gatagagctc   1860
cgcgtcctcg cccacctctc cggggacgaa aacctgatca gggtcttcca ggaggggaag   1920
gacatccaca cccagaccgc aagctggatg ttcggcgtcc ccccggaggc cgtggacccc   1980
ctgatgcgcc gggcgccaa  gacggtgaac ttcggcgtcc tctacggcat gtccgcccat   2040
aggctctccc aggagcttgc catcCcctac gaggaggcg  tggcctttat agagcgctac   2100
ttccaaagct tccccaaggt gcgggcctgg atagaaaaga ccctggagga ggggaggaag   2160
cggggctacg tggaaaccct cttcggaaga aggcgctacg tgcccgacct caacgcccgg   2220
gtgaagagcg tcagggaggc cgcggagcgc atggccttca acatgcccgt ccagggcacc   2280
gccgccgacc tcatgaagct cgccatggtg aagctcttcc ccgcctccg  ggagatgggg   2340 gcccgcatgc tcctccaggt ccacgacgag ctcctcctgg aggcccccca agcgcgggcc   2400
gaggaggtgg cggctttggc caaggaggcc atggagaagg cctatcccct cgccgtgccc   2460
ctggaggtgg aggtggggat ggggggaggac tggctttccg ccaagggtta g           2511
```

<210> SEQ ID NO 162
<211> LENGTH: 836
<212> TYPE: PRT
<213> ORGANISM: Artificial Sequence
<220> FEATURE:
<223> OTHER INFORMATION: Description of Artificial Sequence: Synthetic

<400> SEQUENCE: 162

```
Met Asn Ser Glu Ala Met Leu Pro Leu Phe Glu Pro Lys Gly Arg Val
 1               5                  10                  15

Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
        35                  40                  45

Phe Ala Lys Ser Leu Leu Lys Ala Leu Lys Glu Asp Gly Tyr Lys Ala
    50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
```

-continued

```
                100                 105                 110
Arg Leu Glu Val Pro Gly Tyr Glu Ala Asp Asp Val Leu Ala Thr Leu
            115                 120                 125
Ala Lys Lys Ala Glu Lys Glu Gly Tyr Glu Val Arg Ile Leu Thr Ala
        130                 135                 140
Asp Arg Asp Leu Tyr Gln Leu Val Ser Asp Arg Val Ala Val Leu His
145                 150                 155                 160
Pro Glu Gly His Leu Ile Thr Pro Glu Trp Leu Trp Glu Lys Tyr Gly
                165                 170                 175
Leu Arg Pro Glu Gln Trp Val Asp Phe Arg Ala Leu Val Gly Asp Pro
            180                 185                 190
Ser Asp Asn Leu Pro Gly Val Lys Gly Ile Gly Glu Lys Thr Ala Leu
                195                 200                 205
Lys Leu Leu Lys Glu Trp Gly Ser Leu Glu Asn Leu Leu Lys Asn Leu
        210                 215                 220
Asp Arg Val Lys Pro Glu Asn Val Arg Glu Lys Ile Lys Ala His Leu
225                 230                 235                 240
Glu Asp Leu Arg Leu Ser Leu Glu Leu Ser Arg Val Arg Thr Asp Leu
                245                 250                 255
Pro Leu Glu Val Asp Leu Ala Gln Gly Arg Glu Pro Asp Arg Glu Gly
            260                 265                 270
Leu Arg Ala Phe Leu Glu Arg Leu Glu Phe Gly Ser Leu Leu His Glu
        275                 280                 285
Phe Gly Leu Leu Glu Ala Pro Ala Pro Leu Glu Glu Ala Pro Trp Pro
    290                 295                 300
Pro Pro Glu Gly Ala Phe Val Gly Phe Val Leu Ser Arg Pro Glu Pro
305                 310                 315                 320
Met Trp Ala Glu Leu Lys Ala Leu Ala Ala Cys Arg Asp Gly Arg Val
                325                 330                 335
His Arg Ala Ala Asp Pro Leu Ala Gly Leu Lys Asp Leu Lys Glu Val
            340                 345                 350
Arg Gly Leu Leu Ala Lys Asp Leu Ala Val Leu Ala Ser Arg Glu Gly
        355                 360                 365
Leu Asp Leu Val Pro Gly Asp Asp Pro Met Leu Leu Ala Tyr Leu Leu
    370                 375                 380
Asp Pro Ser Asn Thr Thr Pro Glu Gly Val Ala Arg Arg Tyr Gly Gly
385                 390                 395                 400
Glu Trp Thr Glu Asp Ala Ala His Arg Ala Leu Leu Ser Glu Arg Leu
                405                 410                 415
His Arg Asn Leu Leu Lys Arg Leu Glu Gly Glu Glu Lys Leu Leu Trp
            420                 425                 430
Leu Tyr His Glu Val Glu Lys Pro Leu Ser Arg Val Leu Ala His Met
        435                 440                 445
Glu Ala Thr Gly Val Arg Arg Asp Val Ala Tyr Leu Gln Ala Leu Ser
    450                 455                 460
Leu Glu Leu Ala Glu Glu Ile Arg Arg Leu Glu Glu Val Phe Arg
465                 470                 475                 480
Leu Ala Gly His Pro Phe Asn Leu Asn Ser Arg Asp Gln Leu Glu Arg
                485                 490                 495
Val Leu Phe Asp Glu Leu Arg Leu Pro Ala Leu Gly Lys Thr Gln Lys
            500                 505                 510
Thr Gly Lys Arg Ser Thr Ser Ala Ala Val Leu Glu Ala Leu Arg Glu
        515                 520                 525
```

```
Ala His Pro Ile Val Glu Lys Ile Leu Gln His Arg Glu Leu Thr Lys
    530                 535                 540

Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
        595                 600                 605

Ala Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Val Ala Phe Ile Glu Arg Tyr Phe Gln Ser Phe
    690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Arg Tyr Val Pro Asp
                725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Arg Glu Met Gly Ala Arg Met Leu
    770                 775                 780

Leu Gln Val His Asp Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
                805                 810                 815

Leu Ala Val Pro Leu Glu Val Glu Val Gly Met Gly Glu Asp Trp Leu
            820                 825                 830

Ser Ala Lys Gly
        835

<210> SEQ ID NO 163
<211> LENGTH: 2511
<212> TYPE: DNA
<213> ORGANISM: Artificial Sequence
<220> FEATURE:
<223> OTHER INFORMATION: Description of Artificial Sequence:  Synthetic

<400> SEQUENCE: 163
atgaattccg aggcgatgct tccgctcttt gaacccaaag gccgggtcct cctggtggac      60
ggccaccacc tggcctaccg caccttcttc gccctgaagg cctcaccac gagccggggc     120 gaaccggtgc aggcggtcta cggcttcgcc aagagcctcc tcaaggccct gaaggaggac     180
gggtacaagg ccgtcttcgt ggtctttgac gccaaggccc cctccttccg ccacgaggcc     240
```

-continued

```
tacgaggcct acaaggcggg gagggccccg accccgaggg acttccccg gcagctcgcc      300
ctcatcaagg agctggtgga cctcctgggg tttacccgcc tcgaggtccc cggctacgag    360
gcggacgacg ttctcgccac cctggccaag aaggcggaaa aggagggta cgaggtgcgc    420
atcctcaccg ccgaccgcga cctctaccaa ctcgtctccg accgcgtcgc cgtcctccac    480
cccgagggcc acctcatcac cccggagtgg ctttgggaga agtacggcct caggccggag    540
cagtgggtgg acttccgcgc cctcgtgggg gaccccctccg acaacctccc cggggtcaag   600
ggcatcgggg agaagaccgc cctcaagctc ctcaaggagt ggggaagcct ggaaaacctc    660
ctcaagaacc tggaccgggt aaagccagaa aacgtccggg agaagatcaa ggcccacctg    720
gaagacctca ggctctcctt ggagctctcc cgggtgcgca ccgacctccc cctggaggtg    780
gacctcgccc aggggcggga gcccgaccgg gaggggctta gggccttcct ggagaggctg    840
gagttcggca gctcctcca cgagttcggc ctcctggagg cccccgcccc cctgaggag     900
gccccctggc cccgccgga aggggccttc gtgggcttcg tcctctcccg ccccgagccc    960
atgtgggcgg agcttaaagc cctggccgcc tgcaggacg gccgggtgca ccgggcagca   1020
gacccccttgg cggggctaaa ggacctcaag gaggtccggg gcctcctcgc caaggacctc  1080
gccgtcttgg cctcgaggga ggggctagac ctcgtgcccg gggacgaccc catgctcctc  1140
gcctacctcc tggacccctc caacaccacc cccgaggggg tggcgcggcg ctacgggggg  1200
gagtggacgg aggacgccgc ccaccggggcc ctcctctcgg agaggctcca tcggaacctc  1260
cttaagcgcc tcgaggggga ggagaagctc ctttggctct accacgaggt ggaaaagccc  1320
ctctcccggg tcctggccca catggaggcc accggggtac ggcgggacgt ggcctacctt  1380
caggcccttt cctggagct tgcggaggag atccgccgcc tcgaggagga ggtcttccgc   1440
ttggcgggcc accccttcaa cctcaactcc cgggaccagc tggaaagggt gctctttgac  1500
gagcttaggc ttcccgcctt ggggaagacg caaaagacag gcaagcgctc caccagcgcc  1560
gcggtgctgg aggccctacg ggaggcccac cccatcgtgg agaagatcct ccagcaccgg  1620
gagctcacca agctcaagaa cacctacgtg accccctccc aagcctcgt ccacccgagg   1680
acgggccgcc tccacacccg cttcaaccag acggccacgg ccacggggag gcttagtagc  1740
tccgaccca acctgcagaa catccccgtc cgcacccct tgggccagag gatccgccgg   1800
gccttcgtgg ccgaggcggg ttgggcgttg gtggccctgg actatagcca gatagagctc  1860
cgcgtcctcg cccacctctc cggggacgaa aacctgatca gggtcttcca ggaggggaag  1920
gacatccaca cccagaccgc aagctggatg ttcggcgtcc cccggaggc cgtggacccc  1980
ctgatgcgcc gggcggccaa gacgtgaac ttcggcgtcc tctacggcat gtccgcccat   2040
aggctctccc aggagcttgc catcccctac gaggaggcgg tggctttat agagcgctac   2100
ttccaaagct tccccaaggt gcgggcctgg atagaaaaga ccctggagga ggggaggaag  2160
cggggctacg tggaaaccct cttcggaaga aggcgctacg tgcccgacct caacgcccgg  2220
gtgaagagcg tcagggaggc cgcggagcgc atggccttca acatgcccgt ccagggcacc  2280
gccgccgacc tcatgaagct cgccatggtg aagctcttcc cccgcctccg ggagatgggg  2340
gcccgcatgc tcctccaggt ccacaacgag ctcctcctgg aggcccccca agcgcgggcc  2400
gaggaggtgg cggctttggc caaggaggcc atggagaagg cctatcccct cgccgtgccc  2460
ctggaggtgg aggtgggat gggggaggac tggctttccg ccaagggtta g             2511
```

<210> SEQ ID NO 164
<211> LENGTH: 836

```
<212> TYPE: PRT
<213> ORGANISM: Artificial Sequence
<220> FEATURE:
<223> OTHER INFORMATION: Description of Artificial Sequence: Synthetic

<400> SEQUENCE: 164

Met Asn Ser Glu Ala Met Leu Pro Leu Phe Glu Pro Lys Gly Arg Val
  1               5                  10                  15

Leu Leu Val Asp Gly His His Leu Ala Tyr Arg Thr Phe Phe Ala Leu
                 20                  25                  30

Lys Gly Leu Thr Thr Ser Arg Gly Glu Pro Val Gln Ala Val Tyr Gly
             35                  40                  45

Phe Ala Lys Ser Leu Leu Lys Ala Leu Lys Glu Asp Gly Tyr Lys Ala
         50                  55                  60

Val Phe Val Val Phe Asp Ala Lys Ala Pro Ser Phe Arg His Glu Ala
 65                  70                  75                  80

Tyr Glu Ala Tyr Lys Ala Gly Arg Ala Pro Thr Pro Glu Asp Phe Pro
                 85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
        115                 120                 125

Ala Lys Lys Ala Glu Lys Glu Gly Tyr Glu Val Arg Ile Leu Thr Ala
130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
        195                 200                 205

Lys Leu Leu Lys Glu Trp Gly Ser Leu Glu Asn Leu Leu Lys Asn Leu
210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
        275                 280                 285

Phe Gly Leu Leu Glu Ala Pro Ala Pro Leu Glu Glu Ala Pro Trp Pro
290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Asp Gly Arg Val
                325                 330                 335

His Arg Ala Ala Asp Pro Leu Ala Gly Leu Lys Asp Leu Lys Glu Val
            340                 345                 350

Arg Gly Leu Leu Ala Lys Asp Leu Ala Val Leu Ala Ser Arg Glu Gly
        355                 360                 365

Leu Asp Leu Val Pro Gly Asp Asp Pro Met Leu Leu Ala Tyr Leu Leu
370                 375                 380
```

-continued

```
Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
            405                 410                 415

His Arg Asn Leu Leu Lys Arg Leu Glu Gly Glu Lys Leu Leu Trp
            420                 425                 430

Leu Tyr His Glu Val Glu Lys Pro Leu Ser Arg Val Leu Ala His Met
            435                 440                 445

Glu Ala Thr Gly Val Arg Arg Asp Val Ala Tyr Leu Gln Ala Leu Ser
450                 455                 460

Leu Glu Leu Ala Glu Glu Ile Arg Arg Leu Glu Glu Val Phe Arg
465                 470                 475                 480

Leu Ala Gly His Pro Phe Asn Leu Asn Ser Arg Asp Gln Leu Glu Arg
            485                 490                 495

Val Leu Phe Asp Glu Leu Arg Leu Pro Ala Leu Gly Lys Thr Gln Lys
            500                 505                 510

Thr Gly Lys Arg Ser Thr Ser Ala Ala Val Leu Glu Ala Leu Arg Glu
            515                 520                 525

Ala His Pro Ile Val Glu Lys Ile Leu Gln His Arg Glu Leu Thr Lys
530                 535                 540

Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
            565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
            595                 600                 605

Ala Leu Val Ala Leu Asp Tyr Ser Gln Ile Glu Leu Arg Val Leu Ala
            610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
            645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
            675                 680                 685

Pro Tyr Glu Glu Ala Val Ala Phe Ile Glu Arg Tyr Phe Gln Ser Phe
690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Arg Tyr Val Pro Asp
            725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
            755                 760                 765

Met Val Lys Leu Phe Pro Arg Leu Arg Glu Met Gly Ala Arg Met Leu
770                 775                 780

Leu Gln Val His Asn Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
```

```
                    805                 810                 815
Leu Ala Val Pro Leu Glu Val Glu Val Gly Met Gly Glu Asp Trp Leu
                820                 825                 830
Ser Ala Lys Gly
        835
```

<210> SEQ ID NO 165
<211> LENGTH: 350
<212> TYPE: DNA
<213> ORGANISM: Escherichia coli

<400> SEQUENCE: 165

| | | | | | |
|---|---|---|---|---|---|
| agagtttgat | catggctcag | attgaacgct | ggcggcaggc | ctaacacatg caagtcgaac | 60 |
| ggtaacagga | agaagcttgc | ttctttgctg | acgagtggcg | gacgggtgag taatgtctgg | 120 |
| gaaactgcct | gatggagggg | gataactact | ggaaacggta | gctaataccg cataacgtcg | 180 |
| caagaccaaa | gagggggacc | ttcgggcctc | ttgccatcgg | atgtgcccag atggattag  | 240 |
| ctagtaggtg | gggtaacggc | tcacctaggc | gacgatccct | agctggtctg agaggatgac | 300 |
| cagccacact | ggaactgaga | cacggtccag | actcctacgg | gaggcagcag           | 350 |

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 166
cacgaattcc gaggcgatgc ttccgctc                                28

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 167
tcgacgtcga ctaacccttg gcggaaagcc                              30

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 168
gcatcgcctc ggaattcatg gtc                                     23

<210> SEQ ID NO 169
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 169
caggaggagc tcgttgtgga cctgga                                  26

<210> SEQ ID NO 170
<211> LENGTH: 26

```
<212> TYPE: DNA
<213> ORGANISM: Artificial Sequence
<220> FEATURE:
<223> OTHER INFORMATION: Description of Artificial Sequence: Synthetic

<400> SEQUENCE: 170
ccgtcaacat ttaccatggg tgcgga                                   26

<210> SEQ ID NO 171
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 171
ccgccacctc gtagtcgaca tcctttcgt g                              31

<210> SEQ ID NO 172
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 172
gggtgttccc atgggagtta aactcagg                                 28

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 173
ctgaattctg cagaaaaagg gg                                       22

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 174
agagtttgat cctggctcag                                          20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 175
ctgctgcctc ccgtaggagt                                          20

<210> SEQ ID NO 176
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 176
```

```
ttttcgctgt ctcgctgaaa gcgagacagc gttt                                34
```

<210> SEQ ID NO 177
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 177

```
ttttcgctgt ctcgctgaaa gcgagacagc gaaagacgct cgtgaaacga gcgtctttg    59
```

<210> SEQ ID NO 178
<211> LENGTH: 1011
<212> TYPE: DNA
<213> ORGANISM: Archaeoglobus fulgidus

<400> SEQUENCE: 178

```
atgggtgcgg atattggtga cctctttgag agggaagagg tcgagcttga gtacttctca    60
ggaaagaaaa ttgccgttga tgctttcaac acgctatacc agttcatctc gataataagg   120
cagcctgacg gtacgccgtt aaaggactca caggcagaa tcacctctca cctttccgga    180
atcctataca gagtctccaa catggtcgag gtgggaatca ggccggtgtt tgtattcgac   240
ggagagccac cggagttcaa gaaggctgaa attgaggaga ggaaaagag aagggctgag    300
gcagaggaga tgtggattgc ggcttttgcag gcaggagata aggacgcgaa aaagtatgct   360
caggctgcag ggagggttga cgagtacatt gttgactccg caaagacgct tttaagttac   420
atggggattc cctttgtcga tgccccgtct gaaggagagg cgcaggctgc ttacatggca   480
gcaaaaggcg atgtggagta cacaggaagc caggattacg attctctgct cttcggaagc   540
ccgagactcg ccagaaatct cgcaataacg ggaaaaagga gcttcccgg caaaaatgtc    600
tatgtggatg taaagccgga gataataatt ctggaaagca acctcaaaag gctgggtttg   660
acgagggagc agctcatcga catagcgatt ctggtcggga cggactacaa tgagggtgtg   720
aagggtgtcg cgctcaagaa ggctttgaac tacatcaaga cctacggaga tatttttcagg   780
gcactcaagg ctctgaaagt aaatattgac cacgtagagg agataaggaa tttcttcctg   840
aatcctcctg tgactgacga ctacagaata gagttcaggg agcctgactt tgagaaggcc   900
atcgagttcc tgtgcgagga gcacgacttc agcagggaga gggtcgagaa ggccttggag   960
aagctcaaag ctctgaagtc aacccaggcc acgcttgaga ggtggttctg a           1011
```

<210> SEQ ID NO 179
<211> LENGTH: 336
<212> TYPE: PRT
<213> ORGANISM: Archaeoglobus fulgidus

<400> SEQUENCE: 179

```
Met Gly Ala Asp Ile Gly Asp Leu Phe Glu Arg Glu Val Glu Leu
 1               5                  10                  15

Glu Tyr Phe Ser Gly Lys Lys Ile Ala Val Asp Ala Phe Asn Thr Leu
                20                  25                  30

Tyr Gln Phe Ile Ser Ile Ile Arg Gln Pro Asp Gly Thr Pro Leu Lys
            35                  40                  45

Asp Ser Gln Gly Arg Ile Thr Ser His Leu Ser Gly Ile Leu Tyr Arg
    50                  55                  60

Val Ser Asn Met Val Glu Val Gly Ile Arg Pro Val Phe Val Phe Asp
65                  70                  75                  80
```

Gly Glu Pro Pro Glu Phe Lys Lys Ala Glu Ile Glu Arg Lys Lys
                    85                  90                  95

Arg Arg Ala Glu Ala Glu Glu Met Trp Ile Ala Ala Leu Gln Ala Gly
                100                 105                 110

Asp Lys Asp Ala Lys Lys Tyr Ala Gln Ala Ala Gly Arg Val Asp Glu
            115                 120                 125

Tyr Ile Val Asp Ser Ala Lys Thr Leu Leu Ser Tyr Met Gly Ile Pro
130                 135                 140

Phe Val Asp Ala Pro Ser Glu Gly Glu Ala Gln Ala Ala Tyr Met Ala
145                 150                 155                 160

Ala Lys Gly Asp Val Glu Tyr Thr Gly Ser Gln Asp Tyr Asp Ser Leu
                165                 170                 175

Leu Phe Gly Ser Pro Arg Leu Ala Arg Asn Leu Ala Ile Thr Gly Lys
                180                 185                 190

Arg Lys Leu Pro Gly Lys Asn Val Tyr Val Asp Val Lys Pro Glu Ile
            195                 200                 205

Ile Ile Leu Glu Ser Asn Leu Lys Arg Leu Gly Leu Thr Arg Glu Gln
210                 215                 220

Leu Ile Asp Ile Ala Ile Leu Val Gly Thr Asp Tyr Asn Glu Gly Val
225                 230                 235                 240

Lys Gly Val Gly Val Lys Lys Ala Leu Asn Tyr Ile Lys Thr Tyr Gly
                245                 250                 255

Asp Ile Phe Arg Ala Leu Lys Ala Leu Lys Val Asn Ile Asp His Val
            260                 265                 270

Glu Glu Ile Arg Asn Phe Phe Leu Asn Pro Pro Val Thr Asp Asp Tyr
            275                 280                 285

Arg Ile Glu Phe Arg Glu Pro Asp Phe Glu Lys Ala Ile Glu Phe Leu
            290                 295                 300

Cys Glu Glu His Asp Phe Ser Arg Glu Arg Val Glu Lys Ala Leu Glu
305                 310                 315                 320

Lys Leu Lys Ala Leu Lys Ser Thr Gln Ala Thr Leu Glu Arg Trp Phe
                325                 330                 335

<210> SEQ ID NO 180
<211> LENGTH: 777
<212> TYPE: DNA
<213> ORGANISM: Methanobacterium thermoautotrophicum

<400> SEQUENCE: 180

| | | |
|---|---|---|
| atgggagtta aactcaggga tgttgtatca ccccgcagga tacgccttga ggaccttagg | 60 |
| ggaagaacgg tcgcagtcga tgcagccaac acactctacc agttcctatc aagcataagg | 120 |
| cagagggatg gaacacccct catggattcc agggtagag taacatcaca cctcagcggc | 180 |
| atactctaca ggacggccgc ggtcatggag agggagataa gggtcatata tgtcttcgat | 240 |
| ggaaggtccc accacctcaa gggcgagacc gtgagcagga gggctgatat ccggaagaaa | 300 |
| tctgaggttg agtggaagag ggcccttgag gagggggaca ttgacagggc gaaaaaatat | 360 |
| gctgtaaggt cctcaaggat gtcctcagaa atactggaga gttcaaagag ctcctggaa | 420 |
| cttctgggaa taccctatgt acaggcaccc ggtgagggg aggctcaggc atcatacatg | 480 |
| gttaagatgg gcgatgcatg ggccgtggca tcccaggact atgactgtct cctcttggc | 540 |
| gccccaaggg ttgtaaggaa cctcacccctc agcggaaaac ttgaggaccc cgagatcatt | 600 |
| gaactggagt ccaccctcag gaactctca atcagccaca cacagctcgt ggatatggca | 660 |
| ctactcgtcg ggactgactt caatgagggt gtaaagggga taggcgcaag gagggactc | 720 | aaactcatca gggagaaggg cgacattttc aaagtcatca gggaccttga agcttga      777

<210> SEQ ID NO 181
<211> LENGTH: 258
<212> TYPE: PRT
<213> ORGANISM: Methanobacterium thermoautotrophicum

<400> SEQUENCE: 181

```
Met Gly Val Lys Leu Arg Asp Val Val Ser Pro Arg Arg Ile Arg Leu
 1               5                  10                  15
Glu Asp Leu Arg Gly Arg Thr Val Ala Val Asp Ala Ala Asn Thr Leu
            20                  25                  30
Tyr Gln Phe Leu Ser Ser Ile Arg Gln Arg Asp Gly Thr Pro Leu Met
        35                  40                  45
Asp Ser Arg Gly Arg Val Thr Ser His Leu Ser Gly Ile Leu Tyr Arg
    50                  55                  60
Thr Ala Ala Val Met Glu Arg Glu Ile Arg Val Ile Tyr Val Phe Asp
65                  70                  75                  80
Gly Arg Ser His His Leu Lys Gly Glu Thr Val Ser Arg Arg Ala Asp
                85                  90                  95
Ile Arg Lys Lys Ser Glu Val Glu Trp Lys Arg Ala Leu Glu Glu Gly
            100                 105                 110
Asp Ile Asp Arg Ala Lys Lys Tyr Ala Val Arg Ser Ser Arg Met Ser
        115                 120                 125
Ser Glu Ile Leu Glu Ser Ser Lys Arg Leu Leu Glu Leu Leu Gly Ile
    130                 135                 140
Pro Tyr Val Gln Ala Pro Gly Glu Gly Glu Ala Gln Ala Ser Tyr Met
145                 150                 155                 160
Val Lys Met Gly Asp Ala Trp Ala Val Ala Ser Gln Asp Tyr Asp Cys
                165                 170                 175
Leu Leu Phe Gly Ala Pro Arg Val Val Arg Asn Leu Thr Leu Ser Gly
            180                 185                 190
Lys Leu Glu Asp Pro Glu Ile Ile Glu Leu Glu Ser Thr Leu Arg Glu
        195                 200                 205
Leu Ser Ile Ser His Thr Gln Leu Val Asp Met Ala Leu Leu Val Gly
    210                 215                 220
Thr Asp Phe Asn Glu Gly Val Lys Gly Ile Gly Ala Arg Arg Gly Leu
225                 230                 235                 240
Lys Leu Ile Arg Glu Lys Gly Asp Ile Phe Lys Val Ile Arg Asp Leu
                245                 250                 255
Glu Ala
```

<210> SEQ ID NO 182
<211> LENGTH: 987
<212> TYPE: DNA
<213> ORGANISM: Methanobacterium thermoautotrophicum

<400> SEQUENCE: 182
atgggagtta aactcaggga tgttgtatca ccccgcagga tacgccttga ggaccttagg      60
ggaagaacgg tcgcagtcga tgcagccaac acactctacc agttcctatc aagcataagg     120
cagagggatg gaacacccct catggattcc agggtgtaga taacatcaca cctcagcggc     180
atactctaca ggacggccgc ggtcatggag agggagataa gggtcatata tgtcttcgat     240
ggaaggtccc accacctcaa gggcgagacc gtgagcagga gggctgatat ccggaagaaa     300

-continued

```
tctgaggttg agtggaagag ggcccttgag gaggggggaca ttgacagggc gagaaaatat      360
gctgtaaggt cctcaaggat gtcctcagaa atactggaga gttcaaagag gctcctggaa      420
cttctgggaa taccctatgt acaggcaccc ggtgaggggg aggctcaggc atcatacatg      480
gttaagatgg gcgatgcatg ggccgtggca tcccaggact atgactgtct cctctttggc      540
gccccaaggg ttgtaaggaa ggtcaccctc agcggaaaac ttgaggaccc ccacatcatt      600
gaactggagt ccaccctcag ggccctctca atcagccaca cacagctcgt ggatatggca      660
ctactcgtcg ggactgactt caatgagggt gtaaagggt atggcgcaag gaggggactc       720
aaactcatca gggagaaggg cgacattttc aaagtcatca gggaccttga gctgacata       780 ggtggcgacc cccaggtcct caggaggatc tttctggagc agaggtttc agaggactat       840 gagatcaggt ggagaaaacc tgacgtggaa ggtgttatcg agttcctgtg cactgaacac      900
ggcttttcag aggaccgtgt gagggatgca cttaaaaaat ttgagggtgc atcctccacc      960
cagaagagcc tggaggactg gttctga                                          987
```

<210> SEQ ID NO 183
<211> LENGTH: 328
<212> TYPE: PRT
<213> ORGANISM: Methanobacterium thermoautotrophicum

<400> SEQUENCE: 183

```
Met Gly Val Lys Leu Arg Asp Val Val Ser Pro Arg Arg Ile Arg Leu
  1               5                  10                  15

Glu Asp Leu Arg Gly Arg Thr Val Ala Val Asp Ala Ala Asn Thr Leu
             20                  25                  30

Tyr Gln Phe Leu Ser Ser Ile Arg Gln Arg Asp Gly Thr Pro Leu Met
         35                  40                  45

Asp Ser Arg Gly Arg Val Thr Ser His Leu Ser Gly Ile Leu Tyr Arg
     50                  55                  60

Thr Ala Ala Val Met Glu Arg Glu Ile Arg Val Ile Tyr Val Phe Asp
 65                  70                  75                  80

Gly Arg Ser His His Leu Lys Gly Glu Thr Val Ser Arg Arg Ala Asp
                 85                  90                  95

Ile Arg Lys Lys Ser Glu Val Glu Trp Lys Arg Ala Leu Glu Glu Gly
            100                 105                 110

Asp Ile Asp Arg Ala Arg Lys Tyr Ala Val Arg Ser Ser Arg Met Ser
        115                 120                 125

Ser Glu Ile Leu Glu Ser Ser Lys Arg Leu Leu Glu Leu Leu Gly Ile
    130                 135                 140

Pro Tyr Val Gln Ala Pro Gly Glu Gly Glu Ala Gln Ala Ser Tyr Met
145                 150                 155                 160

Val Lys Met Gly Asp Ala Trp Ala Val Ala Ser Gln Asp Tyr Asp Cys
                165                 170                 175

Leu Leu Phe Gly Ala Pro Arg Val Val Arg Lys Val Thr Leu Ser Gly
            180                 185                 190

Lys Leu Glu Asp Pro His Ile Ile Glu Leu Glu Ser Thr Leu Arg Ala
        195                 200                 205

Leu Ser Ile Ser His Thr Gln Leu Val Asp Met Ala Leu Leu Val Gly
    210                 215                 220

Thr Asp Phe Asn Glu Gly Val Lys Gly Tyr Gly Ala Arg Arg Gly Leu
225                 230                 235                 240

Lys Leu Ile Arg Glu Lys Gly Asp Ile Phe Lys Val Ile Arg Asp Leu
                245                 250                 255
```

```
Glu Ala Asp Ile Gly Gly Asp Pro Gln Val Leu Arg Arg Ile Phe Leu
            260                 265                 270

Glu Pro Glu Val Ser Glu Asp Tyr Glu Ile Arg Trp Arg Lys Pro Asp
        275                 280                 285

Val Glu Gly Val Ile Glu Phe Leu Cys Thr Glu His Gly Phe Ser Glu
        290                 295                 300

Asp Arg Val Arg Asp Ala Leu Lys Lys Phe Glu Gly Ala Ser Ser Thr
305                 310                 315                 320

Gln Lys Ser Leu Glu Asp Trp Phe
                325

<210> SEQ ID NO 184
<211> LENGTH: 340
<212> TYPE: PRT
<213> ORGANISM: Artificial Sequence
<220> FEATURE:
<223> OTHER INFORMATION: Description of Artificial Sequence: Synthetic

<400> SEQUENCE: 184

Met Gly Val Gln Phe Gly Asp Phe Ile Pro Lys Asn Ile Ile Ser Phe
  1               5                  10                  15

Glu Asp Leu Lys Gly Lys Val Ala Ile Asp Gly Met Asn Ala Leu
             20                  25                  30

Tyr Gln Phe Leu Thr Ser Ile Arg Leu Arg Asp Gly Ser Pro Leu Arg
             35                  40                  45

Asn Arg Lys Gly Glu Ile Thr Ser Ala Tyr Asn Gly Val Phe Tyr Lys
         50                  55                  60

Thr Ile His Leu Leu Glu Asn Asp Ile Thr Pro Ile Trp Val Phe Asp
 65                  70                  75                  80

Gly Glu Pro Pro Glu Phe Lys Lys Lys Glu Leu Glu Lys Arg Arg Glu
                 85                  90                  95

Ala Arg Glu Glu Ala Glu Glu Lys Trp Arg Glu Ala Leu Glu Lys Gly
            100                 105                 110

Glu Ile Glu Glu Ala Arg Lys Tyr Ala Gln Arg Ala Thr Arg Val Asn
            115                 120                 125

Glu Met Leu Ile Glu Asp Ala Lys Lys Leu Leu Glu Leu Met Gly Ile
130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175

Leu Leu Phe Gly Ala Pro Arg Leu Val Arg Asn Leu Thr Ile Thr Gly
            180                 185                 190

Lys Arg Lys Leu Pro Gly Lys Asn Val Tyr Val Glu Ile Lys Pro Glu
        195                 200                 205

Leu Ile Ile Leu Glu Glu Val Leu Lys Glu Leu Lys Leu Thr Arg Glu
210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                245                 250                 255

Ser Lys Asp Pro Leu Ala Lys Phe Gln Lys Gln Ser Asp Val Asp Leu
            260                 265                 270

Tyr Ala Ile Lys Glu Phe Phe Leu Asn Pro Pro Val Thr Asp Asn Tyr
        275                 280                 285
```

```
Asn Leu Val Trp Arg Asp Pro Asp Glu Glu Gly Ile Leu Lys Phe Leu
            290                 295                 300
Cys Asp Glu His Asp Phe Ser Glu Glu Arg Val Lys Asn Gly Leu Glu
305                 310                 315                 320
Arg Leu Lys Lys Ala Ile Lys Ser Gly Lys Gln Ser Thr Leu Glu Ser
                325                 330                 335
Trp Phe Lys Arg
            340

<210> SEQ ID NO 185
<211> LENGTH: 326
<212> TYPE: PRT
<213> ORGANISM: Artificial Sequence
<220> FEATURE:
<223> OTHER INFORMATION: Description of Artificial Sequence: Synthetic

<400> SEQUENCE: 185

Met Gly Val Pro Ile Gly Glu Ile Ile Pro Arg Lys Glu Ile Glu Leu
  1               5                  10                  15
Glu Asn Leu Tyr Gly Lys Lys Ile Ala Ile Asp Ala Leu Asn Ala Ile
                 20                  25                  30
Tyr Gln Phe Leu Ser Thr Ile Arg Gln Lys Asp Gly Thr Pro Leu Met
             35                  40                  45
Asp Ser Lys Gly Arg Ile Thr Ser His Leu Ser Gly Leu Phe Tyr Arg
         50                  55                  60
Thr Ile Asn Leu Met Glu Ala Gly Ile Lys Pro Val Tyr Val Phe Asp
 65                  70                  75                  80
Gly Glu Pro Pro Lys Leu Lys Glu Lys Thr Arg Lys Val Arg Arg Glu
                 85                  90                  95
Met Lys Glu Lys Ala Glu Leu Lys Met Lys Glu Ala Ile Lys Lys Glu
                100                 105                 110
Asp Phe Glu Glu Ala Ala Lys Tyr Ala Lys Arg Val Ser Tyr Leu Thr
            115                 120                 125
Pro Lys Met Val Glu Asn Cys Lys Tyr Leu Leu Ser Leu Met Gly Ile
        130                 135                 140
Pro Tyr Val Glu Ala Pro Ser Glu Gly Glu Ala Gln Ala Ser Tyr Met
145                 150                 155                 160
Ala Lys Lys Gly Asp Val Trp Ala Val Ser Gln Asp Tyr Asp Ala
                165                 170                 175
Leu Leu Tyr Gly Ala Pro Arg Val Val Arg Asn Leu Thr Thr Thr Lys
                180                 185                 190
Glu Met Pro Glu Leu Ile Glu Leu Asn Glu Val Leu Glu Asp Leu Arg
            195                 200                 205
Ile Ser Leu Asp Asp Leu Ile Asp Ile Ala Ile Phe Met Gly Thr Asp
        210                 215                 220
Tyr Asn Pro Gly Gly Val Lys Gly Ile Gly Phe Lys Arg Ala Tyr Glu
225                 230                 235                 240
Leu Val Arg Ser Gly Val Ala Lys Asp Val Leu Lys Lys Glu Val Glu
                245                 250                 255
Tyr Tyr Asp Glu Ile Lys Arg Ile Phe Lys Glu Pro Lys Val Thr Asp
            260                 265                 270
Asn Tyr Ser Leu Ser Leu Lys Leu Pro Asp Lys Glu Gly Ile Ile Lys
        275                 280                 285
Phe Leu Val Asp Glu Asn Asp Phe Asn Tyr Asp Arg Val Lys Lys His
290                 295                 300
```

Val Asp Lys Leu Tyr Asn Leu Ile Ala Asn Lys Thr Lys Gln Lys Thr
305                 310                 315                 320

Leu Asp Ala Trp Phe Lys
                325

<210> SEQ ID NO 186
<211> LENGTH: 332
<212> TYPE: PRT
<213> ORGANISM: Artificial Sequence
<220> FEATURE:
<223> OTHER INFORMATION: Description of Artificial Sequence:  Synthetic

<400> SEQUENCE: 186

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Lys Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Glu Leu Glu Lys Arg Arg Glu
                85                  90                  95

Ala Arg Glu Glu Ala Glu Lys Trp Arg Glu Ala Leu Glu Lys Gly
            100                 105                 110

Glu Ile Glu Glu Ala Ala Lys Tyr Ala Lys Arg Val Ser Tyr Leu Thr
        115                 120                 125

Pro Lys Met Val Glu Asn Cys Lys Tyr Leu Leu Ser Leu Met Gly Ile
    130                 135                 140

Pro Tyr Val Glu Ala Pro Ser Glu Gly Glu Ala Gln Ala Ser Tyr Met
145                 150                 155                 160

Ala Lys Lys Gly Asp Val Trp Ala Val Val Ser Gln Asp Tyr Asp Ala
                165                 170                 175

Leu Leu Tyr Gly Ala Pro Arg Val Val Arg Asn Leu Thr Thr Thr Lys
            180                 185                 190

Glu Met Pro Glu Leu Ile Glu Leu Asn Glu Val Leu Glu Asp Leu Arg
        195                 200                 205

Ile Ser Leu Asp Asp Leu Ile Asp Ile Ala Ile Phe Met Gly Thr Asp
    210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Lys Glu Val Glu
                245                 250                 255

Tyr Tyr Asp Glu Ile Lys Arg Ile Phe Lys Glu Pro Lys Val Thr Asp
            260                 265                 270

Asn Tyr Ser Leu Ser Leu Lys Leu Pro Asp Lys Glu Gly Ile Ile Lys
        275                 280                 285

Phe Leu Val Asp Glu Asn Asp Phe Asn Tyr Asp Arg Val Lys Lys His
    290                 295                 300

Val Asp Lys Leu Tyr Asn Leu Ile Ala Asn Lys Thr Lys Gln Lys Thr
305                 310                 315                 320

Leu Asp Ala Trp Phe Lys His His His His His
                325                 330

```
<210> SEQ ID NO 187
<211> LENGTH: 340
<212> TYPE: PRT
<213> ORGANISM: Artificial Sequence
<220> FEATURE:
<223> OTHER INFORMATION: Description of Artificial Sequence: Synthetic

<400> SEQUENCE: 187

Met Gly Val Gln Phe Gly Asp Phe Ile Pro Lys Asn Ile Ile Ser Phe
 1               5                  10                  15

Glu Asp Leu Lys Gly Lys Val Ala Ile Asp Gly Met Asn Ala Leu
                20                  25                  30

Tyr Gln Phe Leu Thr Ser Ile Arg Leu Arg Asp Gly Ser Pro Leu Arg
            35                  40                  45

Asn Arg Lys Gly Glu Ile Thr Ser Ala Tyr Asn Gly Val Phe Tyr Lys
        50                  55                  60

Thr Ile His Leu Leu Glu Asn Asp Ile Thr Pro Ile Trp Val Phe Asp
65                  70                  75                  80

Gly Glu Pro Pro Lys Leu Lys Glu Lys Thr Arg Lys Val Arg Arg Glu
                85                  90                  95

Met Lys Glu Lys Ala Glu Leu Lys Met Lys Glu Ala Ile Lys Lys Glu
            100                 105                 110

Asp Phe Glu Glu Ala Ala Lys Tyr Ala Lys Arg Val Ser Tyr Leu Thr
        115                 120                 125

Pro Lys Met Val Glu Asn Cys Lys Tyr Leu Leu Ser Leu Met Gly Ile
    130                 135                 140

Pro Tyr Val Glu Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175

Leu Leu Phe Gly Ala Pro Arg Leu Val Arg Asn Leu Thr Ile Thr Gly
            180                 185                 190

Lys Arg Lys Leu Pro Gly Lys Asn Val Tyr Val Glu Ile Lys Pro Glu
        195                 200                 205

Leu Ile Ile Leu Glu Glu Val Leu Lys Glu Leu Lys Leu Thr Arg Glu
    210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                245                 250                 255

Ser Lys Asp Pro Leu Ala Lys Phe Gln Lys Gln Ser Asp Val Asp Leu
            260                 265                 270

Tyr Ala Ile Lys Glu Phe Phe Leu Asn Pro Pro Val Thr Asp Asn Tyr
        275                 280                 285

Asn Leu Val Trp Arg Asp Pro Asp Glu Glu Gly Ile Leu Lys Phe Leu
    290                 295                 300

Cys Asp Glu His Asp Phe Ser Glu Glu Arg Val Lys Asn Gly Leu Glu
305                 310                 315                 320

Arg Leu Lys Lys Ala Ile Lys Ser Gly Lys Gln Ser Thr Leu Glu Ser
                325                 330                 335

Trp Phe Lys Arg
            340

<210> SEQ ID NO 188
```

-continued

```
<211> LENGTH: 326
<212> TYPE: PRT
<213> ORGANISM: Artificial Sequence
<220> FEATURE:
<223> OTHER INFORMATION: Description of Artificial Sequence:  Synthetic

<400> SEQUENCE: 188

Met Gly Val Pro Ile Gly Glu Ile Ile Pro Arg Lys Glu Ile Glu Leu
  1               5                  10                  15

Glu Asn Leu Tyr Gly Lys Lys Ile Ala Ile Asp Ala Leu Asn Ala Ile
             20                  25                  30

Tyr Gln Phe Leu Ser Thr Ile Arg Gln Lys Asp Gly Thr Pro Leu Met
         35                  40                  45

Asp Ser Lys Gly Arg Ile Thr Ser His Leu Ser Gly Leu Phe Tyr Arg
     50                  55                  60

Thr Ile Asn Leu Met Glu Ala Gly Ile Lys Pro Val Tyr Val Phe Asp
 65                  70                  75                  80

Gly Glu Pro Pro Glu Phe Lys Lys Lys Glu Leu Glu Lys Arg Arg Glu
                 85                  90                  95

Ala Arg Glu Glu Ala Glu Lys Trp Arg Glu Ala Leu Glu Lys Gly
                100                 105                 110

Glu Ile Glu Glu Ala Arg Lys Tyr Ala Gln Arg Ala Thr Arg Val Asn
            115                 120                 125

Glu Met Leu Ile Glu Asp Ala Lys Lys Leu Leu Glu Leu Met Gly Ile
        130                 135                 140

Pro Ile Val Gln Ala Pro Ser Glu Gly Glu Ala Gln Ala Ser Tyr Met
145                 150                 155                 160

Ala Lys Lys Gly Asp Val Trp Ala Val Val Ser Gln Asp Tyr Asp Ala
                165                 170                 175

Leu Leu Tyr Gly Ala Pro Arg Val Val Arg Asn Leu Thr Thr Thr Lys
            180                 185                 190

Glu Met Pro Glu Leu Ile Glu Leu Asn Glu Val Leu Glu Asp Leu Arg
        195                 200                 205

Ile Ser Leu Asp Asp Leu Ile Asp Ile Ala Ile Phe Met Gly Thr Asp
    210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Lys Glu Val Glu
                245                 250                 255

Tyr Tyr Asp Glu Ile Lys Arg Ile Phe Lys Glu Pro Lys Val Thr Asp
            260                 265                 270

Asn Tyr Ser Leu Ser Leu Lys Leu Pro Asp Lys Glu Gly Ile Ile Lys
        275                 280                 285

Phe Leu Val Asp Glu Asn Asp Phe Asn Tyr Asp Arg Val Lys His
    290                 295                 300

Val Asp Lys Leu Tyr Asn Leu Ile Ala Asn Lys Thr Lys Gln Lys Thr
305                 310                 315                 320

Leu Asp Ala Trp Phe Lys
                325
```